United States Patent
Bell et al.

(10) Patent No.: US 9,408,840 B2
(45) Date of Patent: *Aug. 9, 2016

(54) COMPOUNDS AND METHODS FOR INHIBITING NHE-MEDIATED ANTIPORT IN THE TREATMENT OF DISORDERS ASSOCIATED WITH FLUID RETENTION OR SALT OVERLOAD AND GASTROINTESTINAL TRACT DISORDER

(71) Applicant: Ardelyx, Inc., Fremont, CA (US)

(72) Inventors: Noah Bell, Fremont, CA (US); Christopher Carreras, Fremont, CA (US); Dominique Charmot, Fremont, CA (US); Jeffrey W. Jacobs, Fremont, CA (US); Michael Robert Leadbetter, Fremont, CA (US); Marc Navre, Fremont, CA (US)

(73) Assignee: Ardelyx, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/592,200

(22) Filed: Jan. 8, 2015

(65) Prior Publication Data

US 2015/0190389 A1    Jul. 9, 2015

Related U.S. Application Data

(63) Continuation of application No. 13/804,752, filed on Mar. 14, 2013, now Pat. No. 8,969,377, which is a continuation of application No. 13/172,394, filed on Jun. 29, 2011, now Pat. No. 8,541,448, which is a continuation of application No. PCT/US2009/069852, filed on Dec. 30, 2009.

(60) Provisional application No. 61/237,842, filed on Aug. 28, 2009, provisional application No. 61/169,509, filed on Apr. 15, 2009, provisional application No. 61/141,853, filed on Dec. 31, 2008.

(51) Int. Cl.
| | |
|---|---|
| *A61K 31/18* | (2006.01) |
| *A61K 31/4725* | (2006.01) |
| *A61K 31/472* | (2006.01) |
| *A61K 31/517* | (2006.01) |
| *A61K 31/662* | (2006.01) |
| *A61K 31/675* | (2006.01) |
| *A61K 45/06* | (2006.01) |
| *C07C 311/29* | (2006.01) |
| *C07D 217/04* | (2006.01) |
| *C07D 217/14* | (2006.01) |
| *C07D 401/12* | (2006.01) |
| *C07F 9/38* | (2006.01) |
| *C07F 9/576* | (2006.01) |
| *C07F 9/6558* | (2006.01) |
| *C07D 217/16* | (2006.01) |
| *C07D 215/14* | (2006.01) |
| *C07F 9/60* | (2006.01) |

(52) U.S. Cl.
CPC ............. *A61K 31/4725* (2013.01); *A61K 31/18* (2013.01); *A61K 31/472* (2013.01); *A61K31/517* (2013.01); *A61K 31/662* (2013.01); *A61K 31/675* (2013.01); *A61K 45/06* (2013.01); *C07C 311/29* (2013.01); *C07D 215/14* (2013.01); *C07D 217/04* (2013.01); *C07D 217/14* (2013.01); *C07D 217/16* (2013.01); *C07D 401/12* (2013.01); *C07F 9/3808* (2013.01); *C07F 9/3834* (2013.01); *C07F 9/3882* (2013.01); *C07F 9/5765* (2013.01); *C07F 9/60* (2013.01); *C07F 9/65583* (2013.01)

(58) Field of Classification Search
None
See application file for complete search history.

(56) References Cited

U.S. PATENT DOCUMENTS

| | | |
|---|---|---|
| 6,451,781 B1 | 9/2002 | Kleemann et al. |
| 6,703,405 B2 | 3/2004 | Hofmeister et al. |
| 6,911,453 B2 | 6/2005 | Hofmeister et al. |
| 7,241,775 B2 | 7/2007 | Hofmeister et al. |
| 7,790,742 B2 | 9/2010 | Lang et al. |
| 2003/0171580 A1 | 9/2003 | Hofmeister et al. |

| | | | |
|---|---|---|---|
| 2004/0044211 | A1 | 3/2004 | Hofmeister et al. |
| 2005/0009863 | A1 | 1/2005 | Hofmeister et al. |
| 2007/0135383 | A1 | 6/2007 | Chang et al. |
| 2007/0225323 | A1 | 9/2007 | Lang et al. |
| 2008/0058328 | A1 | 3/2008 | Heinelt et al. |
| 2008/0194621 | A1 | 8/2008 | Lang |
| 2008/0234317 | A1 | 9/2008 | Kleemann et al. |
| 2013/0274285 | A1 | 10/2013 | Bell et al. |

FOREIGN PATENT DOCUMENTS

| | | |
|---|---|---|
| WO | WO 01/17954 A1 | 3/2001 |
| WO | WO 03/048129 A1 | 6/2003 |
| WO | WO 2004/085404 A1 | 10/2004 |
| WO | WO 2006/032372 A1 | 6/2006 |
| WO | WO 2008/137318 A1 | 11/2008 |

OTHER PUBLICATIONS

MedlinePlus entry for Irritable Bowel Syndrome, retrieved from <www.nlm.nih.gov/medlineplus/irritablebowelsyndrome.html> on Aug. 6, 2015, pp. 1-6.*

MedlinePlus entry for Chronic Kidney Disease, retrived from <www.nlm.nih.gov/medlineplus/ency/article/000471.htm> on Aug. 6, 2015, pp. 1-8.*

MedlinePlus entry for End-stage Kidney Diseaes, retrieved from <www.nlm.nih.gov/medlineplus/ency/article/000500.htm> on Aug. 6, 2015, pp. 1-6.*

MedlinePlus entry for Irritable Bowel Syndrome, retrieved from medlineplus/irritablebowelsyndrome.html> on Aug. 6, 2015, pp. 1-6.*

Masereel, B. "An overview of inhibitors of Na+/H+ exchanger," 2003, Elsevier, *European Journal of Medicinal Chemistry*, vol. 38, pp. 547-554.

Li, Xiaoling "Biodegradable polymeric prodrugs of antihypertensive agents," 1991, University of Utah, Department of Pharmaceutics, pp. 1-241.

Weinman, Edward et al.; "Fibroblast Growth Factor-23-mediated Inhibition of Renal Phosphate Transport in Mice Requires Sodium-Hydrogen Exchanger Regulatory Factor-1 (NHERF-1) and Synergizes with Parathyroid Hormone," 2011, ASBMB, *The Journal of Biological Chemistry*, vol. 286, No. 43, pp. 37216-37221.

Ertl et al. "Fast Calculation of Molecular Polar Surface Area as a Sum of Fragment-based Contributions and Its Application to the Prediction of Drug Transport Properties", *Journal of Medicinal Chemistry*, (2000); 43(20); pp. 3714-3717.

Mammen et al. "Effective Inhibitors of Hemagglutination by Influenza Virus Synthesized from Polymers Having Active Ester Groups. Insight into Mechanism of Inhibition", *Journal of Medicinal Chemistry*, (1995); 38; 4179-4190.

Ledoussal, Clara, et al. "Renal salt wasting in mice lacking NHE3 Na+/H+ exchanger but not in mice lacking NHE2." American Journal of Physiology-Renal Physiology, vol. 281, No. 4 (2001): F718-F727.

Spencer, Andrew G., et al. "Intestinal Inhibition of the Na+/H+ Exchanger 3 Prevents Cardiorenal Damage in Rats and Inhibits Na+ Uptake in Humans." Science translational medicine, vol. 6, No. 227 (2014): 227ra36-27ra36.

\* cited by examiner

*Primary Examiner* — Suzanne Ziska
*Assistant Examiner* — Ivan Greene

(74) *Attorney, Agent, or Firm* — Cooley LLP; J. Dean Farmer; Serge R. Banini

(57) ABSTRACT

The present disclosure is directed to compounds of the structure (X):

$$\text{Core} (\text{L-NHE})_n \qquad (X)$$

wherein:
n is 2 or 3;
NHE has the structure

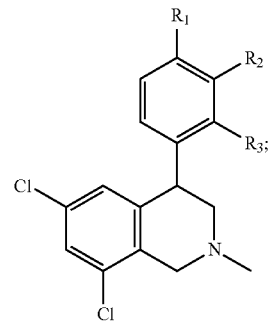

wherein:
$R^1$ is H or —SO$_2$—NR$_7$R$_8$—;
$R^2$ is selected from H, —NR$_7$(CO)R$_8$, —SO$_2$—NR$_7$R$_8$— and —NR$_7$R$_8$;
$R^3$ is hydrogen;
$R^7$ is hydrogen;
$R^8$ is a bond linking to L;
L is a polyalkylene glycol linker; and
Core has the following structure:

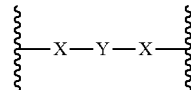

wherein:
X is selected from the group consisting of a bond, —O—, —NH—, NHC(=O)—, —NHC(=O)NH— and —NHSO$_2$—; and
Y is selected from the group consisting of a bond, optionally substituted C$_{1-6}$ alkylene, optionally substituted benzene, pyridinyl, a polyethylene glycol linker and —(CH$_2$)$_{1-6}$O(CH$_2$)$_{1-6}$—, and methods of using such compounds for the treatment of irritable bowel syndrome, chronic kidney disease and end-stage renal disease.

6 Claims, 8 Drawing Sheets

COMPOUNDS AND METHODS FOR INHIBITING NHE-MEDIATED ANTIPORT IN THE TREATMENT OF DISORDERS ASSOCIATED WITH FLUID RETENTION OR SALT OVERLOAD AND GASTROINTESTINAL TRACT DISORDER

CROSS-REFERENCE TO RELATED APPLICATIONS

This application is a continuation application U.S. patent application Ser. No. 13/804,752, filed Mar. 14, 2013, allowed, which is a continuation of U.S. patent application Ser. No. 13/172,394, filed Jun. 29, 2011, now U.S. Pat. No. 8,541,488, which is a continuation of International PCT Patent Application No. PCT/US2009/069852, filed on Dec. 30, 2009, which claims the benefit under 35 U.S.C. §119(e) of U.S. Provisional Patent Application No. 61/141,853, filed Dec. 31, 2008, U.S. Provisional Patent Application No. 61/169,509, filed Apr. 15, 2009, and U.S. Provisional Patent Application No. 61/237,842, filed Aug. 28, 2009. This application is also related to U.S. patent application Ser. No. 13/826,186, allowed, which is a divisional application of U.S. patent application Ser. No. 13/172,394. The contents of each of the foregoing applications are hereby incorporated by reference in their entirety.

BACKGROUND

1. Field

The present disclosure is directed to compounds that are substantially active in the gastrointestinal tract to inhibit NHE-mediated antiport of sodium ions and hydrogen ions, and the use of such compounds in the treatment of disorders associated with fluid retention or salt overload and in the treatment of gastrointestinal tract disorders, including the treatment or reduction of pain associated with a gastrointestinal tract disorder.

2. Description of the Related Art

Disorders Associated with Fluid Retention and Salt Overload

According to the American Heart Association, more than 5 million Americans have suffered from heart failure, and an estimated 550,000 cases of congestive heart failure (CHF) occur each year (Schocken, D. D. et al., *Prevention of heart failure: a scientific statement from the American Heart Association Councils on Epidemiology and Prevention, Clinical Cardiology, Cardiovascular Nursing, and High Blood Pressure Research*; Quality of Care and Outcomes Research Interdisciplinary Working Group; and Functional Genomics and Translational Biology Interdisciplinary Working Group: Circulation, v. 117, no. 19, p. 2544-2565 (2008)). The clinical syndrome of congestive heart failure occurs when cardiac dysfunction prevents adequate perfusion of peripheral tissues. The most common form of heart failure leading to CHF is systolic heart failure, caused by contractile failure of the myocardium. A main cause of CHF is due to ischemic coronary artery disease, with or without infarction. Long standing hypertension, particularly when it is poorly controlled, may lead to CHF. In patients with CHF, neurohumoral compensatory mechanisms (i.e., the sympathetic nervous system and the renin-angiotensin system) are activated in an effort to maintain normal circulation. The renin-angiotensin system is activated in response to decreased cardiac output, causing increased levels of plasma renin, angiotensin II, and aldosterone. As blood volume increases in the heart, cardiac output increases proportionally, to a point where the heart is unable to dilate further. In the failing heart, contractility is reduced, so the heart operates at higher volumes and higher filling pressures to maintain output. Filling pressures may eventually increase to a level that causes transudation of fluid into the lungs and congestive symptoms (e.g., edema, shortness of breath). All of these symptoms are related to fluid volume and salt retention, and this chronic fluid and salt overload further contribute to disease progression.

Compliance with the medication regimen and with dietary sodium restrictions is a critical component of self-management for patients with heart failure and may lengthen life, reduce hospitalizations and improve quality of life. Physicians often recommend keeping salt intake below 2.3 g per day and no more than 2 g per day for people with heart failure. Most people eat considerably more than this, so it is likely that a person with congestive heart failure will need to find ways to reduce dietary salt. A number of drug therapies currently exist for patients suffering from CHF. For example, diuretics may be used or administered to relieve congestion by decreasing volume and, consequently, filling pressures to below those that cause pulmonary edema. By counteracting the volume increase, diuretics reduce cardiac output; however, fatigue and dizziness may replace CHF symptoms. Among the classes or types of diuretics currently being used is thiazides. Thiazides inhibit NaCl transport in the kidney, thereby preventing reabsorption of Na in the cortical diluting segment at the ending portion of the loop of Henle and the proximal portion of the distal convoluted tubule. However, these drugs are not effective when the glomerular filtration rate (GFR) is less than 30 ml/min. Additionally, thiazides, as well as other diuretics, may cause hypokalemia. Also among the classes or types of diuretics currently being used is loop diuretics (e.g., furosemide). These are the most potent diuretics and are particularly effective in treating pulmonary edema. Loop diuretics inhibit the NaKCl transport system, thus preventing reabsorption of Na in the loop of Henle. Patients that have persistent edema despite receiving high doses of diuretics may be or become diuretic-resistant. Diuretic resistance may be caused by poor availability of the drug. In patients with renal failure, which has a high occurrence in the CHF population, endogenous acids compete with loop diuretics such as furosemide for the organic acid secretory pathway in the tubular lumen of the nephron. Higher doses, or continuous infusion, are therefore needed to achieve entrance of an adequate amount of drug into the nephron. However, recent meta-analysis have raised awareness about the long-term risk of chronic use of diuretics in the treatment of CHF. For instance, in a recent study (Ahmed et al., *Int J Cardiol.* 2008 Apr. 10; 125(2): 246-253) it was shown that chronic diuretic use was associated with significantly increased mortality and hospitalization in ambulatory older adults with heart failure receiving angiotensin converting enzyme inhibitor and diuretics.

Angiotensin-converting enzyme ("ACE") inhibitors are an example of another drug therapy that may be used to treat congestive heart failure. ACE inhibitors cause vasodilatation by blocking the renin-angiotensin-aldosterone system. Abnormally low cardiac output may cause the renal system to respond by releasing renin, which then converts angiotensinogen into angiotensin I. ACE converts angiotensin I into angiotensin II. Angiotensin II stimulates the thirst centers in the hypothalamus and causes vasoconstriction, thus increasing blood pressure and venous return. Angiotensin II also causes aldosterone to be released, causing reabsorption of Na and concomitant passive reabsorption of fluid, which in turn causes the blood volume to increase. ACE inhibitors block this compensatory system and improve cardiac performance by decreasing systemic and pulmonary vascular resistance. ACE inhibitors have shown survival benefit and conventionally have been a treatment of choice for CHF. However, since ACE inhibitors lower aldosterone, the K-secreting hormone, one of the side-effects of their use is hyperkalemia. In addition, ACE inhibitors have been show to lead to acute renal failure in certain categories of CHF patients. (See, e.g., C. S. Cruz et al., "Incidence and Predictors of Development of Acute Renal Failure Related to the Treatment of Congestive Heart Failure with ACE Inhibitors, Nephron Clin. Pract., v. 105, no. 2, pp c77-c83 (2007)).

Patients with end stage renal disease ("ESRD"), i.e., stage 5 chronic kidney failure, must undergo hemodialysis three times per week. The quasi-absence of renal function and ability to eliminate salt and fluid results in large fluctuations in body weight as fluid and salt build up in the body (sodium/volume overload). The fluid overload is characterized as interdialytic weight gain. High fluid overload is also worsened by heart dysfunction, specifically CHF. Dialysis is used to remove uremic toxins and also adjust salt and fluid homeostasis. However, symptomatic intradialytic hypotension (SIH) may occur when patients are over-dialyzed. SIH is exhibited in about 15% to 25% of the ESRD population (Davenport, A., C. Cox, and R. Thuraisingham, *Blood pressure control and symptomatic intradialytic hypotension in diabetic haemodialysis patients: a cross-sectional survey*; Nephron Clin. Pract., v. 109, no. 2, p. c65-c71 (2008)). Like in hypertensive and CHF patients, dietary restrictions of salt and fluid are highly recommended but poorly followed because of the poor palatability of low-salt food The cause of primary or "essential" hypertension is elusive. However, several observations point to the kidney as a primary factor. The strongest data for excess salt intake and elevated blood pressure come from INTERSALT, a cross-sectional study of greater than 10,000 participants. For individuals, a significant, positive, independent linear relation between 24-hour sodium excretion and systolic blood pressure was found. Higher individual 24-hour urinary sodium excretions were found to be associated with higher systolic/diastolic blood pressure on average, by 6-3/3-0 mm Hg. Primary hypertension is a typical example of a complex, multifactorial, and polygenic trait. All these monogenic hypertensive syndromes are virtually confined to mutated genes involving gain of function of various components of the renin-angiotensin-aldosterone system, resulting in excessive renal sodium retention. In a broad sense, these syndromes are characterized by increased renal sodium reabsorption arising through either primary defects in sodium transport systems or stimulation of mineralocorticoid receptor activity (Altun, B., and M. Arici, 2006, *Salt and blood pressure: time to challenge*; Cardiology, v. 105, no. 1, p. 9-16 (2006)). A much larger number of controlled studies have been performed on hypertensive subjects during the last three decades to determine whether sodium reduction will reduce established high blood pressure. Meta-analyses of these studies have clearly shown a large decrease in blood pressure in hypertensive patients.

In end stage liver disease (ESLD), accumulation of fluid as ascites, edema or pleural effusion due to cirrhosis is common and results from a derangement in the extracellular fluid volume regulatory mechanisms. Fluid retention is the most frequent complication of ESLD and occurs in about 50% of patients within 10 years of the diagnosis of cirrhosis. This complication significantly impairs the quality of life of cirrhotic patients and is also associated with poor prognosis. The one-year and five-year survival rate is 85% and 56%, respectively (Kashani et al., *Fluid retention in cirrhosis: pathophysiology and management*; QJM, v. 101, no. 2, p. 71-85 (2008)). The most acceptable theories postulate that the initial event in ascites formation in the cirrhotic patient is sinusoidal hypertension. Portal hypertension due to an increase in sinusoidal pressure activates vasodilatory mechanisms. In advanced stages of cirrhosis, arteriolar vasodilation causes underfilling of systemic arterial vascular space. This event, through a decrease in effective blood volume, leads to a drop in arterial pressure. Consequently, baroreceptor-mediated activation of renin-angiotensin aldosterone system, sympathetic nervous system and nonosmotic release of antidiuretic hormone occur to restore the normal blood homeostasis. These events cause further retention of renal sodium and fluid. Splanchnic vasodilation increases splanchnic lymph production, exceeding the lymph transportation system capacity, and leads to lymph leakage into the peritoneal cavity. Persistent renal sodium and fluid retention, alongside increased splanchnic vascular permeability in addition to lymph leakage into the peritoneal cavity, play a major role in a sustained ascites formation.

Thiazolidinediones (TZD's), such as rosiglitazone, are peroxisome proliferator-activated receptor (PPAR) gamma agonist agents used for the treatment of type-2 diabetes and are widely prescribed. Unfortunately, fluid retention has emerged as the most common and serious side-effect of TZD's and has become the most frequent cause of discontinuation of therapy. The incidence of TZD-induced fluid retention ranges from 7% in monotherapy and to as high as 15% when combined with insulin (Yan, T., Soodvilai, S., *PPAR Research* volume 2008, article ID 943614). The mechanisms for such side-effects are not fully understood but may be related in Na and fluid re-absorption in the kidney. However TZD-induced fluid retention is resistant to loop diuretics or thiazide diuretics, and combination of peroxisome proliferator-activated receptor (PPAR) alpha with PPAR gamma agonists, which were proposed to reduce such fluid overload, are associated with major adverse cardiovascular events.

In view of the foregoing, it is recognized that salt and fluid accumulation contribute to the morbidity and mortality of many diseases, including heart failure (in particular, congestive heart failure), chronic kidney disease, end-stage renal disease, liver disease and the like. It is also accepted that salt and fluid accumulation are risk factors for hypertension. Accordingly, there is a clear need for a medicament that, when administered to a patient in need, would result in a reduction in sodium retention, fluid retention, or preferably both. Such a medicament would more preferably also not involve or otherwise impair renal mechanisms of fluid/Na homeostasis.

One option to consider for treating excessive fluid overload is to induce diarrhea. Diarrhea may be triggered by several agents including, for example, laxatives such as sorbitol, polyethyleneglycol, bisacodyl and phenolphthaleine. Sorbitol and polyethyleneglycol triggers osmotic diarrhea with low levels of secreted electrolytes; thus, their utility in removing sodium salt from the GI tract is limited. The mechanism of action of phenolphthalein is not clearly established, but is thought to be caused by inhibition of the Na/K ATPase and the $Cl/HCO_3$ anion exchanger and stimulation of electrogenic anion secretion (see, e.g., Eherer, A. J., C. A. Santa Ana, J. Porter, and J. S. Fordtran, 1993, Gastroenterology, v. 104, no. 4, p. 1007-1012). However, some laxatives, such as phenolphthalein, are not viable options for the chronic treatment of fluid overload, due to the potential risk of carcinogenicity in humans. Furthermore, laxatives may not be used chronically, as they have been shown to be an irritant and cause mucosal damage. Accordingly, it should also be recognized that the induction of chronic diarrhea as part of an effort to control salt and fluid overload would be an undesired treatment modality for most patients. Any medicament utilizing the GI tract for this purpose would therefore need to control diarrhea in order to be of practical benefit.

One approach for the treatment of mild diarrhea is the administration of a fluid-absorbing polymer, such as the natural plant fiber psyllium. Polymeric materials, and more specifically hydrogel polymers, may also be used for the removal of fluid from the gastrointestinal (GI) tract. The use of such polymers is described in, for example, U.S. Pat. No. 4,470,975 and U.S. Pat. No. 6,908,609, the entire contents of which are incorporated herein by reference for all relevant and consistent purposes. However, for such polymers to effectively remove significant quantities of fluid, they must desirably resist the static and osmotic pressure range existing in the GI tract. Many mammals, including humans, make a soft feces with a water content of about 70%, and do so by transporting fluid against the high hydraulic resistance imposed by the fecal mass. Several studies show that the pressure required to dehydrate feces from about 80% to about 60% is between about 500 kPa and about 1000 kPa (i.e., about 5 to about 10 atm). (See, e.g., McKie, A. T., W. Powrie, and R. J. Naftalin, 1990, Am J Physiol, v. 258, no. 3 Pt 1, p. G391-G394; Bleakman, D., and R. J. Naftalin, 1990, Am J Physiol, v. 258, no. 3 Pt 1, p. G377-G390; Zammit, P. S., M. Mendizabal, and R. J. Naftalin, 1994, J Physiol, v. 477 (Pt 3), p. 539-548.) However, the static pressure measured intraluminally is usually between about 6 kPa and about 15 kPa. The rather high pressure needed to dehydrate feces is essentially due to an osmotic process and not a mechanical process produced by muscular forces. The osmotic pressure arises from the active transport of salt across the colonic mucosa that ultimately produces a hypertonic fluid absorption. The osmotic gradient produced drives fluid from the lumen to the serosal side of the mucosa. Fluid-absorbing polymers, such as those described in for example U.S. Pat. Nos. 4,470,975 and 6,908,609, may not be able to sustain such pressure. Such polymers may collapse in a normal colon where the salt absorption process is intact, hence removing a modest quantity of fluid and thereby salt.

Synthetic polymers that bind sodium have also been described. For example, ion-exchange polymeric resins, such as Dowex-type cation exchange resins, have been known since about the 1950's. However, with the exception of Kayexalate™ (or Kionex™), which is a polystyrene sulfonate salt approved for the treatment of hyperkalemia, cation exchange resins have very limited use as drugs, due at least in part to their limited capacity and poor cation binding selectivity. Additionally, during the ion-exchange process, the resins may release a stochiometric amount of exogenous cations (e.g., H, K, Ca), which may in turn potentially cause acidosis (H), hyperkalemia (K) or contribute to vascular calcification (Ca). Such resins may also cause constipation.

Gastrointestinal Tract Disorders

Constipation is characterized by infrequent and difficult passage of stool and becomes chronic when a patient suffers specified symptoms for over 12 non-consecutive weeks within a 12-month period. Chronic constipation is idiopathic if it is not caused by other diseases or by use of medications. An evidence-based approach to the management of chronic constipation in North America (Brandt et al., 2005, Am. J. Gastroenterol. 100(Suppl. 1):S5-S21) revealed that prevalence is approximately 15% of the general population. Constipation is reported more commonly in women, the elderly, non-whites, and individuals from lower socioeconomic groups.

Irritable bowel syndrome (IBS) is a common GI disorder associated with alterations in motility, secretion and visceral sensation. A range of clinical symptoms characterizes this disorder, including stool frequency and form, abdominal pain and bloating. The recognition of clinical symptoms of IBS are yet to be defined, but it is now common to refer to diarrhea-predominant IBS (D-IBS) and constipation-predominant IBS (C-IBS), wherein D-IBS is defined as continuous passage of loose or watery stools and C-IBS as a group of functional disorders which present as difficult, infrequent or seemingly incomplete defecation. The pathophysiology of IBS is not fully understood, and a number of mechanisms have been suggested. Visceral hypersensitivity is often considered to play a major etiologic role and has been proposed to be a biological marker even useful to discriminate IBS from other causes of abdominal pain. In a recent clinical study (Posserud, I. et al, *Gastroenterology,* 2007; 133:1113-1123) IBS patients were submitted to a visceral sensitivity test (Balloon distention) and compared with healthy subjects. It revealed that 61% of the IBS patients had an altered visceral perception as measured by pain and discomfort threshold. Other reviews have documented the role of visceral hypersensitivity in abdominal pain symptomatic of various gastrointestinal tract disorders (Akbar, A, et al, *Aliment. Pharmaco. Ther.,* 2009, 30, 423-435; Bueno et al., *Neurogastroenterol Motility* (2007) 19 (suppl. 1), 89-119). Colonic and rectal distention have been widely used as a tool to assess visceral sensitivity in animal and human studies. The type of stress used to induce visceral sensitivity varies upon the models (see for instance Eutamen, H *Neurogastroenterol Motil.* 2009 Aug. 25. [Epub ahead of print]), however stress such as Partial restraint stress (PRS) is a relatively mild, non-ulcerogenic model that is considered more representative of the IBS setting.

Constipation is commonly found in the geriatric population, particularly patients with osteoporosis who have to take calcium supplements. Calcium supplements have shown to be beneficial in ostoporotic patients to restore bone density but compliance is poor because of calcium-induced constipation effects.

Opioid-induced constipation (OIC) (also referred to as opioid-induced bowel dysfunction or opioid bowel dysfuntion (OBD)) is a common adverse effect associated with opioid therapy. OIC is commonly described as constipation; however, it is a constellation of adverse gastrointestinal (GI) effects, which also includes abdominal cramping, bloating, and gastroesophageal reflux. Patients with cancer may have disease-related constipation, which is usually worsened by opioid therapy. However, OIC is not limited to cancer patients. A recent survey of patients taking opioid therapy for pain of non-cancer origin found that approximately 40% of patients experienced constipation related to opioid therapy (<3 complete bowel movements per week) compared with 7.6% in a control group. Of subjects who required laxative therapy, only 46% of opioid-treated patients (control subjects, 84%) reported achieving the desired treatment results >50% of the time (Pappagallo, 2001, Am. J. Surg. 182(5A Suppl.):11S-18S).

Some patients suffering from chronic idiopathic constipation can be successfully treated with lifestyle modification, dietary changes and increased fluid and fiber intake, and these treatments are generally tried first. For patients who fail to respond to these approaches, physicians typically recommend laxatives, most of which are available over-the-counter. Use of laxatives provided over-the-counter is judged inefficient by about half of the patients (Johanson and Kralstein, 2007, Aliment. Pharmacol. Ther. 25(5):599-608). Other therapeutic options currently prescribed or in clinical development for the treatment of IBS and chronic constipation including OIC are described in, for example: Chang et al., 2006, Curr. Teat. Options Gastroenterol. 9(4):314-323; Gershon and Tack, 2007, Gastroenterology 132(1):397-414; and, Hammerle and Surawicz, 2008, World J. Gastroenterol. 14(17):2639-2649. Such treatments include but are not limited to serotonin receptor ligands, chloride channel activators, opioid receptor antagonists, guanylate-cyclase receptor agonists and nucleotide P2Y(2) receptor agonists. Many of these treatment options are inadequate, as they may be habit forming, ineffective in some patients, may cause long term adverse effects, or otherwise are less than optimal.

Na$^+$/H$^+$ Exchanger (NHE) Inhibitors

A major function of the GI tract is to maintain water/Na homeostasis by absorbing virtually all water and Na to which the GI tract is exposed. The epithelial layer covering the apical surface of the mammalian colon is a typical electrolyte-transporting epithelium, which is able to move large quantities of salt and water in both directions across the mucosa. For example, each day the GI tract processes about 9 liters of fluid and about 800 meq of Na. (See, e.g., Zachos et al., *Molecular physiology of intestinal Na+/H+ exchange*; Annu Rev. Physiol., v. 67, p. 411-443 (2005).) Only about 1.5 liters of this fluid and about 150 meq of this sodium originates from ingestion; rather, the majority of the fluid (e.g., about 7.5 liters) and sodium (about 650 meq) is secreted via the GI organs as part of digestion. The GI tract therefore represents a viable target for modulating systemic sodium and fluid levels.

Many reviews have been published on the physiology and secretory and/or absorption mechanisms of the GI tract (see, e.g., Kunzelmann et al., *Electrolyte transport in the mammalian colon: mechanisms and implications for disease*; Physiol. Rev., v. 82, no. 1, p. 245-289 (2002); Geibel, J. P.; *Secretion and absorption by colonic crypts*; Annu Rev. Physiol, v. 67, p. 471-490 (2005); Zachos et al., supra; Kiela, P. R. et al., *Apical NA+/H+ exchangers in the mammalian gastrointestinal tract*; J. Physiol. Pharmacol., v. 57 Suppl. 7, p. 51-79 (2006)). The two main mechanisms of Na absorption are electroneutral and electrogenic transport. Electroneutral transport is essentially due to the Na$^+$/H$^+$ antiport NHE (e.g., NHE-3) and is responsible for the bulk of Na absorption. Electrogenic transport is provided by the epithelium sodium channel ("ENaC"). Electroneutral transport is located primarily in the ileal segment and proximal colon and electrogenic transport is located in the distal colon. Plasma membrane NHEs contribute to maintenance of intracellular pH and volume, transcellular absorption of NaCl and NaHCO$_3$, and fluid balance carried out by epithelial cells, especially in the kidney, intestine, gallbladder, and salivary glands, as well as regulation of systemic pH. There exists a body of literature devoted to the role and clinical intervention on systemic NHEs to treat disorders related to ischemia and reperfusion for cardioprotection or renal protection. Nine isoforms of NHEs have been identified (Kiela, P. R., et al.; *Apical NA+/H+ exchangers in the mammalian gastrointestinal tract*; J. Physiol. Pharmacol., v. 57 Suppl 7, p. 51-79 (2006)), of which NHE-2, NHE-3 and NHE-8 are expressed on the apical side of the GI tract, with NHE-3 providing a larger contribution to transport. Another, yet to be identified, Cl-dependant NHE has been identified in the crypt of rat cells. In addition, much research has been devoted to identifying inhibitors of NHEs. The primary targets of such research have been NHE-1 and NHE-3. Small molecule NHE inhibitors are, for example, described in: U.S. Pat. Nos. 5,866,610; 6,399,824; 6,911,453; 6,703,405; 6,005,010; 6,736,705; 6,887,870; 6,737,423; 7,326,705; 5,824,691 (WO 94/026709); U.S. Pat. No. 6,399, 824 (WO 02/024637); U.S. Pat. Pub. Nos. 2004/0039001 (WO 02/020496); 2005/0020612 (WO 03/055490); 2004/0113396 (WO 03/051866); 2005/0020612; 2005/0054705; 2008/0194621; 2007/0225323; 2004/0039001; 2004/0224965; 2005/0113396; 2007/0135383; 2007/0135385; 2005/0244367; 2007/0270414; International Publication Nos. WO 01/072742; WO 01021582 (CA2387529); WO 97/024113 (CA02241531) and European Pat. No. EP 0744397 (CA2177007); all of which are incorporated herein by reference in their entirety for all relevant and consistent purposes. However, to-date, such research has failed to develop or recognize the value or importance of NHE inhibitors that are not absorbed (i.e., not systemic) and target the gastrointestinal tract. Such inhibitors could be utilized in the treatment of disorders associated with fluid retention and salt overload and in the treatment of GI tract disorders, including the treatment or reduction of pain associated with a gastrointestinal tract disorder. Such inhibitors would be particular advantageous because they could be delivered with reduced fear of systemic on-target or off-target effects (e.g., little or no risk of renal involvement or other systemic effects.

Accordingly, while progress has been made in the foregoing fields, there remains a need in the art for novel compounds for use in the disorders associated with fluid retention and salt overload and in the treatment of gastrointestinal tract disorders, including the treatment or reduction of pain associated with a gastrointestinal tract disorder. The present invention fulfills this need and provides further related advantages.

BRIEF SUMMARY

In brief, the present invention is directed to compounds that are substantially active in the gastrointestinal tract to inhibit NHE-mediated antiport of sodium ions and hydrogen ions, and the use of such compounds in the treatment of disorders associated with fluid retention and salt overload and in the treatment of gastrointestinal tract disorders, including the treatment or reduction of pain associated with a gastrointestinal tract disorder.

In one embodiment, a compound is provided having: (i) a topological Polar Surface Area (tPSA) of at least about 200 Å$^2$ and a molecular weight of at least about 710 Daltons in the non-salt form; or (ii) a tPSA of at least about 270 Å$^2$, wherein the compound is substantially active in the gastrointestinal tract to inhibit NHE-mediated antiport of sodium ions and hydrogen ions therein upon administration to a patient in need thereof.

In further embodiments, the compound has a molecular weight of at least about 500 Da, at least about 1000 Da, at least about 2500 Da, or at least about 5000 Da. In further embodiments, the compound has a tPSA of at least about 250 Å$^2$, at least about 270 Å$^2$, at least about 300 Å$^2$, at least about 350 Å$^2$, at least about 400 Å$^2$, or at least about 500 Å$^2$.

In further embodiments, the compound is substantially active on the apical side of the epithelium of the gastrointestinal tract to inhibit antiport of sodium ions and hydrogen ions mediated by NHE-3, NHE-2, NHE-8, or a combination thereof. In further embodiments, the compound is substantially systemically non-bioavailable and/or substantially impermeable to the epithelium of the gastrointestinal tract. In further embodiments, the compound is substantially active in the lower gastrointestinal tract. In further embodiments, the compound has (i) a total number of NH and/or OH and/or other potential hydrogen bond donor moieties greater than about 5; (ii) a total number of O atoms and/or N atoms and/or other potential hydrogen bond acceptors greater than about 10; and/or (iii) a Moriguchi partition coefficient greater than about $10^5$ or less than about 10. In further embodiments, the compound has a permeability coefficient, $P_{app}$, of less than about $100 \times 10^{-6}$ cm/s, or less than about $10 \times 10^{-6}$ cm/s, or less than about $1 \times 10^{-6}$ cm/s, or less than about $0.1 \times 10^{-6}$ cm/s. In further embodiments, the compound is substantially localized in the gastrointestinal tract or lumen. In further embodiments, the compound inhibits NHE irreversibly. In further embodiments, the compound is capable of providing a substantially persistent inhibitory action and wherein the compound is orally administered once-a-day. In further embodiments, the compound is substantially stable under physiological conditions in the gastrointestinal tract. In further embodiments, the compound is inert with regard to gastrointestinal flora. In further embodiments, the compound is designed to be delivered to the lower part of the gastrointestinal tract. In further embodiments, the compound is designed to be delivered to the lower part of the gastrointestinal tract past the duodenum. In further embodiments, the compound, when administered at a dose resulting in at least a 10% increase in fecal water content, has a $C_{max}$ that is less than the $IC_{50}$ for NHE-3, less than about 10× the $IC_{50}$, or less than about 100× the $IC_{50}$. In further embodiments, upon administration of the compound to a patient in need thereof, the compound exhibits a maximum concentration detected in the serum, defined as $C_{max}$, that is lower than the NHE inhibitory concentration $IC_{50}$ of the compound. In further embodiments, upon administration of the compound to a patient in need thereof, greater than about 80%, greater than about 90% or greater than about 95% of the amount of compound administered is present in the patient's feces.

In further embodiments, the compound has a structure of Formula (I) or (IX):

NHE—Z                                 (I)

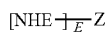                               (IX)

wherein:

NHE is a NHE-inhibiting small molecule that comprises (i) a hetero-atom containing moiety, and (ii) a cyclic or heterocyclic scaffold or support moiety bound directly or indirectly thereto, the heteroatom-containing moiety being selected from a substituted guanidinyl moiety and a substituted heterocyclic moiety, which may optionally be fused with the scaffold or support moiety to form a fused bicyclic structure; and, Z is a moiety having at least one site thereon for attachment to the NHE-inhibiting small molecule, the resulting NHE-Z molecule possessing overall physicochemical properties that render it substantially impermeable or substantially systemically non-bioavailable; and, E is an integer having a value of 1 or more.

In further embodiments, the total number of freely rotatable bonds in the NHE-Z molecule is at least about 10. In further embodiments, the total number hydrogen bond donors in the NHE-Z molecule is at least about 5. In further embodiments, the total number of hydrogen bond acceptors in the NHE-Z molecule is at least about 10. In further embodiments, the total number of hydrogen bond donors and hydrogen bond acceptors in the NHE-Z molecule is at least about 10. In further embodiments, the Log P of the NHE-Z inhibiting compound is at least about 5. In further embodiments, the log P of the NHE-Z inhibiting compound is less than about 1, or less than about 0. In further embodiments, the scaffold is a 5-member or 6-member cyclic or heterocyclic moiety. In further embodiments, the scaffold is aromatic.

In further embodiments, the scaffold of the NHE-inhibiting small molecule is bound to the moiety, Z, and the compound has the structure of Formula (II):

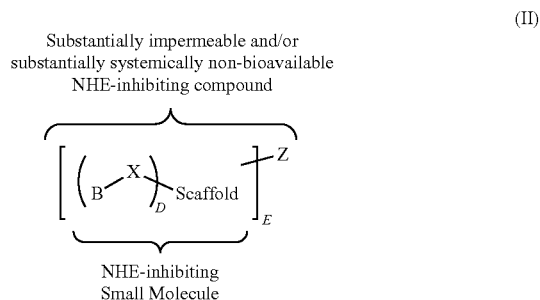

wherein:

Z is a Core having one or more sites thereon for attachment to one or more NHE-inhibiting small molecules, the resulting NHE-Z molecule possessing overall physicochemical properties that render it substantially impermeable or substantially systemically non-bioavailable;

B is the heteroatom-containing moiety of the NHE-inhibiting small molecule, and is selected from a substituted guanidinyl moiety and a substituted heterocyclic moiety, which may optionally be fused with the Scaffold moiety to form a fused, bicyclic structure;

Scaffold is the cyclic or heterocyclic scaffold or support moiety of the NHE-inhibiting small molecule, which is bound directly or indirectly to heteroatom-containing moiety, B, and which is optionally substituted with one or more additionally hydrocarbyl or heterohydrocarbyl moieties;

X is a bond or a spacer moiety selected from a group consisting of substituted or unsubstituted hydrocarbyl or heterohydrocarbyl moieties, and in particular substituted or unsubstituted $C_{1-7}$ hydrocarbyl or heterohydrocarbyl, and substituted or unsubstituted, saturated or unsaturated, cyclic or heterocyclic moieties, which links B and the Scaffold; and, D and E are integers, each independently having a value of 1 or more.

In further embodiments, the compound is an oligomer, dendrimer or polymer, and Z is a Core moiety having two or more sites thereon for attachment to multiple NHE-inhibiting small molecules, either directly or indirectly through a linking moiety, L, and the compound has the structure of Formula (X):

                          (X)

wherein L is a bond or linker connecting the Core to the NHE-inhibiting small molecule, and n is an integer of 2 or more, and further wherein each NHE-inhibiting small molecule may be the same or differ from the others.

In further embodiments, the NHE-inhibiting small molecule has the structure of Formula (IV):

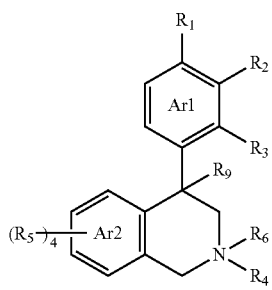

(IV)

or a stereoisomer, prodrug or pharmaceutically acceptable salt thereof, wherein:

each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or a bond linking the NHE-inhibiting small molecule to L, provided at least one is a bond linking the NHE-inhibiting small molecule to L;

$R_4$ is selected from H, $C_1$-$C_7$ alkyl, or a bond linking the NHE-inhibiting small molecule to L;

$R_6$ is absent or selected from H and $C_1$-$C_7$ alkyl; and

Ar1 and Ar2 independently represent an aromatic ring or a heteroaromatic ring. In further embodiments, the NHE-inhibiting small molecule has the following structure:

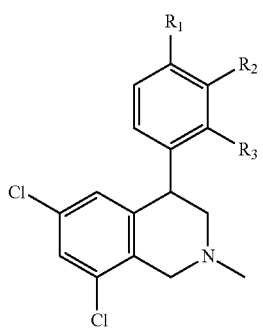

or a stereoisomer, prodrug or pharmaceutically acceptable salt thereof, wherein:

each $R_1$, $R_2$ and $R_3$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or a bond linking the NHE-inhibiting small molecule to L, provided at least one is a bond linking the NHE-inhibiting small molecule to L.

In further embodiments, the NHE-inhibiting small molecule has one of the following structures:

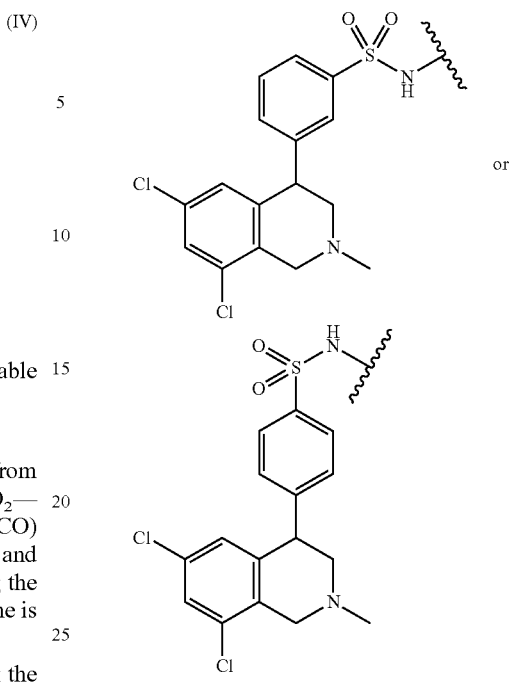

or a stereoisomer, prodrug or pharmaceutically acceptable salt thereof.

In further embodiments, L is a polyalkylene glycol linker. In further embodiments, L is a polyethylene glycol linker.

In further embodiments, n is 2.

In further embodiments, the Core has the following structure:

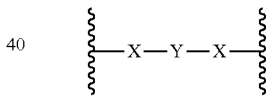

wherein:

X is selected from the group consisting of a bond, —O—, —NH—, —S—, $C_{1-6}$alkylene, —NHC(=O)—, —C(=O)NH—, —NHC(=O)NH—, —$SO_2$NH—, and —NH$SO_2$—;

Y is selected from the group consisting of a bond, optionally substituted $C_{1-8}$alkylene, optionally substituted aryl, optionally substituted heteroaryl, a polyethylene glycol linker, —$(CH_2)_{1-6}O(CH_2)_{1-6}$— and —$(CH_2)_{1-6}NY_1(CH_2)_{1-6}$—; and $Y_1$ is selected from the group consisting of hydrogen, optionally substituted $C_{1-8}$alkyl, optionally substituted aryl or optionally substituted heteroaryl.

In further embodiments, the Core is selected from the group consisting of:

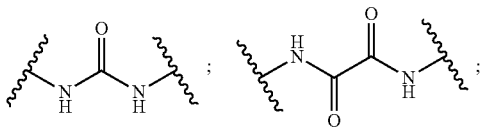

-continued

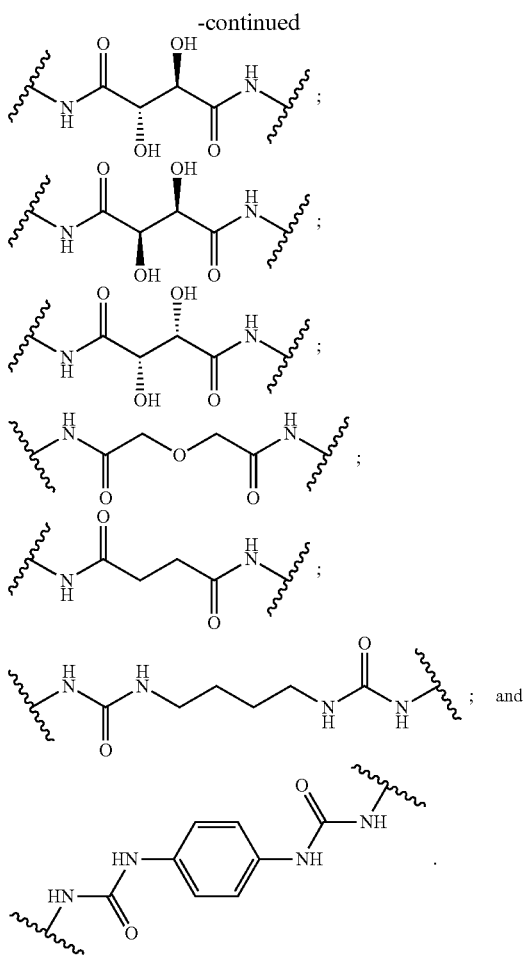

In further embodiments, the compound is an oligomer, and Z is a linking moiety, L, that links two or more NHE-inhibiting small molecules together, when the two or more NHE-inhibiting small molecules may be the same or different, and the compound has the structure of Formula (XI):

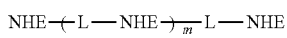
(XI)

wherein L is a bond or linker connecting one NHE-inhibiting small molecule to another, and m is 0 or an integer of 1 or more.

In further embodiments, the compound is an oligomer, dendrimer or polymer, and Z is a backbone, denoted Repeat Unit, to which is bound multiple NHE-inhibiting moieties, and the compound has the structure of Formula (XIIB):

(XIIB)

wherein: L is a bond or a linking moiety; NHE is a NHE-inhibiting small molecule; and n is a non-zero integer.

In another embodiment, a pharmaceutical composition is provided comprising a compound as set forth above, or a stereoisomer, pharmaceutically acceptable salt or prodrug thereof, and a pharmaceutically acceptable carrier, diluent or excipient.

In further embodiments, the composition further comprises a fluid-absorbing polymer. In further embodiments, the fluid-absorbing polymer is delivered directly to the colon. In further embodiments, the fluid-absorbing polymer has a fluid absorbency of at least about 15 g of isotonic fluid per g of polymer under a static pressure of about 5 kPa. In further embodiments, the fluid-absorbing polymer has a fluid absorbency of at least about 15 g of isotonic fluid per g of polymer under a static pressure of about 10 kPa. In further embodiments, the fluid-absorbing polymer is characterized by a fluid absorbency of at least about 10 g/g. In further embodiments, the fluid-absorbing polymer is characterized by a fluid absorbency of at least about 15 g/g. In further embodiments, the fluid-absorbing polymer is superabsorbent. In further embodiments, the fluid-absorbing polymer is a crosslinked, partially neutralized polyelectrolyte hydrogel. In further embodiments, the fluid-absorbing polymer is a crosslinked polyacrylate. In further embodiments, the fluid-absorbing polymer is a polyelectrolyte. In further embodiments, the fluid-absorbing polymer is calcium Carbophil. In further embodiments, the fluid-absorbing polymer is prepared by a high internal phase emulsion process. In further embodiments, the fluid-absorbing polymer is a foam. In further embodiments, the fluid-absorbing polymer is prepared by a aqueous free radical polymerization of acrylamide or a derivative thereof, a crosslinker and a free radical initiator redox system in water. In further embodiments, the fluid-absorbing polymer is a hydrogel. In further embodiments, the fluid-absorbing polymer is an N-alkyl acrylamide. In further embodiments, the fluid-absorbing polymer is a superporous gel. In further embodiments, the fluid-absorbing polymer is naturally occurring. In further embodiments, the fluid-absorbing polymer is selected from the group consisting of xanthan, guar, wellan, hemicelluloses, alkyl-cellulose hydroalkyl-cellulose, carboxy-alkyl-cellulose, carrageenan, dextran, hyaluronic acid and agarose. In further embodiments, the fluid-absorbing polymer is psyllium. In further embodiments, the fluid-absorbing polymer is a polysaccharide that includes xylose and arabinose. In further embodiments, the fluid-absorbing polymer is a polysaccharide that includes xylose and arabinose, wherein the ratio of xylose to arabinose is at least about 3:1, by weight.

In further embodiments, the composition further comprises another pharmaceutically active agent or compound. In further embodiments, the composition further comprises another pharmaceutically active agent or compound selected from the group consisting of a diuretic, cardiac glycoside, ACE inhibitor, angiotensin-2 receptor antagonist, calcium channel blocker, beta blocker, alpha blocker, central alpha agonist, vasodilator, blood thinner, anti-platelet agent, lipid-lowering agent, and peroxisome proliferator-activated receptor (PPAR) gamma agonist agent. In further embodiments, the diuretic is selected from the group consisting of a high ceiling loop diuretic, a benzothiadiazide diuretic, a potassium sparing diuretic, and a osmotic diuretic. In further embodiments, the composition further comprises another pharmaceutically active agent or compound selected from the group consisting of an analgesic peptide or agent. In further embodiments, the composition further comprises another pharmaceutically active agent or compound selected from the group consisting of a laxative agent selected from a bulk-producing agent (e.g. psyllium husk (Metamucil)), methylcellulose (Citrucel), polycarbophil, dietary fiber, apples, stool softeners/surfactant (e.g., docusate, Colace, Diocto), a hydrating or osmotic agent (e.g., dibasic sodium phosphate, magnesium citrate, magnesium hydroxide (Milk of magnesia), magnesium sulfate (which is Epsom salt), monobasic sodium phosphate, sodium biphosphate), a hyperosmotic agent (e.g., glycerin suppositories, sorbitol, lactulose, and polyethylene glycol (PEG)).

In another embodiment, a method for inhibiting NHE-mediated antiport of sodium and hydrogen ions is provided, the method comprising administering to a mammal in need thereof a pharmaceutically effective amount of a compound or pharmaceutical composition as set forth above.

In another embodiment, a method for treating a disorder associated with fluid retention or salt overload is provided, the method comprising administering to a mammal in need thereof a pharmaceutically effective amount of a compound or pharmaceutical composition as set forth above.

In another embodiment, a method for treating a disorder selected from the group consisting of heart failure (such as congestive heart failure), chronic kidney disease, end-stage renal disease, liver disease, and peroxisome proliferator-activated receptor (PPAR) gamma agonist-induced fluid retention is provided, the method comprising administering to a mammal in need thereof a pharmaceutically effective amount of a compound or pharmaceutical composition as set forth above.

In another embodiment, a method for treating hypertension is provided, the method comprising administering to a mammal in need thereof a pharmaceutically effective amount of a compound or pharmaceutical composition as set forth above.

In further embodiments, the method comprises administering a pharmaceutically effective amount of the compound to the mammal in order to increase the mammal's daily fecal output of sodium and/or fluid. In further embodiments, the method comprises administering a pharmaceutically effective amount of the compound to the mammal in order to increase the mammal's daily fecal output of sodium by at least about 30 mmol, and/or fluid by at least about 200 ml. In further embodiments, the mammal's fecal output of sodium and/or fluid is increased without introducing another type of cation in a stoichiometric or near stoichiometric fashion via an ion exchange process. In further embodiments, the method further comprises administering to the mammal a fluid-absorbing polymer to absorb fecal fluid resulting from the use of the compound that is substantially active in the gastrointestinal tract to inhibit NHE-mediated antiport of sodium ions and hydrogen ions therein.

In further embodiments, the compound or composition is administered to treat hypertension. In further embodiments, the compound or composition is administered to treat hypertension associated with dietary salt intake. In further embodiments, administration of the compound or composition allows the mammal to intake a more palatable diet. In further embodiments, the compound or composition is administered to treat fluid overload. In further embodiments, the fluid overload is associated with congestive heart failure. In further embodiments, the fluid overload is associated with end stage renal disease. In further embodiments, the fluid overload is associated with peroxisome proliferator-activated receptor (PPAR) gamma agonist therapy. In further embodiments, the compound or composition is administered to treat sodium overload. In further embodiments, the compound or composition is administered to reduce interdialytic weight gain in ESRD patients. In further embodiments, the compound or composition is administered to treat edema. In further embodiments, the edema is caused by chemotherapy, premenstrual fluid overload or preeclampsia.

In further embodiments, the compound or composition is administered orally, by rectal suppository, or enema.

In further embodiments, the method comprises administering a pharmaceutically effective amount of the compound or composition in combination with one or more additional pharmaceutically active compounds or agents. In further embodiments, the one or more additional pharmaceutically active compounds or agents is selected from the group consisting of a diuretic, cardiac glycoside, ACE inhibitor, angiotensin-2 receptor antagonist, aldosterone antagonist, calcium channel blocker, beta blocker, alpha blocker, central alpha agonist, vasodilator, blood thinner, anti-platelet agent, lipid-lowering agent, and peroxisome proliferator-activated receptor (PPAR) gamma agonist agent. In further embodiments, the diuretic is selected from the group consisting of a high ceiling loop diuretic, a benzothiadiazide diuretic, a potassium sparing diuretic, and a osmotic diuretic. In further embodiments, the pharmaceutically effective amount of the compound or composition, and the one or more additional pharmaceutically active compounds or agents, are administered as part of a single pharmaceutical preparation. In further embodiments, the pharmaceutically effective amount of the compound or composition, and the one or more additional pharmaceutically active compounds or agents, are administered as individual pharmaceutical preparations. In further embodiments, the individual pharmaceutical preparation are administered sequentially. In further embodiments, the individual pharmaceutical preparation are administered simultaneously.

In another embodiment, a method for treating a gastrointestinal tract disorder is provided, the method comprising administering to a mammal in need thereof a pharmaceutically effective amount of a compound or pharmaceutical composition as set forth above.

In further embodiments, the gastrointestinal tract disorder is a gastrointestinal motility disorder. In further embodiments, the gastrointestinal tract disorder is irritable bowel syndrome. In further embodiments, the gastrointestinal tract disorder is chronic constipation. In further embodiments, the gastrointestinal tract disorder is chronic idiopathic constipation. In further embodiments, the gastrointestinal tract disorder is chronic constipation occurring in cystic fibrosis patients. In further embodiments, the gastrointestinal tract disorder is opioid-induced constipation. In further embodiments, the gastrointestinal tract disorder is a functional gastrointestinal tract disorder. In further embodiments, the gastrointestinal tract disorder is selected from the group consisting of chronic intestinal pseudo-obstruction and colonic pseudo-obstruction. In further embodiments, the gastrointestinal tract disorder is Crohn's disease. In further embodiments, the gastrointestinal tract disorder is ulcerative colitis. In further embodiments, the gastrointestinal tract disorder is a disease referred to as inflammatory bowel disease. In further embodiments, the gastrointestinal tract disorder is associated with chronic kidney disease (stage 4 or 5). In further embodiments, the gastrointestinal tract disorder is constipation induced by calcium supplement. In further embodiments, the gastrointestinal tract disorder is constipation, and the constipation to be treated is associated with the use of a therapeutic agent. In further embodiments, the gastrointestinal tract disorder is constipation, and the constipation to be treated is associated with a neuropathic disorder. In further embodiments, the gastrointestinal tract disorder is constipation, and the constipation to be treated is post-surgical constipation (postoperative ileus). In further embodiments, the gastrointestinal tract disorder is constipation, and the constipation to be treated is idiopathic (functional constipation or slow transit constipation). In further embodiments, the gastrointestinal tract disorder is constipation, and the constipation to be treated is associated with neuropathic, metabolic or an endocrine disorder (e.g., diabetes mellitus, renal failure, hypothyroidism, hyperthyroidism, hypocalcaemia, Multiple Sclerosis, Parkinson's disease, spinal cord lesions, neurofibromatosis, autonomic neuropathy, Chagas disease, Hirschsprung's disease or cystic fibrosis, and the like). In further embodiments, the gastrointestinal tract disorder is constipation, and the constipation to be treated is due the use of drugs selected from analgesics (e.g., opioids), antihypertensives, anticonvulsants, antidepressants, antispasmodics and antipsychotics.

In another embodiment, a method for treating irritable bowel syndrome is provided, the method comprising administering to a mammal in need thereof a pharmaceutically effective amount of an NHE-3 inhibitor compound or a pharmaceutical composition comprising an NHE-3 inhibitor compound. In further embodiments, the NHE-3 inhibitor compound or the pharmaceutical composition comprising an NHE-3 inhibitor compound is a compound or pharmaceutical composition as set forth above.

In further embodiments of the above embodiments, the compound or composition is administered to treat or reduce pain associated with a gastrointestinal tract disorder. In further embodiments, the compound or composition is administered to treat or reduce visceral hypersensitivity associated with a gastrointestinal tract disorder. In further embodiments, the compound or composition is administered to treat or reduce inflammation of the gastrointestinal tract. In further embodiments, the compound or composition is administered to reduce gastrointestinal transit time.

In further embodiments, the compound or composition is administered either orally or by rectal suppository.

In further embodiments, the method comprises administering a pharmaceutically effective amount of the compound or composition, in combination with one or more additional pharmaceutically active compounds or agents. In further embodiments, the one or more additional pharmaceutically active agents or compounds are an analgesic peptide or agent. In further embodiments, the one or more additional pharmaceutically active agents or compounds are selected from the group consisting of a laxative agent selected from a bulk-producing agent (e.g. psyllium husk (Metamucil)), methylcellulose (Citrucel), polycarbophil, dietary fiber, apples, stool softeners/surfactant (e.g., docusate, Colace, Diocto), a hydrating or osmotic agent (e.g., dibasic sodium phosphate, magnesium citrate, magnesium hydroxide (Milk of magnesia), magnesium sulfate (which is Epsom salt), monobasic sodium phosphate, sodium biphosphate), and a hyperosmotic agent (e.g., glycerin suppositories, sorbitol, lactulose, and polyethylene glycol (PEG)). In further embodiments, the pharmaceutically effective amount of the compound or composition, and the one or more additional pharmaceutically active compounds or agents, are administered as part of a single pharmaceutical preparation. In further embodiments, the pharmaceutically effective amount of the compound or composition, and the one or more additional pharmaceutically active compounds or agents, are administered as individual pharmaceutical preparations. In further embodiments, the individual pharmaceutical preparation are administered sequentially. In further embodiments, the individual pharmaceutical preparation are administered simultaneously.

These and other aspects of the invention will be apparent upon reference to the following detailed description.

DETAILED DESCRIPTION

Figure 1:
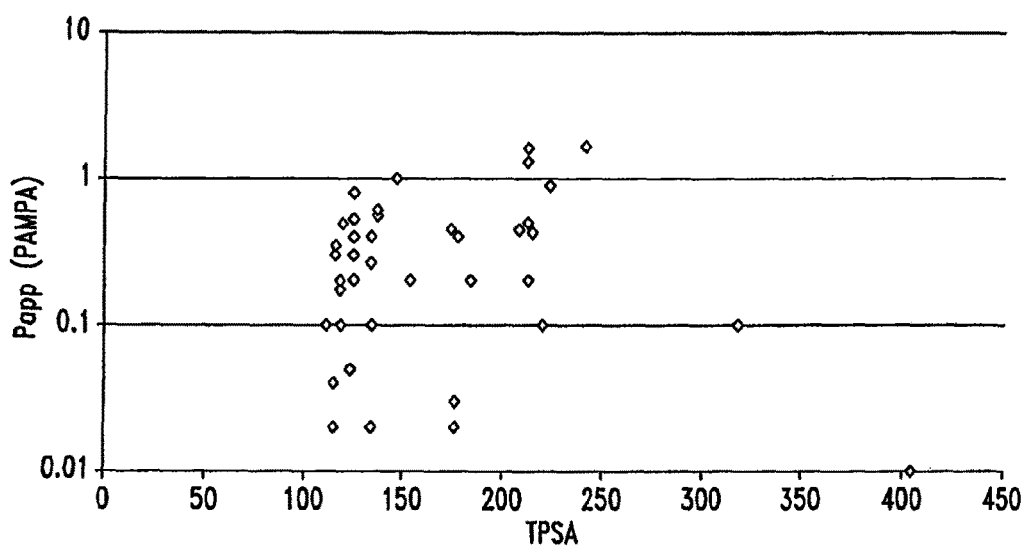
FIG. 1 is a graph that illustrates the relationship between tPSA and Permeability (Papp, as measured in the PAMPA assay) of certain example compounds, as further discussed in the Examples (under the subheading "2. Pharmacological Test Example 2").

In accordance with the present disclosure, and as further detailed herein below, it has been found that the inhibition of NHE-mediated antiport of sodium ions ($Na^+$) and hydrogen ions ($H^+$) in the gastrointestinal tract, and more particularly the gastrointestinal epithelia, is a powerful approach to the treatment of various disorders that may be associated with or caused by fluid retention and/or salt overload, and/or disorders such as heart failure (in particular, congestive heart failure), chronic kidney disease, end-stage renal disease, liver disease, and/or peroxisome proliferator-activated receptor (PPAR) gamma agonist-induced fluid retention. More specifically, it has been found that the inhibition of the NHE-mediated antiport of sodium ions and hydrogen ions in the GI tract increases the fecal excretion of sodium, effectively reducing systemic levels of sodium and fluid. This, in turn, improves the clinical status of a patient suffering from, for example, CHF, ESRD/CKD and/or liver disease. It has further been found that such a treatment may optionally be enhanced by the co-administration of other beneficial compounds or compositions, such as for example a fluid-absorbing polymer. The fluid-absorbing polymer may optimally be chosen so that it does not block or otherwise negatively interfere with the mechanism of action of the co-dosed NHE inhibitor.

Additionally, and also as further detailed herein below, it has further been found that the inhibition of NHE-mediated antiport of sodium ions ($Na^+$) and hydrogen ions ($H^+$) in the gastrointestinal tract, and more particularly the gastrointestinal epithelia, is a powerful approach to the treatment of hypertension, that may be associated with or caused by fluid retention and/or salt overload. More specifically, it has been found that the inhibition of the NHE-mediated antiport of sodium ions and hydrogen ions in the GI tract increases the fecal excretion of sodium, effectively reducing systemic levels of sodium and fluid. This, in turn, improves the clinical status of a patient suffering from hypertension. Such a treatment may optionally be enhanced by the co-administration of other beneficial compounds or compositions, such as for example a fluid-absorbing polymer. The fluid-absorbing polymer may optimally be chosen so that it does not block or otherwise negatively interfere with the mechanism of action of the co-dosed NHE inhibitor. and/or hypertension.

Additionally, and also as further detailed herein below, it has further been found that the inhibition of NHE-mediated antiport of sodium ions ($Na^+$) and hydrogen ions ($H^+$) in the gastrointestinal tract, and more particularly the gastrointestinal epithelia, is a powerful approach to the treatment of various gastrointestinal tract disorders, including the treatment or reduction of pain associated with gastrointestinal tract disorders, and more particularly to the restoration of appropriate fluid secretion in the gut and the improvement of pathological conditions encountered in constipation states. Applicants have further recognized that by blocking sodium ion re-absorption, the compound of the invention restore fluid homeostasis in the GI tract, particularly in situations wherein fluid secretion/absorption is altered in such a way that it results in a high degree of feces dehydration, low gut motility, and/or a slow transit-time producing constipation states and GI discomfort generally. It has further been found that such a treatment may optionally be enhanced by the co-administration of other beneficial compounds or compositions, such as for example a fluid-absorbing polymer. The fluid-absorbing polymer may optimally be chosen so that it does not block or otherwise negatively interfere with the mechanism of action of the co-dosed NHE inhibitor.

Due to the presence of NHEs in other organs or tissues in the body, the method of the present disclosure employs the use of compounds and compositions that are desirably highly selective or localized, thus acting substantially in the gastrointestinal tract without exposure to other tissues or organs. In this way, any systemic effects can be minimized (whether they are on-target or off-target). Accordingly, it is to be noted that, as used herein, and as further detailed elsewhere herein, "substantially active in the gastrointestinal tract" generally refers to compounds that are substantially systemically non-bioavailable and/or substantially impermeable to the layer of epithelial cells, and more specifically epithelium of the GI tract. It is to be further noted that, as used herein, and as further detailed elsewhere herein, "substantially impermeable" more particularly encompasses compounds that are impermeable to the layer of epithelial cells, and more specifically the gastrointestinal epithelium (or epithelial layer). "Gastrointestinal epithelium" refers to the membranous tissue covering the internal surface of the gastrointestinal tract. Accordingly, by being substantially impermeable, a compound has very limited ability to be transferred across the gastrointestinal epithelium, and thus contact other internal organs (e.g., the brain, heart, liver, etc.). The typical mechanism by which a compound can be transferred across the gastrointestinal epithelium is by either transcellular transit (a substance travels through the cell, mediated by either passive or active transport passing through both the apical and basolateral membranes) and/or by paracellular transit, where a substance travels between cells of an epithelium, usually through highly restrictive structures known as "tight junctions".

The compounds of the present disclosure may therefore not be absorbed, and are thus essentially not systemically bioavailable at all (e.g., impermeable to the gastrointestinal epithelium at all), or they show no detectable concentration of the compound in serum. Alternatively, the compounds may: (i) exhibit some detectable permeability to the layer of epithelial cells, and more particularly the epithelium of the GI tract, of less than about 20% of the administered compound (e.g., less than about 15%, about 10%, or even about 5%, and for example greater than about 0.5%, or 1%), but then are rapidly cleared in the liver (i.e., hepatic extraction) via first-pass metabolism; and/or (ii) exhibit some detectable permeability to the layer of epithelial cells, and more particularly the epithelium of the GI tract, of less than about 20% of the administered compound (e.g., less than about 15%, about 10%, or even about 5%, and for example greater than about 0.5%, or 1%), but then are rapidly cleared in the kidney (i.e., renal excretion).

In this regard it is to be still further noted that, as used herein, "substantially systemically non-bioavailable" generally refers to the inability to detect a compound in the systemic circulation of an animal or human following an oral dose of the compound. For a compound to be bioavailable, it must be transferred across the gastrointestinal epithelium (that is, substantially permeable as defined above), be transported via the portal circulation to the liver, avoid substantial metabolism in the liver, and then be transferred into systemic circulation.

As further detailed elsewhere herein, small molecules exhibiting an inhibitory effect on NHE-mediated antiport of sodium and hydrogen ions described herein may be modified or functionalized to render them "substantially active" in the GI tract (or "substantially impermeable" to the GI tract and/or "substantially systemically non-bioavailable" from the GI tract) by, for example, ensuring that the final compound has: (i) a molecular weight of greater than about 500 Daltons (Da) (e.g., greater than about 1000 Da, about 2500 Da, about 5000 Da, or even about 10000 Da) in its non-salt form; and/or (ii) at least about 10 freely rotatable bonds therein (e.g., about 10, about 15 or even about 20); and/or (iii) a Moriguchi Partition Coefficient of at least about $10^5$ (or log P of at least about 5), by for example increasing the hydrophobicity of the compound (e.g., inserting or installing a hydrocarbon chain of a sufficient or suitable length therein), or alternatively a Moriguchi Partition Coefficient of less than 10 (or alternatively a log P of less than about 1, or less than about 0); and/or (iv) a number of hydrogen-bond donors therein greater than about 5, about 10, or about 15; and/or (v) a number of hydrogen-bond acceptors therein greater than about 5, about 10, or about 15; and/or (vi) a total number of hydrogen-bond donors and acceptors therein of greater than about 5, about 10, or about 15; and/or, (vii) a topological polar surface area (tPSA) therein of greater than about 100 Å$^2$, about 120 Å$^2$, about 130 Å$^2$, or about 140 Å$^2$, and in some instances about 150 Å$^2$, about 200 Å$^2$, about 250 Å$^2$, about 270 Å$^2$, about 300 Å$^2$, about 400 Å$^2$, or even about 500 Å$^2$, by for example inserting or installing a sufficiently hydrophilic functional group therein (e.g., a polyalkylene ether or a polyol or an ionizable group, such as a phosphonate, sulfonate, carboxylate, amine, quaternary amine, etc.), the hydrogen-bond donors/acceptor groups also contributing to compound tPSA.

One or more of the above-noted methods for structurally modifying or functionalizing the NHE-inhibiting small molecule may be utilized in order to prepare a compound suitable for use in the methods of the present disclosure, so as to render the compound substantially impermeable or substantially systemically non-bioavailable; that is, one or more of the noted exemplary physical properties may be "engineered" into the NHE-inhibiting small molecule to render the resulting compound substantially impermeable or substantially systemically non-bioavailable, or more generally substantially active, in the GI tract, while still possessing a region or moiety therein that is active to inhibit NHE-mediated antiport of sodium ions and hydrogen ions.

Without being held to any particular theory, the NHE-inhibitors (e.g., NHE-3, -2 and/or -8) of the instant disclosure are believed to act via a distinct and unique mechanism, causing the retention of fluid and ions in the GI tract (and stimulating fecal excretion) rather than stimulating increased secretion of said fluid and ions. For example, lubiprostone (Amitiza® Sucampo/Takeda) is a bicyclic fatty acid prostaglandin E1 analog that activates the Type 2 Chloride Channel (ClC-2) and increases chloride-rich fluid secretion from the serosal to the mucosal side of the GI tract (see, e.g., Pharmacological Reviews for Amitiza®, NDA package). Linaclotide (MD-1100 acetate, Microbia/Forest Labs) is a 14 amino acid peptide analogue of an endogenous hormone, guanylin, and indirectly activates the Cystic Fibrosis Transmembrane Conductance Regulator (CFTR) thereby inducing fluid and electrolyte secretion into the GI (see, e.g., Li et al., J. Exp. Med., vol. 202 (2005), pp. 975-986). The substantially impermeable NHE inhibitors described in the instant disclosure act to inhibit the reuptake of salt and fluid rather than promote secretion. Since the GI tract processes about 9 liters of fluid and about 800 meq of Na each day, it is anticipated that NHE inhibition could permit the removal of substantial quantities of systemic fluid and sodium to resorb edema and resolve CHF symptoms.

I. Substantially Impermeable or Substantially Systemically Non-Bioavailable NHE-Inhibiting Compounds A. General Structure Generally speaking, the present disclosure encompasses essentially any small molecule, which may be monovalent or polyvalent, that is effective or active as a NHE inhibitor and that is substantially active in the GI tract, and more particularly substantially impermeable or substantially systemically non-bioavalable therein, including known NHE inhibitors that may be modified or functionalized in accordance with the present disclosure to alter the physicochemical properties thereof so as to render the overall compound substantially active in the GI tract. In particular, however, the present disclosure encompasses monovalent or polyvalent compounds that are effective or active as NHE-3, NHE-2 and/or NHE-8 inhibitors.

Accordingly, the compounds of the present disclosure may be generally represented by Formula (I):

wherein: (i) NHE represents a NHE-inhibiting small molecule, and (ii) Z represents a moiety having at least one site thereon for attachment to an NHE-inhibiting small molecule, the resulting NHE-Z molecule possessing overall physicochemical properties that render it substantially impermeable or substantially systemically non-bioavailable. The NHE-inhibiting small molecule generally comprises a heteroatom-containing moiety and a cyclic or heterocyclic scaffold or support moiety bound directly or indirectly thereto. In particular, examination of the structures of small molecules reported to-date to be NHE inhibitors suggest, as further illustrated herein below, that most comprise a cyclic or heterocyclic support or scaffold bound directly or indirectly (by, for example, an acyl moiety or a hydrocarbyl or heterohydrocarbyl moiety, such as an alkyl, an alkenyl, a heteroalkyl or a heteroalkenyl moiety) to a heteroatom-containing moiety that is capable of acting as a sodium atom or sodium ion mimic, which is typically selected from a substituted guanidinyl moiety and a substituted heterocyclic moiety (e.g., a nitrogen-containing hetrocyclic moiety). Optionally, the heteroatom-containing moiety may be fused with the scaffold or support moiety to form a fused, bicyclic structure, and/or it may be capable of forming a positive charge at a physiological pH.

In this regard it is to be noted that, while the heteroatom-containing moiety that is capable of acting as a sodium atom or ion mimic may optionally form a positive charge, this should not be understood or interpreted to require that the overall compound have a net positive charge, or only a single positively charged moiety therein. Rather, in various embodiments, the compound may have no charged moieties, or it may have multiple charged moieties therein (which may have positive charges, negative charges, or a combination thereof, the compound for example being a zwitterion). Additionally, it is to be understood that the overall compound may have a net neutral charge, a net positive charge (e.g., +1, +2, +3, etc.), or a net negative charge (e.g., −1, −2, −3, etc.).

The Z moiety may be bound to essentially any position on, or within, the NHE small molecule, and in particular may be: (i) bound to the scaffold or support moiety, (ii) bound to a position on, or within, the heteroatom-containing moiety, and/or (iii) bound to a position on, or within, a spacer moiety that links the scaffold to the heteroatom-containing moiety, provided that the installation of the Z moiety does not significantly adversely impact NHE-inhibiting activity. In one particular embodiment, Z may be in the form of an oligomer, dendrimer or polymer bound to the NHE small molecule (e.g., bound for example to the scaffold or the spacer moiety), or alternatively Z may be in the form of a linker that links multiple NHE small molecules together, and therefore that acts to increase: (i) the overall molecular weight and/or polar surface area of the NHE-Z molecule; and/or, (ii) the number of freely rotatable bonds in the NHE-Z molecule; and/or, (iii) the number of hydrogen-bond donors and/or acceptors in the NHE-Z molecule; and/or, (iv) the Log P value of the NHE-Z molecule to a value of at least about 5 (or alternatively less than 1, or even about 0), all as set forth herein; such that the overall NHE-inhibiting compound (i.e., the NHE-Z compound) is substantially impermeable or substantially systemically non-bioavailable.

The present disclosure is more particularly directed to such a substantially impermeable or substantially systemically non-bioavailable, NHE-inhibiting compound, or a pharmaceutical salt thereof, wherein the compound has the structure of Formula (II):

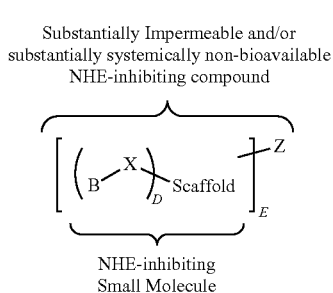

Substantially Impermeable and/or substantially systemically non-bioavailable NHE-inhibiting compound NHE-inhibiting Small Molecule (II)

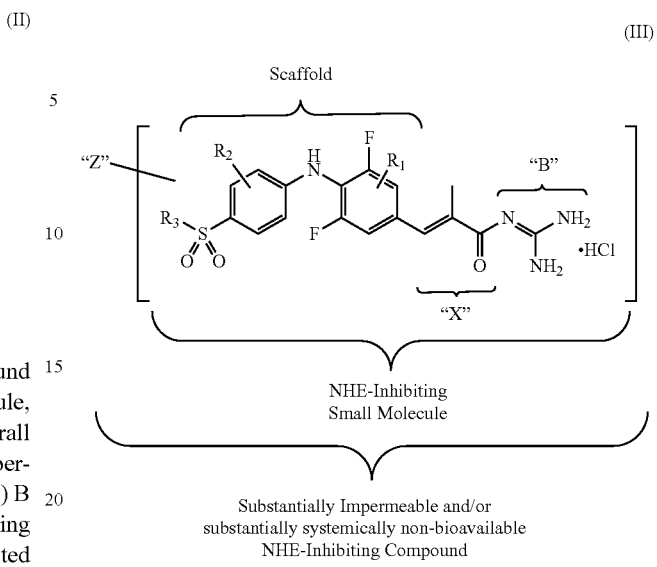

NHE-Inhibiting Small Molecule

Substantially Impermeable and/or substantially systemically non-bioavailable NHE-Inhibiting Compound (III)

wherein: (i) Z, as previously defined above, is a moiety bound to or incorporated in the NHE-inhibiting small molecule, such that the resulting NHE-Z molecule possesses overall physicochemical properties that render it substantially impermeable or substantially systemically non-bioavailable; (ii) B is the heteroatom-containing moiety of the NHE-inhibiting small molecule, and in one particular embodiment is selected from a substituted guanidinyl moiety and a substituted heterocyclic moiety, which may optionally be fused with the Scaffold moiety to form a fused, bicyclic structure; (iii) Scaffold is the cyclic or heterocyclic moiety to which is bound directly or indirectly the hetero-atom containing moiety (e.g., the substituted guanidinyl moiety or a substituted heterocyclic moiety), B, and which is optionally substituted with one or more additionally hydrocarbyl or heterohydrocarbyl moieties; (iv) X is a bond or a spacer moiety selected from a group consisting of substituted or unsubstituted hydrocarbyl or heterohydrocarbyl moieties, and in particular substituted or unsubstituted $C_1$-$C_7$ hydrocarbyl or heterohydrocarbyl (e.g., $C_1$-$C_7$ alkyl, alkenyl, heteroalkyl or heteroalkenyl), and substituted or unsubstituted, saturated or unsaturated, cyclic or heterocyclic moieties (e.g., $C_4$-$C_7$ cyclic or heterocyclic moieties), which links B and the Scaffold; and, (v) D and E are integers, each independently having a value of 1, 2 or more.

In one or more particular embodiments, as further illustrated herein below, B may be selected from a guanidinyl moiety or a moiety that is a guanidinyl bioisostere selected from the group consisting of substituted cyclobutenedione, substituted imidazole, substituted thiazole, substituted oxadiazole, substituted pyrazole, or a substituted amine. More particularly, B may be selected from guanidinyl, acylguanidinyl, sulfonylguanidinyl, or a guanidine bioisostere such as a cyclobutenedione, a substituted or unsubstituted 5- or 6-member heterocycle such as substituted or unsubstituted imidazole, aminoimidazole, alkylimidizole, thiazole, oxadiazole, pyrazole, alkylthioimidazole, or other functionality that may optionally become positively charged or function as a sodium mimetic, including amines (e.g., tertiary amines), alkylamines, and the like, at a physiological pH. In one particularly preferred embodiment, B is a substituted guanidinyl moiety or a substituted heterocyclic moiety that may optionally become positively charged at a physiological pH to function as a sodium mimetic. In one exemplary embodiment, the compound of the present disclosure (or more particularly the pharmaceutically acceptable HCl salt thereof, as illustrated) may have the structure of Formula (III):

wherein Z may be optionally attached to any one of a number of sites on the NHE-inhibiting small molecule, and further wherein the $R_1$, $R_2$ and $R_3$ substituents on the aromatic rings are as detailed elsewhere herein, and/or in U.S. Pat. No. 6,399,824, the entire contents of which are incorporated herein by reference for all relevant and consistent purposes.

In this regard it is to be noted, however, that the substantially impermeable or substantially systemically non-bioavailable NHE-inhibiting compounds of the present disclosure may have a structure other than illustrated above, without departing from the scope of the present disclosure. For example, in various alternative embodiments, one or both of the terminal nitrogen atoms in the guanidine moiety may be substituted with one or more substituents, and/or the modifying or functionalizing moiety Z may be attached to the NHE-inhibiting compound by means of (i) the Scaffold, (ii) the spacer X, or (iii) the heteroatom-containing moiety, B, as further illustrated generally in the structures provided below:

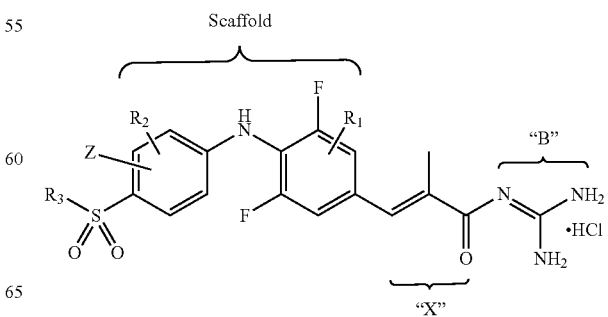

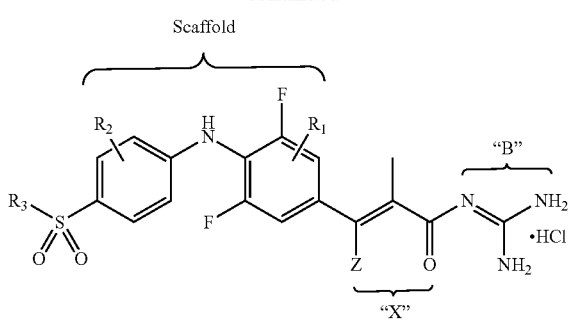

Scaffold

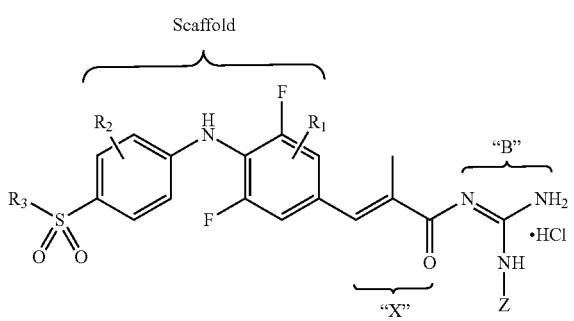

Scaffold

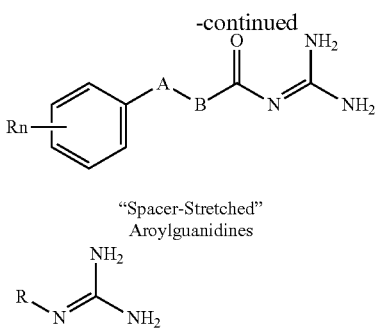

"Spacer-Stretched" Aroylguanidines

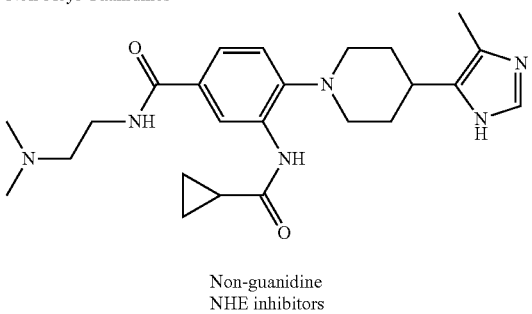

Non-Acyl Guanidines

Non-guanidine NHE inhibitors

In this regard it is to be further noted that, as used herein, "bioisostere" generally refers to a moiety with similar physical and chemical properties to a guanidine moiety, which in turn imparts biological properties to that given moiety similar to, again, a guanidine moiety, in this instance. (See, for example, Ahmad, S. et al., Aminoimidazoles as Bioisosteres of Acylguanidines: Novel, Potent, Selective and Orally Bioavailable Inhibitors of the Sodium Hydrogen Exchanger Isoform-1, *Boorganic & Med. Chem. Lett.*, pp. 177-180 (2004), the entire contents of which is incorporated herein by reference for all relevant and consistent purposes.)

As further detailed below, known NHE-inhibiting small molecules or chemotypes that may serve as suitable starting materials (for modification or functionalization, in order to render the small molecules substantially impermeable or substantially systemically non-bioavailable, and/or used in pharmaceutical preparations in combination with, for example, a fluid-absorbing polymer) may generally be organized into a number of subsets, such as for example:

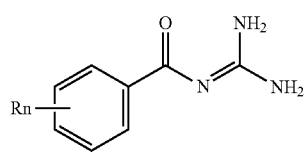

Benzoylguanidines

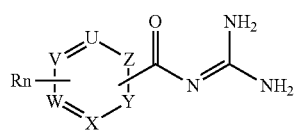

Heteroaroylguanidines wherein: the terminal ring (or, in the case of the non-acyl guanidines, "R"), represent the scaffold or support moiety; the guanidine moiety (or the substituted heterocycle, and more specifically the piperidine ring, in the case of the non-guanidine inhibitors) represents B; and, X is the acyl moiety, or the -A-B-acyl-moiety (or a bond in the case of the non-acyl guanidines and the non-guanidine inhibitors). (See, e.g., Lang, H. J., "*Chemistry of NHE Inhibitors*" in The Sodium-Hydrogen Exchanger, Harmazyn, M., Avkiran, M. and Fliegel, L., Eds., Kluwer Academic Publishers 2003. See also B. Masereel et al., An Overview of Inhibitors of Na+/H+ Exchanger, *European J. of Med. Chem.*, 38, pp. 547-554 (2003), the entire contents of which is incorporated by reference here for all relevant and consistent purposes). Without being held to any particular theory, it has been proposed that a guanidine group, or an acylguanidine group, or a charged guanidine or acylguanidine group (or, in the case of non-guanidine inhibitors, a heterocycle or other functional group that can replicate the molecular interactions of a guanidinyl functionality including, but not limited to, a protonated nitrogen atom in a piperidine ring) at physiological pH may mimic a sodium ion at the binding site of the exchanger or antiporter (See, e.g., Vigne, P.; Frelin, C.; Lazdunski, M. J. Biol. Chem. 1982, 257, 9394).

Although the heteroatom-containing moiety may be capable of forming a positive charge, this should not be understood or interpreted to require that the overall compound have a net positive charge, or only a single positively charged moiety therein, or even that the heteroatom-containing moiety therein be capable of forming a positive charge in all instances. Rather, in various alternative embodiments, the compound may have no charged moieties therein, or it may have multiple charged moieties therein (which may have positive charges, negative charges, or a combination thereof). Additionally, it is to be understood that the overall compound may have a net neutral charge, a net positive charge, or a net negative charge.

In this regard it is to be noted that the U.S. Patents and U.S. Published Applications cited above, or elsewhere herein, are incorporated herein by reference in their entirety, for all relevant and consistent purposes.

In addition to the structures illustrated above, and elsewhere herein, it is to be noted that bioisosteric replacements for guanidine or acylguanidine may also be used. Potentially viable bioisosteric "guanidine replacements" identified to-date have a five- or six-membered heterocyclic ring with donor/acceptor and pKa patterns similar to that of guanidine or acylguanidine (see for example Ahmad, S. et al., Aminoimidazoles as Bioisosteres of Acylguanidines: Novel, Potent, Selective and Orally Bioavailable Inhibitors of the Sodium Hydrogen Exchanger Isoform-1, *Boorganic & Med. Chem. Lett.*, pp. 177-180 (2004), the entire contents of which is incorporated herein by reference for all relevant and consistent purposes), and include those illustrated below:

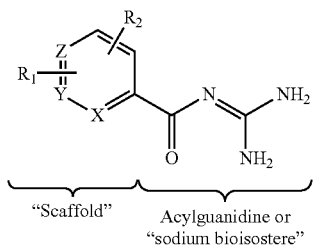

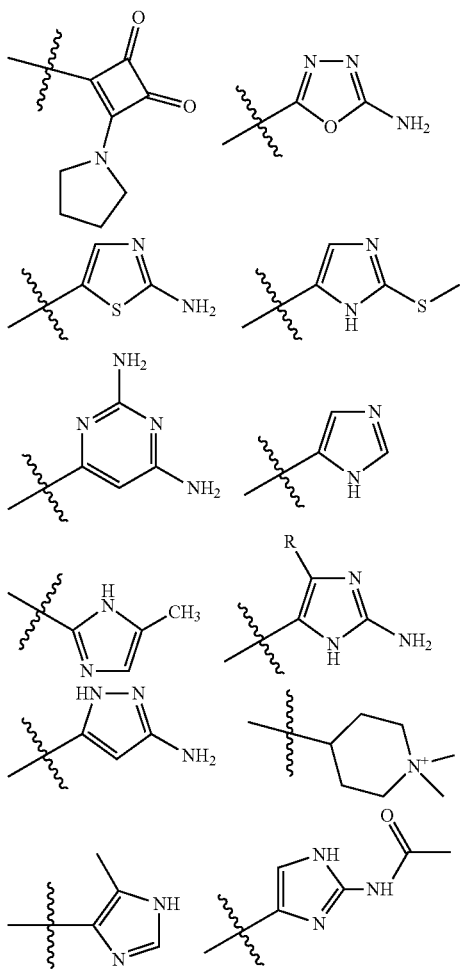

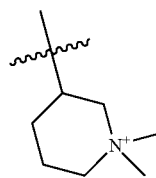

-continued

The above bioisosteric embodiments (i.e., the group of structures above) correspond to "B" in the structure of Formula (II), the broken bond therein being attached to "X" (e.g., the acyl moiety, or alternatively a bond linking the bioisostere to the scaffold), with bonds to Z in Formula (III) not shown here.

It is to be noted that, in the many structures illustrated herein, all of the various linkages or bonds will not be shown in every instance. For example, in one or more of the structures illustrated above, a bond or connection between the NHE-inhibiting small molecule and the modifying or functionalizing moiety Z is not always shown. However, this should not be viewed in a limiting sense. Rather, it is to be understood that the NHE-inhibiting small molecule is bound or connected in some way (e.g., by a bond or linker of some kind) to Z, such that the resulting NHE-Z molecule is suitable for use (i.e., substantially impermeable or substantially systemically non-bioavailable in the GI tract). Alternatively, Z may be incorporated into the NHE-inhibiting small molecule, such as for example by positioning it between the guanidine moiety and scaffold.

It is to be further noted that a number of structures are provided herein for substantially impermeable or substantially systemically non-bioavailable NHE-inhibiting compounds, and/or for NHE-inhibiting small molecules suitable for modification or functionalization in accordance with the present disclosure so as to render them substantially impermeable or substantially systemically non-bioavailable. Due to the large number of structures, various identifiers (e.g., atom identifiers in a chain or ring, identifiers for substituents on a ring or chain, etc.) may be used more than once. An identifier in one structure should therefore not be assumed to have the same meaning in a different structure, unless specifically stated (e.g., "$R_1$" in one structure may or may not be the same as "$R_1$" in another structure). Additionally, it is to be noted that, in one or more of the structures further illustrated herein below, specific details of the structures, including one or more of the identifiers therein, may be provided in a cited reference, the contents of which are specifically incorporated herein by reference for all relevant and consistent purposes.

B. Illustrative Small Molecule Embodiments

The substantially impermeable or substantially systemically non-bioavailable NHE-inhibiting compounds of the present disclosure may in general be derived or prepared from essentially any small molecule possessing the ability to inhibit NHE activity, including small molecules that have already been reported or identified as inhibiting NHE activity but lack impermeability (i.e., are not substantially impermeable). In one particularly preferred embodiment, the compounds utilized in the various methods of the present disclosure are derived or prepared from small molecules that inhibit the NHE-3, -2, and/or -8 isoforms. To-date, a considerable amount of work has been devoted to the study of small molecules exhibiting NHE-1 inhibition, while less has been devoted for example to the study of small molecules exhibiting NHE-3 inhibition. Although the present disclosure is directed generally to substantially impermeable or substantially systemically non-bioavailable NHE-inhibiting compounds, the substantially impermeable or substantially systemically non-bioavailable compounds exhibiting NHE-3, -2, and/or -8 inhibition are of particular interest. However, while it is envisioned that appropriate starting points may be the modification of known NHE-3, -2, and/or -8 inhibiting small molecules, small molecules identified for the inhibition of other NHE subtypes, including NHE-1, may also be of interest, and may be optimized for selectivity and potency for the NHE-3, -2, and/or -8 subtype antiporter.

Small molecules suitable for use (i.e., suitable for modification or functionalization in accordance with the present disclosure) to prepare the substantially impermeable or substantially systemically non-bioavailable NHE-inhibiting compounds of the present disclosure include those illustrated below. In this regard it is to be noted a bond or link to Z (i.e., the modification or functionalization that renders the small molecules substantially impermeable or substantially systemically non-bioavailable) is not specifically shown. As previously noted, the Z moiety may be attached to, or included within, the small molecule at essentially any site or position that does not interfere (e.g., sterically interfere) with the ability of the resulting compound to effectively inhibit the NHE antiport of interest. More particularly, Z may be attached to essentially any site on the NHE-inhibiting small molecule, Z for example displacing all or a portion of a substituent initially or originally present thereon and as illustrated below, provided that the site of installation of the Z moiety does not have a substantially adversely impact on the NHE-inhibiting activity thereof. In one particular embodiment, however, a bond or link extends from Z to a site on the small molecule that effectively positions the point of attachment as far away (based, for example, on the number of intervening atoms or bonds) from the atom or atoms present in the resulting compound that effectively act as the sodium ion mimic (for example, the atom or atoms capable of forming a positive ion under physiological pH conditions). In a preferred embodiment, the bond or link will extend from Z to a site in a ring, and more preferably an aromatic ring, within the small molecule, which serves as the scaffold.

In view of the foregoing, in one particular embodiment, the following small molecule, disclosed in U.S. Patent Application No. 2005/0054705, the entire content of which (and in particular the text of pages 1-2 therein) is incorporated herein by reference for all relevant and consistent purposes, may be suitable for use or modification in accordance with the present disclosure (e.g., bound to or modified to include Z, such that the resulting NHE-Z molecule is substantially impermeable or substantially systemically non-bioavailable).

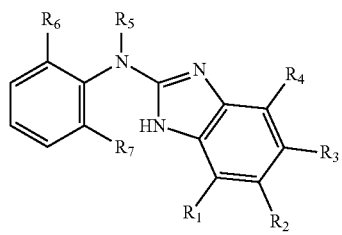

The variables in the structure are defined in the cited patent application, the details of which are incorporated herein by reference. In one particularly preferred embodiment, $R_6$ and $R_7$ are a halogen (e.g., Cl), $R_5$ is lower alkyl (e.g., $CH_3$), and $R_1$-$R_4$ are H, the compound having for example the structure:

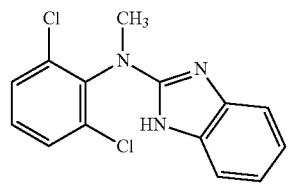 [SMILES: CN(c1nc2ccccc2[nH]1)c1c(Cl)cccc1Cl]

In yet another particular embodiment, the following small molecule, disclosed in Canadian Patent Application No. 2,241,531 (or International Patent Publication No. WO 97/24113), the entire content of which (and in particular pages 1-2 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

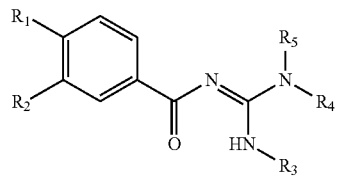

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular page 49 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

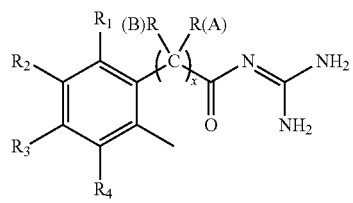

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 118-120 and 175-177 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

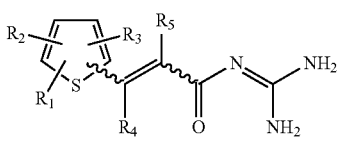

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 129-131 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

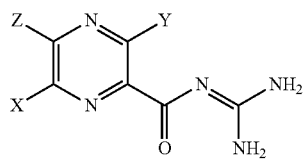

The variables in the structure are defined in the cited patent application, the details of which are incorporated herein by reference. (In this regard it is to be noted that the substituent Z within the structure illustrated above is not to be confused with the moiety Z that, in accordance with the present disclosure, is attached to the NHE-inhibiting small molecule in order effective render the resulting "NHE-Z" molecule substantially impermeable.)

In yet another particular embodiment, the following small molecule, disclosed in Canadian Patent Application No. 2,241,531 (or International Patent Publication No. WO 97/24113), the entire content of which (and in particular pages 127-129 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

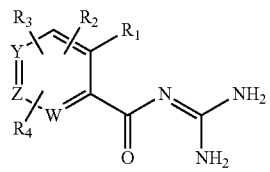

The variables in the structure are defined in the cited patent application, the details of which are incorporated herein by reference. (In this regard it is to be noted that Z within the ring of the structure illustrated above is not to be confused with the moiety Z that, in accordance with the present disclosure, is attached to the NHE-inhibiting small molecule in order effective render the resulting "NHE-Z" molecule substantially impermeable.)

In yet another particular embodiment, the following small molecule, disclosed in Canadian Patent Application No. 2,241,531 (or International Patent Publication No. WO 97/24113), the entire content of which (and in particular pages 134-137 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

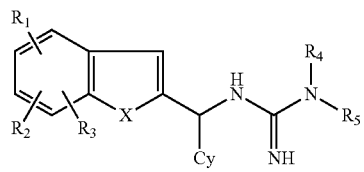

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 31-32 and 137-139 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

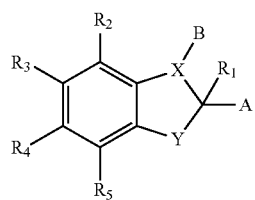

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 37-45 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

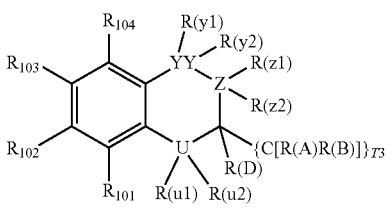

The variables in the structure are defined in the cited patent application, the details of which are incorporated herein by reference. (In this regard it is to be noted that Z within the ring structure illustrated above is not to be confused with the moiety Z that, in accordance with the present disclosure, is attached to the NHE-inhibiting small molecule in order effective render the resulting "NHE-Z" molecule substantially impermeable.)

In yet another particular embodiment, the following small molecule, disclosed in Canadian Patent Application No. 2,241,531 (or International Patent Publication No. WO 97/24113), the entire content of which (and in particular pages 100-102 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

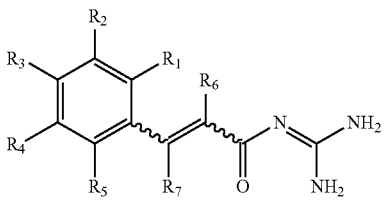

The variables in the structure are defined in the cited patent application, the details of which are incorporated herein by reference (wherein, in particular, the wavy bonds indicate variable length, or a variable number of atoms, therein).

In yet another particular embodiment, the following small molecule, disclosed in Canadian Patent Application No. 2,241,531 (or International Patent Publication No. WO 97/24113), the entire content of which (and in particular pages 90-91 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

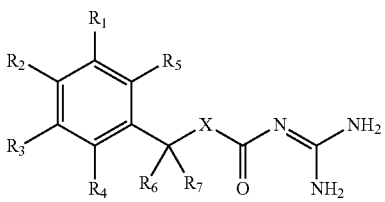

The variables in the structure are defined in the cited patent application, the details of which are incorporated herein by reference.

In yet another particular embodiment, the following small molecule, disclosed in U.S. Pat. No. 5,900,436 (or EP 0822182 B1), the entire contents of which (and in particular column 1, lines 10-55 therein) are incorporated herein by reference for all relevant and consistent purposes, may be suitable for use or modification in accordance with the present disclosure (e.g., bound to or modified to include Z, such that the resulting NHE-Z molecule is substantially impermeable or substantially systemically non-bioavailable).

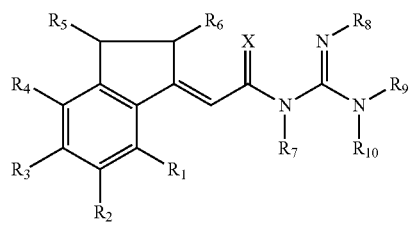

The variables in the structures are defined in the cited patents, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 35-47 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

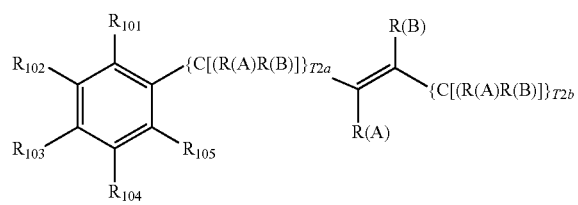

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 154-155 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

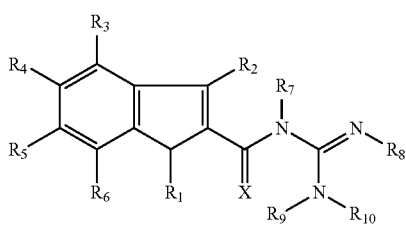

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 132-133 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

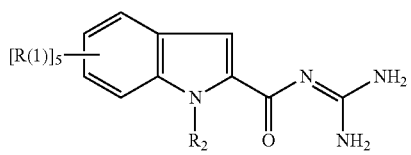

The variables in the structure are defined in the cited patent application, the details of which are incorporated herein by reference.

In yet another particular embodiment, the following small molecule, disclosed in Canadian Patent Application No. 2,241,531 (or International Patent Publication No. WO 97/24113), the entire content of which (and in particular pages 58-65 AND 141-148 therein) is incorporated herein for all relevant and consistent purposes, may be suitable for use or modification in accordance with the present disclosure (e.g., bound to or modified to include Z, such that the resulting NHE-Z molecule is substantially impermeable or substantially systemically non-bioavailable).

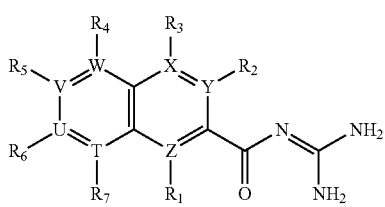

The variables in the structure are defined in the cited patent application, the details of which are incorporated herein by reference. (In this regard it is to be noted that Z within the ring structure illustrated above is not to be confused with the moiety Z that, in accordance with the present disclosure, is attached to the NHE-inhibiting small molecule in order effective render the resulting "NHE-Z" molecule substantially impermeable.)

In yet another particular embodiment, the following small molecule, disclosed in U.S. Pat. Nos. 6,911,453 and 6,703, 405, the entire contents of which (and in particular the text of columns 1-7 and 46 of U.S. Pat. No. 6,911,453 and columns 14-15 of U.S. Pat. No. 6,703,405) are incorporated herein by reference for all relevant and consistent purposes, may be suitable for use or modification in accordance with the present disclosure (e.g., bound to or modified to include Z, such that the resulting NHE-Z molecule is substantially impermeable or substantially systemically non-bioavailable).

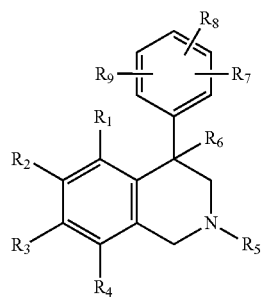

The variables in the structure are defined in the cited patents, the details of which are incorporated herein by reference. A particularly preferred small molecule falling within the above-noted structure is further illustrated below (see, e.g., Example 1 of the U.S. Pat. No. 6,911,453, the entire contents of which are specifically incorporated herein by reference):

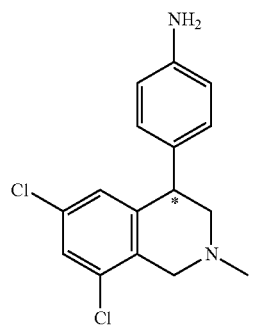 [SMILES: CN1Cc2c(Cl)cc(Cl)cc2C(c2ccc(N)cc2)C1]

In yet another particular embodiment, the following small molecules, disclosed in U.S. Patent Publication Nos. 2004/0039001, 2004/0224965, 2005/0113396 and 2005/0020612, the entire contents of which are incorporated herein by reference for all relevant and consistent purposes, may be suitable for use or modification in accordance with the present disclosure (e.g., bound to or modified to include Z, such that the resulting NHE-Z molecule is substantially impermeable or substantially systemically non-bioavailable).

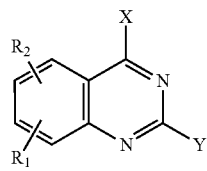

-continued

X = Ar (aryl), Het (heterocycle)

Y =
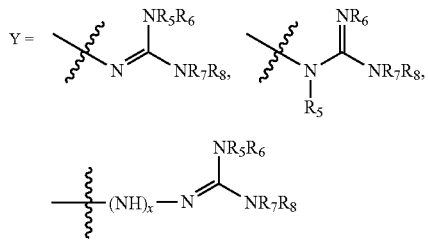

The variables in the structures are defined above and/or in one or more of the cited patent applications, the details of which are incorporated herein by reference, and/or as illustrated above (wherein the broken bonds indicate a point of attachment for the Y moiety to the fused heterocyclic ring). In particular, in various embodiments the combination of X and Y may be as follows:

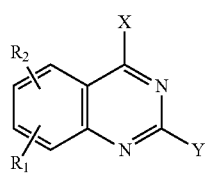

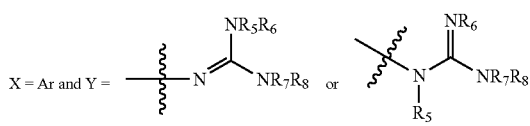

(see, e.g., U.S. 2004/0039001, p. 1 therein)

X = Ar and Y =

(see, e.g., U.S. 2004/0224965, p. 1 therein)

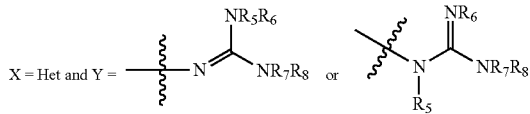

X = Het and Y =

(see, e.g., U.S. 2005/0113396, p. 1 therein)

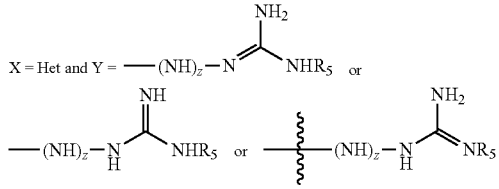

(see, e.g., U.S. 2005/00020612, p. 1 therein)

In a particularly preferred embodiment of the above-noted structure, the small molecule has the general structure:

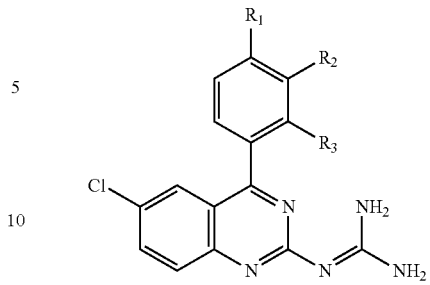

wherein $R_1$, $R_2$ and $R_3$ may be the same or different, but are preferably different, and are independently selected from H, NR'R" (wherein R' and R" are independently selected from H and hydrocarbyl, such as lower alkyl, as defined elsewhere herein) and the structure:

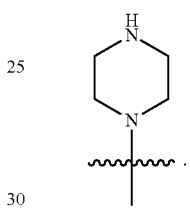

In a more particularly preferred embodiment of the above structure, a small molecule falling within the above-noted structure is further illustrated below (see, e.g., compound I1 on p. 5 of the 2005/0020612 patent application, the entire contents of which are specifically incorporated herein by reference):

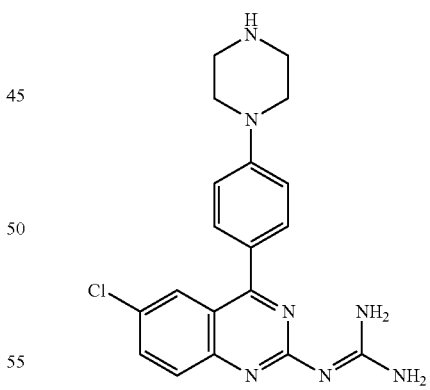

In another particularly preferred embodiment, the following small molecule, disclosed in U.S. Pat. No. 6,399,824, the entire content of which (and in particular the text of Example 1 therein) is incorporated herein by reference for all relevant and consistent purposes, may be particularly suitable for use or modification in accordance with the present disclosure (e.g., bound to or modified to include Z, such that the resulting NHE-Z molecule is substantially impermeable or substantially systemically non-bioavailable).

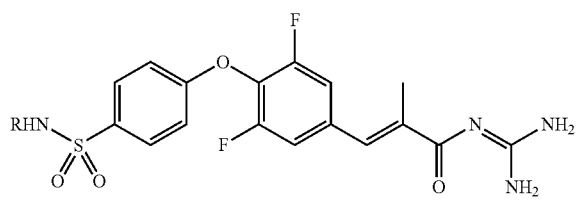

In the structure, R may be preferably selected from H and $(CH_3)_2NCH_2CH_2$—, with H being particularly preferred in various embodiments.

In yet another particular embodiment, the following small molecule, disclosed in U.S. Pat. No. 6,005,010 (and in particular columns 1-3 therein), and/or U.S. Pat. No. 6,166,002 (and in particular columns 1-3 therein), the entire contents of which are incorporated herein by reference for all relevant and consistent purposes, may be suitable for use or modification in accordance with the present disclosure (e.g., bound to or modified to include Z, such that the resulting NHE-Z molecule is substantially impermeable or substantially systemically non-bioavailable).

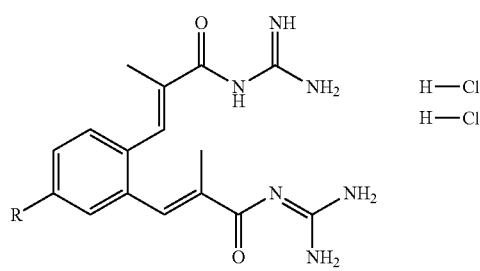

The variable ("R") in the structure is defined in the cited patent application, the details of which are incorporated herein by reference.

In yet another particularly preferred embodiment, the following small molecule, disclosed in U.S. Patent Application No. 2008/0194621, the entire content of which (and in particular the text of Example 1 therein) is incorporated herein by reference for all relevant and consistent purposes, may be particularly suitable for use or modification in accordance with the present disclosure (e.g., bound to or modified to include Z, such that the resulting NHE-Z molecule is substantially impermeable or substantially systemically non-bioavailable).

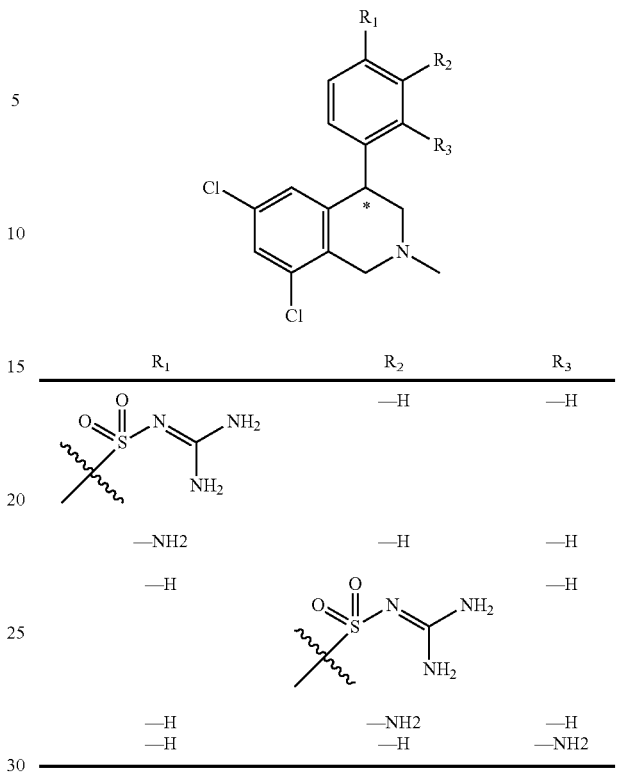

The variables ("$R_1$", "$R_2$ and "$R_3$") in the structure are as defined above, and/or as defined in the cited patent application, the details of which are incorporated herein by reference.

In yet another particularly preferred embodiment, the following small molecule, disclosed in U.S. Patent Application No. 2007/0225323, the entire content of which (and in particular the text of Example 36 therein) is incorporated herein by reference for all relevant and consistent purposes, may be particularly suitable for use or modification in accordance with the present disclosure (e.g., bound to or modified to include Z, such that the resulting NHE-Z molecule is substantially impermeable or substantially systemically non-bioavailable).

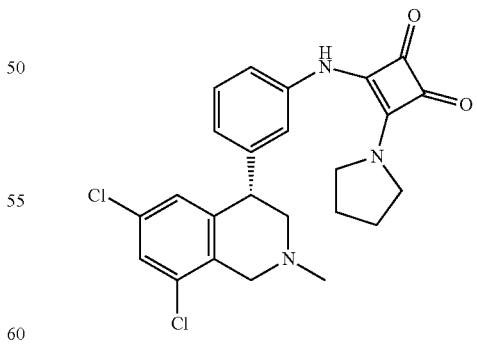

In yet another particularly preferred embodiment, the following small molecule, disclosed in U.S. Pat. No. 6,911,453, the entire content of which (and in particular the text of Example 35 therein) is incorporated herein by reference for all relevant and consistent purposes, may be particularly suitable for use or modification in accordance with the present disclosure (e.g., bound to or modified to include Z, such that the resulting NHE-Z molecule is substantially impermeable or substantially systemically non-bioavailable).

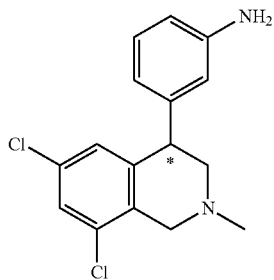 [SMILES: CN1Cc2c(Cl)cc(Cl)cc2C(c2cccc(N)c2)C1]

In one particularly preferred embodiment of the present disclosure, the small molecule may be selected from the group consisting of:

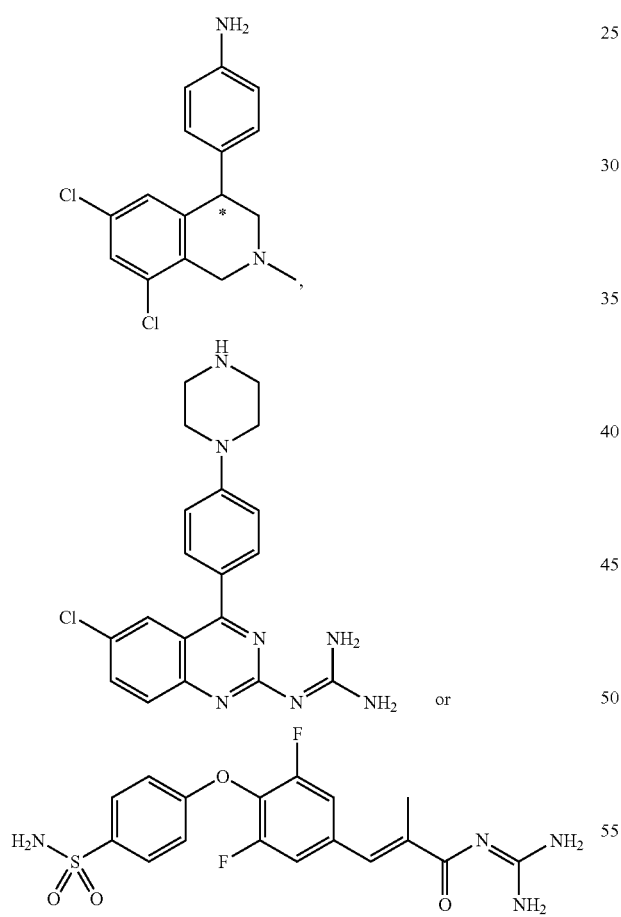

In these structures, a bond or link (not shown) may extend, for example, between the Core and amine-substituted aromatic ring (first structure), the heterocyclic ring or the aromatic ring to which it is bound, or alternatively the chloro-substituted aromatic ring (second structure), or the difluoro-substituted aromatic ring or the sulfonamide-substituted aromatic ring (third structure).

C. Exemplary Small Molecule Selectivity

Shown below are examples of various NHE inhibiting small molecules and their selectivity across the NHE-1, -2 and -3 isoforms. (See, e.g., B. Masereel et al., An Overview of Inhibitors of Na+/H+ Exchanger, *European J. of Med. Chem.*, 38, pp. 547-554 (2003), the entire contents of which is incorporated by reference here for all relevant and consistent purposes). Most of these small molecules were optimized as NHE-1 inhibitors, and this is reflected in their selectivity with respect thereto (IC50's for subtype-1 are significantly more potent (numerically lower) than for subtype-3). However, the data in Table 1 indicates that NHE-3 activity may be engineered into an inhibitor series originally optimized against a different isoform. For example, amiloride is a poor NHE-3 inhibitor and was inactive against this antiporter at the highest concentration tested (IC50>100 µM); however, analogs of this compound, such as DMA and EIPA, have NHE-3 IC50's of 14 and 2.4 uM, respectively. The cinnamoylguanidine S-2120 is over 500-fold more active against NHE-1 than NHE-3; however, this selectivity is reversed in regioisomer S-3226. It is thus possible to engineer NHE-3 selectivity into a chemical series optimized for potency against another antiporter isoform; that is, the inhibitor classes exemplified in the art may be suitably modified for activity and selectivity against NHE-3 (or alternatively NHE-2 and/or NHE-8), as well as being modified to be rendered substantially impermeable or substantially systemically non-bioavailable.

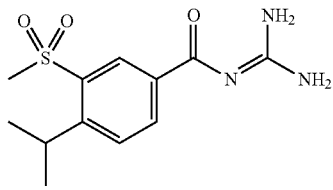

Cariporide

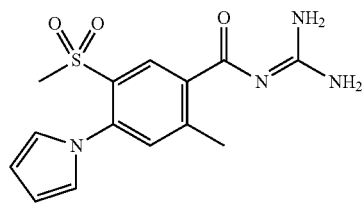

Eniporide

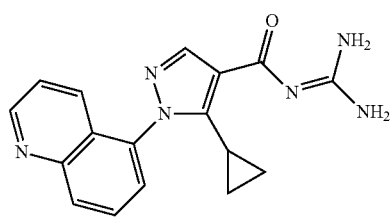

Zoniporide

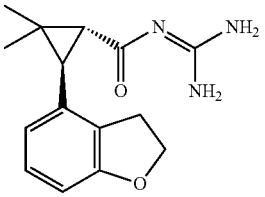

TABLE 1

| Drug[a] | IC$_{50}$ or K$_i$ (μM)[b] | | | |
|---|---|---|---|---|
| | NHE-1 | NHE-2 | NHE-3 | NHE-5 |
| Amiloride | 1-1.6* | 1.0** | >100* | 21 |
| EIPA | 0.01*-0.02** | 0.08*-0.5** | 2.4* | 0.42 |
| HMA | 0.013* | — | 2.4* | 0.37 |
| DMA | 0.023* | 0.25* | 14* | — |
| Cariporide | 0.03-3.4 | 4.3-62 | 1->100 | >30 |
| Eniporide | 0.005-0.38 | 2-17 | 100-460 | >30 |
| Zoniporide | 0.059 | 12 | >500* | — |
| BMS-284640 | 0.009 | 1800 | >30 | 3.36 |
| T-162559 (S) | 0.001 | 0.43 | 11 | — |
| T-162559 (R) | 35 | 0.31 | >30 | — |
| S-3226 | 3.6 | 80** | 0.02 | — |
| S-2120 | 0.002 | 0.07 | 1.32 | — |

*= from rat,
**= from rabbit.
NA = not active
[a]Table adapted from Masereel, B. et al., *European Journal of Medicinal Chemistry*, 2003, 38, 547-54.
[b]K$_i$ values are in italic As previously noted above, the NHE inhibitor small molecules disclosed herein, including those noted above, may advantageously be modified to render them substantially impermeable or substantially systemically non-bioavailable. The compounds as described herein are, accordingly, effectively localized in the gastrointestinal tract or lumen, and in one particular embodiment the colon. Since the various NHE isomforms may be found in many different internal organs (e.g., brain, heart, liver, etc.), localization of the NHE inhibitors in the intestinal lumen is desirable in order to minimize or eliminate systemic effects (i.e., prevent or significantly limit exposure of such organs to these compounds). Accordingly, the present disclosure provides NHE inhibitors, and in particular NHE-3, -2 and/or -8 inhibitors, that are substantially systemically non-bioavailable in the GI tract, and more specifically substantially systemically impermeable to the gut epithelium, as further described below.

D. Preferred Embodiments

In one or more particularly preferred embodiments of the present disclosure, the "NHE-Z" molecule is monovalent; that is, the molecule contains one moiety that effectively acts to inhibit NHE-mediated antiport of sodium ions and hydrogen ions. In such embodiments, the NHE-Z molecule may be selected, for example, from one of the following structures of Formulas (IV), (V), (VI) or (VII):

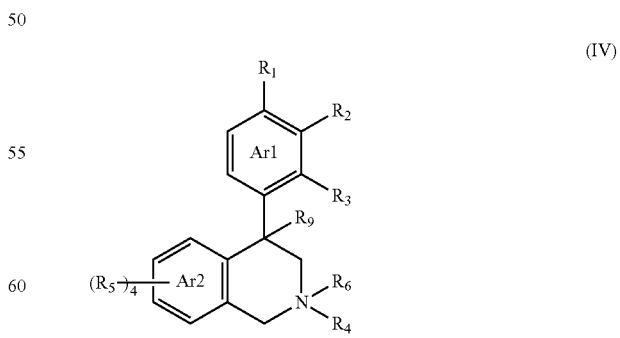

(IV)

wherein: each R$_1$, R$_2$, R$_3$, R$_5$ and R$_9$ are independently selected from H, halogen (e.g., Cl), —NR$_7$(CO)R$_8$, —(CO)NR$_7$R$_8$, —SO$_2$—NR$_7$R$_8$, —NR$_7$SO$_2$R$_8$, —NR$_7$R$_8$, —OR$_7$, —SR$_7$, —O(CO)NR$_7$R$_8$, —NR$_7$(CO)OR$_8$, and —$NR_7SO_2NR_8$, where $R_7$ and $R_8$ are independently selected from H or Z, where Z is selected from substituted or unsubstituted hydrocarbyl, heterohydrocarbyl, polyalkylene glycol and polyols, where substituents thereon are selected from hydroxyls, amines, amidines, carboxylates, phosphonates, sulfonates, and guanidines; $R_4$ is selected from H, $C_1$-$C_7$ alkyl or Z, where Z is selected from substituted or unsubstituted hydrocarbyl, heterohydrocarbyl, a polyalkylene glycol and polyols, where substituents thereon are selected from hydroxyls, amines, amidines, carboxylates, phosphonates, sulfonates, and guanidines; $R_6$ is absent or selected from H and $C_1$-$C_7$ alkyl; and, Ar1 and Ar2 independently represent an aromatic ring, or alternatively a heteroaromatic ring wherein one or more of the carbon atoms therein is replaced with a N, O or S atom;

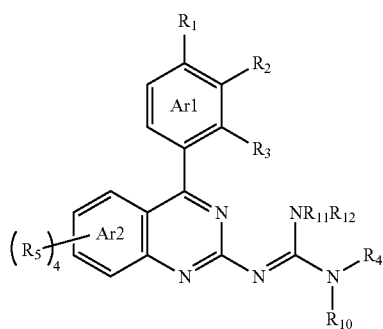

(V)

wherein: each $R_1$, $R_2$, $R_3$, and $R_5$ are independently selected from H, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or Z, where Z is selected from substituted or unsubstituted hydrocarbyl, heterohydrocarbyl, polyalkylene glycol and polyols, where substituents thereon are selected from hydroxyls, amines, amidines, carboxylates, phosphonates, sulfonates, and guanidines, optionally linked to the ring Ar1 by a heterocyclic linker; $R_4$ and $R_{12}$ are independently selected from H and $R_7$, where $R_7$ is as defined above; $R_{10}$ and $R_{11}$, when presented, are independently selected from H and $C_1$-$C_7$ alkyl; and, Ar1 and Ar2 independently represent an aromatic ring, or alternatively a heteroaromatic ring wherein one or more of the carbon atoms therein is replaced with a N, O or S atom;

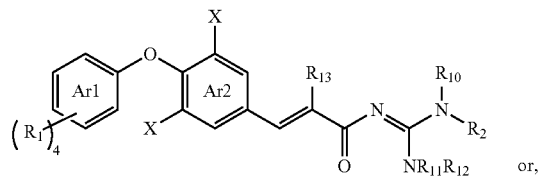

(VI)

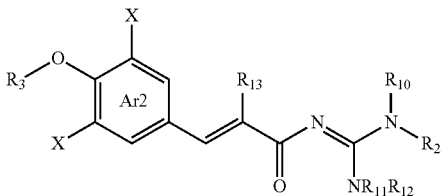

(VII)

wherein: each X is a halogen atom, which may be the same or different; $R_1$ is selected from —$SO_2$—$NR_7R_8$, —$NR_7(CO)R_8$, —$(CO)NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or Z, where Z is selected from substituted or unsubstituted hydrocarbyl, heterohydrocarbyl, polyalkylene glycol and polyols, where substituents thereon are selected from hydroxyls, amines, amidines, carboxylates, phosphonates, sulfonates, and guanidines; $R_3$ is selected from H or $R_7$, where $R_7$ is as described above; $R_{13}$ is selected from substituted or unsubstituted $C_1$-$C_8$ alkyl; $R_2$ and $R_{12}$ are independently selected from H or $R_7$, wherein $R_7$ is as described above; $R_{10}$ and $R_{11}$, when present, are independently selected from H and $C_1$-$C_7$ alkyl; Ar1 represents an aromatic ring, or alternatively a heteroaromatic ring wherein one or more of the carbon atoms therein is replaced with a N, O or S atom; and Ar2 represents an aromatic ring, or alternatively a heteroaromatic ring wherein one or more of the carbon atoms therein is replaced with a N, O or S atom.

In one particular embodiment for the structure of Formula (V), one of $R_1$, $R_2$ and $R_3$ is linked to the ring Ar1, and/or $R_5$ is linked to the ring Ar2, by a heterocyclic linker having the structure:

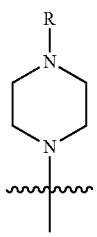

wherein R represents $R_1$, $R_2$, $R_3$, or $R_5$ bound thereto.

In another particular embodiment, the NHE-Z molecule of the present disclosure may have the structure of Formula (IV):

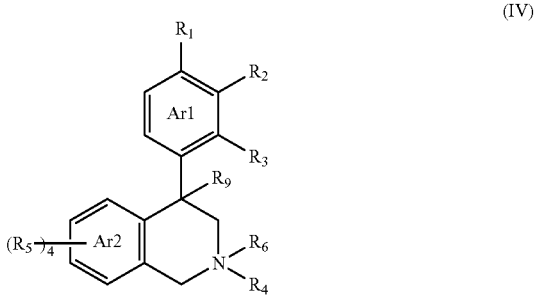

(IV)

wherein: each $R_1$, $R_2$, $R_3$, $R_5$ and $R_9$ are independently selected from H, halogen, $NR_7(CO)R_8$, $-(CO)NR_7R_8$, $-SO_2-NR_7R_8$, $-NR_7SO_2R_8$, $-NR_7R_8$, $-OR_7$, $-SR_7$, $-O(CO)NR_7R_8$, $-NR_7(CO)OR_8$, and $-NR_7SO_2NR_8$, where $R_7$ and $R_8$ are independently selected from H or Z, where Z is selected from substituted hydrocarbyl, heterohydrocarbyl, or polyols and/or substituted or unsubstituted polyalkylene glycol, wherein substituents thereon are selected from the group consisting of phosphinates, phosphonates, phosphonamidates, phosphates, phosphonthioates and phosphonodithioates; $R_4$ is selected from H or Z, where Z is substituted or unsubstituted hydrocarbyl, heterohydrocarbyl, a polyalkylene glycol and a polyol, where substituents thereon are selected from hydroxyls, amines, amidines, carboxylates, phosphonates, sulfonates, and guanidines; $R_6$ is selected from —H and $C_1$-$C_7$ alkyl; and, Ar1 and Ar2 independently represent an aromatic ring, or alternatively a heteroaromatic ring wherein one or more of the carbon atoms therein is replaced with a N, O or S atom.

Additionally, or alternatively, in one or more embodiments of the compounds illustrated above, the compound may optionally have a tPSA of at least about 100 Å$^2$, about 150 Å$^2$, about 200 Å$^2$, about 250 Å$^2$, about 270 Å$^2$, or more and/or a molecular weight of at least about 710 Da.

II. Polyvalent Structures

Macromolecules and Oligomers

A. General Structure

As noted above, the compounds of the present disclosure comprise a NHE-inhibiting small molecule that has been modified or functionalized structurally to alter its physicochemical properties (by the attachment or inclusion of moiety Z), and more specifically the physicochemical properties of the NHE-Z molecule, thus rendering it substantially impermeable or substantially systemically non-bioavailable. In one particular embodiment, and as further detailed elsewhere herein, the NHE-Z compound may be polyvalent (i.e., an oligomer, dendrimer or polymer moiety), wherein Z may be referred to in this embodiment generally as a "Core" moiety, and the NHE-inhibiting small molecule may be bound, directly or indirectly (by means of a linking moiety) thereto, the polyvalent compounds having for example one of the following general structures of Formula (VIII), (IX) and (X):

  (VIII) NHE-Core

  (IX) [NHE$\frac{}{E}$Z

  (X) Core$-$(L$-$NHE)$_n$ wherein: Core (or Z) and NHE are as defined above; L is a bond or linker, as further defined elsewhere herein below, and E and n are both an integer of 2 or more. In various alternative embodiments, however, the NHE-inhibiting small molecule may be rendered substantially impermeable or substantially systemically non-bioavailable by forming a polymeric structure from multiple NHE-inhibiting small molecules, which may be the same or different, connected or bound by a series of linkers, L, which also may be the same or different, the compound having for example the structure of Formula (XI):

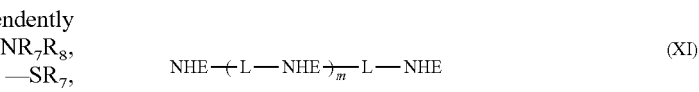  (XI)

wherein: Core (or Z) and NHE are as defined above; L is a bond or linker, as further defined elsewhere herein below, and m is 0 or an integer of 1 or more. In this embodiment, the physicochemical properties, and in particular the molecular weight or polar surface area, of the NHE-inhibiting small molecule is modified (e.g., increased) by having a series of NHE-inhibiting small molecules linked together, in order to render them substantially impermeable or substantially systemically non-bioavailable. In these or yet additional alternative embodiments, the polyvalent compound may be in dimeric, oligomeric or polymeric form, wherein for example Z or the Core is a backbone to which is bound (by means of a linker, for example) multiple NHE-inhibiting small molecules. Such compounds may have, for example, the structures of Formulas (XIIA) or (XIIB):

  (XIIA)

  (XIIB)

wherein: L is a linking moiety; NHE is a NHE-inhibiting small molecule, each NHE as described above and in further detail hereinafter; and n is a non-zero integer (i.e., an integer of 1 or more).

The Core moiety has one or more attachment sites to which NHE-inhibiting small molecules are bound, and preferably covalently bound, via a bond or linker, L. The Core moiety may, in general, be anything that serves to enable the overall compound to be substantially impermeable or substantially systemically non-bioavailable (e.g., an atom, a small molecule, etc.), but in one or more preferred embodiments is an oligomer, a dendrimer or a polymer moiety, in each case having more than one site of attachment for L (and thus for the NHE-inhibiting small molecule). The combination of the Core and NHE-inhibiting small molecule (i.e., the "NHE-Z" molecule) may have physicochemical properties that enable the overall compound to be substantially impermeable or substantially systemically non-bioavailable.

In this regard it is to be noted that the repeat unit in Formulas (XIIA) and (XIIB) generally encompasses repeating units of various polymeric embodiments, which may optionally be produced by methods referred to herein. In each polymeric, or more general polyvalent, embodiment, it is to be noted that each repeat unit may be the same or different, and may or may not be linked to the NHE-inhibiting small molecule by a linker, which in turn may be the same or different when present. In this regard it is to be noted that as used herein, "polyvalent" refers to a molecule that has multiple (e.g., 2, 4, 6, 8, 10 or more) NHE-inhibiting moieties therein.

In this regard it is to be still further noted that, as further illustrated elsewhere herein, certain polyvalent NHE-inhibiting compounds of the present disclosure show unexpectedly higher potency, as measured by inhibition assays (as further detailed elsewhere herein) and characterized by the concentration of said NHE inhibitor resulting in 50% inhibition (i.e., the IC$_{50}$ values). It has been observed that certain multivalent structures, represented generally by Formula (X), above, have an IC$_{50}$ value several fold lower in magnitude than the individual NHE, or L-NHE, structure (which may be referred to as the "monomer" or monovalent form). For example, in one embodiment, multivalent compounds according to Formula (X) were observed to have an IC$_{50}$ value of at least about 5 time lower (i.e. potency about 5 time higher) than the monomer (or monovalent) form (e.g. Examples 46 and 49). In another embodiment, multivalent compounds according to Formula (X) were observed to have an IC$_{50}$ value of at least about 10 time lower (i.e. potency about 10 time higher) than the monomer form (e.g. Examples 87 and 88).

The above noted embodiments are further illustrated herein below. For example, the first representation below of an exemplary oligomer compound, wherein the various parts of the compound corresponding to the structure of Formula (X) are identified, is intended to provide a broad context for the disclosure provided herein. It is to be noted that while each "NHE" moiety (i.e., the NHE small molecule) in the structure below is the same, it is within the scope of this disclosure that each is independently selected and may be the same or different. In the illustration below, the linker moiety is a polyethylene glycol (PEG) motif. PEG derivatives are advantageous due in part to their aqueous solubility, which may help avoid hydrophobic collapse (the intramolecular interaction of hydrophobic motifs that can occur when a hydrophobic molecule is exposed to an aqueous environment (see, e.g., Wiley, R. A.; Rich, D. H. Medicai Research Reviews 1993, 13(3), 327-384). The core moiety illustrated below is also advantageous because it provides some rigidity to the Core-(L-NHE)$_n$ molecule, allowing an increase in distance between the NHE inhibitors while minimally increasing rotational degrees of freedom.

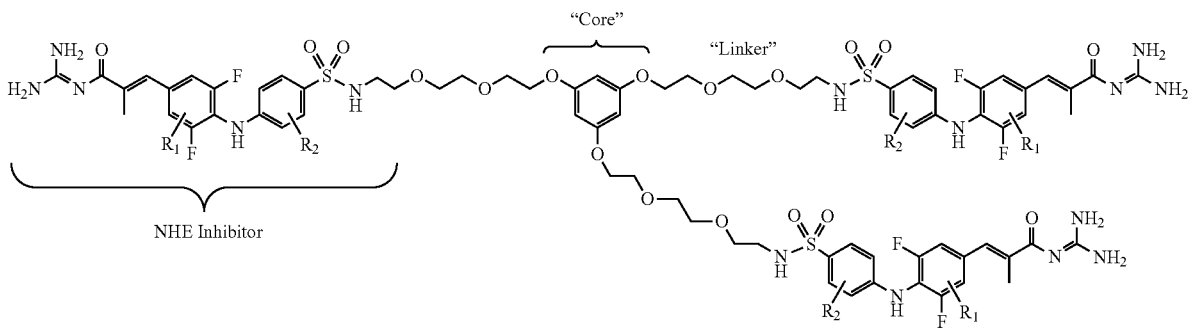

In an alternative embodiment (e.g., Formula (XI), wherein m=0), the structure may be for example:

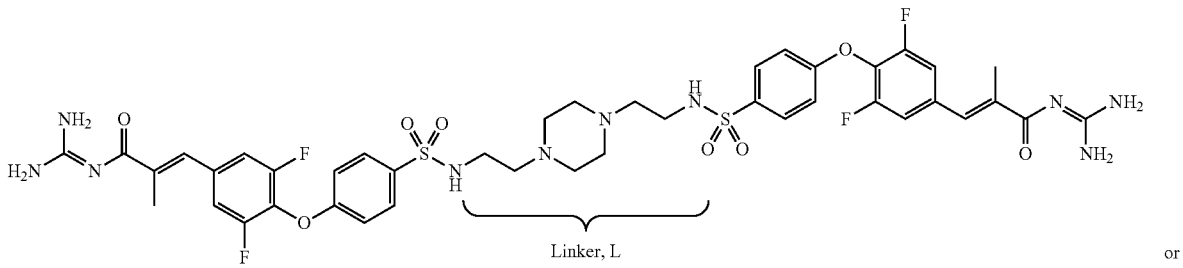

or

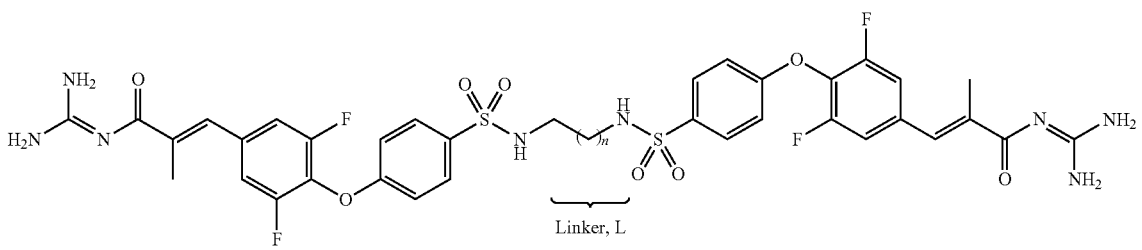

n = 1, 2, 3, 4, 5, 6, etc.

or

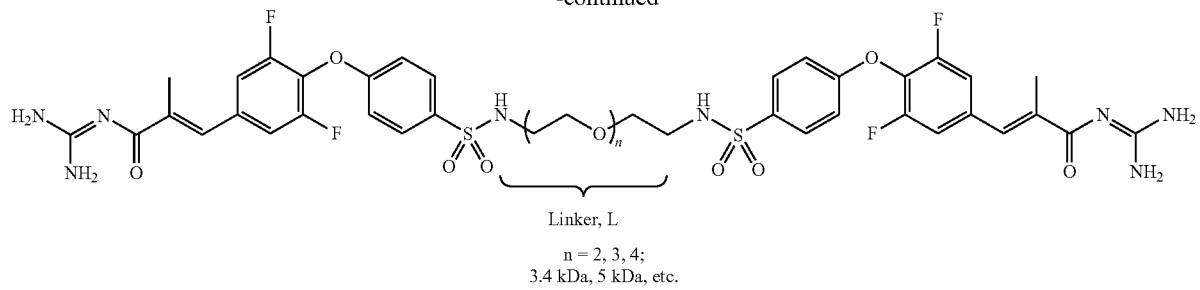

Linker, L n = 2, 3, 4;
3.4 kDa, 5 kDa, etc.

Within the polyvalent compounds utilized for treatments according to the present disclosure, n and m (when m is not zero) may be independently selected from the range of from about 1 to about 10, more preferably from about 1 to about 5, and even more preferably from about 1 to about 2. In alternative embodiments, however, n and m may be independently selected from the range of from about 1 to about 500, preferably from about 1 to about 300, more preferably from about 1 to about 100, and most preferably from about 1 to about 50. In these or other particular embodiments, n and m may both be within the range of from about 1 to about 50, or from about 1 to about 20.

The structures provided above are illustrations of one embodiment of compounds utilized for administration wherein absorption is limited (i.e., the compound is rendered substantially impermeable or substantially systemically non-bioavailable) by means of increasing the molecular weight of the NHE-inhibiting small molecule. In an alternative approach, as noted elsewhere herein, the NHE-inhibiting small molecule may be rendered substantially impermeable or substantially systemically non-bioavailable by means of altering, and more specifically increasing, the topological polar surface area, as further illustrated by the following structures, wherein a substituted aromatic ring is bound to the "scaffold" of the NHE-inhibition small molecule. The selection of ionizable groups such as phosphonates, sulfonates, guanidines and the like may be particularly advantageous at preventing paracellular permeability. Carbohydrates are also advantageous, and though uncharged, significantly increase tPSA while minimally increasing molecular weight.

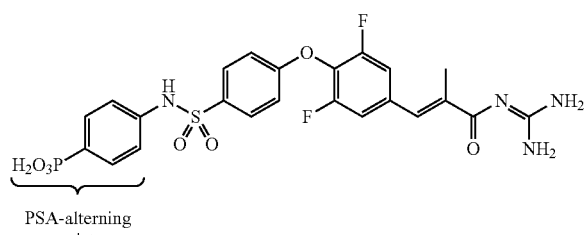

PSA-alterning moiety

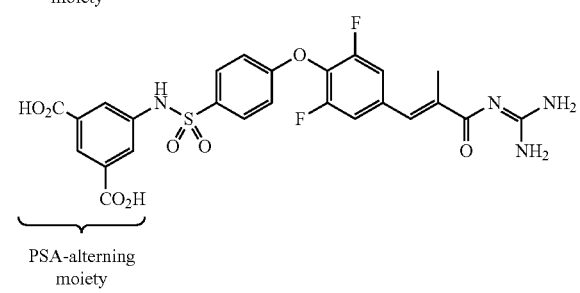

PSA-alterning moiety

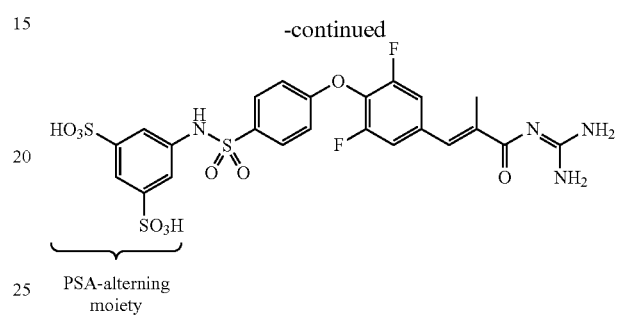

PSA-alterning moiety

It is to be noted, within one or more of the various embodiments illustrated herein, NHE-inhibiting small molecules suitable for use (i.e., suitable for modification or functionalization, in order to render them substantially impermeable or substantially systemically non-bioavailable) may, in particular, be selected independently from one or more of the small molecules described as benzoylguandines, heteroaroylguandines, "spacer-stretched" aroylguandines, non-acyl guanidines and acylguanidine isosteres, above, and as discussed in further detail hereinafter and/or to the small molecules detailed in, for example: U.S. Pat. No. 5,866,610; U.S. Pat. No. 6,399,824; U.S. Pat. No. 6,911,453; U.S. Pat. No. 6,703,405; U.S. Pat. No. 6,005,010; U.S. Pat. No. 6,887,870; U.S. Pat. No. 6,737,423; U.S. Pat. No. 7,326,705; U.S. Pat. No. 5,824,691 (WO94/026709); U.S. Pat. No. 6,399,824 (WO02/024637); US 2004/0339001 (WO02/020496); US 2005/0020612 (WO03/055490); WO01/072742; CA 2387529 (WO01021582); CA 02241531 (WO97/024113); US 2005/0113396 (WO03/051866); US2005/0020612; US2005/0054705; US2008/0194621; US2007/0225323; US2004/0039001; US2004/0224965; US2005/0113396; US2007/0135383; US2007/0135385; US2005/0244367; US2007/0270414; and CA 2177007 (EP 0744397), the entire contents of which are incorporated herein by reference for all relevant and consistent purposes. Again, it is to be noted that when it is said that NHE-inhibiting small molecule is selected independently, it is intended that, for example, the oligomeric structures represented in Formulas (X) and (XI) above can include different structures of the NHE small molecules, within the same oligomer or polymer. In other words, each "NHE" within a given polyvalent embodiment may independently be the same or different than other "NHE" moieties within the same polyvalent embodiment. In designing and making the substantially impermeable or substantially systemically non-bioavailable, NHE-inhibiting compounds that may be utilized for the treatments detailed in the instant disclosure, it may in some cases be advantageous to first determine a likely point of attachment on a small molecule NHE inhibitor, where a core or linker might be installed or attached before making a series of candidate multivalent or polyvalent compounds. This may be done by one skilled in the art via known methods by systematically installing functional groups, or functional groups displaying a fragment of the desired core or linker, onto various positions of the NHE inhibitor small molecule and then testing these adducts to determine whether the modified inhibitor still retains desired biological properties (e.g., NHE inhibition). An understanding of the SAR of the inhibitor also allows the design of cores and/or linkers that contribute positively to the activity of the resulting compounds. For example, the SAR of an NHE inhibitor series may show that installation of an N-alkylated piperazine contributes positively to biochemical activity (increased potency) or pharmaceutical properties (increased solubility); the piperazine moiety may then be utilized as the point of attachment for the desired core or linker via N-alkylation. In this fashion, the resulting compound thereby retains the favorable biochemical or pharmaceutical properties of the parent small molecule. In another example, the SAR of an NHE inhibitor series might indicate that a hydrogen bond donor is important for activity or selectivity. Core or linker moieties may then be designed to ensure this H-bond donor is retained. These cores and/or linkers may be further designed to attenuate or potentiate the pKa of the H-bond donor, potentially allowing improvements in potency and selectivity. In another scenario, an aromatic ring in an inhibitor could be an important pharmacophore, interacting with the biological target via a pi-stacking effect or pi-cation interaction. Linker and core motifs may be similarly designed to be isosteric or otherwise synergize with the aromatic features of the small molecule. Accordingly, once the structure-activity relationships within a molecular series are understood, the molecules of interest can be broken down into key pharmacophores which act as essential molecular recognition elements. When considering the installation of a core or linker motif, said motifs can be designed to exploit this SAR and may be installed to be isosteric and isoelectronic with these motifs, resulting in compounds that retain biological activity but have significantly reduced permeability.

Another way the SAR of an inhibitor series can be exploited in the installation of core or linker groups is to understand which regions of the molecule are insensitive to structural changes. For example, X-ray co-crystal structures of protein-bound inhibitors can reveal those portions of the inhibitor that are solvent exposed and not involved in productive interactions with the target. Such regions can also be identified empirically when chemical modifications in these regions result in a "flat SAR" (i.e., modifications appear to have minimal contribution to biochemical activity). Those skilled in the art have frequently exploited such regions to engineer in pharmaceutical properties into a compound, for example, by installing motifs that may improve solubility or potentiate ADME properties. In the same fashion, such regions are expected to be advantageous places to install core or linker groups to create compounds as described in the instant disclosure. These regions are also expected to be sites for adding, for example, highly polar functionality such as carboxylic acids, phosphonic acids, sulfonic acids, and the like in order to greatly increase tPSA.

Another aspect to be considered in the design of cores and linkers displaying an NHE inhibitor is the limiting or preventing of hydrophobic collapse. Compounds with extended hydrocarbon functionalities may collapse upon themselves in an intramolecular fashion, causing an increased enthalpic barrier for interaction with the desired biological target. Accordingly, when designing cores and linkers, these are preferably designed to be resistant to hydrophobic collapse. For example, conformational constraints such as rigid monocyclic, bicyclic or polycyclic rings can be installed in a core or linker to increase the rigidity of the structure. Unsaturated bonds, such as alkenes and alkynes, may also or alternatively be installed. Such modifications may ensure the NHE-inhibiting compound is accessible for productive binding with its target. Furthermore, the hydrophilicity of the linkers may be improved by adding hydrogen bond donor or acceptor motifs, or ionic motifs such as amines that are protonated in the GI, or acids that are deprotonated. Such modifications will increase the hydrophilicity of the core or linker and help prevent hydrophobic collapse. Furthermore, such modifications will also contribute to the impermeability of the resulting compounds by increasing tPSA.

Specific examples of NHE-inhibiting small molecules modified consistent with the principles detailed above are illustrated below. These moieties display functional groups that facilitate their appendage to "Z" (e.g., a core group, Core, or linking group, L). These functional groups can include electrophiles, which can react with nucleophilic cores or linkers, and nucleophiles, which can react with electrophilic cores or linkers. Small molecule NHE inhibitors may be similarly derivatized with, for example, boronic acid groups which can then react with appropriate cores or linkers via palladium mediated cross-coupling reactions. The NHE inhibitor may also contain olefins which can then react with appropriate cores or linkers via olefin metathesis chemistry, or alkynes or azides which can then react with appropriate cores or linkers via [2+3] cycloaddition. One skilled in the art may consider a variety of functional groups that will allow the facile and specific attachment of an NHE inhibiting small molecule to a desired core or linker. Exemplary functionalized derivatives of NHEs include but are not limited to the following:

Scheme 1
Cinnamoylguanidine NHE-inhibiting Moiety Functionalized to Display Electrophilic or Nucleophilic Groups to Facilitate Reaction with Cores and Linkers

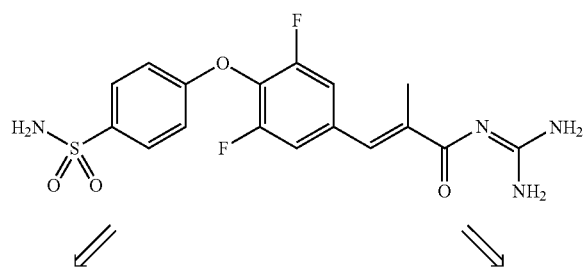

-continued

Electrophilic Intermediates:

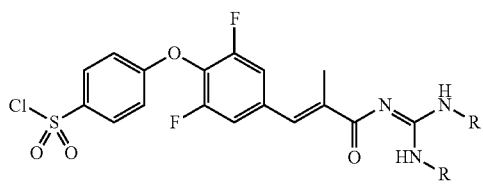

R = —H, —P.G.

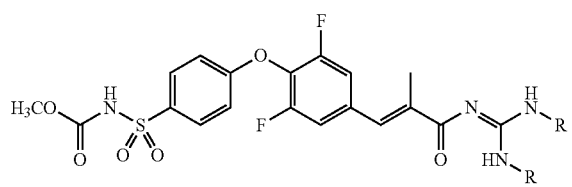

R = —H, —P.G.

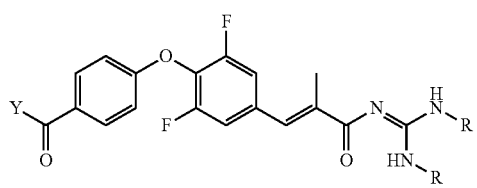

Y = —OH, —NHS, —Cl, etc.

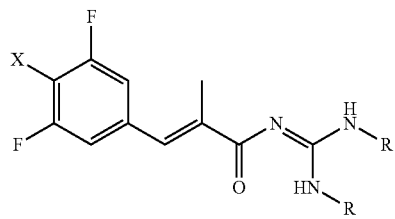

X = —F, —Cl, etc.

Nucleophilic Intermediates:

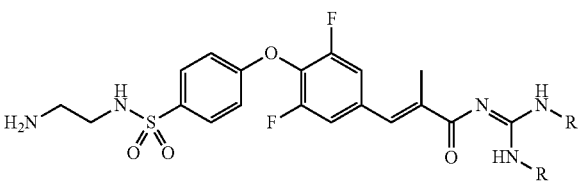

R = —H, —P.G.

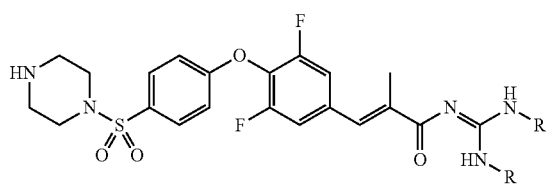

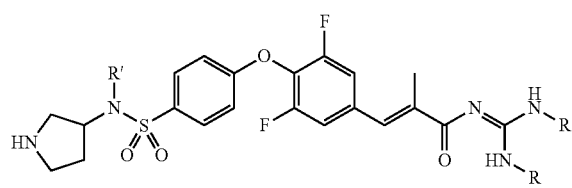

R' = —H, —CH$_3$

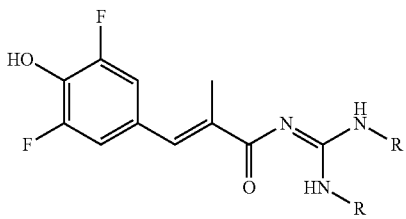

wherein the variables in the above-noted structures (e.g., R, etc.) are as defined in U.S. Pat. No. 6,399,824, the entire contents of which are incorporated herein by reference for all relevant and consistent purposes.

Scheme 2
Tetrahydroisoquinoline NHE-inhibiting Moiety Functionalized to Display Electrophilic or Nucleophilic Groups to Facilitate Reaction with Cores and Linkers

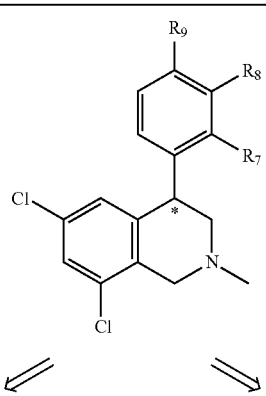

-continued
Nucleophilic Intermediates:
Electrophilic Intermediates:
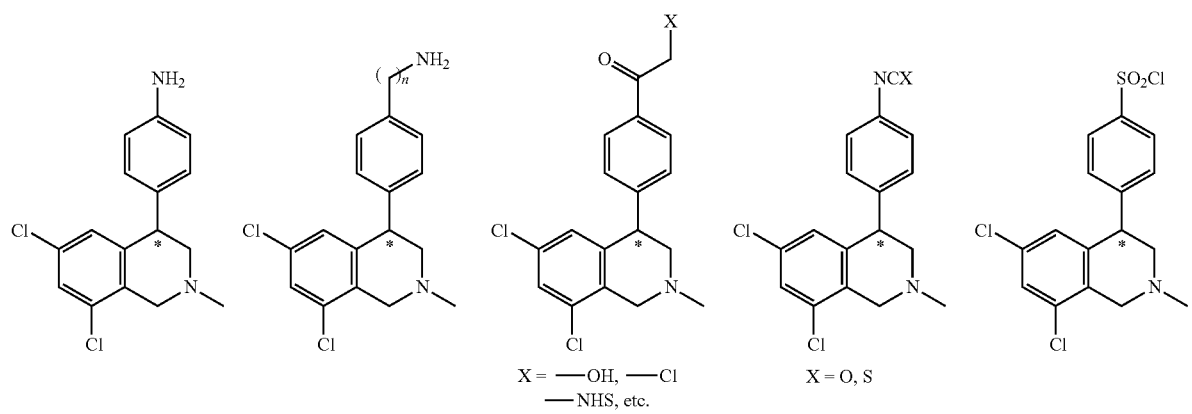
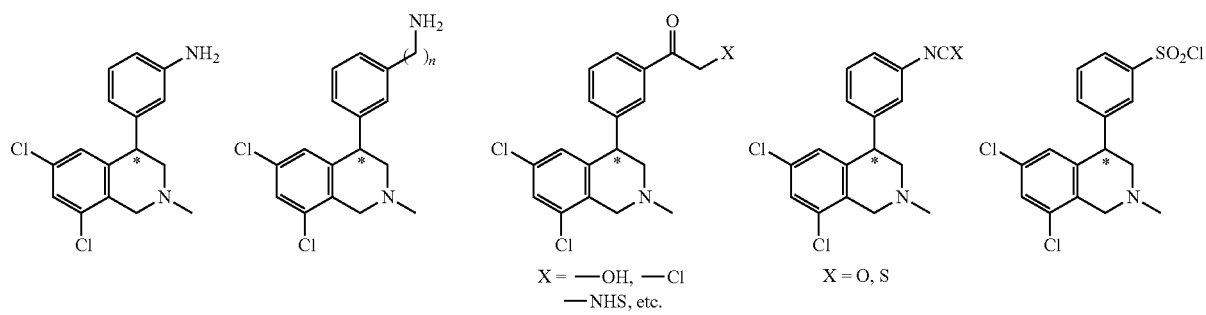
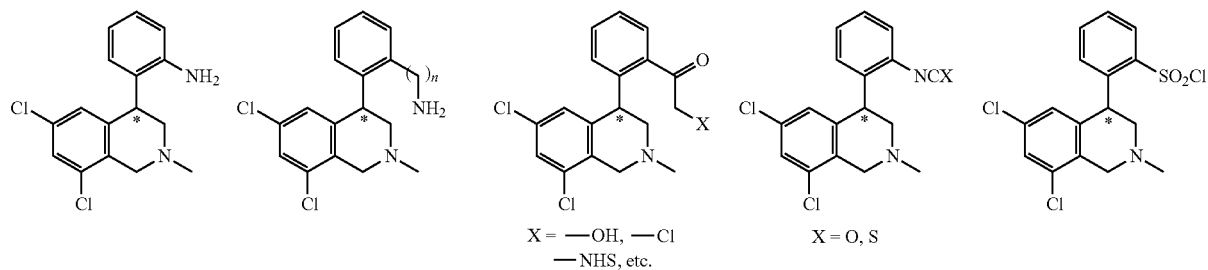
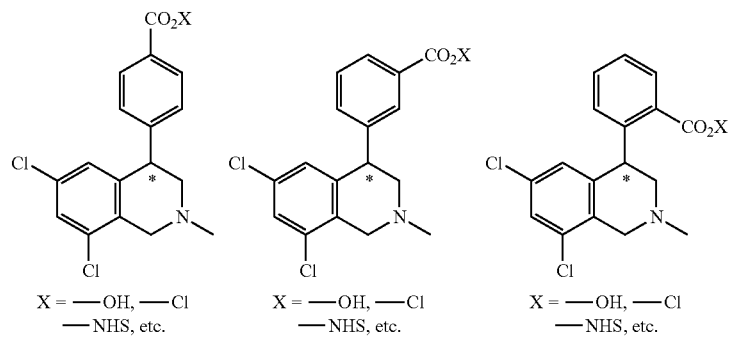
wherein the variables in the above-noted structures (e.g., $R_{7-9}$, etc.) are as defined in U.S. Pat. No. 6,911,453, the entire contents of which (and in particular the text of columns 1-4 therein) are incorporated herein by reference for all relevant and consistent purposes.

Scheme 3
Quinazoline NHE-inhibiting Moiety Functionalized to Display Electrophilic or Nucleophilic Groups to Facilitate Reaction with Cores and Linkers

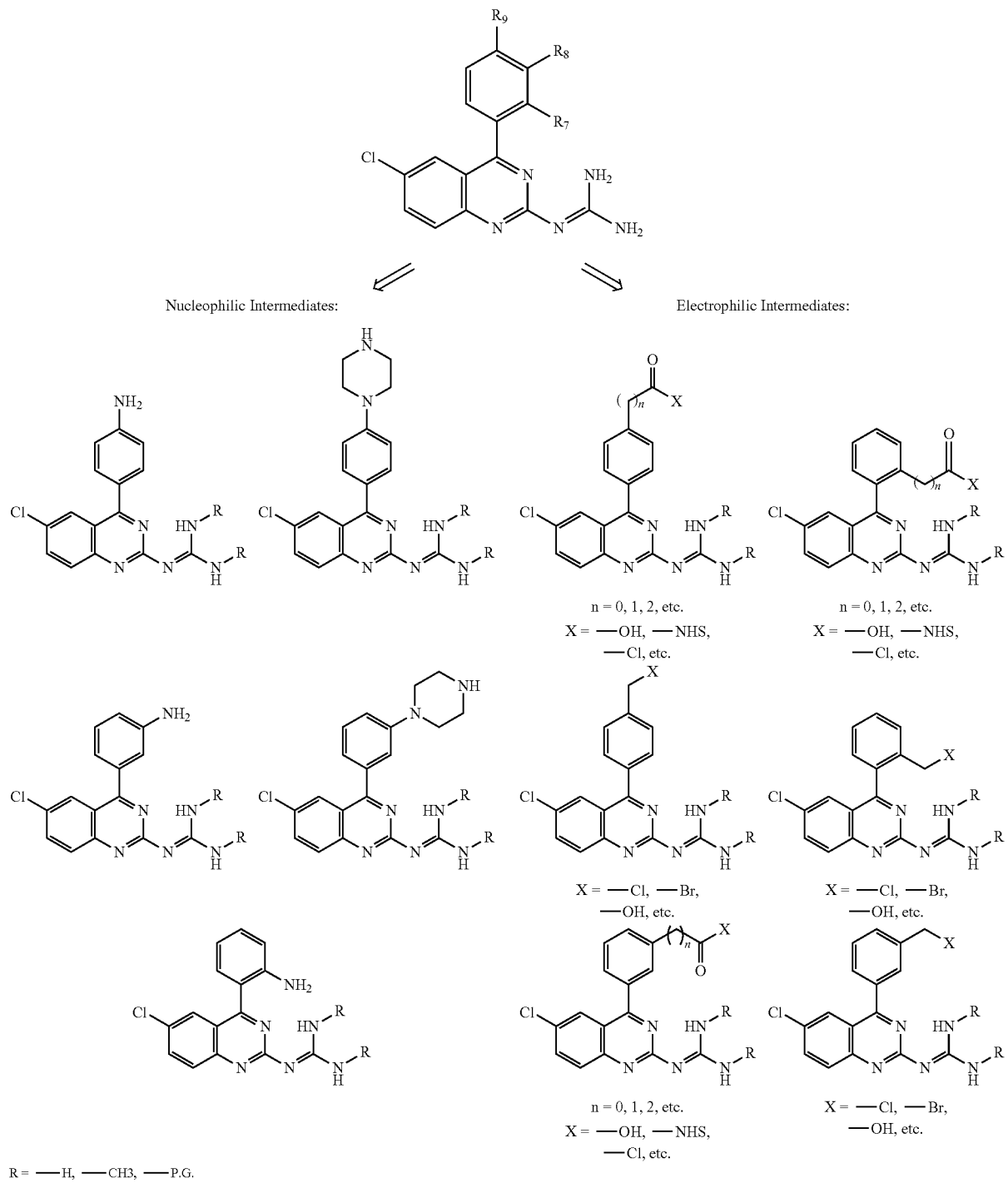

wherein the variables in the above-noted structures (e.g., $R_{7-9}$, etc.) are as defined in U.S. Patent Application No. 2005/0020612 and U.S. Pat. No. 6,911,453, the entire contents of which (and in particular the text of columns 1-4 therein) are incorporated herein by reference for all relevant and consistent purposes.

It is to be noted that one skilled in the art can envision a number of core or linker moieties that may be functionalized with an appropriate electrophile or nucleophile. Shown below are a series of such compounds selected based on several design considerations, including solubility, steric effects, and their ability to confer, or be consistent with, favorable structure-activity relationships. In this regard it is to be further noted, however, that the structures provided below, and above, are for illustration purposes only, and therefore should not be viewed in a limiting sense. Exemplary electrophilic and nucleophilic linker moieties include, but are not limited to, the linker moieties illustrated in the Examples and the following:

Nucleophilic linkers (for use with electrophilic NHE-inhibitory derivatives)

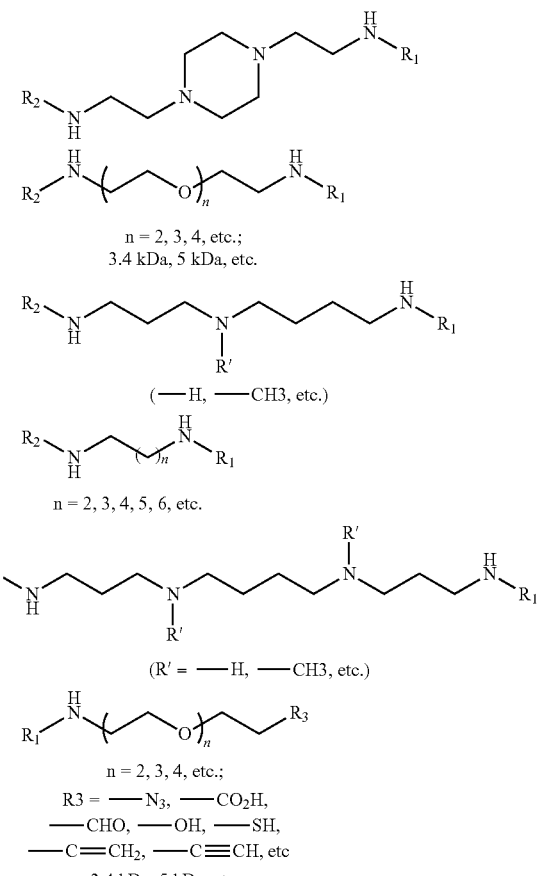

Electrophilic linkers (for use with nucleophilic NHE-inhibitory derivatives)

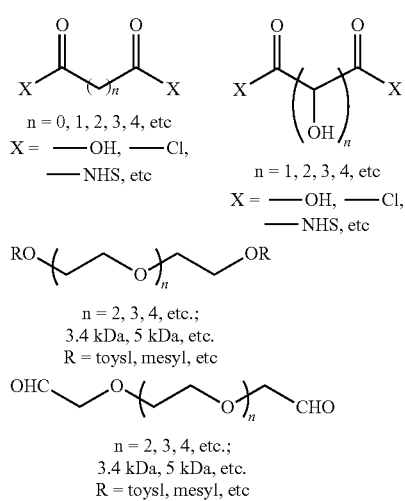

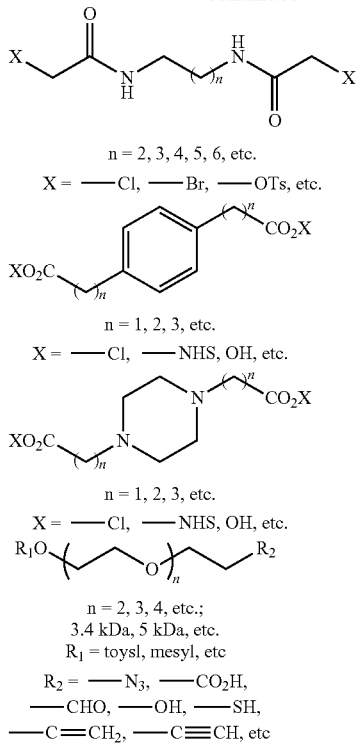

The linking moiety, L, in each of the described embodiments (including embodiments in which a NHE-inhibiting small molecule is linked to a core such as an atom, another small molecule, a polymer moiety, an oligomer moiety, or a non-repeating moiety) can be a chemical linker, such as a bond or other moiety, for example, comprising about 1 to about 200 atoms, or about 1 to about 100 atoms, or about 1 to about 50 atoms, that can be hydrophilic and/or hydrophobic. In one embodiment, the linking moiety can be a polymer moiety grafted onto a polymer backbone, for example, using living free radical polymerization approaches known in the art. Preferred L structures or moieties may also be selected from, for example, oligoethylene glycol, oligopeptide, oligoethyleneimine, oligotetramethylene glycol and oligocaprolactone.

As noted, the core moiety can be an atom, a small molecule, an oligomer, a dendrimer or a polymer moiety, in each case having one or more sites of attachment for L. For example, the core moiety can be a non-repeating moiety (considered as a whole including linking points to the inhibitors), selected for example from the group consisting of alkyl, phenyl, aryl, alkenyl, alkynyl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, and moieties comprising combinations thereof (in each permutation). A non-repeating moiety can include repeating units (e.g., methylene) within portions or segments thereof (e.g., within an alkyl segment), without having discrete repeat units that constitute the moiety as a whole (e.g., in the sense of a polymer or oligomer).

Exemplary core moieties include but are not limited to the core moieties illustrated in the Examples and ether moieties, ester moieties, sulfide moieties, disulfide moieties, amine moieties, aryl moieties, alkoxyl moieties, etc., such as, for example, the following:

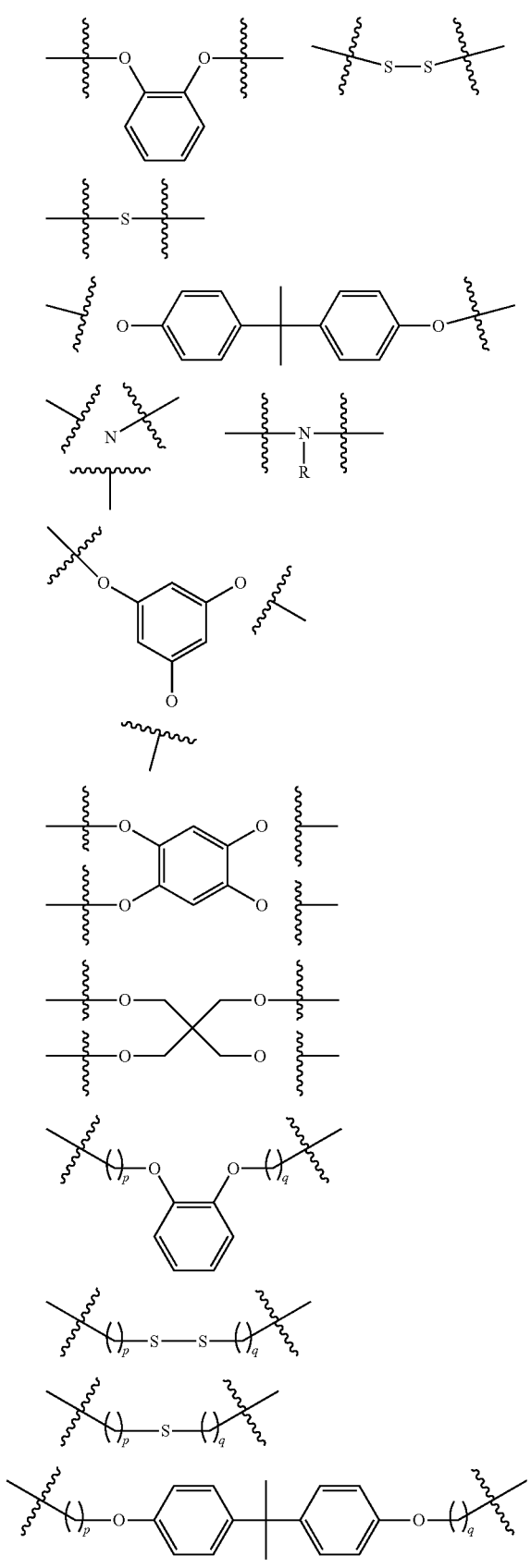
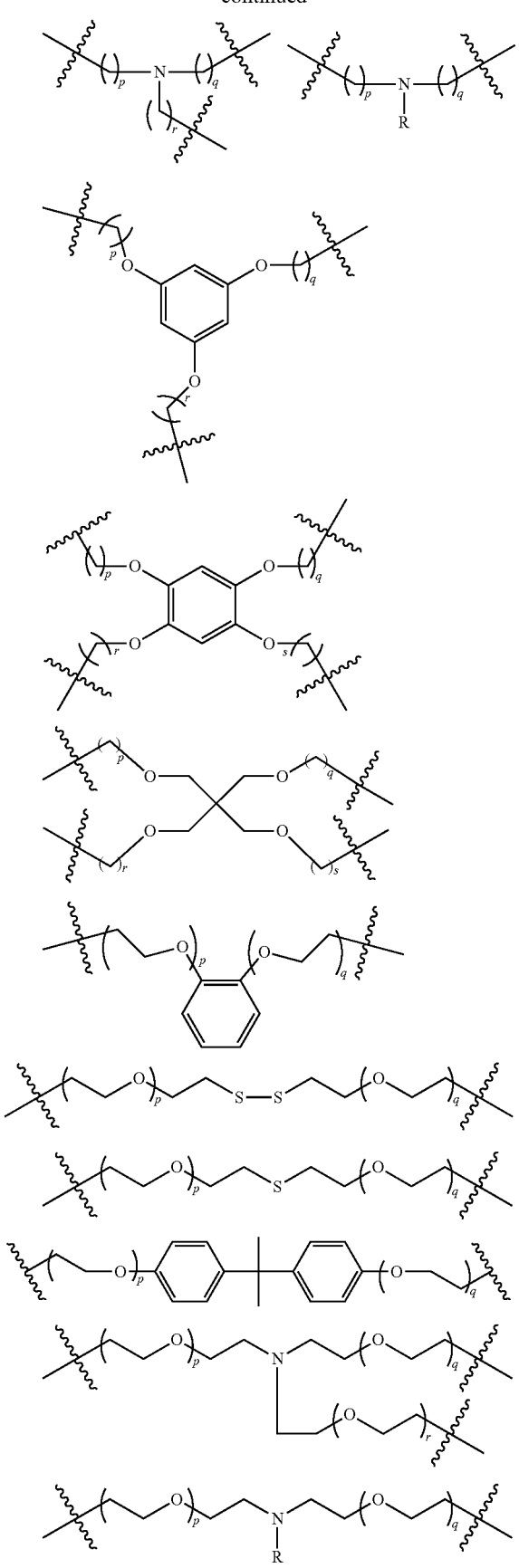

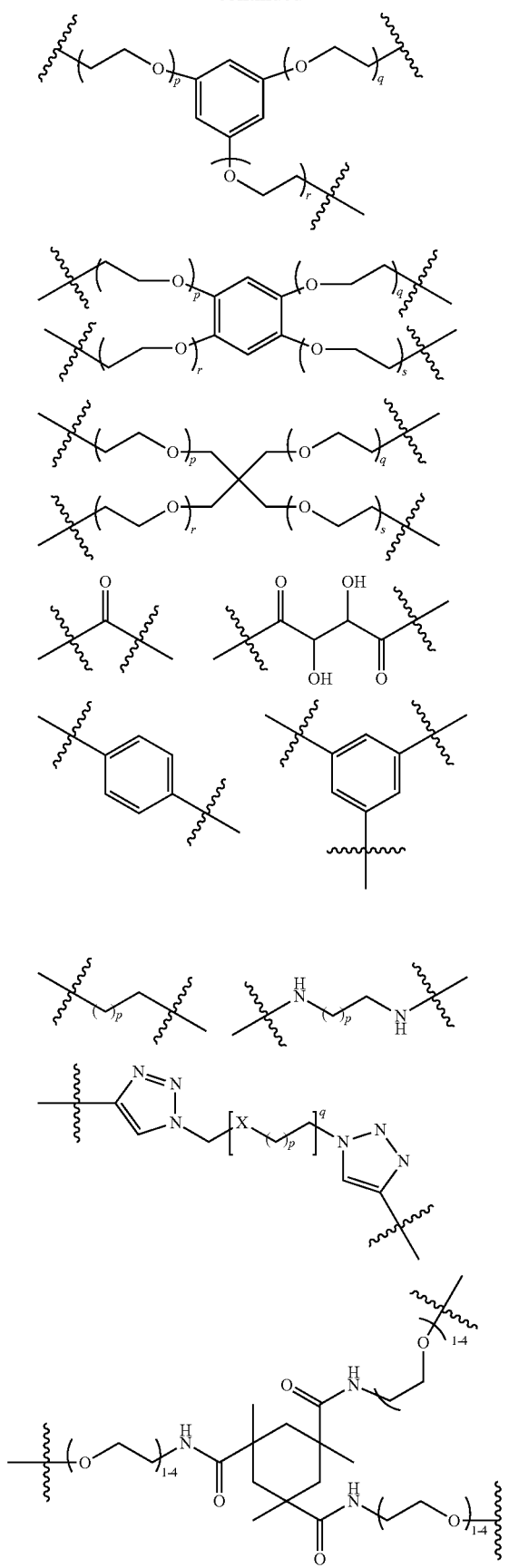
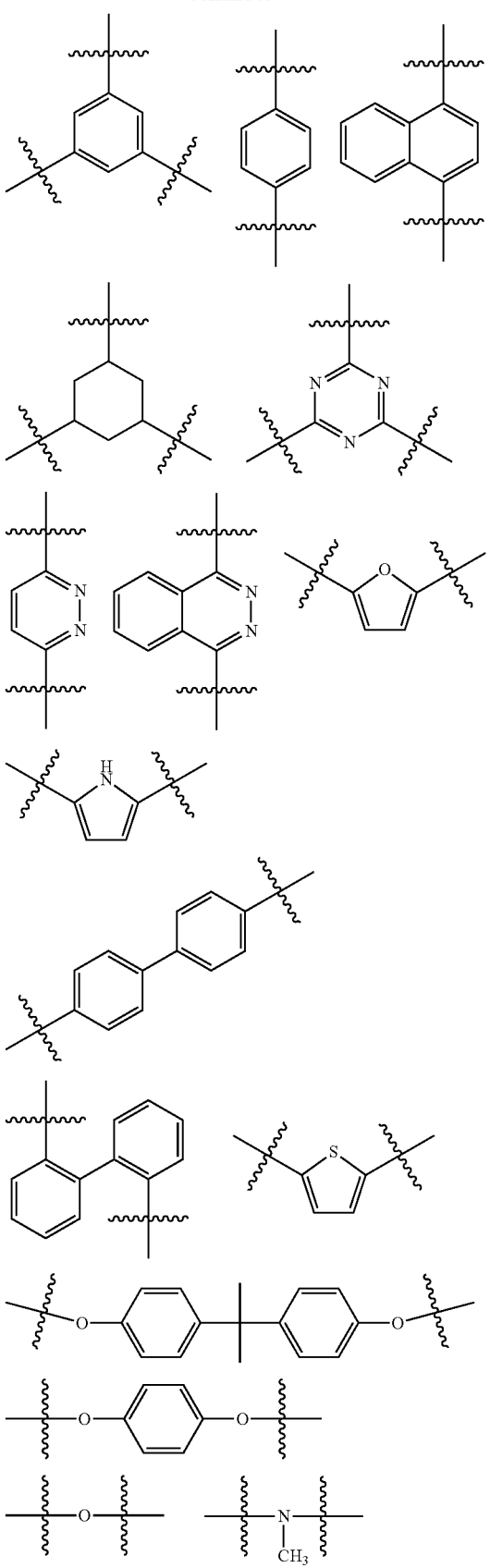

-continued

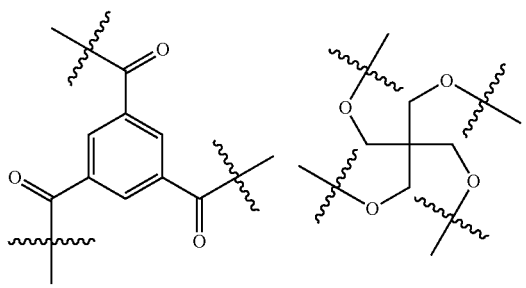

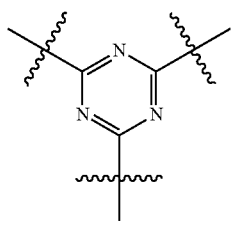

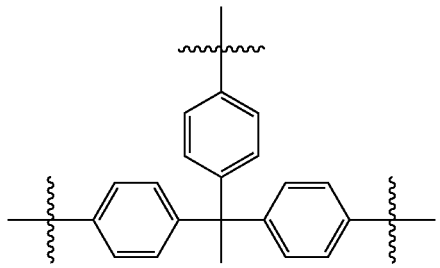

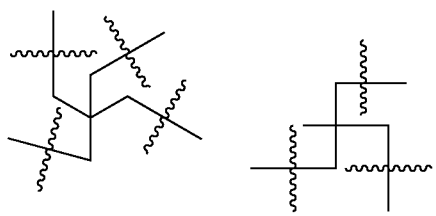

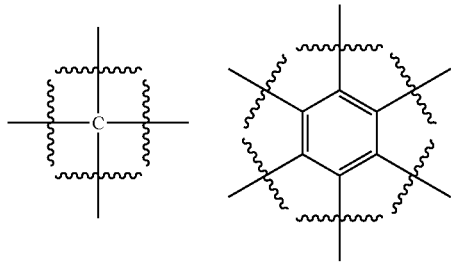

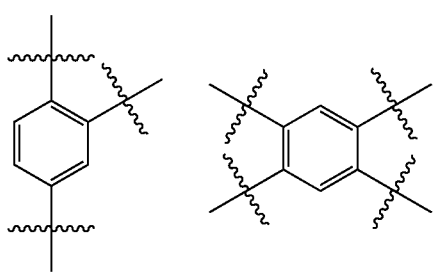

-continued

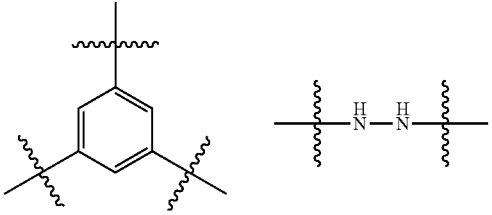

wherein the broken bonds (i.e., those having a wavy bond, through them) are points of connection to either an NHE inhibitor or a linker moiety displaying an NHE inhibitor, where said points of connection can be made using chemistries and functional groups known to the art of medicinal chemistry; and further wherein each p, q, r and s is an independently selected integer ranging from about 0 to about 48, preferably from about 0 to about 36, or from about 0 to about 24, or from about 0 to about 16. In some instances, each p, q, r and s can be an independently selected integer ranging from about 0 to 12. Additionally, R can be a substituent moiety generally selected from halide, hydroxyl, amine, thiol, ether, carbonyl, carboxyl, ester, amide, carbocyclic, heterocyclic, and moieties comprising combinations thereof.

Figure 8:
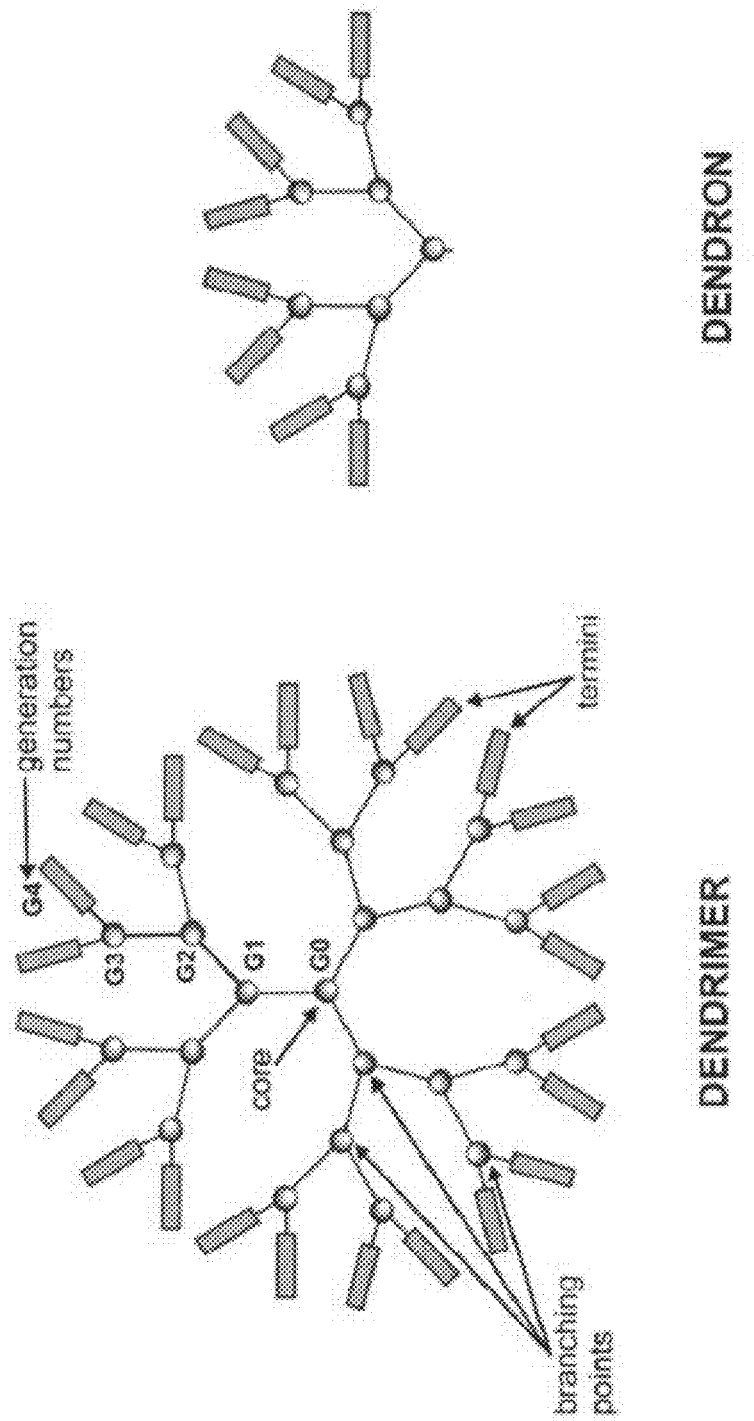
FIG. 8 is a schematic representation of a dendrimer.

In another approach, the core moiety is a dendrimer, defined as a repeatedly branched molecule (see, e.g., J. M. J. Fréchet, D. A. Tomalia, *Dendrimers and Other Dendritic Polymers*, John Wiley & Sons, Ltd. NY, N.Y., 2001) and schematically represented in FIG. 8:

In this approach, the NHE inhibiting small molecule is attached through L to one, several or optionally all termini located at the periphery of the dendrimer. In another approach, a dendrimer building block named dendron, and illustrated above, is used as a core, wherein the NHE inhibitor group is attached to one, several or optionally all termini located at the periphery of the dendron. The number of generations herein is typically between about 0 and about 6, and preferably between about 0 and about 3. (Generation is defined in, for example, J. M. J. Fréchet, D. A. Tomalia, *Dendrimers and Other Dendritic Polymers*, John Wiley & Sons, Ltd. NY, N.Y.) Dendrimer and/or dendron structures are well known in the art and include, for example, those shown in or illustrated by: (i) J. M. J. Fréchet, D. A. Tomalia, *Dendrimers and Other Dendritic Polymers*, John Wiley & Sons, Ltd. NY, N.Y.; (ii) George R Newkome, Charles N. Moorefield and Fritz Vogtle, *Dendrimers and Dendrons: Concepts, Syntheses, Applications*, VCH Verlagsgesellschaft Mbh; and, (iii) Boas, U., Christensen, J. B., Heegaard, P. M. H., *Dendrimers in Medicine and Biotechnology: New Molecular Tools*, Springer, 2006.

In yet another approach, the core moiety may be a polymer moiety or an oligomer moiety. The polymer or oligomer may, in each case, be independently considered and comprise repeat units consisting of a repeat moiety selected from alkyl (e.g., —$CH_2$—), substituted alkyl (e.g., —CHR—, wherein, for example, R is hydroxy), alkenyl, substituted alkenyl, alkynyl, substituted alkynyl, phenyl, aryl, heterocyclic, amine, ether, sulfide, disulfide, hydrazine, and any of the foregoing substituted with oxygen, sulfur, sulfonyl, phosphonyl, hydroxyl, alkoxyl, amine, thiol, ether, carbonyl, carboxyl, ester, amide, alkyl, alkenyl, alkynyl, aryl, heterocyclic, as well as moieties comprising combinations thereof. In still another approach, the core moiety comprises repeat units resulting from the polymerization of ethylenic monomers (e.g., such as those ethylenic monomers listed elsewhere herein below).

Preferred polymers for polymeric moieties useful in constructing substantially impermeable or substantially systemically non-bioavailable NHE-inhibiting compounds that are multivalent, for use in the treatment various treatment methods disclosed herein, can be prepared by any suitable technique, such as by free radical polymerization, condensation polymerization, addition polymerization, ring-opening polymerization, and/or can be derived from naturally occurring polymers, such as saccharide polymers. Further, in some embodiments, any of these polymer moieties may be functionalized.

Examples of polysaccharides useful in preparation of such compounds include but are not limited to materials from vegetable or animal origin, including cellulose materials, hemicellulose, alkyl cellulose, hydroxyalkyl cellulose, carboxymethylcellulose, sulfoethylcellulose, starch, xylan, amylopectine, chondroitin, hyarulonate, heparin, guar, xanthan, mannan, galactomannan, chitin, and/or chitosan. More preferred, in at least some instances, are polymer moieties that do not degrade, or that do not degrade significantly, under the physiological conditions of the GI tract (such as, for example, carboxymethylcellulose, chitosan, and sulfoethylcellulose). When free radical polymerization is used, the polymer moiety can be prepared from various classes of monomers including, for example, acrylic, methacrylic, styrenic, vinylic, and dienic, whose typical examples are given thereafter: styrene, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, and combinations thereof. Functionalized versions of these monomers may also be used and any of these monomers may be used with other monomers as comonomers. For example, specific monomers or comonomers that may be used in this disclosure include methyl methacrylate, ethyl methacrylate, propyl methacrylate (all isomers), butyl methacrylate (all isomers), 2-ethylhexyl methacrylate, isobomyl methacrylate, methacrylic acid, benzyl methacrylate, phenyl methacrylate, methacrylonitrile, α-methylstyrene, methyl acrylate, ethyl acrylate, propyl acrylate (all isomers), butyl acrylate (all isomers), 2-ethylhexyl acrylate, isobomyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N—N-butylacrylamide, N-methylolacrylamide, N-ethylolacrylamide, 4-acryloylmorpholine, vinyl benzoic acid (all isomers), diethylaminostyrene (all isomers), a-methylvinyl benzoic acid (all isomers), diethylamino α-methylstyrene (all isomers), p-vinylbenzene sulfonic acid, p-vinylbenzene sulfonic sodium salt, alkoxy and alkyl silane functional monomers, maleic anhydride, N-phenylmaleimide, N-butylmaleimide, butadiene, isoprene, chloroprene, ethylene, vinyl acetate, vinylformamide, allylamine, vinylpyridines (all isomers), fluorinated acrylate, methacrylates, and combinations thereof. Main chain heteroatom polymer moieties can also be used, including polyethyleneimine and polyethers such as polyethylene oxide and polypropylene oxide, as well as copolymers thereof.

In one particular embodiment, the polymer to which the NHE inhibitor small molecule, NHE, is attached or otherwise a part of is a polyol (e.g., a polymer having a repeat unit of, for example, a hydroxyl-substituted alkyl, such as —CH(OH)—). Polyols, such as mono- and disaccharides, with or without reducing or reducible end groups thereon, may be good candidates, for example, for installing additional functionality that could render the compound substantially impermeable.

In one particular embodiment, the NHE inhibiting small molecule, NHE, is attached at one or both ends of the polymer chain. More specifically, in yet another alternative approach to the polyvalent embodiment of the present disclosure, a macromolecule (e.g., a polymer or oligomer) having one of the following exemplary structures may be designed and constructed as described herein:

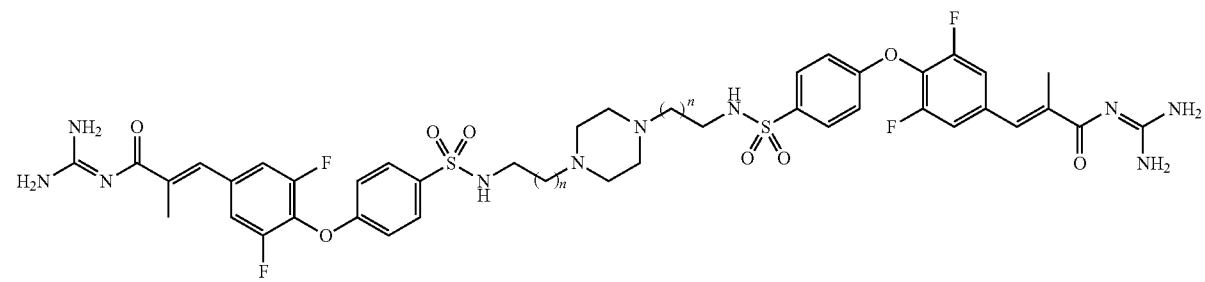

n = 1, 2, 3-10, or more

-continued
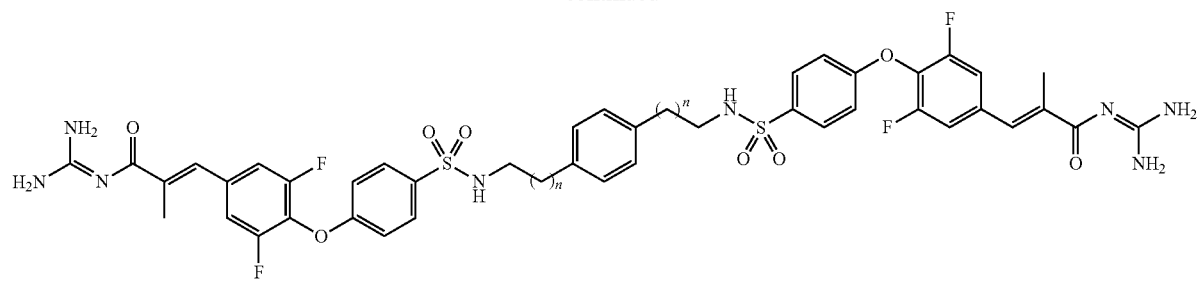
n = 1, 2, 3-10, or more
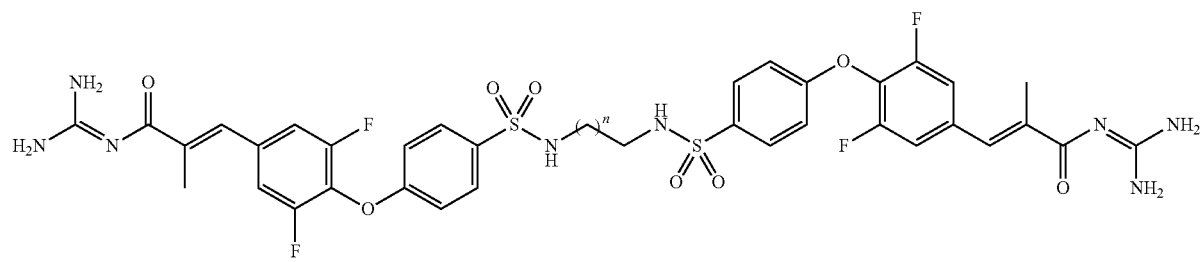
n = 1, 2, 3-10, or more
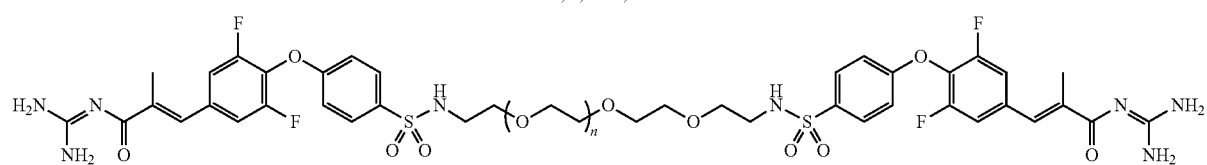
n = 0, 1, 2, 3-10, or more
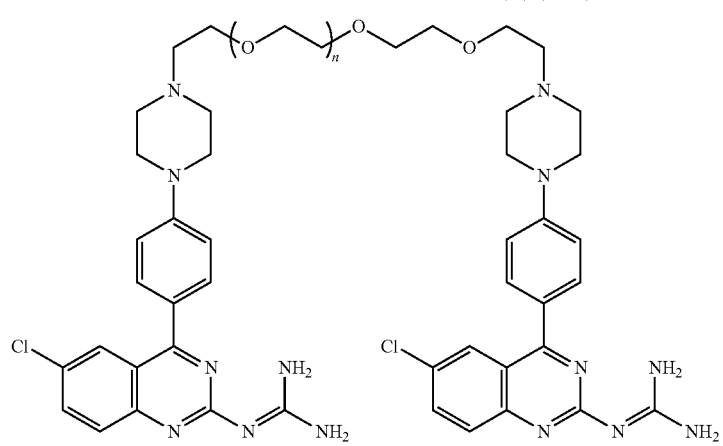
n = 0, 1, 2, 3-10, or more
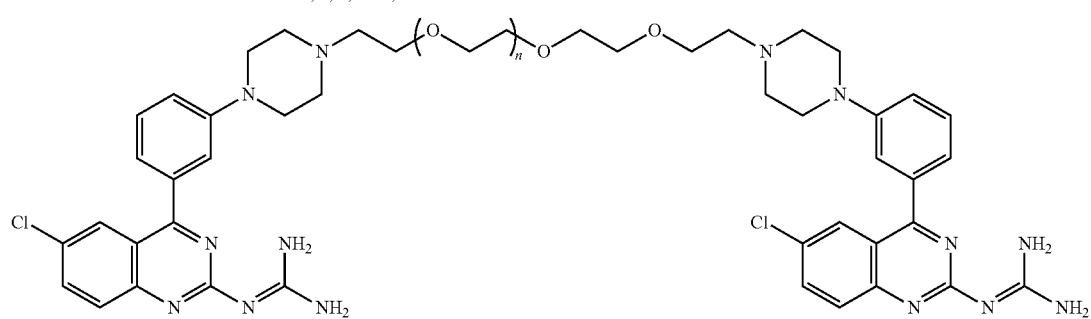
n = 0, 1, 2, 3-10, or more -continued
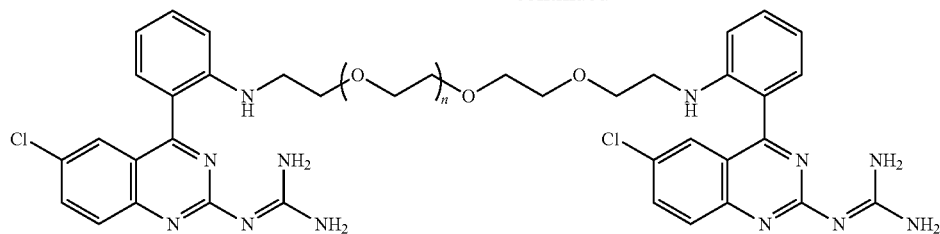
n = 0, 1, 2, 3-10, or more
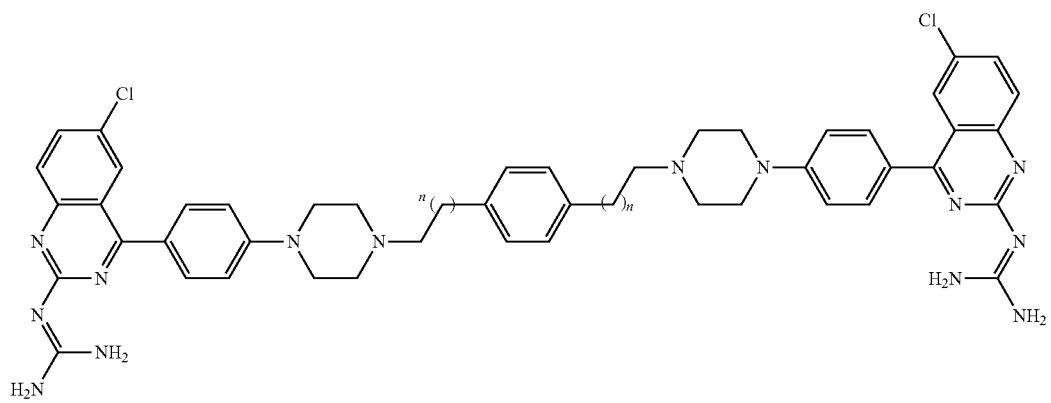
n = 0, 1, 2, 3-10, or more
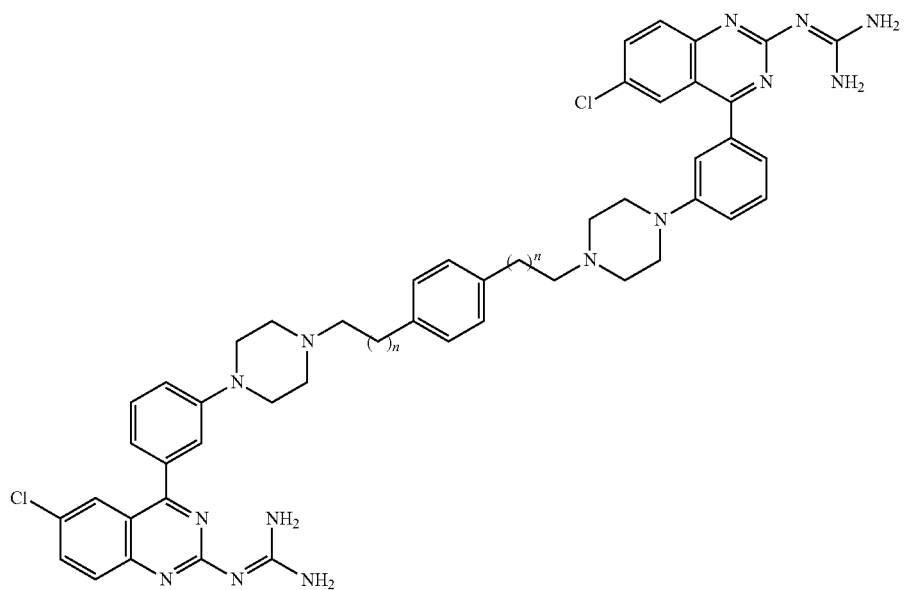
n = 0, 1, 2, 3-10, or more -continued
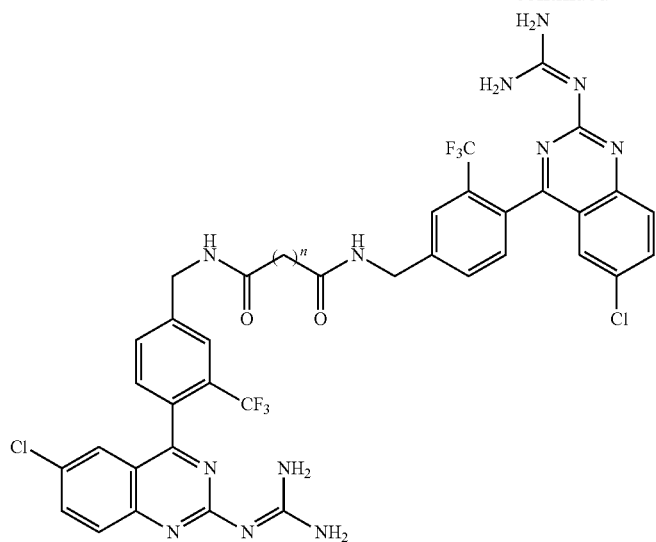
n = 0, 1, 2, 3-10, or more
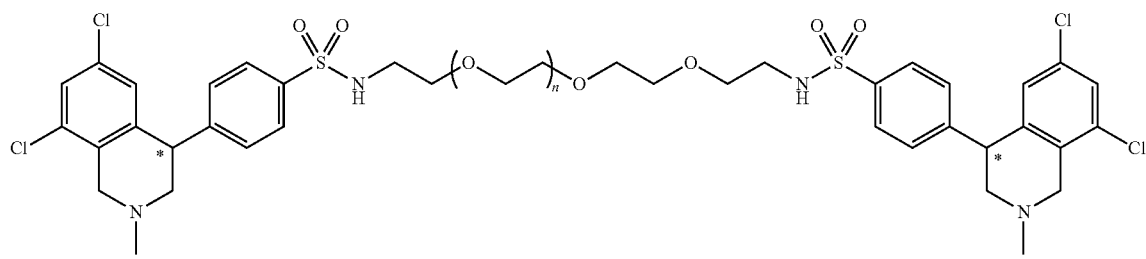
n = 0, 1, 2, 3, 4-10, or more
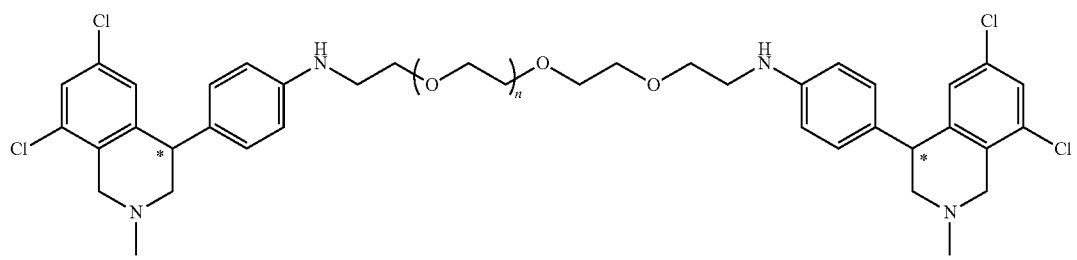
n = 0, 1, 2, 3, 4-10, or more
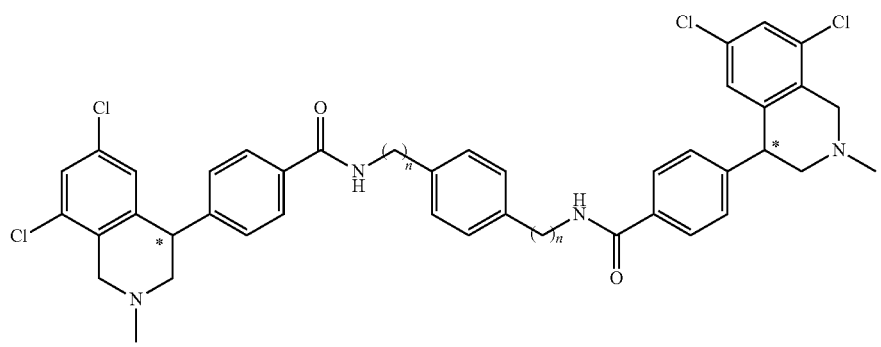
n = 0, 1, 2, 3, 4-10, or more -continued
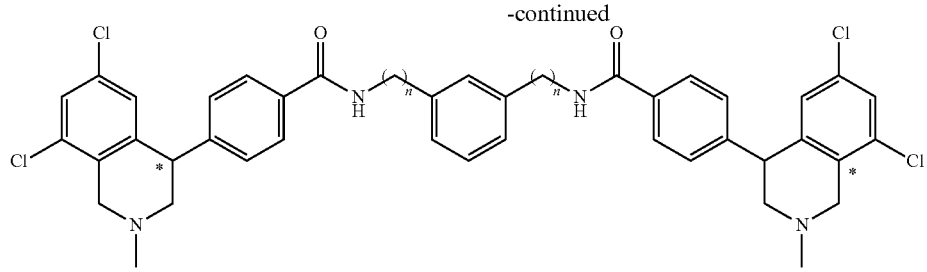
n = 0, 1, 2, 3, 4-10, or more
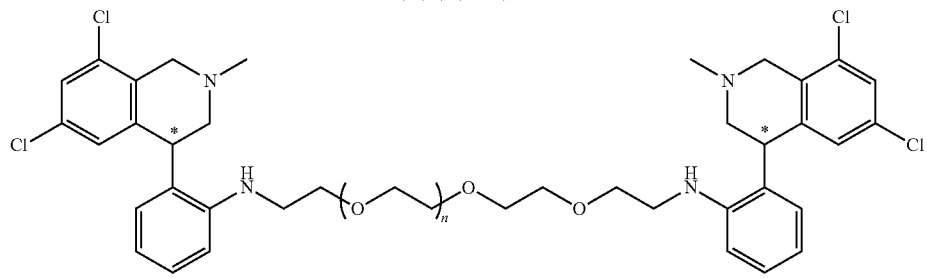
n = 0, 1, 2, 3, 4-10, or more
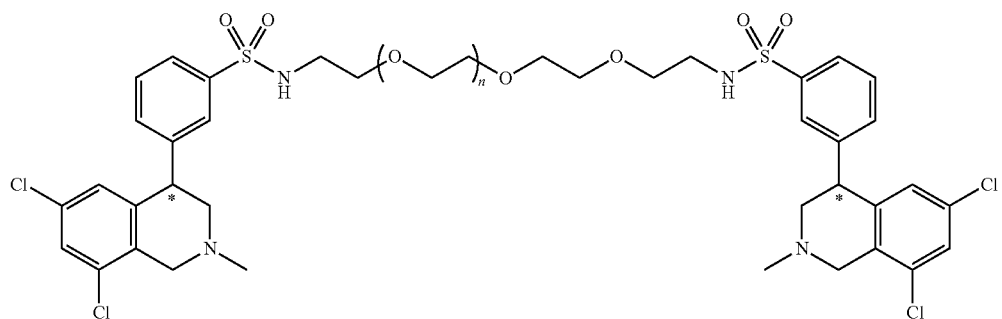
n = 0, 1, 2, 3, 4-10, or more
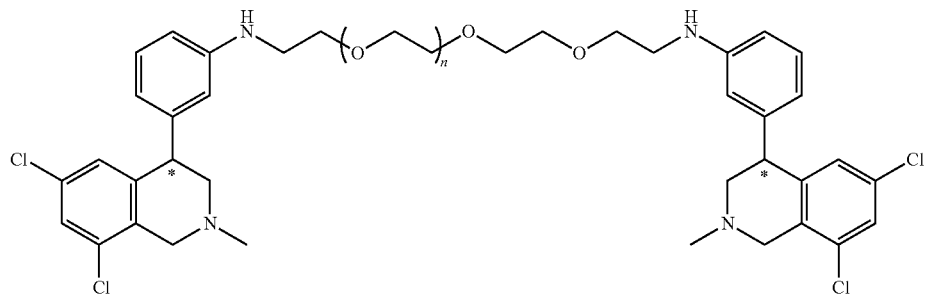
n = 0, 1, 2, 3, 4-10, or more
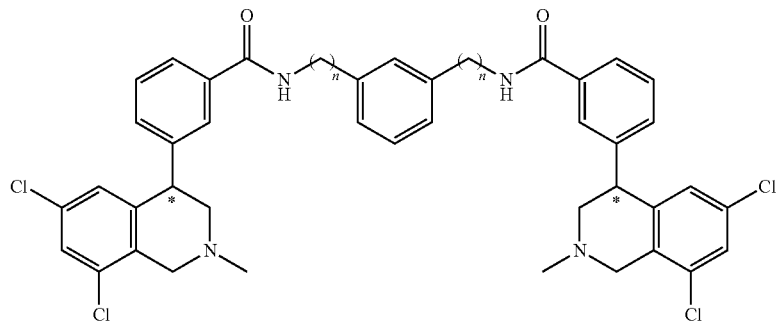
n = 0, 1, 2, 3, 4-10, or more

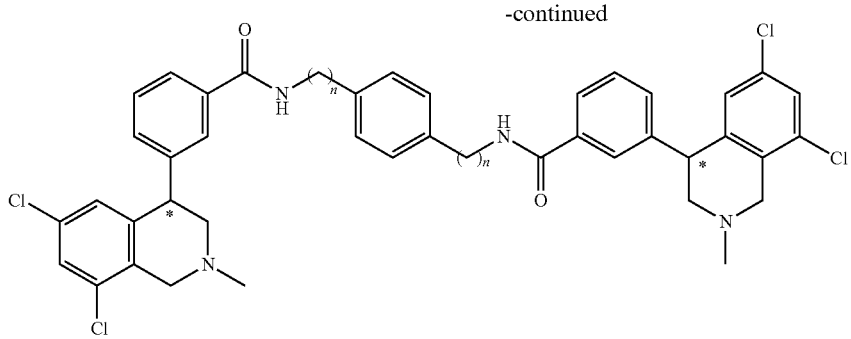

n = 0, 1, 2, 3, 4-10, or more

It is to be further noted that the repeat moiety in Formulas (XIIA) or (XIIB) generally encompasses repeating units of polymers and copolymers produced by methods referred to herein above.

It is to be noted that the various properties of the oligomers and polymers that form the core moiety as disclosed herein above may be optimized for a given use or application using experimental means and principles generally known in the art. For example, the overall molecular weight of the compounds or structures presented herein above may be selected so as to achieve non-absorbability, inhibition persistence and/or potency.

Additionally, with respect to those polymeric embodiments that encompass or include the compounds generally represented by the structure of Formula (I) herein, and/or those disclosed for example in the many patents and patent applications cited herein (see, e.g., U.S. Pat. No. 5,866,610; U.S. Pat. No. 6,399,824; U.S. Pat. No. 6,911,453; U.S. Pat. No. 6,703,405; U.S. Pat. No. 6,005,010; U.S. Pat. No. 6,887,870; U.S. Pat. No. 6,737,423; U.S. Pat. No. 7,326,705; U.S. Pat. No. 5,824,691 (WO94/026709); U.S. Pat. No. 6,399,824 (WO02/024637); US 2004/0339001 (WO02/020496); US 2005/0020612 (WO03/055490); WO01/072742; CA 2387529 (WO01021582); CA 02241531 (WO97/024113); US 2005/0113396 (WO03/051866); US2005/0020612; US2005/0054705; US2008/0194621; US2007/0225323; US2004/0039001; US2004/0224965; US2005/0113396; US2007/0135383; US2007/0135385; US2005/0244367; US2007/0270414; and CA 2177007 (EP 0744397), the entire contents of which are incorporated herein by reference for all relevant and consistent purposes), such as those wherein these compounds or structures are pendants off of a polymeric backbone or chain, the composition of the polymeric backbone or chain, as well as the overall size or molecular weight of the polymer, and/or the number of pendant molecules present thereon, may be selected according to various principles known in the art in view of the intended application or use.

With respect to the polymer composition of the NHE inhibiting compound, it is to be noted that a number of polymers can be used including, for example, synthetic and/or naturally occurring aliphatic, alicyclic, and/or aromatic polymers. In preferred embodiments, the polymer moiety is stable under physiological conditions of the GI tract. By "stable" it is meant that the polymer moiety does not degrade or does not degrade significantly or essentially does not degrade under the physiological conditions of the GI tract. For instance, at least about 90%, preferably at least about 95%, and more preferably at least about 98%, and even more preferably at least about 99% of the polymer moiety remains un-degraded or intact after at least about 5 hours, at least about 12 hours, at least about 18 hours, at least about 24 hours, or at least about 48 hours of residence in a gastrointestinal tract. Stability in a gastrointestinal tract can be evaluated using gastrointestinal mimics, e.g., gastric mimics or intestinal mimics of the small intestine, which approximately model the physiological conditions at one or more locations therein.

Polymer moieties detailed herein for use as the core moiety can be hydrophobic, hydrophilic, amphiphilic, uncharged or non-ionic, negatively or positively charged, or a combination thereof. Additionally, the polymer architecture of the polymer moiety can be linear, grafted, comb, block, star and/or dendritic, preferably selected to produce desired solubility and/or stability characteristics as described above.

Additionally or alternatively, modifications may be made to NHE-inhibiting small molecules that increase tPSA, thus contributing to the impermeability of the resulting compounds. Such modifications preferably include addition of di-anions, such as phosphonates, malonates, sulfonates and the like, and polyols such as carbohydrates and the like. Exemplary derivatives of NHEs with increased tPSA include but are not limited to the following:

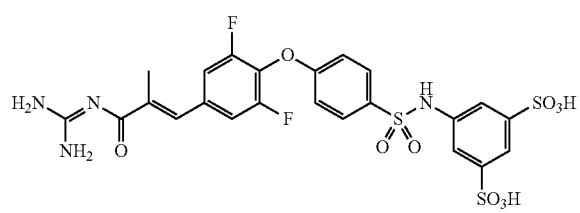

81
-continued
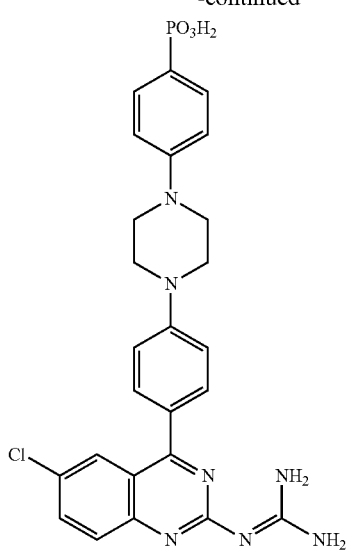
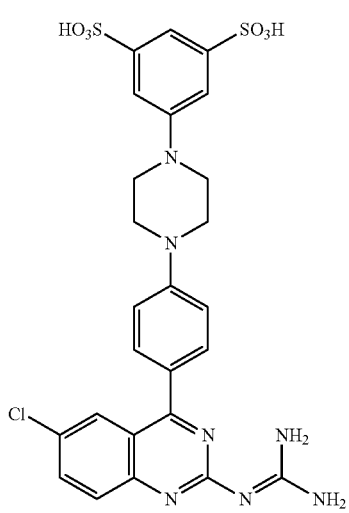
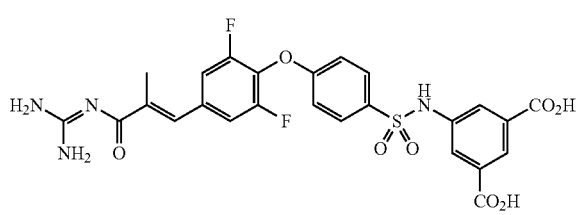
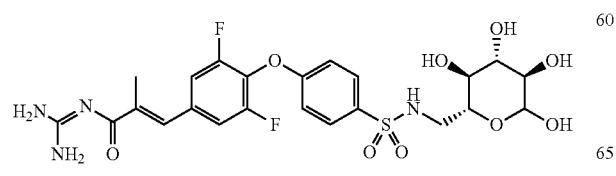
82
-continued
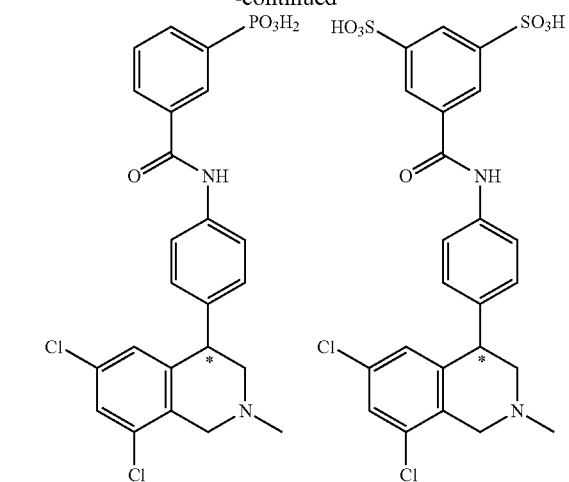
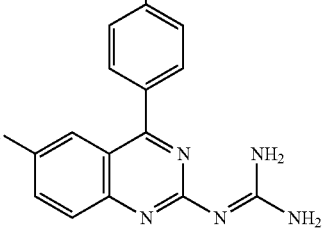
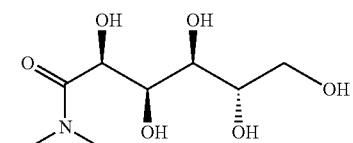
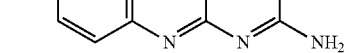

-continued

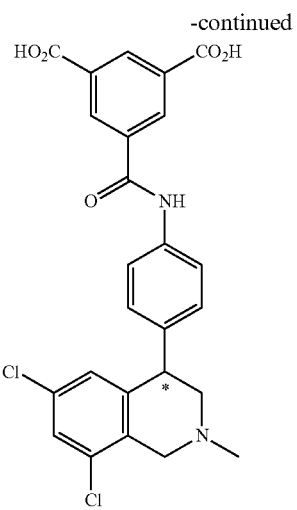

B. Preferred Embodiments

In one or more particularly preferred embodiments of the present disclosure, the "NHE-Z" molecule is polyvalent; that is, the molecule contains two or more moieties that effectively acts to inhibit NHE-mediated antiport of sodium ions and hydrogen ions. In such embodiments, the NHE-Z molecule may be selected, for example, from one of the following Formulas (IV), (V), (VI) or (VII):

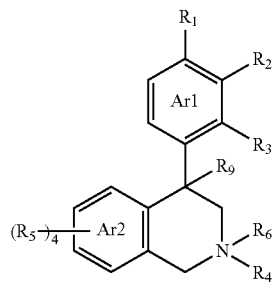

(IV)

wherein: each $R_1$, $R_2$, $R_3$, $R_5$ and $R_9$ are independently selected from H, halogen, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or L, provided at least one is L, wherein L is selected from the group consisting of substituted or unsubstituted hydrocarbyl, heterohydrocarbyl, polyalkylene glycol and polyols, and further wherein L links the repeat unit to at least one other repeat unit and/or at least one other Core moiety independently selected from substituted or unsubstituted hydrocarbyl, heterohydrocarbyl, polyalkylene glycol, polyols, polyamines, or polyacrylamides, of the polyvalent compound; $R_4$ is selected from H, $C_1$-$C_7$ alkyl or L, where L is as described above; $R_6$ is absent or selected from H and $C_1$-$C_7$ alkyl; and, Ar1 and Ar2 independently represent an aromatic ring, or alternatively a heteroaromatic ring wherein one or more of the carbon atoms therein is replaced with a N, O or S atom;

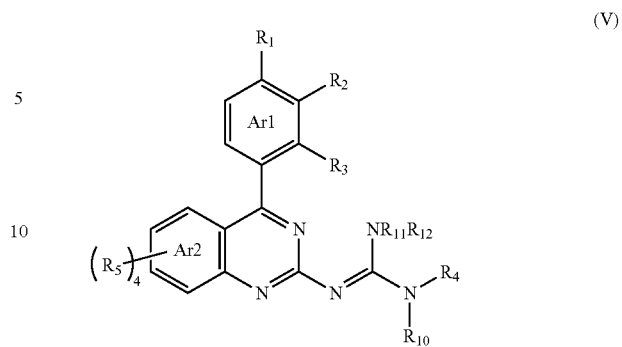

(V)

wherein: each $R_1$, $R_2$, $R_3$, and $R_5$ are optionally linked to the ring Ar1 by a heterocyclic linker, and further are independently selected from H, —$NR_7(CO)R_8$, —$(CO)NR_7R_8$, —$SO_2$—$NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or L, provided at least one is L, wherein L is selected from the group consisting of substituted or unsubstituted hydrocarbyl, heterohydrocarbyl, polyalkylene glycol and polyols, and further wherein L links the repeat unit to at least one other repeat unit and/or at least one other Core moiety independently selected from substituted or unsubstituted hydrocarbyl, heterohydrocarbyl, polyalkylene glycol, polyols, polyamines, or polyacrylamides, of the polyvalent compound; $R_4$ and $R_{12}$ are independently selected from H or L, where L is as defined above; $R_{10}$ and $R_{11}$, when presented, are independently selected from H and $C_1$-$C_7$ alkyl; and, Ar1 and Ar2 independently represent an aromatic ring, or alternatively a heteroaromatic ring wherein one or more of the carbon atoms therein is replaced with a N, O or S atom;

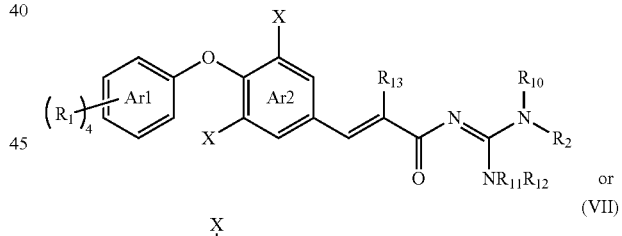

(VI)

or

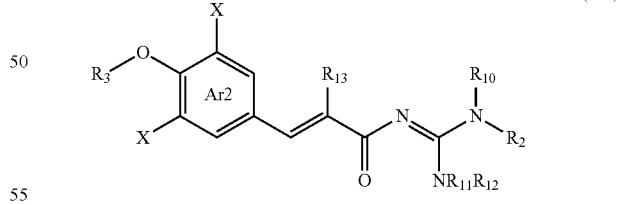

(VII)

wherein: each X is a halogen atom, which may be the same or different; $R_1$ is selected from —$SO_2$—$NR_7R_8$, —$NR_7(CO)R_8$, —$(CO)NR_7R_8$, —$NR_7SO_2R_8$, —$NR_7R_8$, —$OR_7$, —$SR_7$, —$O(CO)NR_7R_8$, —$NR_7(CO)OR_8$, and —$NR_7SO_2NR_8$, where $R_7$ and $R_8$ are independently selected from H or L, provided at least one is L, wherein L is selected from the group consisting of substituted or unsubstituted hydrocarbyl, heterohydrocarbyl, polyalkylene glycol and polyols, and further wherein L links the repeat unit to at least one other repeat unit and/or at least one other Core moiety independently selected from substituted or unsubstituted hydrocarbyl, heterohydrocarbyl, polyalkylene glycol, polyols, polyamines, or polyacrylamides, of the polyvalent compound; $R_3$ is selected from H or L, where L is as described above; $R_{13}$ is selected from substituted or unsubstituted $C_1$-$C_8$ alkyl; $R_2$ and $R_{12}$ are independently selected from H or L, wherein L is as described above; $R_{10}$ and $R_{11}$, when present, are independently selected from H and $C_1$-$C_7$ alkyl; Ar1 represents an aromatic ring, or alternatively a heteroaromatic ring wherein one or more of the carbon atoms therein is replaced with a N, O or S atom; and Ar2 represents an aromatic ring, or alternatively a heteroaromatic ring wherein one or more of the carbon atoms therein is replaced with a N, O or S atom.

In one particular embodiment for the structure of Formula (V), one of $R_1$, $R_2$ and $R_3$ is linked to the ring Ar1, and/or $R_5$ is linked to the ring Ar2, by a heterocyclic linker having the structure:

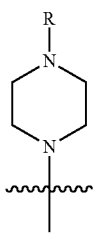

wherein R represents $R_1$, $R_2$, $R_3$, or $R_5$ bound thereto.

In one particular embodiment, the NHE-inhibiting small molecule has the structure of Formula (IV):

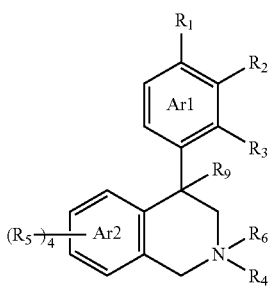

(IV)

or a stereoisomer, prodrug or pharmaceutically acceptable salt thereof, wherein: each $R_1$, $R_2$, $R_3$, $R_5$ and $R_9$ are independently selected from H, halogen, —$NR_7(CO)R_8$, —(CO)$NR_7R_8$, —$SO_2$—$NR_7R_8$, —$NR_7SO_2R_8$, —$NR_7R_8$, —$OR_7$, —$SR_7$, —O(CO)$NR_7R_8$, —$NR_7(CO)OR_8$, and —$NR_7SO_2NR_8$, where $R_7$ and $R_8$ are independently selected from H or a bond linking the NHE-inhibiting small molecule to L, provided at least one is a bond linking the NHE-inhibiting small molecule to L; $R_4$ is selected from H, $C_1$-$C_7$ alkyl, or a bond linking the NHE-inhibiting small molecule to L; $R_6$ is absent or selected from H and $C_1$-$C_7$ alkyl; and Ar1 and Ar2 independently represent an aromatic ring or a heteroaromatic ring.

In further particular embodiments of the above embodiment, the NHE-inhibiting small molecule has the following structure:

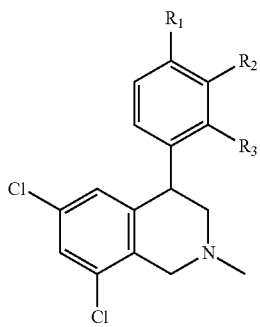

or a stereoisomer, prodrug or pharmaceutically acceptable salt thereof, wherein: each $R_1$, $R_2$ and $R_3$ are independently selected from H, halogen, —$NR_7(CO)R_8$, —(CO)$NR_7R_8$, —$SO_2$—$NR_7R_8$, —$NR_7SO_2R_8$, —$NR_7R_8$, —$OR_7$, —$SR_7$, —O(CO)$NR_7R_8$, —$NR_7(CO)OR_8$, and —$NR_7SO_2NR_8$, where $R_7$ and $R_8$ are independently selected from H or a bond linking the NHE-inhibiting small molecule to L, provided at least one is a bond linking the NHE-inhibiting small molecule to L.

In further particular embodiments of the above embodiment, the NHE-inhibiting small molecule has one of the following structures:

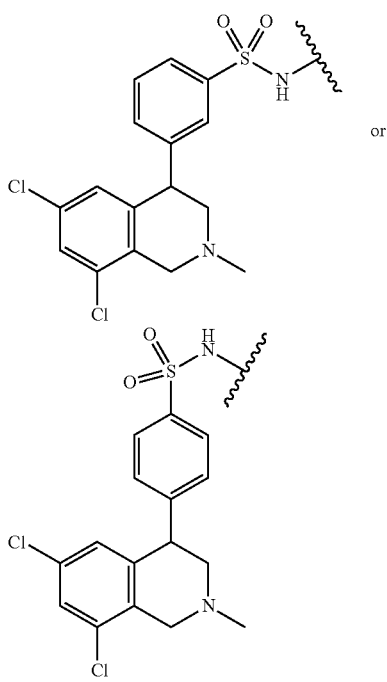

or or a stereoisomer, prodrug or pharmaceutically acceptable salt thereof.

In further particular embodiments of the above embodiment, L is a polyalkylene glycol linker, such as a polyethylene glycol linker.

In further particular embodiments of the above embodiment, n is 2.

In further particular embodiments of the above embodiment, the Core has the following structure:

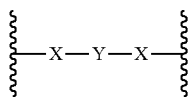

wherein: X is selected from the group consisting of a bond, —O—, —NH—, —S—, C$_{1-6}$alkylene, —NHC(=O)—, —C(=O)NH—, —NHC(=O)NH—, —SO$_2$NH—, and —NHSO$_2$—; Y is selected from the group consisting of a bond, optionally substituted C$_{1-8}$alkylene, optionally substituted aryl, optionally substituted heteroaryl, a polyethylene glycol linker, —(CH$_2$)$_{1-6}$O(CH$_2$)$_{1-6}$— and —(CH$_2$)$_{1-6}$NY$_1$(CH$_2$)$_{1-6}$—; and Y$_1$ is selected from the group consisting of hydrogen, optionally substituted C$_{1-8}$alkyl, optionally substituted aryl or optionally substituted heteroaryl.

In further particular embodiments of the above embodiment, the Core is selected from the group consisting of:

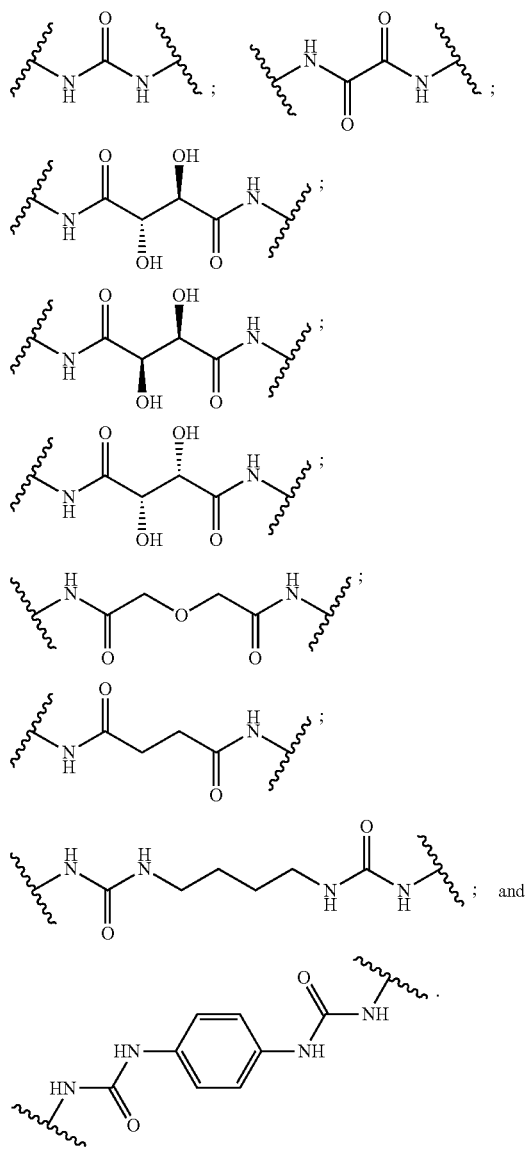

III. Terminology, Physical and Performance Properties

A. Terminology

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —NH$_2$ radical.
"Cyano" refers to the —CN radical.
"Hydroxy" or "hydroxyl" refers to the —OH radical.
"Imino" refers to the =NH substituent.
"Nitro" refers to the —NO$_2$ radical.
"Oxo" refers to the =O substituent.
"Thioxo" refers to the =S substituent.
"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms (C$_1$-C$_{12}$ alkyl), preferably one to eight carbon atoms (C$_1$-C$_8$ alkyl) or one to six carbon atoms (C$_1$-C$_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butyryl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group may be optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$-$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_b R_d$ where $R_d$ is an alkylene chain as defined above and $R_g$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_b R_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_b R_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$, —$(CH_2CH_2O)_{2-10}R_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

In accordance with the present disclosure, the compounds described herein are designed to be substantially active or localized in the gastrointestinal lumen of a human or animal subject. The term "gastrointestinal lumen" is used interchangeably herein with the term "lumen," to refer to the space or cavity within a gastrointestinal tract (GI tract, which can also be referred to as the gut), delimited by the apical membrane of GI epithelial cells of the subject. In some embodiments, the compounds are not absorbed through the layer of epithelial cells of the GI tract (also known as the GI epithelium). "Gastrointestinal mucosa" refers to the layer(s) of cells separating the gastrointestinal lumen from the rest of the body and includes gastric and intestinal mucosa, such as the mucosa of the small intestine. A "gastrointestinal epithelial cell" or a "gut epithelial cell" as used herein refers to any epithelial cell on the surface of the gastrointestinal mucosa that faces the lumen of the gastrointestinal tract, including, for example, an epithelial cell of the stomach, an intestinal epithelial cell, a colonic epithelial cell, and the like.

"Substantially systemically non-bioavailable" and/or "substantially impermeable" as used herein (as well as variations thereof) generally refer to situations in which a statistically significant amount, and in some embodiments essentially all of the compound of the present disclosure (which includes the NHE-inhibitor small molecule), remains in the gastrointestinal lumen. For example, in accordance with one or more embodiments of the present disclosure, preferably at least about 70%, about 80%, about 90%, about 95%, about 98%, about 99%, or even about 99.5%, of the compound remains in the gastrointestinal lumen. In such cases, localization to the gastrointestinal lumen refers to reducing net movement across a gastrointestinal layer of epithelial cells, for example, by way of both transcellular and paracellular transport, as well as by active and/or passive transport. The compound in such embodiments is hindered from net permeation of a layer of gastrointestinal epithelial cells in transcellular transport, for example, through an apical membrane of an epithelial cell of the small intestine. The compound in these embodiments is also hindered from net permeation through the "tight junctions" in paracellular transport between gastrointestinal epithelial cells lining the lumen.

In this regard it is to be noted that, in one particular embodiment, the compound is essentially not absorbed at all by the GI tract or gastrointestinal lumen. As used herein, the terms "substantially impermeable" or "substantially systemically non-bioavailable" refers to embodiments wherein no detectable amount of absorption or permeation or systemic exposure of the compound is detected, using means generally known in the art.

In this regard it is to be further noted, however, that in alternative embodiments "substantially impermeable" or "substantially systemically non-bioavailable" provides or allows for some limited absorption in the GI tract, and more particularly the gut epithelium, to occur (e.g., some detectable amount of absorption, such as for example at least about 0.1%, 0.5%, 1% or more and less than about 30%, 20%, 10%, 5%, etc., the range of absorption being for example between about 1% and 30%, or 5% and 20%, etc.; stated another way, "substantially impermeable" or "substantially systemically non-bioavailable" refers to compounds that exhibit some detectable permeability to an epithelium layer of cells in the GI tract of less than about 20% of the administered compound (e.g., less than about 15%, about 10%, or even about 5%, and for example greater than about 0.5%, or 1%), but then are cleared by the liver (i.e., hepatic extraction) and/or the kidney (i.e., renal excretion).

B. Permeability

In this regard it is to be noted that, in various embodiments, the ability of the compound to be substantially systemically non-bioavailable is based on the compound charge, size, and/or other physicochemical parameters (e.g., polar surface area, number of hydrogen bond donors and/or acceptors therein, number of freely rotatable bonds, etc.). More specifically, it is to be noted that the absorption character of a compound can be selected by applying principles of pharmacodynamics, for example, by applying Lipinski's rule, also known as "the rule of five." Although not a rule, but rather a set of guidelines, Lipinski shows that small molecule drugs with (i) a molecular weight, (ii) a number of hydrogen bond donors, (iii) a number of hydrogen bond acceptors, and/or (iv) a water/octanol partition coefficient (Moriguchi Log P), greater than a certain threshold value, generally do not show significant systemic concentration (i.e., are generally not absorbed to any significant degree). (See, e.g., Lipinski et al., *Advanced Drug Delivery Reviews*, 46, 2001 3-26, incorporated herein by reference.) Accordingly, substantially systemically non-bioavailable compounds (e.g., substantially systemically non-bioavailable NHE inhibitor compounds) can be designed to have molecular structures exceeding one or more of Lipinski's threshold values. (See also Lipinski et al., *Experimental and Computational Approaches to Estimate Solubility and Permeability in Drug Discovery and Development Settings*, Adv. Drug Delivery Reviews, 46:3-26 (2001); and Lipinski, *Drug-like Properties and the Causes of Poor Solubility and Poor Permeability*, J. Pharm. & Toxicol. Methods, 44:235-249 (2000), incorporated herein by reference.) In some embodiments, for example, a substantially impermeable or substantially systemically non-bioavailable NHE inhibitor compound of the present disclosure can be constructed to feature one or more of the following characteristics: (i) a MW greater than about 500 Da, about 1000 Da, about 2500 Da, about 5000 Da, about 10,000 Da or more (in the non-salt form of the compound); (ii) a total number of NH and/or OH and/or other potential hydrogen bond donors greater than about 5, about 10, about 15 or more; (iii) a total number of O atoms and/or N atoms and/or other potential hydrogen bond acceptors greater than about 5, about 10, about 15 or more; and/or (iv) a Moriguchi partition coefficient greater than about $10^5$ (i.e., Log P greater than about 5, about 6, about 7, etc.), or alternatively less than about 10 (i.e., a Log P of less than 1, or even 0).

In view of the foregoing, and as previously noted herein, essentially any known NHE inhibitor small molecule (described herein and/or in the art) can be used in designing a substantially systemically non-bioavailable NHE inhibitor molecular structure, in accordance with the present disclosure. In addition to the parameters noted above, the molecular polar surface area (i.e., "PSA"), which may be characterized as the surface belonging to polar atoms, is a descriptor that has also been shown to correlate well with passive transport through membranes and, therefore, allows prediction of transport properties of drugs. It has been successfully applied for the prediction of intestinal absorption and Caco2 cell monolayer penetration. (For Caco2 cell monolayer penetration test details, see for example the description of the Caco2 Model provided in Example 31 of U.S. Pat. No. 6,737,423, the entire contents of which are incorporated herein by reference for all relevant and consistent purposes, and the text of Example 31 in particular, which may be applied for example to the evaluation or testing of the compounds of the present disclosure.) PSA is expressed in $Å^2$ (squared angstroms) and is computed from a three-dimensional molecular representation. A fast calculation method is now available (see, e.g., Ertl et al., *Journal of Medicinal Chemistry*, 2000, 43, 3714-3717, the entire contents of which are incorporated herein by reference for all relevant and consistent purposes) using a desktop computer and commercially available chemical graphic tools packages, such as ChemDraw. The term "topological PSA" (tPSA) has been coined for this fast-calculation method. tPSA is well correlated with human absorption data with common drugs (see, e.g., Table 2, below):

TABLE 2

| name | % FA$^a$ | TPSA$^b$ |
| --- | --- | --- |
| metoprolol | 102 | 50.7 |
| nordiazepam | 99 | 41.5 |
| diazepam | 97 | 32.7 |
| oxprenolol | 97 | 50.7 |
| phenazone | 97 | 26.9 |
| oxazepam | 97 | 61.7 |
| alprenolol | 96 | 41.9 |
| practolol | 95 | 70.6 |
| pindolol | 92 | 57.3 |
| ciprofloxacin | 69 | 74.6 |
| metolazone | 64 | 92.5 |
| tranexamic acid | 55 | 63.3 |
| atenolol | 54 | 84.6 |
| sulpiride | 36 | 101.7 |
| mannitol | 26 | 121.4 |
| foscarnet | 17 | 94.8 |
| sulfasalazine | 12 | 141.3 |
| olsalazine | 2.3 | 139.8 |
| lactulose | 0.6 | 197.4 |
| raffinose | 0.3 | 268.7 |

(from Ertl et al., *J. Med. Chem.*, 2000, 43:3714-3717). Accordingly, in some preferred embodiments, the compounds of the present disclosure may be constructed to exhibit a tPSA value greater than about 100 $Å^2$, about 120 $Å^2$, about 130 $Å^2$, or about 140 $Å^2$, and in some instances about 150 $Å^2$, about 200 $Å^2$, about 250 $Å^2$, about 270 $Å^2$, about 300 $Å^2$, about 400 $Å^2$, or even about 500 $Å^2$, such that the compounds are substantially impermeable or substantially systemically non-bioavailable (as defined elsewhere herein).

Because there are exceptions to Lipinski's "rule," or the tPSA model, the permeability properties of the compounds of the present disclosure may be screened experimentally. The permeability coefficient can be determined by methods known to those of skill in the art, including for example by Caco-2 cell permeability assay and/or using an artificial membrane as a model of a gastrointestinal epithelial cell. (As previously noted above, see for example U.S. Pat. No. 6,737,423, Example 31 for a description of the Caco-2 Model, which is incorporated herein by reference). A synthetic membrane impregnated with, for example, lecithin and/or dodecane to mimic the net permeability characteristics of a gastrointestinal mucosa, may be utilized as a model of a gastrointestinal mucosa. The membrane can be used to separate a compartment containing the compound of the present disclosure from a compartment where the rate of permeation will be monitored. Also, parallel artificial membrane permeability assays (PAMPA) can be performed. Such in vitro measurements can reasonably indicate actual permeability in vivo. (See, for example, Wohnsland et al., *J. Med. Chem.*, 2001, 44:923-930; Schmidt et al., Millipore Corp. Application Note, 2002, n° AN1725EN00, and n° AN1728EN00, incorporated herein by reference.) Accordingly, in some embodiments, the compounds utilized in the methods of the present disclosure may have a permeability coefficient, $P_{app}$, of less than about $100 \times 10^{-6}$ cm/s, or less than about $10 \times 10^{-6}$ cm/s, or less than about $1 \times 10^{-6}$ cm/s, or less than about $0.1 \times 10^{-6}$ cm/s, when measured using means known in the art (such as for example the permeability experiment described in Wohnsland et al., *J. Med. Chem.*, 2001, 44. 923-930, the contents of which is incorporated herein by reference).

As previously noted, in accordance with the present disclosure, NHE inhibitor small molecules are modified as described above to hinder the net absorption through a layer of gut epithelial cells, rendering them substantially systemically non-bioavailable. In some particular embodiments, the compounds of the present disclosure comprise an NHE-inhibiting small molecule linked, coupled or otherwise attached to a moiety Z, which may be an oligomer moiety, a polymer moiety, a hydrophobic moiety, a hydrophilic moiety, and/or a charged moiety, which renders the overall compound substantially impermeable or substantially systemically non-bioavailable. In some preferred embodiments, the NHE-inhibiting small molecule is coupled to a multimer or polymer portion or moiety, such that the resulting NHE-Z molecule is substantially impermeable or substantially systemically non-bioavailable. The multimer or polymer portion or moiety may be of a molecular weight greater than about 500 Daltons (Da), about 1000 Da, about 2500 Da, about 5000 Da, about 10,000 Da or more, and in particular may have a molecular weight in the range of about 1000 Daltons (Da) to about 500,000 Da, preferably in the range of about 5000 to about 200,000 Da, and more preferably may have a molecular weight that is sufficiently high to essentially preclude any net absorption through a layer of gut epithelial cells of the compound. For example, an NHE-inhibiting small molecule may be linked to at least one repeat unit of a polymer portion or moiety according, for example, to the structure of Formula (XIIA) or Formula (XIIB), as illustrated herein. In these or other particular embodiments, the NHE-inhibiting small molecule is modified as described herein to substantially hinder its net absorption through a layer of gut epithelial cells and may comprise, for example, a NHE-inhibiting compound linked, coupled or otherwise attached to a substantially impermeable or substantially systemically non-bioavailable "Core" moiety, as described above.

C. Persistent Inhibitory Effect

In other embodiments, the substantially impermeable or substantially systemically non-bioavailable NHE-inhibiting compounds utilized in the treatment methods of the present disclosure may additionally exhibit a persistent inhibitor effect. This effect manifests itself when the inhibitory action of a compound at a certain concentration in equilibrium with the epithelial cell (e.g., at or above its inhibitory concentration, IC) does not revert to baseline (i.e., sodium transport without inhibitor) after the compound is depleted by simple washing of the luminal content.

This effect can be interpreted as a result of the tight binding of the NHE-inhibiting compounds to the NHE protein at the intestinal apical side of the gut epithelial cell. The binding can be considered as quasi-irreversible to the extent that, after the compound has been contacted with the gut epithelial cell and subsequently washed off said gut epithelial cell, the flux of sodium transport is still significantly lower than in the control without the compound. This persistent inhibitory effect has the clear advantage of maintaining drug activity within the GI tract even though the residence time of the active in the upper GI tract is short, and when no entero-biliary recycling process is effective to replenish the compound concentration near its site of action.

Such a persistent inhibitory effect has an obvious advantage in terms of patient compliance, but also in limiting drug exposure within the GI tract.

The persistence effect can be determined using in vitro methods; in one instance, cell lines expressing NHE transporters are split in different vials and treated with a NHE-inhibiting compound and sodium solution to measure the rate of sodium uptake. The cells in one set of vials are washed for different periods of time to remove the inhibitor, and sodium uptake measurement is repeated after the washing. Compounds that maintain their inhibitory effect after multiple/lengthy washing steps (compared to the inhibitory effect measured in the vials where washing does not occur) are persistent inhibitors. Persistence effect can also be characterized ex vivo by using the everted sac technique, whereby transport of Na is monitored using an excised segment of GI perfused with a solution containing the inhibitor and shortly after flushing the bathing solution with a buffer solution free from inhibitor. A persistence effect can also be characterized in vivo by observing the time needed for sodium balance to return to normal when the inhibitor treatment is discontinued. The limit of the method resides in the fact that apical cells (and therefore apical NHE transporters) are sloughed off after a period of 3 to 4 days, the typical turnover time of gut epithelial cells. A persistence effect can be achieved by increasing the residence time of the active compound at the apical surface of the gut epithelial cells; this can be obtained by designing NHE antiport inhibitors with several NHE inhibiting moieties built-in the small molecule or oligomer (wherein "several" as used herein typically means at least about 2, about 4, about 6 or more). Examples of such structures in the context of analogs of the antibiotic vancomycin are given in Griffin, et al., *J. Am. Chem. Soc.*, 2003, 125, 6517-6531. Alternatively the compound comprises groups that contribute to increase the affinity towards the gut epithelial cell so as to increase the time of contact with the gut epithelial cell surface. Such groups are referred to as being "mucoadhesive." More specifically, the Core or L moiety can be substituted by such mucoadhesive groups, such as polyacrylates, partially deacetylated chitosan or polyalkylene glycol. (See also Patil, S. B. et al., *Curr. Drug. Deliv.*, 2008, Oct. 5(4), pp. 312-8.)

D. GI Enzyme Resistance

Because the compounds utilized in the treatment methods of the present disclosure are preferably substantially systemically non-bioavailable, and/or preferably exhibit a persistent inhibitory effect, it is also desirable that, during their prolonged residence time in the gut, these compounds sustain the hydrolytic conditions prevailing in the upper GI tract. In such embodiments, compounds of the present disclosure are resistant to enzymatic metabolism. For example, administered compounds are preferably resistant to the activity of P450 enzymes, glucurosyl transferases, sulfotransferases, glutathione S-transferases, and the like, in the intestinal mucosa, as well as gastric (e.g., gastric lipase, and pepsine), pancreatic (e.g., trypsin, triglyceride pancreatic lipase, phospholipase A2, endonucleases, nucleotidases, and alpha-amylase), and brush-border enzymes (e.g., alkaline phosphatase, glycosidases, and proteases) generally known in the art.

The compounds that are utilized in methods of the present disclosure are also preferably resistant to metabolism by the bacterial flora of the gut; that is, the compounds are not substrates for enzymes produced by bacterial flora. In addition, the compounds administered in accordance with the methods of the present disclosure may be substantially inactive towards the gastrointestinal flora, and do not disrupt bacterial growth or survival. As a result, in various embodiments herein, the minimal inhibitory concentration (or "MIC") against GI flora is desirably greater than about 15 µg/ml, about 30 µg/ml, about 60 µg/ml, about 120 µg/ml, or even about 240 µg/ml, the MIC in various embodiments being for example between about 16 and about 32 µg/ml, or between about 64 and about 128 µg/ml, or greater than about 256 µg/ml.

To one skilled in the art of medicinal chemistry, metabolic stability can be achieved in a number of ways. Functionality susceptible to P450-mediated oxidation can be protected by, for example, blocking the point of metabolism with a halogen or other functional group. Alternatively, electron withdrawing groups can be added to a conjugated system to generally provide protection to oxidation by reducing the electrophilicity of the compound. Proteolytic stability can be achieved by avoiding secondary amide bonds, or by incorporating changes in stereochemistry or other modifications that prevent the drug from otherwise being recognized as a substrate by the metabolizing enzyme.

E. Sodium and/or Fluid Output

It is also to be noted that, in various embodiments of the present disclosure, one or more of the NHE-Z inhibiting compounds (monovalent or divalent) detailed herein, when administered either alone or in combination with one or more additional pharmaceutically active compounds or agents (including, for example, a fluid-absorbing polymer) to a patient in need thereof, may act to increase the patient's daily fecal output of sodium by at least about 20, about 30 mmol, about 40 mmol, about 50 mmol, about 60 mmol, about 70 mmol, about 80 mmol, about 90 mmol, about 100 mmol, about 125 mmol, about 150 mmol or more, the increase being for example within the range of from about 20 to about 150 mmol/day, or from about 25 to about 100 mmol/day, or from about 30 to about 60 mmol/day Additionally, or alternatively, it is also to be noted that, in various embodiments of the present disclosure, one or more of the NHE-Z inhibiting compounds (monovalent or divalent) detailed herein, when administered either alone or in combination with one or more additional pharmaceutically active compounds or agents (including, for example, a fluid-absorbing polymer) to a patent in need thereof, may act to increase the patient's daily fluid output by at least about 100 ml, about 200 ml, about 300 ml, about 400 ml, about 500 ml, about 600 ml, about 700 ml, about 800 ml, about 900 ml, about 1000 ml or more, the increase being for example within the range of from about 100 to about 1000 ml/day, or from about 150 to about 750 ml/day, or from about 200 to about 500 ml/day (assuming isotonic fluid).

F. $C_{max}$ and $IC_{50}$

It is also to be noted that, in various embodiments of the present disclosure, one or more of the NHE-Z inhibiting compounds (monovalent or divalent) detailed herein, when administered either alone or in combination with one or more additional pharmaceutically active compounds or agents (including, for example, a fluid-absorbing polymer) to a patient in need thereof at a dose resulting in at least a 10% increase in fecal water content, has a $C_{max}$ that is less than the $IC_{50}$ for NHE-3, more specifically, less than about 10× (10 times) the $IC_{50}$, and, more specifically still, less than about 100× (100 times) the $IC_{50}$.

Additionally, or alternatively, it is also to be noted that, in various embodiments of the present disclosure, one or more of the NHE-Z inhibiting compounds (monovalent or divalent) detailed herein, when administered either alone or in combination with one or more additional pharmaceutically active compounds or agents (including, for example, a fluid-absorbing polymer) to a patient in need thereof, may have a $C_{max}$ of less than about 10 ng/ml, about 7.5 ng/ml, about 5 ng/ml, about 2.5 ng/ml, about 1 ng/ml, or about 0.5 ng/ml, the $C_{max}$ being for example within the range of about 1 ng/ml to about 10 ng/ml, or about 2.5 ng/ml to about 7.5 ng/ml.

Additionally, or alternatively, it is also to be noted that, in various embodiments of the present disclosure, one or more of the NHE-Z inhibiting compounds (monovalent or divalent) detailed herein, when administered either alone or in combination with one or more additional pharmaceutically active compounds or agents (including, for example, a fluid-absorbing polymer) to a patient in need thereof, may have a $IC_{50}$ of less than about 10 µM, about 7.5 µM, about 5 µM, about 2.5 µM, about 1 µM, or about 0.5 µM, the $IC_{50}$ being for example within the range of about 1 µM to about 10 µM, or about 2.5 µM to about 7.5 µM.

Additionally, or alternatively, it is also to be noted that, in various embodiments of the present disclosure, one or more of the NHE-Z inhibiting compounds (monovalent or divalent) detailed herein, when administered to a patient in need thereof, may have a ratio of $IC_{50}:C_{max}$, wherein $IC_{50}$ and $C_{max}$ are expressed in terms of the same units, of at least about 10, about 50, about 100, about 250, about 500, about 750, or about 1000.

Additionally, or alternatively, it is also to be noted that, in various embodiments of the present disclosure, wherein one or more of the NHE-Z inhibiting compounds (monovalent or divalent) as detailed herein is orally administered to a patent in need thereof, within the therapeutic range or concentration, the maximum compound concentration detected in the serum, defined as $C_{max}$, is lower than the NHE inhibitory concentration $IC_{50}$ of said compound. As previously noted, as used herein, $IC_{50}$ is defined as the quantitative measure indicating the concentration of the compound required to inhibit 50% of the NHE-mediated Na/H antiport activity in a cell based assay.

IV. Pharmaceutical Compositions and Methods of Treatment

A. Compositions and Methods

1. Fluid Retention and/or Salt Overload Disorders

A pharmaceutical composition or preparation that may be used in accordance with the present disclosure for the treatment of various disorders associated with fluid retention and/or salt overload in the gastrointestinal tract (e.g., hypertension, heart failure (in particular, congestive heart failure), chronic kidney disease, end-stage renal disease, liver disease and/or peroxisome proliferator-activated receptor (PPAR) gamma agonist-induced fluid retention) comprises, in general, the substantially impermeable or substantially systemically non-bioavailable NHE-inhibiting compound of the present disclosure, as well as various other optional components as further detailed herein below (e.g., pharmaceutically acceptable excipients, etc.). The compounds utilized in the treatment methods of the present disclosure, as well as the pharmaceutical compositions comprising them, may accordingly be administered alone, or as part of a treatment protocol or regiment that includes the administration or use of other beneficial compounds (as further detailed elsewhere herein). In some particular embodiments, the NHE-inhibiting compound, including any pharmaceutical composition comprising the compound, is administered with a fluid-absorbing polymer (as more fully described below).

A "subject" or "mammal" is preferably a human, but can also be an animal in need of treatment with a compound of the disclosure, e.g., companion animals (e.g., dogs, cats, and the like), farm animals (e.g., cows, pigs, horses and the like) and laboratory animals (e.g., rats, mice, guinea pigs and the like).

Subjects "in need of treatment" with a compound of the present disclosure, or subjects "in need of NHE inhibition" include subjects with diseases and/or conditions that can be treated with substantially impermeable or substantially systemically non-bioavailable NHE-inhibiting compounds, with or without a fluid-absorbing polymer, to achieve a beneficial therapeutic and/or prophylactic result. A beneficial outcome includes a decrease in the severity of symptoms or delay in the onset of symptoms, increased longevity and/or more rapid or more complete resolution of the disease or condition. For example, a subject in need of treatment may be suffering from hypertension; from salt-sensitive hypertension which may result from dietary salt intake; from a risk of a cardiovascular disorder (e.g., myocardial infarction, congestive heart failure and the like) resulting from hypertension; from heart failure (e.g., congestive heart failure) resulting in fluid or salt overload; from chronic kidney disease resulting in fluid or salt overload, from end stage renal disease resulting in fluid or salt overload; from liver disease resulting in fluid or salt overload; from peroxisome proliferator-activated receptor (PPAR) gamma agonist-induced fluid retention; or from edema resulting from congestive heart failure or end stage renal disease. In various embodiments, a subject in need of treatment typically shows signs of hypervolemia resulting from salt and fluid retention that are common features of congestive heart failure, renal failure or liver cirrhosis. Fluid retention and salt retention manifest themselves by the occurrence of shortness of breath, edema, ascites or interdialytic weight gain. Other examples of subjects that would benefit from the treatment are those suffering from congestive heart failure and hypertensive patients and, particularly, those who are resistant to treatment with diuretics, i.e., patients for whom very few therapeutic options are available. A subject "in need of treatment" also includes a subject with hypertension, salt-sensitive blood pressure and subjects with systolic/diastolic blood pressure greater than about 130-139/85-89 mm Hg.

Administration of NHE inhibitors, with or without administration of fluid-absorbing polymers, may be beneficial for patients put on "non-added salt" dietary regimen (i.e., 60-100 mmol of Na per day), to liberalize their diet while keeping a neutral or slightly negative sodium balance (i.e., the overall uptake of salt would be equal of less than the secreted salt). In that context, "liberalize their diet" means that patients treated may add salt to their meals to make the meals more palatable, or/and diversify their diet with salt-containing foods, thus maintaining a good nutritional status while improving their quality of life.

The treatment methods described herein may also help patients with edema associated with chemotherapy, pre-menstrual fluid overload and preeclampsia (pregnancy-induced hypertension).

Accordingly, it is to be noted that the present disclosure is further directed to methods of treatment involving the administration of the compound of the present disclosure, or a pharmaceutical composition comprising such a compound. Such methods may include, for example, a method for treating hypertension, the method comprising administering to the patient a substantially impermeable or substantially systemically non-bioavailable NHE-inhibiting compound, or a composition comprising it. The method may be for reducing fluid overload associated with heart failure (in particular, congestive heart failure), the method comprising administering to the patient a substantially impermeable or substantially systemically non-bioavailable NHE-inhibiting compound or pharmaceutical composition comprising it. The method may be for reducing fluid overload associated with end stage renal disease, the method comprising administering to the patient a substantially impermeable or substantially systemically non-bioavailable NHE-inhibiting compound or composition comprising it. The method may be for reducing fluid overload associated with peroxisome proliferator-activated receptor (PPAR) gamma agonist therapy, the method comprising administering to the patient a substantially impermeable or substantially systemically non-bioavailable NHE-inhibiting compound or composition comprising it. Additionally, or alternatively, the method may be for decreasing the activity of an intestinal NHE transporter in a patient, the method comprising: administering to the patient a substantially impermeable or substantially systemically non-bioavailable NHE-inhibiting compound, or a composition comprising it.

2. Gastrointestinal Tract Disorders

A pharmaceutical composition or preparation that may be used in accordance with the present disclosure for the treatment of various gastrointestinal tract disorders, including the treatment or reduction of pain associated with gastrointestinal tract disorders, comprises, in general, any small molecule, which may be monovalent or polyvalent, that is effective or active as an NHE-inhibitor and that is substantially active in the GI tract, in particular, the substantially impermeable or substantially systemically non-bioavailable NHE-inhibiting compound of the present disclosure, as well as various other optional components as further detailed herein below (e.g., pharmaceutically acceptable excipients, etc.). The compounds utilized in the treatment methods of the present disclosure, as well as the pharmaceutical compositions comprising them, may accordingly be administered alone, or as part of a treatment protocol or regiment that includes the administration or use of other beneficial compounds (as further detailed elsewhere herein). In some particular embodiments, the NHE-inhibiting compound, including any pharmaceutical composition comprising the compound, is administered with a fluid-absorbing polymer (as more fully described below).

A "subject" is preferably a human, but can also be an animal in need of treatment with a compound of the disclosure, e.g., companion animals (e.g., dogs, cats, and the like), farm animals (e.g., cows, pigs, horses and the like) and laboratory animals (e.g., rats, mice, guinea pigs and the like).

Subjects "in need of treatment" with a compound of the present disclosure, or subjects "in need of NHE inhibition" include subjects with diseases and/or conditions that can be treated with substantially impermeable or substantially systemically non-bioavailable NHE-inhibiting compounds, with or without a fluid-absorbing polymer, to achieve a beneficial therapeutic and/or prophylactic result. A beneficial outcome includes a decrease in the severity of symptoms or delay in the onset of symptoms, increased longevity and/or more rapid or more complete resolution of the disease or condition. For example, a subject in need of treatment is suffering from a gastrointestinal tract disorder; the patient is suffering from a disorder selected from the group consisting of: a gastrointestinal motility disorder, irritable bowel syndrome, chronic constipation, chronic idiopathic constipation, chronic constipation occurring in cystic fibrosis patients, chronic constipation occurring in chronic kidney disease patients, calcium-induced constipation in osteoporotic patients, opioid-induced constipation, a functional gastrointestinal tract disorder, gastroesophageal reflux disease, functional heartburn, dyspepsia, functional dyspepsia, non-ulcer dyspepsia, gastroparesis, chronic intestinal pseudo-obstruction, Crohn's disease, ulcerative colitis and related diseases referred to as inflammatory bowel syndrome, colonic pseudo-obstruction, and the like.

In various preferred embodiments, the constipation to be treated is: associated with the use of a therapeutic agent; associated with a neuropathic disorder; post-surgical constipation (postoperative ileus); associated with a gastrointestinal tract disorder; idiopathic (functional constipation or slow transit constipation); associated with neuropathic, metabolic or endocrine disorder (e.g., diabetes mellitus, renal failure, hypothyroidism, hyperthyroidism, hypocalcaemia, Multiple Sclerosis, Parkinson's disease, spinal cord lesions, neurofibromatosis, autonomic neuropathy, Chagas disease, Hirschsprung's disease or cystic fibrosis, and the like). Constipation may also be the result of surgery (postoperative ileus) or due the use of drugs such as analgesics (e.g., opioids), antihypertensives, anticonvulsants, antidepressants, antispasmodics and antipsychotics.

Accordingly, it is to be noted that the present disclosure is further directed to methods of treatment involving the administration of the compound of the present disclosure, or a pharmaceutical composition comprising such a compound. Such methods may include, for example, a method for increasing gastrointestinal motility in a patient, the method comprising administering to the patient a substantially non-permeable or substantially non-bioavailable NHE-inhibiting compound, or a composition comprising it. Additionally, or alternatively, the method may be for decreasing the activity of an intestinal NHE transporter in a patient, the method comprising: administering to the patient a substantially non-permeable or substantially non-bioavailable NHE-inhibiting compound, or a composition comprising it. Additionally, or alternatively, the method may be for treating a gastrointestinal tract disorder, a gastrointestinal motility disorder, irritable bowel syndrome, chronic calcium-induced constipation in osteoporotic patients, chronic constipation occurring in cystic fibrosis patients, chronic constipation occurring in chronic kidney disease patients, a functional gastrointestinal tract disorder, gastroesophageal reflux disease, functional heartburn, dyspepsia, functional dyspepsia, non-ulcer dyspepsia, gastroparesis, chronic intestinal pseudo-obstruction, colonic pseudo-obstruction, Crohn's disease, ulcerative colitis, inflammatory bowel disease, the method comprising administering an antagonist of the intestinal NHE, and more specifically a substantially non-permeable or substantially non-bioavailable NHE-inhibiting compound, or composition, either orally or by rectal suppository. Additionally, or alternatively, the method may be for treating or reducing pain, including visceral pain, pain associated with a gastrointestinal tract disorder or pain associated with some other disorder, the method comprising administering to a patient a substantially non-permeable or substantially non-bioavailable NHE-inhibiting compound, or composition. Additionally, or alternatively, the method may be for treating inflammation, including inflammation of the gastrointestinal tract, e.g., inflammation associated with a gastrointestinal tract disorder or infection or some other disorder, the method comprising administering to a patient a substantially non-permeable or substantially non-bioavailable NHE-inhibiting compound, or composition.

B. Combination Therapies

1. Fluid Retention and/or Salt Overload Disorders

As previously noted, the compounds described herein can be used alone or in combination with other agents. For example, the compounds can be administered together with a diuretic (i.e., High Ceiling Loop Diuretics, Benzothiadiazide Diuretics, Potassium Sparing Diuretics, Osmotic Diuretics), cardiac glycoside, ACE inhibitor, angiotensin-2 receptor antagonist, calcium channel blocker, beta blocker, alpha blocker, central alpha agonist, vasodilator, blood thinner, anti-platelet agent, lipid-lowering agent, peroxisome proliferator-activated receptor (PPAR) gamma agonist agent or compound or with a fluid-absorbing polymer as more fully described below. The agent can be covalently attached to a compound described herein or it can be a separate agent that is administered together with or sequentially with a compound described herein in a combination therapy.

Combination therapy can be achieved by administering two or more agents, e.g., a substantially non-permeable or substantially systemically non-bioavailable NHE-inhibiting compound described herein and a diuretic, cardiac glycoside, ACE inhibitor, angiotensin-2 receptor antagonist, calcium channel blocker, beta blocker, alpha blocker, central alpha agonist, vasodilator, blood thinner, anti-platelet agent or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc. The compounds described herein can be used in combination therapy with a diuretic. Among the useful analgesic agents are, for example: High Ceiling Loop Diuretics [Furosemide (Lasix), Ethacrynic Acid (Edecrin), Bumetanide (Bumex)], Benzothiadiazide Diuretics [Hydrochlorothiazide (Hydrodiuril), Chlorothiazide (Diuril), Clorthalidone (Hygroton), Benzthiazide (Aguapres), Bendroflumethiazide (Naturetin), Methyclothiazide (Aguatensen), Polythiazide (Renese), Indapamide (Lozol), Cyclothiazide (Anhydron), Hydroflumethiazide (Diucardin), Metolazone (Diulo), Quinethazone (Hydromox), Trichlormethiazide (Naqua)], Potassium Sparing Diuretics [Spironolactone (Aldactone), Triamterene (Dyrenium), Amiloride (Midamor)], and Osmotic Diuretics [Mannitol (Osmitrol)]. Diuretic agents in the various classes are known and described in the literature.

Cardiac glycosides (cardenolides) or other digitalis preparations can be administered with the compounds of the disclosure in co-therapy. Among the useful cardiac glycosides are, for example: Digitoxin (Crystodigin), Digoxin (Lanoxin) or Deslanoside (Cedilanid-D). Cardiac glycosides in the various classes are described in the literature.

Angiotensin Converting Enzyme Inhibitors (ACE Inhibitors) can be administered with the compounds of the disclosure in co-therapy. Among the useful ACE inhibitors are, for example: Captopril (Capoten), Enalapril (Vasotec), Lisinopril (Prinivil). ACE inhibitors in the various classes are described in the literature. Angiotensin-2 Receptor Antagonists (also referred to as $AT_1$-antagonists or angiotensin receptor blockers, or ARB's) can be administered with the compounds of the disclosure in co-therapy. Among the useful Angiotensin-2 Receptor Antagonists are, for example: Candesartan (Atacand), Eprosartan (Teveten), Irbesartan (Avapro), Losartan (Cozaar), Telmisartan (Micardis), Valsartan (Diovan). Angiotensin-2 Receptor Antagonists in the various classes are described in the literature.

Calcium channel blockers such as Amlodipine (Norvasc, Lotrel), Bepridil (Vascor), Diltiazem (Cardizem, Tiazac), Felodipine (Plendil), Nifedipine (Adalat, Procardia), Nimodipine (Nimotop), Nisoldipine (Sular), Verapamil (Calan, Isoptin, Verelan) and related compounds described in, for example, EP 625162B1, U.S. Pat. No. 5,364,842, U.S. Pat. No. 5,587,454, U.S. Pat. No. 5,824,645, U.S. Pat. No. 5,859,186, U.S. Pat. No. 5,994,305, U.S. Pat. No. 6,087,091, U.S. Pat. No. 6,136,786, WO 93/13128 A1, EP 1336409 A1, EP 835126 A1, EP 835126 B1, U.S. Pat. No. 5,795,864, U.S. Pat. No. 5,891,849, U.S. Pat. No. 6,054,429, WO 97/01351 A1, the entire contents of which are incorporated herein by reference for all relevant and consistent purposes, can be used with the compounds of the disclosure.

Beta blockers can be administered with the compounds of the disclosure in co-therapy. Among the useful beta blockers are, for example: Acebutolol (Sectral), Atenolol (Tenormin), Betaxolol (Kerlone), Bisoprolol/hydrochlorothiazide (Ziac), Bisoprolol (Zebeta), Carteolol (Cartrol), Metoprolol (Lopressor, Toprol XL), Nadolol (Corgard), Propranolol (Inderal), Sotalol (Betapace), Timolol (Blocadren). Beta blockers in the various classes are described in the literature.

PPAR gamma agonists such as thiazolidinediones (also called glitazones) can be administered with the compounds of the disclosure in co-therapy. Among the useful PPAR agonists are, for example: rosiglitazone (Avandia), pioglitazone (Actos) and rivoglitazone.

Aldosterone antagonists can be administered with the compounds of the disclosure in co-therapy. Among the useful Aldosterone antagonists are, for example: eplerenone, spironolactone, and canrenone.

Alpha blockers can be administered with the compounds of the disclosure in co-therapy. Among the useful Alpha blockers are, for example: Doxazosin mesylate (Cardura), Prazosin hydrochloride (Minipress). Prazosin and polythiazide (Minizide), Terazosin hydrochloride (Hytrin). Alpha blockers in the various classes are described in the literature.

Central alpha agonists can be administered with the compounds of the disclosure in co-therapy. Among the useful Central alpha agonists are, for example: Clonidine hydrochloride (Catapres), Clonidine hydrochloride and chlorthalidone (Clorpres, Combipres), Guanabenz Acetate (Wytensin), Guanfacine hydrochloride (Tenex), Methyldopa (Aldomet), Methyldopa and chlorothiazide (Aldochlor), Methyldopa and hydrochlorothiazide (Aldoril). Central alpha agonists in the various classes are described in the literature.

Vasodilators can be administered with the compounds of the disclosure in co-therapy. Among the useful vasodilators are, for example: Isosorbide dinitrate (Isordil), Nesiritide (Natrecor), Hydralazine (Apresoline), Nitrates/nitroglycerin, Minoxidil (Loniten). Vasodilators in the various classes are described in the literature. Blood thinners can be administered with the compounds of the disclosure in co-therapy. Among the useful blood thinners are, for example: Warfarin (Coumadin) and Heparin. Blood thinners in the various classes are described in the literature.

Anti-platelet agents can be administered with the compounds of the disclosure in co-therapy. Among the useful anti-platelet agents are, for example: Cyclooxygenase inhibitors (Aspirin), Adenosine diphosphate (ADP) receptor inhibitors [Clopidogrel (Plavix), Ticlopidine (Ticlid)], Phosphodiesterase inhibitors [Cilostazol (Pletal)], Glycoprotein IIB/IIIA inhibitors [Abciximab (ReoPro), Eptifibatide (Integrilin), Tirofiban (Aggrastat), Defibrotide], Adenosine reuptake inhibitors [Dipyridamole (Persantine)]. Anti-platelet agents in the various classes are described in the literature. Lipid-lowering agents can be administered with the compounds of the disclosure in co-therapy. Among the useful lipid-lowering agents are, for example: Statins (HMG CoA reductase inhibitors), [Atorvastatin (Lipitor), Fluvastatin (Lescol), Lovastatin (Mevacor, Altoprev), Pravastatin (Pravachol), Rosuvastatin Calcium (Crestor), Simvastatin (Zocor)], Selective cholesterol absorption inhibitors [ezetimibe (Zetia)], Resins (bile acid sequestrant or bile acid-binding drugs) [Cholestyramine (Questran, Questran Light, Prevalite, Locholest, Locholest Light), Colestipol (Colestid), Colesevelam Hcl (WelChol)], Fibrates (Fibric acid derivatives) [Gemfibrozil (Lopid), Fenofibrate (Antara, Lofibra, Tricor, and Triglide), Clofibrate (Atromid-S)], Niacin (Nicotinic acid). Lipid-lowering agents in the various classes are described in the literature.

The compounds of the disclosure can be used in combination with peptides or peptide analogs that activate the Guanylate Cyclase-receptor in the intestine and results in elevation of the intracellular second messenger, or cyclic guanosine monophosphate (cGMP), with increased chloride and bicarbonate secretion into the intestinal lumen and concomitant fluid secretion. Example of such peptides are Linaclotide (MD-1100 Acetate), endogenous hormones guanylin and uroguanylin and enteric bacterial peptides of the heat stable enterotoxin family (ST peptides) and those described in U.S. Pat. No. 5,140,102, U.S. Pat. No. 5,489,670, U.S. Pat. No. 5,969,097, WO 2006/001931A2, WO 2008/002971A2, WO 2008/106429A2, US 2008/0227685A1 and U.S. Pat. No. 7,041,786, the entire contents of which are incorporated herein by reference for all relevant and consistent purposes.

The compounds of the disclosure can be used in combination with type-2 chloride channel agonists, such as Amitiza (Lubiprostone) and other related compounds described in U.S. Pat. No. 6,414,016, the entire contents of which are incorporated herein by reference for all relevant and consistent purposes.

The compounds of the disclosure can be used in combination with P2Y2 receptor agonists, such as those described in EP 1196396B1 and U.S. Pat. No. 6,624,150, the entire contents of which are incorporated herein by reference for all relevant and consistent purposes.

Other agents include natriuretic peptides such as nesiritide, a recombinant form of brain-natriuretic peptide (BNP) and an atrial-natriuretic peptide (ANP). Vasopressin receptor antagonists such as tolvaptan and conivaptan may be co-administered as well as phosphate binders such as renagel, renleva, phoslo and fosrenol. Other agents include phosphate transport inhibitors (as described in U.S. Pat. Nos. 4,806,532; 6,355,823; 6,787,528; 7,119,120; 7,109,184; U.S. Pat. Pub. No. 2007/021509; 2006/0280719; 2006/0217426; International Pat. Pubs. WO 2001/005398, WO 2001/087294, WO 2001/082924, WO 2002/028353, WO 2003/048134, WO 2003/057225, WO2003/080630, WO 2004/085448, WO 2004/085382; European Pat. Nos. 1465638 and 1485391; and JP Patent No. 2007131532, or phosphate transport antagonists such as Nicotinamide.

2. Gastrointestinal Tract Disorders

As previously noted, the compounds described herein can be used alone or in combination with other agents. For example, the compounds can be administered together with an analgesic peptide or compound. The analgesic peptide or compound can be covalently attached to a compound described herein or it can be a separate agent that is administered together with or sequentially with a compound described herein in a combination therapy.

Combination therapy can be achieved by administering two or more agents, e.g., a substantially non-permeable or substantially non-bioavailable NHE-inhibiting compound described herein and an analgesic peptide or compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

The compounds described herein can be used in combination therapy with an analgesic agent, e.g., an analgesic compound or an analgesic peptide. The analgesic agent can optionally be covalently attached to a compound described herein. Among the useful analgesic agents are, for example: Ca channel blockers, 5HT3 agonists (e.g., MCK-733), 5HT4 agonists (e.g., tegaserod, prucalopride), and 5HT1 receptor antagonists, opioid receptor agonists (loperamide, fedotozine, and fentanyl), NK1 receptor antagonists, CCK receptor agonists (e.g., loxiglumide), NK1 receptor antagonists, NK3 receptor antagonists, norepinephrine-serotonin reuptake inhibitors (NSR1), vanilloid and cannabanoid receptor agonists, and sialorphin. Analgesics agents in the various classes are described in the literature.

Opioid receptor antagonists and agonists can be administered with the compounds of the disclosure in co-therapy or linked to the compound of the disclosure, e.g., by a covalent bond. For example, opioid receptor antagonists such as naloxone, naltrexone, methyl nalozone, nalmefene, cypridime, beta funaltrexamine, naloxonazine, naltrindole, and nor-binaltorphimine are thought to be useful in the treatment of opioid-induced constipaption (OIC). It can be useful to formulate opioid antagonists of this type in a delayed or sustained release formulation, such that initial release of the antagonist is in the mid to distal small intestine and/or ascending colon. Such antagonists are described in U.S. Pat. No. 6,734,188 (WO 01/32180 A2), the entire contents of which are incorporated herein by reference for all relevant and consistent purposes. Enkephalin pentapeptide (HOE825; Tyr-D-Lys-Gly-Phe-L-homoserine) is an agonist of the μ- and γ-opioid receptors and is thought to be useful for increasing intestinal motility (*Eur. J. Pharm.*, 219:445, 1992), and this peptide can be used in conjunction with the compounds of the disclosure. Also useful is trimebutine which is thought to bind to mu/delta/kappa opioid receptors and activate release of motilin and modulate the release of gastrin, vasoactive intestinal peptide, gastrin and glucagons. K-opioid receptor agonists such as fedotozine, ketocyclazocine, and compounds described in US 2005/0176746 (WO 03/097051 A2), the entire contents of which are incorporated herein by reference for all relevant and consistent purposes, can be used with or linked to the compounds of the disclosure. In addition, μ-opioid receptor agonists, such as morphine, diphenyloxylate, frakefamide (H-Tyr-D-Ala-Phe(F)-Phe-NH$_2$; disclosed in WO 01/019849 A1, the entire contents of which are incorporated herein by reference for all relevant and consistent purposes) and loperamide can be used. Tyr-Arg (kyotorphin) is a dipeptide that acts by stimulating the release of met-enkephalins to elicit an analgesic effect (J. Biol. Chem. 262: 8165, 1987). Kyotorphin can be used with or linked to the compounds of the disclosure. CCK receptor agonists such as caerulein from amphibians and other species are useful analgesic agents that can be used with or linked to the compounds of the disclosure.

Conotoxin peptides represent a large class of analgesic peptides that act at voltage gated Ca channels, NMDA receptors or nicotinic receptors. These peptides can be used with or linked to the compounds of the disclosure.

Peptide analogs of thymulin (U.S. Pat. No. 7,309,690 or FR 2830451, the entire contents of which are incorporated herein by reference for all relevant and consistent purposes) can have analgesic activity and can be used with or linked to the compounds of the disclosure.

CCK (CCKa or CCKb) receptor antagonists, including loxiglumide and dexloxiglumide (the R-isomer of loxiglumide) (U.S. Pat. No. 5,130,474 or WO 88/05774, the entire contents of which are incorporated herein by reference for all relevant and consistent purposes) can have analgesic activity and can be used with or linked to the compounds of the disclosure.

Other useful analgesic agents include 5-HT4 agonists such as tegaserod/zelnorm and lirexapride. Such agonists are described in: EP 1321142 A1, WO 03/053432A1, EP 505322 A1, EP 505322 B1, EP 507672 A1, EP 507672 B1, U.S. Pat. No. 5,510,353 and U.S. Pat. No. 5,273,983, the entire contents of which are incorporated herein by reference for all relevant and consistent purposes.

Calcium channel blockers such as ziconotide and related compounds described in, for example, EP 625162B1, U.S. Pat. No. 5,364,842, U.S. Pat. No. 5,587,454, U.S. Pat. No. 5,824,645, U.S. Pat. No. 5,859,186, U.S. Pat. No. 5,994,305, U.S. Pat. No. 6,087,091, U.S. Pat. No. 6,136,786, WO 93/13128 A1, EP 1336409 A1, EP 835126 A1, EP 835126 B1, U.S. Pat. No. 5,795,864, U.S. Pat. No. 5,891,849, U.S. Pat. No. 6,054,429, WO 97/01351 A1, the entire contents of which are incorporated herein by reference for all relevant and consistent purposes, can be used with or linked to the compounds of the disclosure.

Various antagonists of the NK-1, NK-2, and NK-3 receptors (for a review see Giardina et al. 2003 Drugs 6:758) can be can be used with or linked to the compounds of the disclosure.

NK1 receptor antagonists such as: aprepitant (Merck & Co Inc), vofopitant, ezlopitant (Pfizer, Inc.), R-673 (Hoffmann-La Roche Ltd), SR-14033 and related compounds described in, for example, EP 873753 A1, U.S. 20010006972 A1, U.S. 20030109417 A1, WO 01/52844 A1, the entire contents of which are incorporated herein by reference for all relevant and consistent purposes, can be used with or linked to the compounds of the disclosure.

NK-2 receptor antagonists such as nepadutant (Menarini Ricerche SpA), saredutant (Sanofi-Synthelabo), SR-144190 (Sanofi-Synthelabo) and UK-290795 (Pfizer Inc) can be used with or linked to the compounds of the disclosure.

NK3 receptor antagonists such as osanetant (Sanofi-Synthelabo), talnetant and related compounds described in, for example, WO 02/094187 A2, EP 876347 A1, WO 97/21680 A1, U.S. Pat. No. 6,277,862, WO 98/11090, WO 95/28418, WO 97/19927, and Boden et al. (J Med. Chem. 39:1664-75, 1996), the entire contents of which are incorporated herein by reference for all relevant and consistent purposes, can be used with or linked to the compounds of the disclosure.

Norepinephrine-serotonin reuptake inhibitors such as milnacipran and related compounds described in WO 03/077897 A1, the entire contents of which are incorporated herein by reference for all relevant and consistent purposes, can be used with or linked to the compounds of the disclosure.

Vanilloid receptor antagonists such as arvanil and related compounds described in WO 01/64212 A1, the entire contents of which are incorporated herein by reference for all relevant and consistent purposes, can be used with or linked to the compounds of the disclosure.

The compounds can be used in combination therapy with a phosphodiesterase inhibitor (examples of such inhibitors can be found in U.S. Pat. No. 6,333,354, the entire contents of which are incorporated herein by reference for all relevant and consistent purposes).

The compounds can be used alone or in combination therapy to treat disorders associated with chloride or bicarbonate secretion that may lead to constipation, e.g., Cystic Fibrosis.

The compounds can also or alternatively be used alone or in combination therapy to treat calcium-induced constipation effects. Constipation is commonly found in the geriatric population, particularly patients with osteoporosis who have to take calcium supplements. Calcium supplements have shown to be beneficial in ostoporotic patients to restore bone density but compliance is poor because of constipation effects associated therewith.

The compounds of the current disclosure have can be used in combination with an opioid. Opioid use is mainly directed to pain relief, with a notable side-effect being GI disorder, e.g. constipation. These agents work by binding to opioid receptors, which are found principally in the central nervous system and the gastrointestinal tract. The receptors in these two organ systems mediate both the beneficial effects, and the undesirable side effects (e.g. decrease of gut motility and ensuing constipation). Opioids suitable for use typically belong to one of the following exemplary classes: natural opiates, alkaloids contained in the resin of the opium poppy including morphine, codeine and thebaine; semi-synthetic opiates, created from the natural opioids, such as hydromorphone, hydrocodone, oxycodone, oxymorphone, desomorphine, diacetylmorphine (Heroin), nicomorphine, dipropanoylmorphine, benzylmorphine and ethylmorphine; fully synthetic opioids, such as fentanyl, pethidine, methadone, tramadol and propoxyphene; endogenous opioid peptides, produced naturally in the body, such as endorphins, enkephalins, dynorphins, and endomorphins.

The compound of the disclosure can be used alone or in combination therapy to alleviate GI disorders encountered with patients with renal failure (stage 3-5). Constipation is the second most reported symptom in that category of patients (Murtagh et al., 2006; Murtagh et al., 2007a; Murtagh et al., 2007b). Without being held by theory, it is believed that kidney failure is accompanied by a stimulation of intestinal Na re-absorption (Hatch and Freel, 2008). A total or partial inhibition of such transport by administration of the compounds of the disclosure can have a therapeutic benefit to improve GI transit and relieve abdominal pain. In that context, the compounds of the disclosure can be used in combination with Angiotensin-modulating agents: Angiotensin Converting Enzyme (ACE) inhibitors (e.g. captopril, enalopril, lisinopril, ramipril) and Angiotensin II receptor antagonist therapy (also referred to as $AT_1$-antagonists or angiotensin receptor blockers, or ARB's); diuretics such as loop diuretics (e.g. furosemide, bumetanide), Thiazide diuretics (e.g. hydrochlorothiazide, chlorthalidone, chlorthiazide) and potassium-sparing diuretics: amiloride; beta blockers: bisoprolol, carvedilol, nebivolol and extended-release metoprolol; positive inotropes: Digoxin, dobutamine; phosphodiesterase inhibitors such as milrinone; alternative vasodilators: combination of isosorbide dinitrate/hydralazine; aldosterone receptor antagonists: spironolactone, eplerenone; natriuretic peptides: Nesiritide, a recombinant form of brain-natriuretic peptide (BNP), atrial-natriuretic peptide (ANP); vasopressin receptor antagonists: Tolvaptan and conivaptan; phosphate binder (Renagel, Renleva, Phoslo, Fosrenol); phosphate transport inhibitor such as those described in U.S. Pat. No. 4,806,532, U.S. Pat. No. 6,355,823, U.S. Pat. No. 6,787,528, WO 2001/005398, WO 2001/087294, WO 2001/082924, WO 2002/028353, WO 2003/048134, WO 2003/057225, U.S. Pat. No. 7,119,120, EP 1465638, US Appl. 2007/021509, WO 2003/080630, U.S. Pat. No. 7,109,184, US Appl. 2006/0280719, EP 1485391, WO 2004/085448, WO 2004/085382, US Appl. 2006/0217426, JP 2007/131532, the entire contents of which are incorporated herein by reference for all relevant and consistent purposes, or phosphate transport antagonist (Nicotinamide).

The compounds of the disclosure can be used in combination with peptides or peptide analogs that activate the Guanylate Cyclase-receptor in the intestine and results in elevation of the intracellular second messenger, or cyclic guanosine monophosphate (cGMP), with increased chloride and bicarbonate secretion into the intestinal lumen and concomitant fluid secretion. Example of such peptides are Linaclotide (MD-1100 Acetate), endogenous hormones guanylin and uroguanylin and enteric bacterial peptides of the heat stable enterotoxin family (ST peptides) and those described in U.S. Pat. No. 5,140,102, U.S. Pat. No. 5,489,670, U.S. Pat. No. 5,969,097, WO 2006/001931A2, WO 2008/002971A2, WO 2008/106429A2, US 2008/0227685A1 and U.S. Pat. No. 7,041,786, the entire contents of which are incorporated herein by reference for all relevant and consistent purposes.

The compounds of the disclosure can be used in combination with type-2 chloride channel agonists, such as Amitiza (Lubiprostone) and other related compounds described in U.S. Pat. No. 6,414,016, the entire contents of which are incorporated herein by reference for all relevant and consistent purposes.

The compounds of the disclosure can be used in combination with P2Y2 receptor agonists, such as those described in EP 1196396B1 and U.S. Pat. No. 6,624,150, the entire contents of which are incorporated herein by reference for all relevant and consistent purposes.

The compounds of the disclosure can be used in combination with laxative agents such as bulk-producing agents, e.g. psyllium husk (Metamucil), methylcellulose (Citrucel), polycarbophil, dietary fiber, apples, stool softeners/surfactant such as docusate (Colace, Diocto); hydrating agents (osmotics), such as dibasic sodium phosphate, magnesium citrate, magnesium hydroxide (Milk of magnesia), magnesium sulfate (which is Epsom salt), monobasic sodium phosphate, sodium biphosphate; hyperosmotic agents: glycerin suppositories, sorbitol, lactulose, and polyethylene glycol (PEG). The compounds of the disclosure can be also be used in combination with agents that stimulate gut peristalsis, such as Bisacodyl tablets (Dulcolax), Casanthranol, Senna and Aloin, from Aloe Vera.

In one embodiment, the compounds of the disclosure accelerate gastrointestinal transit, and more specifically in the colon, without substantially affecting the residence time in the stomach, i.e. with no significant effect on the gastric emptying time. Even more specifically the compounds of the invention restore colonic transit without the side-effects associated with delayed gastric emptying time, such as nausea. The GI and colonic transit are measured in patients using methods reported in, for example: Burton D D, Camilleri M, Mullan B P, et al., *J. Nucl. Med.*, 1997; 38:1807-1810; Cremonini F, Mullan B P, Camilleri M, et al., *Aliment. Pharmacol. Ther.*, 2002; 16:1781-1790; Camilleri M, Zinsmeister A R, *Gastroenterology*, 1992; 103:36-42; Bouras E P, Camilleri M, Burton D D, et al., *Gastroenterology*, 2001; 120:354-360; Coulie B, Szarka L A, Camilleri M, et al., *Gastroenterology*, 2000; 119:41-50; Prather C M, Camilleri M, Zinsmeister A R, et al., *Gastroenterology*, 2000; 118:463-468; and, Camilleri M, McKinzie S, Fox J, et al., *Clin. Gastroenterol. Hepatol.*, 2004; 2:895-904.

C. Polymer Combination Therapy

The NHE-inhibiting compounds described therein may be administered to patients in need thereof in combination with a fluid-absorbing polymer ("FAP"). The intestinal fluid-absorbing polymers useful for administration in accordance with embodiments of the present disclosure may be administered orally in combination with non-absorbable NHE-inhibitors (e.g., a NHE-3 inhibitor) to absorb the intestinal fluid resulting from the action of the sodium transport inhibitors. Such polymers swell in the colon and bind fluid to impart a consistency to stools that is acceptable for patients. The fluid-absorbing polymers described herein may be selected from polymers with laxative properties, also referred to as bulking agents (i.e., polymers that retain some of the intestinal fluid in the stools and impart a higher degree of hydration in the stools and facilitate transit). The fluid-absorbing polymers may also be optionally selected from pharmaceutical polymers with anti-diarrhea function, i.e., agents that maintain some consistency to the stools to avoid watery stools and potential incontinence.

The ability of the polymer to maintain a certain consistency in stools with a high content of fluid can be characterized by its "water holding power." Wenzl et al. (in *Determinants of decreased fecal consistency in patients with diarrhea*; Gastroenterology, v. 108, no. 6, p. 1729-1738 (1995)) studied the determinants that control the consistency of stools of patients with diarrhea and found that they were narrowly correlated with the water holding power of the feces. The water holding power is determined as the water content of given stools to achieve a certain level of consistency (corresponding to "formed stool" consistency) after the reconstituted fecal matter has been centrifuged at a certain g number. Without being held to any particular theory, has been found that the water holding power of the feces is increased by ingestion of certain polymers with a given fluid absorbing profile. More specifically, it has been found that the water-holding power of said polymers is correlated with their fluid absorbancy under load (AUL); even more specifically the AUL of said polymers is greater than 15 g of isotonic fluid/g of polymer under a static pressure of 5 kPa, even more preferably under a static pressure of 10 kPa.

The FAP utilized in the treatment method of the present disclosure preferably has a AUL of at least about 10 g, about 15 g, about 20 g, about 25 g or more of isotonic fluid/g of polymer under a static pressure of about 5 kPa, and preferably about 10 kPA, and may have a fluid absorbency of about 20 g, about 25 g or more, as determined using means generally known in the art. Additionally or alternatively, the FAP may impart a minimum consistency to fecal matter and, in some embodiments, a consistency graded as "soft" in the scale described in the test method below, when fecal non water-soluble solid fraction is from 10% to 20%, and the polymer concentration is from 1% to 5% of the weight of stool. The determination of the fecal non water-soluble solid fraction of stools is described in Wenz et al. The polymer may be uncharged or may have a low charge density (e.g., 1-2 meq/gr). Alternatively or in addition, the polymer may be delivered directly to the colon using known delivery methods to avoid premature swelling in the esophagus.

In one embodiment of the present disclosure, the FAP is a "superabsorbent" polymer (i.e., a lightly crosslinked, partially neutralized polyelectrolyte hydrogel similar to those used in baby diapers, feminine hygiene products, agriculture additives, etc.). Superabsorbent polymers may be made of a lightly crosslinked polyacrylate hydrogel. The swelling of the polymer is driven essentially by two effects: (i) the hydration of the polymer backbone and entropy of mixing and (ii) the osmotic pressure arising from the counter-ions (e.g., Na ions) within the gel. The gel swelling ratio at equilibrium is controlled by the elastic resistance inherent to the polymer network and by the chemical potential of the bathing fluid, i.e., the gel will de-swell at higher salt concentration because the background electrolyte will reduce the apparent charge density on the polymer and will reduce the difference of free ion concentrations inside and outside the gel that drives osmotic pressure. The swelling ratio SR (g of fluid per g of dry polymer and synonymously "fluid absorbency") may vary from 1000 in pure water down to 30 in 0.9% NaCl solution representative of physiological saline (i.e., isotonic). SR may increase with the degree of neutralization and may decrease with the crosslinking density. SR generally decreases with an applied load with the extent of reduction dependent on the strength of the gel, i.e., the crosslinking density. The salt concentration within the gel, as compared with the external solution, may be lower as a result of the Donnan effect due to the internal electrical potential.

The fluid-absorbing polymer may include crosslinked polyacrylates which are fluid absorbent such as those prepared from $\alpha,\beta$-ethylenically unsaturated monomers, such as monocarboxylic acids, polycarboxylic acids, acrylamide and their derivatives. These polymers may have repeating units of acrylic acid, methacrylic acid, metal salts of acrylic acid, acrylamide, and acrylamide derivatives (such as 2-acrylamido-2-methylpropanesulfonic acid) along with various combinations of such repeating units as copolymers. Such derivatives include acrylic polymers which include hydrophilic grafts of polymers such as polyvinyl alcohol. Examples of suitable polymers and processes, including gel polymerization processes, for preparing such polymers are disclosed in U.S. Pat. Nos. 3,997,484; 3,926,891; 3,935,099; 4,090,013; 4,093,776; 4,340,706; 4,446,261; 4,683,274; 4,459,396; 4,708,997; 4,076,663; 4,190,562; 4,286,082; 4,857,610; 4,985,518; 5,145,906; 5,629,377 and 6,908,609 which are incorporated herein by reference for all relevant and consistent purposes (in addition, see Buchholz, F. L. and Graham, A. T., "Modern Superabsorbent Polymer Technology," John Wiley & Sons (1998), which is also incorporated herein by reference for all relevant and consistent purposes). A class of preferred polymers for treatment in combination with NHE-inhibitors is polyelectrolytes.

The degree of crosslinking can vary greatly depending upon the specific polymer material; however, in most applications the subject superabsorbent polymers are only lightly crosslinked, that is, the degree of crosslinking is such that the polymer can still absorb over 10 times its weight in physiological saline (i.e., 0.9% saline). For example, such polymers typically include less than about 0.2 mole % crosslinking agent.

In some embodiments, the FAP's utilized for treatment are Calcium Carbophil (Registry Number: 9003-97-8, also referred as Carbopol EX-83), and Carpopol 934P. In some embodiments, the fluid-absorbing polymer is prepared by high internal phase emulsion ("HIPE") processes. The HIPE process leads to polymeric foam slabs with a very large porous fraction of interconnected large voids (about 100 microns) (i.e., open-cell structures). This technique produces flexible and collapsible foam materials with exceptional suction pressure and fluid absorbency (see U.S. Pat. Nos. 5,650,222; 5,763,499 and 6,107,356, which are incorporated herein for all relevant and consistent purposes). The polymer is hydrophobic and, therefore, the surface should be modified so as to be wetted by the aqueous fluid. This is accomplished by post-treating the foam material by a surfactant in order to reduce the interfacial tension. These materials are claimed to be less compliant to loads, i.e., less prone to de-swelling under static pressure.

In some embodiments, fluid-absorbing gels are prepared by aqueous free radical polymerization of acrylamide or a derivative thereof, a crosslinker (e.g., methylene-bis-acrylamide) and a free radical initiator redox system in water. The material is obtained as a slab. Typically the swelling ratio of crosslinked polyacrylamide at low crosslinking density (e.g., 2%-4% expressed as weight % of methylene-bis-acrylamide) is between 25 and 40 (F. Horkay, *Macromolecules*, 22, pp. 2007-09 (1989)). The swelling properties of these polymers have been extensively studied and are essentially the same of those of crosslinked polyacrylic acids at high salt concentration. Under those conditions, the osmotic pressure is null due to the presence of counter-ions and the swelling is controlled by the free energy of mixing and the network elastic energy. Stated differently, a crosslinked polyacrylamide gel of same crosslink density as a neutralized polyacrylic acid will exhibit the same swelling ratio (i.e., fluid absorbing properties) and it is believed the same degree of deswelling under pressure, as the crosslinked polyelectrolyte at high salt content (e.g., 1 M). The properties (e.g., swelling) of neutral hydrogels will not be sensitive to the salt environment as long as the polymer remains in good solvent conditions. Without being held to any particular theory, it is believed that the fluid contained within the gel has the same salt composition than the surrounding fluid (i.e., there is no salt partitioning due to Donnan effect).

Another subclass of fluid-absorbing polymers that may be utilized is hydrogel materials that include N-alkyl acrylamide polymers (e.g., N-isopropylacrylamide (NIPAM)). The corresponding aqueous polyNIPAM hydrogel shows a temperature transition at about 35° C. Above this temperature the hydrogel may collapse. The mechanism is generally reversible and the gel re-swells to its original swelling ratio when the temperature reverts to room temperature. This allows production of nanoparticles by emulsion polymerization (R. Pelton, *Advances in Colloid and Interface Science*, 85, pp. 1-33, (2000)). The swelling characteristics of poly-NIPAM nanoparticles below the transition temperature have been reported and are similar to those reported for bulk gel of polyNIPAM and equivalent to those found for polyacrylamide (i.e. 30-50 g/g) (W. McPhee, *Journal of Colloid and Interface Science*, 156, pp. 24-30 (1993); and, K. Oh, *Journal of Applied Polymer Science*, 69, pp. 109-114 (1997)).

In some embodiments, the FAP utilized for treatment in combination with a NHE-inhibitor is a superporous gel that may delay the emptying of the stomach for the treatment of obesity (J. Chen, *Journal of Controlled Release*, 65, pp. 73-82 (2000), or to deliver proteins. Polyacrylate-based SAP's with a macroporous structure may also be used. Macroporous SAP and superporous gels differ in that the porous structure remains almost intact in the dry state for superporous gels, but disappears upon drying for macroporous SAP's. The method of preparation is different although both methods use a foaming agent (e.g., carbonate salt that generates $CO_2$ bubbles during polymerization). Typical swelling ratios, SR, of superporous materials are around 10. Superporous gels keep a large internal pore volume in the dry state.

Macroporous hydrogels may also be formed using a method whereby polymer phase separation in induced by a non-solvent. The polymer may be poly-NIPAM and the non-solvent utilized may be glucose (see, e.g., Z. Zhang, *J. Org. Chem.*, 69, 23 (2004)) or NaCl (see, e.g., Cheng et al., *Journal of Biomedical Materials Research—Part A*, Vol. 67, Issue 1, 1 Oct. 2003, Pages 96-103). The phase separation induced by the presence of NaCl leads to an increase in swelling ratio. These materials are preferred if the swelling ratio of the material, SR, is maintained in salt isotonic solution and if the gels do not collapse under load. The temperature of "service" should be shifted beyond body temperature, e.g. by diluting NIPAM in the polymer with monomer devoid of transition temperature phenomenon.

In some embodiments, the fluid-absorbing polymer may be selected from certain naturally-occurring polymers such as those containing carbohydrate moieties. In a preferred embodiment, such carbohydrate-containing hydrogels are non-digestible, have a low fraction of soluble material and a high fraction of gel-forming materials. In some embodiments, the fluid-absorbing polymer is selected from xanthan, guar, wellan, hemicelluloses, alkyl-cellulose, hydro-alkyl-cellulose, carboxy-alkyl-cellulose, carrageenan, dextran, hyaluronic acid and agarose. In a preferred embodiment, the gel forming polymer is psyllium. Psyllium (or "ispaghula") is the common name used for several members of the plant genus *Plantago* whose seeds are used commercially for the production of mucilage. Most preferably, the fluid-absorbing polymer is in the gel-forming fraction of psyllium, i.e., a neutral saccharide copolymer of arabinose (25%) and xylose (75%) as characterized in (J. Marlett, *Proceedings of the Nutrition Society*, 62, pp. 2-7-209 (2003); and, M. Fischer, *Carbohydrate* Research, 339, 2009-2012 (2004)), and further described in U.S. Pat. Nos. 6,287,609; 7,026,303; 5,126,150; 5,445,831; 7,014,862; 4,766,004; 4,999,200, each of which is incorporated herein for all relevant and consistent purposes, and over-the-counter psyllium-containing agents such as those marketed under the name Metamucil (The Procter and Gamble company). Preferably the a psyllium-containing dosage form is suitable for chewing, where the chewing action disintegrates the tablet into smaller, discrete particles prior to swallowing but which undergoes minimal gelling in the mouth, and has acceptable mouthfeel and good aesthetics as perceived by the patient.

The psyllium-containing dosage form includes physically discrete unit suitable as a unitary dosage for human subjects and other mammals, each containing a predetermined quantity of active material (e.g. the gel-forming polysaccharide) calculated to produce the desired therapeutic effect. Solid oral dosage forms that are suitable for the present compositions include tablets, pills, capsules, lozenges, chewable tablets, troches, cachets, pellets, wafer and the like.

In some embodiments, the FAP is a polysaccharide particle wherein the polysaccharide component includes xylose and arabinose. The ratio of the xylose to the arabinose may be at least about 3:1 by weight, as described in U.S. Pat. Nos. 6,287,609; 7,026,303 and 7,014,862, each of which is incorporated herein for all relevant and consistent purposes.

The fluid-absorbing polymers described herein may be used in combination with the NHE-inhibiting compounds or a pharmaceutical composition containing the compound. The NHE inhibitor and the FAP may also be administered with other agents including those described under the heading "Combination Therapies" without departing from the scope of the present disclosure. As described above, the NHE inhibitor may be administered alone without use of a fluid-absorbing polymer to resolve symptoms without eliciting significant diarrhea or fecal fluid secretion that would require the co-administration of a fluid-absorbing polymer.

The fluid-absorbing polymers described herein may be selected so as to not induce any substantial interaction with the NHE-inhibiting compounds or a pharmaceutical composition containing the compound. As used herein, "no substantial interaction" generally means that the co-administration of the FAP polymer would not substantially alter (i.e., neither substantially decrease nor substantially increase) the pharmacological property of the NHE-inhibiting compounds administered alone. For example, FAPs containing negatively charged functionality, such as carboxylates, sulfonates, and the like, may potentially interact ionically with positively charged NHE inhibitors, preventing the inhibitor from reaching its pharmacological target. In addition, it may be possible that the shape and arrangement of functionality in a FAP could act as a molecular recognition element, and sequestor NHE inhibitors via "host-guest" interactions via the recognition of specific hydrogen bonds and/or hydrophobic regions of a given inhibitor. Accordingly, in various embodiments of the present disclosure, the FAP polymer may be selected, for co-administration or use with a compound of the present disclosure, to ensure that (i) it does not ionically interact with or bind with the compound of the present disclosure (by means of, for example, a moiety present therein possessing a charge opposite that of a moiety in the compound itself), and/or (ii) it does not possess a charge and/or structural conformation (or shape or arrangement) that enables it to establish a "host-guest" interaction with the compound of the present disclosure (by means of, for example, a moiety present therein that may act as a molecular recognition element and sequester the NHE inhibitor or inhibiting moiety of the compound).

D. Dosage

It is to be noted that, as used herein, an "effective amount" (or "pharmaceutically effective amount") of a compound disclosed herein, is a quantity that results in a beneficial clinical outcome of the condition being treated with the compound compared with the absence of treatment. The amount of the compound or compounds administered will depend on the degree, severity, and type of the disease or condition, the amount of therapy desired, and the release characteristics of the pharmaceutical formulation. It will also depend on the subject's health, size, weight, age, sex and tolerance to drugs. Typically, the compound is administered for a sufficient period of time to achieve the desired therapeutic effect.

In embodiments wherein both an NHE-inhibitor compound and a fluid-absorbing polymer are used in the treatment protocol, the NHE-inhibitor and FAP may be administered together or in a "dual-regimen" wherein the two therapeutics are dosed and administered separately. When the NHE inhibitor and the fluid-absorbing polymer are dosed separately, the typical dosage administered to the subject in need of the NHE inhibitor is typically from about 5 mg per day and about 5000 mg per day and, in other embodiments, from about 50 mg per day and about 1000 mg per day. Such dosages may induce fecal excretion of sodium (and its accompanying anions), from about 10 mmol up to about 250 mmol per day, from about 20 mmol to about 70 mmol per day or even from about 30 mmol to about 60 mmol per day.

The typical dose of the fluid-absorbing polymer is a function of the extent of fecal secretion induced by the non-absorbable NHE inhibitor. Typically the dose is adjusted according to the frequency of bowel movements and consistency of the stools. More specifically the dose is adjusted so as to avoid liquid stools and maintain stool consistency as "soft" or semi-formed, or formed. To achieve the desired stool consistency and provide abdominal relief to patients, typical dosage ranges of the fluid-absorbing polymer to be administered in combination with the NHE inhibitor, are from about 2 g to about 50 g per day, from about 5 g to about 25 g per day or even from about 10 g to about 20 g per day. When the NHE-inhibitor and the FAP are administered as a single dosage regimen, the daily uptake may be from about 2 g to about 50 g per day, from about 5 g to about 25 g per day, or from about 10 g to about 20 g per day, with a weight ratio of NHE inhibitor to fluid-absorbing polymer being from about 1:1000 to 1:10 or even from about 1:500 to 1:5 or about 1:100 to 1:5.

A typical dosage of the substantially impermeable or substantially systemically non-bioavailable, NHE-inhibiting compound when used alone without a FAP may be between about 0.2 mg per day and about 2 g per day, or between about 1 mg and about 1 g per day, or between about 5 mg and about 500 mg, or between about 10 mg and about 250 mg per day, which is administered to a subject in need of treatment.

The frequency of administration of therapeutics described herein may vary from once-a-day (QD) to twice-a-day (BID) or thrice-a-day (TID), etc., the precise frequency of administration varying with, for example, the patient's condition, the dosage, etc. For example, in the case of a dual-regimen, the NHE-inhibitor could be taken once-a-day while the fluid-absorbing polymer could be taken at each meal (TID).

E. Modes of Administration

The substantially impermeable or substantially systemically non-bioavailable, NHE-inhibiting compounds of the present disclosure with or without the fluid-absorbing polymers described herein may be administered by any suitable route. The compound is preferably administrated orally (e.g., dietary) in capsules, suspensions, tablets, pills, dragees, liquids, gels, syrups, slurries, and the like. Methods for encapsulating compositions (such as in a coating of hard gelatin or cyclodextran) are known in the art (Baker, et al., "Controlled Release of Biological Active Agents", John Wiley and Sons, 1986). The compounds can be administered to the subject in conjunction with an acceptable pharmaceutical carrier as part of a pharmaceutical composition. The formulation of the pharmaceutical composition will vary according to the route of administration selected. Suitable pharmaceutical carriers may contain inert ingredients which do not interact with the compound. The carriers are biocompatible, i.e., non-toxic, non-inflammatory, non-immunogenic and devoid of other undesired reactions at the administration site. Examples of pharmaceutically acceptable carriers include, for example, saline, commercially available inert gels, or liquids supplemented with albumin, methyl cellulose or a collagen matrix. Standard pharmaceutical formulation techniques can be employed, such as those described in Remington's Pharmaceutical Sciences, Mack Publishing Company, Easton, Pa.

Pharmaceutical preparations for oral use can be obtained by combining a compound of the present disclosure with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of a suitable material, such as gelatin, as well as soft, sealed capsules made of a suitable material, for example, gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

It will be understood that, certain compounds of the disclosure may be obtained as different stereoisomers (e.g., diastereomers and enantiomers) or as isotopes and that the disclosure includes all isomeric forms, racemic mixtures and isotopes of the disclosed compounds and a method of treating a subject with both pure isomers and mixtures thereof, including racemic mixtures, as well as isotopes. Stereoisomers can be separated and isolated using any suitable method, such as chromatography.

F. Delayed Release

NHE proteins show considerable diversity in their patterns of tissue expression, membrane localization and functional roles. (See, e.g., *The sodium-hydrogen exchanger—From molecule To Its Role In Disease*, Karmazyn, M., Avkiran, M., and Fliegel, L., eds., Kluwer Academics (2003).)

In mammals, nine distinct NHE genes (NHE-1 through -9) have been described. Of these nine, five (NHE-1 through -5) are principally active at the plasma membrane, whereas NHE-6, -7 and -9 reside predominantly within intracellular compartments. NHE-1 is ubiquitously expressed and is chiefly responsible for restoration of steady state intracellular pH following cytosolic acidification and for maintenance of cell volume. Recent findings show that NHE-1 is crucial for organ function and survival (e.g. NHE-1-null mice exhibit locomotor abnormalities, epileptic-like seizures and considerable mortality before weaning).

In contrast with NHE-1 expressed at the basolateral side of the nephrons and gut epithelial cells, NHE-2 through -4 are predominantly expressed on the apical side of epithelia of the kidney and the gastrointestinal tract. Several lines of evidence show that NHE-3 is the major contributor of renal bulk Na+ and fluid re-absorption by the proximal tubule. The associated secretion of H+ by NHE-3 into the lumen of renal tubules is also essential for about ⅔ of renal $HCO_3^-$ re-absorption. Complete disruption of NHE-3 function in mice causes a sharp reduction in $HCO_3^-$, Na+ and fluid re-absorption in the kidney, which is consistently associated with hypovolemia and acidosis.

In one embodiment, the novel compounds of the invention are intended to target the apical NHE antiporters (e.g. NHE-3, NHE-2 and NHE-8) without substantial permeability across the layer of gut epithelial cells, and/or without substantial activity towards NHEs that do not reside predominantly in the GI tract. This invention provides a method to selectively inhibit GI apical NHE antiporters and provide the desired effect of salt and fluid absorption inhibition to correct abnormal fluid homeostasis leading to constipations states. Because of their absence of systemic exposure, said compounds do not interfere with other key physiological roles of NHEs highlighted above. For instance, the compounds of the invention are expected to treat constipation in patients in need thereof, without eliciting undesired systemic effects, such as for example salt wasting or bicarbonate loss leading to hyponatriemia and acidosis among other disorders.

In another embodiment, the compounds of the invention are delivered to the small bowel with little or no interaction with the upper GI such as the gastric compartment and the duodenum. The applicant found that an early release of the compounds in the stomach or the duodenum can have an untoward effect on gastric secretion or bicarbonate secretion (also referred to as "bicarbonate dump"). In this embodiment the compounds are designed so as to be released in an active form past the duodenum. This can be accomplished by either a prodrug approach or by specific drug delivery systems.

As used herein, "prodrug" is to be understood to refer to a modified form of the compounds detailed herein that is inactive (or significantly less active) in the upper GI, but once administered is metabolised in vivo into an active metabolite after getting past, for example, the duodenum. Thus, in a prodrug approach, the activity of the NHE inhibitor can be masked with a transient protecting group that is liberated after compound passage through the desired gastric compartment. For example, acylation or alkylation of the essential guanidinyl functionality of the NHE inhibitor would render it biochemically inactive; however, cleavage of these functional groups by intestinal amidases, esterases, phosphatases, and the like, as well enzymes present in the colonic flora, would liberate the active parent compound. Prodrugs can be designed to exploit the relative expression and localization of such phase I metabolic enzymes by carefully optimizing the structure of the prodrug for recognition by specific enzymes. As an example, the anti-inflammatory agent sulfasalazine is converted to 5-aminosalicylate in the colon by reduction of the diazo bond by intestinal bacteria.

In a drug delivery approach the NHE-inhibitor compounds of the invention are formulated in certain pharmaceutical compositions for oral administration that release the active in the targeted areas of the GI, i.e., jejunum, ileum or colon, or preferably the distal ileum and colon, or even more preferably the colon.

Methods known from the skilled-in-the-art are applicable. (See, e.g., Kumar, P. and Mishra, B., Colon Targeted Drug Delivery Systems—An Overview, *Curr. Drug Deliv.*, 2008, 5 (3), 186-198; Jain, S. K. and Jain, A., Target-specific Drug Release to the Colon., *Expert Opin. Drug Deliv.*, 2008, 5 (5), 483-498; Yang, L., Biorelevant Dissolution Testing of Colon-Specific Delivery Systems Activated by Colonic Microflora, *J. Control Release*, 2008, 125 (2), 77-86; Siepmann, F.; Siepmann, J.; Walther, M.; MacRae, R. J.; and Bodmeier, R., Polymer Blends for Controlled Release Coatings, *J. Control Release* 2008, 125 (1), 1-15; Patel, M.; Shah, T.; and Amin, A., Therapeutic Opportunities in Colon-Specific Drug-Delivery Systems, *Crit. Rev. Ther. Drug Carrier Syst.*, 2007, 24 (2), 147-202; Jain, A.; Gupta, Y.; Jain, S. K., Perspectives of Biodegradable Natural Polysaccharides for Site-specific Drug Delivery to the Colon., *J. Pharm. Sci.*, 2007, 10 (1), 86-128; Van den, M. G., Colon Drug Delivery, *Expert Opin. Drug Deliv.*, 2006, 3 (1), 111-125; Basit, A. W., Advances in Colonic Drug Delivery, *Drugs* 2005, 65 (14), 1991-2007; Chourasia, M. K.; Jain, S. K., Polysaccharides for Colon-Targeted Drug Delivery, *Drug Deliv.* 2004, 11 (2), 129-148; Shareef, M. A.; Khar, R. K.; Ahuja, A.; Ahmad, F. J.; and Raghava, S., Colonic Drug Delivery: An Updated Review, *AAPS Pharm. Sci.* 2003, 5 (2), E17; Chourasia, M. K.; Jain, S. K., Pharmaceutical Approaches to Colon Targeted Drug Delivery Systems, *J. Pharm. Sci.* 2003, 6 (1), 33-66; and, Sinha, V. R.; Kumria, R., Colonic Drug Delivery: Prodrug Approach, *Pharm. Res.* 2001, 18 (5), 557-564. Typically the active pharmaceutical ingredient (API) is contained in a tablet/capsule designed to release said API as a function of the environment (e.g., pH, enzymatic activity, temperature, etc.), or as a function of time. One example of this approach is Eudracol™ (Pharma Polymers Business Line of Degussa's Specialty Acrylics Business Unit), where the API-containing core tablet is layered with various polymeric coatings with specific dissolution profiles. The first layer ensures that the tablet passes through the stomach intact so it can continue through the small intestine. The change from an acidic environment in the stomach to an alkaline environment in the small intestine initiates the release of the protective outer layer. As it travels through the colon, the next layer is made permeable by the alkalinity and intestinal fluid. This allows fluid to penetrate to the interior layer and release the active ingredient, which diffuses from the core to the outside, where it can be absorbed by the intestinal wall. Other methods are contemplated without departing from the scope of the present disclosure.

In another example, the pharmaceutical compositions of the invention can be used with drug carriers including pectin and galactomannan, polysaccharides that are both degradable by colonic bacterial enzymes. (See, e.g., U.S. Pat. No. 6,413, 494, the entire contents of which are incorporated herein by reference for all relevant and consistent purposes.) While pectin or galactomannan, if used alone as a drug carrier, are easily dissolved in simulated gastric fluid and simulated intestinal fluid, a mixture of these two polysaccharides prepared at a pH of about 7 or above produces a strong, elastic, and insoluble gel that is not dissolved or disintegrated in the simulated gastric and intestinal fluids, thus protecting drugs coated with the mixture from being released in the upper GI tract. When the mixture of pectin and galactomannan arrives in the colon, it is rapidly degraded by the synergic action of colonic bacterial enzymes. In yet another aspect, the compositions of the invention may be used with the pharmaceutical matrix of a complex of gelatin and an anionic polysaccharide (e.g., pectinate, pectate, alginate, chondroitin sulfate, polygalacturonic acid, tragacanth gum, arabic gum, and a mixture thereof), which is degradable by colonic enzymes (U.S. Pat. No. 6,319,518).

In yet other embodiments, fluid-absorbing polymers that are administered in accordance with treatment methods of the present disclosure are formulated to provide acceptable/pleasant organoleptic properties such as mouthfeel, taste, and/or to avoid premature swelling/gelation in the mouth and in the esophagus and provoke choking or obstruction. The formulation may be designed in such a way so as to ensure the full hydration and swelling of the FAP in the GI tract and avoid the formation of lumps. The oral dosages for the FAP may take various forms including, for example, powder, granulates, tablets, wafer, cookie and the like, and are most preferably delivered to the small bowel with little or no interaction with the upper GI such as the gastric compartment and the duodenum.

The above-described approaches or methods are only some of the many methods reported to selectively deliver an active in the lower part of the intestine, and therefore should not be viewed to restrain or limit the scope of the disclosure.

The following non-limiting examples are provided to further illustrate the present disclosure.

EXAMPLES

Exemplary Compound Synthesis

Example 1

2-(3-(6,8-dichloro-2-methyl-1,2,3,4-tetrahydroisoquinolin-4-yl)phenylsulfonamido)ethylphosphonic acid

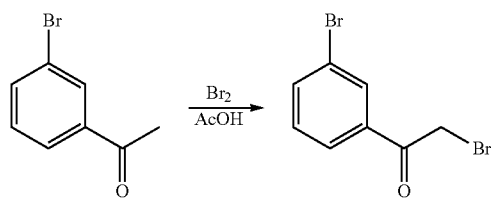

Intermediate 1.1:
2-bromo-1-(3-bromophenyl)ethanone

Into a 500-mL 3-necked round-bottom flask, was placed a solution of 1-(3-bromophenyl)ethanone (40 g, 202.02 mmol, 1.00 equiv) in acetic acid (200 mL). This was followed by the addition of a solution of $Br_2$ (32 g, 200.00 mmol) in acetic acid (50 mL) dropwise with stirring at 60° C. The resulting solution was stirred for 3 h at 60° C. in an oil bath. The resulting mixture was concentrated under vacuum. The crude product was re-crystallized from petroleum ether:ethyl acetate in the ratio of 8:1. This resulted in 24 g (43%) of 2-bromo-1-(3-bromophenyl)ethanone as a yellow solid.

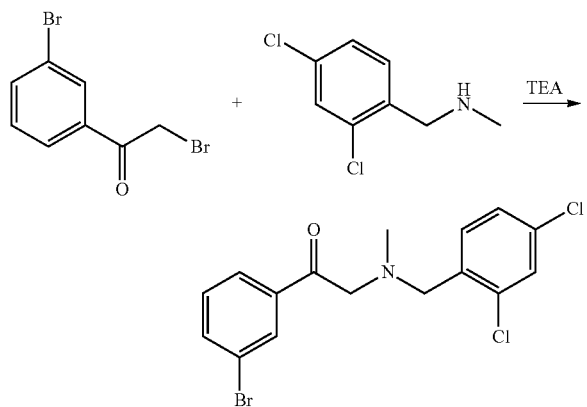

Intermediate 1.2: 1-(3-bromophenyl)-2-((2,4-dichlorobenzyl)(methyl)amino)ethanone Into a 1 L 3-necked round-bottom flask purged and maintained with an inert atmosphere of nitrogen, was placed a solution of 2-bromo-1-(3-bromophenyl)ethanone (55 g, 199.28 mmol, 1.00 equiv) in 1,4-dioxane (300 mL), TEA (40 g, 396.04 mmol, 1.99 equiv), and (2,4-dichlorophenyl)-N-methylmethanamine (38 g, 201.06 mmol, 1.01 equiv). The resulting solution was stirred for 2 h at 25° C. in an oil bath. The solids were filtered out and the filtrate was used without any further purification.

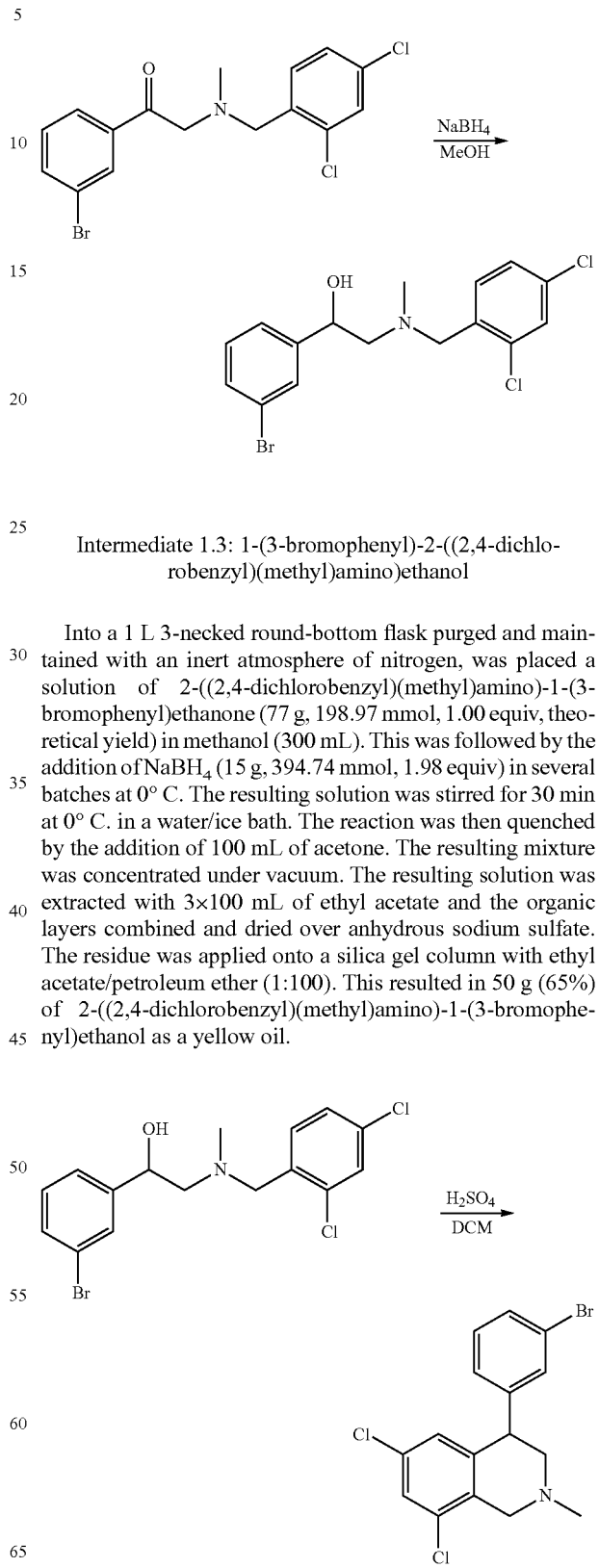

Intermediate 1.3: 1-(3-bromophenyl)-2-((2,4-dichlorobenzyl)(methyl)amino)ethanol Into a 1 L 3-necked round-bottom flask purged and maintained with an inert atmosphere of nitrogen, was placed a solution of 2-((2,4-dichlorobenzyl)(methyl)amino)-1-(3-bromophenyl)ethanone (77 g, 198.97 mmol, 1.00 equiv, theoretical yield) in methanol (300 mL). This was followed by the addition of $NaBH_4$ (15 g, 394.74 mmol, 1.98 equiv) in several batches at 0° C. The resulting solution was stirred for 30 min at 0° C. in a water/ice bath. The reaction was then quenched by the addition of 100 mL of acetone. The resulting mixture was concentrated under vacuum. The resulting solution was extracted with 3×100 mL of ethyl acetate and the organic layers combined and dried over anhydrous sodium sulfate. The residue was applied onto a silica gel column with ethyl acetate/petroleum ether (1:100). This resulted in 50 g (65%) of 2-((2,4-dichlorobenzyl)(methyl)amino)-1-(3-bromophenyl)ethanol as a yellow oil.

Intermediate 1.4: 4-(3-bromophenyl)-6,8-dichloro-2-methyl-1,2,3,4-tetrahydroisoquinoline Into a 500-mL 3-necked round-bottom flask, was placed a solution of 2-((2,4-dichlorobenzyl)(methyl)amino)-1-(3-bromophenyl)ethanol (25 g, 64.27 mmol, 1.00 equiv) in dichloromethane (100 mL). This was followed by the addition of sulfuric acid (100 mL) dropwise with stirring at 0-5° C. The resulting solution was stirred for 4 h at room temperature. The resulting solution was diluted with of ice water. The pH value of the solution was adjusted to 8 with sodium hydroxide. The resulting solution was extracted with 3×300 mL of dichloromethane and the organic layers combined and dried over anhydrous sodium sulfate and concentrated under vacuum. The crude product was re-crystallized from petroleum ether:ethyl acetate in the ratio of 8:1. This resulted in 15 g (63%) of 4-(3-bromophenyl)-6,8-dichloro-2-methyl-1,2,3,4-tetrahydroisoquinoline as a white solid.

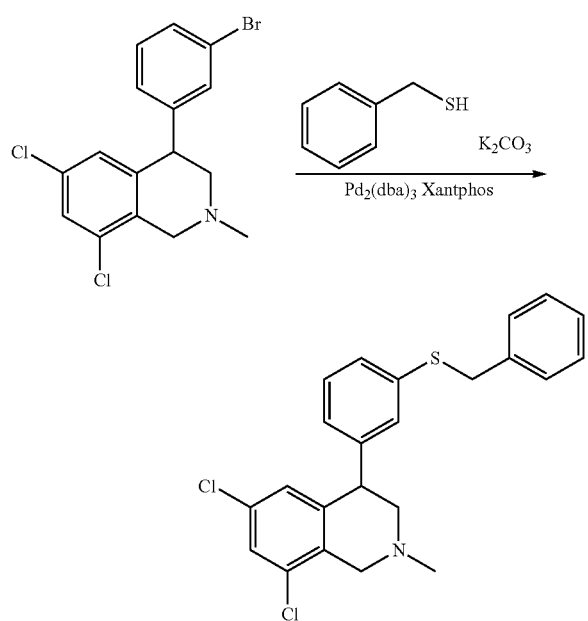

Intermediate 1.5: 4-(3-(benzylthio)phenyl)-6,8-dichloro-2-methyl-1,2,3,4-tetrahydroisoquinoline Into a 250-mL 3-necked round-bottom flask purged and maintained with an inert atmosphere of nitrogen, was placed a solution of potassium carbonate (930 mg, 0.50 equiv) in xylene (50 mL). This was followed by the addition of phenylmethanethiol (2.5 g, 1.50 equiv) dropwise with stirring at 0° C. The resulting solution was stirred for 1 h at 25° C. Into another 100-mL 3-necked round-bottom flask purged and maintained with an inert atmosphere of nitrogen, was added a solution of 4-(3-bromophenyl)-6,8-dichloro-2-methyl-1,2,3,4-tetrahydroisoquinoline (5.0 g, 1 equiv) in xylene (50 mL), Pd$_2$(dba)$_3$ (300 mg), Xantphos (300 mg). The resulting solution was stirred for 30 min at 25° C. and then added to the above reaction solution. The mixture was stirred overnight at 140° C. The resulting mixture was concentrated under vacuum. The residue was applied onto a silica gel column with ethyl acetate/petroleum ether (1:100~1:50). This resulted in 2.5 g (45%) of 4-(3-(benzylthio)phenyl)-6,8-dichloro-2-methyl-1,2,3,4-tetrahydroisoquinoline as a yellow oil.

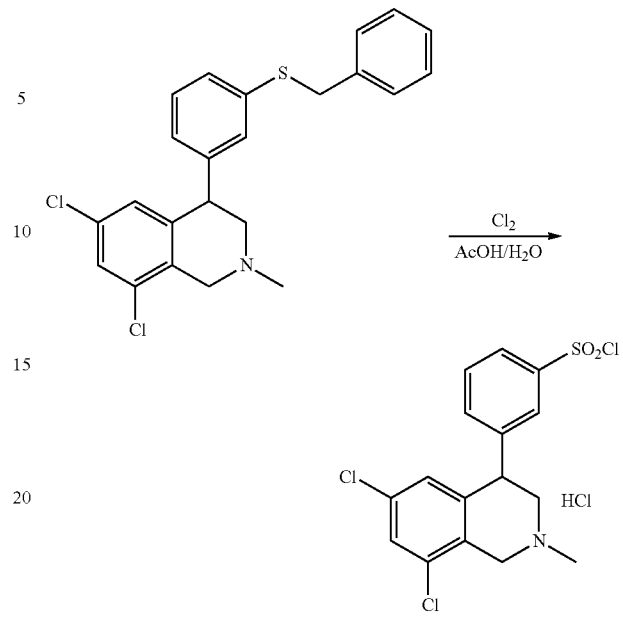

Intermediate 1.6: 3-(6,8-dichloro-2-methyl-1,2,3,4-tetrahydroisoquinolin-4-yl)benzene-1-sulfonyl chloride Into a 250-mL 3-necked round-bottom flask, was placed a solution of 4-(3-(benzylthio)phenyl)-6,8-dichloro-2-methyl-1,2,3,4-tetrahydroisoquinoline (8 g, 13.53 mmol, 1.00 equiv, 70%) in acetic acid/water (80/8 mL). Cl$_2$(g) was introduced and the resulting solution was stirred for 1 h at room temperature. The resulting mixture was concentrated under vacuum. This resulted in 5.0 g (90%) of 3-(6,8-dichloro-2-methyl-1,2,3,4-tetrahydroisoquinolin-4-yl)benzene-1-sulfonyl chloride hydrochloride as a yellowish solid.

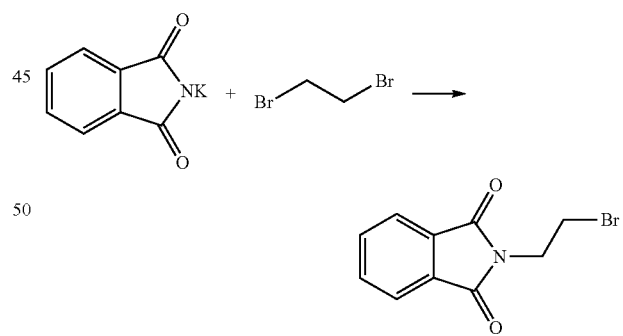

Intermediate 1.7: 2-(2-bromoethyl)isoindoline-1,3-dione

Into a 500-mL round-bottom flask, was placed a solution of 1,2-dibromoethane (30 g, 159.57 mmol, 2.95 equiv) in N,N-dimethylformamide (200 mL). This was followed by the addition of potassium phthalimide (10 g, 54.05 mmol, 1.00 equiv) in several batches. The resulting solution was stirred for 24 h at 60° C. The reaction was then quenched by the addition of 500 mL of water. The resulting solution was extracted with 2×200 mL of ethyl acetate and the organic layers combined and dried over anhydrous sodium sulfate and concentrated under vacuum. The residue was applied onto a silica gel column with ethyl acetate/petroleum ether (1:10). This resulted in 8 g (57%) of 2-(2-bromoethyl)isoindoline-1,3-dione as a white solid.

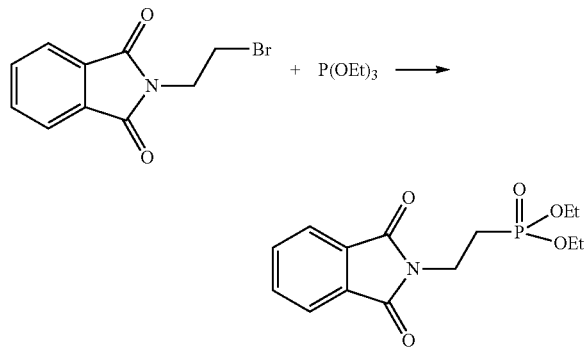

Intermediate 1.8: diethyl 2-(1,3-dioxoisoindolin-2-yl)ethylphosphonate

Into a 50-mL round-bottom flask purged and maintained with an inert atmosphere of nitrogen, was placed 2-(2-bromoethyl)isoindoline-1,3-dione (8 g, 31.50 mmol, 1.00 equiv) and triethyl phosphite (6.2 g, 37.35 mmol, 1.19 equiv). The resulting solution was stirred for 18 h at 130° C. The resulting mixture was concentrated under vacuum. The crude product was re-crystallized from ether:n-hexane (1:2). This resulted in 5 g (48%) of diethyl 2-(1,3-dioxoisoindolin-2-yl)ethylphosphonate as a white solid.

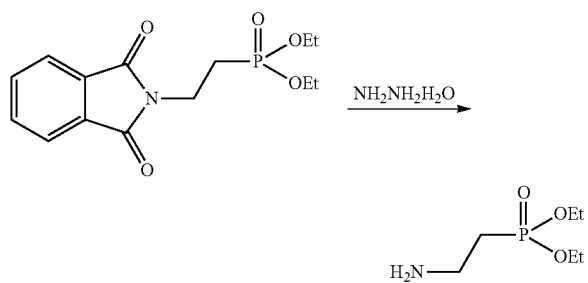

Intermediate 1.9: diethyl 2-aminoethylphosphonate

Into a 500-mL round-bottom flask purged and maintained with an inert atmosphere of nitrogen, was placed a solution of diethyl 2-(1,3-dioxoisoindolin-2-yl)ethylphosphonate (5 g, 16.08 mmol, 1.00 equiv) in ethanol (200 mL) and hydrazine hydrate (8 g, 160.00 mmol, 9.95 equiv). The resulting solution was stirred for 12 h at room temperature. The solids were filtered and the resulting mixture was concentrated under vacuum. The residue was applied onto a silica gel column and eluted with dichloromethane/methanol (9:1). This resulted in 1.5 g (51%) of diethyl 2-aminoethylphosphonate as colorless oil.

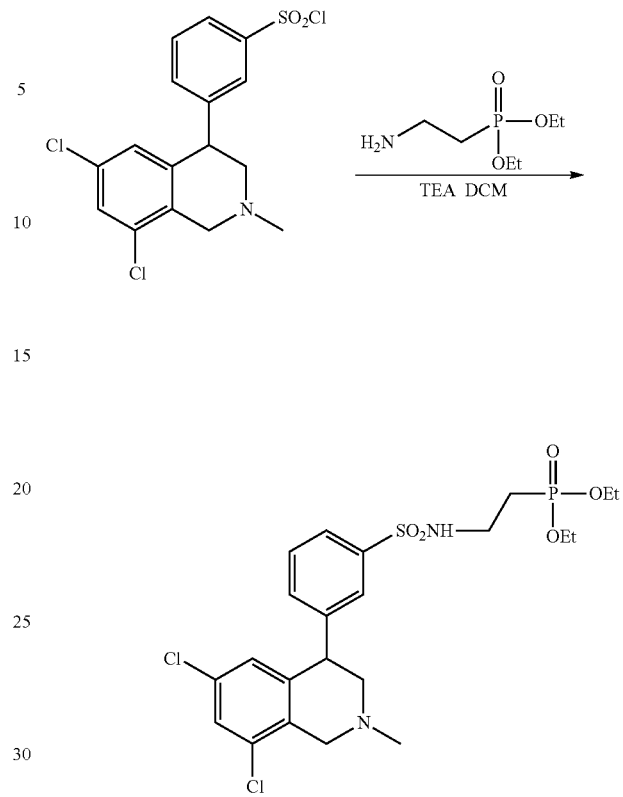

Intermediate 1.10: Diethyl 2-(3-(6,8-dichloro-2-methyl-1,2,3,4-tetrahydroisoquinolin-4-yl)phenylsulfonamido)ethylphosphonate Into a 50-mL round-bottom flask, was placed a solution of diethyl 2-aminoethylphosphonate (100 mg, 0.55 mmol, 1.00 equiv) in dichloromethane (10 mL) with TEA (220 mg, 2.18 mmol, 3.94 equiv). This was followed by the addition of 3-(6,8-dichloro-2-methyl-1,2,3,4-tetrahydroisoquinolin-4-yl)benzene-1-sulfonyl chloride (300 mg, 0.60 mmol, 1.08 equiv, 78%) in several batches. The resulting solution was stirred for 2 h at room temperature. The reaction progress was monitored by LCMS. The resulting mixture was concentrated under vacuum. The residue was applied onto a silica gel column with dichloromethane:methanol (50:1). This resulted in 0.07 g (24%) of the title compound as a colorless oil.

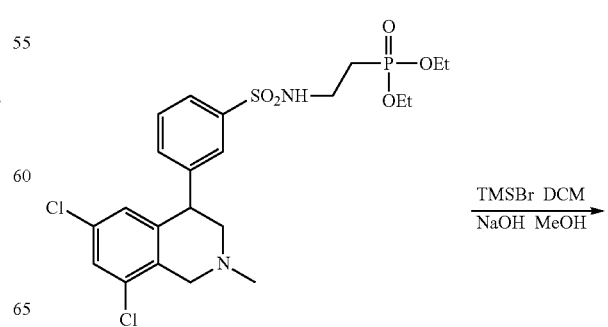

-continued

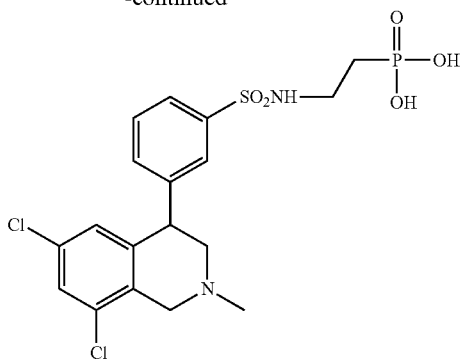

Compound 1: 2-(3-(6,8-dichloro-2-methyl-1,2,3,4-tetrahydroisoquinolin-4-yl)phenylsulfonamido)ethylphosphonic acid To a solution of Intermediate 1.10 (70 mg, 0.13 mmol, 1.00 equiv) in dichloromethane (10 mL) was added bromotrimethylsilane (200 mg, 1.32 mmol, 10.04 equiv). The resulting solution was stirred overnight at 40° C. in an oil bath. The reaction progress was monitored by LCMS. The resulting mixture was concentrated under vacuum. To the above was added methanol. The resulting mixture was concentrated under vacuum. This was followed by the addition of a solution of sodium hydroxide (11 mg, 0.28 mmol, 2.10 equiv) in methanol (2 mL). The resulting solution was stirred for an additional 1 h at room temperature. The resulting mixture was concentrated under vacuum. The solid was dried in an oven under reduced pressure. This resulted in 52.3 mg (73%) of the title compound as a sodium salt. $^1$H-NMR (300 MHz, CD$_3$OD, ppm): 7.82 (d, J=7.5 Hz, 1H), 7.73 (s, 1H), 7.56 (m, 1H), 7.48 (d, J=8.1 Hz, 1H), 7.41 (s, 1H), 6.88 (s, 1H), 4.54 (s, 1H), 3.97 (m, 2H), 3.17 (m, 3H), 2.97 (m, 1H), 2.67 (s, 3H), 1.68 (m, 2H). MS (ES, m/z): 479 [M+H]$^+$.

Example 2

4-(3-(6,8-dichloro-2-methyl-1,2,3,4-tetrahydroisoquinolin-4-yl)phenylsulfonamido)phenylphosphonic acid

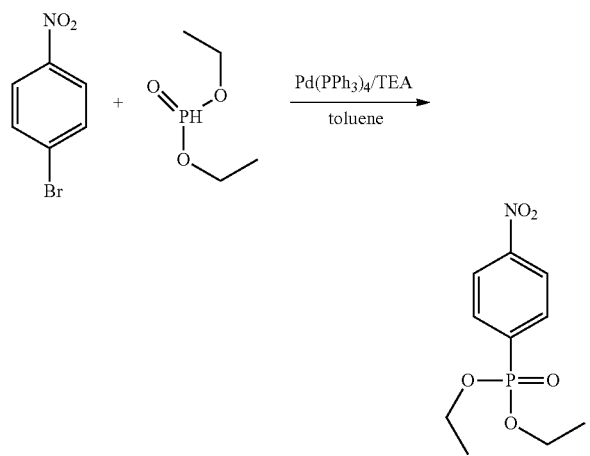

Intermediate 2.1: diethyl 4-nitrophenylphosphonate

Into a 100-mL 3-necked round-bottom flask purged and maintained with an inert atmosphere of nitrogen, was placed a solution of diethyl phosphonate (3.02 g, 21.88 mmol, 1.10 equiv) in toluene (10 mL), Pd(PPh$_3$)$_4$ (1.15 g, 1.00 mmol, 0.05 equiv), TEA (2.21 g, 21.88 mmol, 1.10 equiv), 1-bromo-4-nitrobenzene (4 g, 19.90 mmol, 1.00 equiv). The resulting solution was stirred for 15 h at 90° C. The solids were filtered out and the resulting mixture was concentrated under vacuum. The residue was applied onto a silica gel column and eluted with ethyl acetate/petroleum ether (1:2). This resulted in 3.53 g (68%) of diethyl 4-nitrophenylphosphonate as a yellow liquid.

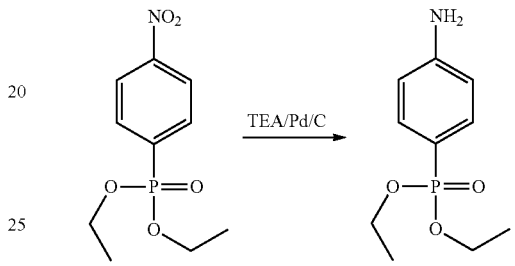

Intermediate 2.2: diethyl 4-aminophenylphosphonate

Into a 50-mL round-bottom flask, was placed a solution of diethyl 4-nitrophenylphosphonate (1.07 g, 4.13 mmol, 1.00 equiv), TEA (3 mL), Palladium carbon (0.025 g). This was followed by the addition of formic acid (2 mL) dropwise with stirring at room temperature. The resulting solution was heated to reflux for 3 hr. The reaction was then quenched by the addition of 5 mL of water and the solids were filtered out. The resulting filtrate was extracted with 5×10 mL of dichloromethane and the organic layers combined and dried over anhydrous sodium sulfate. This resulted in 800 mg (85%) of diethyl 4-aminophenylphosphonate as a white solid.

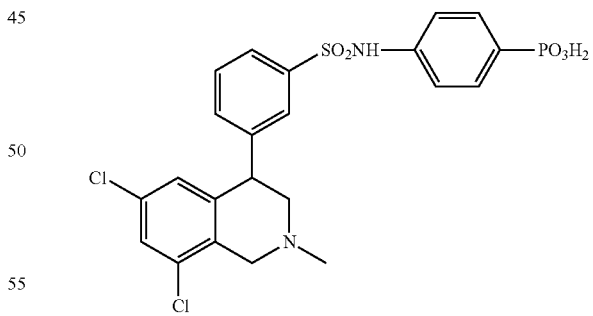

Compound 2: 4-(3-(6,8-dichloro-2-methyl-1,2,3,4-tetrahydroisoquinolin-4-yl)phenyl-sulfonamido)phenylphosphonic acid Compound 2 was prepared in an analogous manner to that of Compound 1 using diethyl 4-aminophenylphosphonate (Intermediate 2.2) as the amine. $^1$H-NMR (300 MHz, CD$_3$OD, ppm): 7.86 (d, 1H), 7.69 (m, 3H), 7.55 (m, 3H), 7.21

(m, 2H), 6.73 (s, 1H), 4.70 (m, 2H), 4.48 (d, 1H), 3.79 (m, 1H), 3.46 (m, 1H), 3.09 (s, 3H). MS (ES, m/z): 527 [M+H]+.

Example 3

4-(3-(6,8-dichloro-2-methyl-1,2,3,4-tetrahydroisoquinolin-4-yl)phenylsulfonamido)benzylphosphonic acid

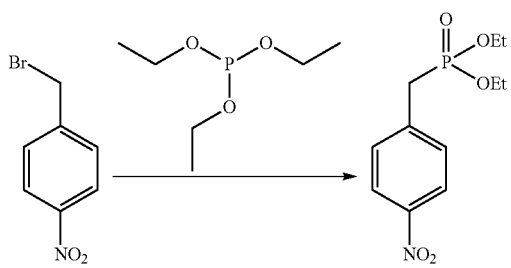

Intermediate 3.1: diethyl 4-nitrobenzylphosphonate

Into a 250-mL round-bottom flask, was placed 1-(bromomethyl)-4-nitrobenzene (15 g, 69.77 mmol, 1.00 equiv), triethyl phosphite (70 mL). The resulting solution was stirred for 2 h at 110° C. in an oil bath. The resulting mixture was concentrated under vacuum. The residue was applied onto a silica gel column with ethyl acetate/petroleum ether (1:10-1:1). This resulted in 17 g (89%) of the title compound as a yellow oil.

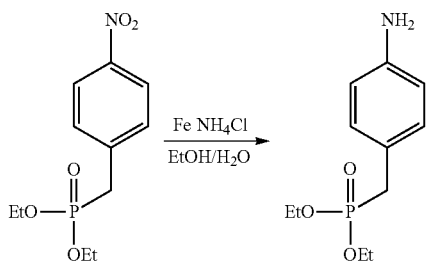

Intermediate 3.2: diethyl 4-aminobenzylphosphonate

Into a 100-mL 3-necked round-bottom flask, was placed a solution of diethyl 4-nitrobenzylphosphonate (5 g, 18.32 mmol, 1.00 equiv) in ethanol (50 mL) and a solution of NH$_4$Cl (2.9 g, 54.72 mmol, 2.99 equiv) in water (50 mL) was added. This was followed by the addition of Fe (4.1 g, 73.21 mmol, 4.00 equiv), while the temperature was maintained at reflux. The resulting solution was heated to reflux for 1 hr. The solids were filtered out. The resulting mixture was concentrated under vacuum. The resulting solution was extracted with 3×20 mL of ethyl acetate and the organic layers combined and dried over anhydrous sodium sulfate. The solids were filtered out. The resulting mixture was concentrated under vacuum. The residue was applied onto a silica gel column and eluted with ethyl acetate/petroleum ether (1:3). This resulted in 2.5 g (56%) of the title compound as a yellow solid.

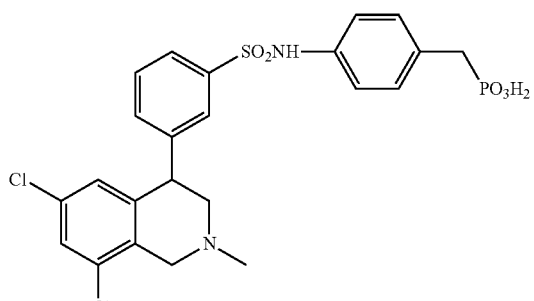

Compound 3: 4-(3-(6,8-dichloro-2-methyl-1,2,3,4-tetrahydroisoquinolin-4-yl)phenylsulfonamido)benzylphosphonic acid Compound 3 was prepared in an analogous manner to that of Compound 1 using diethyl 4-aminobenzylphosphonate (Intermediate 3.2) as the amine. $^1$H-NMR (300 MHz, CD$_3$OD, ppm): 7.89 (d, J=7.8 Hz, 1H), 7.61~7.66 (m, 1H), 7.52~7.54 (m, 2H), 7.21~7.20 (m, 2H), 7.11 (s, 1H), 6.95 (d, J=8.1 Hz, 2H), 6.73 (s, 1H), 4.51~4.59 (m, 3H), 3.33 (s, 1H), 3.03~2.89 (m, 6H). MS (ES, m/z): 541 [M+H]$^+$.

Example 4

3-(3-(6,8-dichloro-2-methyl-1,2,3,4-tetrahydroisoquinolin-4-yl)phenylsulfonamido)propylphosphonic acid

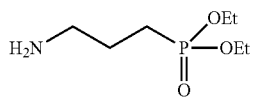

Intermediate 4.1: 3-diethyl 3-aminopropylphosphonate

Following the procedures outlined in Example 1, substituting dibromopropane for dibromoethane gave the title compound.

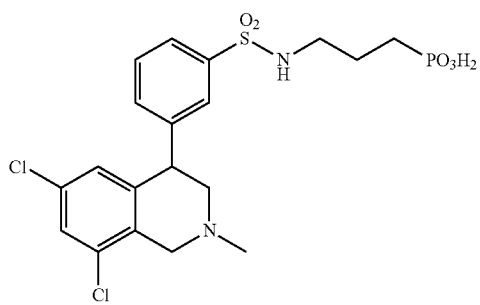

Compound 4 3-(3-(6,8-dichloro-2-methyl-1,2,3,4-tetrahydroisoquinolin-4-yl)phenylsulfonamido)propylphosphonic acid Compound 4 was prepared in an analogous manner to that of Compound 1 using 3-diethyl 3-aminopropylphosphonate (Intermediate 4.1) as the amine. ¹H-NMR (300 MHz, CD₃OD, ppm): 7.87 (d, J=8.1 Hz, 1H), 7.77 (s, 1H), 7.61~7.66 (m, 1H), 7.51~7.54 (m, 2H), 6.88 (s, 1H), 4.77~4.83 (m, 1H), 4.65 (d, J=16.2 Hz, 1H), 4.44 (d, J=15.6 Hz, 1H), 3.78~3.84 (m, 1H), 3.50~3.57 (m, 1H), 3.08 (s, 3H), 2.93~2.97 (m, 2H), 1.61~1.72 (m, 2H), 1.48~1.59 (m, 2H). MS (ES, m/z): 493 [M+H]⁺.

Example 5

(3-(6,8-dichloro-2-methyl-1,2,3,4-tetrahydroiso-quinolin-4-yl)phenylsulfonamido)methylphosphonic acid

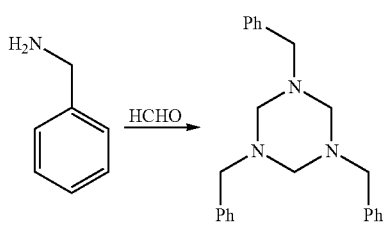

Intermediate 5.1: 1,3,5-tribenzyl-1,3,5-triazinane

Into a 100-mL 3-necked round-bottom flask was placed benzylamine (10 g, 93.46 mmol, 1.00 equiv), followed by the addition of formaldehyde (9.0 g, 1.20 equiv, 37%) dropwise with stirring at 0-10° C. To the precipitated gum was added 3M aqueous sodium hydroxide (20 mL), and the mixture was stirred. After standing in ice for 0.3 h, ether (30 mL) was added, and the mixture stirred until all precipitate dissolved. The aqueous phase was separated and extracted with ether. The solvents were removed under vacuum to afford 12 g (36%) of 1,3,5-tribenzyl-1,3,5-triazinane as colorless oil.

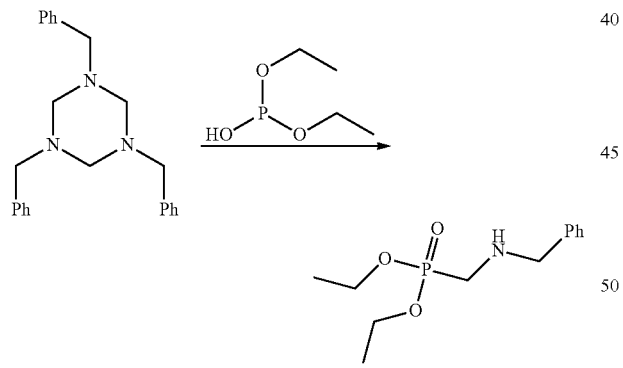

Intermediate 5.2: diethyl (benzylamino)methylphosphonate

Into a 50-mL 3-necked round-bottom flask purged and maintained with an inert atmosphere of nitrogen, was placed 1,3,5-tribenzyl-1,3,5-triazinane (3.0 g, 8.40 mmol, 1.00 equiv) and diethyl phosphite (3.5 g, 25.36 mmol, 3.00 equiv). The resulting solution was stirred for 3 h at 100° C. The residue was applied onto a silica gel column with ethyl acetate/petroleum ether (1:20 to 1:1). This resulted in 2.0 g (90%) of diethyl (benzylamino)methylphosphonate as a colorless oil.

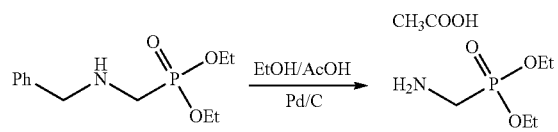

Intermediate 5.3: Diethyl aminomethylphosphonate

A 250-mL pressure tank reactor was purged, flushed and maintained with a hydrogen atmosphere, then, was added a solution of diethyl (benzylamino)methylphosphonate (3.5 g, 13.62 mmol, 1.00 equiv) in ethanol (180 mL), acetic acid (10 mL) and Palladium carbon (0.2 g, 0.10 equiv). The resulting solution was stirred for 24 h at 50° C. under 20 atm pressure. The solids were filtered out. The resulting mixture was concentrated under vacuum. This resulted in 2.0 g (crude) of the title compound as brown oil which was used without further purification.

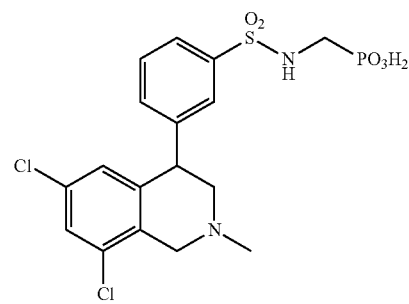

Compound 5: (3-(6,8-dichloro-2-methyl-1,2,3,4-tetrahydroisoquinolin-4-yl)phenylsulfonamido)methylphosphonic acid Compound 5 was prepared in an analogous manner to that of Compound 1 using diethyl aminomethylphosphonate (Intermediate 5.3) as the amine. ¹H-NMR (300 MHz, CD₃OD, ppm): 7.89 (d, J=7.8 Hz, 1H), 7.74 (s, 1H), 7.63~7.66 (m, 1H), 7.57~7.61 (m, 2H), 6.97 (s, 1H), 4.80~4.89 (m, 1H), 4.55~4.67 (m, 2H), 3.83~3.89 (m, 1H), 3.55~3.66 (m, 1H), 3.02~3.11 (m, 5H). MS (ES, m/z): 465 [M+H]⁺.

Example 6

4-((3-(6,8-dichloro-2-methyl-1,2,3,4-tetrahydroiso-quinolin-4-yl)phenylsulfonamido)methyl)ben-zylphosphonic acid

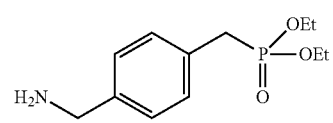 [SMILES: CCOP(=O)(Cc1ccc(CN)cc1)OCC]

Intermediate 6.1: 4-diethyl 4-(aminomethyl)benzylphosphonate

Following the procedures outlined in Example 1, substituting 1,4-bis(bromomethyl)benzene for dibromoethane gave the title compound.

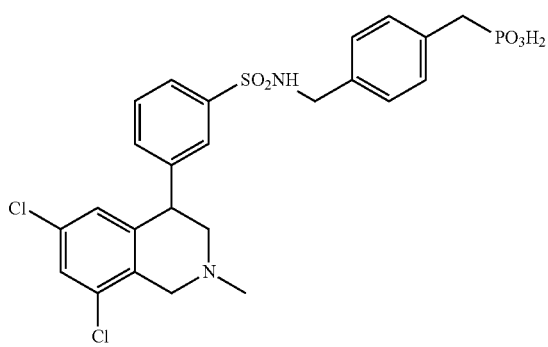

Compound 6 4-((3-(6,8-dichloro-2-methyl-1,2,3,4-tetrahydroisoquinolin-4-yl)phenylsulfonamido)methyl)benzylphosphonic acid Compound 6 was prepared in an analogous manner to that of Compound 1 using 4-diethyl 4-(aminomethyl)benzylphosphonate (Intermediate 6.1) as the amine. $^1$H-NMR (300 MHz, CD$_3$OD, ppm): 7.85~7.88 (m, 1H), 7.54~7.59 (m, 2H), 7.37~7.42 (m, 2H), 7.198~7.22 (m, 2H), 7.06~7.09 (m, 1H), 6.77 (s, 1H), 4.64 (m, J=16.2 Hz, 1H), 4.49~4.53 (m, 1H), 4.37 (m, J=16.5, 1H), 4.17 (s, 2H), 3.45~3.56 (m, 1H), 3.11~3.27 (m, 1H), 3.09~3.10 (m, 4H), 2.96~2.97 (m, 1H). MS (ES, m/z): 555 [M+H]$^+$.

Example 7

3-(3-(6,8-dichloro-2-methyl-1,2,3,4-tetrahydroisoquinolin-4-yl)phenylsulfonamido)propane-1-sulfonic acid

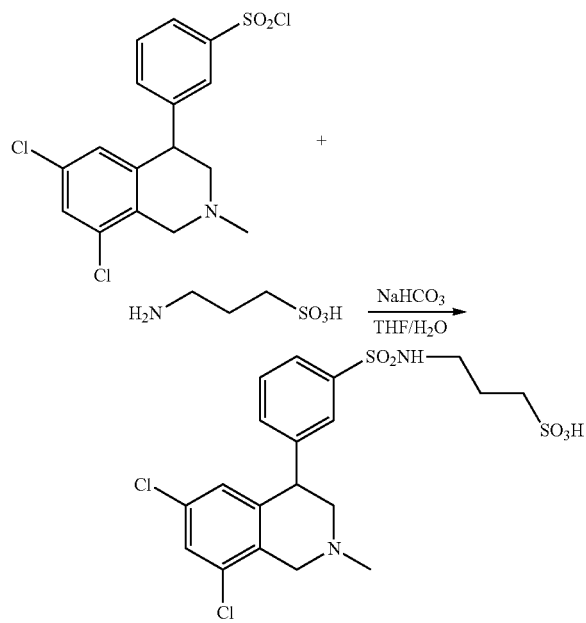

Compound 7: 3-(3-(6,8-dichloro-2-methyl-1,2,3,4-tetrahydroisoquinolin-4-yl)phenylsulfonamido)propane-1-sulfonic acid Into a 50-mL round-bottom flask, was placed a solution of 3-aminopropane-1-sulfonic acid (180 mg, 1.29 mmol, 1.00 equiv) in tetrahydrofuran/water (10/10 mL) with sodium bicarbonate (430 mg, 5.12 mmol). This was followed by the addition of 3-(6,8-dichloro-2-methyl-1,2,3,4-tetrahydroisoquinolin-4-yl)benzene-1-sulfonyl chloride (500 mg, 1.29 mmol, 0.99 equiv) in several batches. The resulting solution was stirred for 4 h at room temperature. The reaction progress was monitored by LCMS. The pH value of the solution was adjusted to 6 with 1M hydrogen chloride. The resulting mixture was concentrated under vacuum. The crude product (500 mg) was purified by preparative HPLC to give 26.7 mg of the title compound (4%) as a TFA salt. $^1$H-NMR (300 MHz, DMSO, ppm): 10.28 (s, 1H), 7.53~7.79 (m, 6H), 6.83 (s, 1H), 4.74 (s, 2H), 4.51 (s, 1H), 3.90 (s, 1H), 3.06 (s, 3H), 2.86~2.93 (m, 2H), 2.33~2.44 (m, 2H), 1.58~1.63 (m, 2H). MS (ES, m/z): 493 [M+H]$^+$.

Example 8

2-(3-(6,8-dichloro-2-methyl-1,2,3,4-tetrahydroisoquinolin-4-yl)-N-(phosphonomethyl)phenylsulfonamido)acetic acid

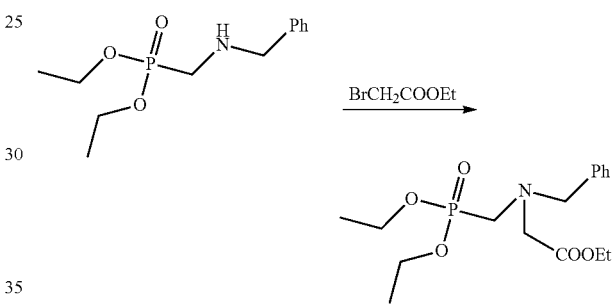

Intermediate 8.1: ethyl 2-(benzyl((diethoxyphosphoryl)methyl)amino)acetate

Into a 500-mL 3-necked round-bottom flask, was placed a solution of diethyl (benzylamino)methylphosphonate (intermediate 5.2) (12 g, 46.69 mmol, 1.00 equiv) in acetonitrile (150 mL), DIEA (12 g, 2.00 equiv). This was followed by the addition of ethyl 2-bromoacetate (8.4 g, 50.30 mmol, 1.10 equiv) dropwise with stirring. The mixture was stirred for 30 min at room temperature. The resulting solution was heated to reflux for 6 hr. The resulting mixture was cooled to room temperature and concentrated under vacuum. The residue was applied onto a silica gel column with ethyl acetate/petroleum ether (1:20 to 1:5). This resulted in 8.0 g (50%) of ethyl 2-(benzyl((diethoxyphosphoryl)methyl)amino)acetate as yellow oil.

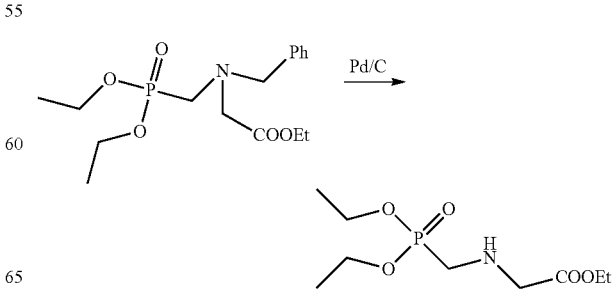

Intermediate 8.2: ethyl 2-((diethoxyphosphoryl)methylamino)acetate

A 250-mL pressure tank reactor was purged, flushed and maintained with a hydrogen atmosphere, then, was added a solution of ethyl 2-(benzyl((diethoxyphosphoryl)methyl)amino)acetate (8.0 g, 23.32 mmol, 1.00 equiv) in ethanol (180 mL), acetic acid (10 mL), Pd/C (0.9 g). The resulting solution was stirred at 20 atm for 32 h at 50° C. The solids were filtered out, and the resulting mixture was concentrated under vacuum. This resulted in 6.0 g (82%) of the acetic acid salt of ethyl 2-((diethoxyphosphoryl)methylamino)acetate as a brown oil.

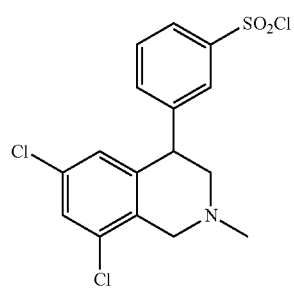

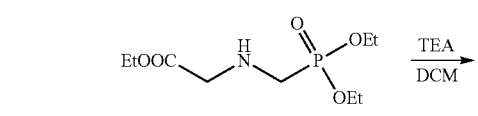

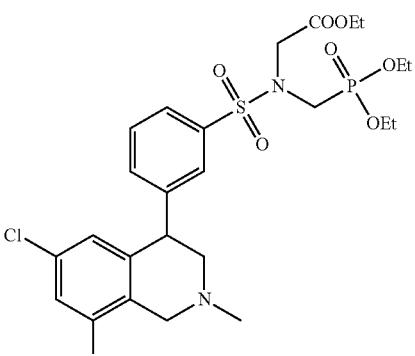

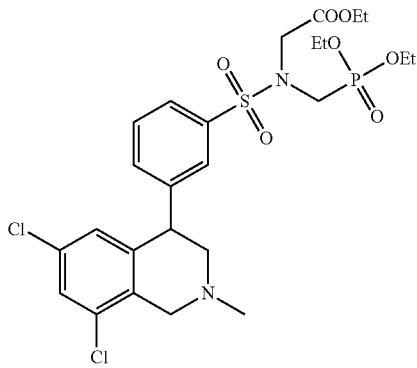

Intermediate 8.3: ethyl 2-(3-(6,8-dichloro-2-methyl-1,2,3,4-tetrahydroisoquinolin-4-yl)-N-((diethoxyphosphoryl)methyl)phenylsulfonamido)acetate Into a 50-mL round-bottom flask, was placed a solution of ethyl 2-((diethoxyphosphoryl)methylamino)acetate (320 mg, 1.26 mmol, 1.00 equiv) in pyridine (10 mL). 3-(6,8-dichloro-2-methyl-1,2,3,4-tetrahydroisoquinolin-4-yl)benzene-1-sulfonyl chloride (500 mg, 1.28 mmol, 1.01 equiv) was added and the resulting solution was stirred overnight at room temperature. The reaction progress was monitored by LCMS. The resulting mixture was concentrated under vacuum. The crude product (400 mg) was purified by preparative HPLC to give 200 mg (24%) of the title compound as a TFA salt.

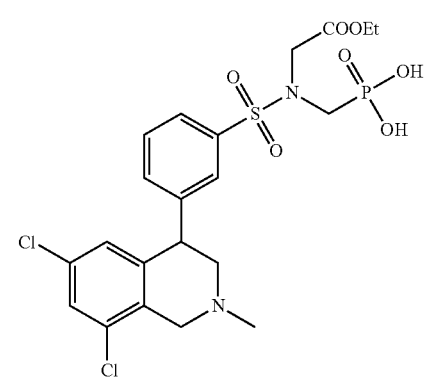

Intermediate 8.4: (3-(6,8-dichloro-2-methyl-1,2,3,4-tetrahydroisoquinolin-4-yl)-N-(2-ethoxy-2-oxoethyl)phenylsulfonamido)methylphosphonic acid Into a 50-mL round-bottom flask, was placed a solution of Intermediate 8.3 (200 mg, 0.33 mmol, 1.00 equiv) in dichloromethane (6 mL). Bromotrimethylsilane (502 mg, 3.30 mmol, 10.01 equiv) was added and the resulting solution was stirred overnight at 40° C. in an oil bath. The reaction progress was monitored by LCMS. The resulting mixture was concentrated under vacuum. The residue was dissolved in 10 mL of methanol. The resulting mixture was concentrated under vacuum. This resulted in 180 mg (99%) of the title compound as a yellow solid.

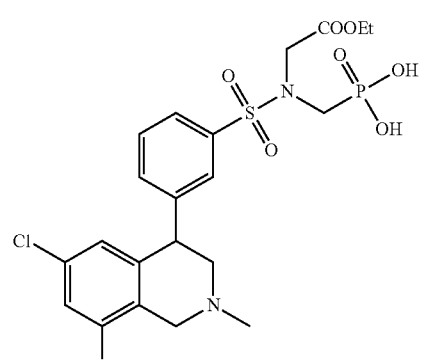

-continued

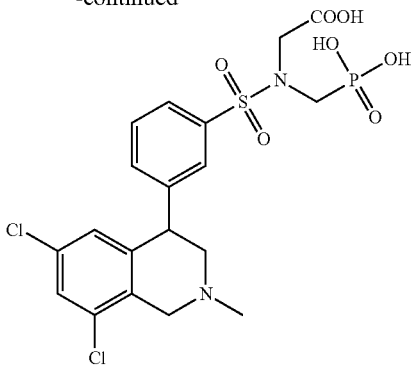

Compound 8: 2-(3-(6,8-dichloro-2-methyl-1,2,3,4-tetrahydroisoquinolin-4-yl)-N-(phosphonomethyl)phenylsulfonamido)acetic acid Into a 50-mL round-bottom flask, was placed a solution of (3-(6,8-dichloro-2-methyl-1,2,3,4-tetrahydroisoquinolin-4-yl)-N-(2-ethoxy-2-oxoethyl)phenylsulfonamido)methylphosphonic acid (Intermediate 8.4) (180 mg, 0.33 mmol, 1.00 equiv) in tetrahydrofuran/water (5/5 mL). This was followed by the addition of lithium hydroxide (39 mg, 1.62 mmol, 4.97 equiv) in several batches at room temperature. The resulting solution was stirred for 4 h at room temperature. The reaction progress was monitored by LCMS. The resulting mixture was concentrated under vacuum. The pH value of the solution was adjusted to 6 with 1M hydrogen chloride. The resulting mixture was concentrated under vacuum. The crude product (150 mg) was purified by preparative HPLC giving 59.2 mg (35%) of the title compound as a TFA salt. $^1$H-NMR (300 MHz, DMSO+D$_2$O, ppm): 7.73~7.74 (m, 1H), 7.67~7.68 (m, 1H), 7.58~7.62 (m, 2H), 7.49 (s, 1H), 7.00 (s, 1H), 4.71~4.75 (m, 1H), 4.49 (d, J=16.2 Hz, 1H), 4.33 (d, J=15.9 Hz, 1H), 4.07 (s, 2H), 3.62~3.64 (m, 1H), 3.45~3.54 (m, 2H), 3.31~3.40 (m, 1H), 2.88 (s, 3H). MS (ES, m/z): 523 [M+H]$^+$.

Example 9

2-(3-(6,8-dichloro-2-methyl-1,2,3,4-tetrahydroisoquinolin-4-yl)phenylsulfonamido)succinic acid

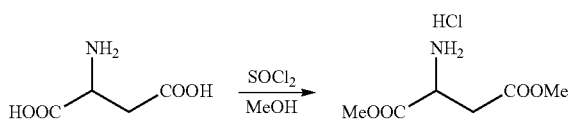 [SMILES: "MeOH" ; Cl ; NC(CC(=O)O)C(=O)O ; "SOCl2" ; COC(=O)CC(N)C(=O)OC]

Intermediate 9.1: Dimethyl 2-aminosuccinate hydrochloride

Into a 100-mL round-bottom flask, was placed a solution of 2-aminosuccinic acid (3 g, 22.56 mmol, 1.00 equiv) in methanol (20 mL). This was followed by the addition of thionyl chloride (10 g, 84.75 mmol, 3.76 equiv) dropwise with stirring at 0-5° C. The resulting solution was heated to reflux for 2 h in an oil bath. The resulting mixture was concentrated under vacuum. This resulted in 4.2 g (95%) of the title compound as a white solid.

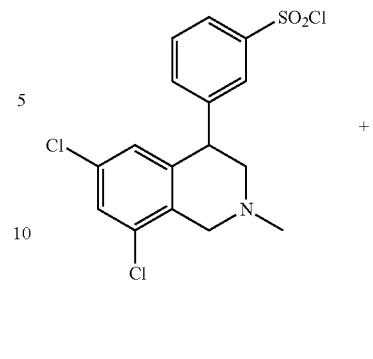

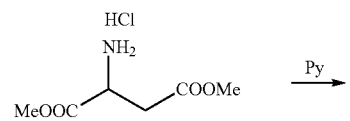

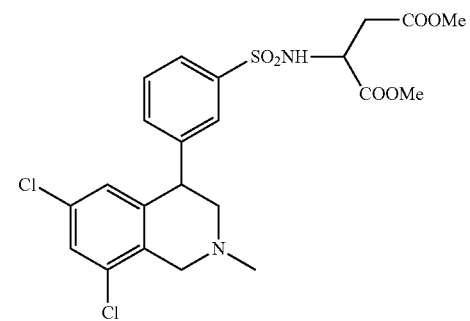

Intermediate 9.2: Dimethyl 2-(3-(6,8-dichloro-2-methyl-1,2,3,4-tetrahydroisoquinolin-4-yl)phenylsulfonamido)succinate Into a 50-mL round-bottom flask, was placed a solution of dimethyl 2-aminosuccinate hydrochloride (107 mg, 0.54 mmol, 1.00 equiv) in pyridine (5 mL). This was followed by the addition of 3-(6,8-dichloro-2-methyl-1,2,3,4-tetrahydroisoquinolin-4-yl)benzene-1-sulfonyl chloride (300 mg, 0.69 mmol, 1.27 equiv, 90%) in several batches. The resulting solution was stirred overnight at room temperature. The resulting mixture was concentrated under vacuum. The residue was applied onto a silica gel column with dichloromethane:methanol (50:1). This resulted in 200 mg (72%) of the title compound as a colorless oil

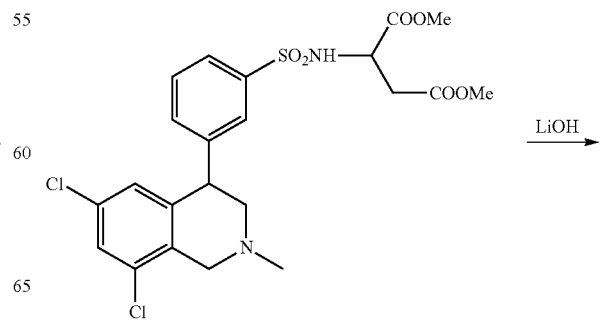

-continued

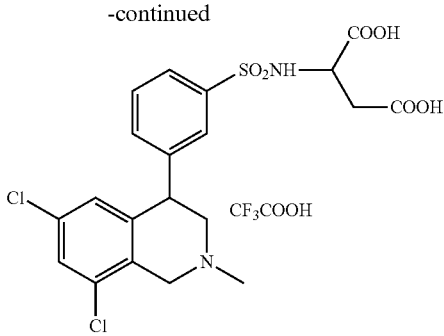

Compound 9: 2-(3-(6,8-dichloro-2-methyl-1,2,3,4-tetrahydroisoquinolin-4-yl)phenylsulfonamido)succinic acid Into a 50-mL round-bottom flask, was placed a solution of Intermediate 9.2 (100 mg, 0.19 mmol, 1.00 equiv) in tetrahydrofuran (5 mL) and water (5 mL). This was followed by the addition of LiOH (23 mg, 0.96 mmol, 4.93 equiv) in several batches at room temperature. The resulting solution was stirred for 2 h at room temperature. The reaction progress was monitored by LCMS. The resulting mixture was concentrated under vacuum. The pH value of the solution was adjusted to 6 with hydrogen chloride (1 mol/L). The solids were collected by filtration. The crude product (200 mg) was purified by preparative HPLC to give 12.1 mg (10%) the title compound as a TFA salt. $^1$H-NMR (300 MHz, CD$_3$OD, ppm): 7.89 (d, J=7.2 Hz, 1H), 7.80 (d, J=6.3 Hz, 1H), 7.64~7.52 (m, 3H), 6.95 (s, 1H), 4.78~4.70 (m, 2H), 4.55~4.50 (m, 1H), 4.23~4.17 (m, 1H), 3.87~3.82 (m, 1H), 3.63~3.57 (m, 1H), 3.12 (s, 3H), 2.79~2.65 (m, 2H). MS (ES, m/z): 487 [M-CF$_3$COOH+H]$^+$.

Example 10

2-(4-(6,8-dichloro-2-methyl-1,2,3,4-tetrahydroisoquinolin-4-yl)phenylsulfonamido)ethylphosphonic acid

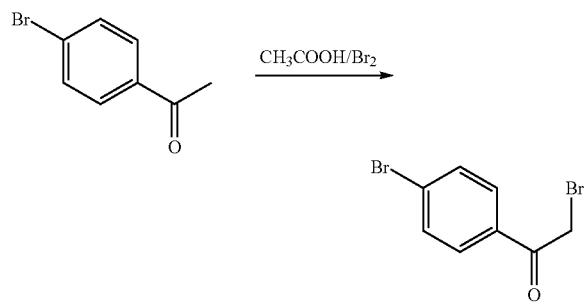

Intermediate 10.1: 2-bromo-1-(4-bromophenyl)ethanone

Into a 250-mL 3-necked round-bottom flask, was placed a solution of 1-(4-bromophenyl)ethanone (10.0 g, 50.25 mmol, 1.00 equiv) in acetic acid (50 mL). This was followed by the addition of a solution of bromine (8.2 g, 1.05 equiv) in acetic acid (50 mL) dropwise with stirring at 60° C. over 90 min. The resulting solution was stirred for 3 h at 60° C. The resulting mixture was concentrated under vacuum. The crude product was re-crystallized from petroleum ether/ethyl acetate in the ratio of 7:1. This resulted in 9.3 g (67%) of the title compound as a yellow solid.

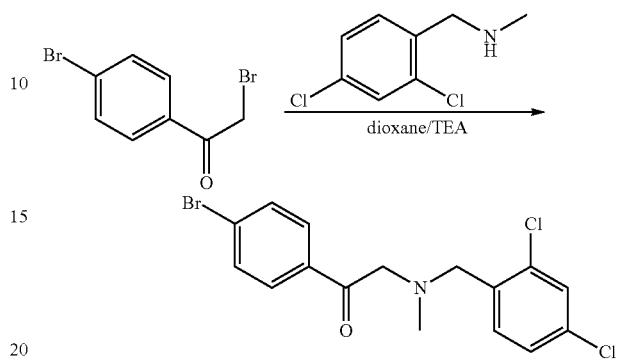

Intermediate 10.2: 1-(4-bromophenyl)-2-((2,4-dichlorobenzyl)(methyl)amino)ethanone Into a 250-mL 3-necked round-bottom flask purged and maintained with an inert atmosphere of nitrogen, was placed a solution of 2-bromo-1-(4-bromophenyl)ethanone (9.3 g, 33.45 mmol, 1.00 equiv) in dioxane (100 mL), triethylamine (5.0 g, 1.50 equiv), and (2,4-dichlorophenyl)-N-methyl-methanamine (6.4 g, 33.68 mmol, 1.00 equiv). The resulting solution was stirred for 2 h at 25° C. The solids were filtered out. The filtrate was used for next step directly.

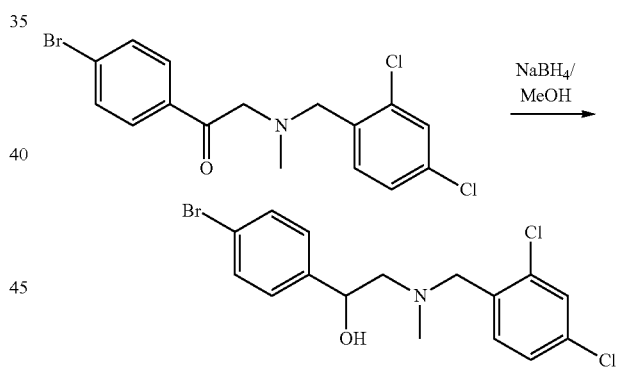

Intermediate 10.3: 2-((2,4-dichlorobenzyl)(methyl)amino)-1-(4-bromophenyl)ethanol Into a 500-mL 3-necked round-bottom flask purged and maintained with an inert atmosphere of nitrogen, was placed a solution of the crude Intermediate 10.2 in fresh methanol (100 mL). This was followed by the addition of sodium borohydride (2.5 g, 65.79 mmol, 2.00 equiv) in several batches at 0-5° C. The resulting solution was stirred for 1 h at 25° C. The reaction was then quenched by the addition of sat. NH$_4$Cl. The resulting mixture was concentrated under vacuum. The resulting solution was extracted with EtOAc (2×100 mL) and the organic layers combined and concentrated under vacuum. The crude product was re-crystallized from petroleum ether/ethyl acetate (60 mL) in the ratio of 7:1. This resulted in 6.5 g (50%) of the title compound as a white solid. MS (ES, m/z): 390 [M+H]$^+$.

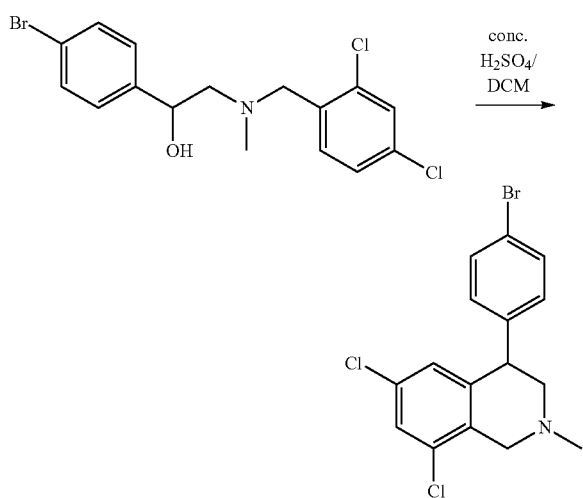

Intermediate 10.4: 4-(4-bromophenyl)-6,8-dichloro-2-methyl-1,2,3,4-tetrahydroisoquinoline Into a 50-mL 3-necked round-bottom flask, was placed a solution of 2-((2,4-dichlorobenzyl)(methyl)amino)-1-(4-bromophenyl)ethanol (1.0 g, 2.57 mmol, 1.00 equiv) in dichloromethane (3 mL). This was followed by the addition of conc.H$_2$SO$_4$ (2 mL) dropwise with stirring at 0-5° C. The resulting solution was stirred for 3 h at 20° C. The reaction was then quenched by the addition of water/ice. The pH value of the solution was adjusted to 9 with sodium hydroxide. The resulting solution was extracted with dichloromethane (2×30 mL) and the organic layers combined and dried over anhydrous sodium sulfate and concentrated under vacuum. This resulted in 0.9 g of the title compound which was used without further purification. MS (ES, m/z): 372 [M+H]$^+$.

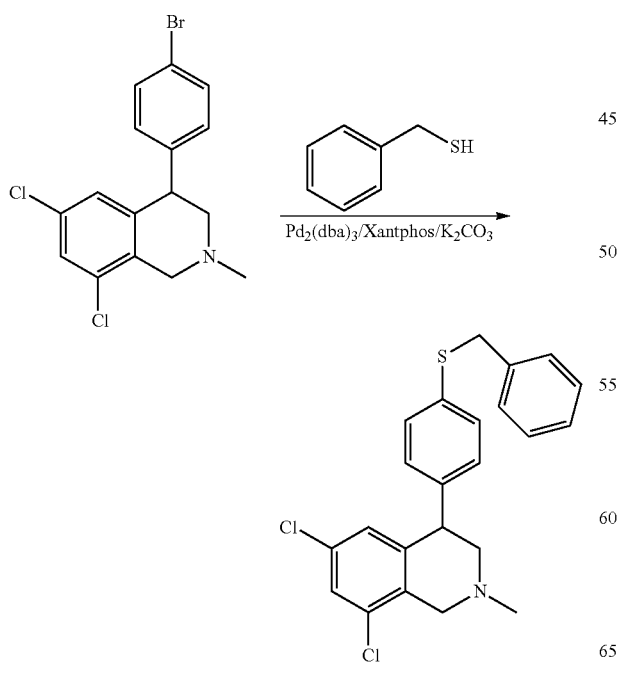

Intermediate 10.5: 4-(4-(benzylthio)phenyl)-6,8-dichloro-2-methyl-1,2,3,4-tetrahydroisoquinoline Into a 250-mL 3-necked round-bottom flask purged and maintained with an inert atmosphere of nitrogen, was placed K$_2$CO$_3$ (800 mg, 0.50 equiv) and xylene (50 mL). This was followed by the addition of phenylmethanethiol (1.75 g, 1.00 equiv) dropwise with stirring at 0° C. The resulting mixture was then allowed to warm to room temperature and stirred for 1 h. Into another 250-mL 3-necked round-bottom flask purged and maintained with an inert atmosphere of nitrogen, was placed 4-(4-bromophenyl)-6,8-dichloro-2-methyl-1,2,3,4-tetrahydroisoquinoline (4.8 g, 0.80 equiv), Xantphos (200 mg, 0.08 equiv) and Pd$_2$(dba)$_3$ (200 mg, 0.08 equiv) in xylene (30 mL). The mixture was stirred at room temperature for 20 min and transferred to the previously formed potassium thiolate. The dark solution was then purged with nitrogen and heated to 130° C. for 15 h. After cooling to room temperature, the mixture was concentrated under reduced pressure. The crude product was then purified by silica gel chromatography with ethyl acetate/petroleum ether (1:80~1:50) to afford 1.8 g (30%) of the title compound as yellow oil. MS (ES, m/z): 414 [M+H]$^+$.

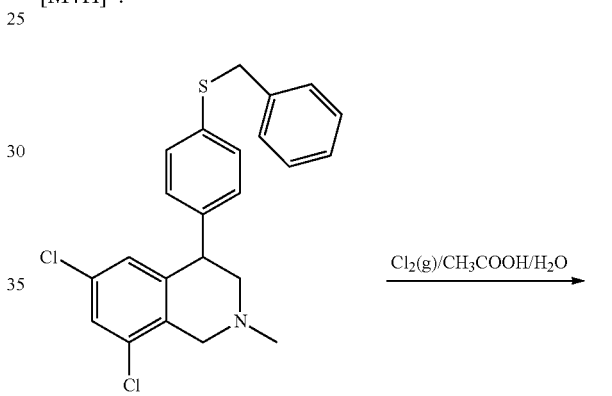

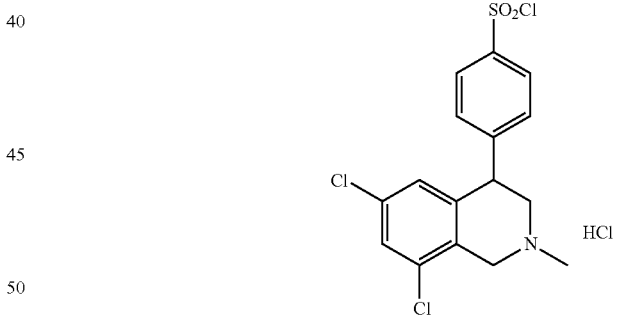

Compound 10.6: 4-(6,8-dichloro-2-methyl-1,2,3,4-tetrahydroisoquinolin-4-yl)benzene-1-sulfonyl chloride Into a 50-mL 3-necked round-bottom flask, was placed a solution of 4-(4-(benzylthio)phenyl)-6,8-dichloro-2-methyl-1,2,3,4-tetrahydroisoquinoline (250 mg, 0.60 mmol, 1.00 equiv) in acetic acid (8 mL), water (1 mL). To the above Cl$_2$(g) was introduced and the resulting solution was stirred for 30 min at 25° C. The resulting mixture was concentrated under vacuum. This resulted in 200 mg (85%) of the title compound as a yellow solid. MS (ES, m/z): 390 [M−HCl+H]$^+$.

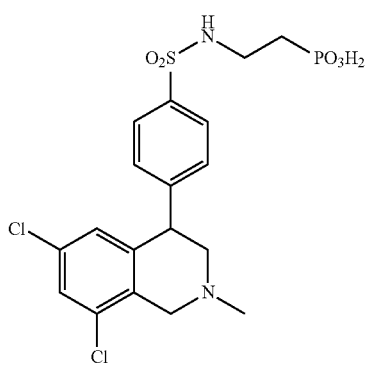

Compound 10: 2-(4-(6,8-dichloro-2-methyl-1,2,3,4-tetrahydroisoquinolin-4-yl)phenylsulfonamido)ethylphosphonic acid Following the procedures outlined in Example 1, 4-(6,8-dichloro-2-methyl-1,2,3,4-tetrahydroisoquinolin-4-yl)benzene-1-sulfonyl chloride (intermediate 10.6) was converted to compound 10. Purification by preparative HPLC gave a TFA salt of the title compound as a white solid. $^1$H-NMR (CD$_3$OD, 300 MHz, ppm): 7.93 (d, J=8.4 Hz, 2H), 7.58~7.51 (m, 3H), 6.89 (s, 1H), 4.89~4.80 (m, 2H), 4.56~4.51 (m, 1H), 3.95~3.90 (m, 1H), 3.69~3.65 (m, 1H), 3.21~3.10 (m, 5H), 2.01~1.89 (m, 2H). MS (ES, m/z): 479 [M+H]$^+$.

Example 11

(4-(6,8-dichloro-2-methyl-1,2,3,4-tetrahydroisoquinolin-4-yl)phenylsulfonamido)methylphosphonic acid

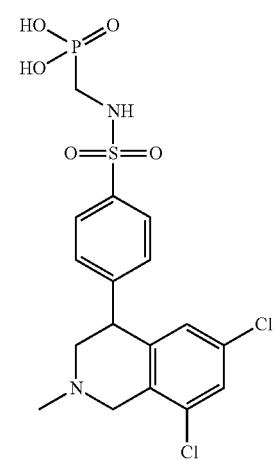 [SMILES: CN1Cc2c(Cl)cc(Cl)cc2C(c2ccc(S(=O)(=O)NCP(=O)(O)O)cc2)C1]

Compound 11: (4-(6,8-dichloro-2-methyl-1,2,3,4-tetrahydroisoquinolin-4-yl)phenylsulfonamido)methylphosphonic acid Following the procedures outlined in Example 1, compound 11 was made using 4-(6,8-dichloro-2-methyl-1,2,3,4-tetrahydroisoquinolin-4-yl)benzene-1-sulfonyl chloride (intermediate 10.6) and diethyl aminomethylphosphonate (intermediate 5.3). Purification by preparative HPLC gave a TFA salt of the title compound. $^1$H-NMR (300 MHz, DMSO+D$_2$O, ppm): 7.87 (d, J=8.4 Hz, 2H), 7.68 (d, J=1.5 Hz, 1H), 7.48 (d, J=9.4 Hz, 2H), 6.80 (s, 1H), 4.74~4.66 (m, 1H), 4.46~4.40 (m, 1H), 3.82~3.77 (m, 1H), 3.69~3.39 (m, 1H), 3.01 (s, 3H), 2.91~2.74 (m, 2H). MS 465 [M+H]$^+$.

Example 12

3-(4-(6,8-dichloro-2-methyl-1,2,3,4-tetrahydroisoquinolin-4-yl)phenylsulfonamido)propylphosphonic acid

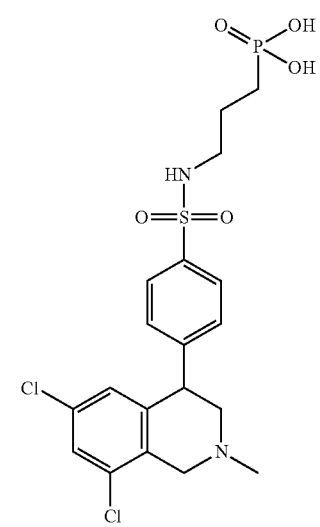 [SMILES: CN1Cc2c(Cl)cc(Cl)cc2C(c2ccc(S(=O)(=O)NCCCP(=O)(O)O)cc2)C1]

Compound 12: 3-(4-(6,8-dichloro-2-methyl-1,2,3,4-tetrahydroisoquinolin-4-yl)phenylsulfonamido)propylphosphonic acid Following the procedures outlined in Example 1, compound 12 was made using 4-(6,8-dichloro-2-methyl-1,2,3,4-tetrahydroisoquinolin-4-yl)benzene-1-sulfonyl chloride (intermediate 10.6) and 3-diethyl 3-aminopropylphosphonate (intermediate 4.1). Purification by preparative HPLC gave a TFA salt of the title compound $^1$H-NMR (300 MHz, CD$_3$OD, ppm): 7.90 (d, J=8.4, 2H), 7.55 (s, 1H), 7.46 (d, J=8.1 Hz, 2H), 6.88 (s, 1H), 4.77~4.82 (m, 1H), 4.71 (d, J=16.2 Hz, 1H), 4.47 (d, J=15.9 Hz, 1H), 3.80~3.86 (m, 1H), 3.54~3.61 (m, 1H), 3.11 (s, 3H), 2.95~2.99 (m, 2H), 1.53~1.71 (m, 4H). MS 493 [M+H]⁺.

Example 13

(4-(4-(6,8-dichloro-2-methyl-1,2,3,4-tetrahydroisoquinolin-4-yl)phenylsulfonamido)phenyl)methylphosphonic acid

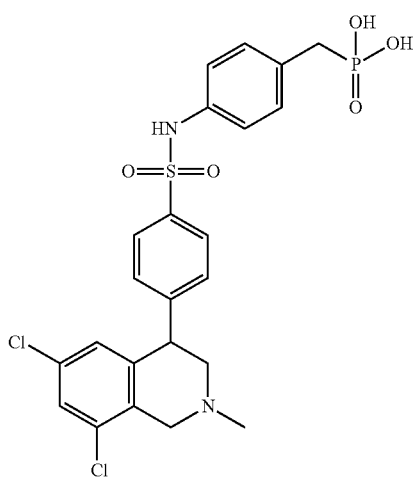 [SMILES: CN1Cc2c(Cl)cc(Cl)cc2C(c2ccc(S(=O)(=O)Nc3ccc(CP(=O)(O)O)cc3)cc2)C1]

Compound 13: (4-(4-(6,8-dichloro-2-methyl-1,2,3,4-tetrahydroisoquinolin-4-yl)phenylsulfonamido)phenyl)methylphosphonic acid Following the procedures outlined in Example 1, compound 13 was made using 4-(6,8-dichloro-2-methyl-1,2,3,4-tetrahydroisoquinolin-4-yl)benzene-1-sulfonyl chloride (intermediate 10.6) and 4-aminobenzylphosphonate (intermediate 3.2). Purification by preparative HPLC gave a TFA salt of the title compound. ¹H-NMR (300 MHz, DMSO+ D₂O, ppm): 7.69 (d, J=8.4 Hz, 2H), 7.46~7.46 (m, 1H), 7.34 (d, J=8.4 Hz, 2H), 7.07 (d, J=7.8 Hz, 2H), 6.94 (d, J=8.1 Hz, 2H), 6.71~6.71 (m, 1H), 4.36~4.40 (m, 1H), 3.65~3.80 (m, 2H), 2.95~3.01 (m, 1H), 2.72~2.79 (m, 3H), 2.41 (s, 3H). MS (ES, m/z): 541 [M+H]⁺.

Example 14

(4-((4-(6,8-dichloro-2-methyl-1,2,3,4-tetrahydroisoquinolin-4-yl)phenylsulfonamido)methyl)phenyl)methylphosphonic acid

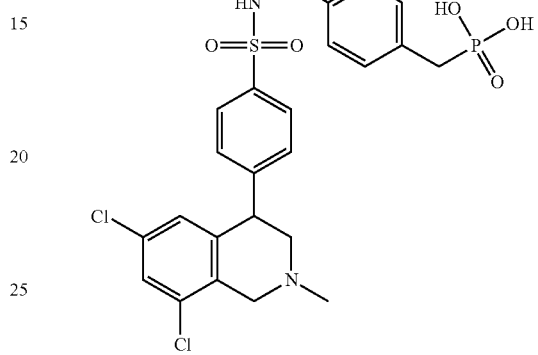

Compound 14: (4-((4-(6,8-dichloro-2-methyl-1,2,3,4-tetrahydroisoquinolin-4-yl)phenylsulfonamido)methyl)phenyl)methylphosphonic acid Following the procedures outlined in Example 1, compound 14 was made using 4-(6,8-dichloro-2-methyl-1,2,3,4-tetrahydroisoquinolin-4-yl)benzene-1-sulfonyl chloride (intermediate 10.6) and 4-(aminomethyl)benzylphosphonate (intermediate 6.1). Purification by preparative HPLC gave a TFA salt of the title compound. ¹H-NMR (300 MHz, DMSO+ D₂O, ppm): 7.71 (d, J=8.4 Hz, 2H), 7.50 (m, 1H), 7.40 (d, J=8.4 Hz, 2H), 7.06~7.15 (m, 4H), 6.86~6.87 (m, 1H), 4.38~4.40 (m, 1H), 3.95 (s, 2H), 3.75 (d, J=16.2 Hz, 1H), 3.53 (m, 1H), 2.85~2.92 (m, 3H), 2.69~2.75 (m, 1H), 2.41 (s, 3H). MS (ES, m/z): 555 [M+H]⁺.

Example 15

3,3'-(4-(6,8-dichloro-2-methyl-1,2,3,4-tetrahydroisoquinolin-4-yl)phenylsulfonylazanediyl)dipropanoic acid

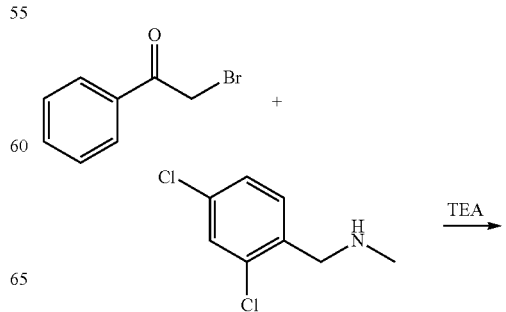

-continued

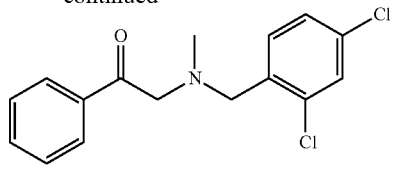

Intermediate 15.1: 2-((2,4-dichlorobenzyl)(methyl)amino)-1-phenylethanone

Into a 50-mL 3-necked round-bottom flask purged and maintained with an inert atmosphere of nitrogen, was placed a solution of 2-bromo-1-phenylethanone (1 g, 5.05 mmol, 1.00 equiv) in 1,4-dioxane (20 mL) and (2,4-dichlorophenyl)-N-methylmethanamine (1.1 g, 5.82 mmol, 1.15 equiv). Triethylamine (2 g, 19.80 mmol, 3.92 equiv) was added dropwise with stirring at 20° C. The resulting solution was stirred for 1 h at 20° C. in an oil bath. The solids were filtered out. The resulting mixture was concentrated under vacuum. The residue was applied onto a silica gel column with ethyl acetate/petroleum ether (1:50). This resulted in 1.4 g (90%) of the title compound as a yellow oil.

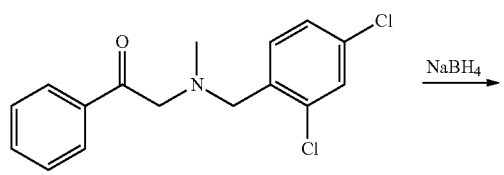

Intermediate 15.2: 2-((2,4-dichlorobenzyl)(methyl)amino)-1-phenylethanol

Into a 250 ml 3-necked roundbottom flask purged and maintained with an inert atmosphere of nitrogen, was placed a solution of 2-((2,4-dichlorobenzyl)(methyl)amino)-1-phenylethanone (4.3 g, 14.01 mmol, 1.00 equiv) in methanol (50 mL). This was followed by the addition of NaBH$_4$ (1.5 g, 39.47 mmol, 2.82 equiv) in several batches at 0° C. The resulting solution was stirred for 30 min at 0° C. in a water/ice bath. The reaction was then quenched by the addition of 20 mL of acetone. The resulting mixture was concentrated under vacuum. The residue was applied onto a silica gel column with ethyl acetate/petroleum ether (1:80~1:20). This resulted in 3.4 g (79%) of the title compound as a white solid.

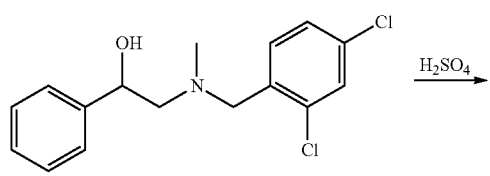

-continued

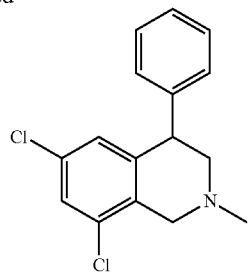

Intermediate 15.3: 6,8-dichloro-2-methyl-4-phenyl-1,2,3,4-tetrahydroisoquinoline Into a 100-mL 3-necked round-bottom flask, was placed a solution of 2-((2,4-dichlorobenzyl)(methyl)amino)-1-phenylethanol (3.4 g, 11.00 mmol, 1.00 equiv) in dichloromethane (15 mL). This was followed by the addition of sulfuric acid (15 mL) dropwise with stirring at 0° C. The resulting solution was stirred for 2 h at 0° C. in a water/ice bath. The pH value of the solution was adjusted to 7 with 1M sodium hydroxide. The resulting solution was extracted with ethyl acetate (3×60 mL) and the combined organic layers dried over anhydrous sodium sulfate and concentrated under vacuum. The residue was applied onto a silica gel column with petroleum ether:ethyl acetate (80:1). This resulted in 1.6 g (50%) of the title compound as a colorless oil.

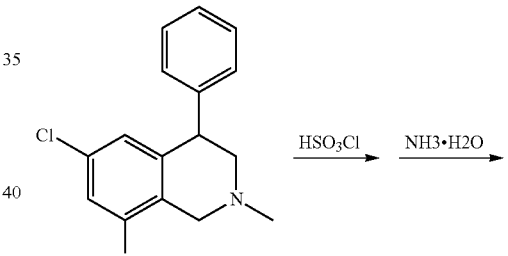

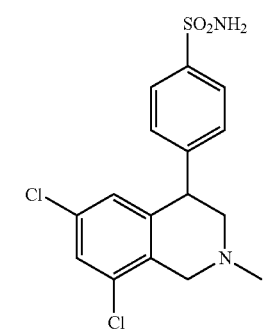

Intermediate 15.4: 4-(6,8-dichloro-2-methyl-1,2,3,4-tetrahydroisoquinolin-4-yl)benzenesulfonamide Into a 100-mL 3-necked round-bottom flask purged and maintained with an inert atmosphere of nitrogen, was placed chlorosulfonic acid (4 mL). This was followed by the dropwise addition of a solution of 6,8-dichloro-2-methyl-4-phenyl-1,2,3,4-tetrahydroisoquinoline (1.6 g, 5.5 mmol, 1.00 equiv) in dichloromethane (30 mL) at 0° C. The resulting solution was stirred for 1 h at 0° C. in a water/ice bath and for an additional 1 h at 25° C. in an oil bath. To this was added chlorosulfonic acid (16 mL) dropwise at 25° C. The resulting solution was stirred for an additional 1 h at 25° C. To the resulting mixture was cooled to 0° C. and aqueous ammonia (120 mL) was added dropwise. The resulting solution was stirred for an additional 3 h 90° C. in an oil bath. The resulting mixture was concentrated under vacuum. The residue was dissolved in 20 mL of water. The resulting solution was extracted with dichloromethane (3×30 mL) and the combined organic layers concentrated under vacuum. The residue was applied onto a silica gel column with dichloromethane/methanol (100:1). The crude product (0.5 g) was purified by preparative HPLC to give 53 mg (3%) of the title compound as a TFA salt. $^1$H-NMR (300 MHz, CDCl$_3$, ppm): 7.89 (1H, d, J=8.4 Hz), 7.35 (2H, d, J=8.4 Hz), 7.30 (1H, m), 6.77 (1H, s), 4.87 (1H, s), 4.39 (1H, s), 3.69 (2H, m), 2.98 (1H, t), 2.67 (1H, dd), 2.55 (3H, s). MS (ES, m/z): 371 [M+H]$^+$.

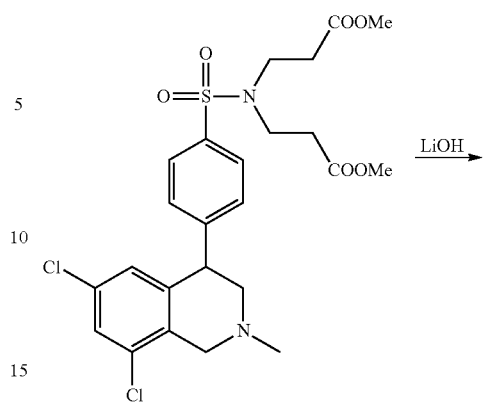

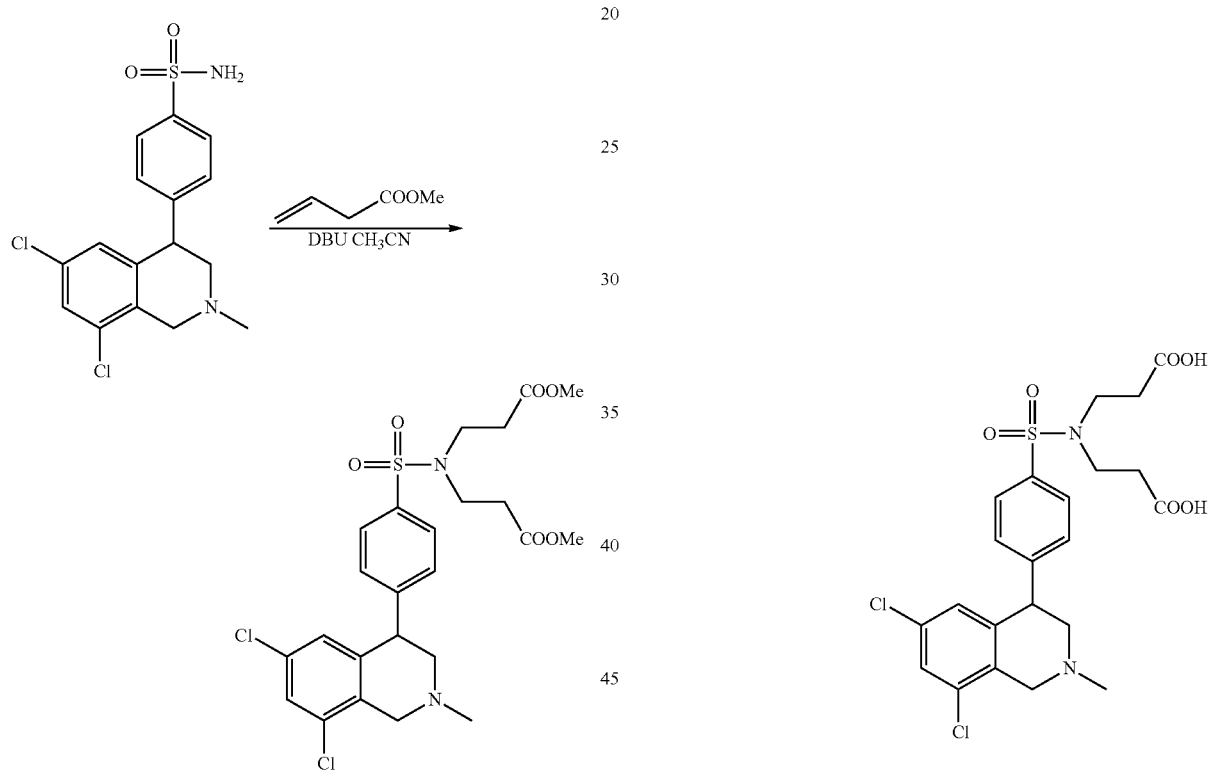

Intermediate 15.5: dimethyl 3,3'-(4-(6,8-dichloro-2-methyl-1,2,3,4-tetrahydroisoquinolin-4-yl)phenylsulfonylazanediyl)dipropanoate Into a 50-mL 3-necked round-bottom flask purged and maintained with an inert atmosphere of nitrogen, was placed a solution of 4-(6,8-dichloro-2-methyl-1,2,3,4-tetrahydroisoquinolin-4-yl)benzenesulfonamide (Compound 15.4, 100 mg, 0.27 mmol, 1.00 equiv) in acetonitrile (5 mL). Methyl but-3-enoate (40 mg, 0.40 mmol, 1.48 equiv) was added, along with 1,8-Diazabicyclo[5.4.0]undec-7-ene (DBU, 20 mg, 0.13 mmol, 0.49 equiv). The resulting solution was stirred overnight at 25° C. in an oil bath. Removing the solvent under vacuum gave the title compound which was used without further purification.

Compound 15: 3,3'-(4-(6,8-dichloro-2-methyl-1,2,3,4-tetrahydroisoquinolin-4-yl)phenylsulfonylazanediyl)dipropanoic acid Into a 50-mL 3-necked round-bottom flask purged and maintained with an inert atmosphere of nitrogen, was placed a solution of Intermediate 15.5 (140 mg, 0.26 mmol, 1.00 equiv, theoretical yield) in tetrahydrofuran (5 mL) and water (5 mL). LiOH (20 mg, 0.83 mmol, 3.23 equiv) was added and the resulting solution was stirred for 1 h at room temperature. The resulting mixture was concentrated under vacuum. The residue was applied onto a silica gel column with dichloromethane/methanol (100:1~20:1). This resulted in 0.015 g (11%) of the title compound as a white solid. $^1$H-NMR (300 MHz, CD$_3$OD, ppm): 7.84 (d, J=8.1 Hz, 2H), 7.41 (d, J=8.4 Hz, 2H), 7.35 (s, 1H), 6.84 (s, 1H), 4.39 (t, 1H), 3.77 (d, 1H), 3.67 (d, 1H), 3.45 (m, 1H), 3.33 (m, 4H), 2.69 (d, 1H), 3.0 (m, 1H), 2.47 (m, 6H). MS (ES, m/z): 515 [M+H]⁺.

Example 16

N,N',N''-(2,2',2''-nitrilotris(ethane-2,1-diyl))tris(3-(6,8-dichloro-2-methyl-1,2,3,4-tetrahydroisoquinolin-4-yl)benzenesulfonamide

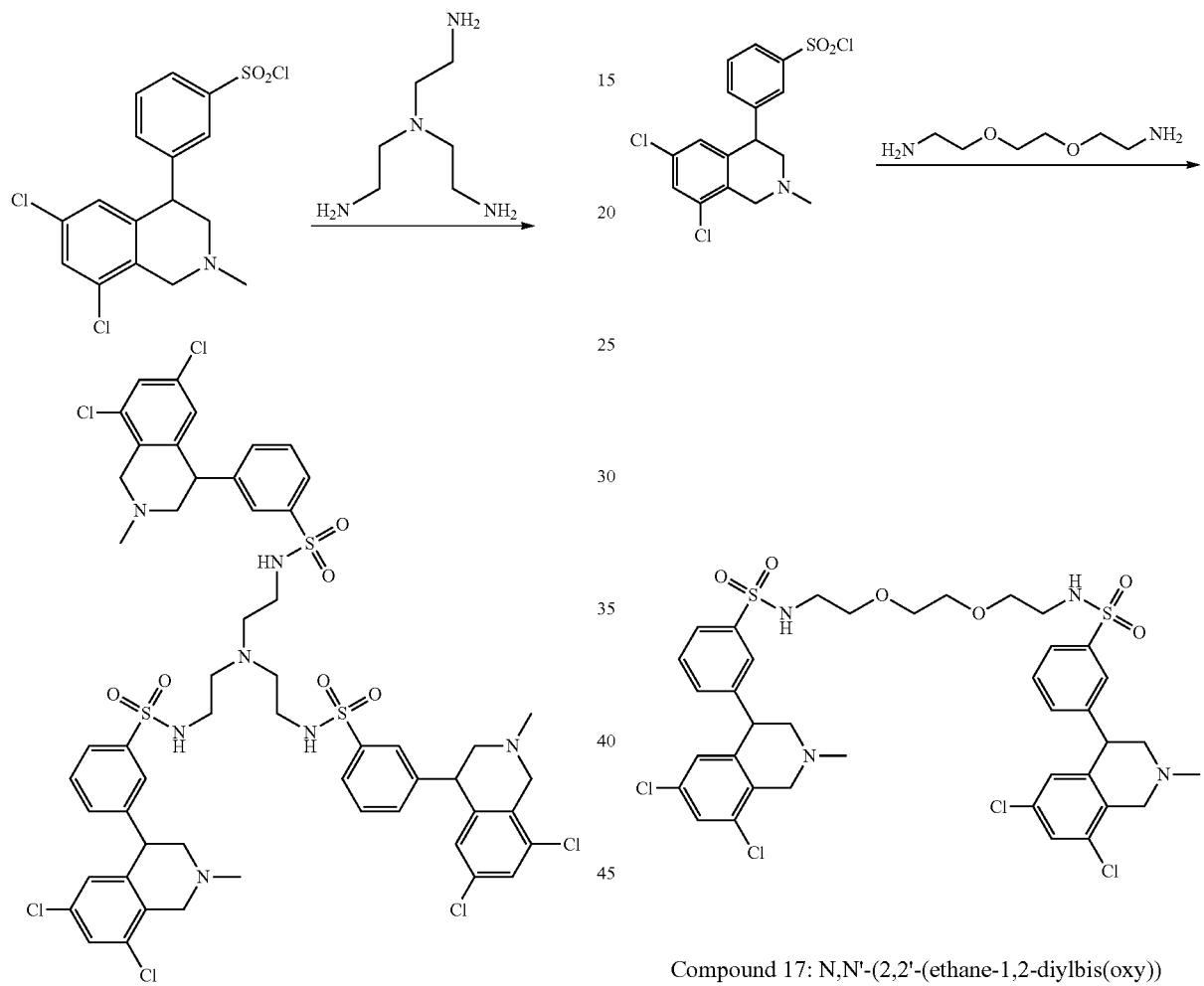

Compound 16: N,N',N''-(2,2',2''-nitrilotris(ethane-2,1-diyl))tris(3-(6,8-dichloro-2-methyl-1,2,3,4-tetrahydroisoquinolin-4-yl)benzenesulfonamide)

To a solution of 3-(6,8-dichloro-2-methyl-1,2,3,4-tetrahydroisoquinolin-4-yl)benzene-1-sulfonyl chloride (intermediate 1.6) (100 mg, 0.235 mmol) in DMF (1.5 mL) was added TEA (94.94 mg, 0.94 mmol) and a solution of N1,N1-bis(2-aminoethyl)ethane-1,2-diamine (11.45 mg, 0.0783 mmol) in 0.1 mL DMF. The reaction was stirred for 40 minutes at which point LCMS indicated no starting material remained. The solvent was removed and the residue dissolved in 50% acetic acid in water and purified by preparative HPLC to yield the title compound (25.4 mg) as a TFA salt. ¹H-NMR (400 MHz, d₆-DMSO): δ7.77 (s, 1H), 7.75 (s, 1H), 7.64 (s, 1H), 7.59 (m, 3H), 6.76 (s, 1H), 4.70 (m, 1H), 4.38 (m, 1H), 3.90 (br m, 8H), 3.26 (m, 1H), 3.95 (s, 3H), 2.65 (m, 2H). MS (m/z): 1210.01 (M+H).

Example 17

N,N'-(2,2'-(ethane-1,2-diylbis(oxy))bis(ethane-2,1-diyl))bis(3-(6,8-dichloro-2-methyl-1,2,3,4-tetrahydroisoquinolin-4-yl)benzenesulfonamide)

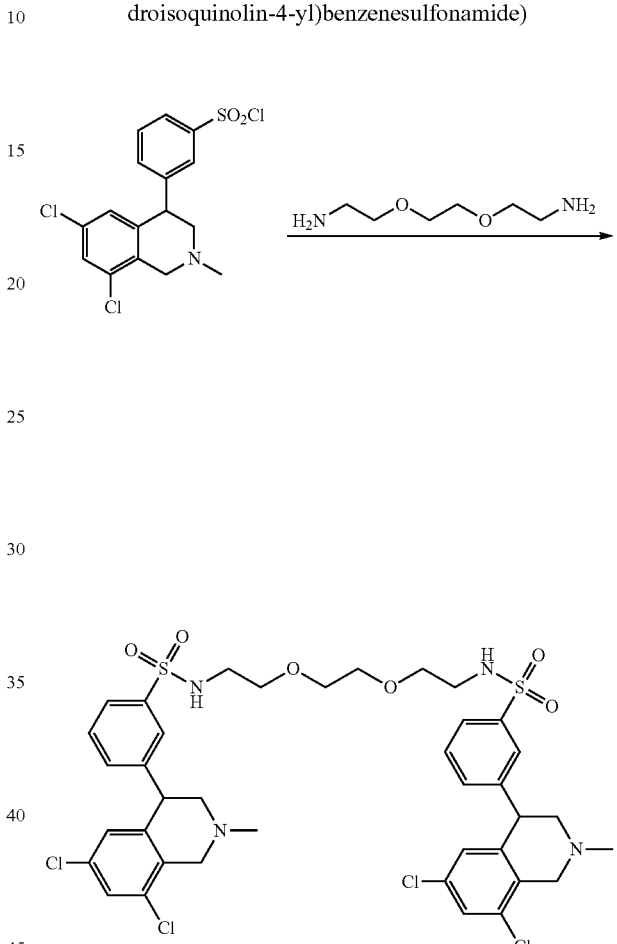

Compound 17: N,N'-(2,2'-(ethane-1,2-diylbis(oxy)) bis(ethane-2,1-diyl))bis(3-(6,8-dichloro-2-methyl-1,2,3,4-tetrahydroisoquinolin-4-yl)benzenesulfonamide)

To a solution of 2,2'-(ethane-1,2-diylbis(oxy))diethanamine (26.17 mg, 0.176 mmol) in chloroform (0.223 mL) at 0° C. was added diisopropylethylamine (DIEA, 182 mg, 1.412 mmol) and a solution of 3-(6,8-dichloro-2-methyl-1,2,3,4-tetrahydroisoquinolin-4-yl)benzene-1-sulfonyl chloride (intermediate 1.6) (150 mg, 0.353 mmol) in chloroform (0.706 mL). The resulting solution was stirred for 10 minutes at which point the solvent was removed and the residue taken up in 50% isopropanol/water mixture and purified by preparative HPLC. The title compound was obtained (44.5 mg) as a TFA salt. ¹H-NMR (400 MHz, CD₃OD): δ 7.87 (d, 1H), 7.78 (d, 1H), 7.64 (t, 1H), 7.55 (d, 1H), 7.51 (d, 1H), 6.81 (s, 1H), 4.47 (d, 1H), 3.83 (dd, 1H), 3.59 (t, 1H), 3.43 (m, 2H), 3.12 (s, 4H), 3.01 (q, 2H). MS (m/z): 857.17 (M+H).

Example 18

N,N'-(1,4-phenylenebis(methylene))bis(3-(6,8-dichloro-2-methyl-1,2,3,4-tetrahydroisoquinolin-4-yl)benzenesulfonamide)

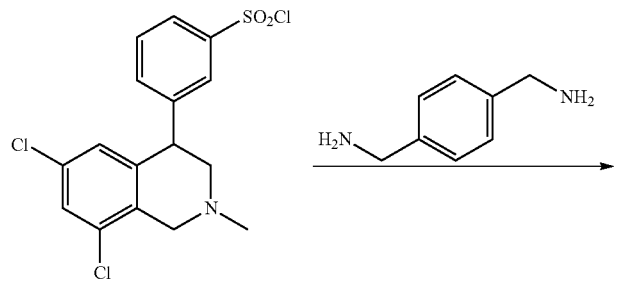

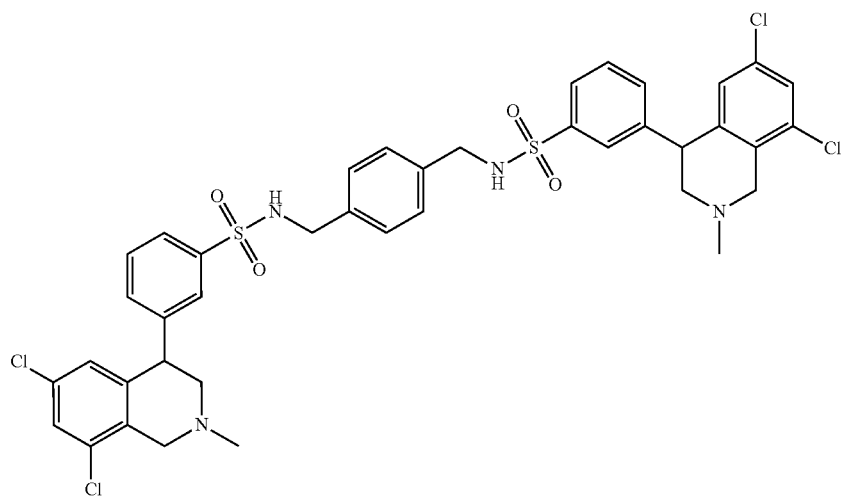

Compound 18: N,N'-(1,4-phenylenebis(methylene))bis(3-(6,8-dichloro-2-methyl-1,2,3,4-tetrahydroisoquinolin-4-yl)benzenesulfonamide)

Following the procedures outlined in Example 17, compound 18 was made using 1,4-phenylenedimethanamine as the amine. Purification by preparative HPLC gave the title compound as a TFA salt. $^1$H-NMR (400 MHz, CD$_3$OD): δ 7.87 (d, 2H), 7.67 (s, 2H), 7.52 (m, 4H), 7.49 (d, 2H), 7.09 (s, 4H), 6.82 (s, 2H), 4.78 (m, 7H), 4.43 (d, 2H), 4.00 (s, 4H), 3.82 (dd, 2H), 3.51 (t, 2H), 3.11 (s, 6H). MS (m/z): 845.03 (M+H).

Example 19

N,N'-(butane-1,4-diyl)bis(3-(6,8-dichloro-2-methyl-1,2,3,4-tetrahydroisoquinolin-4-yl)benzenesulfonamide)

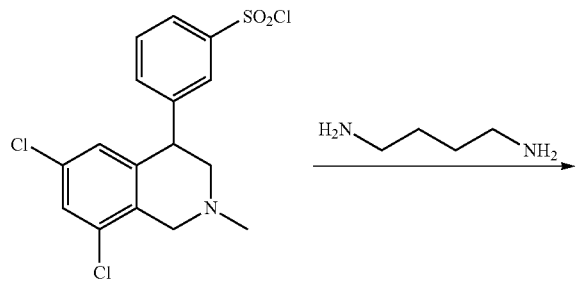

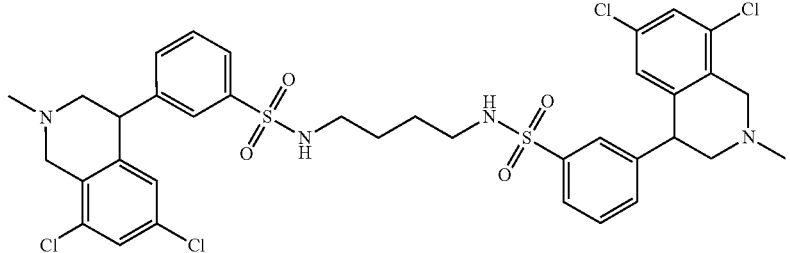

Compound 19: N,N'-(butane-1,4-diyl)bis(3-(6,8-dichloro-2-methyl-1,2,3,4-tetrahydroisoquinolin-4-yl)benzenesulfonamide)

Following the procedures outlined in Example 17, compound 19 was made using butane-1,4-diamine as the amine. Purification by preparative HPLC gave the title compound as a TFA salt. $^1$H-NMR (400 MHz, CD$_3$OD): δ 7.85 (d, 2H), 7.80 (s, 2H), 7.63 (t, 2H), 7.54 (t, 4H), 6.82 (s, 2H), 4.49 (d, 1H), 3.88 (dd, 2H), 3.58 (t, 2H), 3.14 (s, 6H), 2.81 (m, 4H), 1.42 (m, 4H). MS (m/z): 797.19 (M+H).

Example 20

N,N'-(dodecane-1,12-diyl)bis(3-(6,8-dichloro-2-methyl-1,2,3,4-tetrahydroisoquinolin-4-yl)benzenesulfonamide)

Compound 20: N,N'-(dodecane-1,12-diyl)bis(3-(6,8-dichloro-2-methyl-1,2,3,4-tetrahydroisoquinolin-4-yl)benzenesulfonamide)

Following the procedures outlined in Example 17, compound 20 was made using dodecane-1,12-diamine as the amine. Purification by preparative HPLC gave the title compound as a TFA salt. $^1$H-NMR (400 MHz, CD$_3$OD): δ7.85 (d, 2H), 7.71 (s, 2H), 7.63 (t, 2H), 7.54 (m, 4H), 6.81 (s, 2H), 4.74 (m, 2H), 4.51 (d, 2H), 3.86 (dd, 2H), 3.29 (t, 2H), 3.13 (s, 7H), 2.79 (t, 4H), 1.39 (m, 4H), 1.22 (m, 20H). MS (m/z): 909.28 (M+H).

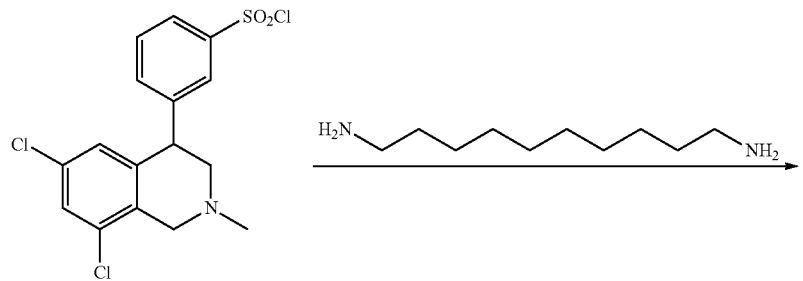

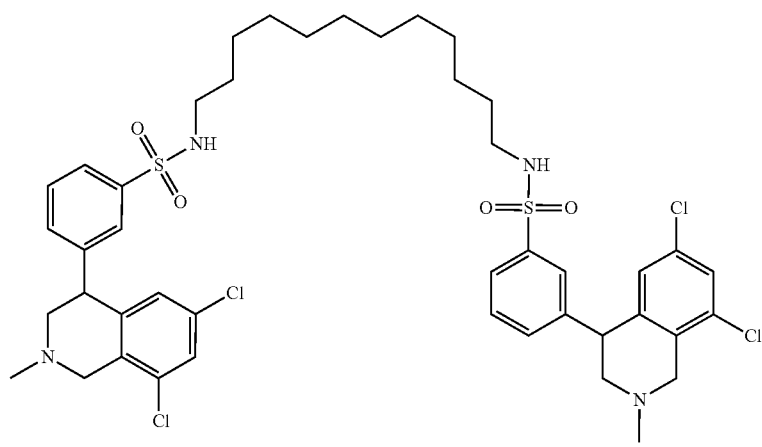

Example 21

N,N',N'',N'''-(3,3',3'',3'''-(butane-1,4-diylbis(azanetriyl))tetrakis(propane-3,1-diyl))tetrakis(3-(6,8-dichloro-2-methyl-1,2,3,4-tetrahydroisoquinolin-4-yl)benzenesulfonamide)

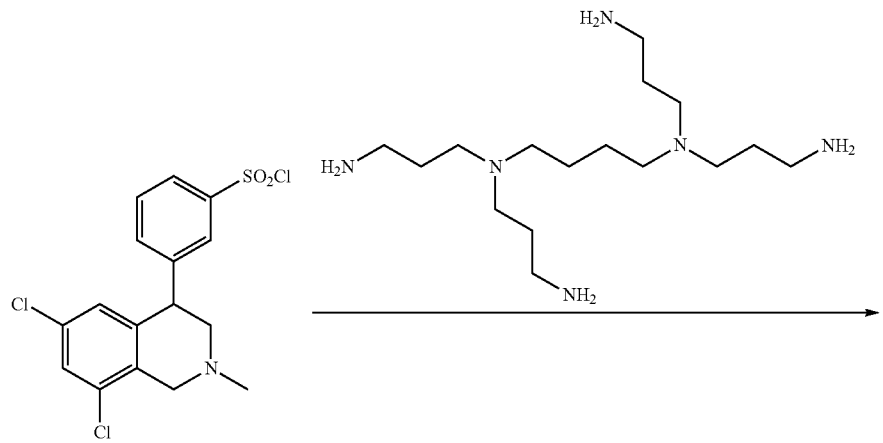

Compound 21: N,N',N'',N'''-(3,3',3'',3'''-(butane-1,4-diylbis(azanetriyl))tetrakis(propane-3,1-diyl))tetrakis(3-(6,8-dichloro-2-methyl-1,2,3,4-tetrahydroisoquinolin-4-yl)benzenesulfonamide)

To a solution of 3-(6,8-dichloro-2-methyl-1,2,3,4-tetrahydroisoquinolin-4-yl)benzene-1-sulfonyl chloride (intermediate 1.6) (150 mg, 0.352 mmol) in THF/H$_2$O (0.704 mL, 50% v/v) was added DIEA (181.6 mg, 1.41 mmol) and finally N1,N1'-(butane-1,4-diyl)bis(N1-(3-aminopropyl)propane-1,3-diamine) (27.94 mg, 0.08825 mmol). The reaction mixture was stirred vigorously for 1 hour at which point the solvent was removed. The resulting residue was brought up in 50% acetonitrile/water and purified by preparative HPLC to give the title compound (117 mg) as a TFA salt. $^1$H-NMR (400 MHz, CD$_3$OD): δ7.85 (d, 2H), 7.78 (s, 2H), 7.62 (t, 2H), 7.36 (m, 4H), 6.79 (s, 2H), 4.78 (m, 4H), 4.47 (d, 2H), 3.86 (dd, 2H), 3.55 (t, 2H), 3.12 (s, 6H), 2.94 (m, 4H), 1.90 (m, 4H), 1.85 (m, 2H). MS (m/z): 1732.90 (M+H).

Example 22

N,N'-(butane-1,4-diyl)bis(4-(6,8-dichloro-2-methyl-1,2,3,4-tetrahydroisoquinolin-4-yl)benzenesulfonamide)

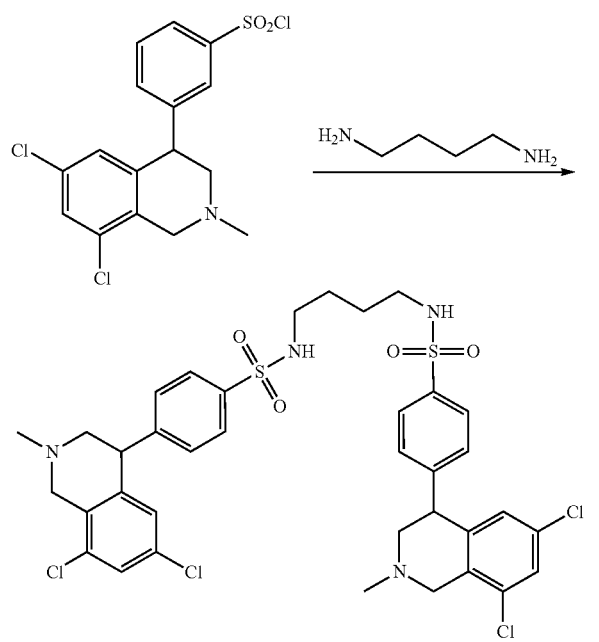

Compound 22: N,N'-(butane-1,4-diyl)bis(4-(6,8-dichloro-2-methyl-1,2,3,4-tetrahydroisoquinolin-4-yl)benzenesulfonamide)

To a solution of 4-(6,8-dichloro-2-methyl-1,2,3,4-tetrahydroisoquinolin-4-yl)benzene-1-sulfonyl chloride (intermediate 10.6) (150 mg, 0.353 mmol) in chloroform (0.706 mL) was added DIEA (182 mg, 1.412 mmol) and a solution of butane-1,4-diamine (15.5 mg, 0.176 mmol) in chloroform (0.176 mL). The reaction was stirred overnight at which point the solvent was removed and the resulting residue brought up in 50% IPA/H$_2$O. Purification by preparative HPLC gave the title compound (18.4 mg) as a TFA salt. $^1$H-NMR (400 MHz, CD$_3$OD): δ7.86 (d, 4H), 7.53 (s, 2H), 7.45 (d, 4H), 6.84 (s, 2H), 4.73 (m, 3H), 4.46 (d, 2H), 3.86 (dd, 2H), 3.57 (t, 2H), 3.12 (s, 6H), 2.84 (m, 4H), 1.41 (m, 4H). MS (m/z): 797.15 (M+H).

Example 23

N,N'-(dodecane-1,12-diyl)bis(4-(6,8-dichloro-2-methyl-1,2,3,4-tetrahydroisoquinolin-4-yl)benzenesulfonamide)

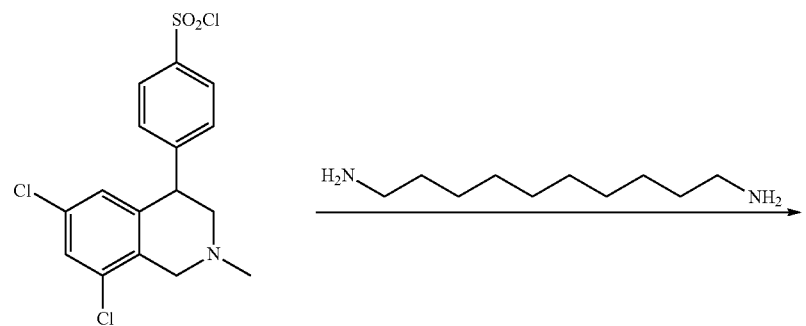

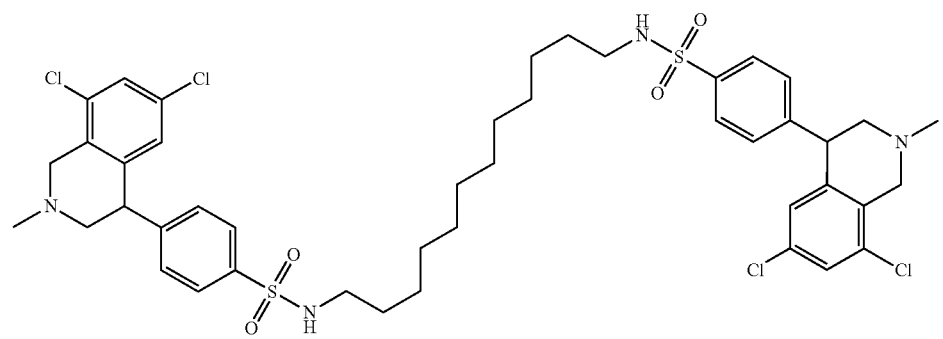

Compound 23: N,N'-(dodecane-1,12-diyl)bis(4-(6,8-dichloro-2-methyl-1,2,3,4-tetrahydroisoquinolin-4-yl)benzenesulfonamide)

Following the procedures outlined in Example 22, compound 23 was made using dodecane-1,12-diamine as the amine. Purification by preparative HPLC gave the title compound as a TFA salt. $^1$H-NMR (400 MHz, CD$_3$OD): 7.89 (d, 4H), 7.54 (m, 2H), 7.42 (m, 4H), 6.82 (s, 2H), 4.85 (m, 3H), 4.72 (d, 2H), 3.85 (dd, 2H), 3.59 (t, 2H), 3.13 (m, 8H), 2.85 (m, 4H), 1.89 (m, 5H), 1.33 (m, 23H). MS (m/z): 909.21 (M+H).

Example 24

N,N',N''-(2,2',2''-nitrilotris(ethane-2,1-diyl))tris(4-(6,8-dichloro-2-methyl-1,2,3,4-tetrahydroisoquinolin-4-yl)benzenesulfonamide)

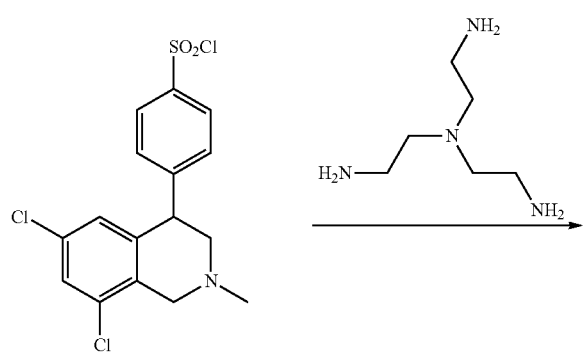

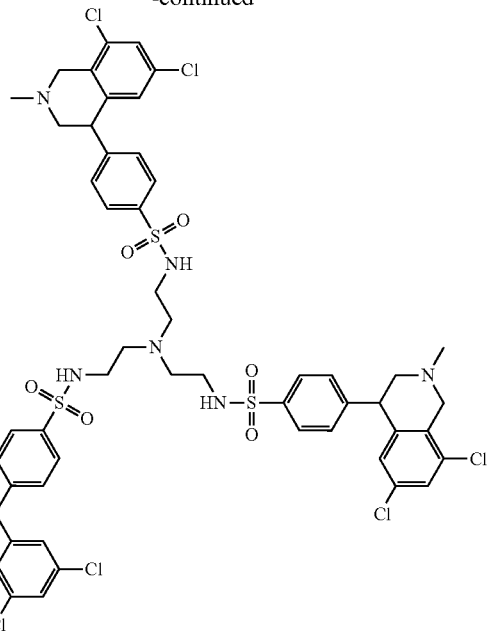

Compound 24: N,N',N''-(2,2',2''-nitrilotris(ethane-2,1-diyl))tris(4-(6,8-dichloro-2-methyl-1,2,3,4-tetrahydroisoquinolin-4-yl)benzenesulfonamide)

To a solution of 4-(6,8-dichloro-2-methyl-1,2,3,4-tetrahydroisoquinolin-4-yl)benzene-1-sulfonyl chloride (intermediate 10.6) (150 mg, 0.353 mmol) in THF/H$_2$O solution (50% v/v, 0.704 mL) was added DIEA (182.2 mg, 1.412 mmol) and N1,N1-bis(2-aminoethyl)ethane-1,2-diamine (17.0 mg, 0.116 mmol). The reaction was stirred vigorously at room temperature for 40 minutes at which point the solvent was removed. The resulting residue was dissolved in acetonitrile/water (50% v/v) and purified by preparative HPLC to give the title compound (57.6 mg) as a TFA salt. $^1$H-NMR (400 MHz, CD$_3$OD): 7.94 (d, 6H), 7.51 (t, 9H), 6.83 (s, 3H), 4.78 (m, 6H), 4.45 (d, 3H), 3.83 (dd, 3H), 3.49 (t, 3H), 3.30 (m, 6H), 3.29 (m, 21H), 3.12 (s, 9H). MS (m/z): 1208.09 (M+H).

Example 25

N,N',N'',N'''-(3,3',3'',3'''-(butane-1,4-diylbis(azanetriyl))tetrakis(propane-3,1-diyl))tetrakis(4-(6,8-dichloro-2-methyl-1,2,3,4-tetrahydroisoquinolin-4-yl)benzenesulfonamide)

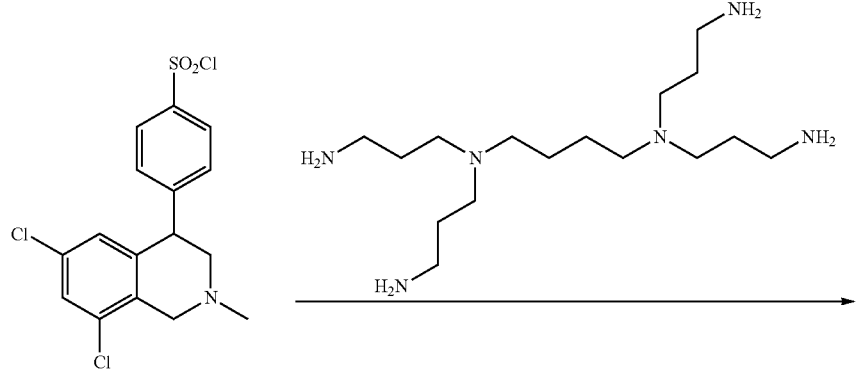

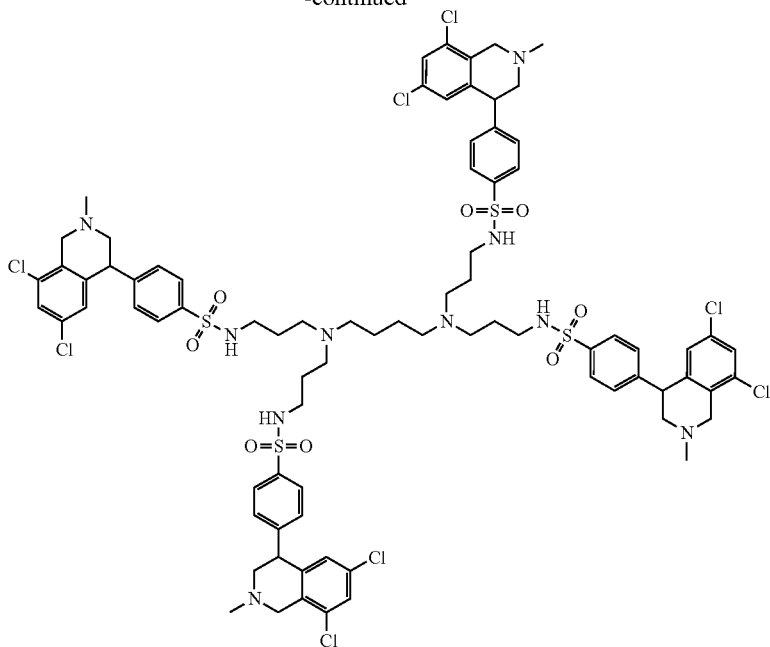

Compound 25: N,N',N'',N'''-(3,3',3'',3'''-(butane-1,4-diylbis(azanetriyl))tetrakis(propane-3,1-diyl))tetrakis(4-(6,8-dichloro-2-methyl-1,2,3,4-tetrahydroisoquinolin-4-yl)benzenesulfonamide)

Following the procedure outlined in Example 24, Compound 25 was made using N1,N1'-(butane-1,4-diyl)bis(N1-(3-aminopropyl)propane-1,3-diamine) as the amine. Purification by preparative HPLC gave the title compound as a TFA salt. $^1$H-NMR (400 MHz, CD$_3$OD): 7.88 (d, 8H), 7.51 (s, 4H), 7.48 (d, 8H), 6.81 (s, 4H), 4.75 (m, 8H), 4.47 (d, 4H), 3.85 (dd, 4H), 3.58 (t, 4H), 3.13 (s, 12H), 2.98 (t, 8H), 1.97 (m, 8H), 1.88 (m, 4H). MS (m/z): 1733.02 (M+H).

Example 26

N,N'-(1,4-phenylenebis(methylene))bis(4-(6,8-dichloro-2-methyl-1,2,3,4-tetrahydroisoquinolin-4-yl)benzenesulfonamide)

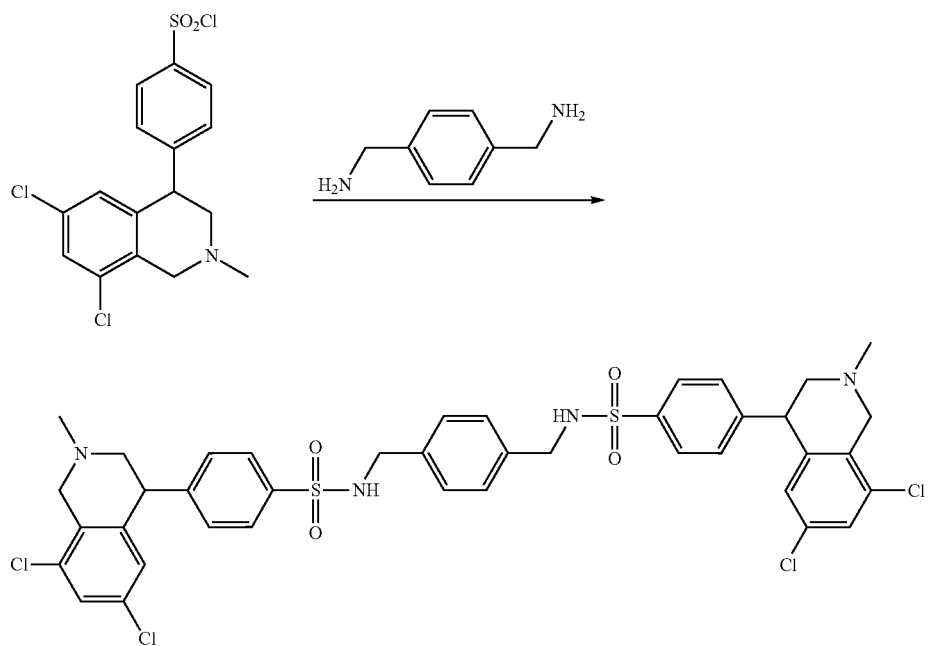

Compound 26: N,N'-(1,4-phenylenebis(methylene))bis(4-(6,8-dichloro-2-methyl-1,2,3,4-tetrahydroisoquinolin-4-yl)benzenesulfonamide)

Following the procedure outlined in Example 24, compound 26 was made using 1,4-phenylenedimethanamine as the amine. Purification by preparative HPLC gave the title compound as a TFA salt. $^1$H-NMR (400 MHz, CD$_3$OD): 7.76 (d, 4H), 7.54 (s, 2H), 7.39 (d, 4H), 7.08 (s, 4H), 6.82 (s, 2H), 4.72 (m, 3H), 4.47 (d, 2H), 4.07 (s, 4H), 3.88 (dd, 2H), 3.61 (t, 2H), 3.16 (s, 6H). MS (m/z): 845.07 (M+H).

Example 27

N,N'-(2,2'-(ethane-1,2-diylbis(oxy))bis(ethane-2,1-diyl))bis(4-(6,8-dichloro-2-methyl-1,2,3,4-tetrahydroisoquinolin-4-yl)benzenesulfonamide)

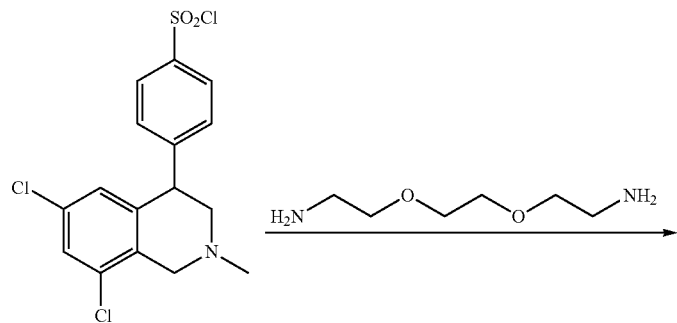

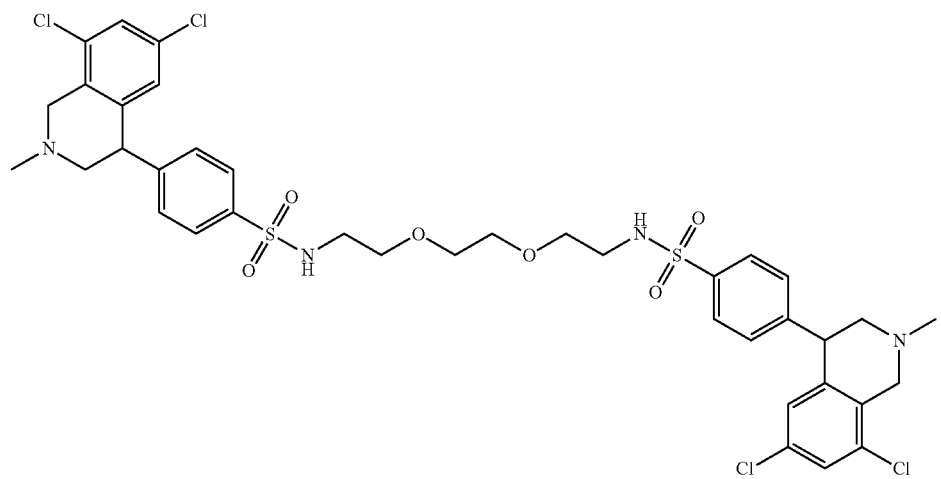

Compound 27: N,N'-(2,2'-(ethane-1,2-diylbis(oxy))bis(ethane-2,1-diyl))bis(4-(6,8-dichloro-2-methyl-1,2,3,4-tetrahydroisoquinolin-4-yl)benzenesulfonamide)

Following the procedure outlined in Example 24, compound 27 was made using 2,2'-(ethane-1,2-diylbis(oxy))diethanamine as the amine. Purification by preparative HPLC gave the title compound as a TFA salt. $^1$H-NMR (400 MHz, CD$_3$OD): 7.89 (d. 4H), 7.52 (s, 2H), 7.47 (d, 4H), 6.82 (s, 2H), 4.77 (m, 4H), 4.47 (d, 2H), 3.86 (dd, 2H), 3.59 (t, 2H), 3.43 (t, 8H), 3.13 (s, 6H), 3.06 (t, 4H). MS (m/z): 857.15 (M+H).

Example 28

N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide

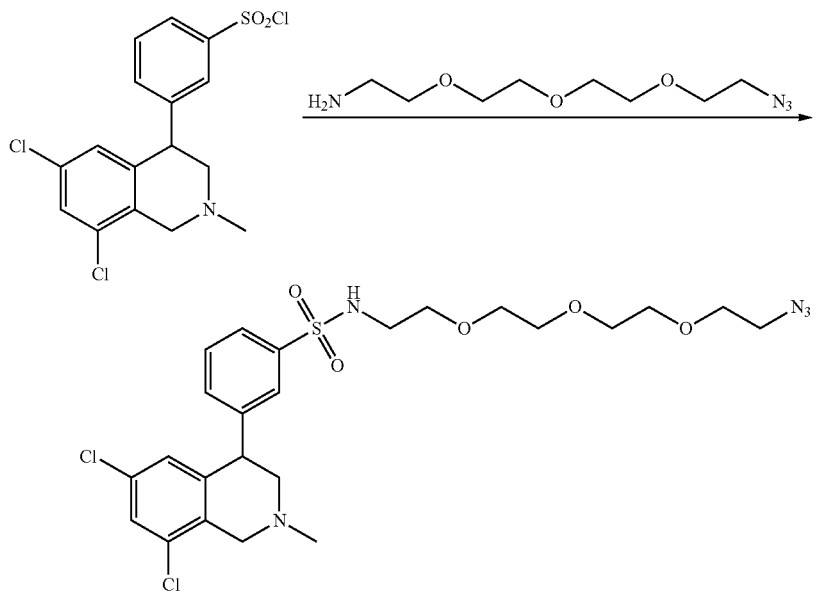

Intermediate 28.1 N-(2-(2-(2-(2-azidoethoxy)ethoxy)ethoxy)ethyl)-3-(6,8-dichloro-2-methyl-1,2,3,4-tetrahydroisoquinolin-4-yl)benzenesulfonamide To a solution of 3-(6,8-dichloro-2-methyl-1,2,3,4-tetrahydroisoquinolin-4-yl)benzene-1-sulfonyl chloride (intermediate 1.6) (600 mg, 1.41 mmol) in chloroform (2.82 mL) was added DIEA (545.7 mg, 4.24 mmol) and 2-(2-(2-(2-azidoethoxy)ethoxy)ethoxy)ethanamine (616.3 mg, 2.82 mmol). The reaction was stirred overnight at which point the mixture was diluted with 50 mL DCM and washed with NaHCO$_3$ (50 mL). The aqueous layer was extracted with DCM (2×50 mL) and the combined organic fractions washed with water (200 mL), brine (200 mL), and dried over Na$_2$SO$_4$. Removing the solvent gave the title compound as an oil which was used without further purification.

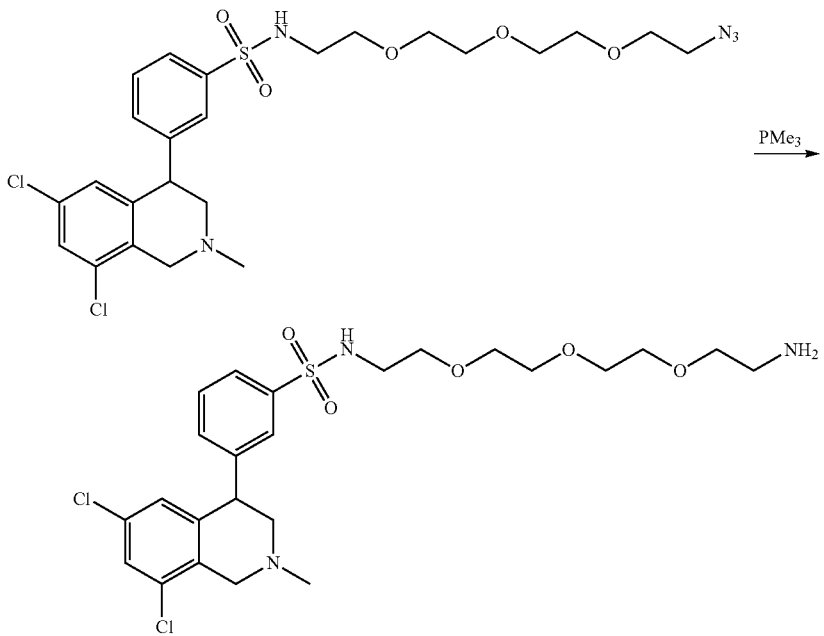

Compound 28: N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide N-(2-(2-(2-(2-azidoethoxy)ethoxy)ethoxy)ethyl)-3-(6,8-dichloro-2-methyl-1,2,3,4-tetrahydroisoquinolin-4-yl)benzenesulfonamide (intermediate 28.1) (1.035 g, assume 1.41 mmol) was dissolved in a 10:1 THF:water solution (26.5 mL) and placed under $N_2$. $PMe_3$ (165 mg, 2.18 mmol) was added and the reaction stirred overnight. The solvent was removed and the resulting residue brought up in EtOAc (100 mL) and washed with $NaHCO_3$ (100 mL) and brine (100 mL). After drying the organic layer over $Na_2SO_4$, the solvent was removed to give 446 mg of the title compound (58% over two steps) as an oil. A portion of the crude product was purified by preparative HPLC to give the title compound as a TFA salt. $^1$H-NMR (400 mHz, CD3OD) δ 7.87 (m, 1H), 7.73 (m, 1H), 7.67 (t, j=7.7 Hz, 1H), 7.54 (m, 2H), 6.82 (s, 1H), 4.8-4.6 (m, 4H), 4.46 (m, 1H), 3.86 (m, 1H), 3.69 (m, 2H), 3.66 (s, 3H), 3.61 (m, 2H), 3.55 (m, 2H), 3.12 (m, 4H), 3.03 (t, j=5.4 Hz, 1H). MS (m/z): 546.18 (M+H).

Example 29

N1,N8-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)octanediamide

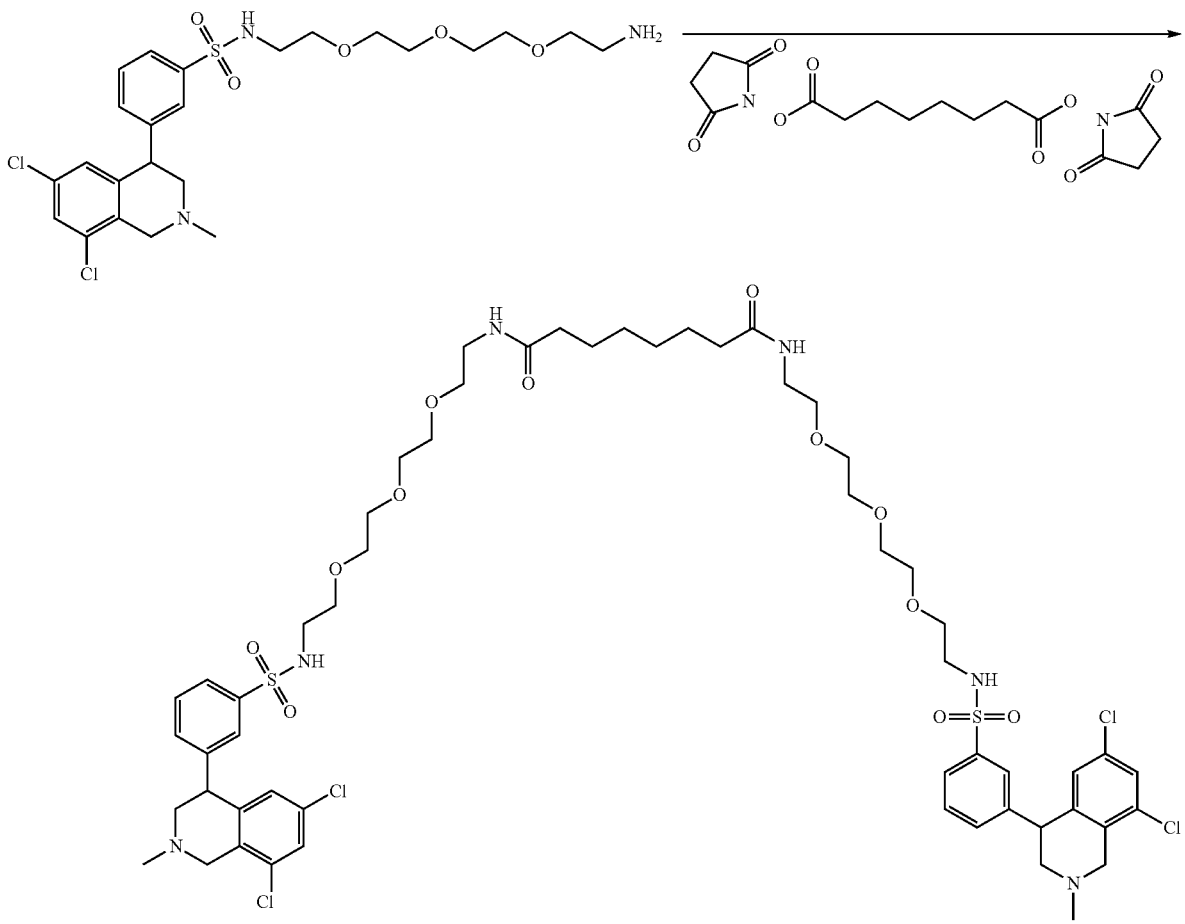

Compound 29: N1,N8-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)octanediamide To a solution of N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (compound 28) (54.5 mg, 0.1 mmol) in DMF (0.20 mL) was added DIEA (15.5 mg, 0.12 mmol) and bis(2,5-dioxopyrrolidin-1-yl) octanedioate (18.4 mg, 0.05 mmol). The reaction was stirred at room temperature for 3 hours at which point an additional 0.03 mmol of compound 28 was added. After a further hour the solvent was removed and the resulting residue dissolved in acetonitrile/water (1:1) and purified by preparative HPLC to give the title compound (17.4 mg) as a TFA salt. $^1$H-NMR (400 MHz, CD$_3$OD): 7.89 (d, 2H), 7.78 (s, 2H), 7.64 (t, 2H), 7.52 (m, 4H), 6.83 (s, 2H), 4.81 (m, 4H), 4.45 (d, 2H), 3.89 (dd, 2H), 3.61 (m, 18H), 3.55 (m, 10H), 3.47 (m, 5H), 3.33 (m, 5H), 3.14 (s, 7H), 3.04 (t, 4H), 2.16 (t, 4H), 1.55 (m, 4H), 1.29 (m, 4H). MS (m/z): 1231.87 (M+H).

Example 30

2-(N-(4-(6,8-dichloro-2-methyl-1,2,3,4-tetrahydroisoquinolin-4-yl)phenyl)sulfamoylamino)ethylphosphonic acid

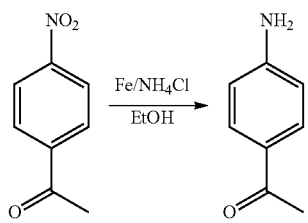

Intermediate 30.1: 1-(4-aminophenyl)ethanone

Into a 100-mL 3-necked round-bottom flask, was placed a solution of 1-(4-nitrophenyl)ethanone (6 g, 36.36 mmol, 1.00 equiv) in ethanol (100 mL), water (15 mL). This was followed by the addition of NH$_4$Cl (3.85 g, 72.64 mmol, 2.00 equiv) in several batches. To this was added Fe (10.18 g, 181.79 mmol, 5.00 equiv) in several batches, while the temperature was maintained at reflux. The resulting mixture was heated to reflux for 2 h. The solids were filtered out and the resulting filtrate was concentrated under vacuum. The residue was diluted with 50 mL of water. The resulting solution was extracted with 3×50 mL of ethyl acetate and the organic layers combined and dried over anhydrous sodium sulfate and concentrated under vacuum to give 3.1 g (60%) of 1-(4-aminophenyl)ethanone as a yellow solid.

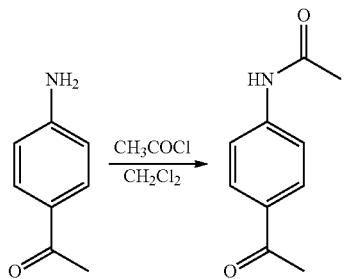

Intermediate 30.2: N-(4-acetylphenyl)acetamide

Into a 100-mL 3-necked round-bottom flask purged and maintained with an inert atmosphere of nitrogen, was placed a solution of 1-(4-aminophenyl)ethanone (3.1 g, 22.96 mmol, 1.00 equiv) in dichloromethane (30 mL), triethylamine (4.64 g, 45.94 mmol, 2.00 equiv). This was followed by the addition of acetyl chloride (1.79 g, 22.95 mmol, 1.00 equiv) dropwise with stirring at 0° C. The resulting solution was stirred for 30 min at 0° C. The reaction was then quenched by the addition of 2 mL of water. The resulting mixture was washed with 3×50 mL of saturated aqueous sodium chloride. The mixture was dried over anhydrous sodium sulfate and concentrated under vacuum to give 3.0 g (74%) of N-(4-acetylphenyl)acetamide as a white solid.

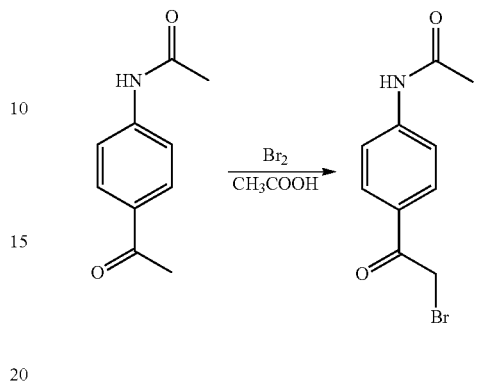

Intermediate 30.3: N-(4-(2-bromoacetyl)phenyl)acetamide

Into a 100-mL 3-necked round-bottom flask, was placed a solution of N-(4-acetylphenyl)acetamide (1 g, 5.65 mmol, 1.00 equiv) in acetic acid (10 mL). This was followed by the addition of a solution of bromine (910 mg, 5.69 mmol, 1.01 equiv) in acetic acid (2 mL) dropwise with stirring at 50° C. The resulting solution was stirred for 1.5 h at 50° C. The reaction was then quenched by the addition of 100 mL of water/ice. The solids were collected by filtration and dried under vacuum. This resulted in 0.5 g (33%) of N-(4-(2-bromoacetyl)phenyl)acetamide as a white solid.

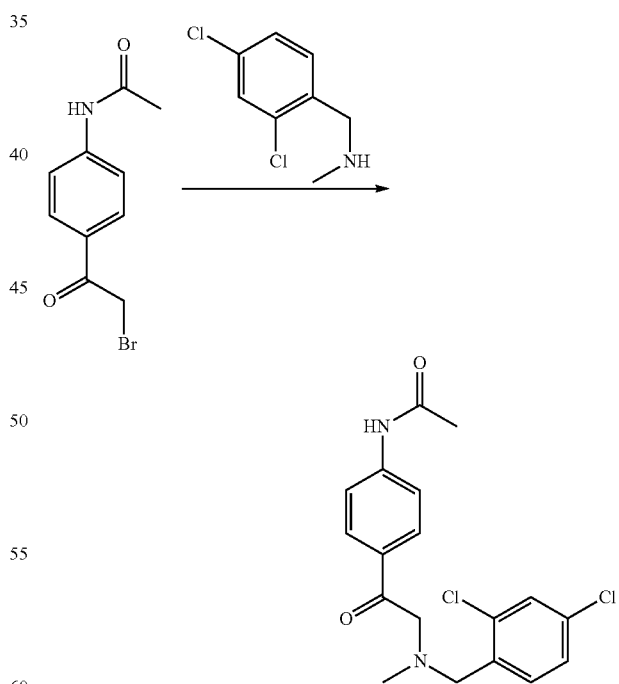

Intermediate 30.4: N-(4-(2-((2,4-dichlorobenzyl)(methyl)amino)acetyl)phenyl)acetamide Into a 100-mL 3-necked round-bottom flask purged and maintained with an inert atmosphere of nitrogen, was placed a solution of N-(4-(2-bromoacetyl)phenyl)acetamide (1 g, 3.91 mmol, 1.00 equiv) in 1,4-dioxane (40 mL). This was followed by the addition of triethylamine (1.58 g, 15.64 mmol, 4.00 equiv) dropwise with stirring at 20° C. To this was added (2,4-dichlorophenyl)-N-methylmethanamine (880 mg, 4.63 mmol, 1.19 equiv) dropwise with stirring at 20° C. The resulting solution was stirred for 4 h at 20° C. The solids were filtered out. The resulting mixture was concentrated under vacuum to give 1.5 g (84%) of N-(4-(2-((2,4-dichlorobenzyl)(methyl)amino)acetyl)phenyl)acetamide as a white solid.

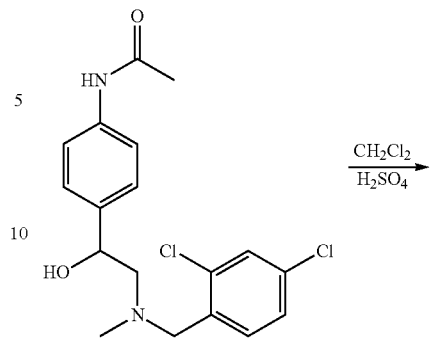

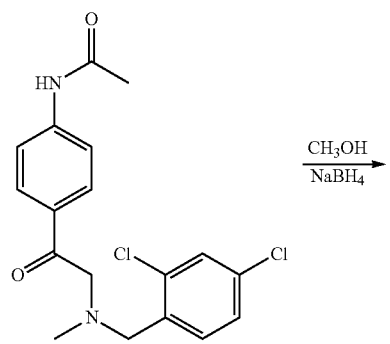

Intermediate 30.5: N-(4-(2-((2,4-dichlorobenzyl)(methyl)amino)-1-hydroxyethyl)phenyl)acetamide Into a 100-mL 3-necked round-bottom flask purged and maintained with an inert atmosphere of nitrogen, was placed a solution of N-(4-(2-((2,4-dichlorobenzyl)(methyl)amino)acetyl)phenyl)acetamide (1.5 g, 4.11 mmol, 1.00 equiv) in methanol (20 mL). This was followed by the addition of NaBH₄ (300 mg, 7.89 mmol, 2.06 equiv) in several batches at 0-5° C. The resulting solution was stirred for 2 h at 0-5° C. The reaction was then quenched by the addition of 5 mL of acetone. The resulting mixture was concentrated under vacuum. The residue was applied onto a silica gel column with ethyl acetate/petroleum ether (1:10-1:5). This resulted in 1.2 g (76%) of N-(4-(2-((2,4-dichlorobenzyl)(methyl)amino)-1-hydroxyethyl)phenyl)acetamide as yellow oil.

Intermediate 30.6: N-(4-(6,8-dichloro-2-methyl-1,2,3,4-tetrahydroisoquinolin-4-yl)phenyl)acetamide Into a 100-mL 3-necked round-bottom flask, was placed a solution of N-(4-(2-((2,4-dichlorobenzyl)(methyl)amino)-1-hydroxyethyl)phenyl)acetamide (500 mg, 1.36 mmol, 1.00 equiv) in dichloromethane (3 mL). This was followed by the addition of sulfuric acid (3 mL) dropwise with stirring at 0° C. The resulting solution was stirred for 5 h at 0-5° C. The reaction was then quenched by the addition of 20 mL of water/ice. The pH value of the solution was adjusted to 7-8 with sodium hydroxide. The resulting solution was extracted with 3×20 mL of ethyl acetate and the organic layers combined and concentrated under vacuum. The residue was applied onto a silica gel column with ethyl acetate/petroleum ether (1:10-1:5). This resulted in 25 mg (5%) of N-(4-(6,8-dichloro-2-methyl-1,2,3,4-tetrahydroisoquinolin-4-yl)phenyl)acetamide as a white solid. $^1$H-NMR (300 HMz, CDCl₃, ppm): δ 7.46-7.49 (2H, d, J=8.4 Hz), 7.23-7.29 (1H, m), 7.12-7.15 (2H, d, J=8.4 Hz), 6.80 (1H, s), 4.314 (1H, s), 3.92 (1H, d), 3.58-3.63 (1H, d), 3.06 (1H, s), 2.61-2.68 (1H, m), 2.57 (3H, s), 2.20 (3H, s). MS (ES, m/z): 349 [M+H]⁺.

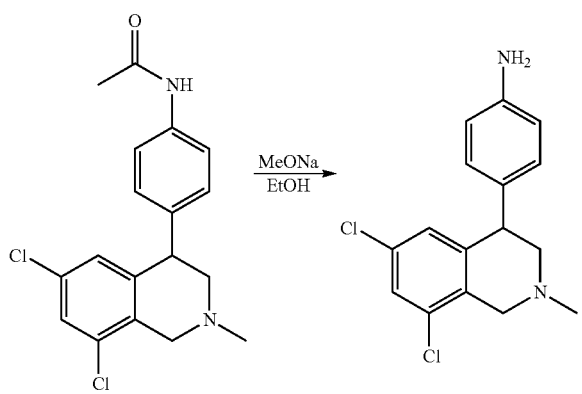 [SMILES: "MeONa" ; "EtOH" ; CC(=O)Nc1ccc(C2CN(C)Cc3c(Cl)cc(Cl)cc32)cc1 ; CN1Cc2c(Cl)cc(Cl)cc2C(c2ccc(N)cc2)C1]

Intermediate 30.7: 4-(6,8-dichloro-2-methyl-1,2,3,4-tetrahydroisoquinolin-4-yl)benzenamine Into a 100-mL 3-necked round-bottom flask purged and maintained with an inert atmosphere of nitrogen, was placed a solution of N-(4-(6,8-dichloro-2-methyl-1,2,3,4-tetrahydroisoquinolin-4-yl)phenyl)acetamide (2 g, 5.73 mmol, 1.00 equiv) in ethanol (20 mL). This was followed by the addition of sodium methanolate (5 g, 92.59 mmol, 16.16 equiv) in several batches, while the temperature was maintained at reflux. The resulting solution was heated to reflux overnight. The reaction was then quenched by the addition of 50 mL of water/ice. The resulting solution was extracted with 3×50 mL of ethyl acetate and the organic layers combined and concentrated under vacuum. This resulted in 1.5 g (85%) of 4-(6,8-dichloro-2-methyl-1,2,3,4-tetrahydroisoquinolin-4-yl)benzenamine as yellow oil. $^1$H-NMR (300 MHz, DMSO, ppm): δ 7.42-7.42 (1H, d, J=1.5 Hz), 6.83-6.86 (2H, d, J=8.1 Hz), 6.78-6.78 (1H, d, J=1.2 Hz), 6.48-6.51 (2H, d, J=8.4 Hz), 4.98 (2H, s), 4.02-4.06 (1H, m), 3.62-3.67 (1H, d, J=16.2 Hz), 3.43-3.48 (1H, d, J=15.9 Hz), 2.80-2.86 (1H, m), 2.37 (3H, s). MS (ES, m/z): 307 [M+H]$^+$.

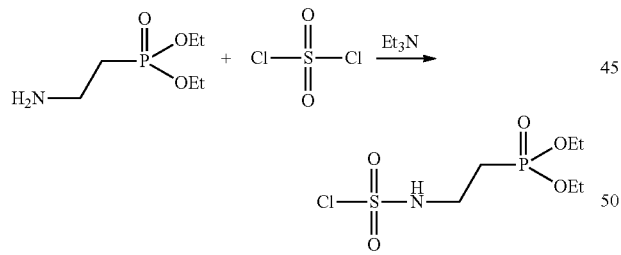

Intermediate 30.8: diethyl 2-(chlorosulfonylamino)ethylphosphonate

Into a 100-mL round-bottom flask purged and maintained with an inert atmosphere of nitrogen, was placed a solution of sulfuryl dichloride (1.1 g, 8.15 mmol, 1.47 equiv) in dichloromethane (10 mL). This was followed by the addition of a solution of diethyl 2-aminoethylphosphonate (intermediate 1.9) (1.0 g, 5.52 mmol, 1.00 equiv) and triethylamine (800 mg, 7.92 mmol, 1.43 equiv) in dichloromethane (20 mL) dropwise with stirring at 0° C. The resulting solution was stirred for 2 h at 0° C. The reaction was then quenched by the addition of ice water. The organic layer was washed with saturated sodium chloride (20 mL), dried over anhydrous sodium sulfate and concentrated under vacuum. This resulted in 0.5 g (crude) of the title compound as a colorless oil.

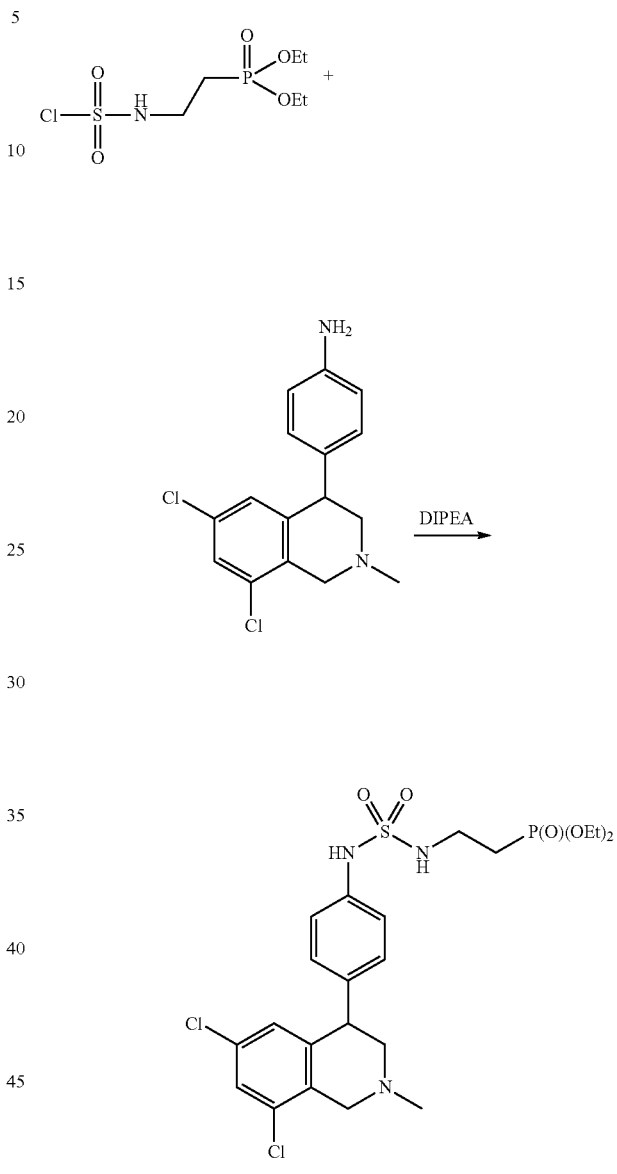

Intermediate 30.9: diethyl 2-(N-(4-(6,8-dichloro-2-methyl-1,2,3,4-tetrahydroisoquinolin-4-yl)phenyl)sulfamoylamino)ethylphosphonate Into a 50-mL round-bottom flask purged and maintained with an inert atmosphere of nitrogen, was placed diethyl 2-(chlorosulfonylamino)ethylphosphonate (intermediate 30.8) (670 mg, 2.40 mmol, 1.47 equiv), 4-(6,8-dichloro-2-methyl-1,2,3,4-tetrahydroisoquinolin-4-yl)benzenamine (intermediate 30.7) (500 mg, 1.63 mmol, 1.00 equiv), N-ethyl-N-isopropylpropan-2-amine (400 mg, 3.10 mmol, 1.91 equiv) in acetonitrile (20 mL). The resulting solution was stirred for 3 h at 60° C. The resulting mixture was concentrated under vacuum and the residue was applied to a silica gel column and eluted with dichloromethane/methanol (20:1). This resulted in 150 mg (16%) of the title compound as a light yellow solid.

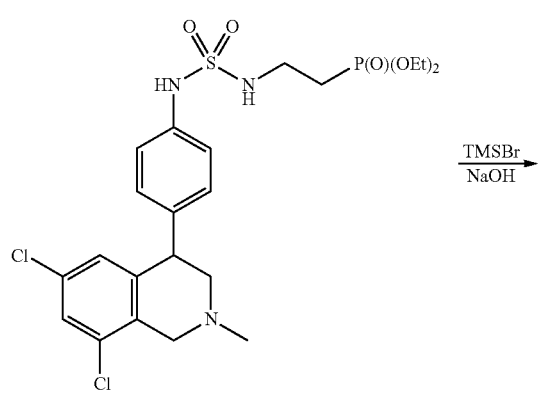

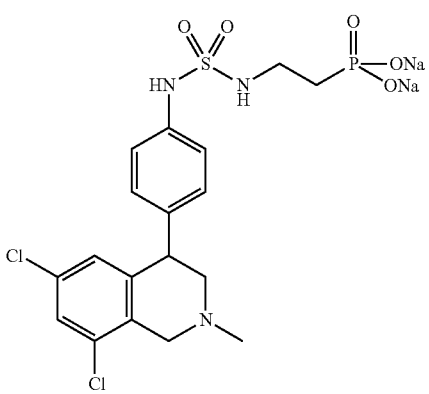

Compound 30: 2-(N-(4-(6,8-dichloro-2-methyl-1,2,3,4-tetrahydroisoquinolin-4-yl)phenyl)sulfamoylamino)ethylphosphonic acid Into a 50-mL round-bottom flask purged and maintained with an inert atmosphere of nitrogen, was placed a solution of diethyl 2-(N-(4-(6,8-dichloro-2-methyl-1,2,3,4-tetrahydroisoquinolin-4-yl)phenyl)sulfamoylamino)ethylphosphonate (100 mg, 0.18 mmol, 1.00 equiv) in dichloromethane (5 mL) and bromotrimethylsilane (275 mg, 1.80 mmol, 9.89 equiv). The resulting solution was stirred overnight at 39° C. The resulting mixture was concentrated under vacuum and the residue was dissolved in dichloromethane (5 mL). This was followed by the addition of a solution of sodium hydroxide (14.5 mg, 0.36 mmol, 2.00 equiv) in methanol (0.2 mL) dropwise with stirring. The solids were collected by filtration and dried under reduced pressure. This gave 40 mg (40%) of a sodium salt of the title compound as a white solid. $^1$H-NMR (300 MHz, d$_6$-DMSO, ppm): δ 9.78 (1H, brs), 7.54 (1H, s), 7.47 (1H, brs), 7.09-7.17 (4H, m), 6.82 (1H, s), 4.31 (1H, brs), 3.88 (2H, brs), 3.13 (1H, brs), 3.04 (2H, brs), 2.90 (1H, brs), 2.58 (3H, s), 1.65-1.77 (2H, m). MS (m/z): 494 [M+H]$^+$.

Example 31

2-(N-(3-(6,8-dichloro-2-methyl-1,2,3,4-tetrahydroisoquinolin-4-yl)phenyl)sulfamoylamino)ethylphosphonic acid

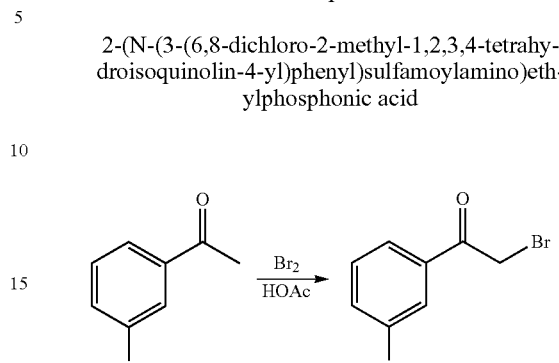

Intermediate 31.1:
2-bromo-1-(3-nitrophenyl)ethanone

Into a 500-mL 3-necked round-bottom flask, was placed a solution of 1-(3-nitrophenyl)ethanone (50 g, 303.03 mmol, 1.00 equiv) in acetic acid (300 mL), Br$_2$ (53.5 g, 331.6 mmol, 1.00 equiv). The resulting solution was stirred for 2 h at 60° C. in an oil bath. The reaction was then quenched by the addition of ice and the solids were collected by filtration. The crude product was re-crystallized from ethyl acetate/petroleum ether in the ratio of 1:10. This resulted in 25 g (34%) of 2-bromo-1-(3-nitrophenyl)ethanone as a white solid.

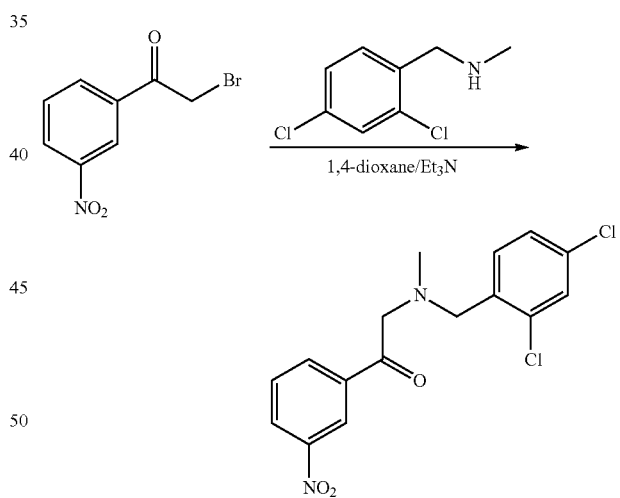

Intermediate 31.2: 2-((2,4-dichlorobenzyl)(methyl)amino)-1-(3-nitrophenyl)ethanone Into a 100-mL 3-necked round-bottom flask purged and maintained with an inert atmosphere of nitrogen, was placed a solution of 2-bromo-1-(3-nitrophenyl)ethanone (2 g, 8.23 mmol, 1.00 equiv), triethylamine (3.4 g, 4.00 equiv), (2,4-dichlorophenyl)-N-methylmethanamine (1.9 g, 10.05 mmol, 1.20 equiv), 1,4-dioxane (50 mL). The resulting solution was stirred for 2 h at room temperature at which time it was judged to be complete by LCMS. The mixture was concentrated under vacuum and the residue was applied onto a silica gel column with ethyl acetate/petroleum ether (1:100~1:50). This resulted in 1.5 g (50%) of 2-((2,4-dichlorobenzyl)(methyl)amino)-1-(3-nitrophenyl)ethanone as a yellow solid.

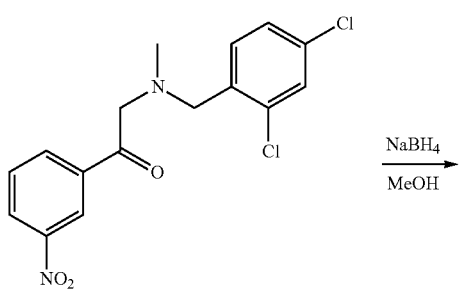

Intermediate 31.3: 2-((2,4-dichlorobenzyl)(methyl)amino)-1-(3-nitrophenyl)ethanol Into a 500-mL 3-necked round-bottom flask, was placed a solution of 2-((2,4-dichlorobenzyl)(methyl)amino)-1-(3-nitrophenyl)ethanone (28 g, 1.00 equiv, Crude) in methanol (280 mL), NaBH₄ (6.38 mg, 0.17 mmol, 2.00 equiv). The resulting solution was stirred for 0.5 h at 0° C. The reaction progress was monitored by LCMS. The reaction was then quenched by the addition of 10 mL of acetone. The resulting mixture was concentrated under vacuum. The residue was applied onto a silica gel column with ethyl acetate/petroleum ether (1:10~1:5). This resulted in 14 g of 2-((2,4-dichlorobenzyl)(methyl)amino)-1-(3-nitrophenyl)ethanol as a yellow solid.

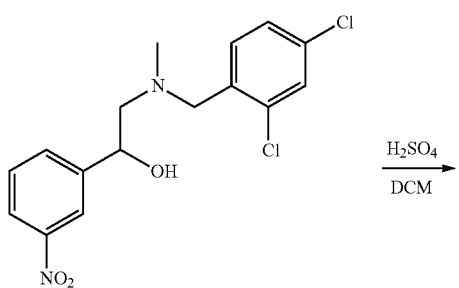

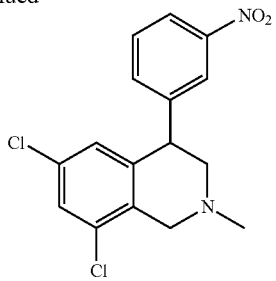

Intermediate 31.4: 6,8-dichloro-2-methyl-4-(3-nitrophenyl)-1,2,3,4-tetrahydroisoquinoline Into a 500-mL 3-necked round-bottom flask, was placed a solution of 2-((2,4-dichlorobenzyl)(methyl)amino)-1-(3-nitrophenyl)ethanol (14 g, 39.55 mmol, 1.00 equiv) in dichloromethane (140 mL), sulfuric acid (140 mL). The resulting solution was stirred overnight at room temperature. The reaction progress was monitored by LCMS. The resulting solution was diluted with 100 mL of ice. The pH value of the solution was adjusted to 8-9 with sat. sodium hydroxide (100 mL). The resulting solution was extracted with 2×500 mL of ethyl acetate and the organic layers combined and dried over sodium sulfate. The residue was applied onto a silica gel column with ethyl acetate/petroleum ether (1:10~1:5). This resulted in 7 g (51%) of 6,8-dichloro-2-methyl-4-(3-nitrophenyl)-1,2,3,4-tetrahydroisoquinoline as a yellow solid.

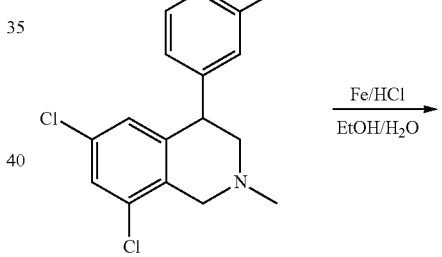

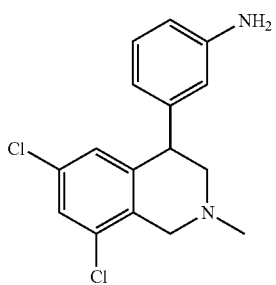

Intermediate 31.5: 3-(6,8-dichloro-2-methyl-1,2,3,4-tetrahydroisoquinolin-4-yl)benzenamine Into a 100-mL 3-necked round-bottom flask purged and maintained with an inert atmosphere of nitrogen, was placed 6,8-dichloro-2-methyl-4-(3-nitrophenyl)-1,2,3,4-tetrahydroisoquinoline (200 mg, 0.59 mmol, 1.00 equiv), Fe (360 mg, 6.43 mmol, 8.60 equiv), hydrogen chloride (0.02 mL), ethanol (0.6 mL), water (0.2 mL). The resulting solution was stirred for 0.5 h at 80° C. in an oil bath. The solids were filtered out. The resulting mixture was concentrated under vacuum.

This resulted in 0.2 g (crude) of 3-(6,8-dichloro-2-methyl-1,2,3,4-tetrahydroisoquinolin-4-yl)benzenamine as yellow oil.

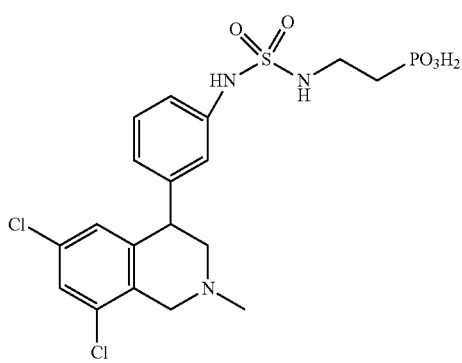

Compound 31: 2-(N-(3-(6,8-dichloro-2-methyl-1,2,3,4-tetrahydroisoquinolin-4-yl)phenyl)sulfamoylamino)ethylphosphonic acid Following the procedures outlined in Example 30, substituting 3-(6,8-dichloro-2-methyl-1,2,3,4-tetrahydroisoquinolin-4-yl)aniline (intermediate 31.5) for 4-(6,8-dichloro-2-methyl-1,2,3,4-tetrahydroisoquinolin-4-yl)aniline gave the title compound as a sodium salt. $^1$H-NMR (300 MHz, D$_2$O+ DMSO-d$_6$, ppm): δ 7.67 (s, 1H), 7.33 (t, J=8.1 Hz, 1H), 7.07-7.15 (m, 2H), 6.81-6.86 (m, 2H), 4.39-4.66 (m, 3H), 3.75-3.81 (m, 1H), 3.45-3.50 (m, 1H), 3.02-3.08 (m, 5H), 1.67-1.78 (m, 2H). MS (ES, m/z): 494.0 [M+H]$^+$.

Example 32

3-(N-(4-(6,8-dichloro-2-methyl-1,2,3,4-tetrahydroisoquinolin-4-yl)phenyl)sulfamoylamino)propylphosphonic acid

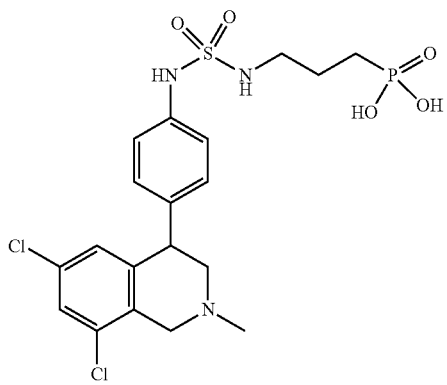 [SMILES: CN1Cc2c(Cl)cc(Cl)cc2C(c2ccc(NS(=O)(=O)NCCCP(=O)(O)O)cc2)C1]

Compound 32: 3-(N-(4-(6,8-dichloro-2-methyl-1,2,3,4-tetrahydroisoquinolin-4-yl)phenyl)sulfamoylamino)propylphosphonic acid Following the procedures outlined in Example 30, substituting 3-diethyl 3-aminopropylphosphonate (intermediate 4.1) for diethyl 2-aminoethylphosphonate gave the title compound as a sodium salt. $^1$H-NMR (300 MHz, CD$_3$OD, ppm): δ 7.47 (s, 1H), 7.28 (s, 4H), 6.81 (s, 1H), 4.73-4.77 (m, 2H), 4.57 (m, 1H), 3.81 (s, 1H), 3.66 (s, 1H), 3.18 (s, 3H), 3.06 (s, 2H), 1.74 (m, 4H), 1.20-1.35 (m, 1H). MS (ES, m/z): 508 [M+H]$^+$ Example 33

3-(N-(3-(6,8-dichloro-2-methyl-1,2,3,4-tetrahydroisoquinolin-4-yl)phenyl)sulfamoylamino)propylphosphonic acid

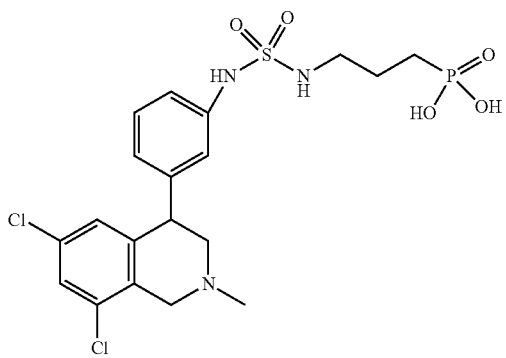 [SMILES: CN1Cc2c(Cl)cc(Cl)cc2C(c2cccc(NS(=O)(=O)NCCCP(=O)(O)O)c2)C1]

Compound 33: 3-(N-(3-(6,8-dichloro-2-methyl-1,2,3,4-tetrahydroisoquinolin-4-yl)phenyl)sulfamoylamino)propylphosphonic acid Following the procedures outlined in Example 30, substituting 3-diethyl 3-aminopropylphosphonate (intermediate 4.1) for diethyl 2-aminoethylphosphonate and 3-(6,8-dichloro-2-methyl-1,2,3,4-tetrahydroisoquinolin-4-yl) aniline (intermediate 31.5) for 4-(6,8-dichloro-2-methyl-1,2,3,4-tetrahydroisoquinolin-4-yl)aniline gave the title compound as a sodium salt. $^1$H-NMR (300 MHz, CD$_3$OD, ppm): δ 7.54 (s, 1H), 7.38 (s, 1H), 7.25 (s, 1H), 7.11 (s, 1H), 6.94 (m, 2H), 4.66 (s, 1H), 4.55-4.51 (m, 1H), 3.89 (s, 1H), 3.65 (m, 2H), 3.18 (s, 3H), 3.05 (s, 2H), 1.71 (m, 4H). MS (ES, m/z): 508 [M+H]$^+$.

Example 34

(2S)-2-(3-(4-(6,8-dichloro-2-methyl-1,2,3,4-tetrahydroisoquinolin-4-yl)phenyl)ureido)succinic acid

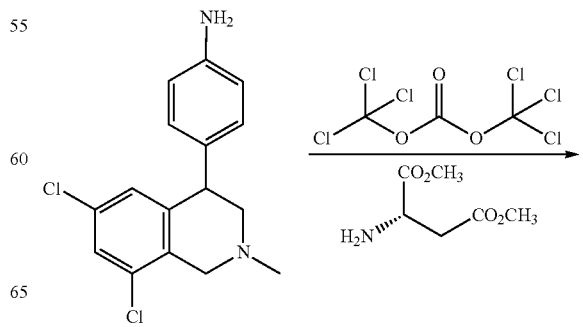

Intermediate 34.1: (2S)-dimethyl 2-(3-(4-(6,8-dichloro-2-methyl-1,2,3,4-tetrahydroisoquinolin-4-yl)phenyl)ureido)succinate

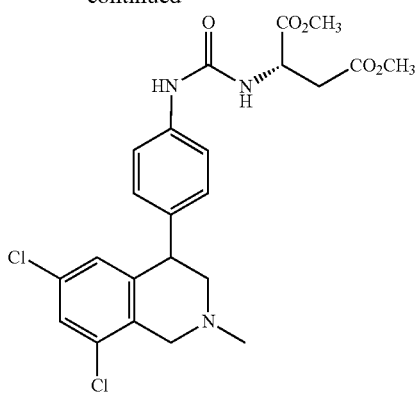

Into a 50-mL 3-necked round-bottom flask purged and maintained with an inert atmosphere of nitrogen, was placed a solution of 4-(6,8-dichloro-2-methyl-1,2,3,4-tetrahydroisoquinolin-4-yl)benzenamine (intermediate 30.7) (200 mg, 0.65 mmol, 1.00 equiv) in dichloromethane (10 mL), triethylamine (1.2 mL). This was followed by the addition of bis(trichloromethyl) carbonate (200 mg, 0.67 mmol, 1.03 equiv) slowly with stirring at 0-5° C. The resulting solution was stirred for 1 h at room temperature. To this was added triethylamine (1 mL) followed by (S)-dimethyl 2-aminosuccinate (200 mg, 1.24 mmol, 1.91 equiv) in several batches. The resulting solution was stirred for 2 h at room temperature. The resulting mixture was concentrated under vacuum and the residue was applied onto a silica gel column and eltued with ethyl acetate/petroleum ether (1:10-1:5). This resulted in 50 mg (15%) of (2S)-dimethyl 2-(3-(4-(6,8-dichloro-2-methyl-1,2,3,4-tetrahydroisoquinolin-4-yl)phenyl)ureido)succinate as yellow oil.

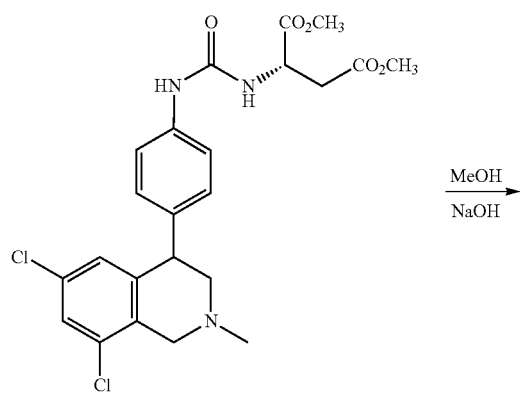

MeOH / NaOH →

Compound 34: (2S)-2-(3-(4-(6,8-dichloro-2-methyl-1,2,3,4-tetrahydroisoquinolin-4-yl)phenyl)ureido)succinic acid

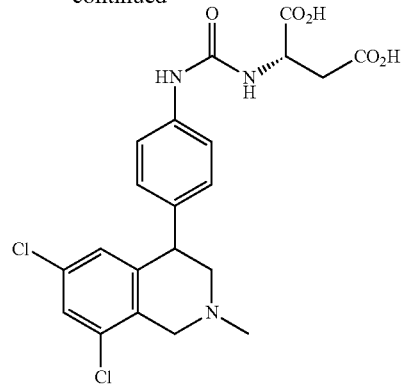

Into a 50-mL round-bottom flask, was placed a solution of (2S)-dimethyl 2-(3-(4-(6,8-dichloro-2-methyl-1,2,3,4-tetrahydroisoquinolin-4-yl)phenyl)ureido)succinate (100 mg, 0.20 mmol, 1.00 equiv) in methanol (5 mL), water (1 mL), sodium hydroxide (30 mg, 0.75 mmol, 3.71 equiv). The resulting solution was stirred for 3 h at room temperature and then concentrated under vacuum. The pH of the solution was adjusted to 3-4 with 1N hydrochloric acid. The solids were collected by filtration and the residue was lyophilized. This resulted in 16 mg (16%) of (2S)-2-(3-(4-(6,8-dichloro-2-methyl-1,2,3,4-tetrahydroisoquinolin-4-yl)phenyl)ureido)succinic acid as a white solid. $^1$H-NMR (300 MHz, DMSO, ppm): δ 8.98 (s, 1H), 7.66 (s, 1H), 7.38-7.44 (d, J=17.1 Hz, 2H), 7.12-7.15 (d, J=8.4 Hz, 2H), 6.78 (s, 1H), 6.60-6.63 (s, 1H), 4.48-4.54 (m, 4H), 3.63-3.66 (s, 2H), 3.01 (s, 1H), 2.51-2.84 (m, 2H). MS (ES, m/z): 466 [M+H]$^+$.

Example 35

(2S)-2-(3-(3-(6,8-dichloro-2-methyl-1,2,3,4-tetrahydroisoquinolin-4-yl)phenyl)ureido)succinic acid

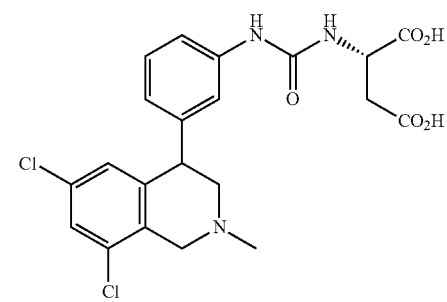 [SMILES: CN1Cc2c(Cl)cc(Cl)cc2C(c2cccc(NC(=O)N[C@@H](CC(=O)O)C(=O)O)c2)C1]

Compound 35: (2S)-2-(3-(3-(6,8-dichloro-2-methyl-1,2,3,4-tetrahydroisoquinolin-4-yl)phenyl)ureido)succinic acid Following the procedures outlined in Example 34, substituting 3-(6,8-dichloro-2-methyl-1,2,3,4-tetrahydroisoquinolin-4-yl)aniline (intermediate 31.5) for 4-(6,8-dichloro-2-methyl-1,2,3,4-tetrahydroisoquinolin-4-yl)aniline gave, after purification by preparative HPLC, the title compound as a TFA salt. $^1$H-NMR (300 MHz, DMSO, ppm): δ 8.88 (s, 1H), 7.54 (s, 1H), 7.31-7.18 (m, 3H), 6.83-6.78 (m, 2H), 6.53-6.51 (m, 1H), 4.49-4.47 (m, 1H), 4.29 (m, 1H), 3.87 (m, 2H), 3.32 (m, 2H), 2.76-2.59 (m, 2H), 2.50 (s, 3H). MS 466 [M+H]$^+$.

Example 36

(2S)-2-(3-(4-(6,8-dichloro-2-methyl-1,2,3,4-tetrahydroisoquinolin-4-yl)phenyl)ureido)pentanedioic acid

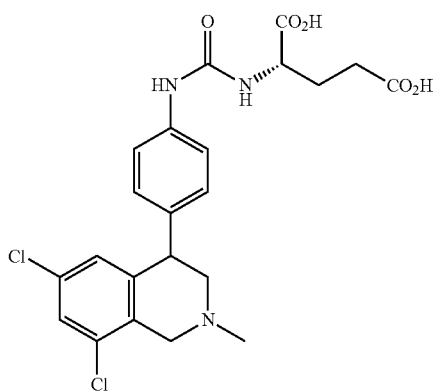 [SMILES: CN1Cc2c(Cl)cc(Cl)cc2C(c2ccc(NC(=O)N[C@@H](CCC(=O)O)C(=O)O)cc2)C1]

Compound 36: (2S)-2-(3-(4-(6,8-dichloro-2-methyl-1,2,3,4-tetrahydroisoquinolin-4-yl)phenyl)ureido)pentanedioic acid Following the procedures outlined in Example 34, substituting (S)-diethyl 2-aminopentanedioate for (S)-dimethyl 2-aminosuccinate gave the title compound. $^1$H-NMR (300 MHz, DMSO, ppm) δ 12.32 (s, 2H), 8.63 (s, 1H), 7.47 (s, 1H), 7.30-7.33 (d, J=8.1 Hz, 2H), 7.06-7.09 (d, J=5.4 Hz, 2H), 6.79 (s, 1H), 6.45-6.48 (d, J=8.1 Hz, 1H), 4.19-4.20 (s, 2H), 3.68 (s, 2H), 2.95 (s, 1H), 2.68 (s, 1H), 2.45 (s, 3H), 2.27-2.30 (s, 2H), 1.99-2.02 (s, 1H), 1.76-7.78 (s, 1H). MS (ES, m/z): 480 [M+H]$^+$.

Example 37

(2S)-2-(3-(3-(6,8-dichloro-2-methyl-1,2,3,4-tetrahydroisoquinolin-4-yl)phenyl)ureido)pentanedioic acid

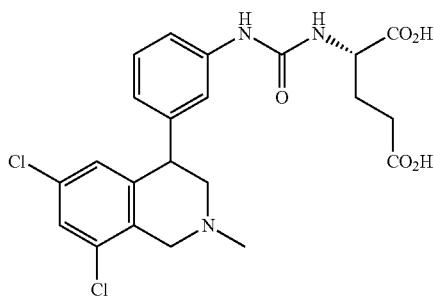 [SMILES: CN1Cc2c(Cl)cc(Cl)cc2C(c2cccc(NC(=O)N[C@@H](CCC(=O)O)C(=O)O)c2)C1]

Compound 37: (2S)-2-(3-(3-(6,8-dichloro-2-methyl-1,2,3,4-tetrahydroisoquinolin-4-yl)phenyl)ureido)pentanedioic acid Following the procedures outlined in Example 34, substituting 3-(6,8-dichloro-2-methyl-1,2,3,4-tetrahydroisoquinolin-4-yl)aniline (intermediate 31.5) for 4-(6,8-dichloro-2-methyl-1,2,3,4-tetrahydroisoquinolin-4-yl)aniline and (S)-diethyl 2-aminopentanedioate for (S)-dimethyl 2-aminosuccinate gave, after purification by preparative HPLC, the title compound as a TFA salt. $^1$H-NMR (300 MHz, DMSO-d$_6$, ppm): δ 8.74 (s, 1H), 7.67 (s, 1H), 7.42 (m, 1H), 7.27-7.25 (m, 2H), 6.79 (m, 2H), 6.52-6.49 (m, 1H), 4.63-4.58 (m, 1H), 4.44 (m, 2H), 4.20-4.16 (m, 1H), 3.72-3.64 (m, 2H), 2.99 (s, 3H), 2.34-2.27 (m, 2H), 2.01-1.97 (m, 2H), 1.82-1.77 (m, 2H). MS 480 [M+H]$^+$.

Example 38

(3-(4-(6,8-dichloro-2-methyl-1,2,3,4-tetrahydroisoquinolin-4-yl)phenyl)ureido)methylphosphonic acid

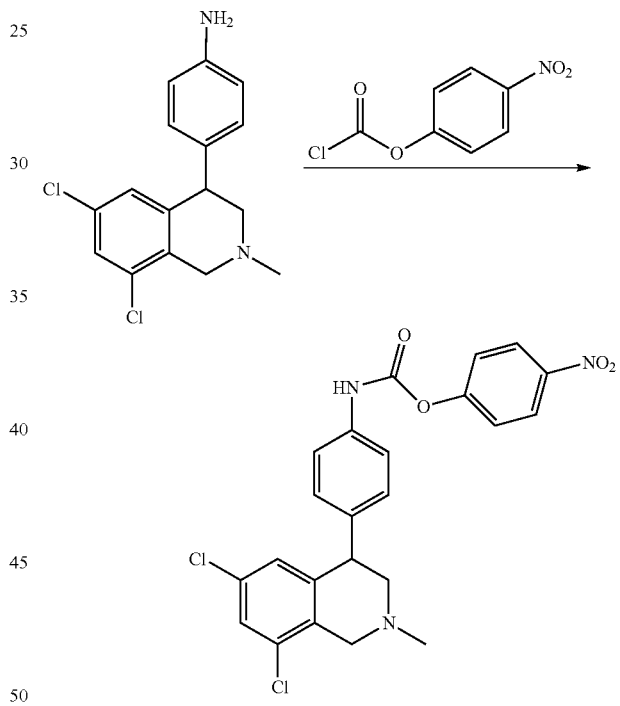

Intermediate 38.1: 4-nitrophenyl 4-(6,8-dichloro-2-methyl-1,2,3,4-tetrahydroisoquinolin-4-yl)phenylcarbamate Into a 50-mL round-bottom flask purged and maintained with an inert atmosphere of nitrogen, was placed a solution of 4-(6,8-dichloro-2-methyl-1,2,3,4-tetrahydroisoquinolin-4-yl)benzenamine (intermediate 30.7) (300 mg, 0.98 mmol, 1.00 equiv) in dichloromethane (10 mL). This was followed by the addition of 4-nitrophenyl chloroformate (230 mg, 1.14 mmol, 1.20 equiv) in several batches at room temperature. The resulting solution was stirred for 3 h at room temperature. The solids were collected by filtration. This resulted in 0.3 g (65%) of 4-nitrophenyl 4-(6,8-dichloro-2-methyl-1,2,3,4-tetrahydroisoquinolin-4-yl)phenylcarbamate as a yellow solid.

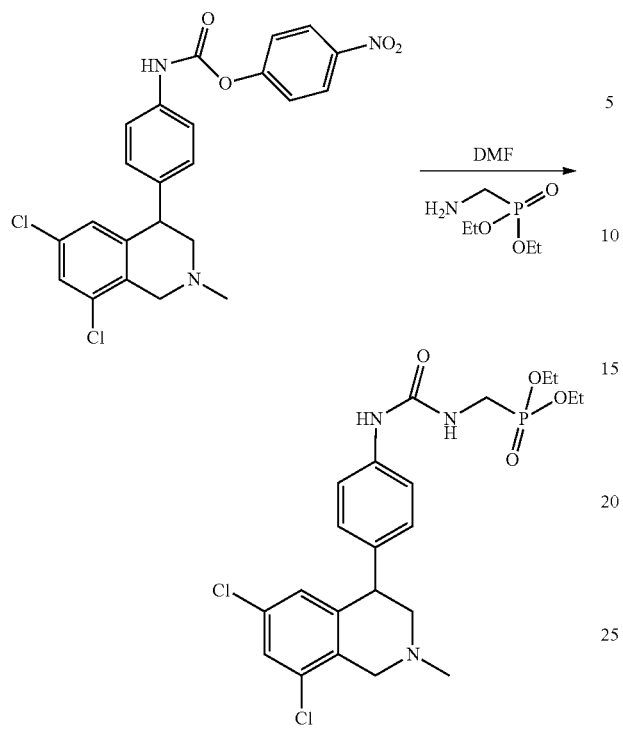

Intermediate 38.2: diethyl (3-(4-(6,8-dichloro-2-methyl-1,2,3,4-tetrahydroisoquinolin-4-yl)phenyl)ureido)methylphosphonate Into a 50-mL round-bottom flask purged and maintained with an inert atmosphere of nitrogen, was placed a solution of 4-nitrophenyl 4-(6,8-dichloro-2-methyl-1,2,3,4-tetrahydroisoquinolin-4-yl)phenylcarbamate (200 mg, 0.42 mmol, 1.00 equiv) in N,N-dimethylformamide (6 mL), a solution of diethyl aminomethylphosphonate (144 mg, 0.63 mmol, 1.50 equiv) in N,N-dimethylformamide (1 mL) and triethylamine (64 mg). The resulting solution was stirred overnight at room temperature. The reaction was then quenched by the addition of 10 mL of water. The resulting solution was extracted with 3×10 mL of ethyl acetate and the organic layers combined and dried over anhydrous sodium sulfate and concentrated under vacuum. This resulted in 40 mg (17%) of diethyl (3-(4-(6,8-dichloro-2-methyl-1,2,3,4-tetrahydroisoquinolin-4-yl)phenyl)ureido)methylphosphonate as a solid.

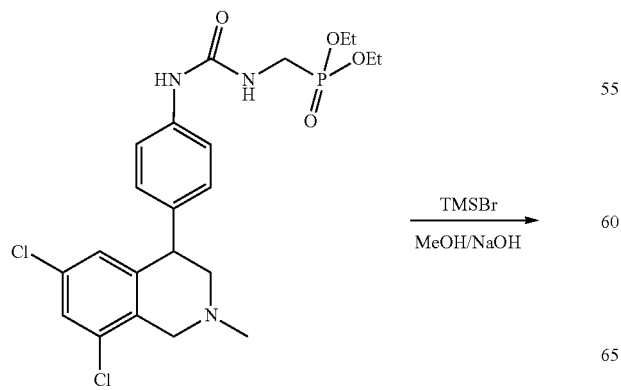

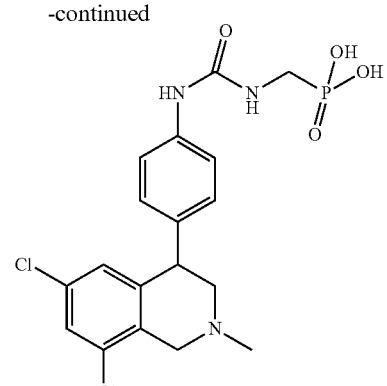

Compound 38: (3-(4-(6,8-dichloro-2-methyl-1,2,3,4-tetrahydroisoquinolin-4-yl)phenyl)ureido)methylphosphonic acid Into a 50-mL round-bottom flask purged and maintained with an inert atmosphere of nitrogen, was placed a solution of diethyl (3-(4-(6,8-dichloro-2-methyl-1,2,3,4-tetrahydroisoquinolin-4-yl)phenyl)ureido)methylphosphonate (40 mg, 0.08 mmol, 1.00 equiv) in dichloromethane (5 mL) and bromotrimethylsilane (0.15 mL). The resulting solution was stirred overnight at room temperature. The resulting mixture was concentrated under vacuum. To the above was added methanol (5 mL) and sodium hydroxide (5 mg). The resulting mixture was stirred 0.5 h at room temperature. The solids were collected by filtration and the residue was lyophilized. This resulted in 17.4 mg (42%) a sodium salt of the title compound as a yellow solid. $^1$H-NMR (300 MHz, CD$_3$OD+DCl, ppm): δ 7.46-7.49 (m, 3H), 7.20-7.23 (d, J=8.7 Hz, 2H), 6.80 (s, 1H), 4.77-4.83 (d, J=15.9 Hz, 1H), 4.65-4.71 (m, 1H), 4.50-4.55 (d, J=16.2 Hz, 1H), 3.79-3.85 (m, 1H), 3.56-3.69 (m, 3H), 3.32 (s, 3H). MS (ES, m/z): 444 [M+H]$^+$.

Example 39

(3-(3-(6,8-dichloro-2-methyl-1,2,3,4-tetrahydroisoquinolin-4-yl)phenyl)ureido)methylphosphonic acid

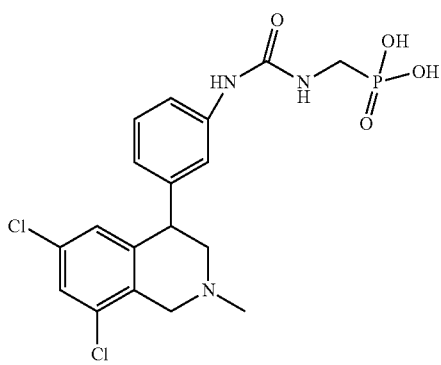 [SMILES: CN1Cc2c(Cl)cc(Cl)cc2C(c2cccc(NC(=O)NCP(=O)(O)O)c2)C1]

Compound 39: (3-(3-(6,8-dichloro-2-methyl-1,2,3,4-tetrahydroisoquinolin-4-yl)phenyl)ureido)methylphosphonic acid Following the procedures outlined in Example 38, substituting 3-(6,8-dichloro-2-methyl-1,2,3,4-tetrahydroisoquinolin-4-yl)aniline (intermediate 31.5) for 4-(6,8-dichloro-2-methyl-1,2,3,4-tetrahydroisoquinolin-4-yl)aniline gave the title compound as a sodium salt. $^1$H-NMR (300 MHz, CD$_3$OD, ppm): δ 7.47 (s, 1H), 7.37 (m, 3H), 6.96 (m, 1H), 6.82 (s, 1H), 4.81 (m, 1H), 4.70 (m, 1H), 4.54 (m, 1H), 3.83 (m, 1H), 3.65 (m, 3H), 3.19 (s, 3H).

Example 40

2-(3-(3-(4-(6,8-dichloro-2-methyl-1,2,3,4-tetrahydroisoquinolin-4-yl)phenyl)ureido)propyl)malonic acid

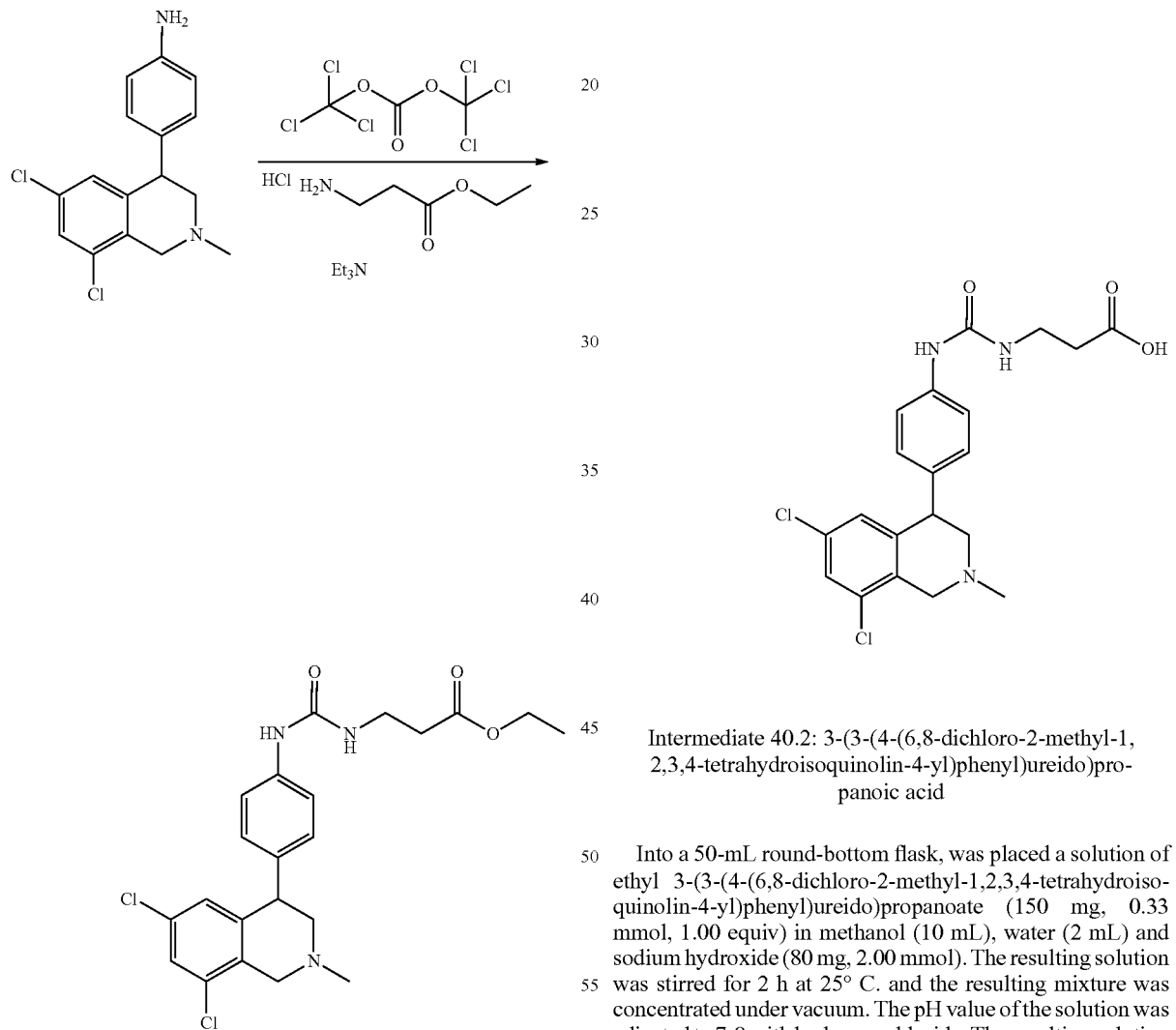

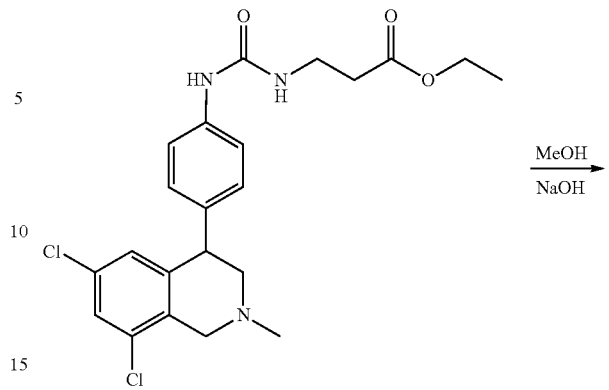

Intermediate 40.1: ethyl 3-(3-(4-(6,8-dichloro-2-methyl-1,2,3,4-tetrahydroisoquinolin-4-yl)phenyl)ureido)propanoate Following the procedures outlined in Example 34, substituting ethyl 3-aminopropanoate for (S)-dimethyl 2-aminosuccinate gave the title compound as a yellow oil.

Intermediate 40.2: 3-(3-(4-(6,8-dichloro-2-methyl-1,2,3,4-tetrahydroisoquinolin-4-yl)phenyl)ureido)propanoic acid Into a 50-mL round-bottom flask, was placed a solution of ethyl 3-(3-(4-(6,8-dichloro-2-methyl-1,2,3,4-tetrahydroisoquinolin-4-yl)phenyl)ureido)propanoate (150 mg, 0.33 mmol, 1.00 equiv) in methanol (10 mL), water (2 mL) and sodium hydroxide (80 mg, 2.00 mmol). The resulting solution was stirred for 2 h at 25° C. and the resulting mixture was concentrated under vacuum. The pH value of the solution was adjusted to 7-8 with hydrogen chloride. The resulting solution was extracted with chloroform (3×10 ml) and the organic layers combined and dried over sodium sulfate. This resulted in 31.5 mg (22%) of 3-(3-(4-(6,8-dichloro-2-methyl-1,2,3,4-tetrahydroisoquinolin-4-yl)phenyl)ureido)propanoic acid as a white solid. $^1$H-NMR (300 MHz, DMSO, ppm): δ 8.56 (1H, s), 7.45 (1H, s), 7.29-7.32 (2H, d, J=8.1 Hz), 7.04-7.07 (2H, d, J=8.4 Hz), 6.79 (1H, s), 6.21 (1H, s), 4.16 (1H, m), 3.56-3.58 (2H, d, J=5.4 Hz), 3.27-3.29 (2H, d, J=6 Hz), 2.82-2.87 (1H, m), 2.59 (2H, s), 2.38-2.40 (4H, m). MS (ES, m/z): 422 [M+H]$^+$.

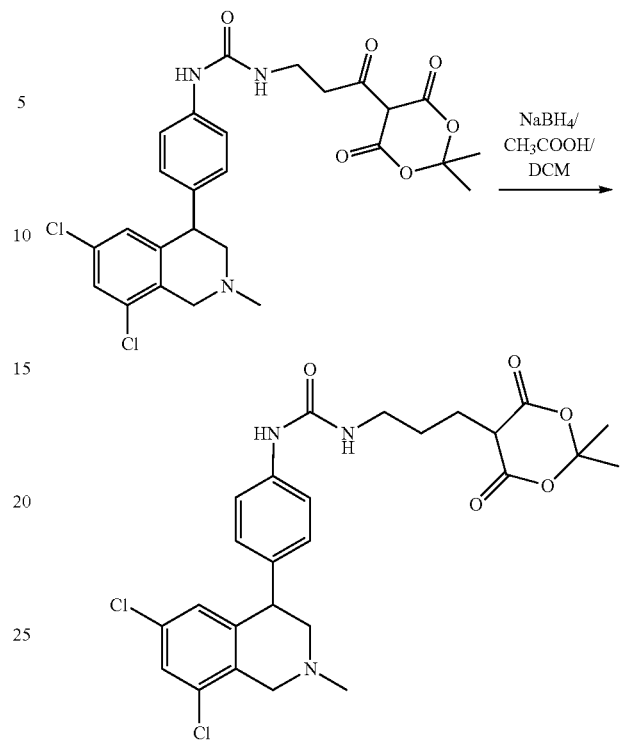

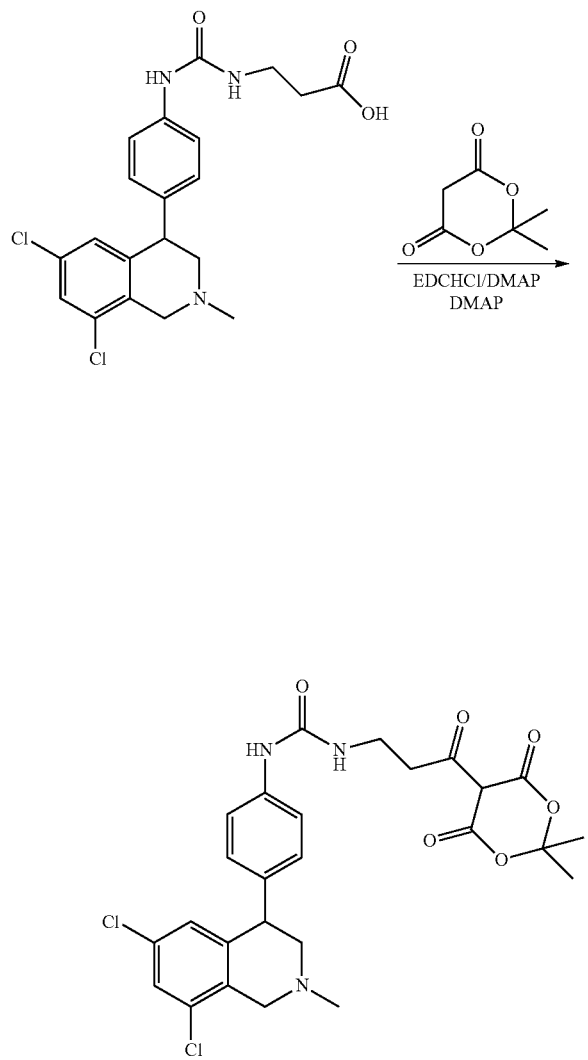

Intermediate 40.3: 1-(4-(6,8-dichloro-2-methyl-1,2,3,4-tetrahydroisoquinolin-4-yl)phenyl)-3-(3-(2,2-dimethyl-4,6-dioxo-1,3-dioxan-5-yl)-3-oxopropyl)urea Into a 50-mL round-bottom flask purged and maintained with an inert atmosphere of nitrogen, was placed a solution of 3-(3-(4-(6,8-dichloro-2-methyl-1,2,3,4-tetrahydroisoquinolin-4-yl)phenyl)ureido)propanoic acid (200 mg, 0.47 mmol, 1.00 equiv) in dichloromethane (20 mL), N-(3-dimethylaminopropyl)-N'-ethylcarbodiimide hydrochloride (136 mg, 0.71 mmol, 1.50 equiv) and 4-dimethylaminopyridine (115 mg, 0.94 mmol, 1.99 equiv). This was followed by the addition of a solution of 2,2-dimethyl-1,3-dioxane-4,6-dione (102 mg, 0.71 mmol, 1.49 equiv) in dichloromethane (2 mL) dropwise with stirring at 0° C. The resulting solution was stirred for 3 h at room temperature. The resulting mixture was washed with KHSO$_4$ (2×10 mL). The mixture was dried over anhydrous sodium sulfate and concentrated under vacuum. This resulted in 240 mg (92%) of 1-(4-(6,8-dichloro-2-methyl-1,2,3,4-tetrahydroisoquinolin-4-yl)phenyl)-3-(3-(2,2-dimethyl-4,6-dioxo-1,3-dioxan-5-yl)-3-oxopropyl)urea as a yellow solid.

Intermediate 40.4: 1-(4-(6,8-dichloro-2-methyl-1,2,3,4-tetrahydroisoquinolin-4-yl)phenyl)-3-(3-(2,2-dimethyl-4,6-dioxo-1,3-dioxan-5-yl)propyl)urea Into a 50-mL round-bottom flask purged and maintained with an inert atmosphere of nitrogen, was placed a solution of 1-(4-(6,8-dichloro-2-methyl-1,2,3,4-tetrahydroisoquinolin-4-yl)phenyl)-3-(3-(2,2-dimethyl-4,6-dioxo-1,3-dioxan-5-yl)-3-oxopropyl)urea (150 mg, 0.27 mmol, 1.00 equiv) in dichloromethane (10 mL) and acetic acid (1 mL) Sodium borohydride (42 mg, 1.11 mmol, 4.04 equiv) was added and the resulting solution was stirred overnight at room temperature. The resulting mixture was washed with saturated aqueous sodium chloride (3×10 mL). The mixture was dried over anhydrous sodium sulfate and concentrated under vacuum. This resulted in 30 mg (21%) of 1-(4-(6,8-dichloro-2-methyl-1,2,3,4-tetrahydroisoquinolin-4-yl)phenyl)-3-(3-(2,2-dimethyl-4,6-dioxo-1,3-dioxan-5-yl)propyl)urea as a yellow solid.

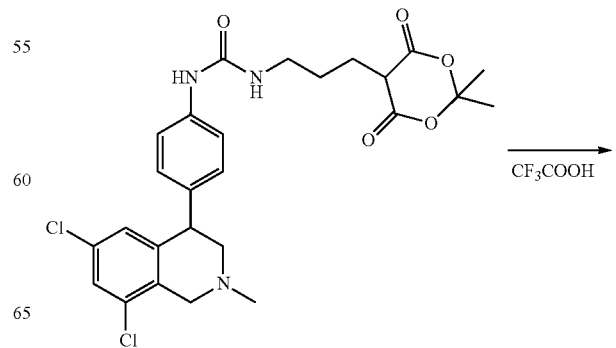

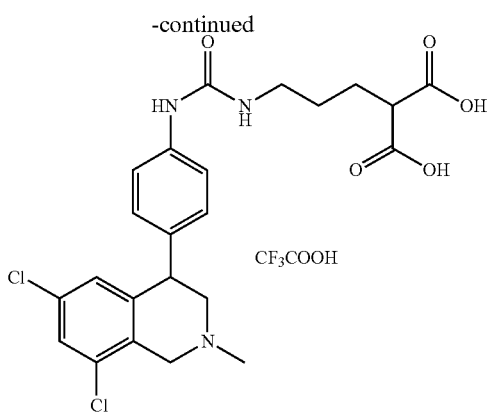

Compound 40: 2-(3-(3-(4-(6,8-dichloro-2-methyl-1,2,3,4-tetrahydroisoquinolin-4-yl)phenyl)ureido)propyl)malonic acid Into a 50-mL round-bottom flask, was placed a solution of 1-(4-(6,8-dichloro-2-methyl-1,2,3,4-tetrahydroisoquinolin-4-yl)phenyl)-3-(3-(2,2-dimethyl-4,6-dioxo-1,3-dioxan-5-yl)propyl)urea (100 mg, 0.19 mmol, 1.00 equiv) in 2,2,2-trifluoroacetic acid (10 mL), and water (2 mL). The resulting solution was stirred overnight at room temperature. The resulting mixture was concentrated under vacuum. The residue was applied onto a silica gel column with methanol:water (60%). The residue was lyophilized. This resulted in 36.3 mg (30%) of a TFA salt of the title compound as a white solid. $^1$H-NMR (300 MHz, DMSO, ppm): δ 8.55 (s, 1H), 7.64 (s, 1H), 7.39-7.42 (d, J=8.7 Hz, 2H), 7.09-7.12 (d, J=8.4 Hz, 2H), 6.79 (s, 1H), 6.23-6.27 (m, 1H), 4.33-4.50 (m, 3H), 3.62 (s, 1H), 3.19 (m, 1H), 3.08-3.10 (d, J=5.7 Hz, 2H), 2.94 (s, 3H), 1.70-1.77 (d, J=23.1 Hz, 2H), 1.41-1.46 (d, J=12 Hz, 2H). MS (ES, m/z): 494 [M+H]$^+$.

Example 41

N,N'-(butane-1,4-diyl)bis[(E)-N-(diaminomethylene)-3-(3,5-difluoro-4-(4-sulfamoylphenoxy)phenyl)-2-methylacrylamide]

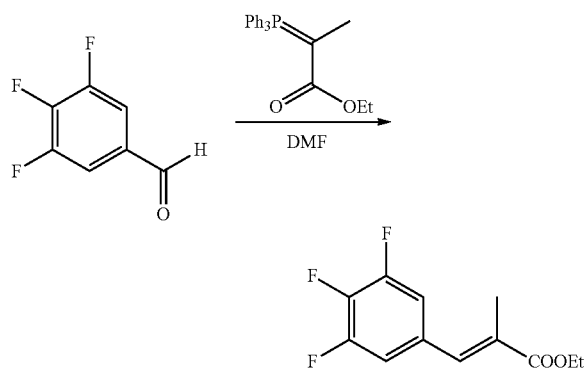

Intermediate 41.1 (E)-ethyl 2-methyl-3-(3,4,5-trifluorophenyl)acrylate

To a solution of dry DMF (50 mL) under N$_2$ was added 3,4,5-trifluorobenzaldehyde (4.26 g, 26.6 mmol) followed by ethyl 2-(triphenylphosphoranylidene)propionate (10.6 g, 29.3 mmol) in portions, keeping the solution at room temperature. After 1 hour, TLC (10% EtOAC in Hexanes) showed complete conversion, and the solvent was removed by rotary evaporation. The resulting material was brought up in 50 mL methyl t-butyl ether (MBTE) and the precipitate removed by filtration and washed with additional MBTE (3×50 mL). After concentration, the resulting filtrate was applied onto a silica gel column (25% EtOAc in hexanes) resulting in 6.0 g of the title compound (93%) as a white powder.

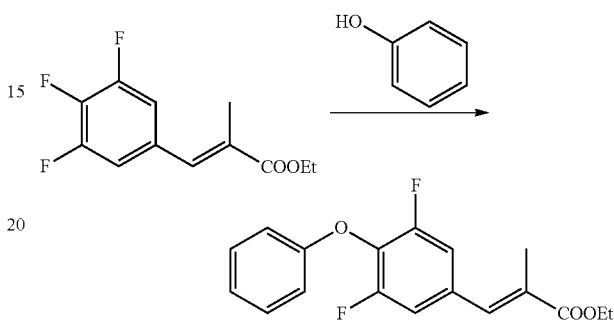

Intermediate 41.2 (E)-ethyl 3-(3,5-difluoro-4-phenoxyphenyl)-2-methylacrylate

To a solution of (E)-ethyl 2-methyl-3-(3,4,5-trifluorophenyl)acrylate (Intermediate 41.1, 6.0 g, 24.56 mmol) in dry DMF (25 mL) under N$_2$ was added phenol (2.774 g, 29.5 mmol) and K$_2$CO$_3$ (10.2 g, 73.68 mmol). The resulting solution was brought to 120° C. and stirred for 3 hours at which point TLC indicated complete conversion. The solvent was removed by rotary evaporation and the resulting residue brought up in EtOAc (200 mL) and washed with water (2×200 mL), 1N NaOH (2×200 mL) and brine (200 mL). The organic layer was dried over Na$_2$SO$_4$ and concentrated to yield 6.94 g (89%) of the title compound as tan crystals.

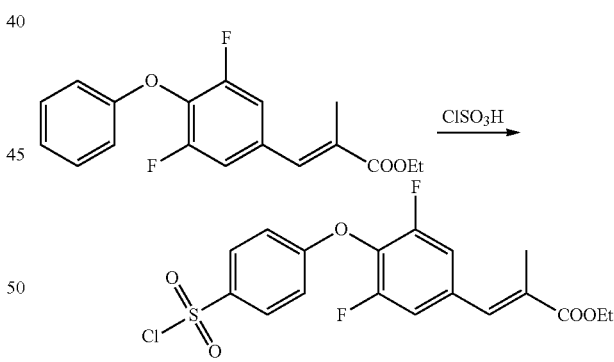

Intermediate 41.3 (E)-ethyl 3-(4-(4-(chlorosulfonyl)phenoxy)-3,5-difluorophenyl)-2-methylacrylate To a solution of (E)-ethyl 3-(3,5-difluoro-4-phenoxyphenyl)-2-methylacrylate (intermediate 41.2) (1 g, 3.14 mmol) in DCM (3.14 mL) under N$_2$ was added chlorosulfonic acid (0.419 mL, 6.28 mmol) dropwise. After 1 hour an additional 0.209 mL chlorosulfonic acid was added. After an additional hour the reaction mixture was quenched with ice-water and extracted into EtOAc (2×200 mL). The combined organic layers were dried briefly (<10 min) over Na$_2$SO$_4$ and concentrated to recover 1.283 g of the title compound (98%) as a yellow oil.

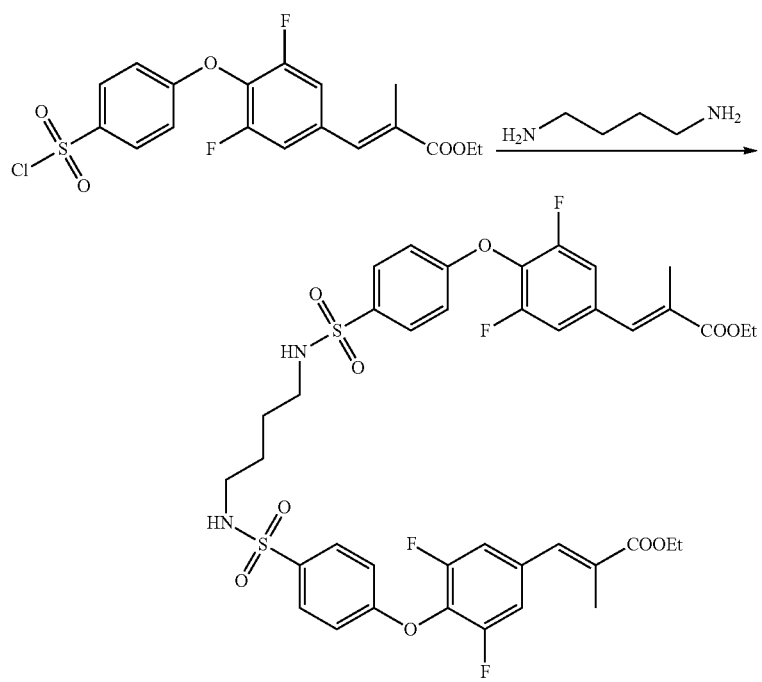

Intermediate 41.4 N,N'-(butane-1,4-diyl)bis[4-(2,6-difluoro-4-(2-carboethoxypropenyl)phenoxy)benzenesulfonamide]

To a solution of (E)-ethyl 3-(4-(4-(chlorosulfonyl)phenoxy)-3,5-difluorophenyl)-2-methylacrylate (Intermediate 41.3) (104.3 mg, 0.25 mmol) in chloroform (0.5 mL) was added DIEA (0.0869 mL, 0.5 mmol) and a solution of butane-1,4-diamine (12.6 uL, 0.125 mmol) and DIEA (0.087 mL, 0.5 mmol) in chloroform (0.125 mL). After one hour the solvent was removed and the resulting residue brought up in EtOAc (40 mL), washed with water (2×40 mL), brine (40 mL) and dried over $Na_2SO_4$. Removing the solvent gave 118 mg of the title compound which was used without further purification.

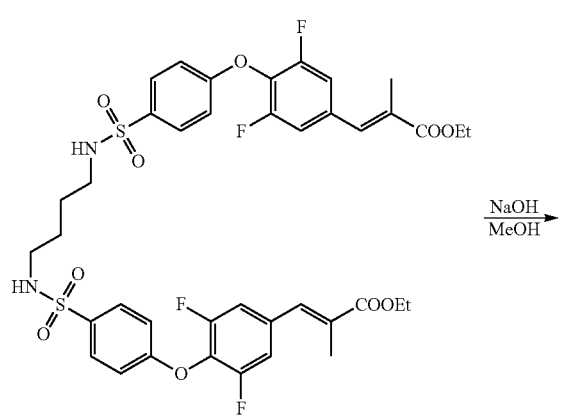

-continued

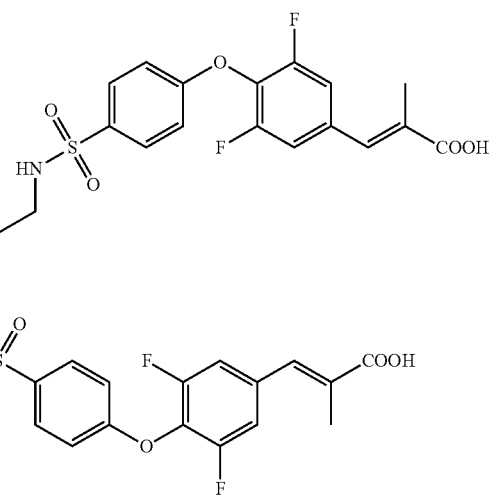

Intermediate 41.5: N,N'-(butane-1,4-diyl)bis[4-(2,6-difluoro-4-(2-carboxypropenyl)phenoxy)benzenesulfonamide]

To a solution of Intermediate 41.4 (118 mg, 0.139 mmol) in MeOH (1.39 mL) was added a NaOH (0.3M in water, 0.278 mL, 0.835 mmol). The reaction was placed under $N_2$ and heated at 60° C. for 30 minutes. After cooling the reaction mixture was diluted with water (20 mL), partitioned with EtOAc (20 mL) and acidified with HCl. After extracting with EtOAc (2×20 mL) the combined organic phases were dried over $Na_2SO_4$ and the solvent removed to give 40.7 mg of the title compound.

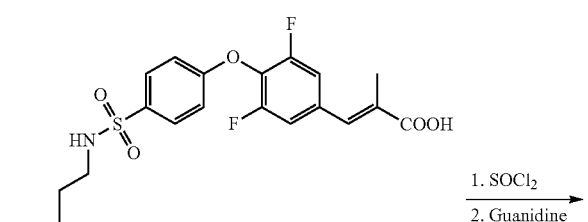

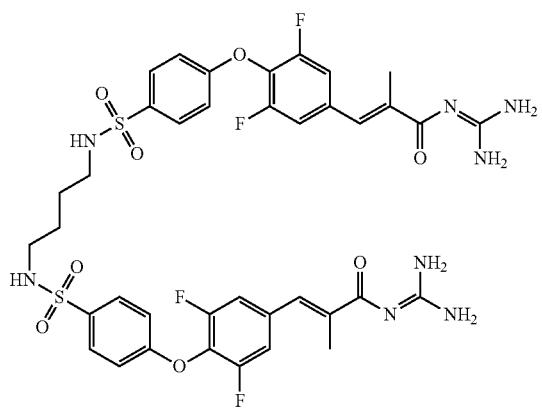

Compound 41: N,N'-(butane-1,4-diyl)bis[(E)-N-(diaminomethylene)-3-(3,5-difluoro-4-(4-sulfamoylphenoxy)phenyl)-2-methylacrylamide]

Thionyl chloride (2 mL) was added to intermediate 41.5 (40.7 mg, 0.051 mmol) and was heated at 80° under $N_2$. After 70 minutes, the solvent was removed in vacuo. The residue was brought up in toluene (2 mL) and the toluene was also removed in vacuo. The bis-acid chloride was dissolved in DME (0.5 mL) and added to guanidine free base (1.4 mmol, prepared as follows: To a slurry of guanidine hydrochloride (480 mg, 5.0 mmol) was added 25% NaOMe in MeOH (1.03 mL, 4.5 mmol). The mixture was stirred for 30 minutes and then filtered. A portion of the filtrate (0.40 mL) was concentrated to dryness.) in DME (1 mL). After 15 minutes, water (10 mL) was added and the mixture was extracted with EtOAc (3×25 mL). The organic layer was dried ($Na_2SO_4$) and concentrated. The crude product was purified by preparative HPLC to give the title compound (7.8 mg) as the TFA salt. $^1$H-NMR (400 mHz, CD3OD) δ 7.80 (d, 4H), 7.44 (s, 2H), 7.30 (d, 4H), 7.11 (d, 4H), 2.80 (m, 4H), 2.18 (s, 6H), 1.44 (m, 4H). MS (m/z): 875.16 (M+H).

Example 42

N,N'-(1,4-phenylenebis(methylene))bis[(E)-N-(diaminomethylene)-3-(3,5-difluoro-4-(4-sulfamoylphenoxy)phenyl)-2-methylacrylamide]

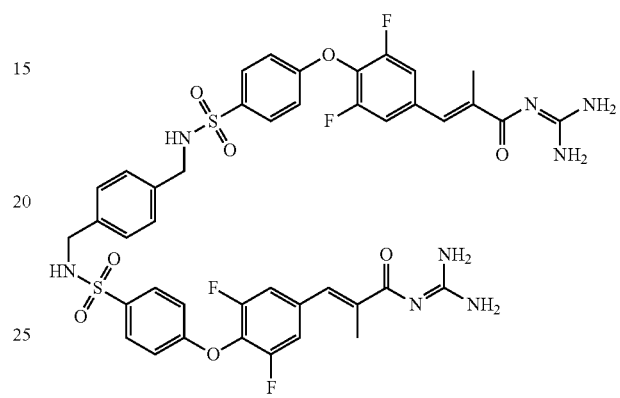

Compound 42: N,N'-(1,4-phenylenebis(methylene))bis[(E)-N-(diaminomethylene)-3-(3,5-difluoro-4-(4-sulfamoylphenoxy)phenyl)-2-methylacrylamide])

Following the procedures outlined in Example 41, compound 42 was made using 1,4-phenylenedimethanamine as the amine. Purification by preparative HPLC gave the title compound as a TFA salt. $^1$H-NMR (400 mHz, CD3OD) δ 7.87 (d, 4H), 7.44 (s, 2H), 7.31 (d, 4H), 7.06 (d, 6H), 7.04 (s, 2H), 4.02 (s, 4H), 2.19 (s, 6H). MS (m/z): 924.21 (M+H)

Example 43

N,N'-(2,2'-(ethane-1,2-diylbis(oxy))bis(ethane-2,1-diyl))bis[(E)-N-(diaminomethylene)-3-(3,5-difluoro-4-(4-sulfamoylphenoxy)phenyl)-2-methylacrylamide]

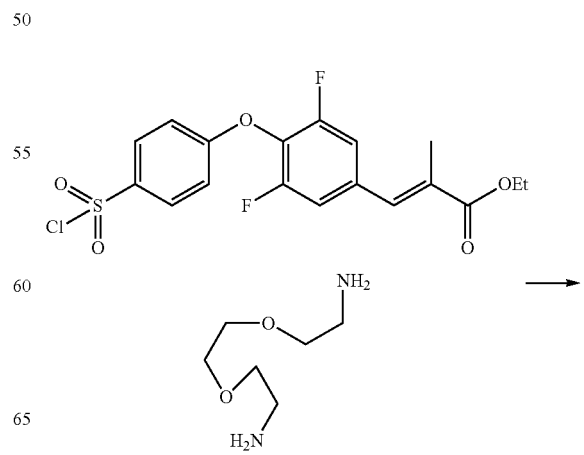

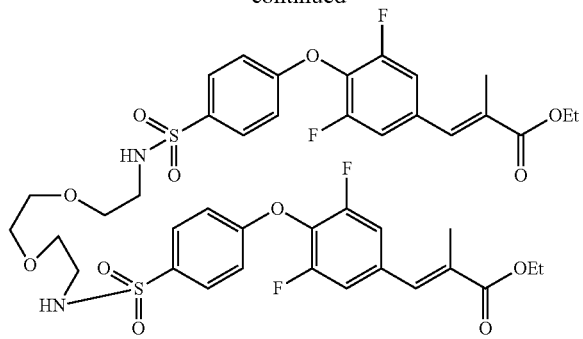

Intermediate 43.1 N,N'-(2,2'-(ethane-1,2-diylbis(oxy))bis(ethane-2,1-diyl))bis((E)-4-(2,6-difluoro-4-(2-carboethoxypropenyl)phenoxy)benzenesulfonamide)

To a solution of (E)-ethyl 3-(4-(4-(chlorosulfonyl)phenoxy)-3,5-difluorophenyl)-2-methylacrylate (intermediate 41.3) (225 mg, 0.54 mmol) in DCM (3 mL) was added a solution of 2,2'-(ethane-1,2-diylbis(oxy))diethanamine (38 mg, 0.26 mmol) and triethylamine (101 mg, 1.0 mmol) in DCM (2 mL) dropwise. After 30 minutes, 1N HCl was added (10 mL) and the reaction mixture was extracted with DCM (3×15 mL). The combined organic layers were dried (Na$_2$SO$_4$) and concentrated to give the title compound (262 mg).

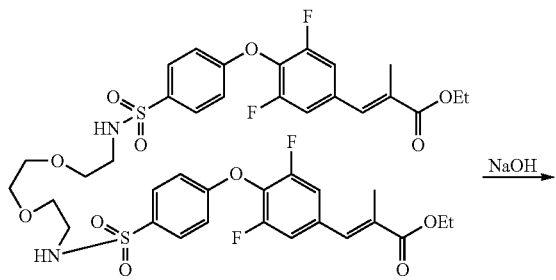

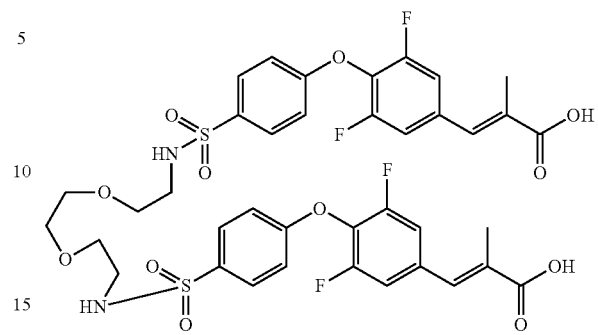

Intermediate 43.2 N,N'-(2,2'-(ethane-1,2-diylbis(oxy))bis(ethane-2,1-diyl))bis((E)-4-(2,6-difluoro-4-(2-carboxypropenyl)phenoxy)benzenesulfonamide)

A solution of the intermediate 43.1 (262 mg, 0.29 mmol) and 3N NaOH (0.6 mL, 1.8 mmol) in methanol (3 mL) was heated at 65° C. for 1 hour. The reaction mixture was cooled to RT and the methanol removed at reduced pressure and 1N HCl (3 mL, 3 mmol) was added to the residue. The product was extracted into DCM (3×15 mL). The combined organic layers were dried (Na$_2$SO$_4$) and concentrated to give the title compound (173 mg).

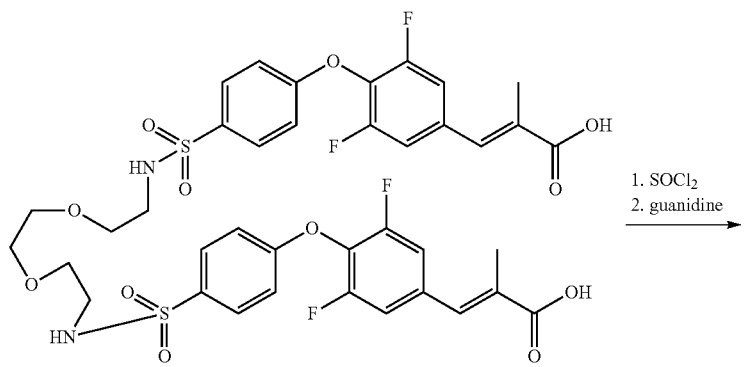

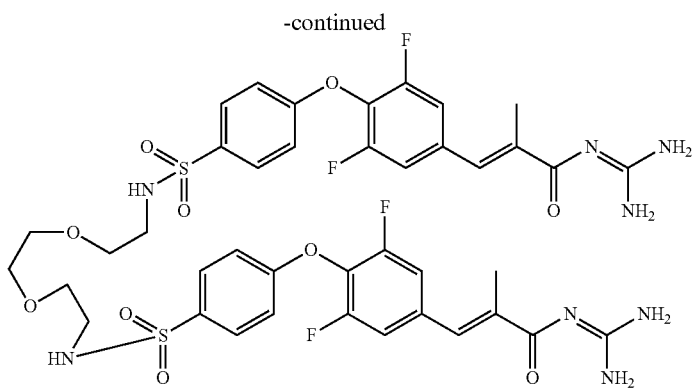

Compound 43: N,N'-(2,2'-(ethane-1,2-diylbis(oxy))bis(ethane-2,1-diyl))bis[(E)-N-(diaminomethylene)-3-(3,5-difluoro-4-(4-sulfamoylphenoxy)phenyl)-2-methylacrylamide]

Thionyl chloride (1 mL) was added to intermediate 43.2 (63 mg, 0.074 mmol) and was heated at 80°. After 2 hours, the solvent was removed in vacuo. The bis-acid chloride was dissolved in DME (1 mL) and added to guanidine free base (1.4 mmol, prepared as follows: To a slurry of guanidine hydrochloride (480 mg, 5.0 mmol) was added 25% NaOMe in MeOH (1.03 mL, 4.5 mmol). The mixture was stirred for 30 minutes and then filtered. A portion of the filtrate (0.40 mL) was concentrated to dryness.) in DME (1 mL). After 15 minutes, water (10 mL) was added and the mixture was extracted with EtOAc (3×25 mL). The organic layer was dried (Na₂SO₄) and concentrated. The crude product was purified by preparative HPLC to give the title compound (20 mg) as the TFA salt. ¹H-NMR (400 mHz, CD3OD) δ 7.83 (d, j=8.8 Hz, 4H), 7.43 (s, 2H), 7.30 (d, j=8.9 Hz, 4H), 7.11 (d, j=8.6 Hz, 4H), 3.42 (t, j=5.5 Hz, 8H), 3.03 (t, j=5.4 Hz, 4H), 2.17 (s, 6H). MS (m/z): 935.08 (M+H).

Example 44

N,N'-(2,2'-(2,2'-oxybis(ethane-2,1-diyl)bis(oxy))bis(ethane-2,1-diyl))bis[(E)-N-(diaminomethylene)-3-(3,5-difluoro-4-(4-sulfamoylphenoxy)phenyl)-2-methylacrylamide]

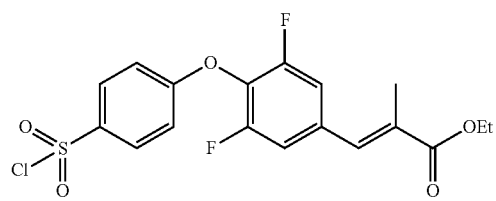

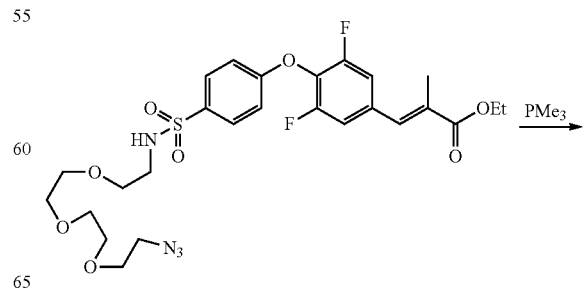

Intermediate 44.1: (E)-ethyl 3-(4-(4-(N-(2-(2-(2-(2-azidoethoxy)ethoxy)ethoxy)ethyl)sulfamoyl)phenoxy)-3,5-difluorophenyl)-2-methylacrylate To a solution of (E)-ethyl 3-(4-(4-(chlorosulfonyl)phenoxy)-3,5-difluorophenyl)-2-methylacrylate (intermediate 41.3) (250 mg, 0.60 mmol) in DCM (3 mL) was added a solution of 2-(2-(2-(2-azidoethoxy)ethoxy)ethoxy)ethanamine (157 mg, 0.72 mmol) and triethylamine (72 mg, 0.72 mmol) in DCM (2 mL). After 15 minutes, water (10 mL) was added and the reaction mixture was extracted with DCM (2×25 mL). The combined organic layers were washed with water (10 mL), brine (10 mL), dried (Na₂SO₄) and concentrated. The crude material was purified by flash chromatography on silica gel eluting with 50% EtOAc in DCM to give the title compound (169 mg).

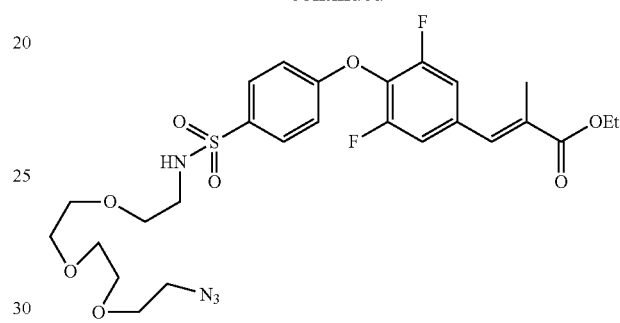

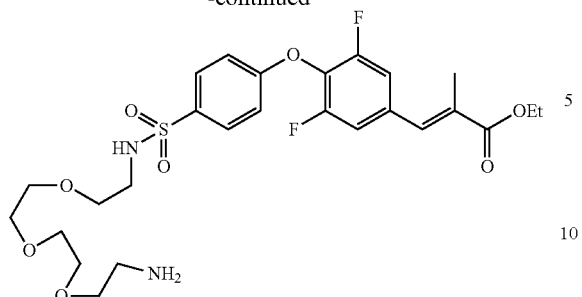

Intermediate 44.2: (E)-ethyl 3-(4-(4-(N-(2-(2-(2-(2-aminoethoxy)ethoxy)ethoxy)ethyl)sulfamoyl)phenoxy)-3,5-difluorophenyl)-2-methylacrylate To a solution of (E)-ethyl 3-(4-(4-(N-(2-(2-(2-(2-azidoethoxy)ethoxy)ethoxy)ethyl)sulfamoyl)phenoxy)-3,5-difluorophenyl)-2-methylacrylate (169 mg, 0.28 mmol) in THF (6 ml) and water (0.6 mL) under nitrogen was added trimethylphosphine (26 mg, 0.34 mmol). After stirring for 3 hours, the solvents were removed at reduced pressure and. The residue was dissolved in water (5 mL) and extracted with EtOAc (3×25 mL). The combined organic layers were dried (Na$_2$SO$_4$) and concentrated to give the title compound (162 mg).

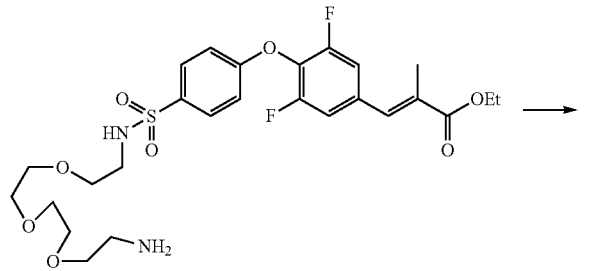
→

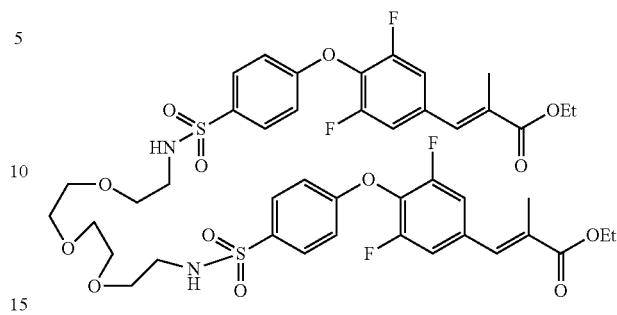

Intermediate 44.3: N,N'-(2,2'-(2,2'-oxybis(ethane-2,1-diyl)bis(oxy))bis(ethane-2,1-diyl))bis[4-(2,6-difluoro-4-(2-carboethoxypropenyl)phenoxy)benzenesulfonamide]

A solution of (E)-ethyl 3-(4-(4-(chlorosulfonyl)phenoxy)-3,5-difluorophenyl)-2-methylacrylate (intermediate 41.3) (71 mg, 0.17 mmol) in EtOAc (1 mL) was added to a solution of (E)-ethyl 3-(4-(4-(N-(2-(2-(2-(2-aminoethoxy)ethoxy)ethoxy)ethyl)sulfamoyl)phenoxy)-3,5-difluorophenyl)-2-methylacrylate (84 mg, 0.15 mmol) and triethylamine (22 mg, 0.22 mmol) in DCM (1 mL) with stirring. After 30 minutes, water (10 mL) was added and the product extracted into DCM (3×15 mL). The combined organic layers were dried (Na$_2$SO$_4$) and concentrated to give the title compound (177 mg).

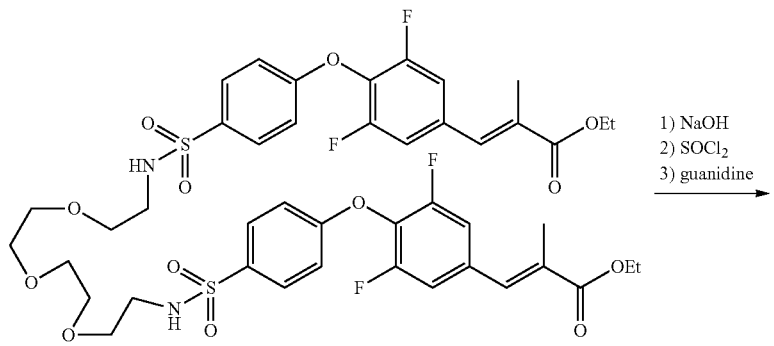

1) NaOH
2) SOCl$_2$
3) guanidine
→

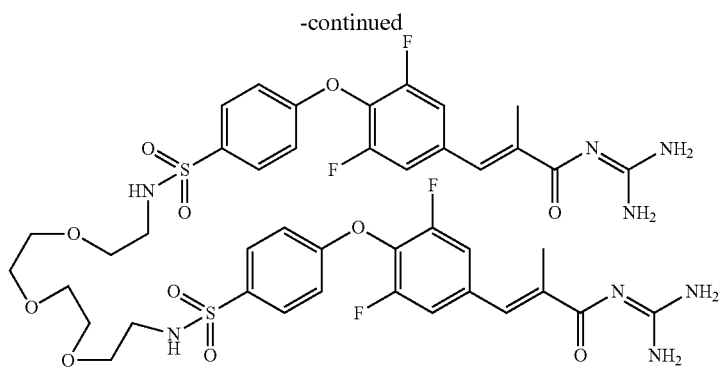

Compound 44 N,N'-(2,2'-(2,2'-oxybis(ethane-2,1-diyl)bis(oxy))bis(ethane-2,1-diyl))bis[(E)-N-(diaminomethylene)-3-(3,5-difluoro-4-(4-sulfamoylphenoxy)phenyl)-2-methylacrylamide]

Following the procedures outlined in Example 43, intermediate 44.3 was converted to the bis-guanidine and gave, after purification by preparative HPLC, the title compound (21 mg) as a TFA salt. $^1$H-NMR (400 mHz, CD3OD) δ 7.84 (d, j=8.8 Hz, 4H), 7.44 (s, 2H), 7.30 (d, j=8.8 Hz, 4H), 7.10 (d, j=8.8 Hz, 4H), 3.54 (m, 4H), 3.48 (m, 4H), 3.43 (t, j=5.5 Hz, 4H), 3.04 (t, j=5.5 Hz, 4H), 2.17 (d, j=1.2 Hz, 6H). MS (m/z): 979.05 (M+H).

Example 45

(E)-3-(4-(4-(N-(2-(2-(2-(2-aminoethoxy)ethoxy)ethoxy)ethyl)sulfamoyl)phenoxy)-3,5-difluorophenyl)-N-(diaminomethylene)-2-methylacrylamide

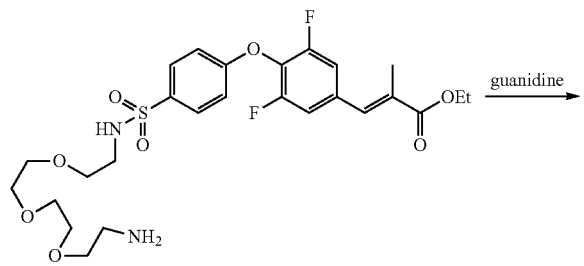

Compound 45: (E)-3-(4-(4-(N-(2-(2-(2-(2-aminoethoxy)ethoxy)ethoxy)ethyl)sulfamoyl)phenoxy)-3,5-difluorophenyl)-N-(diaminomethylene)-2-methylacrylamide A 4.3 M solution of guanidine free base in methanol was prepared. A 25% solution of NaOMe in MeOH (1.03 mL, 4.5 mmol) was added to guanidine hydrochloride (480 mg, 5.0 mmol), and the mixture was stirred for 30 minutes. The mixture was filtered (0.2µ, PTFE) to give the guanidine free base solution. A portion (0.3 mL, 1.3 mmol) was added to (E)-ethyl 3-(4-(4-(N-(2-(2-(2-(2-aminoethoxy)ethoxy)ethoxy)ethyl)sulfamoyl)phenoxy)-3,5-difluorophenyl)-2-methylacrylate (74 mg, 0.13 mmol) with stirring. After 15 minutes, water (10 mL) was added and the product extracted with DCM (4×20 mL). The combined organic layers were dried (Na$_2$SO$_4$) and concentrated. The crude product was purified by preparative HPLC to give the title compound (34 mg) as a TFA salt. $^1$H-NMR (400 mHz, d6-DMSO) δ 11.14 (s, 1H), 8.38 (br s, 4H), 7.78 (d, j=9.0 Hz, 2H), 7.5 (m, 3H), 7.45 (d, j=9.1, 2H), 7.42 (s, 1H), 7.19 (d, j=8.8 Hz, 2H), 3.55 (m, 6H), 3.44 (m, 4H), 3.36 (m, 2H), 2.95 (m, 2H), 2.87 (m, 2H), 2.11 (s, 3H). MS (m/z): 586.11 (M+H).

Example 46

N,N'-(13-oxo-3,6,9,17,20,23-hexaoxa-12,14-diazapentacosane-1,25-diyl)bis[(E)-N-(diaminomethylene)-3-(3,5-difluoro-4-(4-sulfamoylphenoxy)phenyl)-2-methylacrylamide]

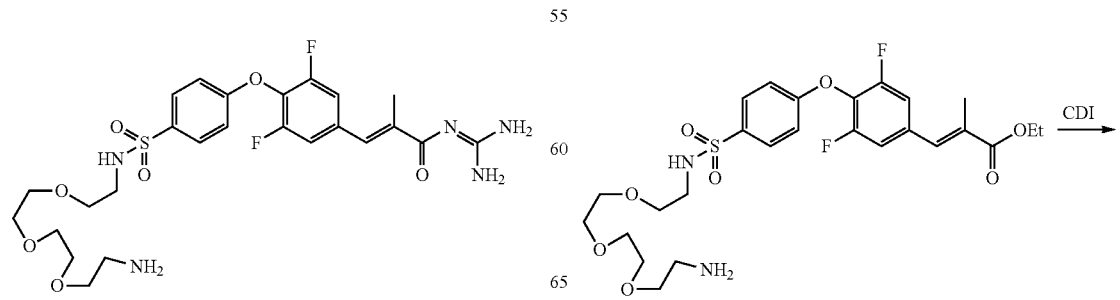

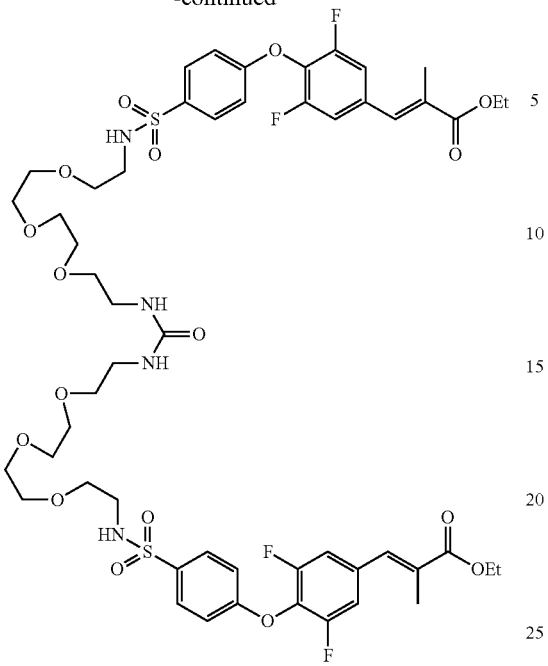

Intermediate 46.1 N,N'-(13-oxo-3,6,9,17,20,23-hexaoxa-12,14-diazapentacosane-1,25-diyl)bis[4-(2,6-difluoro-4-(2-carboethoxypropenyl)phenoxy)benzenesulfonamide]

Carbonyldiimidisole (16.2 mg, 0.10 mmol) was added to a solution of (E)-ethyl 3-(4-(4-(N-(2-(2-(2-(2-aminoethoxy)ethoxy)ethoxy)ethyl)sulfamoyl)phenoxy)-3,5-difluorophenyl)-2-methylacrylate (intermediate 44.2) (125 mg, 0.22 mmol) in DMF (2 mL) and stirred for 23 hours at which time the solvent was removed under vacuum. The residue was dissolved in EtOAc, washed with water (4×10 mL), dried (Na$_2$SO$_4$) and concentrated to give the title compound (132 mg).

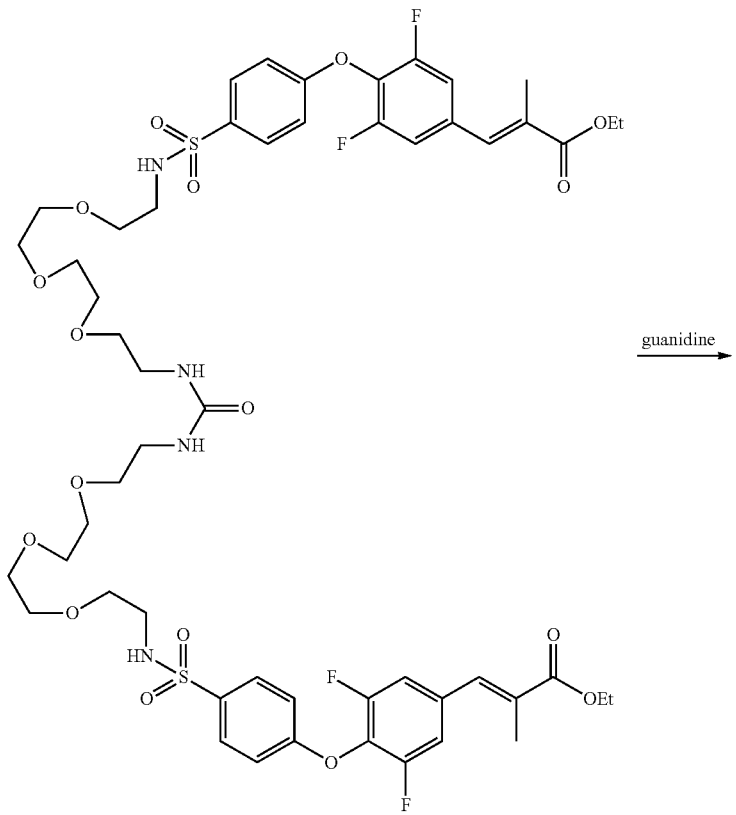

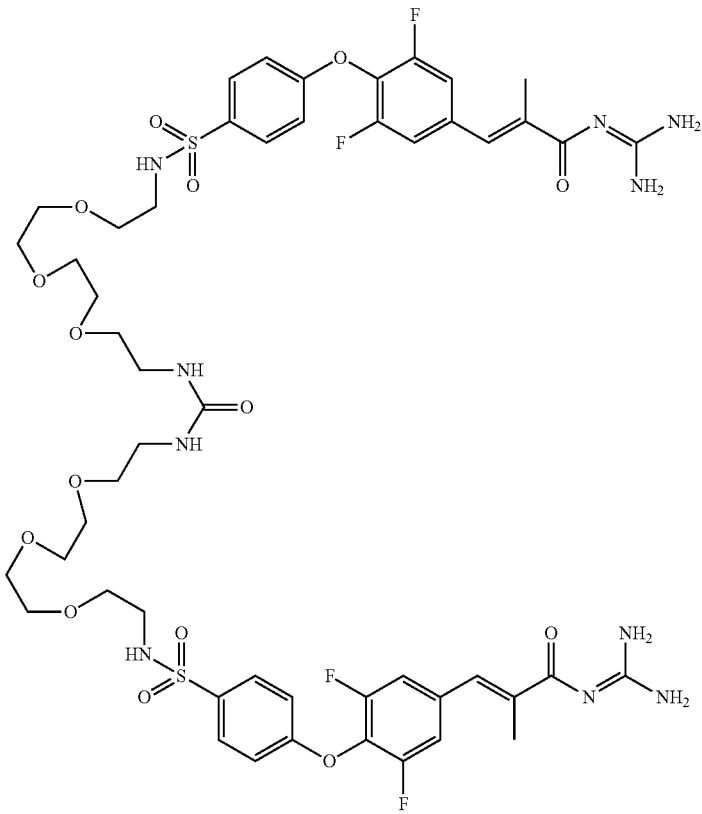

Compound 46: N,N'-(13-oxo-3,6,9,17,20,23-hexaoxa-12,14-diazapentacosane-1,25-diyl)bis[(E)-N-(diaminomethylene)-3-(3,5-difluoro-4-(4-sulfamoylphenoxy)phenyl)-2-methylacrylamide]

A solution of 4.4 M guanidine in methanol (Example 45) (0.5 mL, 2.2 mmol) was added to a solution of intermediate 46.1 (65 mg, 0.055 mmol) in DMF, and stirred for 4 hours. The reaction was quenched with 50% aqueous AcOH, and then concentrated to dryness. The residue was purified by preparative HPLC to give the title compound (35 mg) as a TFA salt. $^1$H-NMR (400 mHz, CD3OD) δ 7.84 (d, j=8.2 Hz, 4H), 7.43 (d, j=1.4 Hz, 2H), 7.30 (d, j=9.0 Hz, 4H), 7.11 (d, j=9.0 Hz, 4H), 3.57 (m, 12H), 3.46 (m, 12H), 3.26 (t, J=5.4 Hz, 4H), 3.04 (t, j=5.4 Hz, 4H), 2.17 (d, j=1.3 Hz, 6H). MS (m/z): 1197.07 (M+H).

Example 47

N,N'-(13,20 dioxo-3,6,9,24,27,30-hexaoxa-12,21-diazadotricontane-1,32-diyl)bis[(E)-N-(diaminomethylene)-3-(3,5-difluoro-4-(4-sulfamoylphenoxy)phenyl)-2-methylacrylamide]

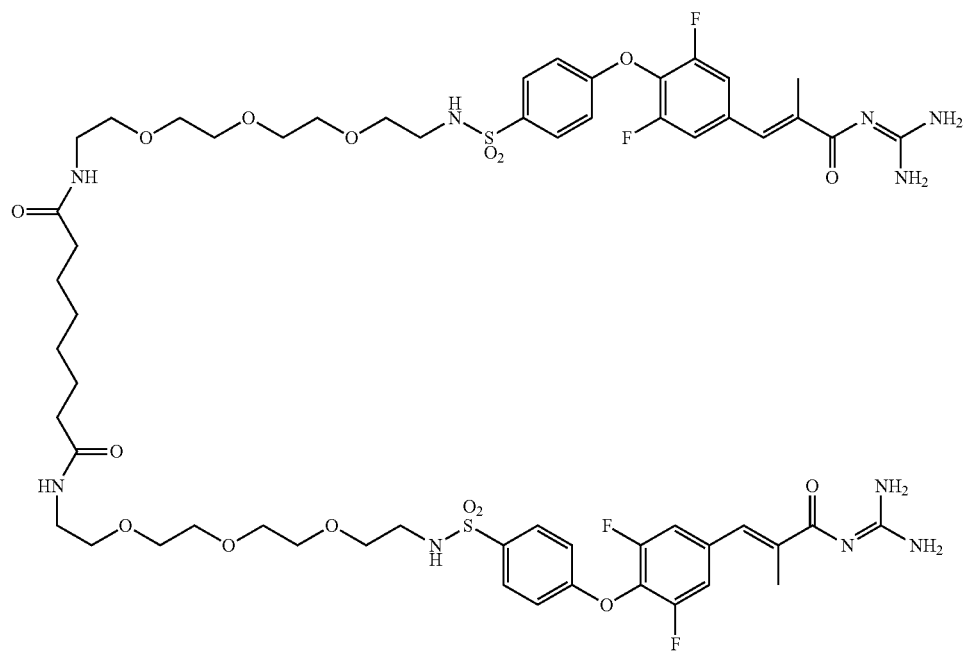 [SMILES: C/C(=C\c1cc(F)c(Oc2ccc(S(=O)(=O)NCCOCCOCCOCCNC(=O)CCCCCCC(=O)NCCOCCOCCOCCNS(=O)(=O)c3ccc(Oc4c(F)cc(/C=C(\C)C(=O)N=C(N)N)cc4F)cc3)cc2)c(F)c1)C(=O)N=C(N)N]

Compound 47: N,N'-(13,20 dioxo-3,6,9,24,27,30-hexaoxa-12,21-diazadotricontane-1,32-diyl)bis[(E)-N-(diaminomethylene)-3-(3,5-difluoro-4-(4-sulfamoylphenoxy)phenyl)-2-methylacrylamide]

Following the procedures in Example 46, substituting subaric acid bis(N-hydroxysuccinimide ester) for carbonyldiimidazole gave the title compound as a TFA salt. $^1$H-NMR (400 mHz, CD3OD) δ 7.84 (m, 4H), 7.43 (m, 2H), 7.30 (m, 4H), 7.11 (m, 4H), 3.58 (m, 12H), 3.50 (m, 8H), 3.32 (m, 4H), 3.05 (t, j=5.4 Hz, 4H), 2.18 (d, j=1.6 Hz, 6H), 2.15 (m, 4H), 1.56 (m, 4H), 1.29 (m, 4H). MS (m/z): 1309.12 (M+H).

Example 48

(E)-N-(diaminomethylene)-3-(3,5-difluoro-4-(4-(N-(2-(2-(2-(2-(4-(hydroxymethyl)-1H-1,2,3-triazol-1-yl)ethoxy)ethoxy)ethoxy)ethyl)sulfamoyl)phenoxy)phenyl)-2-methylacrylamide

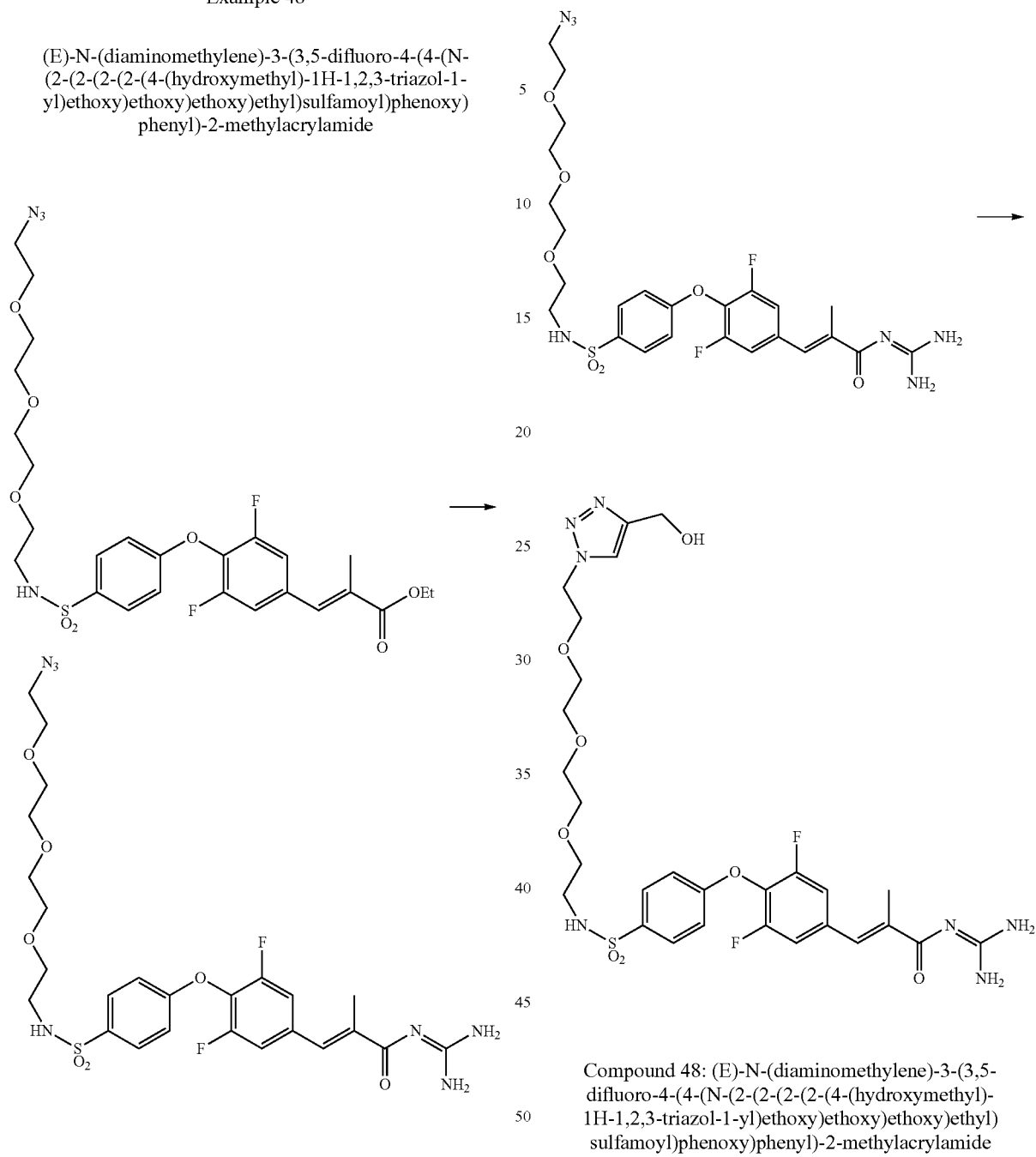

Compound 48: (E)-N-(diaminomethylene)-3-(3,5-difluoro-4-(4-(N-(2-(2-(2-(2-(4-(hydroxymethyl)-1H-1,2,3-triazol-1-yl)ethoxy)ethoxy)ethoxy)ethyl)sulfamoyl)phenoxy)phenyl)-2-methylacrylamide

Intermediate 48.1: (E)-3-(4-(4-(N-(2-(2-(2-(2-azidoethoxy)ethoxy)ethoxy)ethyl)sulfamoyl)phenoxy)-3,5-difluorophenyl)-N-(diaminomethylene)-2-methylacrylamide To (E)-ethyl 3-(4-(4-(N-(2-(2-(2-(2-azidoethoxy)ethoxy)ethoxy)ethyl)sulfamoyl)phenoxy)-3,5-difluorophenyl)-2-methylacrylate (250 mg, 0.42 mmol) was added 4.4 M guanidine in in methanol (as prepared in example 45) (1.0 mL, 4.4 mmol) and the reaction was stirred at RT. After 30 minutes, water (10 mL) was added, and the mixture was extracted with DCM (4×25 mL). The aqueous phase was adjusted to pH 7, and extracted with DCM (2×25 mL). The combined organic extracts were dried ($Na_2SO_4$) and concentrated to give the title compound (245 mg).

To a mixture of (E)-3-(4-(4-(N-(2-(2-(2-(2-azidoethoxy)ethoxy)ethoxy)ethyl)sulfamoyl)phenoxy)-3,5-difluorophenyl)-N-(diaminomethylene)-2-methylacrylamide (70 mg, 0.11 mmol) and propargyl alcohol (6.4 mg, 0.11 mmol) in t-butanol (0.22 mL) and water (0.22 mL) was added 1 M sodium ascorbate (11 μL, 0.011 mmol) and 0.3 M copper sulfate (3.6 μL, 0.0011 mmol) and the reaction was stirred at RT. After 14 hours, the product was purified by preparative HPLC to give the title compound (22 mg) as a TFA salt. $^1$H-NMR (400 mHz, CD3OD) δ 7.93 (s, 1H), 7.84 (m, 2H), 7.44 (s, 1H), 7.30 (m, 2H), 7.11 (m, 2H), 4.64 (d, j=0.6 Hz, 2H), 4.55 (t, j=5.0 Hz, 2H), 3.86 (t, j=5.0 Hz, 2H), 3.57 (m, 4H), 3.52-3.42 (m, 6H), 3.03 (t, j=5.4 Hz, 2H), 2.18 (d, j=1.3 Hz, 3H). MS (m/z): 668.14 (M+H).

Example 49

N,N'-(2,2'-(2,2'-(2,2'-(2,2'-(4,4'-oxybis(methylene)bis(1H-1,2,3-triazole-4,1-diyl))bis(ethane-2,1-diyl))bis(oxy)bis(ethane-2,1-diyl))bis(oxy)bis(ethane-2,1-diyl))bis(oxy)bis(ethane-2,1-diyl))bis[(E)-N-(diaminomethylene)-3-(3,5-difluoro-4-(4-sulfamoylphenoxy)phenyl)-2-methylacrylamide]

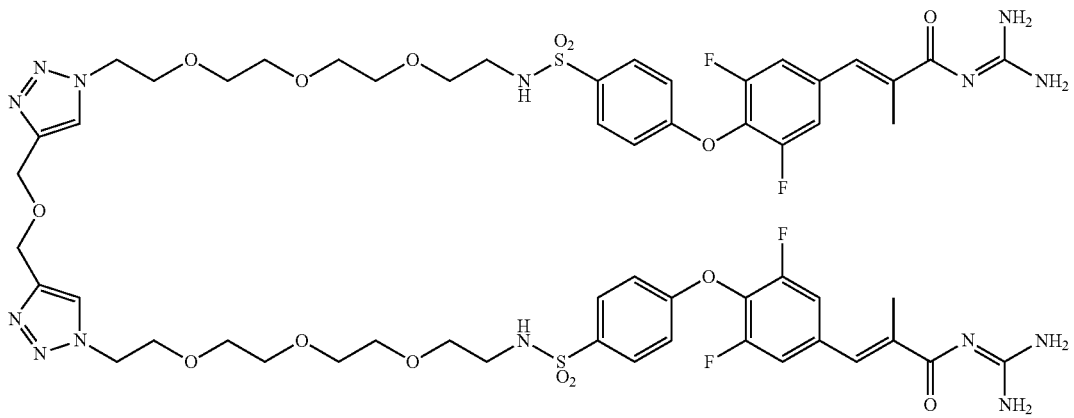 [SMILES: C/C(=C\c1cc(F)c(Oc2ccc(S(=O)(=O)NCCOCCOCCOCCn3cc(COCc4cn(CCOCCOCCOCCNS(=O)(=O)c5ccc(Oc6c(F)cc(/C=C(\C)C(=O)N=C(N)N)cc6F)cc5)nn4)nn3)cc2)c(F)c1)C(=O)N=C(N)N]

Compound 49: N,N'-(2,2'-(2,2'-(2,2'-(2,2'-(4,4'-oxybis(methylene)bis(1H-1,2,3-triazole-4,1-diyl))bis(ethane-2,1-diyl))bis(oxy)bis(ethane-2,1-diyl))bis(oxy)bis(ethane-2,1-diyl))bis[(E)-N-(diaminomethylene)-3-(3,5-difluoro-4-(4-sulfamoylphenoxy)phenyl)-2-methylacrylamide]

Following the procedures in example 48, substituting propargyl ether for propargyl alcohol gave the title compound as a TFA salt. $^1$H-NMR (400 mHz, CD3OD) δ 8.00 (s, 2H), 7.83 (m, 4H), 7.43 (s, 2H), 7.30 (m, 4H), 7.10 (m, 4H), 4.61 (s, 4H), 4.55 (m, 4H), 3.86 (m, 4H), 3.58-3.50 (m, 8H), 3.50-3.40 (m, 12H), 3.01 (m, 4H), 2.17 (d, j=1.3 Hz, 6H). MS (m/z): 1317.09 (M+H).

Example 50

N,N'-(2,2'-(piperazine-1,4-diyl)bis(ethane-2,1-diyl))di-((E)-N-(diaminomethylene)-3-(3,5-difluoro-4-(4-sulfamoylphenoxy)phenyl)-2-methylacrylamide)

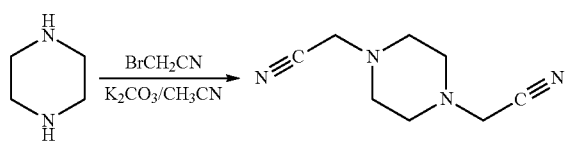

Intermediate 50.1:
2,2'-(piperazine-1,4-diyl)diacetonitrile

To a solution of piperazine (6 g, 69.77 mmol, 1.00 equiv) in acetonitrile (150 mL) was added potassium carbonate (19.2 g, 139.13 mmol, 2.00 equiv) and the mixture was stirred. To this was added dropwise a solution of 2-bromoacetonitrile (16.7 g, 140.34 mmol, 2.00 equiv) in acetonitrile (100 mL) and the suspension was stirred for 4 h at room temperature. The solids were filtered out and the resulting solution was concentrated under vacuum. The crude product was purified by re-crystallization from methanol resulting in 7.75 g (68%) of Intermediate 50.1 as a white solid.

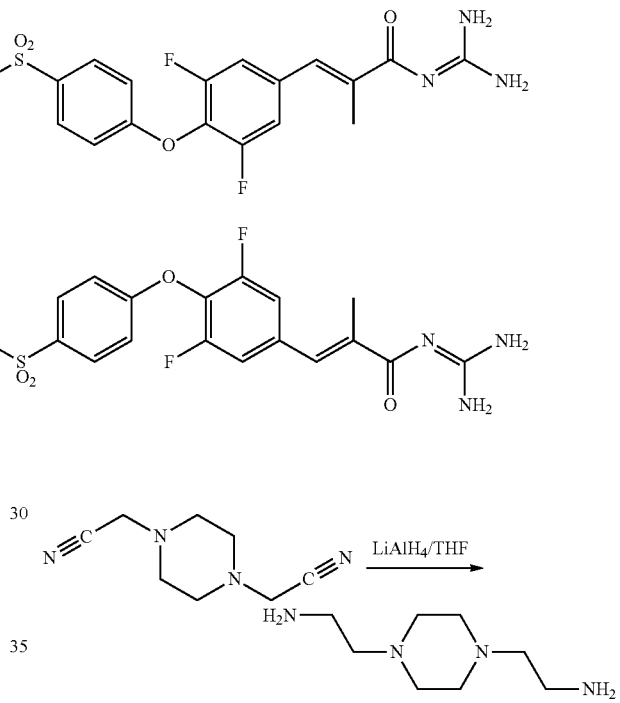

Intermediate 50.2:
2,2'-(piperazine-1,4-diyl)diethanamine

To a suspension of lithium aluminum hydride (LiAlH$_4$; 700 mg, 18.42 mmol, 4.30 equiv) in tetrahydrofuran (40 mL) cooled to 0° C. was added dropwise a solution of Intermediate 50.1 (700 mg, 4.27 mmol, 1.00 equiv) in tetrahydrofuran (10 mL). The mixture was stirred for 15 minutes at 0° C. and heated to reflux for 3 h. The reaction was cooled, the pH adjusted to 8-9 with potassium hydroxide (50%), and the solids filtered out. The resulting mixture was concentrated under vacuum and the resulting solids washed with hexane to afford 0.3 g (41%) of Intermediate 50.2 as a yellow solid.

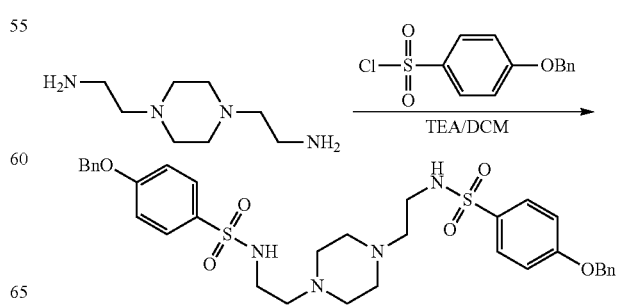

Intermediate 50.3: N,N'-(2,2'-(piperazine-1,4-diyl) bis(ethane-2,1-diyl))bis(4-(benzyloxy)benzene-sulfonamide)

To Intermediate 50.2 (500 mg, 2.91 mmol, 1.00 equiv) in dichloromethane (10 mL) was added triethylamine (1.46 g, 0.01 mmol, 2.00 equiv) and 4-(benzyloxy)benzene-1-sulfonyl chloride (2.0 g, 0.01 mmol, 2.40 equiv) and the resulting solution was stirred for 2 h at room temperature. The reaction was diluted with dichloromethane, washed with 3×10 mL of water, dried over sodium sulfate then filtered and concentrated under vacuum to afford 0.9 g (47%) of Intermediate 50.3 as a yellow solid.

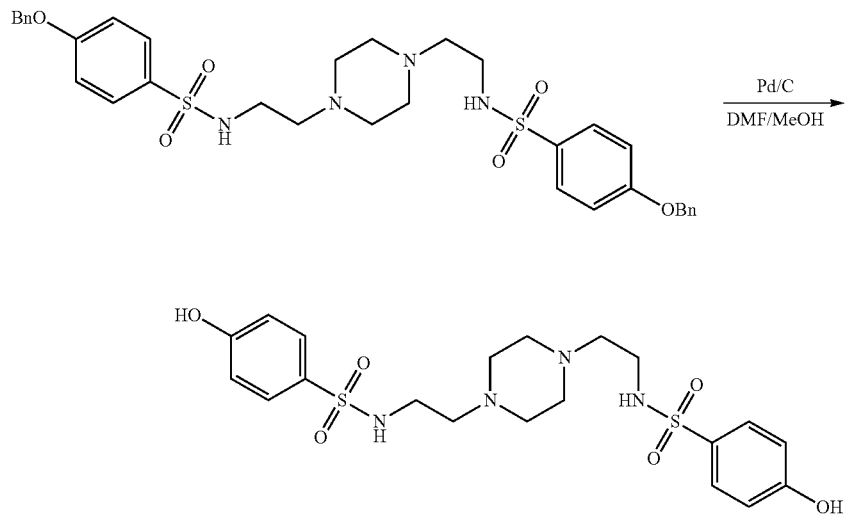

Intermediate 50.4: N,N'-(2,2'-(piperazine-1,4-diyl) bis(ethane-2,1-diyl))bis(4-hydroxybenzenesulfonamide)

To intermediate 50.3 (3 g, 4.52 mmol, 1.00 equiv) in N,N-dimethylformamide (500 mL) and methanol (100 mL) was added Palladium on carbon (1 g) and the suspension stirred under hydrogen gas for 4 h at room temperature. The solids were filtered out and the resulting mixture was concentrated under vacuum to afford 1.5 g (69%) of Intermediate 50.4 as a gray solid.

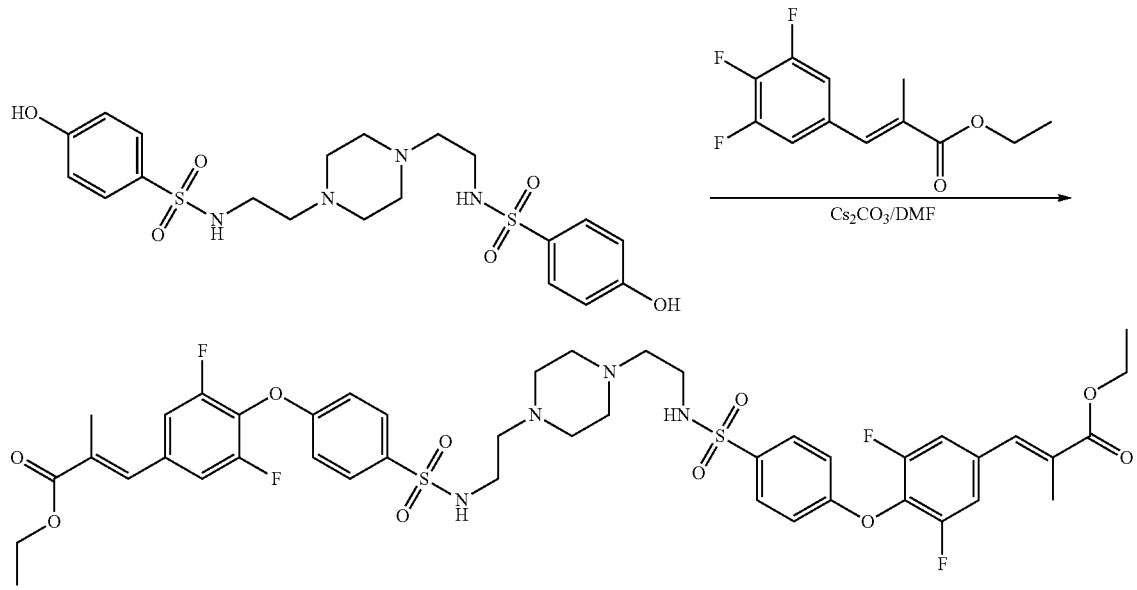

Intermediate 50.5: N,N'-(2,2'-(piperazine-1,4-diyl)bis(ethane-2,1-diyl))bis((E)-ethyl 3-(3,5-difluoro-4-(4-sulfamoylphenoxy)phenyl)-2-methylacrylate)

To Intermediate 50.4 (1 g, 2.06 mmol, 1.00 equiv) in N,N-dimethylformamide (30 mL) was added $Cs_2CO_3$ (1.45 g, 4.45 mmol, 2.16 equiv) and the resulting suspension stirred for 2 h at room temperature. To this was added a solution of (E)-ethyl 2-methyl-3-(3,4,5-trifluorophenyl)acrylate (intermediate 41.1) (1.1 g, 4.51 mmol, 2.19 equiv) in N,N-dimethylformamide (10 mL) dropwise with stirring. The reaction was stirred for 0.5 h at room temperature and then overnight at 90° C. The resulting mixture was concentrated under vacuum, the residue was applied onto a silica gel column and then eluted with dichloromethane:methanol (100:1) to afford 390 mg (20%) of Intermediate 50.5 as a yellow solid.

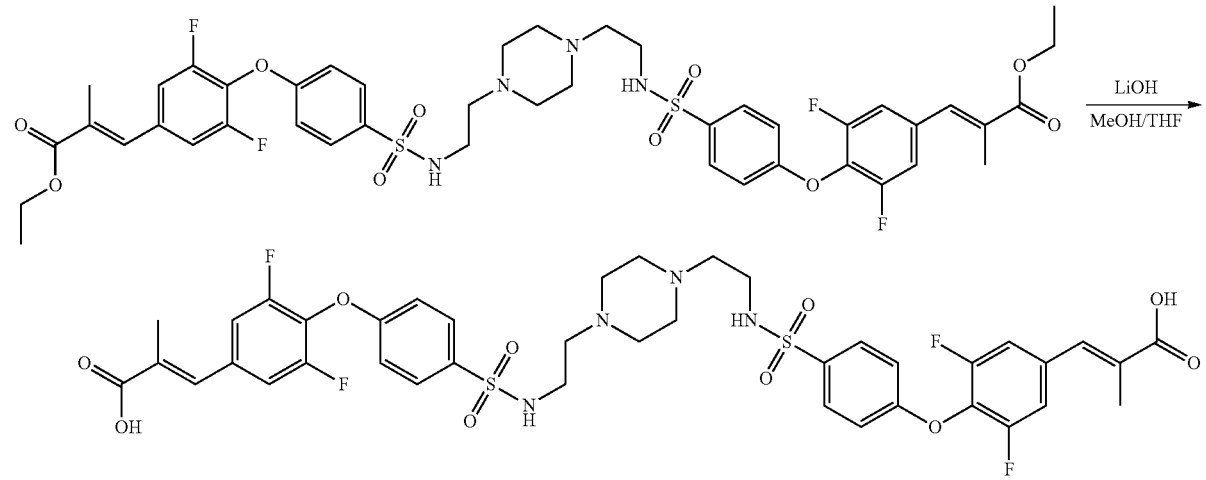

Intermediate 50.6: N,N'-(2,2'-(piperazine-1,4-diyl)bis(ethane-2,1-diyl))di-((E)-3-(3,5-difluoro-4-(4-sulfamoylphenoxy)phenyl)-2-methylacrylic acid)

To Intermediate 50.5 (170 mg, 0.16 mmol, 1.00 equiv, 90%) in 1:1 methanol/tetrahydrofuran (20 mL) was added lithium hydroxide (4 equiv, 30 mg) and the reaction was stirred for 2 h at 27° C. The pH value of the solution was adjusted to 1-2 with aqueous hydrochloric acid (6 mol/L) and the solids were collected by filtration. The residue was washed with ethyl acetate (2×5 mL) and then dried under vacuum to afford 150 mg (94%) of Intermediate 50.6 as a white solid.

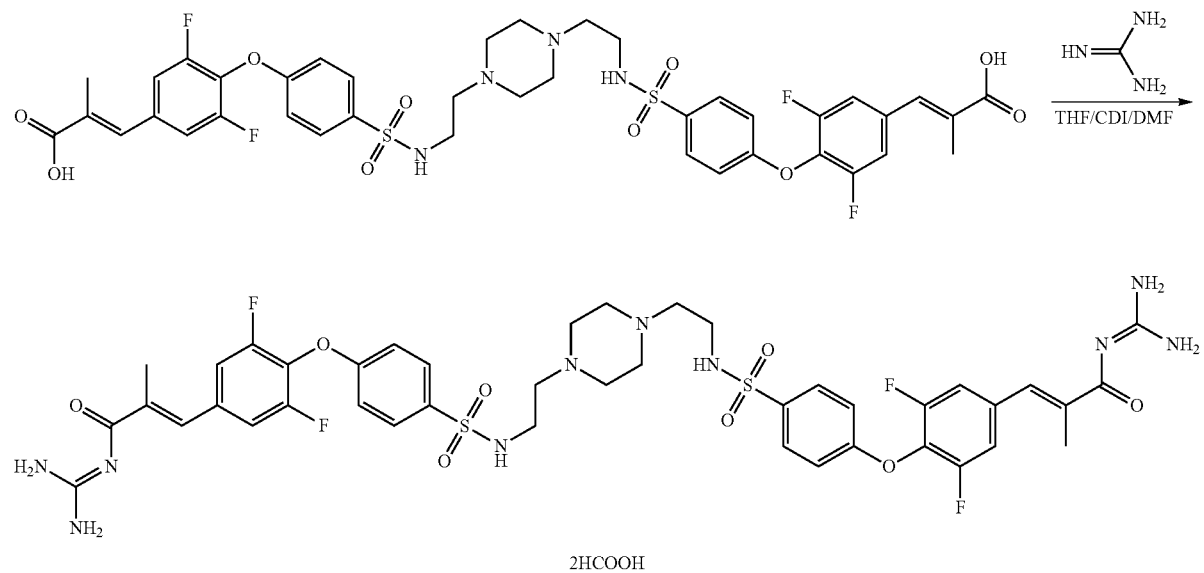

Compound 50: N,N'-(2,2'-(piperazine-1,4-diyl)bis(ethane-2,1-diyl))di-((E)-N-(diaminomethylene)-3-(3,5-difluoro-4-(4-sulfamoylphenoxy)phenyl)-2-methylacrylamide)

To a solution of Intermediate 50.6 (100 mg, 0.09 mmol, 1.00 equiv, 80%) in tetrahydrofuran (30 mL) was added carbonyl diimidazole (CDI; 58 mg, 0.36 mmol, 4.00 equiv) and the resulting solution was stirred for 1 h at 25° C. To this was added guanidine (2M in methanol, 10 ml) and the resulting solution was stirred for an additional 14 h at 30° C. The resulting mixture was concentrated under vacuum, the residue was applied onto a silica gel column and eluted with dichloromethane:methanol (10:1). The crude product (230 mg) was then purified by reverse-phase (C18) preparative-HPLC to afford 16 mg (17%) of a formate salt of the title compound as a white solid. $^1$H-NMR (300 MHz, CD$_3$OD, ppm): 7.89-7.92 (4H, d, J=8.7 Hz), 7.50 (2H, s), 7.34-7.36 (4H, d, J=8.7 Hz), 7.16-7.19 (4H, d, J=8.7 Hz), 2.88-3.16 (16H, m), 2.20 (6H, s); MS (ES, m/z): 959 [M+H]$^+$ Example 51

(E)-4-(4-(4-(3-(diaminomethyleneamino)-2-methyl-3-oxoprop-1-enyl)-2,6-difluorophenoxy)phenylsulfonamido)phenylphosphonic acid

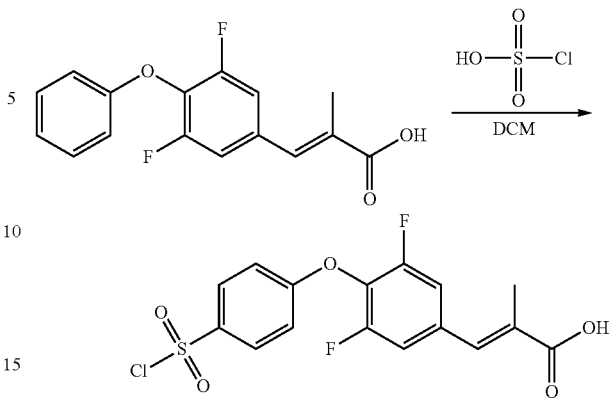

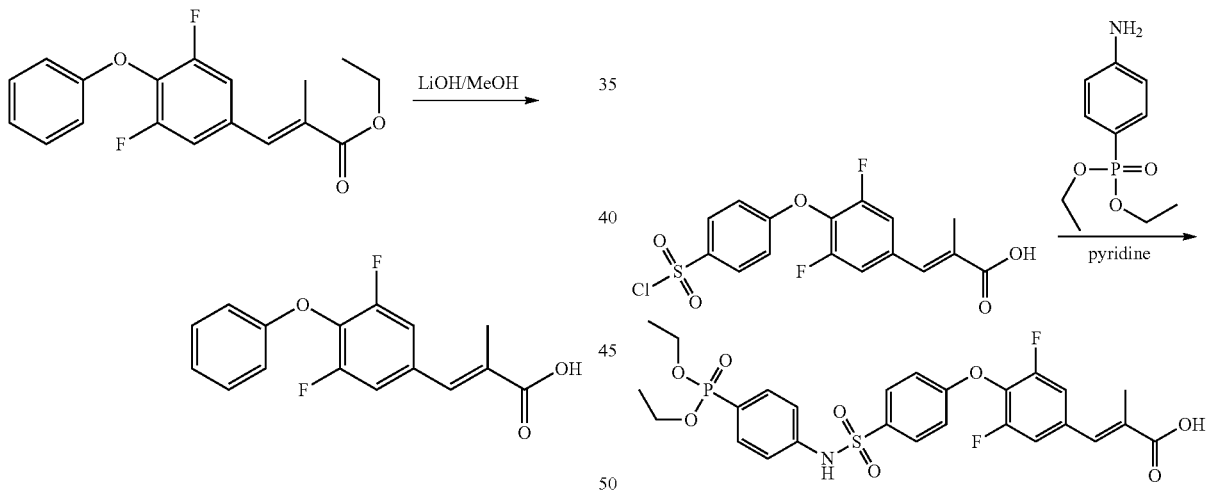

Intermediate 51.1: (E)-3-(3,5-difluoro-4-phenoxyphenyl)-2-methylacrylic acid

To a solution of (E)-ethyl 3-(3,5-difluoro-4-phenoxyphenyl)-2-methylacrylate (intermediate 41.2) (900 mg, 2.83 mmol, 1.00 equiv) in methanol (20 mL) was added methanolic 2M LiOH (50 mL) and the resulting solution stirred for 2 h. The resulting mixture was concentrated under vacuum, the pH value of the solution was adjusted to 5-6 with aqueous HCl (6 mol/L) and the mixture was extracted with 3×20 mL of ethyl acetate. The organic layers were combined, washed with 2×10 mL of sodium chloride (sat.) and then dried over anhydrous sodium sulfate. The solids were filtered out and the solution was concentrated to afford 0.7 g (85%) of Intermediate 51.1 as a white solid.

Intermediate 51.2: (E)-3-(4-(4-(chlorosulfonyl)phenoxy)-3,5-difluorophenyl)-2-methylacrylic acid To Intermediate 51.1 (1 g, 3.14 mmol, 1.00 equiv) in dichloromethane (15 mL) at 0-5° C. was added dropwise a solution of sulfurochloridic acid (8.5 g, 73.28 mmol, 23.00 equiv) in dichloromethane (5 mL). The reaction was stirred overnight at 25° C. in an oil bath, and then quenched by the addition of 200 mL of water/ice. The mixture was extracted with 4×50 mL of dichloromethane and the organic layers combined and dried over anhydrous sodium sulfate to afford 1.1 g (90%) of Intermediate 51.2 as a yellow solid.

Intermediate 51.3: (E)-3-(4-(4-(N-(4-(diethoxyphosphoryl)phenyl)sulfamoyl)phenoxy)-3,5-difluorophenyl)-2-methylacrylic acid To diethyl 4-aminophenylphosphonate (intermediate 2.2) (150 mg, 0.66 mmol, 1.00 equiv) in pyridine (3 mL) was added Intermediate 51.2 (300 mg, 0.77 mmol, 1.22 equiv) in several portions. The mixture was stirred for 3 h at 30° C. and then concentrated, the pH value of the solution adjusted to 3 with aqueous HCl (1 mol/L) and the resulting mixture extracted with 3×30 mL of ethyl acetate. The organic layers were combined, dried over anhydrous sodium sulfate, concentrated, applied onto a silica gel column and eluted with dichloromethane:methanol (50:1) to afford 100 mg (26%) of Intermediate 51.3 as a yellowish solid.

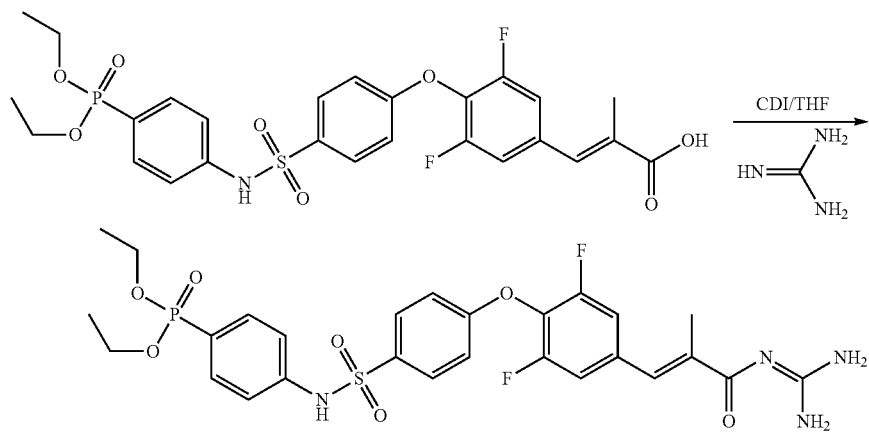

Intermediate 51.4: (E)-diethyl 4-(4-(4-(3-(diaminomethyleneamino)-2-methyl-3-oxoprop-1-enyl)-2,6-difluorophenoxy)phenylsulfonamido)phenylphosphonate To Intermediate 51.3 (150 mg, 0.26 mmol, 1.00 equiv) in tetrahydrofuran (2 mL) was added CDI (120 mg, 0.74 mmol, 1.40 equiv) and the reaction stirred for 2 h at RT. To this was added guanidine (1M in DMF; 0.8 ml) and the reaction was stirred overnight at 30° C. The resulting mixture was concentrated under vacuum and the crude product was purified by reverse phase (C18) Prep-HPLC to afford 40 mg (25%) of Intermediate 51.4 as a White solid.

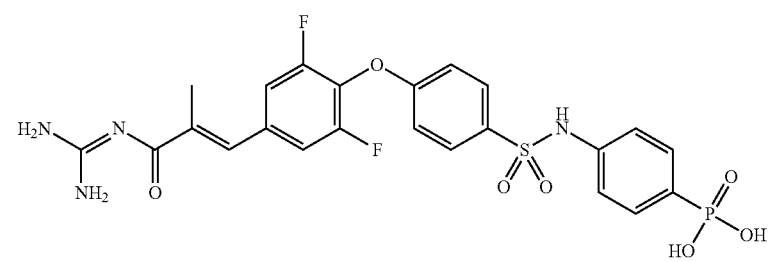

Compound 51: (E)-4-(4-(4-(3-(diaminomethyleneamino)-2-methyl-3-oxoprop-1-enyl)-2,6-difluorophenoxy)phenylsulfonamido)phenylphosphonic acid To Intermediate 51.4 (40 mg, 0.06 mmol, 1.00 equiv) in tetrahydrofuran (2 mL) was added bromotrimethylsilane (15 mg, 0.09 mmol, 1.37 equiv) dropwise with stirring and the resulting solution was stirred at 40° C. overnight. The resulting mixture was concentrated, diluted with methanol (2 mL) and then concentrated under vacuum. This operation was repeated four times. The crude product (75 mg) was purified by reverse phase (C18) Prep-HPLC to afford 12.5 mg of a formate salt of the title compound as a white solid. $^1$H-NMR (300 MHz, DMSO, ppm): 10.54 (s, 1H), 7.82-7.79 (d, J=8.4

Hz, 2H), 7.52-7.40 (m, 5H), 7.18-7.10 (m, 4H), 2.08 (s, 3H); $^{31}$P-NMR (400 MHz, DMSO, ppm): 11.29; MS (ES, m/z): 567 [M+H]$^+$ Example 52

(E)-4-((4-(4-(3-(diaminomethyleneamino)-2-methyl-3-oxoprop-1-enyl)-2,6-difluorophenoxy)phenylsulfonamido)methyl)benzylphosphonic acid

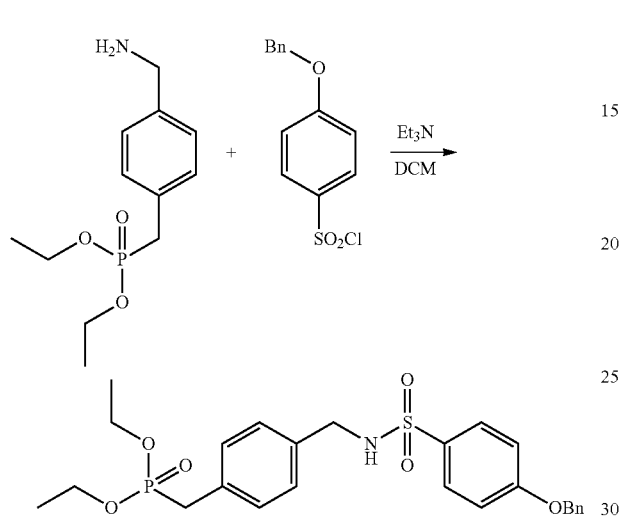

Intermediate 52.1: diethyl 4-((4-(benzyloxy)phenylsulfonamido)methyl)benzylphosphonate To 4-diethyl 4-(aminomethyl)benzylphosphonate (intermediate 6.1) (60 mg, 0.23 mmol, 1.00 equiv) in dichloromethane (10 mL), triethylamine (47 mg, 0.47 mmol, 2.00 equiv) was added dropwise a solution of 4-(benzyloxy)benzene-1-sulfonyl chloride (72 mg, 0.26 mmol, 1.10 equiv) in dichloromethane (5 mL) and the resulting solution was stirred for 1 h at 25° C. The reaction mixture was concentrated, the residue applied onto a silica gel column and then eluted with ethyl acetate/petroleum ether (1:1). The isolated product was washed with 2×50 mL of n-hexane resulting in 50 mg (43%) of Intermediate 52.1 as a white solid.

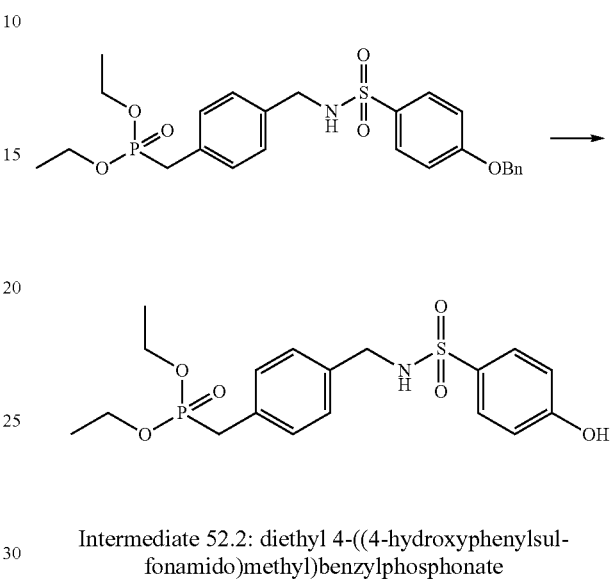

Intermediate 52.2: diethyl 4-((4-hydroxyphenylsulfonamido)methyl)benzylphosphonate To Intermediate 52.1 (1.2 g, 2.39 mmol, 1.00 equiv) in methanol (20 mL) in N,N-dimethylformamide (5 mL) was added Palladium on carbon (0.9 g) and the suspension stirred overnight at 30° C. under a hydrogen atmosphere. The reaction was filtered and concentrated under vacuum to afford 1 g (91%) of Intermediate 52.2 as brown oil.

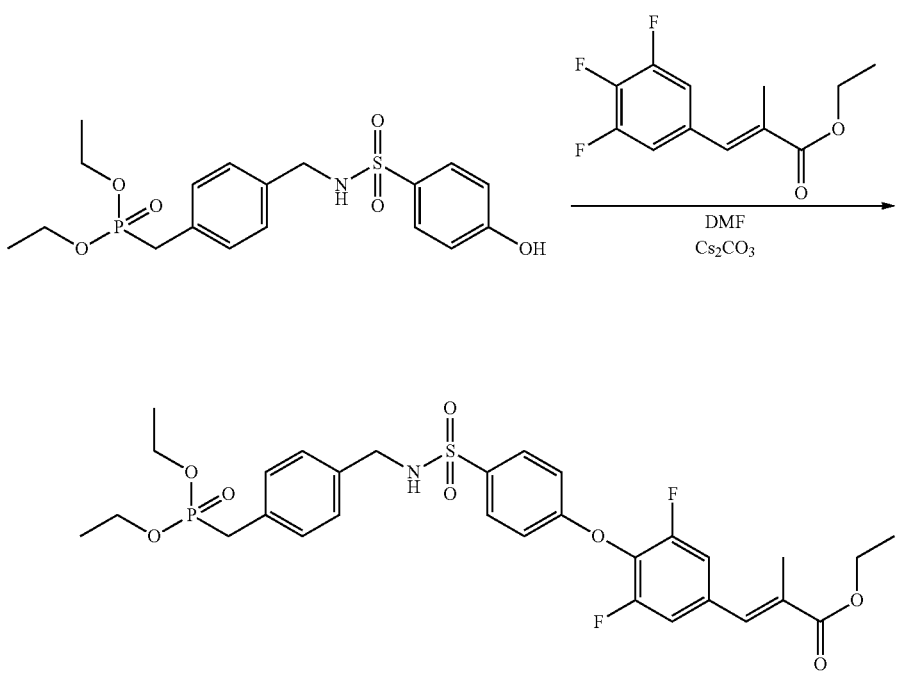

Intermediate 52.3: (E)-ethyl 3-(4-(4-(N-(4-((diethoxyphosphoryl)methyl)benzyl)-sulfamoyl)phenoxy)-3,5-difluorophenyl)-2-methylacrylate To Intermediate 52.2 (100 mg, 0.24 mmol, 1.00 equiv) in N,N-dimethylformamide (10 mL) was added Cs₂CO₃ (160 mg, 0.49 mmol, 2.10 equiv) and the mixture was stirred for 1.5 h at room temperature. To this was added a solution of (E)-ethyl 2-methyl-3-(3,4,5-trifluorophenyl)acrylate (intermediate 41.1) (60 mg, 0.25 mmol, 1.10 equiv) in N,N-dimethylformamide (5 mL) and the reaction was stirred overnight at 90° C. The solids were filtered out and the filtrate was concentrated under vacuum, the residue applied onto a silica gel column and eluted with dichloromethane/methanol (200:1) to afford 50 mg (23%) of Intermediate 52.3 as yellow oil.

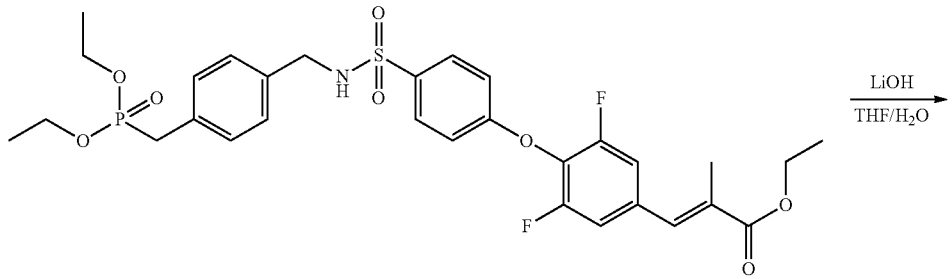

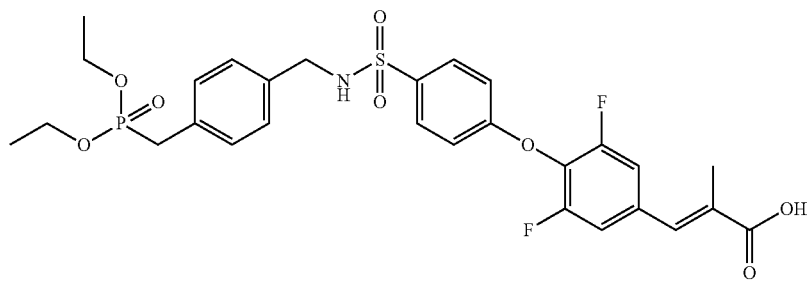

Intermediate 52.4: (E)-3-(4-(4-(N-(4-((diethoxyphosphoryl)methyl)benzyl)sulfamoyl)-phenoxy)-3,5-difluorophenyl)-2-methylacrylic acid To Intermediate 52.3 (700 mg, 1.10 mmol, 1.00 equiv) in tetrahydrofuran (20 mL) and water (20 mL) was added LiOH (700 mg, 29.17 mmol, 30.00 equiv) and the resulting solution was stirred for 1 h at 25° C. The reaction was concentrated, the pH value of the solution was adjusted to 4-5 with aqueous HCl (2 mol/L) and the mixture was extracted with 2×150 mL of ethyl acetate. The organic layers were combined, dried over anhydrous sodium sulfate, concentrated, the residue applied onto a silica gel column and then eluted with ethyl acetate/petroleum ether (1:1-2:1) to afford 250 mg (35%) of Intermediate 52.4 as a white solid.

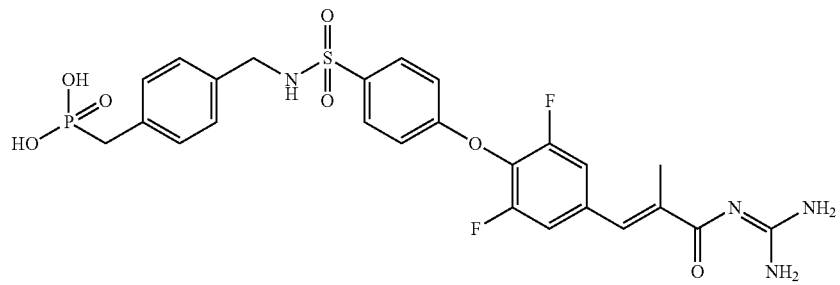 [SMILES: C/C(=C\c1cc(F)c(Oc2ccc(S(=O)(=O)NCc3ccc(CP(=O)(O)O)cc3)cc2)c(F)c1)C(=O)N=C(N)N]

Compound 52: (E)-4-((4-(4-(3-(diaminomethyleneamino)-2-methyl-3-oxoprop-1-enyl)-2,6-difluorophenoxy)phenylsulfonamido)methyl)benzylphosphonic acid Compound 52 was prepared from Intermediate 52.4 using the procedures described under Example 51, except preparative HPLC was not required, affording 84 mg (89%) of a white solid.; $^1$H-NMR (300 MHz, CD$_3$OD, ppm): 7.83-7.80 (d, J=8.7 Hz, 2H), 7.52 (s, 1H), 7.38-7.36 (d, J=8.7 Hz, 2H), 7.23-7.20 (m, 2H), 7.17-7.09 (m, 4H), 4.06 (s, 2H), 3.11 (s, 1H), 3.04 (s, 1H), 2.23-2.23 (s, 3H). MS (ES, m/z): 595 [M+H]$^+$.

Example 53

(E)-4-(4-(4-(3-(diaminomethyleneamino)-2-methyl-3-oxoprop-1-enyl)-2,6-difluorophenoxy)phenylsulfonamido)benzylphosphonic acid

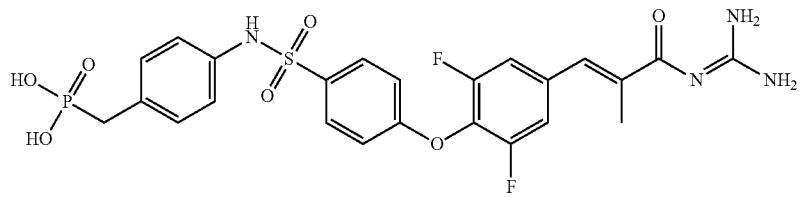 [SMILES: C/C(=C\c1cc(F)c(Oc2ccc(S(=O)(=O)Nc3ccc(CP(=O)(O)O)cc3)cc2)c(F)c1)C(=O)N=C(N)N]

Compound 53: (E)-4-(4-(4-(3-(diaminomethyleneamino)-2-methyl-3-oxoprop-1-enyl)-2,6-difluorophenoxy)phenylsulfonamido)benzylphosphonic acid Compound 53 was prepared from diethyl 4-aminobenzylphosphonate (intermediate 3.2) using the procedures described in Example 52 except the final product was purified by preparative HPLC. $^1$H-NMR (300 MHz, CD$_3$OD, ppm): 7.77-7.74 (d, J=8.7 Hz, 2H), 7.46 (s, 1H), 7.33-7.31 (d, J=8.7 Hz, 2H), 7.21-7.19 (m, 2H), 7.06-7.11 (m, 4H), 3.04-2.97 (d, J=21.6 Hz, 2H), 2.19 (s, 3H); $^{31}$P-NMR (400 MHz, CD$_3$OD, ppm): 22.49. MS (ES, m/z): 581 [M+H]$^+$.

Example 54

(E)-3-(4-(4-(3-(diaminomethyleneamino)-2-methyl-3-oxoprop-1-enyl)-2,6-difluorophenoxy)phenylsulfonamido)propylphosphonic acid

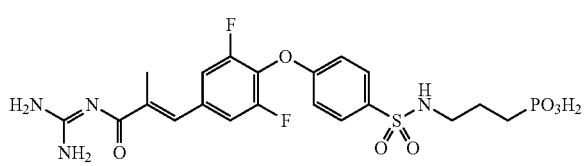

Compound 54: (E)-3-(4-(4-(3-(diaminomethyleneamino)-2-methyl-3-oxoprop-1-enyl)-2,6-difluorophenoxy)phenylsulfonamido)propylphosphonic acid Compound 54 was prepared from diethyl 3-aminopropylphosphonate (intermediate 4.1) using the procedures described under Example 51. $^1$H-NMR (400 MHz, DMSO, ppm): 7.81-7.78 (d, J=8.4 Hz, 2H), 7.57 (s, 1H), 7.42-7.39 (d, J=9.3 Hz, 2H), 7.22-7.19 (d, J=8.7 Hz, 2H), 2.75-2.77 (q, 2H), 2.10 (s, 3H), 1.59-1.42 (m, 4H). MS (ES, m/z): 533 [M+H]$^+$

Example 55

(E)-2-(4-(4-(3-(diaminomethyleneamino)-2-methyl-3-oxoprop-1-enyl)-2,6-difluorophenoxy)phenylsulfonamido)ethylphosphonic acid

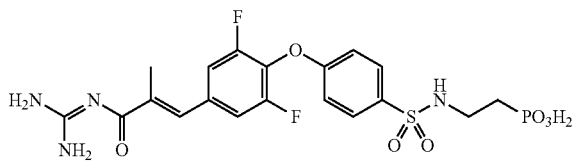

Compound 55: (E)-2-(4-(4-(3-(diaminomethyleneamino)-2-methyl-3-oxoprop-1-enyl)-2,6-difluorophenoxy)phenylsulfonamido)ethylphosphonic acid Compound 55 was prepared from diethyl 2-aminoethylphosphonate (intermediate 1.9) using the procedures described under Example 51, except purification of the final product by preparative HPLC was not required.; $^1$H-NMR (400 MHz, DMSO, ppm): 11.02 (s, 1H), 8.28 (s, 4H), 7.79-7.82 (d, J=9.2 Hz, 2H), 7.62-7.65 (t, 1H), 7.54-7.49 (m, 3H), 7.26-7.24 (d, J=8.8 Hz, 2H), 3.42-3.58 (m, 2H), 2.15 (s, 3H), 1.73-1.65 (m, 2H); $^{31}$P-NMR (400 MHz, DMSO, ppm): 21.36. MS (ES, m/z): 519 [M+H]$^+$

Example 56

(E)-(4-(4-(3-(diaminomethyleneamino)-2-methyl-3-oxoprop-1-enyl)-2,6-difluorophenoxy)phenylsulfonamido)methylphosphonic acid

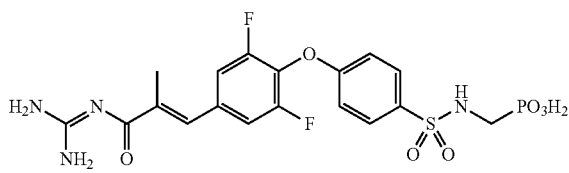

Compound 56: (E)-(4-(4-(3-(diaminomethyleneamino)-2-methyl-3-oxoprop-1-enyl)-2,6-difluorophenoxy)phenylsulfonamido)methylphosphonic acid Compound 56 was prepared from diethyl aminomethylphosphonate (intermediate 5.3) using the procedures described under Example 51, except purification of the final product by Flash-Prep-HPLC with CH$_3$CN:water (10:100). $^1$H-NMR (300 MHz, DMSO, ppm): δ 7.84-7.81 (d, J=8.1 Hz, 2H), 7.57 (s, 1H), 7.45-7.42 (d, J=9.3 Hz, 3H), 7.18-7.15 (d, J=8.4 Hz, 2H), 3.04-3.01 (m, 2H), 2.08 (s, 3H). MS (ES, m/z): 505 [M+H]$^+$.

Example 57

(E)-2-(4-(4-(3-(diaminomethyleneamino)-2-methyl-3-oxoprop-1-enyl)-2,6-difluorophenoxy)-N-(phosphonomethyl)phenylsulfonamido)acetic acid

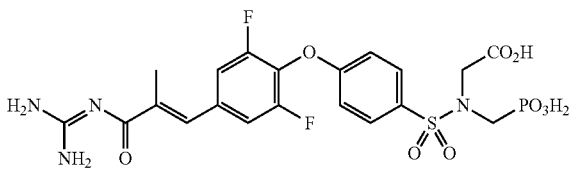

Compound 57: (E)-2-(4-(4-(3-(diaminomethyleneamino)-2-methyl-3-oxoprop-1-enyl)-2,6-difluorophenoxy)-N-(phosphonomethyl)phenyl-sulfonamido)acetic acid Compound 57 was prepared from ethyl 2-((diethoxyphosphoryl)methylamino)acetate (intermediate 8.2) using the procedures described under Example 51. $^1$H-NMR (300 MHz, DMSO, ppm): δ 8.33 (s, 4H), 7.84-7.81 (d, J=8.1 Hz, 2H), 7.52-7.50 (d, J=7.8 Hz, 2H), 7.19-7.16 (d, J=8.4 Hz, 2H), 4.11 (s, 2H), 2.14 (s, 3H); MS (ES, m/z): 563 [M+H]$^+$.

Example 58

(E)-N-(diaminomethylene)-3-(3,5-difluoro-4-(4-(N-(2-methoxyethylcarbamoyl)sulfamoyl)phenoxy)phenyl)-2-methylacrylamide

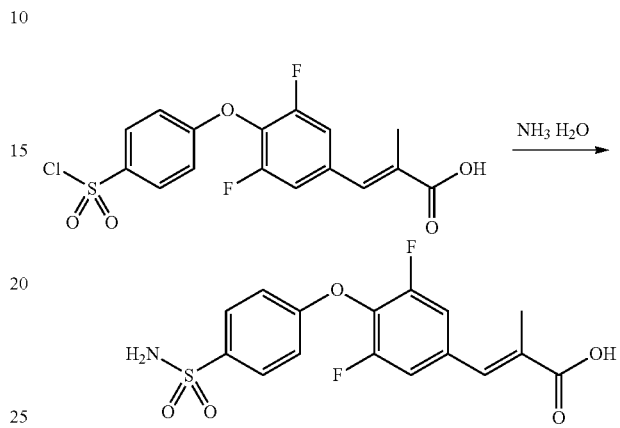

Intermediate 58.1: (E)-3-(3,5-difluoro-4-(4-sulfamoylphenoxy)phenyl)-2-methylacrylic acid (E)-3-(4-(4-(chlorosulfonyl)phenoxy)-3,5-difluorophenyl)-2-methylacrylic acid (Intermediate 51.2) was converted to intermediate 58.1 using procedures outlined in Example 58, with aqueous ammonia as the amine. The title compound was obtained as a yellow solid.

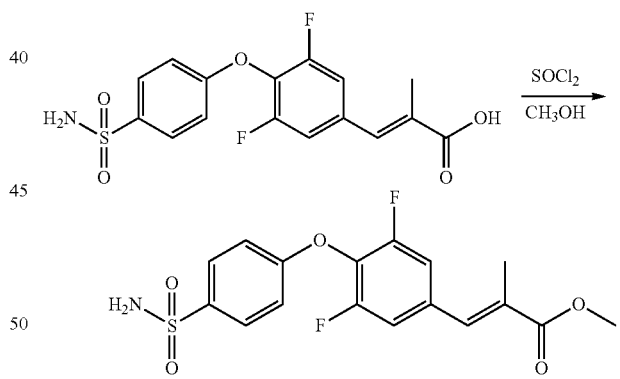

Intermediate 58.2: (E)-methyl 3-(3,5-difluoro-4-(4-sulfamoylphenoxy)phenyl)-2-methylacrylate Into a 50-mL round-bottom flask, was placed a solution of intermediate 58.1 (2 g, 5.42 mmol, 1.00 equiv) in methanol (60 mL). This was followed by the addition of thionyl chloride (2.5 g, 21.19 mmol, 4.00 equiv) dropwise with stirring at 0° C. The resulting solution was stirred for 3 h at 50° C. The resulting mixture was concentrated under vacuum. The pH value of the solution was adjusted to 7 with ammonia (2 mol/L). The resulting solution was extracted with 10 mL of ethyl acetate and the organic layers combined and dried over anhydrous sodium sulfate and concentrated under vacuum.

The residue was applied onto a silica gel column with petroleum ether/ethyl acetate (30:1-1:1). This resulted in 2.1 g (97%) of the title compound as a white solid.

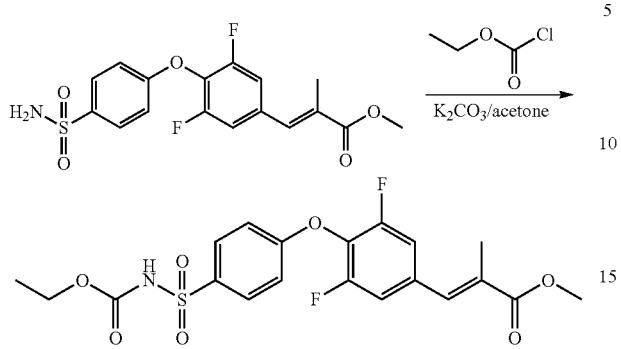

Intermediate 58.3: (E)-methyl 3-(4-(4-(N-(ethoxycarbonyl)sulfamoyl)phenoxy)-3,5-difluorophenyl)-2-methylacrylate Into a 50-mL round-bottom flask, was placed a solution of intermediate 58.2 (280 mg, 0.73 mmol, 1.00 equiv) in acetone (20 mL). This was followed by the addition of potassium carbonate (200 mg, 1.45 mmol, 2.00 equiv). The mixture was stirred for 3 h at room temperature. To this was added ethyl chloroformate (90 mg, 0.83 mmol, 1.20 equiv). The resulting solution was stirred for 6 h at 65° C. The resulting mixture was concentrated under vacuum. The pH value of the solution was adjusted to 2-3 with hydrogen chloride (1 mol/L). The resulting solution was extracted with 2×50 ml of ethyl acetate and the organic layers combined. The mixture was dried over anhydrous sodium sulfate and concentrated under vacuum. This resulted in 300 mg (72%) of the title compound as yellow oil.

Intermediate 58.4: (E)-methyl 3-(3,5-difluoro-4-(4-(N-(2-methoxyethylcarbamoyl)-sulfamoyl)phenoxy)phenyl)-2-methylacrylate Into a 100-mL round-bottom flask, was placed a solution of intermediate 58.3 (300 mg, 0.66 mmol, 1.00 equiv) in toluene (20 mL), 2-methoxyethanamine (100 mg, 1.33 mmol, 1.10 equiv). The resulting solution was stirred for 1 h at 110° C. The resulting mixture was concentrated under vacuum. The residue was applied onto a silica gel column with petroleum ether/ethyl acetate (1:1). This resulted in 0.3 g (92%) of the title compound as a yellow solid.

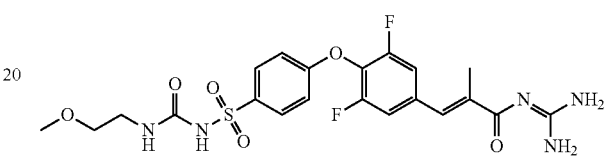

Compound 58: (E)-N-(diaminomethylene)-3-(3,5-difluoro-4-(4-(N-(2-methoxyethylcarbamoyl)sulfamoyl)phenoxy)phenyl)-2-methylacrylamide Intermediate 58.4 was converted to compound 58 using the procedures described under Example 52. Purification by preparative HPLC gave a TFA salt of the title compound. $^1$H-NMR (300 MHz, DMSO, ppm): δ10.62 (s, 1H), 8.33 (s, 3H), 7.94-7.91 (d, J=8.7 Hz, 2H), 7.55-7.52 (d, J=9 Hz, 2H),

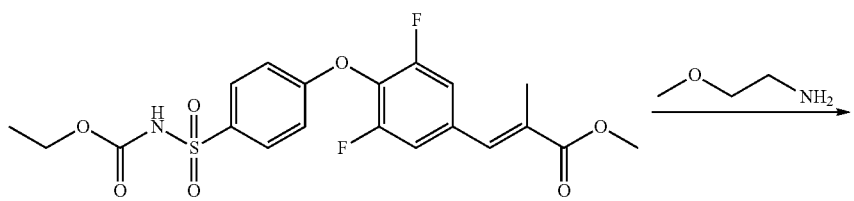

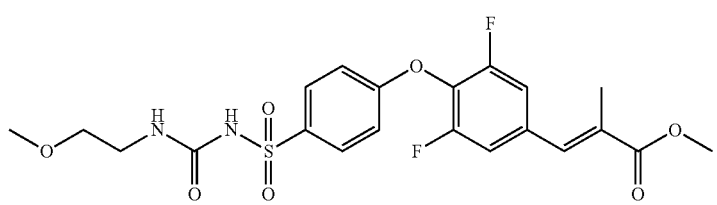

7.45 (s, 1H), 7.26-7.22 (d, J=9 Hz, 2H), 6.55 (s, 1H), 3.37-3.27 (m, 2H), 3.21 (s, 3H), 3.15-3.12 (m, 2H), 2.16 (s, 3H). MS (ES, m/z): 512 [M+H]+.

Example 59

(E)-2-(4-(4-(3-(diaminomethyleneamino)-2-methyl-3-oxoprop-1-enyl)-2,6-difluorophenoxy)phenylsulfonamido)succinic acid

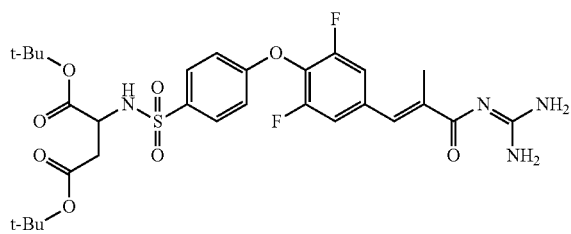 [SMILES: C/C(=C\c1cc(F)c(Oc2ccc(S(=O)(=O)NC(CC(=O)OC(C)(C)C)C(=O)OC(C)(C)C)cc2)c(F)c1)C(=O)N=C(N)N]

Intermediate 59.1: (E)-di-tert-butyl 2-(4-(4-(3-(diaminomethyleneamino)-2-methyl-3-oxoprop-1-enyl)-2,6-difluorophenoxy)phenylsulfonamido)succinate Intermediate 59.1 was prepared from di-tert-butyl 2-aminosuccinate using the procedures described under Example 51.

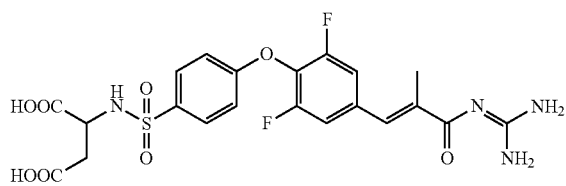 [SMILES: C/C(=C\c1cc(F)c(Oc2ccc(S(=O)(=O)NC(CC(=O)O)C(=O)O)cc2)c(F)c1)C(=O)N=C(N)N]

Compound 59: (E)-2-(4-(4-(3-(diaminomethyleneamino)-2-methyl-3-oxoprop-1-enyl)-2,6-difluorophenoxy)phenylsulfonamido)succinic acid Into a 50-mL round-bottom flask, was placed a solution of intermediate 59.1 (100 mg, 0.16 mmol, 1.00 equiv) in tetrahydrofuran (5 mL). This was followed by the addition of 2,2,2-trifluoroacetic acid (10 mL) dropwise with stirring. The resulting solution was stirred for 3 h at room temperature. The resulting mixture was concentrated under vacuum. This resulted in 63.6 mg (64%) of a TFA salt of the title compound as a light yellow solid. $^1$H-NMR (300 MHz, DMSO, ppm): δ 8.26 (s, 4H), 7.82-7.79 (d, J=8.7 Hz, 2H), 7.49-7.45 (m, 3H), 7.19-7.16 (d, J=8.4 Hz, 2H), 4.00-3.96 (m, 1H), 2.65-2.60 (m, 1H), 2.48-2.41 (m, 1H), 2.13 (s, 3H). MS (ES, m/z): 527 [M+H]+.

Example 60

4-(3-(6-chloro-2-(diaminomethyleneamino)quinazolin-4-yl)phenyl)piperazine-1-carboximidamide

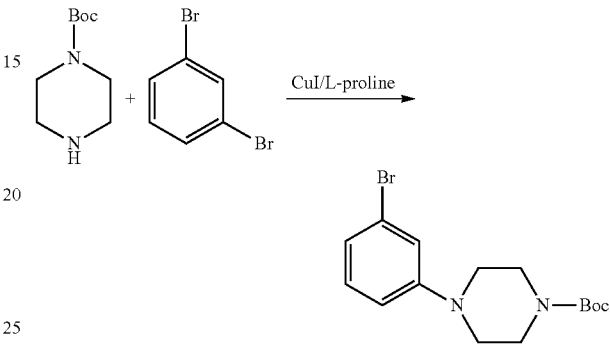

Intermediate 60.1: tert-butyl 4-(3-bromophenyl)piperazine-1-carboxylate

Into a 250-mL round-bottom flask purged and maintained with an inert atmosphere of nitrogen, was placed copper(I) iodide (1.0 g, 5.26 mmol, 0.20 equiv), L-proline (930 mg, 8.09 mmol, 0.30 equiv) in DMSO (50 mL). The resulting solution was stirred for 15 min at room temperature. Then, tert-butyl piperazine-1-carboxylate (5 g, 26.88 mmol, 1.00 equiv), 1,3-dibromobenzene (9.5 g, 40.25 mmol, 1.50 equiv), potassium carbonate (7.4 g, 53.62 mmol, 1.99 equiv) was added. The resulting solution was stirred overnight at 90° C. The reaction was then quenched by the addition of 100 mL of water. The resulting solution was extracted with 2×100 mL of ethyl acetate and the organic layers combined and dried over anhydrous sodium sulfate and concentrated under vacuum. The residue was applied onto a silica gel column with ethyl acetate/petroleum ether (1:6). This resulted in 2.9 g of tert-butyl 4-(3-bromophenyl)piperazine-1-carboxylate as a white solid.

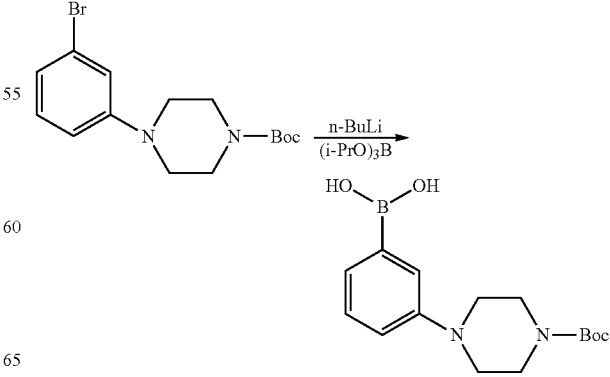

Intermediate 60.2: 3-(4-(tert-butoxycarbonyl)piperazin-1-yl)phenylboronic acid Into a 250-mL 3-necked round-bottom flask purged and maintained with an inert atmosphere of nitrogen, was placed a solution of tert-butyl 4-(3-bromophenyl)piperazine-1-carboxylate (3.8 g, 11.14 mmol, 1.00 equiv) in toluene/tetrahydrofuran=1:1 (40 mL). This was followed by the addition of n-BuLi (4.9 mL, 2.5M/L) dropwise with stirring at −70° C. The resulting solution was stirred for 30 min at −70° C. To this was added triisopropyl borate (2.5 g, 13.30 mmol, 1.19 equiv) dropwise with stirring at −70° C. The mixture was warmed to 0° C., the reaction was then quenched by the addition of 13 mL of saturated ammonium chloride and 3.4 mL of water. Phosphoric acid (85 wt %, 1.5 g, 1.2 equiv) was added and the mixture was stirred for 30 min. The organic layer was separated and dried over anhydrous sodium sulfate and concentrated under vacuum. The residue was dissolved in 20 mL of toluene. The product was precipitated by the addition of 80 mL of heptane. The solids were washed with 20 mL of heptane and collected by filtration. This resulted in 2.9 g (85%) of 3-(4-(tert-butoxycarbonyl)piperazin-1-yl)phenylboronic acid as a white solid.

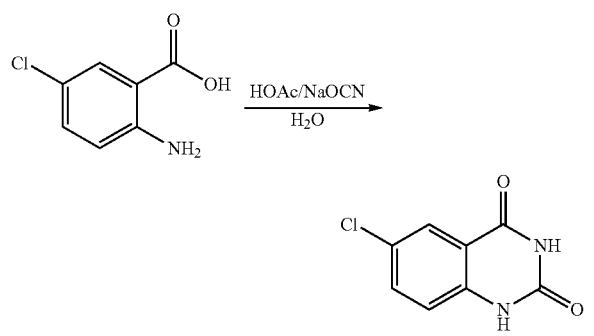

Intermediate 60.3: 6-chloroquinazoline-2,4(1H,3H)-dione

Into a 500-mL 3-necked round-bottom flask, was placed a solution of 2-amino-5-chlorobenzoic acid (10 g, 58.48 mmol, 1.00 equiv) in water (100 mL), acetic acid (8 g, 133.33 mmol, 2.24 equiv). This was followed by the addition of NaOCN (8.2 g, 126.15 mmol, 2.13 equiv). The mixture was stirred for 30 mins at 30° C. To this was added sodium hydroxide (86 g, 2.15 mol, 37.00 equiv). The resulting solution was stirred overnight at 30° C. The solids were collected by filtration. The residue was dissolved in water. The pH value of the solution was adjusted to 7 with hydrogen chloride (12 mol/L). The solids were collected by filtration. This resulted in 5 g (44%) of 6-chloroquinazoline-2,4(1H,3H)-dione as a white solid.

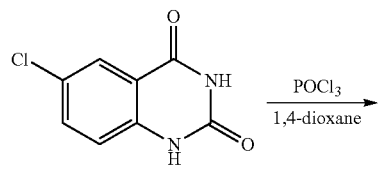

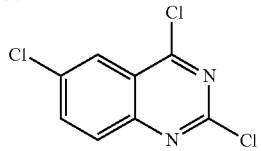

Intermediate 60.4: 2,4,6-trichloroquinazoline

Into a 50-mL round-bottom flask, was placed a solution of 6-chloroquinazoline-2,4(1H,3H)-dione (2.2 g, 11.22 mmol, 1.00 equiv) in 1,4-dioxane (20 mL), phosphoryl trichloride (17 g, 111.84 mmol, 10.00 equiv). The resulting solution was stirred overnight at 120° C. in an oil bath. The resulting mixture was concentrated under vacuum. The reaction was then quenched by the addition of 200 mL of water. The resulting solution was extracted with 3×200 mL of ethyl acetate and the organic layers combined. The residue was applied onto a silica gel column with ethyl acetate/petroleum ether (1:50). This resulted in 1.8 g (69%) of 2,4,6-trichloroquinazoline as a white solid.

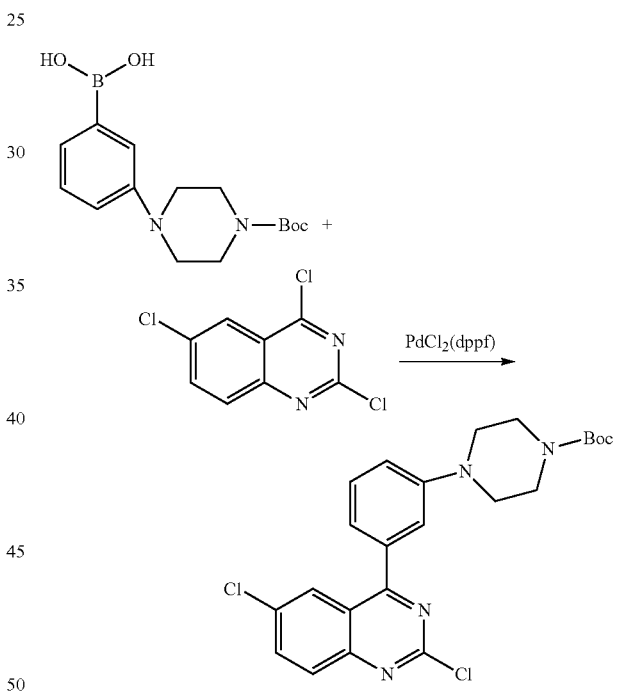

Intermediate 60.5: tert-butyl 4-(3-(2,6-dichloroquinazolin-4-yl)phenyl)piperazine-1-carboxylate Into a 50-mL round-bottom flask purged and maintained with an inert atmosphere of nitrogen, was placed a solution of 3-(4-(tert-butoxycarbonyl)piperazin-1-yl)phenylboronic acid (intermediate 60.2) (960 mg, 3.14 mmol, 1.00 equiv), 2,4,6-trichloroquinazoline (800 mg, 3.43 mmol, 1.09 equiv), PdCl$_2$(dppf).CH$_2$Cl$_2$ (130 mg, 0.16 mmol, 0.05 equiv), Potassium Carbonate (860 mg, 6.23 mmol, 1.99 equiv) in N,N-dimethylformamide (30 mL). The resulting solution was stirred for 3 h at 85° C. The reaction was then quenched by the addition of 50 mL of saturated brine. The resulting solution was extracted with 2×30 mL of ethyl acetate and the organic layers combined and dried over anhydrous sodium sulfate and concentrated under vacuum. The residue was applied onto a silica gel column with ethyl acetate/petroleum ether (1:6). This resulted in 0.45 g (31%) of tert-butyl 4-(3-(2,6-dichloroquinazolin-4-yl)phenyl)piperazine-1-carboxylate as a yellow solid.

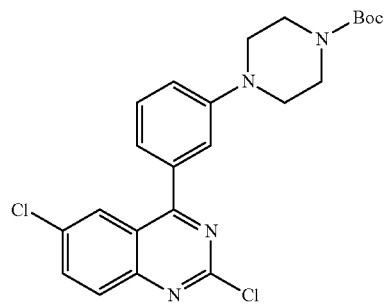

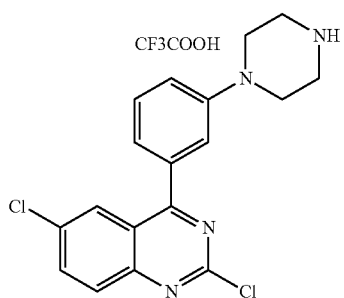

Intermediate 60.6: 2,6-dichloro-4-(3-(piperazin-1-yl)phenyl)quinazoline 2,2,2-trifluoroacetate To intermediate 60.5 (100 mg, 0.22 mmol, 1.00 equiv) was added dichloromethane (10 mL) and 2,2,2-trifluoroacetic acid (124 mg, 1.09 mmol, 5.00 equiv) and the resulting solution was stirred for 3 h at 40° C. The reaction was then concentrated under vacuum to afford 70 mg of Intermediate 60.6 as yellow solid.

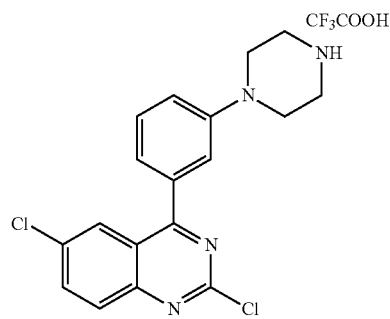

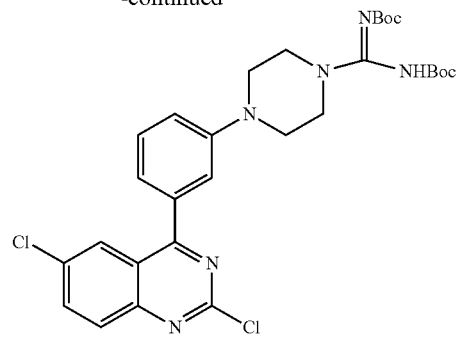

Intermediate 60.7: tert-butyl (4-(3-(2,6-dichloroquinazolin-4-yl)phenyl)piperazin-1-yl)methanediylidenedicarbamate To Intermediate 60.6 (70 mg, 0.15 mmol, 1.00 equiv) in dichloromethane (10 mL) was added N-tert-butoxycarbonyl-N'-tert-butoxycarbonyl-N''-trifluoromethanesulfonylguanidine (91 mg, 0.23 mmol, 1.57 equiv) and triethylamine (38 mg, 0.38 mmol, 2.54 equiv) and the resulting solution was stirred for 3 h at 40° C. The mixture was then concentrated under vacuum, the residue applied onto a silica gel column and eluted with ethyl acetate/petroleum ether (1:8) to afford 70 mg (77%) of Intermediate 60.7 as a yellow solid.

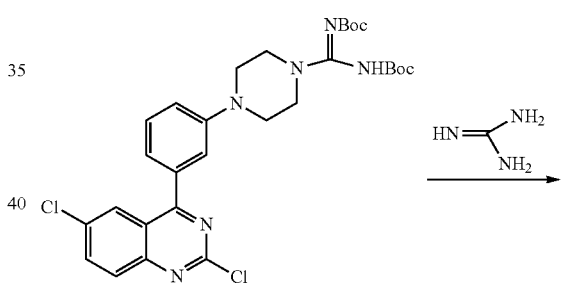

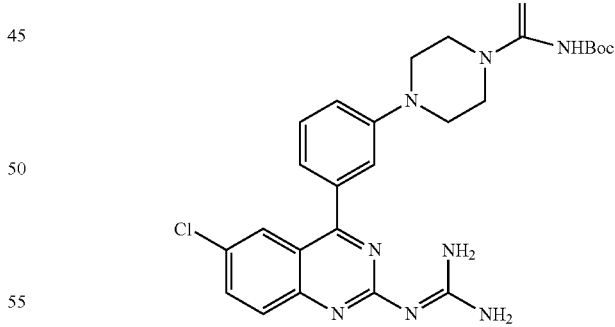

Intermediate 60.8: tert-butyl (4-(3-(6-chloro-2-(diaminomethyleneamino)quinazolin-4-yl)phenyl)piperazin-1-yl)methanediylidenedicarbamate To Intermediate 60.7 (70 mg, 0.12 mmol, 1.00 equiv) in NMP (1.5 mL) was added guanidine (0.24 mL, 2.00 equiv, 1 mol/L) and 1,4-diaza-bicyclo[2.2.2]octane (26 mg, 0.23 mmol, 1.99 equiv) and the resulting solution stirred for 1.5 h at 25° C. The reaction was quenched by the addition of 20 mL of water and the resulting solution was extracted with 2×20 mL of ethyl acetate. The organic layers were combined, dried over anhydrous sodium sulfate, concentrated, the residue applied onto a silica gel column and eluted with dichloromethane/methanol (5:1) to afford 30 mg (41%) of Intermediate 60.8 as a yellow solid.

7.39 (m, 3H), 3.71 (d, J=4.8 Hz, 4H), 3.44 (d, J=4.8 Hz, 4H). MS (ES, m/z): 424.0 [M+H]$^+$.

Example 61

2-(4-(4-(6-chloro-2-(diaminomethyleneamino)quinazolin-4-yl)phenyl)piperazin-1-yl)acetic acid

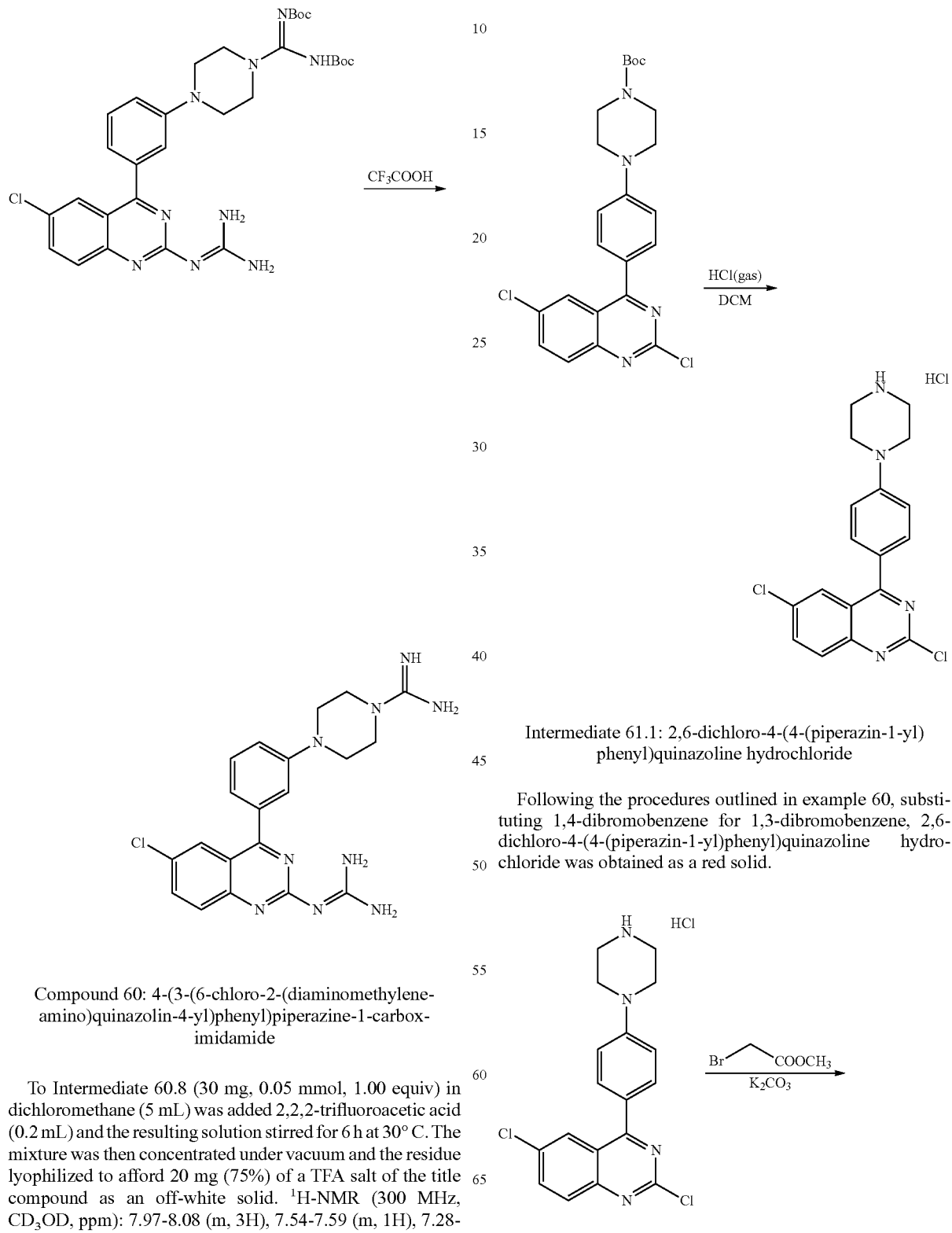

Compound 60: 4-(3-(6-chloro-2-(diaminomethyleneamino)quinazolin-4-yl)phenyl)piperazine-1-carboximidamide To Intermediate 60.8 (30 mg, 0.05 mmol, 1.00 equiv) in dichloromethane (5 mL) was added 2,2,2-trifluoroacetic acid (0.2 mL) and the resulting solution stirred for 6 h at 30° C. The mixture was then concentrated under vacuum and the residue lyophilized to afford 20 mg (75%) of a TFA salt of the title compound as an off-white solid. $^1$H-NMR (300 MHz, CD$_3$OD, ppm): 7.97-8.08 (m, 3H), 7.54-7.59 (m, 1H), 7.28-

Intermediate 61.1: 2,6-dichloro-4-(4-(piperazin-1-yl)phenyl)quinazoline hydrochloride Following the procedures outlined in example 60, substituting 1,4-dibromobenzene for 1,3-dibromobenzene, 2,6-dichloro-4-(4-(piperazin-1-yl)phenyl)quinazoline hydrochloride was obtained as a red solid.

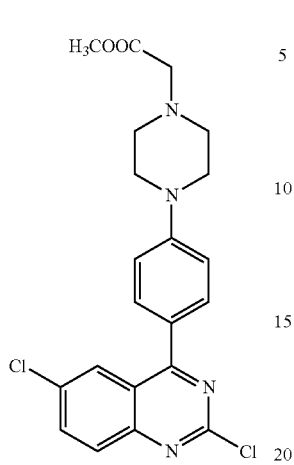
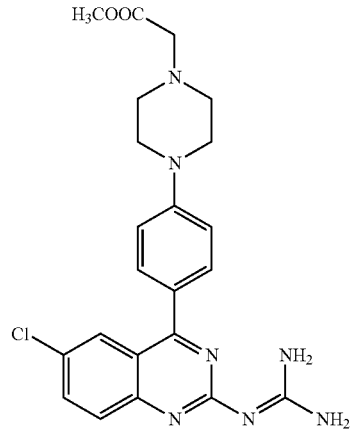

Intermediate 61.2: methyl 2-(4-(4-(2,6-dichloro-quinazolin-4-yl)phenyl)piperazin-1-yl)acetate Intermediate 61.3: methyl 2-(4-(4-(6-chloro-2-(di-aminomethyleneamino)quinazolin-4-yl)phenyl)piperazin-1-yl)acetate To methyl 2-bromoacetate (116 mg, 0.76 mmol, 3.00 equiv) in N,N-dimethylformamide (10 mL) was added potassium carbonate (140 mg, 1.01 mmol, 4.00 equiv) followed by the portion-wise addition of Intermediate 61.1 (100 mg, 0.25 mmol, 1.00 equiv) and the reaction was stirred for 4 h at 30° C. The mixture was concentrated under vacuum and the residue applied onto a silica gel column, eluting with ethyl acetate/petroleum ether (1:5) to afford 60 mg (55%) of Intermediate 61.2 as a yellow solid.

To Intermediate 61.2 (60 mg, 0.14 mmol, 1.00 equiv) in NMP (5 mL) was added 1,4-diaza-bicyclo[2.2.2]octane (DABCO; 15 mg, 0.13 mmol, 1.00 equiv), guanidine (0.3 mL of a 1M solution in NMP, 2.00 equiv) and the resulting solution was stirred for 2 h at 30° C. The reaction was diluted with 10 mL of water, extracted with 4×10 mL of ethyl acetate and the organic layers combined and dried over anhydrous sodium sulfate and then concentrated under vacuum. The residue was applied onto a silica gel column and eluted with dichloromethane/methanol (50:1-20:1) to afford 30 mg (47%) of Intermediate 61.3 as a yellow solid.

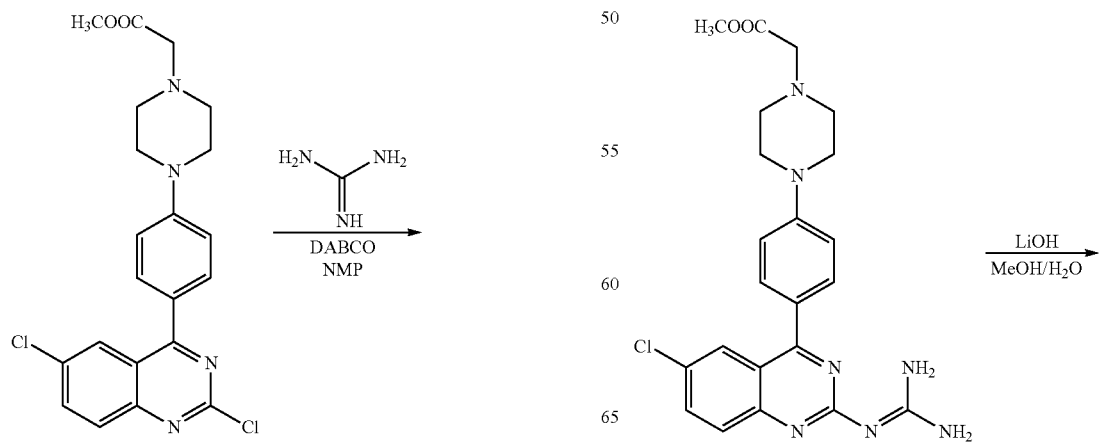

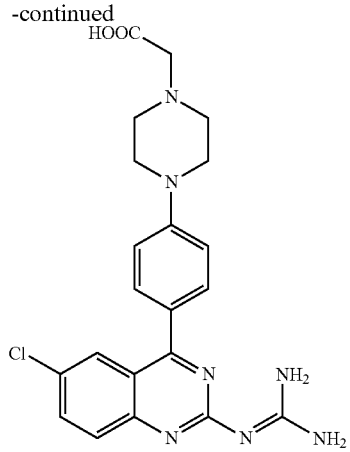

Compound 61: 2-(4-(4-(6-chloro-2-(diaminomethyl-eneamino)quinazolin-4-yl)phenyl)piperazin-1-yl) acetic acid To Intermediate 61.3 (20 mg, 0.04 mmol, 1.00 equiv) in methanol (5 mL) was added a solution of LiOH (32 mg, 1.33 mmol, 30.00 equiv) in water (1 mL) and the reaction was stirred for 3 h at 25° C. The solution was concentrated under vacuum, the pH value adjusted to 6 with aqueous HCl (1 mol/L) and the resulting solids were collected by filtration to afford 15.6 mg (80%) of compound 61 as a yellow solid. $^1$H-NMR (300 MHz, DMSO ppm): 8.07-8.06 (t, 1H), 7.96-7.93 (t, 2H), 7.72-7.69 (d, J=8.7 Hz, 2H), 7.22-7.19 (d, J=8.7 Hz, 2H), 3.58-3.54 (m, 4H), 3.43-3.36 (m, 6H). MS (ES, m/z): 440 [M+H]$^+$.

Example 62

2-(4-(3-(6-chloro-2-(diaminomethyleneamino)quinazolin-4-yl)phenyl)piperazin-1-yl)acetic acid

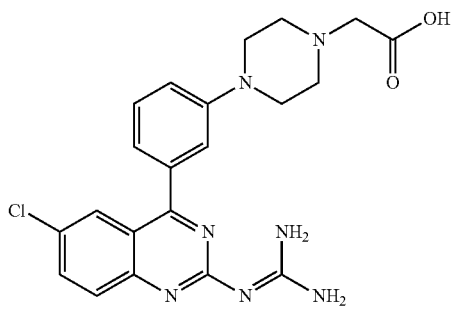 [SMILES: NC(N)=Nc1nc(-c2cccc(N3CCN(CC(=O)O)CC3)c2)c2cc(Cl)ccc2n1]

Compound 62: 2-(4-(3-(6-chloro-2-(diaminomethyl-eneamino)quinazolin-4-yl)phenyl)piperazin-1-yl) acetic acid Compound 62 was prepared from intermediate 60.6, using the procedures described for Example 61. $^1$H-NMR (300 HHz, DMSO-d$_6$, ppm): 7.80-7.86 (m, 3H), 7.41-7.46 (m, 1H), 7.16-7.22 (m, 2H), 7.08-7.10 (m, 1H), 3.13 (brs, 4H), 2.71 (brs, 4H). MS (ES, m/z): 440 [M+H]$^+$;

Example 63

2-(6-chloro-4-(3-(4-((2R,3S,4R,5R)-2,3,4,5,6-pentahydroxyhexanoyl)piperazin-1-yl)phenyl)quinazolin-2-yl)guanidine

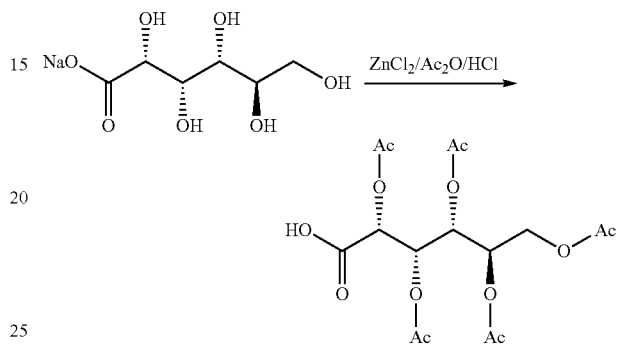

Intermediate 63.1: (2R,3S,4R,5R)-2,3,4,5,6-pentaacetoxyhexanoic acid

Into a 50-mL 3-necked round-bottom flask, was placed ZnCl$_2$ (0.5 g, 0.50 equiv), acetic anhydride (5 mL). To the above was added sodium (2S,3R,4S,5R)-2,3,4,5,6-pentahydroxyhexanoate (1.6 g, 6.97 mmol, 1.00 equiv, 95%) at −5° C. Anhydrous HCl was introduced in for 0.5 h at 0° C. The resulting solution was stirred overnight at room temperature. The reaction mixture was cooled to 0° C. The reaction was then quenched by the addition of 8 g of ice. The mixture was stirred for 1 h at room temperature. The resulting solution was diluted with 20 mL of water. The resulting solution was extracted with 3×20 mL of dichloromethane and the organic layers combined and dried over anhydrous sodium sulfate and concentrated under vacuum. This resulted in 1.0 g (35%) of (2R,3S,4R,5R)-2,3,4,5,6-pentaacetoxyhexanoic acid as a yellow liquid.

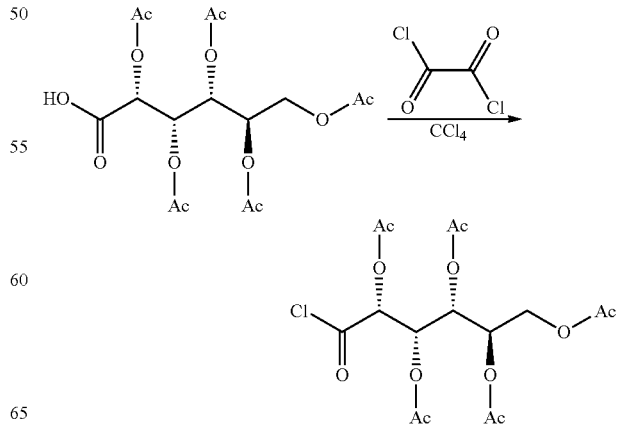

Intermediate 63.2: (2R,3R,4S,5R)-6-chloro-6-oxo-hexane-1,2,3,4,5-pentayl pentaacetate Into a 50-mL 3-necked round-bottom flask, was placed a solution of (2R,3S,4R,5R)-2,3,4,5,6-pentaacetoxyhexanoic acid (intermediate 63.1) (610 mg, 1.35 mmol, 1.00 equiv, 90%) in CCl$_4$ (30 mL). This was followed by the addition of oxalyl dichloride (3 mL) dropwise with stirring. The resulting solution was heated to reflux for 3 h in an oil bath. The resulting mixture was concentrated under vacuum. This resulted in 0.62 g (crude) of intermediate 63.2 as yellow oil.

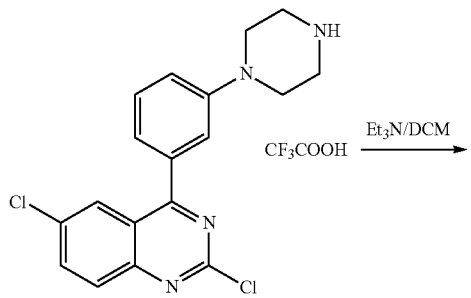

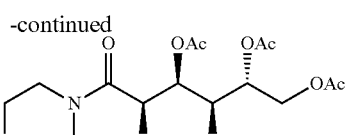

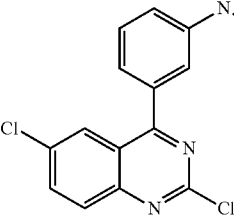

Intermediate 63.3: 2-(6-chloro-4-(3-(4-((2R,3S,4R,5R)-2,3,4,5,6-pentahydroxyhexanoyl)piperazin-1-yl)phenyl)quinazolin-2-yl)guanidine 2,2,2-trifluoroacetate To Intermediate 60.6 (150 mg, 0.32 mmol, 1.00 equiv) in dichloromethane (5 mL) was added triethylamine (96 mg, 0.95 mmol, 2.99 equiv) and the solution cooled to 0° C. Intermediate 63.2 (407 mg, 0.96 mmol, 3.02 equiv) in dichloromethane (5 mL) was then added dropwise and the reaction was stirred for 1 h at room temperature. The resulting mixture was concentrated under vacuum, the residue applied onto a silica gel column and then eluted with ethyl acetate/petroleum ether (1:2) to afford 150 mg (62%) of Intermediate 63.3 as a yellow solid.

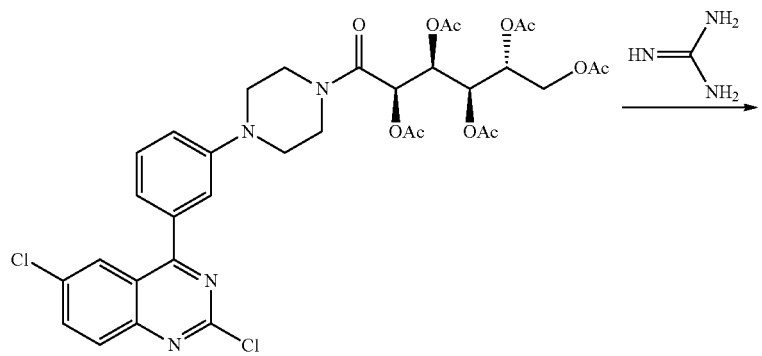

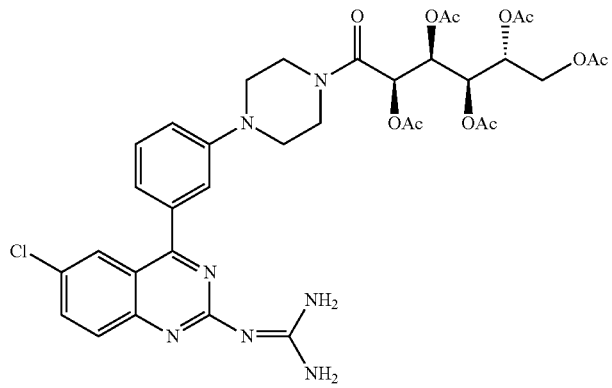

Intermediate 63.4: (2R,3R,4S,5R)-6-(4-(3-(6-chloro-2-(diaminomethyleneamino)-quinazolin-4-yl)phenyl)piperazin-1-yl)-6-oxohexane-1,2,3,4,5-pentayl pentaacetate To Intermediate 63.3 (150 mg, 0.20 mmol, 1.00 equiv) in NMP (5 mL) was added guanidine (0.8 mL of a 1 mol/L solution in NMP; 4.0 equiv) and 1,4-diaza-bicyclo[2.2.2]octane (DABCO; 44.8 mg, 0.40 mmol, 2.00 equiv) and the resulting solution was stirred for 1.5 h at 30° C. The reaction was quenched by the addition of 10 mL of water and then extracted with 2×10 mL of ethyl acetate. The organic layers combined, dried over anhydrous sodium sulfate, concentrated, applied onto a silica gel column and then eluted with dichloromethane/methanol (10:1) to afford 30 mg (19%) of Intermediate 63.4 as a yellow solid.

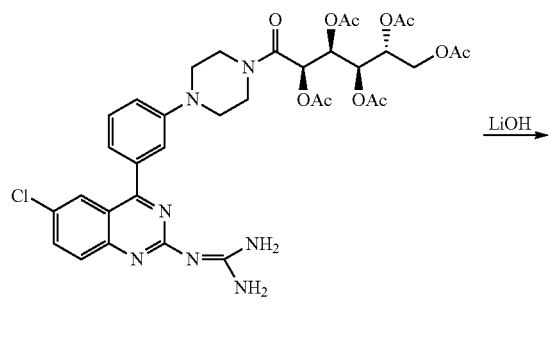

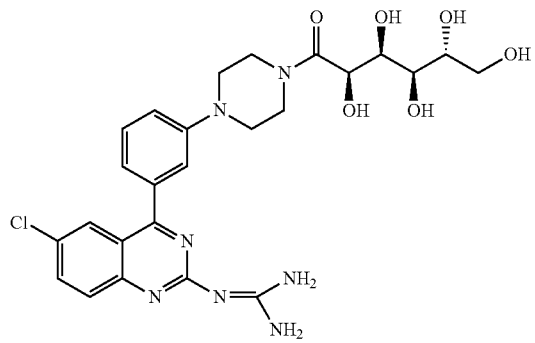

Compound 63: 2-(6-chloro-4-(3-(4-((2R,3S,4R,5R)-2,3,4,5,6-pentahydroxyhexanoyl)piperazin-1-yl)phenyl)quinazolin-2-yl)guanidine To Intermediate 63.4 (25 mg, 0.03 mmol, 1.00 equiv) in methanol (5 mL), was added a solution of LiOH (3.9 mg, 0.16 mmol, 5.03 equiv) in water (0.2 mL) and the resulting solution was stirred for 0.5 h at 0° C. The pH value of the solution was adjusted to 7 with aqueous HCl (5%), the resulting mixture was concentrated under vacuum and then purified by Prep-HPLC to afford 10 mg (45%) a TFA salt of compound 63 as a yellow solid. LCMS (ES, m/z): 560.0 [M+H]$^+$; $^1$H-NMR (300 MHz, CD$_3$OD, ppm): 7.96-8.09 (m, 3H), 7.52- 7.57 (m, 1H), 7.25-7.39 (m, 3H), 4.73 (d, J=5.1 Hz, 1H), 4.07-4.09 (m, 1H), 3.62-3.89 (m, 8H). MS (ES, m/z): 560.0 [M+H]$^+$

Example 64

3-(4-(3-(6-chloro-2-(diaminomethyleneamino)quinazolin-4-yl)phenyl)piperazin-1-yl)propanoic acid

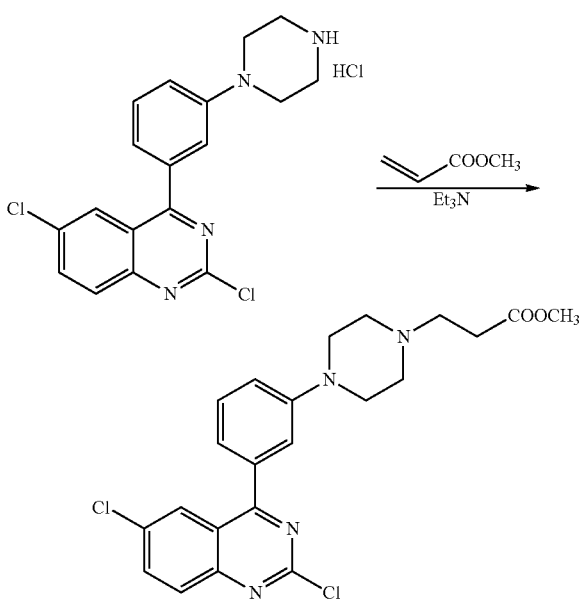

Intermediate 64.1: methyl 3-(4-(3-(2,6-dichloroquinazolin-4-yl)phenyl)piperazin-1-yl)propanoate To Intermediate 60.6 (200 mg, 0.51 mmol, 1.00 equiv) in tetrahydrofuran (10 mL) was added methyl acrylate (253 mg, 2.94 mmol, 5.81 equiv) and triethylamine (253 mg, 2.50 mmol, 4.95 equiv) and the resulting mixture was stirred for 3 h at room temperature. The reaction was concentrated under vacuum, the residue applied onto a silica gel column and then eluted with ethyl acetate/petroleum ether (1:3) to afford 100 mg (44%) of Intermediate 64.1 as a yellow solid.

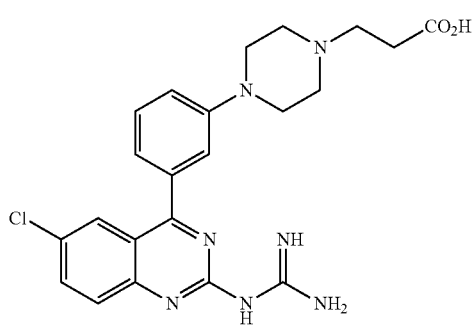 [SMILES: N=C(N)Nc1nc(-c2cccc(N3CCN(CCC(=O)O)CC3)c2)c2cc(Cl)ccc2n1]

Compound 64: 3-(4-(3-(6-chloro-2-(diaminomethyleneamino)quinazolin-4-yl)phenyl)piperazin-1-yl)propanoic acid Compound 64 was prepared from Intermediate 64.1 using the procedures described in Example 61, affording 25 mg of the title compound as a yellow solid.; $^1$H-NMR (300 MHz, DMSO-d6, ppm): δ 7.89-7.92 (m, 3H), 7.42-7.47 (m, 1H), 7.35 (brs, 1H), 7.15-7.24 (m, 2H), 3.25 (brs, 4H), 2.63-2.74 (m, 6H), 2.31-2.35 (m, 2H). LCMS (ES, m/z): 454.0 [M+H]$^+$

Example 65

1-(4-(3-(4-(3-aminopropyl)piperazin-1-yl)phenyl)-6-chloroquinazolin-2-yl)guanidine

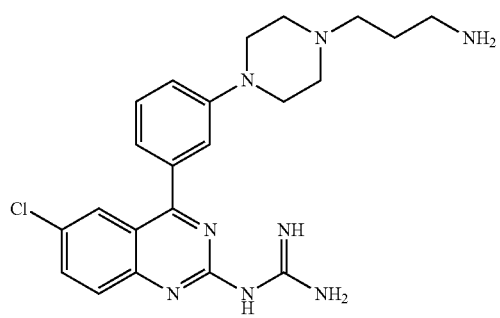 [SMILES: N=C(N)Nc1nc(-c2cccc(N3CCN(CCCN)CC3)c2)c2cc(Cl)ccc2n1]

Compound 65: 1-(4-(3-(4-(3-aminopropyl)piperazin-1-yl)phenyl)-6-chloroquinazolin-2-yl)guanidine A hydrochloride salt of the title compound was prepared using procedures similar to those outlined in Example 61, starting with intermediate 60.6 and tert-butyl 3-bromopropylcarbamate. MS (ES, m/z): 439 [M+H]$^+$

Example 66

4-(4-(6-chloro-2-(diaminomethyleneamino)quinazolin-4-yl)phenyl)piperazine-1-carboximidamide

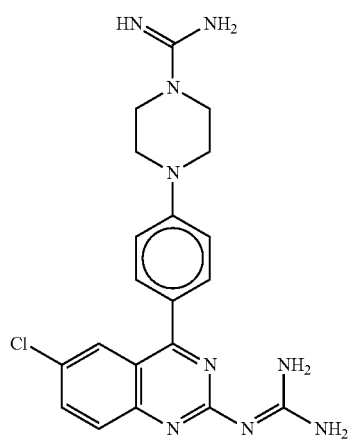

Compound 66: 4-(4-(6-chloro-2-(diaminomethyleneamino)quinazolin-4-yl)phenyl)piperazine-1-carboximidamide A TFA salt of Compound 66 was prepared from Intermediate 61.1, using the procedures described in Example 60. MS (ES, m/z): 424 [M+H]$^+$

Example 67

2-(4-(3-(4-(3-guanidinopropyl)piperazin-1-yl)phenyl)-6-chloroquinazolin-2-yl)guanidine

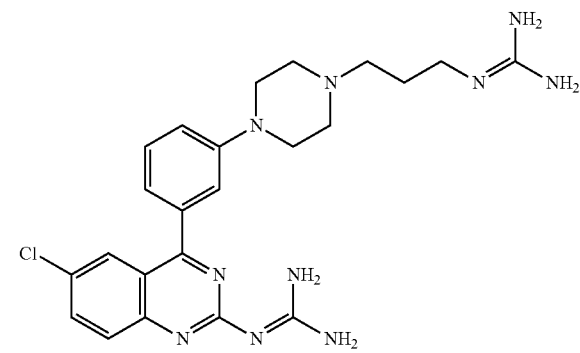 [SMILES: NC(N)=NCCCN1CCN(c2cccc(-c3nc(N=C(N)N)nc4ccc(Cl)cc34)c2)CC1]

Compound 67: 2-(4-(3-(4-(3-guanidinopropyl)piperazin-1-yl)phenyl)-6-chloroquinazolin-2-yl)guanidine A hydrochloride salt of Compound 67 was prepared from Compound 65 using the procedures outlined in Example 60. MS (ES, m/z): 481 [M+H]$^+$

Example 68

2-(6-chloro-4-(3-(4-(2-hydroxyethyl)piperazin-1-yl)phenyl)quinazolin-2-yl)guanidine

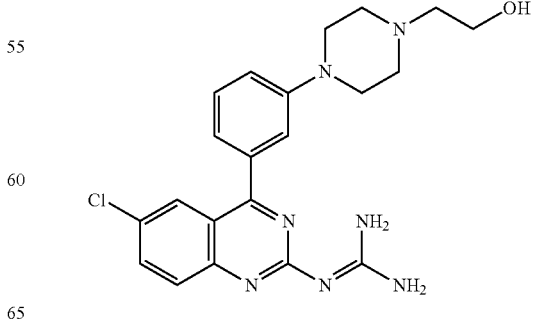

253

Compound 68: 2-(6-chloro-4-(3-(4-(2-hydroxyethyl)piperazin-1-yl)phenyl)quinazolin-2-yl)guanidine A TFA salt of Compound 68 was prepared from Compound 60.6 and ethylene oxide using the procedures outlined in Example 61. MS (ES, m/z): 426 [M+H]⁺

Example 69

2-(6-chloro-4-(4-(4-(2-hydroxyethyl)piperazin-1-yl)phenyl)quinazolin-2-yl)guanidine

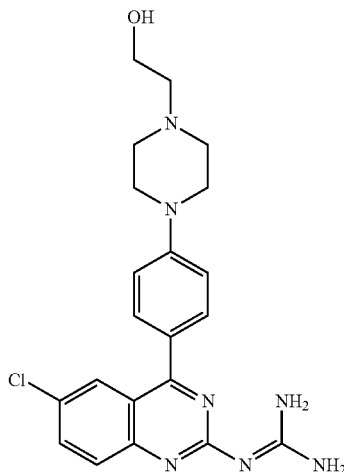 [SMILES: NC(N)=Nc1nc(-c2ccc(N3CCN(CCO)CC3)cc2)c2cc(Cl)ccc2n1]

Compound 69: 2-(6-chloro-4-(4-(4-(2-hydroxyethyl)piperazin-1-yl)phenyl)quinazolin-2-yl)guanidine a TFA salt of Compound 69 was prepared from Intermediate 61.1 using the procedures described in Example 68. MS (ES, m/z): 426 [M+H]⁺

Example 70

4-(4-(3-(6-chloro-2-(diaminomethyleneamino)quinazolin-4-yl)phenyl)piperazin-1-yl)butanoic acid 2,2,2-trifluoroacetic acid salt

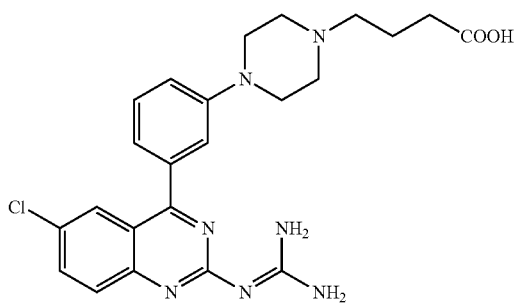 [SMILES: NC(N)=Nc1nc(-c2cccc(N3CCN(CCCC(=O)O)CC3)c2)c2cc(Cl)ccc2n1]

Compound 70: 4-(4-(3-(6-chloro-2-(diaminomethyleneamino)quinazolin-4-yl)phenyl)piperazin-1-yl)butanoic acid Compound 70 was prepared from Intermediate 60.6 and methyl 4-bromobutanoate using the procedures described in

254

Example 61. Purification by silica gel column with methanol:water (0~0.04) gave a TFA salt of the title compound as a yellow solid. ¹H-NMR (300 MHz, DMSO, ppm): δ 11.33 (s, 1H), 8.09-8.19 (m, 2H), 7.96-7.96 (s, 1H), 7.53-7.58 (m, 1H), 7.25-7.37 (m, 3H), 4.0 (s, 4H), 3.16 (s, 6H), 2.34-2.39 (m, 2H), 1.92 (s, 2H); MS (ES, m/z): 468 [M+H]

Examples 71-104

Examples 71-104 were prepared using methods described in Examples 1-70. Characterization data (mass spectra) for compounds 71-104 are provided in Table 3.

Example 71

(E)-3-(4-(4-(3-(diaminomethyleneamino)-2-methyl-3-oxoprop-1-enyl)-2,6-difluorophenoxy)phenylsulfonamido)propane-1-sulfonic acid

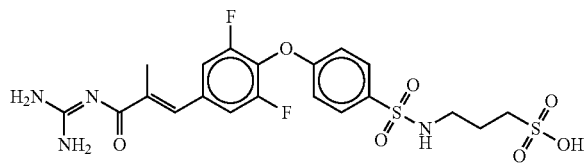

Example 72

2-(4-(6,8-dichloro-2-methyl-1,2,3,4-tetrahydroisoquinolin-4-yl)-N-(phosphonomethyl)phenylsulfonamido)acetic acid

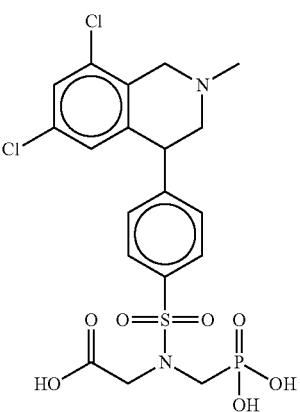

Example 73

4-(4-(4-(6-chloro-2-(diaminomethyleneamino)quinazolin-4-yl)phenyl)piperazin-1-yl)butanoic acid

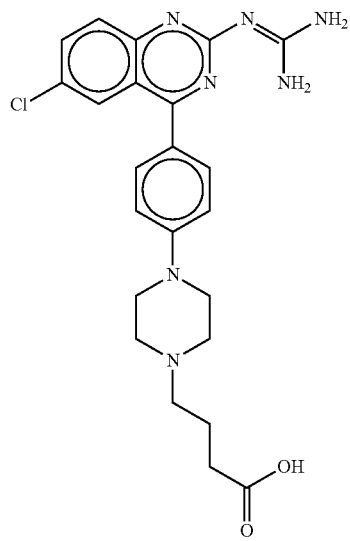

Example 74

(E)-N-(diaminomethylene)-3-(4-(4-(N-(ethylcarbamoyl)sulfamoyl)phenoxy)-3,5-difluorophenyl)-2-methylacrylamide

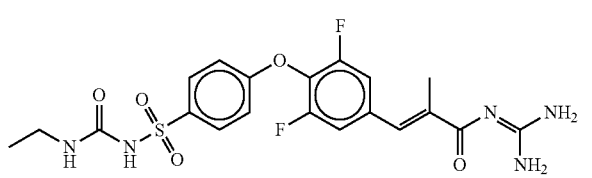

Example 75

(E)-N-(diaminomethylene)-3-(4-(4-(N-(2-(dimethylamino)ethylcarbamoyl)sulfamoyl)phenoxy)-3,5-difluorophenyl)-2-methylacrylamide

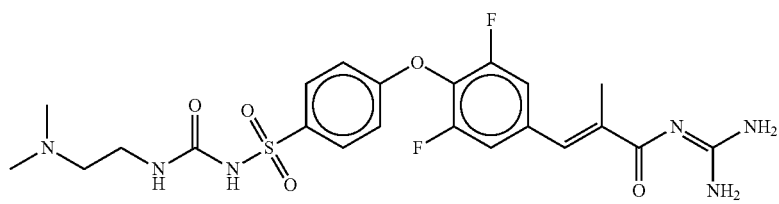

Example 76

4-(4-(6,8-dichloro-2-methyl-1,2,3,4-tetrahydroisoquinolin-4-yl)phenylsulfonamido)phenylphosphonic acid

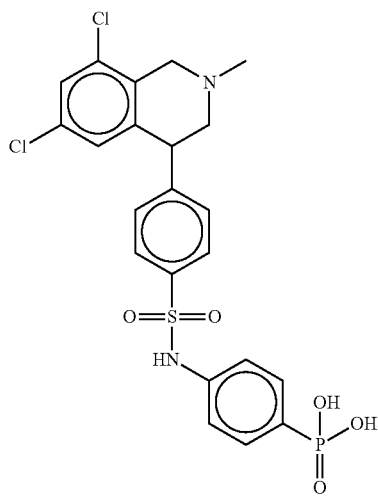

Example 77
(E)-N-(diaminomethylene)-3-(3,5-difluoro-4-(4-(N-methyl-N-((2S,3R,4R,5R)-2,3,4,5,6-pentahydroxyhexyl)sulfamoyl)phenoxy)phenyl)-2-methylacrylamide
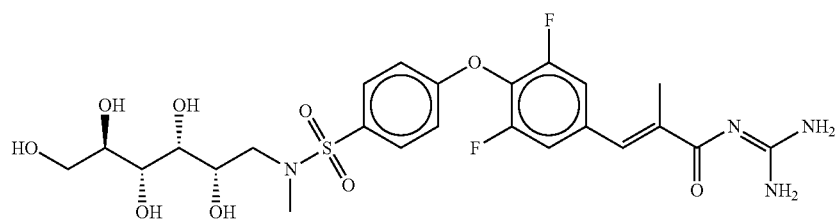
Example 78
3-(4-(6,8-dichloro-2-methyl-1,2,3,4-tetrahydroisoquinolin-4-yl)phenylsulfonamido)propane-1-sulfonic acid
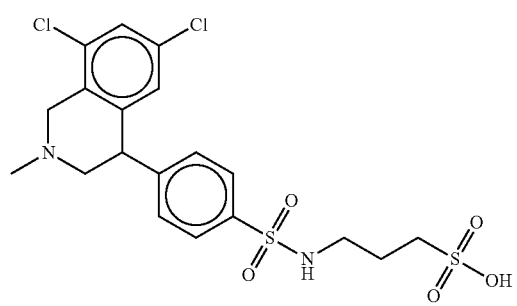
Example 79
2-(4-(4-(4-(3-aminopropyl)piperazin-1-yl)phenyl)-6-chloroquinazolin-2-yl)guanidine
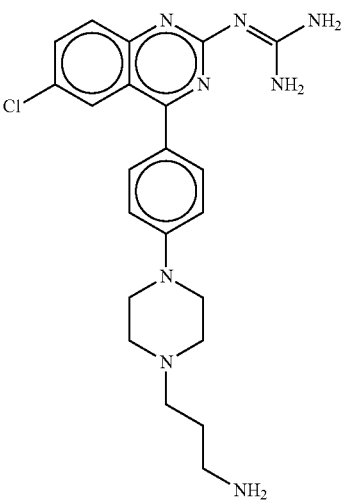

Example 80

3-(6,8-dichloro-2-methyl-1,2,3,4-tetrahydroisoquino-
lin-4-yl)-N-(2-(2-(2-(2-(4-(hydroxymethyl)-1H-1,2,
3-triazol-1-yl)ethoxy)ethoxy)ethoxy)ethyl)benzene-
sulfonamide

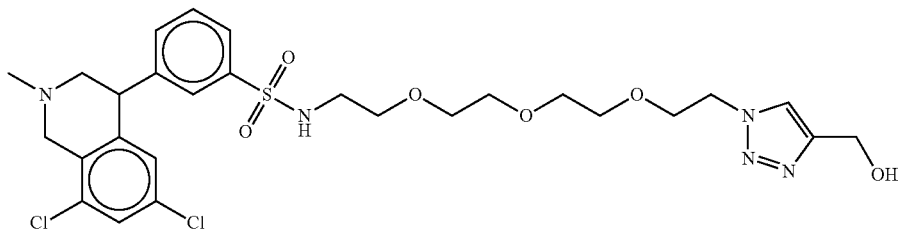

Example 81

N,N'-(2,2'-(2,2'-(2,2'-(2,2'-(4,4'-oxybis(methylene)
bis(1H-1,2,3-triazole-4,1-diyl))bis(ethane-2,1-diyl))
bis(oxy)bis(ethane-2,1-diyl))bis(oxy)bis(ethane-2,1-
diyl))bis(oxy)bis(ethane-2,1-diyl))bis(3-(6,8-
dichloro-2-methyl-1,2,3,4-tetrahydroisoquinolin-4-
yl)benzenesulfonamide)

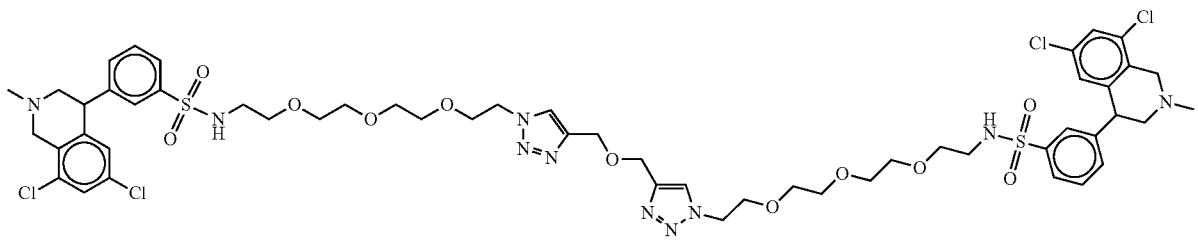

Example 82

N-(2-(2-(2-(2-aminoethoxy)ethoxy)ethoxy)ethyl)-4-
(6,8-dichloro-2-methyl-1,2,3,4-tetrahydroisoquino-
lin-4-yl)benzenesulfonamide

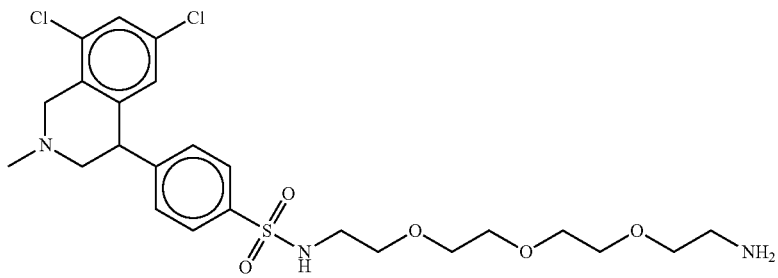

Example 83
1-(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-1H-1,2,3-triazole-4,5-dicarboxylic acid
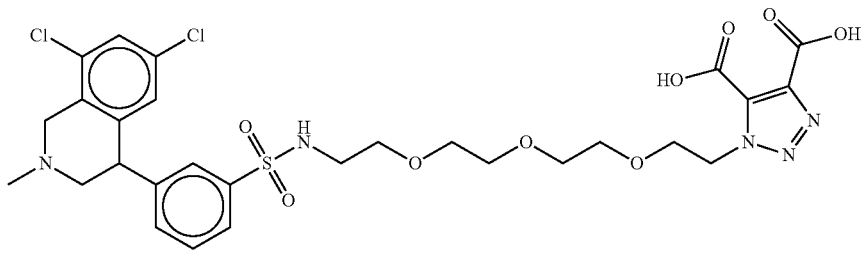
Example 84
(E)-3-(4-(4-(N-(2-(2-(2-aminoethoxy)ethoxy)ethyl)sulfamoyl)phenoxy)-3,5-difluorophenyl)-N-(diaminomethylene)-2-methylacrylamide
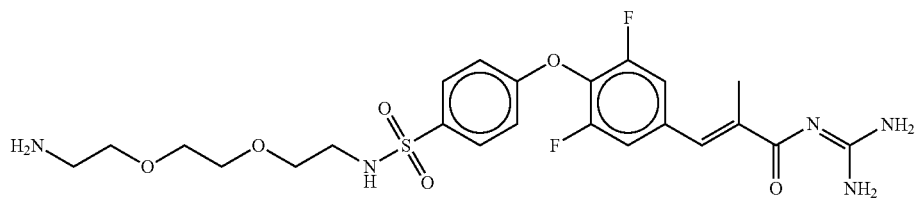
Example 85
2-(4-(4-(4-(2-aminoethyl)piperazin-1-yl)phenyl)-6-chloroquinazolin-2-yl)guanidine
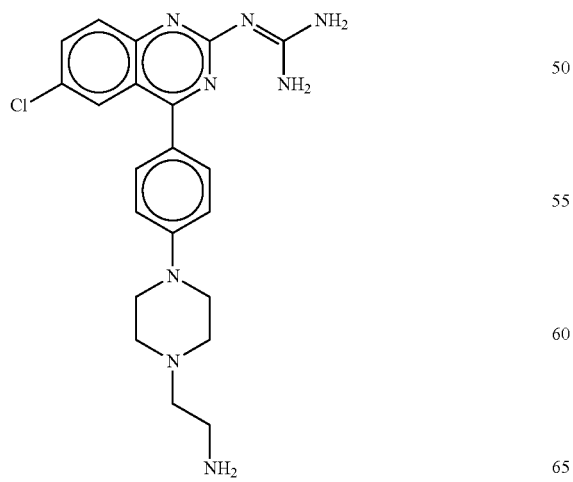

Example 86

(E)-3-(4-(4-(N-(2-(2-(2-(2-aminoethoxy)ethoxy)ethoxy)ethylcarbamoyl)sulfamoyl)phenoxy)-3,5-difluorophenyl)-N-(diaminomethylene)-2-methylacrylamide

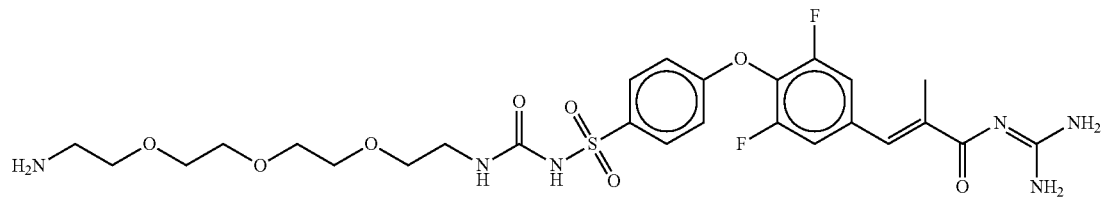

Example 87

N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide

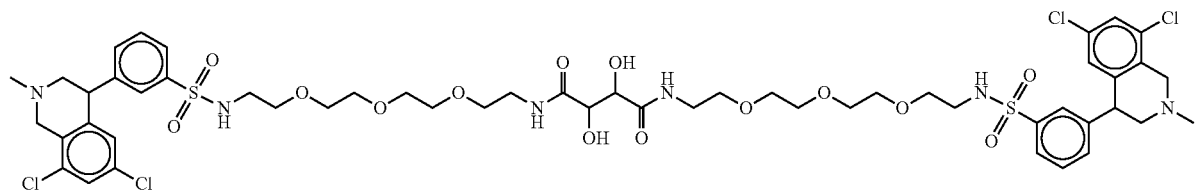

Example 88

N1,N4-bis(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide

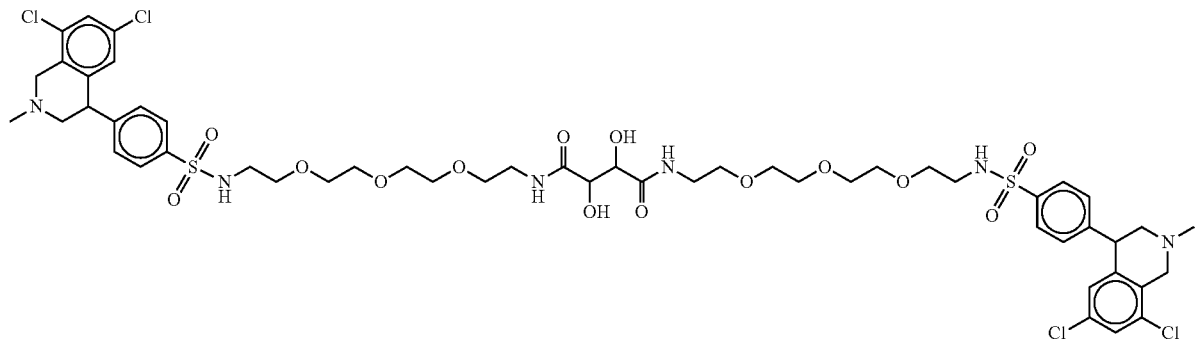

Example 89
1-(4-(4-(4-(3-guanidinopropyl)piperazin-1-yl)phenyl)-6-chloroquinazolin-2-yl)guanidine
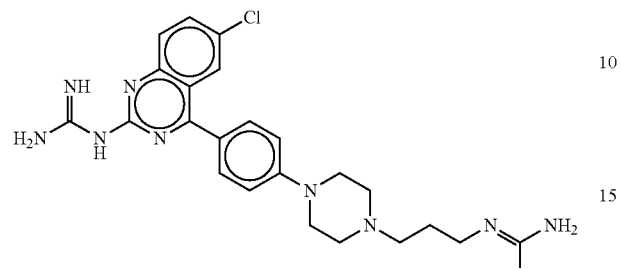
Example 90
(E)-2-(4-(2-(4-(4-(3-(diaminomethyleneamino)-2-methyl-3-oxoprop-1-enyl)-2,6-difluorophenoxy)phenylsulfonamido)ethyl)piperazin-1-yl)acetic acid
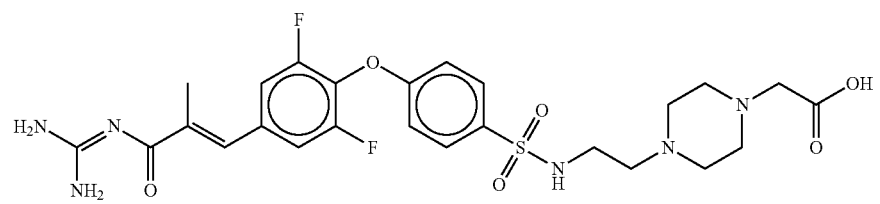
Example 91
N-(1-amino-1-imino-5,8,11-trioxa-2-azatridecan-13-yl)-3-(6,8-dichloro-2-methyl-1,2,3,4-tetrahydroisoquinolin-4-yl)benzenesulfonamide
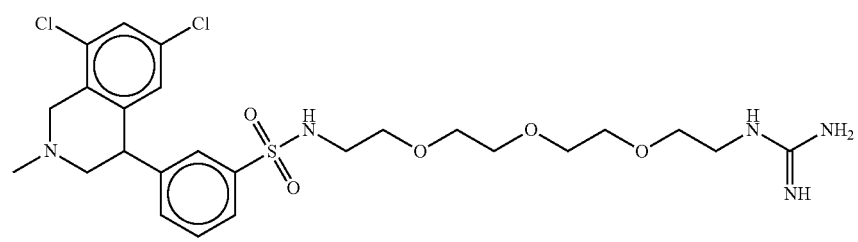

Example 92

N-(1-amino-1-imino-5,8,11-trioxa-2-azatridecan-13-yl)-4-(6,8-dichloro-2-methyl-1,2,3,4-tetrahydroisoquinolin-4-yl)benzenesulfonamide

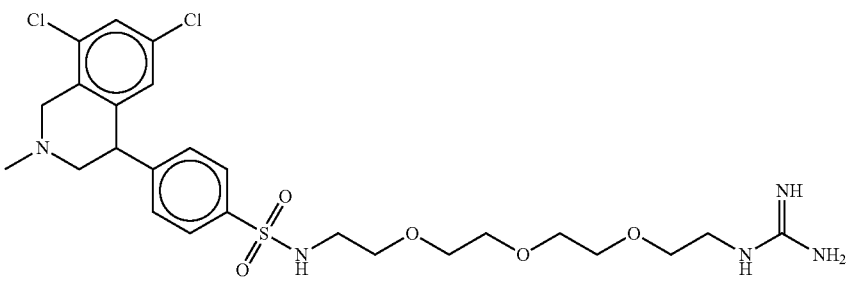

Example 93

(E)-1-(3-(3,5-difluoro-4-phenoxyphenyl)-2-methylallyl)guanidine

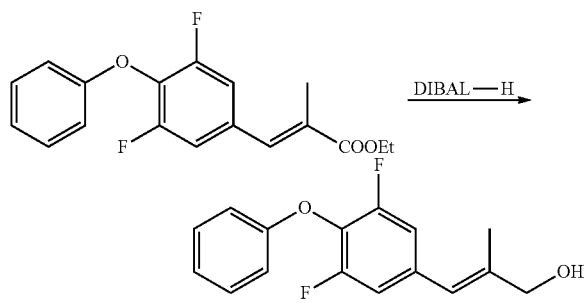

Intermediate 93.1 (E)-3-(3,5-difluoro-4-phenoxyphenyl)-2-methylprop-2-en-1-ol

To a solution of (E)-ethyl 3-(3,5-difluoro-4-phenoxyphenyl)-2-methylacrylate (Intermediate 41.2) (800 mg, 2.51 mmol) in dry DCM (25 mL) under $N_2$ at −78° C. was added a solution of DIBAL-H (8.79 mL, 1M in DCM) dropwise over several minutes. The reaction was allowed to warm to room temperature over 2 hours. The reaction mixture was cooled to 0° C., quenched with 25 mL of Rochelle's Salt solution (10% w/v in water), and stirred vigorously for 1 hour. The resulting suspension was diluted with water (20 mL) and extracted with DCM (3×30 mL). The combined organic layers were dried over $Na_2SO_4$ and concentrated. The resulting oil was applied onto a silica gel column (50% EtOAc in hexanes) to yield 566 mg of the title compound (82%) as a yellow oil.

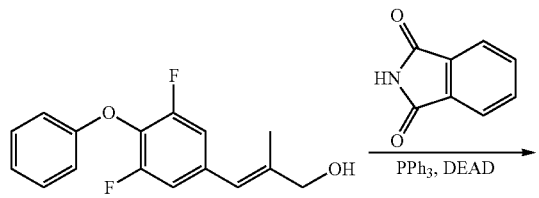

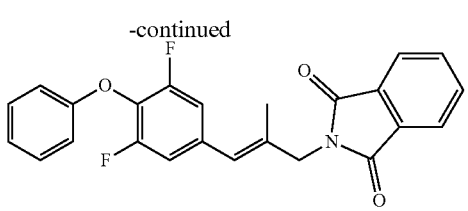

Intermediate 93.2 (E)-2-(3-(3,5-difluoro-4-phenoxyphenyl)-2-methylallyl)isoindoline-1,3-dione To a solution of (E)-3-(3,5-difluoro-4-phenoxyphenyl)-2-methylprop-2-en-1-ol (Intermediate 93.1) (410 mg, 1.49 mmol) in dry toluene (7.45 mL) under $N_2$ was added $PPh_3$ and phthalimide. The resulting solution was cooled to 0° C. and diethyl azodicarboxylate (DEAD, 0.748 mL) was added dropwise over several minutes. The reaction was allowed to warm to room temperature and stirred overnight. After diluting with EtOAc (20 mL), the organic layer was washed with water (2×30 mL), brine (30 mL) and dried over $Na_2SO_4$. After removal of solvent, the resulting residue was applied to a silica gel column (15% EtOAc in hexanes) to yield 385 mg of the title compound (63%) as an oil.

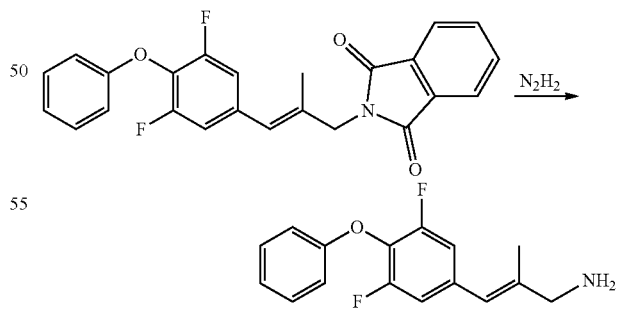

Intermediate 93.3 (E)-3-(3,5-difluoro-4-phenoxyphenyl)-2-methylprop-2-en-1-amine To a solution of (E)-2-(3-(3,5-difluoro-4-phenoxyphenyl)-2-methylallyl)isoindoline-1,3-dione (Intermediate 93.2, 100 mg, 0.25 mmol) in methanol (1 mL) was added hydrazine hydrate (25 mg, 0.5 mmol) and the reaction stirred at 50° C. overnight. The white solid was filtered with DCM, and the solvent removed from the filtrate. The residue was brought up in DCM and filtered. This was repeated until no further precipitate formed to give 49.5 mg of the title compound (71%) as a yellow oil, a 10 mg portion of which was diluted with 1N HCl and freeze dried to give 7.8 mg of the title compound as an HCl salt. $^1$H-NMR (400 MHz, $d_6$-DMSO): δ 8.25 (s, 2H), 7.37 (t, 2H), 7.20 (d, 2H), 7.12 (t, 1H), 6.97 (s, 1H), 3.57 (s, 2H), 1.96 (s, 3H). MS (m/z): 258.96 (M-NH$_2$).

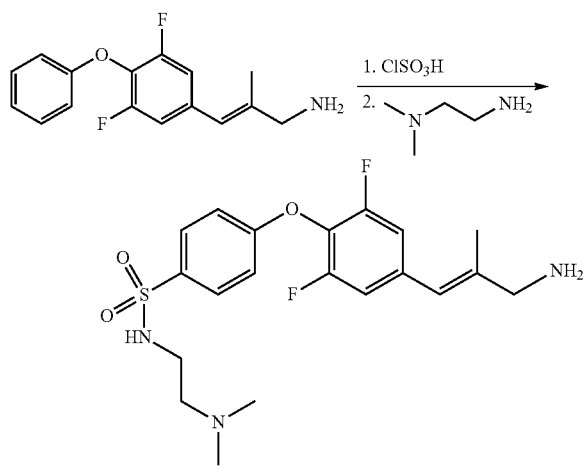

Intermediate 93.4: (E)-4-(4-(3-amino-2-methylprop-1-enyl)-2,6-difluorophenoxy)-N-(2-(dimethylamino)ethyl)benzenesulfonamide To a solution of (E)-3-(3,5-difluoro-4-phenoxyphenyl)-2-methylprop-2-en-1-amine (intermediate 93.3, 100 mg, 0.364 mmol) in DCM (0.364 mL, 1M) was added chlorosulfonic acid (2.91 mmol, 194.3 uL) in 4 portions dropwise every 20 minutes. The reaction was stirred an additional 20 minutes and then quenched into a solution of N1,N1-dimethylethane-1,2-diamine (3.78 mL) in DCM (12 mL) at 0° C. The resulting solution was warmed to room temperature and stirred for 30 minutes. Upon completion the solvent was removed and the residue brought up in 1:1 Acetonitrile:water solution and purified by preparative HPLC to give 74.5 mg of the title compound (31%) as a TFA salt.

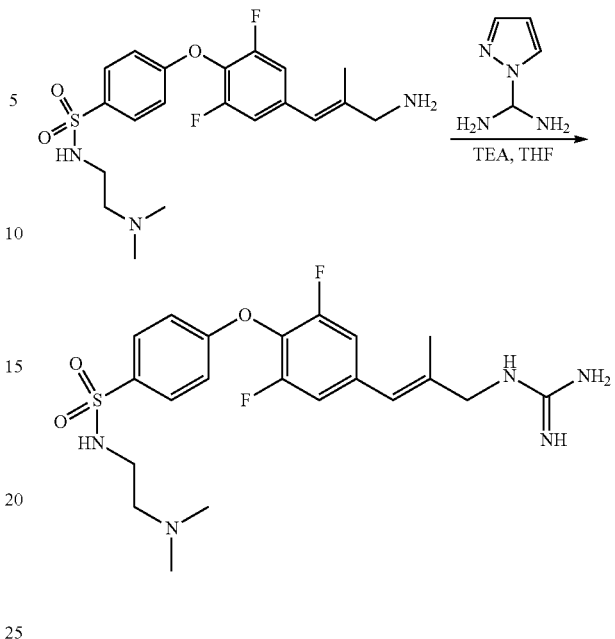

Compound 93: (E)-4-(2,6-difluoro-4-(3-guanidino-2-methylprop-1-enyl)phenoxy)-N-(2-(dimethylamino)ethyl)benzenesulfonamide To a solution of (E)-4-(4-(3-amino-2-methylprop-1-enyl)-2,6-difluorophenoxy)-N-(2-(dimethylamino)ethyl)benzenesulfonamide (Intermediate 93.4, 39.3 mg, 0.092 mmol) in dry THF (460 uL, 0.2M) under N$_2$ was added TEA (0.276 mmol, 27.9 mg) and (1H-pyrazol-1-yl)methanediamine hydrochloride (0.102 mmol, 14.9 mg). The resulting solution was stirred for 1 hour, at which point LCMS indicated complete conversion. The solvent was removed and the resulting residue brought up in 1:1 ACN:water and purified by preparative HPLC to give 16.9 mg of the title compound (26%) as a TFA salt. $^1$H-NMR (400 MHz, CD$_4$OD): δ 7.87 (d, 2H), 7.12 (d, 2H), 7.08 (d, 2H), 3.92 (s, 2H), 3.62 (m, 2H), 3.29 (m, 2H), 3.17 (t, 2H), 2.01 (s, 6H), 1.91 (s, 3H). MS (m/z): 468.12 (M+H)$^+$.

Example 94

N-(2-(2-(2-(2-(4,5-bis(hydroxymethyl)-1H-1,2,3-triazol-1-yl)ethoxy)ethoxy)ethoxy)ethyl)-3-(6,8-dichloro-2-methyl-1,2,3,4-tetrahydroisoquinolin-4-yl)benzenesulfonamide

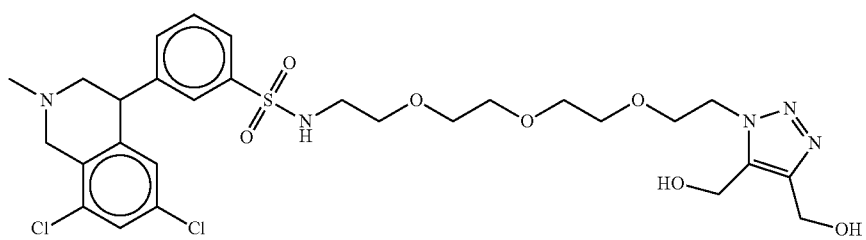

Example 95

N-(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)acetamide

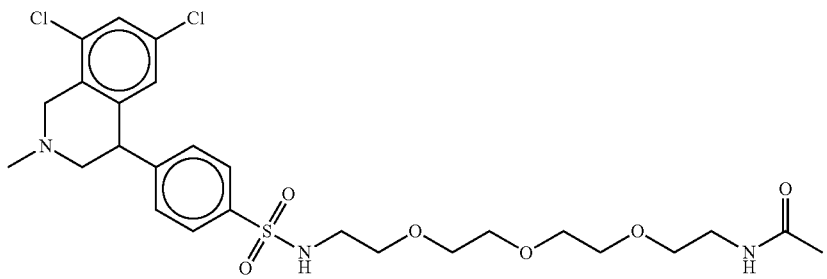

Example 96

N-(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)acetamide

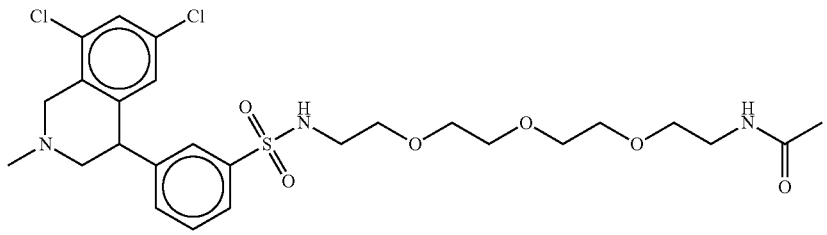

Example 97

N1,N31-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-4,7,10,13,16,19,22,25,28-nonaoxahentriacontane-1,31-diamide

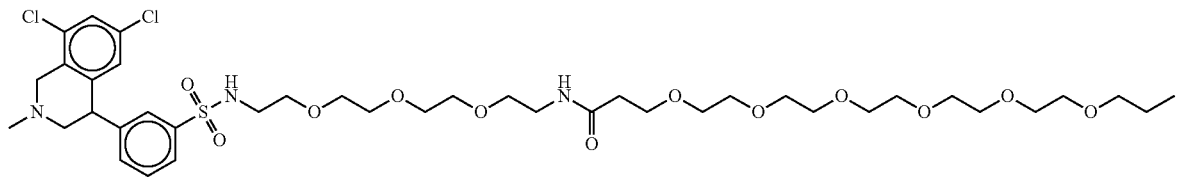

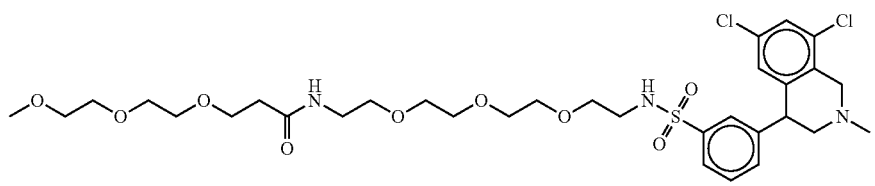

Example 98

N1,N31-bis(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)-4,7,10,13,16,19,22,25,28-nonaoxahentriacontane-1,31-diamide

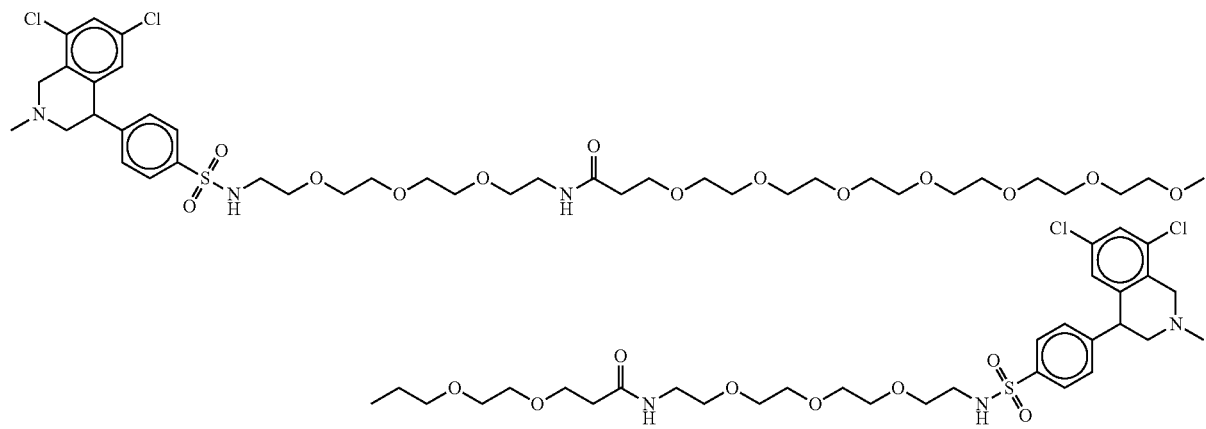

Example 99

(E)-3-(4-(4-(N-(1-amino-1-imino-5,8,11-trioxa-2-azatridecan-13-yl)sulfamoyl)phenoxy)-3,5-difluorophenyl)-N-(diaminomethylene)-2-methylacrylamide

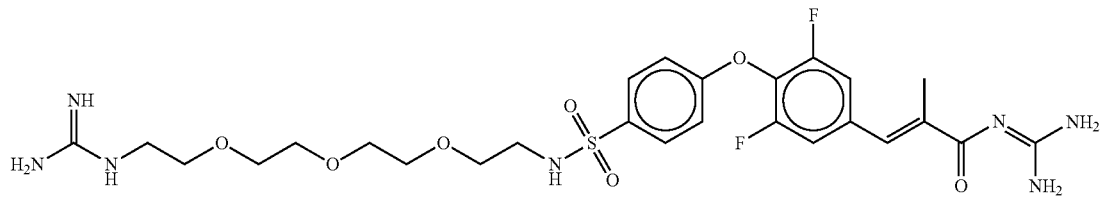

Example 100

N,N'-(13-oxo-3,6,9,17,20,23-hexaoxa-12,14-diazapentacosane-1,25-diyl)bis(3-(6,8-dichloro-2-methyl-1,2,3,4-tetrahydroisoquinolin-4-yl)benzenesulfonamide)

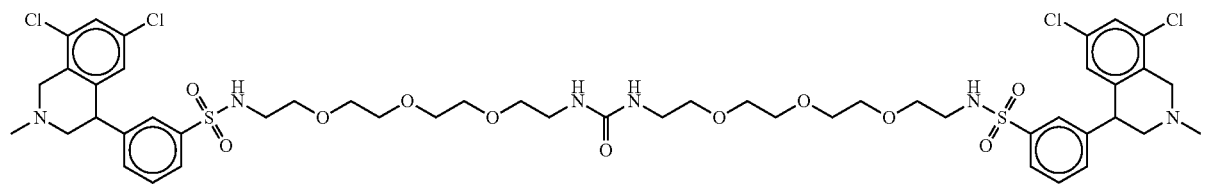

Example 101

(E)-N-(diaminomethylene)-3-(3,5-difluoro-4-(4-(N-(2-oxo-6,9,12-trioxa-3-azatetradecan-14-yl)sulfamoyl)phenoxy)phenyl)-2-methylacrylamide

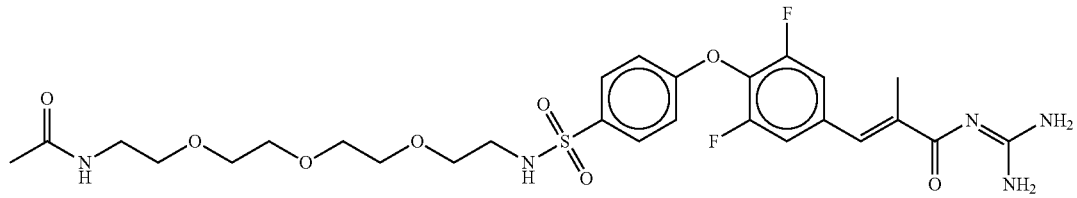

Example 102

N1,N31-bis(2-(2-(2-(2-(4-(4-((E)-3-(diaminomethyleneamino)-2-methyl-3-oxoprop-1-enyl)-2,6-difluorophenoxy)phenylsulfonamido)ethoxy)ethoxy)ethoxy)ethyl)-4,7,10,13,16,19,22,25,28-nonaoxahentriacontane-1,31-diamide

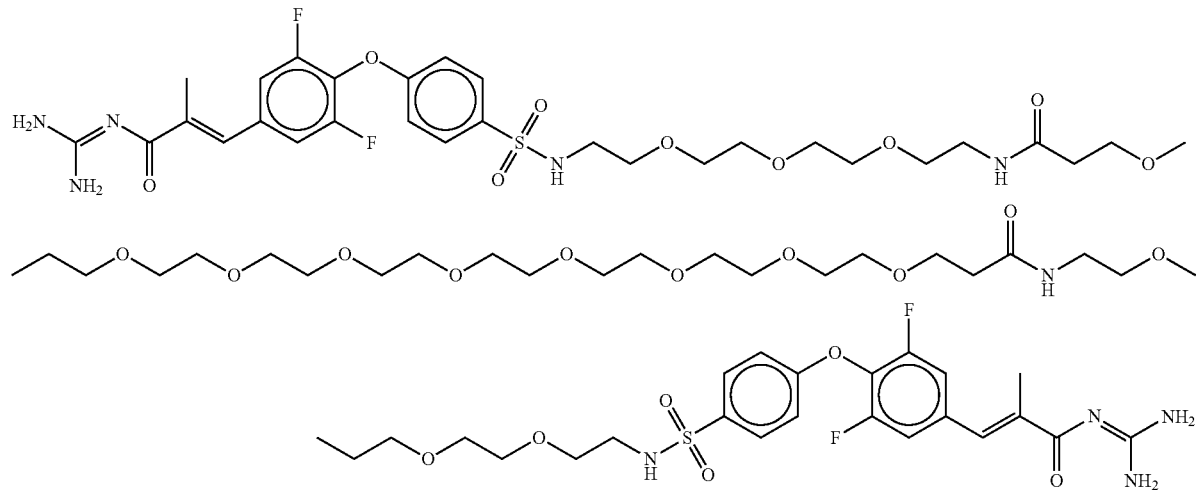

Example 103

N,N'-(13-oxo-3,6,9,17,20,23-hexaoxa-12,14-diazapentacosane-1,25-diyl)bis(4-(6,8-dichloro-2-methyl-1,2,3,4-tetrahydroisoquinolin-4-yl)benzenesulfonamide)

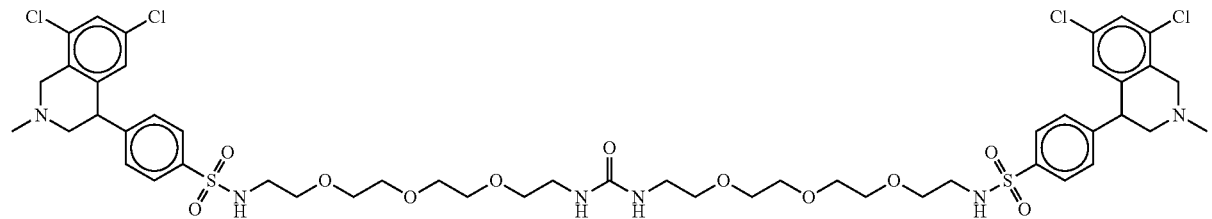

Example 104
N1,N4-bis(20-(4-(4-((E)-3-(diaminomethyleneamino)-2-methyl-3-oxoprop-1-enyl)-2,6-difluorophenoxy)phenylsulfonamido)-3,6,9,12,15,18-hexaoxaicosyl)-2,3-dihydroxysuccinamide
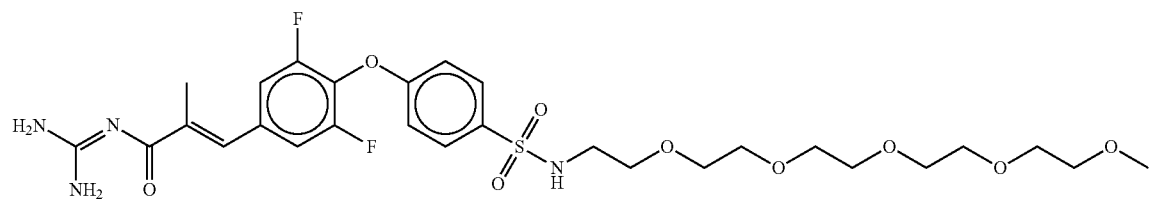
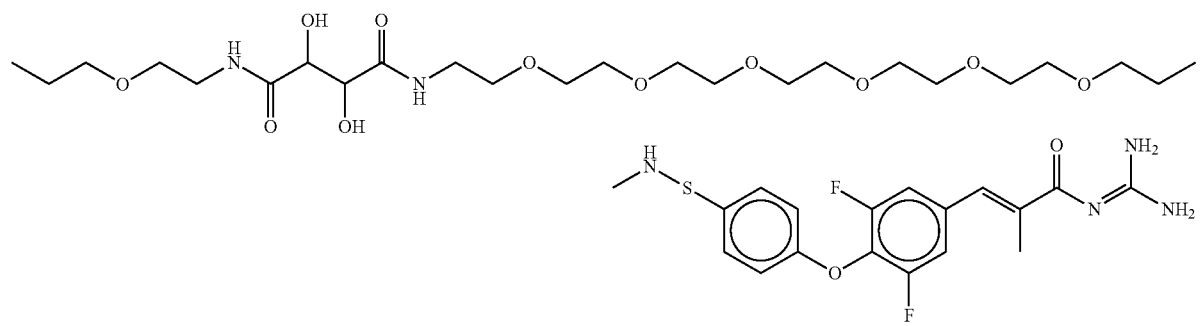
TABLE 3
Analytical Data for Example Compounds 71-104
| Example | [M + H]$^+$ |
|---|---|
| 71 | 533 |
| 72 | 523 |
| 73 | 468 |
| 74 | 482 |
| 75 | 525 |
| 76 | 527 |
| 77 | 589 |
| 78 | 493 |
| 79 | 439 |
| 80 | 628 |
| 81 | 1239.1 |
| 82 | 546.3 |
| 83 | 686 |
| 84 | 542 |
| 85 | 425 |
| 86 | 629 |
| 87 | 604 [M + 2]/2 |
| 88 | 604 [M + 2]/2 |
| 89 | 481 |
| 90 | 581 |
| 91 | 588 |
| 92 | 588 |
| 94 | 658 |
| 95 | 588 |
| 96 | 588 |
| 97 | 1571 |
| 98 | 1571 |
| 99 | 628 |
| 100 | 1117 |
| 101 | 628 |
| 102 | 1649 |
| 103 | 1117 |
| 104 | 1549 |

Example 105

4-/3-(6,8-dichloro-2-methyl-1,2,3,4-tetrahydroiso-quinolin-4-yl)-polyethylimino-sulfonamide

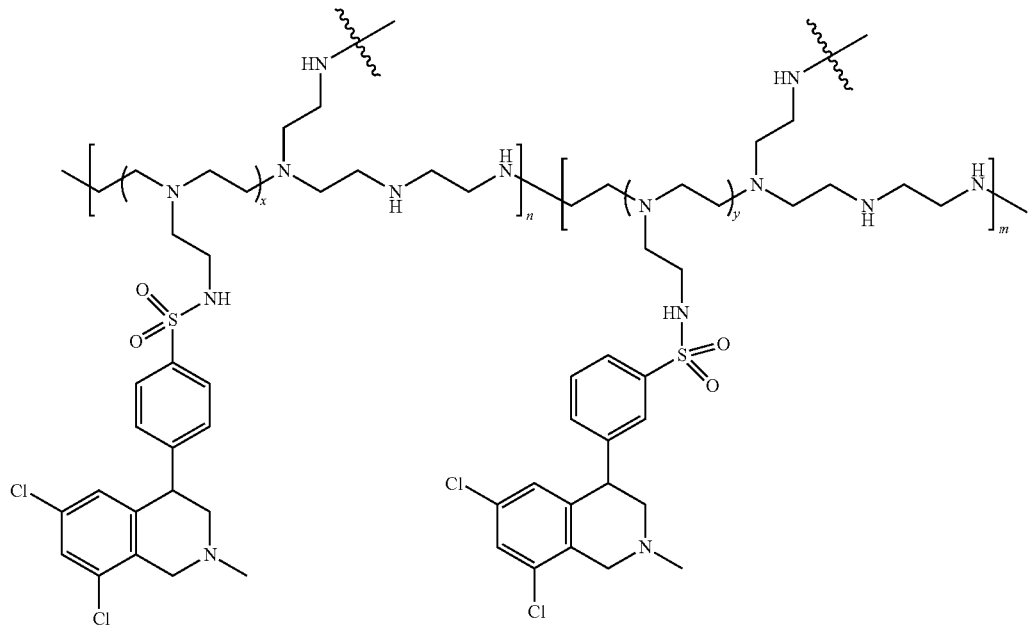

Example 105 is prepared from polyethylamine according to the procedures in described in Examples 1-70, where "x," "y," "n" and "m" are determined by the stoichiometry of the sulfonylchloride and polyethylamine.

Example 106

As illustrated below, other polymeric nucleophiles are employed using the procedures described in Examples 1-70 to prepare polyvalent compounds:

Other polymeric nucleophiles

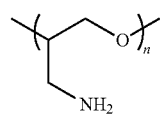
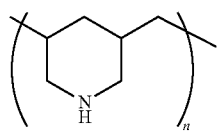

Example 107

As illustrated below, polymeric electrophiles are used with nucleophilic Intermediates to prepare polyvalent compounds using, for example, the procedures outlined in Example 68.

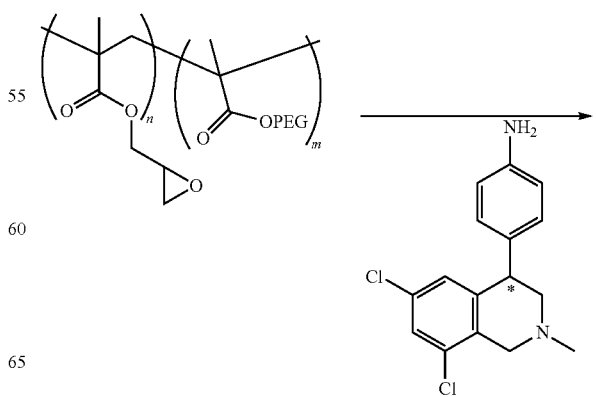

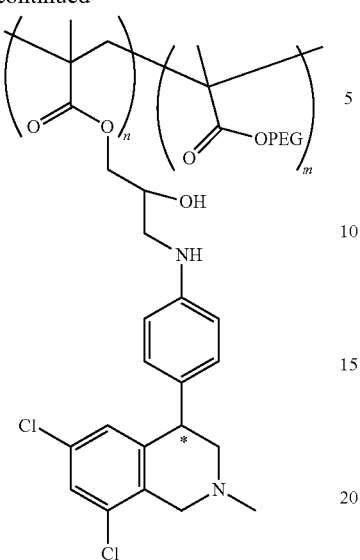
Example 108-147
General Procedure for Copolymerization of Intermediate 108.1 and Intermediate 108.2 with Other Monomers
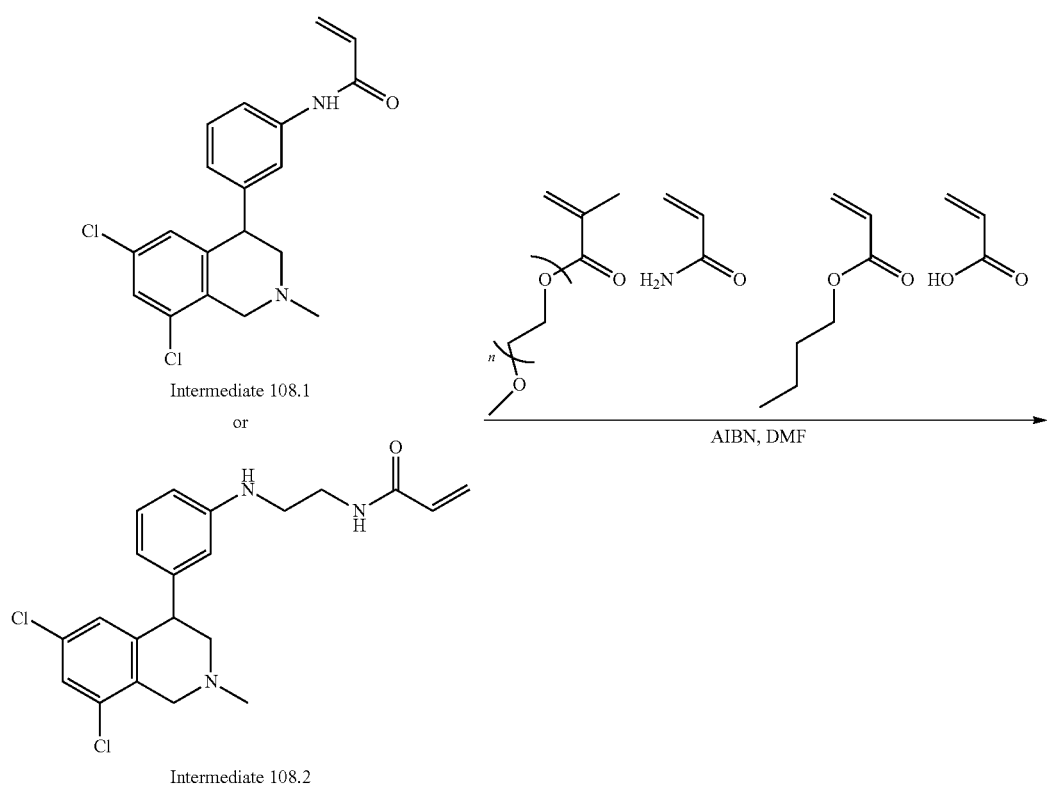

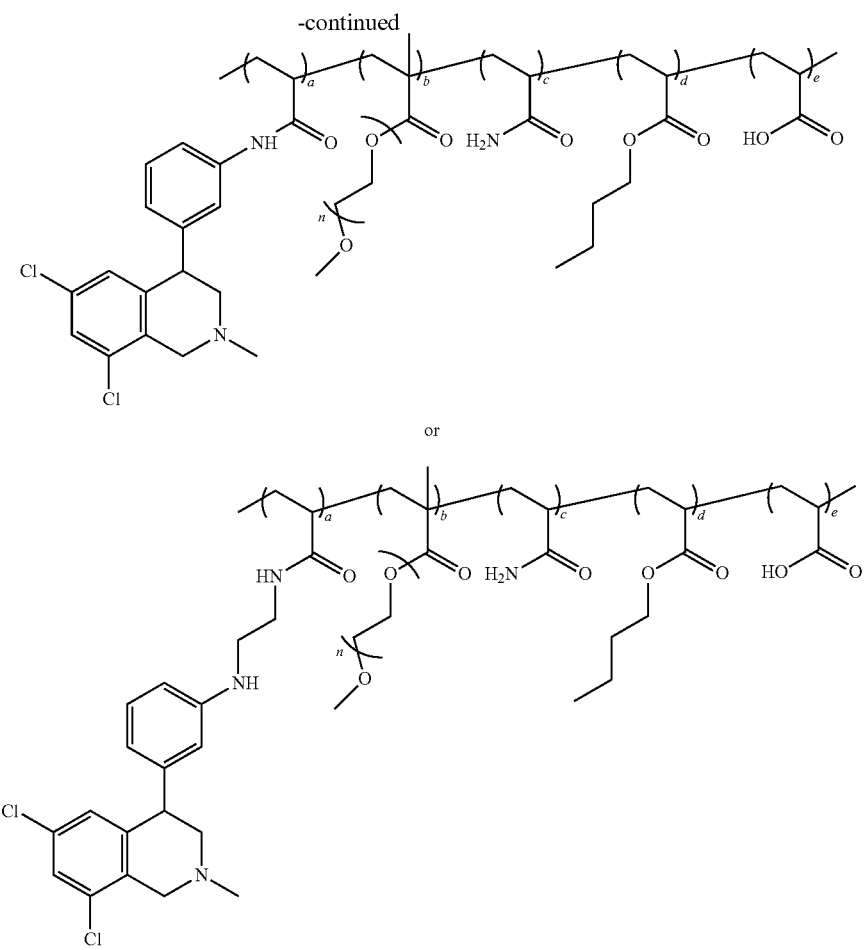

Intermediate 108.1: N-(3-(6,8-dichloro-2-methyl-1,2,3,4-tetrahydroisoquinolin-4-yl)phenyl)acrylamide Intermediate 108.1 (Int 108.1) was prepared from intermediate 30.7 and acrylic acid using procedures described in Examples 1-70. MS (m/z): 361.1 (M+H)

Intermediate 108.2: N-(2-(3-(6,8-dichloro-2-methyl-1,2,3,4-tetrahydroisoquinolin-4-yl)phenylamino)ethyl)acrylamide Intermediate 108.2 (Int 108.2) was prepared from intermediate 30.7 using procedures described in Examples 1-70. MS (m/z): 404.1 (M+H)

A 20-mL vial is charged with a total of 1 g of Intermediate 108.1 or Intermediate 108.2 and other monomers, a total of 9 g of isopropanol/dimethylformamide solvent mixture, and 20 mg of azobisisobutyronitrile. The mixture is degassed for 1 min and is sealed under a nitrogen atmosphere. The stoichiometry for each example is shown in Table 1. The reaction mixture is heated in an oil bath to 70° C. under stirring. After 8 h at 70° C. the reaction mixture is cooled down to ambient temperature and then 10 mL of water is added. The solution is then transferred to a dialysis bag (MWCO 1000) for dialysis against DI water for 2 days. The resulting solution is freeze-dried to afford copolymers.

TABLE 4

Examples of conditions that can be used to create copolymers from acrylamide-functionalized NHE inhibitors and substituted acrylamides and methacrylates

| | Monomer (mg) | | | | | |
|---|---|---|---|---|---|---|
| Example | Int 108.1 Or Int 108.2 | acryl amide | Poly(ethylene glycol) methyl ether methacrylate | butyl acrylate | acrylic acid | Solvent (g) IPA/DMF |
| 108 | 10 | 990 | 0 | 0 | 0 | 0/9 |
| 109 | 50 | 950 | 0 | 0 | 0 | 0/9 |
| 110 | 100 | 900 | 0 | 0 | 0 | 0/9 |
| 111 | 250 | 750 | 0 | 0 | 0 | 0/9 |
| 112 | 500 | 500 | 0 | 0 | 0 | 0/9 |
| 113 | 10 | 990 | 0 | 0 | 0 | 2.25/6.75 |
| 114 | 50 | 950 | 0 | 0 | 0 | 2.25/6.75 |
| 115 | 100 | 900 | 0 | 0 | 0 | 2.25/6.75 |
| 116 | 250 | 750 | 0 | 0 | 0 | 2.25/6.75 |
| 117 | 500 | 500 | 0 | 0 | 0 | 2.25/6.75 |
| 118 | 10 | 990 | 0 | 0 | 0 | 4.5/4.5 |
| 119 | 50 | 950 | 0 | 0 | 0 | 4.5/4.5 |
| 120 | 100 | 900 | 0 | 0 | 0 | 4.5/4.5 |
| 121 | 250 | 750 | 0 | 0 | 0 | 4.5/4.5 |
| 122 | 500 | 500 | 0 | 0 | 0 | 4.5/4.5 |
| 123 | 10 | 990 | 0 | 0 | 0 | 6.75/2.25 |
| 124 | 50 | 950 | 0 | 0 | 0 | 6.75/2.25 |
| 125 | 100 | 900 | 0 | 0 | 0 | 6.75/2.25 |
| 126 | 250 | 750 | 0 | 0 | 0 | 6.75/2.25 |
| 127 | 500 | 500 | 0 | 0 | 0 | 6.75/2.25 |

TABLE 4-continued

Examples of conditions that can be used to create copolymers from acrylamide-functionalized NHE inhibitors and substituted acrylamides and methacrylates

| Example | Int 108.1 Or Int 108.2 | acryl amide | Poly(ethylene glycol) methyl ether methacrylate | butyl acrylate | acrylic acid | Solvent (g) IPA/DMF |
|---|---|---|---|---|---|---|
| | Monomer (mg) | | | | | |
| 128 | 10 | 990 | 0 | 0 | 0 | 9/0 |
| 129 | 50 | 950 | 0 | 0 | 0 | 9/0 |
| 130 | 100 | 900 | 0 | 0 | 0 | 9/0 |
| 131 | 250 | 750 | 0 | 0 | 0 | 9/0 |
| 132 | 500 | 500 | 0 | 0 | 0 | 9/0 |
| 133 | 10 | 0 | 990 | 0 | 0 | 6.75/2.25 |
| 134 | 50 | 0 | 950 | 0 | 0 | 6.75/2.25 |
| 135 | 100 | 0 | 900 | 0 | 0 | 6.75/2.25 |
| 136 | 250 | 0 | 750 | 0 | 0 | 6.75/2.25 |
| 137 | 500 | 0 | 500 | 0 | 0 | 6.75/2.25 |
| 138 | 100 | 775 | 0 | 25 | 0 | 6.75/2.25 |
| 139 | 100 | 750 | 0 | 50 | 0 | 6.75/2.25 |
| 140 | 100 | 700 | 0 | 100 | 0 | 6.75/2.25 |
| 141 | 100 | 650 | 0 | 150 | 0 | 6.75/2.25 |
| 142 | 100 | 600 | 0 | 200 | 0 | 6.75/2.25 |
| 143 | 100 | 800 | 0 | 0 | 10 | 6.75/2.25 |
| 144 | 100 | 800 | 0 | 0 | 25 | 6.75/2.25 |
| 145 | 100 | 800 | 0 | 0 | 50 | 6.75/2.25 |
| 146 | 100 | 800 | 0 | 0 | 100 | 6.75/2.25 |
| 147 | 100 | 800 | 0 | 0 | 150 | 6.75/2.25 |

Example 148

Synthesis of 2-Methyl-acrylic acid 3-trimethylsilanyl-prop-2-ynyl ester

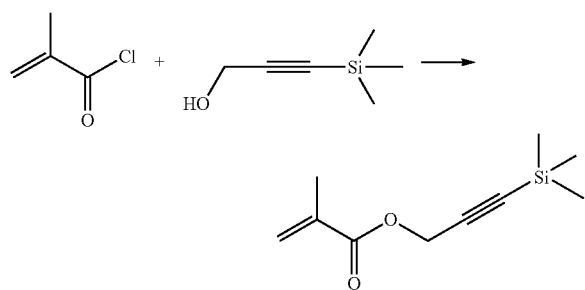

A solution of trimethylsilyl propyn-1-ol (1 g, 7.8 mmol) and Et$_3$N (1.4 mL, 10 mmol) in Et$_2$O (10 mL) is cooled to −20° C. and a solution of methacryloyl chloride (0.9 mL, 9.3 mmol) in Et$_2$O (5 mL) is added dropwise over 1 h. The mixture is stirred at this temperature for 30 min, and then allowed to warm to ambient temperature overnight. Any precipitated ammonium salts can be removed by filtration, and volatile components can be removed under reduced pressure. The crude product is then purified by flash chromatography.

Examples 149-154

General Procedure for synthesis of poly N-(2-hydroxypropyl)methacrylamide-co-prop-2-ynyl methacrylate

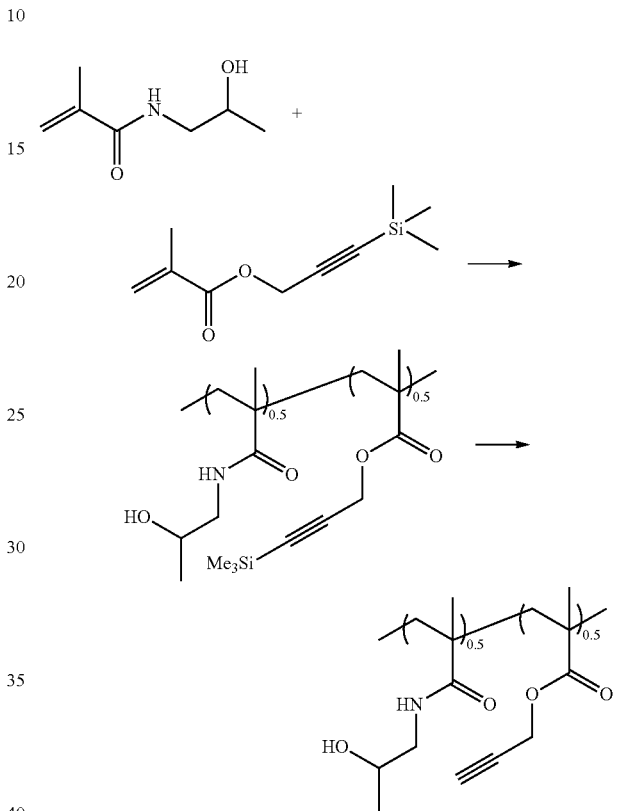

General Procedure for copolymerization of N-(2-hydroxypropyl)methacrylamide and 3-(trimethylsilyl)prop-2-ynyl methacrylate A 100-mL round bottom flask equipped with a reflux condenser is charged with a total 5 g of N-(2-hydroxypropyl) methacrylamide and 3-(trimethylsilyl)prop-2-ynyl methacrylate, 45 g of isopropanol/dimethylformamide solvent mixture, and 100 mg of azobisisobutyronitrile. The mixture is degassed for 1 min and maintained under nitrogen atmosphere during the reaction. Stoichiometry for each example is shown in Table 5. The reaction mixture is heated in an oil bath to 70° C. under stirring, and after 8 h the reaction mixture is cooled to ambient temperature and then 30 mL of solvent is evaporated under vacuum. The resulting solution is then precipitated into 250 mL of Et$_2$O. The precipitate is collected, redissolved in 10 mL of DMF, and precipitated again into 250 mL of Et$_2$O. The resulting precipitate is dried under vacuum to afford copolymers.

General Procedure for Removal of Trimethyl Silyl Group

The trimethyl silyl protected polymer (4 g), acetic acid (1.5 equiv. mol/mol with respect to the alkyne-trimethylsilyl groups), and 200 mL of THF is mixed in a 500 mL flask. The mixture is cooled to −20° C. under nitrogen atmosphere and followed by addition of 0.20 M solution of tetra-n-butylammonium fluoride trihydrate (TBAF.3H$_2$O) in THF (1.5 equiv. mol/mol with respect to the alkyne-trimethylsilyl groups) over a course of 5 min. The solution is stirred at this temperature for 30 min and then warmed to ambient temperature for an additional 8 hours. The resulting mixture is passed through a short silica pad and then precipitated in Et$_2$O. The resulting precipitate is dried under vacuum to afford copolymers.

TABLE 5

Examples of copolymerization conditions that can be used to prepared polymethacrylates

| | Monomer (g) | | |
|---|---|---|---|
| Example | N-(2-hydroxypropyl) methacrylamide | 3-(trimethylsilyl) prop-2-ynyl methacrylate | Solvent (g) IPA/DMF |
| 149 | 2.5 | 2.5 | 0/45 |
| 150 | 2.5 | 2.5 | 11.25/33.75 |
| 151 | 2.5 | 2.5 | 22.5/22.5 |
| 152 | 2.5 | 2.5 | 33.75/11.25 |
| 153 | 2.5 | 2.5 | 45/0 |

Examples 154-167

General procedure for post-modification of Examples 149-153 by [2+3] cycloaddition Polymer 154 (54 mg) containing 0.1 mmol of alkyne moiety, a total of 0.1 mmol of azido-compounds (Intermediate 28.1, 13-azido-2,5,8,11-tetraoxatridecane, N-(2-azidoethyl)-3-(dimethylamino)propanamide and 1-azidodecane, corresponding ratios shown in Table 6), 0.05 mmol of diisopropylethylamine, and 1 mL of DMF is mixed at ambient temperature and degassed for 1 min. While maintaining a nitrogen atmosphere, copper iodide (10 mg, 0.01 mmol) is then added to the mixture. The solution is stirred at ambient temperature for 3 days and then passed through a short neutral alumina pad. The resulting solution is diluted with 10 mL of DI water, dialyzed against DI water for 2 days, and lyophilized to afford copolymers.

TABLE 6

Examples of compounds that can be prepared from polymeric alkynes and varying ratios of substituted azides via [3 + 2] cycloaddition

| | Azido compounds (mmol) | | | |
|---|---|---|---|---|
| Example | Intermediate 28.1 | 13-azido-2,5,8,11-tetraoxatridecane | N-(2-azidoethyl)-3-(dimethylamino) propanamide | 1-azidodecane |
| 155 | 0.002 | 0.098 | 0 | 0 |
| 156 | 0.005 | 0.095 | 0 | 0 |
| 157 | 0.01 | 0.09 | 0 | 0 |
| 158 | 0.025 | 0.075 | 0 | 0 |

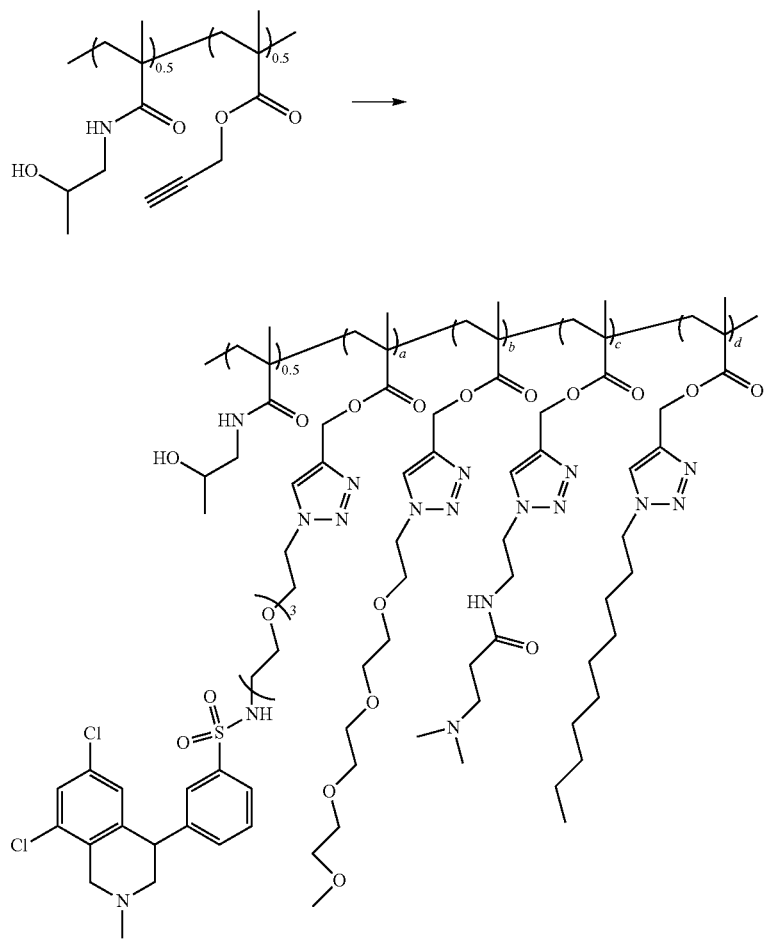

TABLE 6-continued

Examples of compounds that can be prepared from polymeric alkynes and varying ratios of substituted azides via [3 + 2] cycloaddition

| Example | Intermediate 28.1 | 13-azido-2,5,8,11-tetraoxatridecane | N-(2-azidoethyl)-3-(dimethylamino)propanamide | 1-azidodecane |
|---|---|---|---|---|
| 159 | 0.05 | 0.05 | 0 | 0 |
| 160 | 0.01 | 0.088 | 0.002 | 0 |
| 161 | 0.01 | 0.085 | 0.005 | 0 |
| 162 | 0.01 | 0.08 | 0.01 | 0 |
| 163 | 0.01 | 0.07 | 0.02 | 0 |
| 164 | 0.01 | 0.088 | 0 | 0.002 |
| 165 | 0.01 | 0.085 | 0 | 0.005 |
| 166 | 0.01 | 0.08 | 0 | 0.01 |
| 167 | 0.01 | 0.07 | 0 | 0.02 |

Example 168

N1,N4-bis(2-(2-(2-(3-(6,8-dichloro-2-methyl-1,2,3,4-tetrahydroisoquinolin-4-yl)phenylsulfonamido)ethoxy)ethoxy)ethyl)-2,3-dihydroxysuccinamide

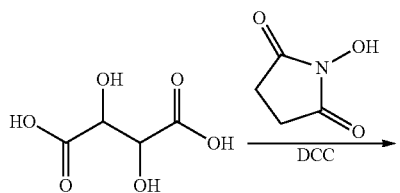

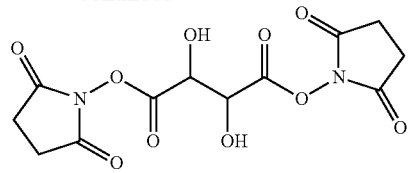

Intermediate 168.1, bis(2,5-dioxopyrrolidin-1-yl) 2,3-dihydroxysuccinate

To a 500 ml 3-necked roundbottom flask was added 2,3-dihydroxysuccinic acid (10.0 g, 66.62 mmol, 1.00 equiv), N,N'-Dicyclohexyl carbodiimide (DCC; 30.0 g, 145.42 mmol, 2.18 equiv) and tetrahydrofuran (THF; 100 mL). This was followed by the addition of a solution of N-hydroxysuccinimide (NHS; 16.5 g, 143.35 mmol, 2.15 equiv) in THF (100 mL) at 0-10° C. The resulting solution was warmed to room temperature and stirred for 16 h. The solids were filtered out and the filtrate was concentrated under vacuum. The crude product was re-crystallized from N,N-dimethylformamide (DMF)/ethanol in the ratio of 1:10. This resulted in 5.2 g (22%) of the title compound as a white solid. $^1$H-NMR (300 MHz, DMSO, ppm) δ 6.70 (d, J=7.8 Hz, 2H), 4.89 (d, J=7.2 Hz, 2H), 2.89 (s, 8H). MS (m/z): 367 [M+Na]$^+$.

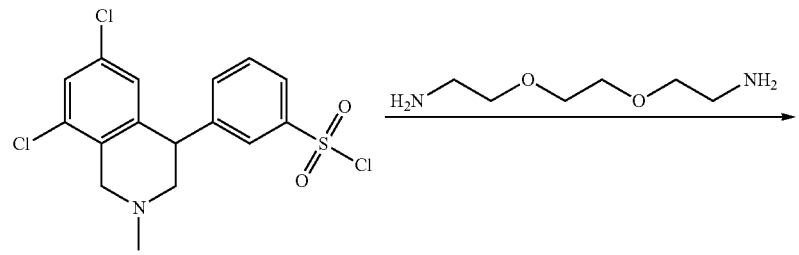

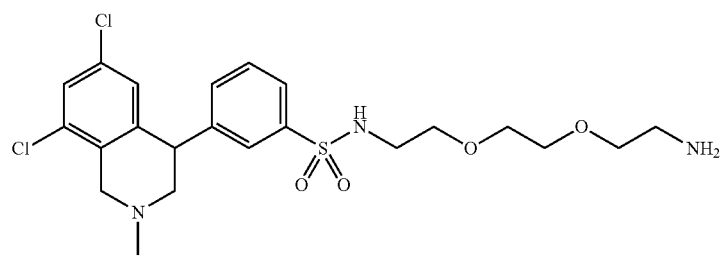

Intermediate 168.2 N-(2-(2-(2-aminoethoxy)ethoxy)ethyl)-3-(6,8-dichloro-2-methyl-1,2,3,4-tetrahydroisoquinolin-4-yl)benzenesulfonamide To a 50-mL 3-necked round-bottom flask was added 2-(2-(2-aminoethoxy)ethoxy)ethanamine (3.2 g, 21.59 mmol, 21.09 equiv) and dichloromethane (DCM; 20 mL). This was followed by the addition of a solution of 3-(6,8-dichloro-2-methyl-1,2,3,4-tetrahydroisoquinolin-4-yl)benzene-1-sulfonyl chloride (Intermediate 1.6) (400 mg, 1.02 mmol, 1.00 equiv) in DMF (5 mL) dropwise with stirring. The resulting solution was stirred for 5 h at which time it was diluted with 100 mL of ethyl acetate. The resulting mixture was washed successively with 2×10 mL of water and 1×10 mL of Brine. The organic layer was dried over anhydrous sodium sulfate and concentrated under vacuum. This resulted in 300 mg (58%) of N-(2-(2-(2-aminoethoxy)ethoxy)ethyl)-3-(6,8-dichloro-2-methyl-1,2,3,4-tetrahydroisoquinolin-4-yl)benzenesulfonamide as a yellow oil.

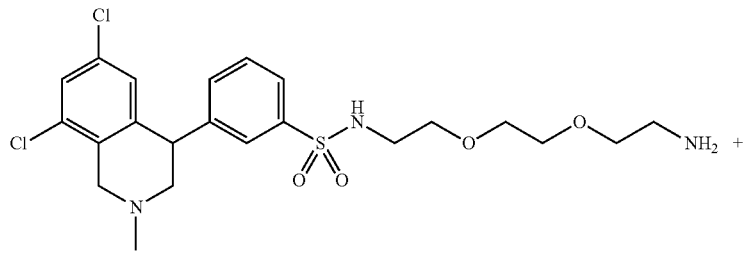

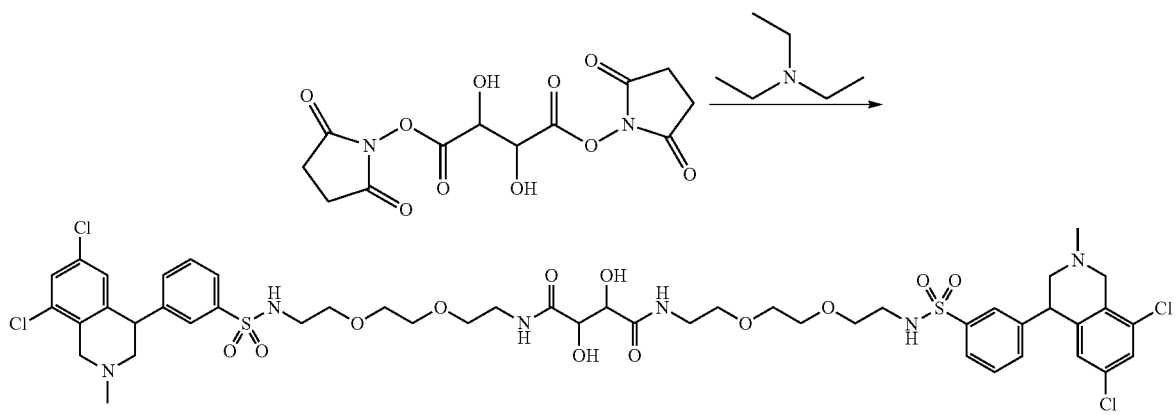

Compound 168, N1,N4-bis(2-(2-(2-(3-(6,8-dichloro-2-methyl-1,2,3,4-tetrahydroisoquinolin-4-yl)phenylsulfonamido)ethoxy)ethoxy)ethyl)-2,3-dihydroxysuccinamide Into a 50-mL round-bottom flask was placed a solution of N-(2-(2-(2-aminoethoxy)ethoxy)ethyl)-3-(6,8-dichloro-2-methyl-1,2,3,4-tetrahydroisoquinolin-4-yl)benzenesulfonamide (300 mg, 0.60 mmol, 1.00 equiv) in DMF (5 mL), bis(2,5-dioxopyrrolidin-1-yl) 2,3-dihydroxysuccinate (92.5 mg, 0.27 mmol, 0.45 equiv) and triethylamine (TEA; 1.0 g, 9.88 mmol, 16.55 equiv). The resulting solution was stirred overnight at room temperature and then concentrated under vacuum. The crude product (300 mg) was purified by Prep-HPLC with the following conditions: Column, SunFire Prep C18, 5 um, 19*150 mm; mobile phase, Water with 0.05% TFA and CH$_3$CN (20% CH$_3$CN up to 40% in 5 min, up to 100% in 2 min); Detector, uv 220&254 nm. This resulted in 192.4 mg (28%) of a TFA salt of the title compound as a white solid. $^1$H-NMR (300 MHz, DMSO, ppm) δ 7.92 (d, J=7.8 Hz, 2H), 7.82 (m, 2H), 7.67 (t, J=7.8 Hz, 2H), 7.57 (m, 2H), 7.55 (d, J=6.9 Hz, 2H), 6.86 (m, 2H), 4.84 (s, 2H), 4.79 (s, 2H), 4.54 (d, 2H), 4.48 (s, 2H), 3.92 (m, 2H), 3.53 (m, 22H), 3.18 (s, 6H), 3.07 (t, J=5.4 Hz, 4H). MS (m/z): 1119 [M+H]$^+$.

Example 169

N1,N4-bis(2-(3-(6,8-dichloro-2-methyl-1,2,3,4-tetrahydroisoquinolin-4-yl)phenylsulfonamido)ethyl)-2,3-dihydroxysuccinamide

Intermediate 169.1, N-(2-aminoethyl)-3-(6,8-dichloro-2-methyl-1,2,3,4-tetrahydroisoquinolin-4-yl)benzenesulfonamide Into a 50-mL 3-necked round-bottom flask purged and maintained with an inert atmosphere of nitrogen, was placed a solution of 3-(6,8-dichloro-2-methyl-1,2,3,4-tetrahydroisoquinolin-4-yl)benzene-1-sulfonyl chloride (intermediate 1.6) (100 mg, 0.26 mmol, 1.00 equiv) in DCM (5 mL). This was followed by the addition of a solution of ethane-1,2-diamine (307 mg, 5.11 mmol, 19.96 equiv) in DCM/DMF (10/1 mL). The resulting solution was stirred for 5 h at room temperature. The mixture was concentrated under vacuum. The resulting solution was diluted with 50 mL of ethyl acetate and washed with 2×10 mL of water and then 1×10 mL of Brine. The organic layer was dried over anhydrous sodium sulfate and concentrated under vacuum to afford 90 mg (76%) of N-(2-aminoethyl)-3-(6,8-dichloro-2-methyl-1,2,3,4-tetrahydroisoquinolin-4-yl)benzenesulfonamide as yellow oil.

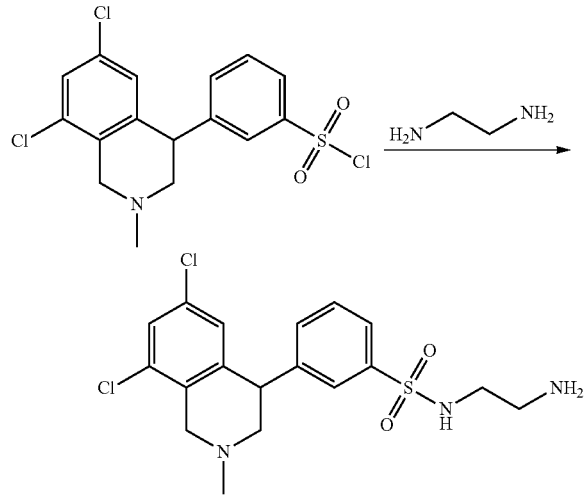

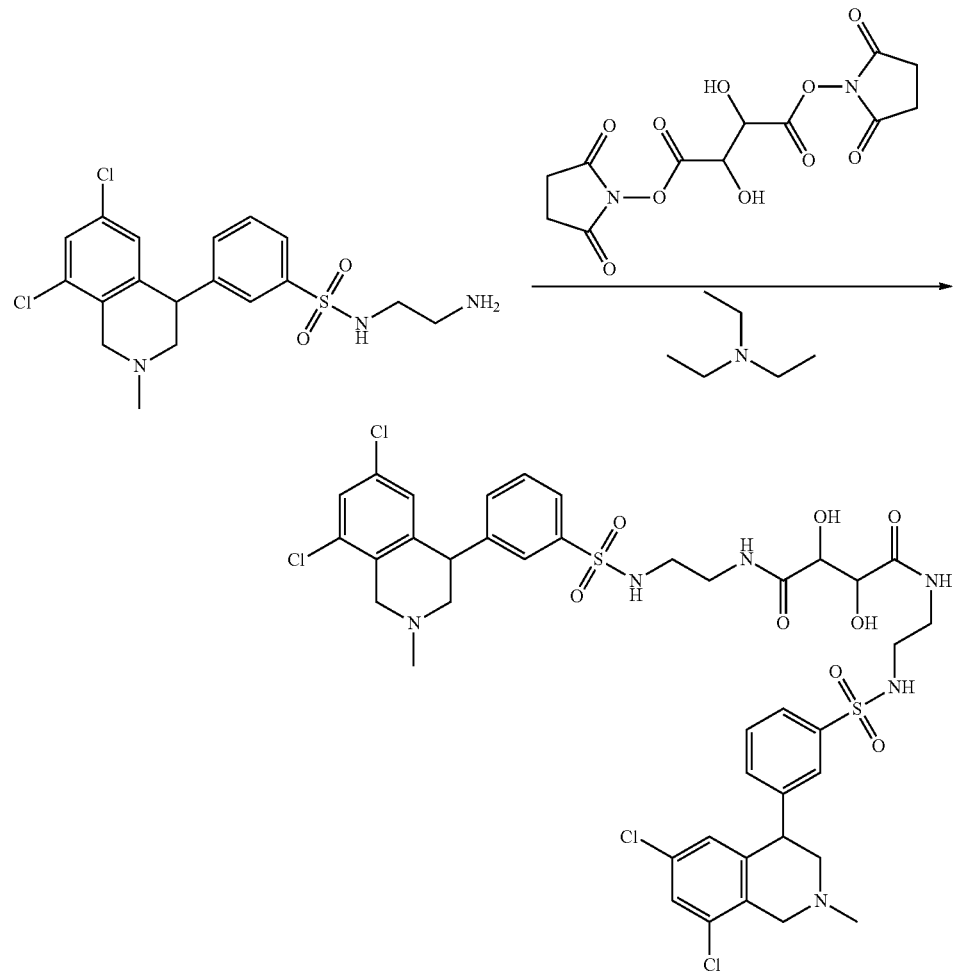

Compound 169, N1,N4-bis(2-(3-(6,8-dichloro-2-methyl-1,2,3,4-tetrahydroisoquinolin-4-yl)phenylsulfonamido)ethyl)-2,3-dihydroxysuccinamide Into a 50-mL round-bottom flask purged and maintained with an inert atmosphere of nitrogen, was placed a solution of N-(2-aminoethyl)-3-(6,8-dichloro-2-methyl-1,2,3,4-tetrahydroisoquinolin-4-yl)benzenesulfonamide (250 mg, 0.60 mmol, 1.00 equiv) in DMF (5 mL), bis(2,5-dioxopyrrolidin-1-yl) 2,3-dihydroxysuccinate (Intermediate 168.1) (92 mg, 0.27 mmol, 0.44 equiv) and triethylamine (280 mg, 2.77 mmol, 4.55 equiv) and the resulting solution was stirred overnight at room temperature. The resulting mixture was concentrated under vacuum, the residue diluted with 100 mL of ethyl acetate and then washed with 2×10 mL of water. The organic layer was dried over anhydrous sodium sulfate and concentrated under vacuum. The crude product was purified by Prep-HPLC with the following conditions: Column, SunFire Prep C18, 5 um, 19*150 mm; mobile phase, Water with 0.05% TFA and $CH_3CN$ (25% $CH_3CN$ up to 35% in 5 min, up to 100% in 2.5 min); Detector, uv 220&254 nm. This resulted in 88.4 mg (15%) of a TFA salt of N1,N4-bis(2-(3-(6,8-dichloro-2-methyl-1,2,3,4-tetrahydroisoquinolin-4-yl)phenylsulfonamido)ethyl)-2,3-dihydroxysuccinamide as a white solid. $^1$H-NMR (400 MHz, $CD_3OD$, ppm) δ 7.67 (d, J=7.6 Hz, 2H), 7.61 (s, 2H), 7.44 (t, J=7.6 Hz, 2H), 7.37 (d, J=7.6 Hz, 2H), 7.25 (d, J=2 Hz, 2H), 6.72 (s, 2H), 4.33 (t, J=6.4 Hz, 2H), 4.30 (s, 2H), 3.64 (m, 4H), 3.21 (s, 4H), 2.98 (m, 2H), 2.90 (m, 4H), 2.65 (m, 2H), 2.42 (s, 6H). MS (m/z): 943 [M+H]$^+$.

Example 170

N1,N4-bis(2-(2-(2-(2-(3-(6,8-dichloro-2-ethyl-1,2,3,4-tetrahydroisoquinolin-4-yl)phenylsulfonamido)ethoxy)ethoxy)ethoxy)ethyl)-2,3-dihydroxysuccinamide

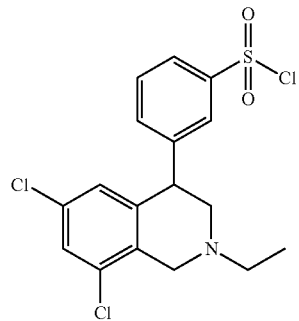 [SMILES: CCN1Cc2c(Cl)cc(Cl)cc2C(c2cccc(S(=O)(=O)Cl)c2)C1]

Intermediate 170.1, 3-(6,8-dichloro-2-ethyl-1,2,3,4-tetrahydroisoquinolin-4-yl)benzene-1-sulfonyl chloride Using procedures outlined in Example 1 to prepare intermediate 1.6, substituting N-(2,4-dichlorobenzyl)ethanamine for 1-(2,4-dichlorophenyl)-N-methylmethanamine, the title compound was prepared as a hydrochloride salt.

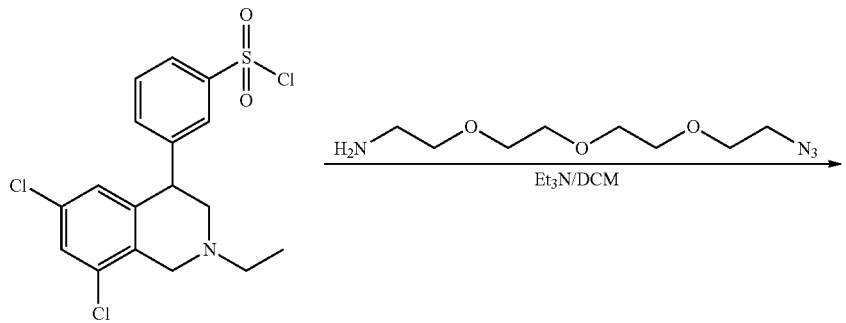

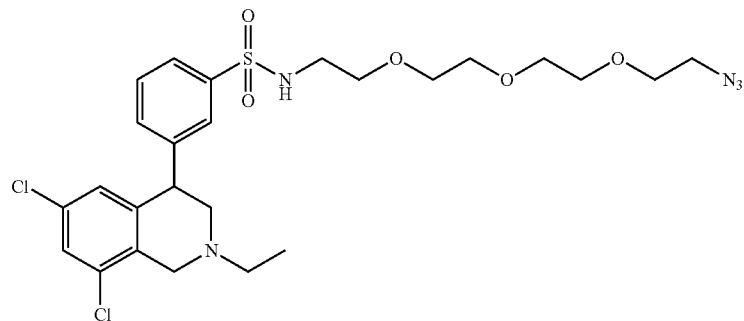

Intermediate 170.2 N-(2-(2-(2-(2-azidoethoxy)ethoxy)ethoxy)ethyl)-3-(6,8-dichloro-2-ethyl-1,2,3,4-tetrahydroisoquinolin-4-yl)benzenesulfonamide To 2-(2-(2-(2-azidoethoxy)ethoxy)ethoxy)ethanamine (300 mg, 1.51 mmol, 1.00 equiv) in DCM (10 mL) was added TEA (375 mg, 3.00 equiv) followed by the portionwise addition of 3-(6,8-dichloro-2-ethyl-1,2,3,4-tetrahydroisoquinolin-4-yl)benzene-1-sulfonyl chloride (500 mg, 1.23 mmol, 1.00 equiv). The resulting solution was stirred for 1 h at room temperature and then concentrated under vacuum. The residue was applied onto a silica gel column and eluted with ethyl acetate/petroleum ether (1:2) to afford 0.4 g (41%) of N-(2-(2-(2-(2-azidoethoxy)ethoxy)ethoxy)ethyl)-3-(6,8-dichloro-2-ethyl-1,2,3,4-tetrahydroisoquinolin-4-yl)benzenesulfonamide as yellow oil.

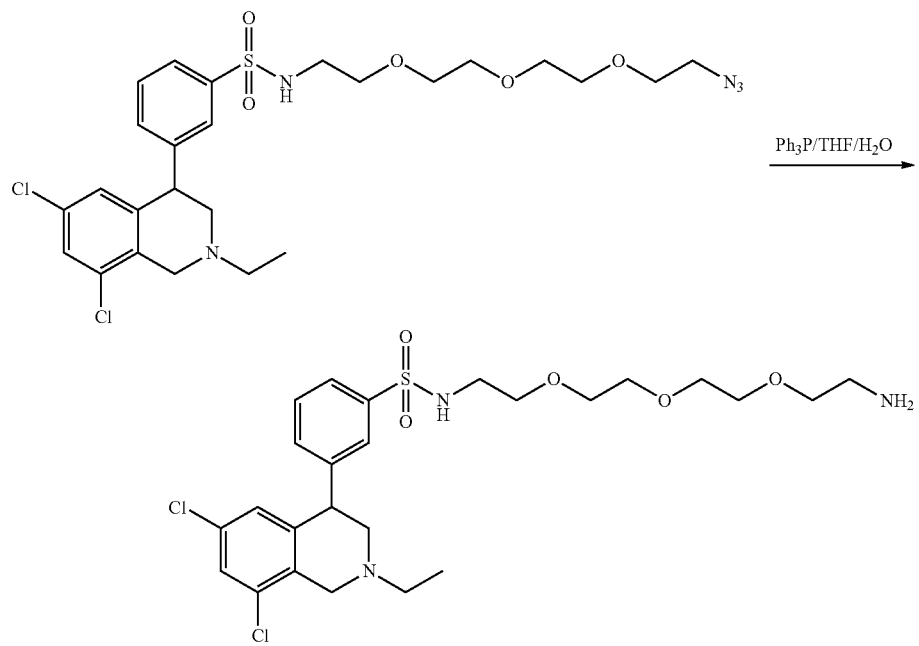

Intermediate 170.3, N-(2-(2-(2-(2-aminoethoxy)ethoxy)ethoxy)ethyl)-3-(6,8-dichloro-2-ethyl-1,2,3,4-tetrahydroisoquinolin-4-yl)benzenesulfonamide Into a 100-mL round-bottom flask, was placed N-(2-(2-(2-(2-azidoethoxy)ethoxy)ethoxy)ethyl)-3-(6,8-dichloro-2-ethyl-1,2,3,4-tetrahydroisoquinolin-4-yl)benzenesulfonamide (400 mg, 0.68 mmol, 1.00 equiv), triphenylphosphine (400 mg, 2.20 equiv), THF (10 mL) and water (1 mL) and the reaction was stirred overnight at room temperature. The resulting mixture was concentrated under vacuum and applied onto a preparative thin-layer chromatography (TLC) plate, eluting with DCM:methanol (5:1). This resulted in 350 mg (73%) of N-(2-(2-(2-(2-aminoethoxy)ethoxy)ethoxy)ethyl)-3-(6,8-dichloro-2-ethyl-1,2,3,4-tetrahydroisoquinolin-4-yl)benzenesulfonamide as yellow oil.

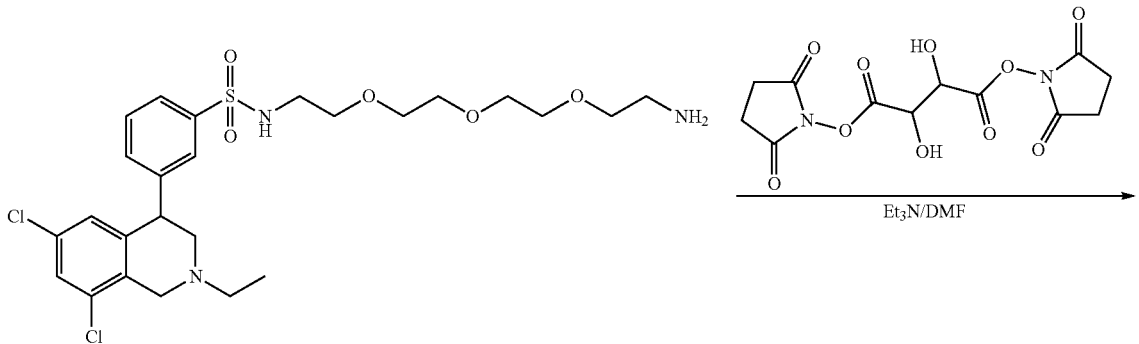

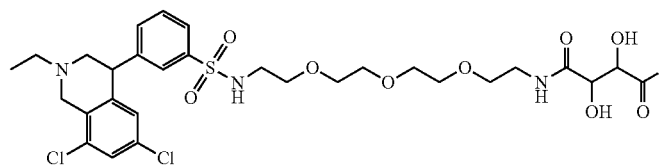
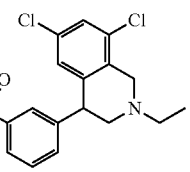

Compound 170, N1,N4-bis(2-(2-(2-(2-(3-(6,8-dichloro-2-ethyl-1,2,3,4-tetrahydroisoquinolin-4-yl)phenylsulfonamido)ethoxy)ethoxy)ethoxy)ethyl)-2,3-dihydroxysuccinamide Into a 50-mL 3-necked round-bottom flask purged and maintained with an inert atmosphere of nitrogen, was placed a solution of N-(2-(2-(2-(2-aminoethoxy)ethoxy)ethoxy)ethyl)-3-(6,8-dichloro-2-ethyl-1,2,3,4-tetrahydroisoquinolin-4-yl)benzenesulfonamide (100 mg, 0.18 mmol, 1.00 equiv) in DMF (3 mL), bis(2,5-dioxopyrrolidin-1-yl) 2,3-dihydroxysuccinate (Intermediate 168.1) (25 mg, 0.07 mmol, 0.45 equiv) and triethylamine (75 mg, 4.50 equiv). The resulting solution was stirred overnight at room temperature. The reaction progress was monitored by LCMS. The resulting mixture was concentrated under vacuum. The crude product was purified by Flash-Prep-HPLC with water: methanol (1:10-1:100). This resulted in 12.1 mg (5%) of N1,N4-bis(2-(2-(2-(2-(3-(6,8-dichloro-2-ethyl-1,2,3,4-tetrahydroisoquinolin-4-yl)phenylsulfonamido)ethoxy)ethoxy)ethoxy)ethyl)-2,3-dihydroxysuccinamide as yellow oil. $^1$H-NMR (300 MHz, DMSO, ppm): δ 7.70-7.60 (m, 8H), 7.53-7.49 (m, 6H), 6.88 (s, 2H), 5.61-5.59 (m, 2H), 4.38 (m, 2H), 4.24-4.22 (m, 2H), 3.78-3.72 (m, 2H), 3.58-3.48 (m, 2H), 3.43 (m, 7H), 3.43-3.40 (m, 11H), 3.27-3.20 (m, 5H), 2.91-2.87 (m, 6H), 2.76-2.70 (m, 2H), 2.61-2.55 (m, 3H), 1.04-0.99 (m, 6H). MS (m/z): 1235 [M+H]$^+$.

Example 171

3,3'-(2,2'-(2,2'-(2,2'-oxybis(ethane-2,1-diyl)bis(oxy))bis(ethane-2,1-diyl))bis(6,8-dichloro-1,2,3,4-tetrahydroisoquinoline-4,2-diyl))dianiline

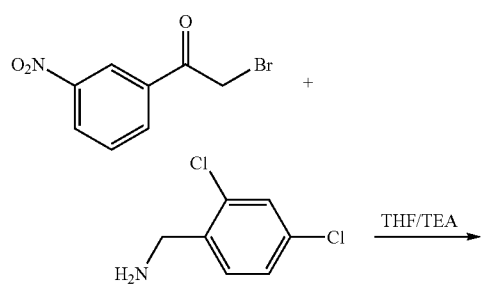

Intermediate 171.1, 2-(2,4-dichlorobenzylamino)-1-(3-nitrophenyl)ethanone

Into a 250-mL 3-necked round-bottom flask purged and maintained with an inert atmosphere of nitrogen, was placed a solution of 2-bromo-1-(3-nitrophenyl)ethanone (10.0 g, 41.15 mmol, 1.00 equiv) in THF (150 mL), (2,4-dichlorophenyl)methanamine (7.16 g, 40.91 mmol, 1.00 equiv) and triethylamine (5.96 g, 59.01 mmol, 1.50 equiv). The resulting solution was stirred for 2 h at 25° C. The solids were filtered out. The filtrate was concentrated to dryness and used for next step, assuming theoretical yield.

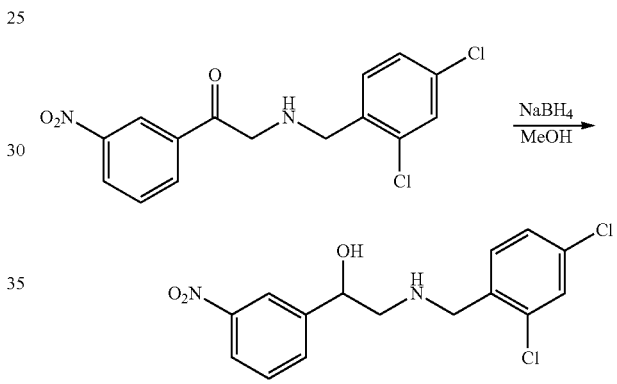

Intermediate 171.2, 2-(2,4-dichlorobenzylamino)-1-(3-nitrophenyl)ethanol

Into a 500-mL 3-necked round-bottom flask purged and maintained with an inert atmosphere of nitrogen, was placed a solution of intermediate 171.1 (40.91 mmol, 1.00 equiv) in methanol (150 mL). This was followed by the addition of NaBH$_4$ (2.5 g, 65.79 mmol, 1.50 equiv) in several batches at 0° C. The resulting solution was stirred for 2 h at 25° C. The reaction was then quenched by the addition of aqueous NH$_4$Cl. The resulting mixture was concentrated under vacuum, and the solids were collected by filtration. The crude product was purified by re-crystallization from ethyl acetate. This resulted in 3.5 g (23%) of 2-(2,4-dichlorobenzylamino)-1-(3-nitrophenyl)ethanol as a yellowish solid.

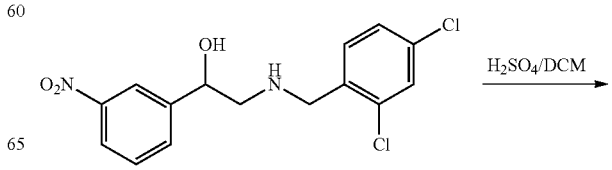

Intermediate 171.3, 6,8-dichloro-4-(3-nitrophenyl)-1,2,3,4-tetrahydroisoquinoline

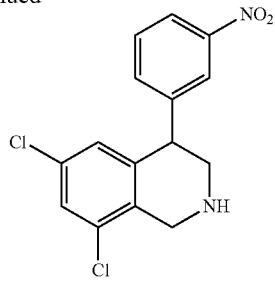

To 2-(2,4-dichlorobenzylamino)-1-(3-nitrophenyl)ethanol (intermediate 171.2) (500 mg, 1.47 mmol, 1.00 equiv) in DCM (10 mL) was added conc. sulfuric acid (4 mL) dropwise with stirring at 0-5° C. The resulting solution was stirred for 12 h at room temperature. The reaction was then quenched by the addition of water/ice. The pH value of the solution was adjusted to 10 with sodium hydroxide. The resulting solution was extracted with 2×50 mL of DCM and the organic layers combined and dried over anhydrous sodium sulfate and concentrated under vacuum. This resulted in 300 mg (63%) of 6,8-dichloro-4-(3-nitrophenyl)-1,2,3,4-tetrahydroisoquinoline as yellow oil.

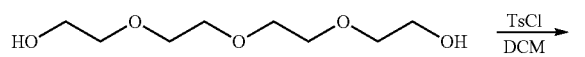

Intermediate 171.4, 2,2'-(2,2'-oxybis(ethane-2,1-diyl)bis(oxy))bis(ethane-2,1-diyl)bis(4-methylbenzenesulfonate)

Into a 250-mL 3-necked round-bottom flask, was placed a solution of tetraethylene glycol (10 g, 51.55 mmol, 1.00 equiv) in DCM (100 mL). This was followed by the addition of a solution of 4-methylbenzene-1-sulfonyl chloride (21.4 g, 112.63 mmol, 2.20 equiv) in DCM (50 mL) dropwise with stirring at 5° C. To this was added N,N-dimethylpyridin-4-amine (15.7 g, 128.69 mmol, 2.50 equiv). The resulting solution was stirred for 2 h at room temperature at which time it was diluted with 100 mL of water. The resulting solution was extracted with 3×100 mL of DCM and the organic layers combined. The resulting mixture was washed with 1×100 mL of brine and then concentrated under vacuum. The residue was applied onto a silica gel column and eluted with ethyl acetate/petroleum ether (1:2) to afford 11 g (43%) of the title compound as white oil.

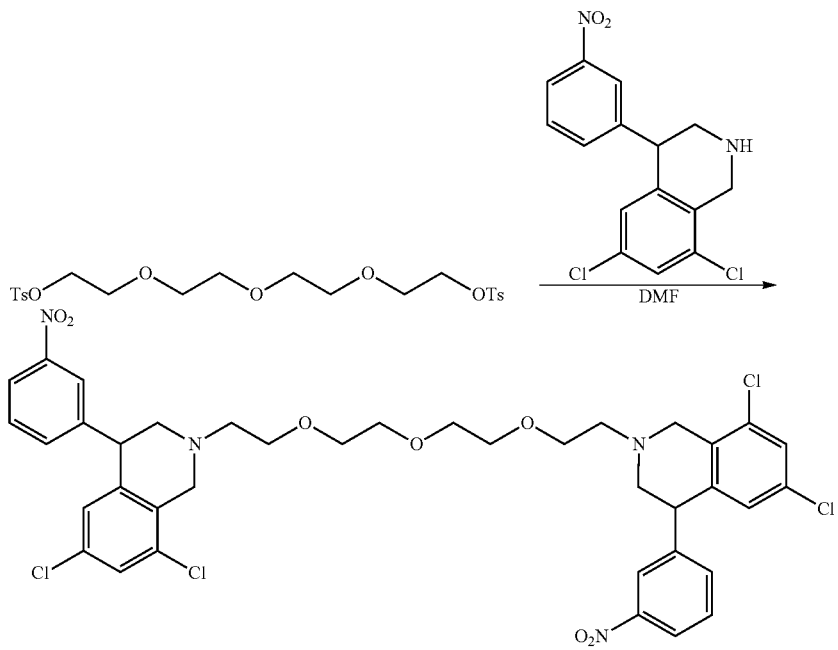

Intermediate 171.5, 2,2'-(2,2'-(2,2'-oxybis(ethane-2,1-diyl)bis(oxy))bis(ethane-2,1-diyl))bis(6,8-dichloro-4-(3-nitrophenyl)-1,2,3,4-tetrahydroisoquinoline To 6,8-dichloro-4-(3-nitrophenyl)-1,2,3,4-tetrahydroisoquinoline (intermediate 171.3) (171 mg, 0.53 mmol, 2.50 equiv) in DMF (2 mL) was added potassium carbonate (87 mg, 0.63 mmol, 3.00 equiv) and intermediate 171.4 (106 mg, 0.21 mmol, 1.00 equiv) and the resulting solution was stirred at 50° C. After stirring overnight, the resulting solution was diluted with 20 ml of water. The resulting mixture was extracted with 3×20 ml of ethyl acetate and the organic layers combined and concentrated under vacuum. The crude product was purified by Prep-HPLC with methanol:water (1:1). This resulted in 10 mg (2%) of 2,2'-(2,2'-(2,2'-oxybis(ethane-2,1-diyl)bis(oxy))bis(ethane-2,1-diyl))bis(6,8-dichloro-4-(3-nitrophenyl)-1,2,3,4-tetrahydroisoquinoline) as a light yellow solid.

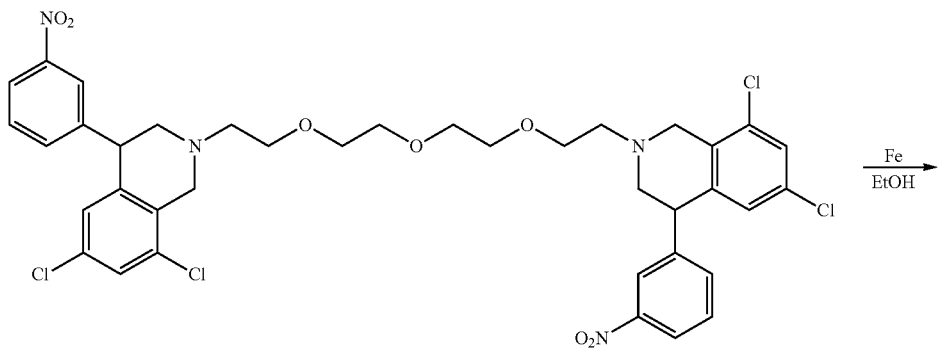

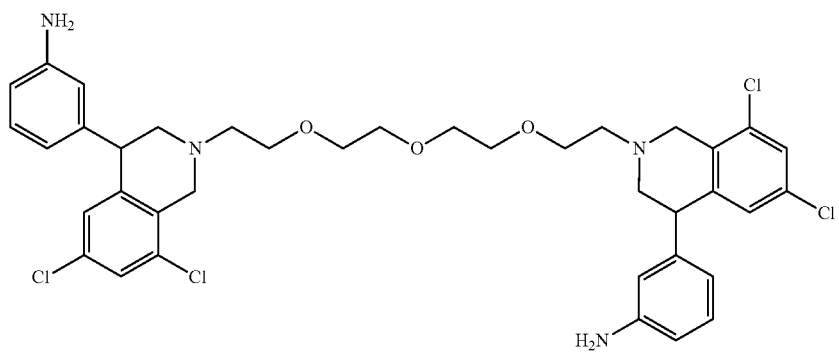

Compound 171, 3,3'-(2,2'-(2,2'-(2,2'-oxybis(ethane-2,1-diyl)bis(oxy))bis(ethane-2,1-diyl))bis(6,8-dichloro-1,2,3,4-tetrahydroisoquinoline-4,2-diyl))dianiline To intermediate 171.5 (50 mg, 0.06 mmol, 1.00 equiv) in ethanol (5 mL) was added iron (34 mg, 0.61 mmol, 9.76 equiv) followed by the addition of hydrogen chloride (5 mL) dropwise with stirring. The resulting solution was stirred for 2 h at room temperature and then for an additional 4 h at 55° C. The reaction progress was monitored by LCMS. The solids were filtered out and the resulting solution was diluted with 10 mL of water. The resulting mixture was concentrated under vacuum and the pH of the solution was adjusted to 9-10 with sodium carbonate. The resulting solution was extracted with 3×50 mL of ethyl acetate and the organic layers combined, washed with 50 mL of brine and then concentrated under vacuum. The crude product was purified by Prep-HPLC with $H_2O:CH_3CN$ (10:1). This resulted in 5 mg (11%) of 3,3'-(2,2'-(2,2'-(2,2'-oxybis(ethane-2,1-diyl)bis(oxy))bis(ethane-2,1-diyl))bis(6,8-dichloro-1,2,3,4-tetrahydroisoquinoline-4,2-diyl))dianiline as a yellow solid.). $^1$H-NMR (400 MHz, $CD_3OD$, ppm) δ 7.27 (m, 2H), 7.06 (m, 2H), 6.80 (s, 2H), 6.63 (d, 2H), 6.54 (m, 4H), 4.14 (m, 2H), 4.02 (d, 2H), 3.65 (m, 12H), 3.19 (m, 3H), 2.81 (s, 4H), 2.71 (m, 2H). MS (m/z): 745 [M+H]$^+$.

Example 172

N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide

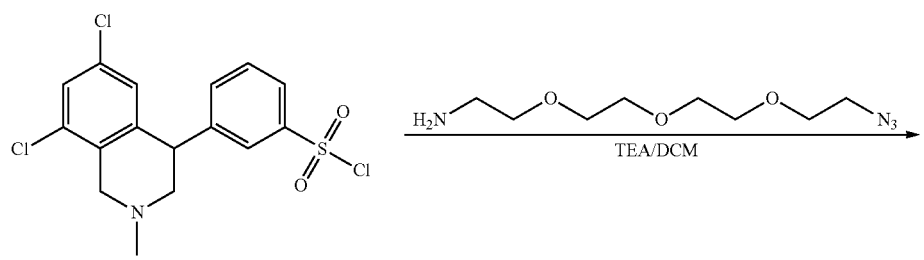

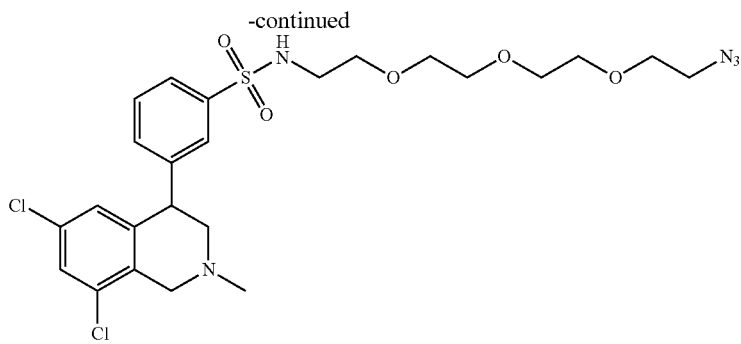

Intermediate 28.1: N-(2-(2-(2-(2-azidoethoxy)ethoxy)ethoxy)ethyl)-3-(6,8-dichloro-2-methyl-1,2,3,4-tetrahydroisoquinolin-4-yl)benzenesulfonamide To 2-(2-(2-(2-azidoethoxy)ethoxy)ethoxy)ethanamine (1.5 g, 6.87 mmol, 1.79 equiv) in DCM (20 mL) was added triethylamine (1.5 g, 14.82 mmol, 3.86 equiv) and 3-(6,8-dichloro-2-methyl-1,2,3,4-tetrahydroisoquinolin-4-yl)benzene-1-sulfonyl chloride (1.5 g, 3.84 mmol, 1.00 equiv). The reaction was stirred overnight at room temperature at which time the resulting mixture was concentrated under vacuum. The residue was dissolved in 100 mL of ethyl acetate and then was washed with 2×20 mL of water, dried over anhydrous sodium sulfate and concentrated under vacuum. This resulted in 1.8 g (85%) of N-(2-(2-(2-(2-azidoethoxy)ethoxy)ethoxy)ethyl)-3-(6,8-dichloro-2-methyl-1,2,3,4-tetrahydroisoquinolin-4-yl)benzenesulfonamide as yellow oil.

Compound 28, N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide To N-(2-(2-(2-(2-azidoethoxy)ethoxy)ethoxy)ethyl)-3-(6,8-dichloro-2-methyl-1,2,3,4-tetrahydroisoquinolin-4-yl)benzenesulfonamide (1.8 g, 3.26 mmol, 1.00 equiv) in THF (30 mL) was added triphenylphosphine (2.6 g, 9.91 mmol, 3.04 equiv). The resulting solution was stirred overnight at room temperature and then concentrated under vacuum. The crude product (5.0 g) was purified by Flash-Prep-HPLC with the following conditions: Column, silica gel; mobile phase, methanol:water=1:9 increasing to methanol:water=9:1 within 30 min; Detector, UV 254 nm. 1.2 g product was obtained. This resulted in 1.2 g (64%) of N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide as yellow oil.

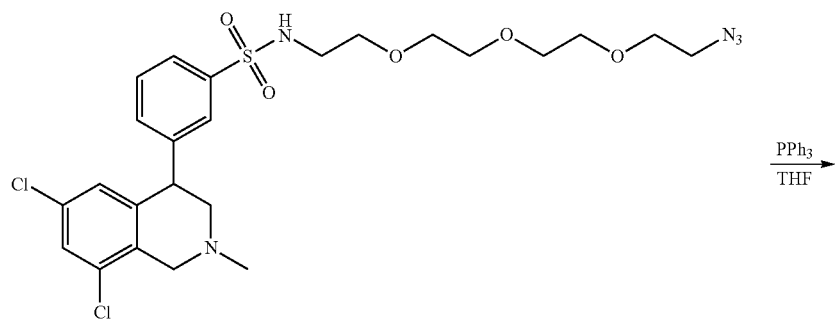

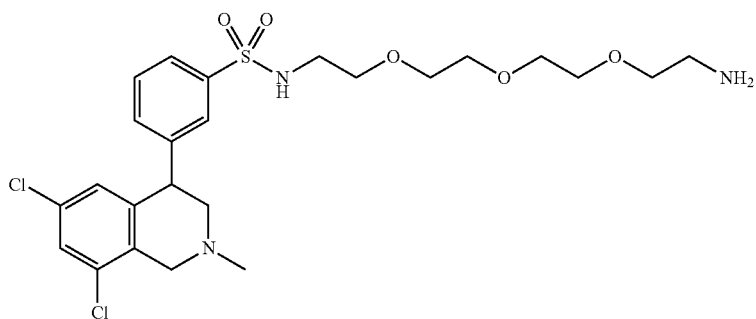

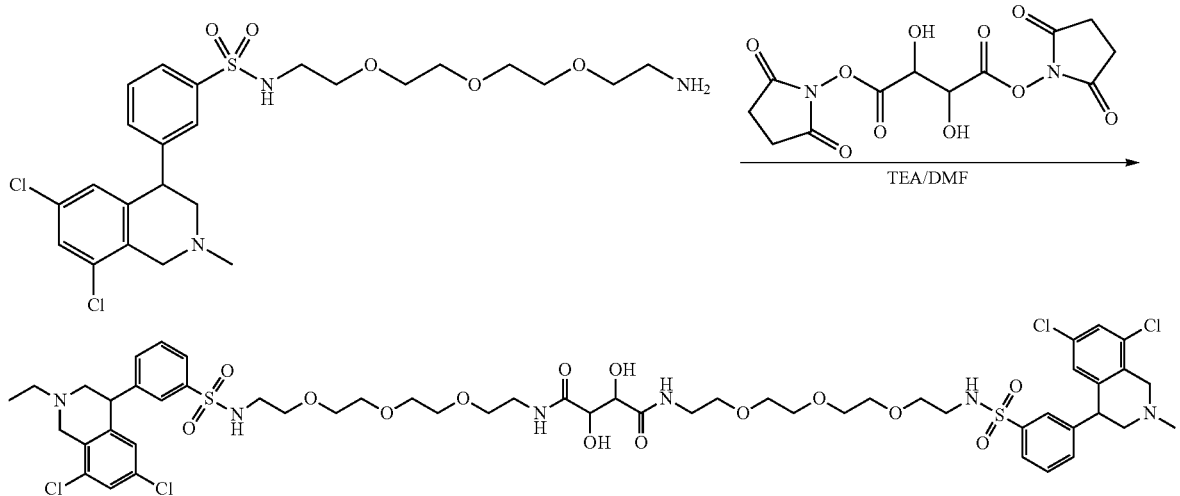

Compound 172, N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide To N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (compound 28) (1.2 g, 2.28 mmol, 1.00 equiv) in DMF (8 mL) was added bis(2,5-dioxopyrrolidin-1-yl) 2,3-dihydroxysuccinate (intermediate 168.1) (393 mg, 1.14 mmol, 0.50 equiv) and triethylamine (1.5 g, 14.82 mmol, 6.50 equiv) and the resulting solution was stirred overnight at room temperature. The mixture was concentrated under vacuum and the crude product was purified by Flash-Prep-HPLC with the following conditions: Column, silica gel; mobile phase, methanol:water=1:9 increasing to methanol:water=9:1 within 30 min; Detector, UV 254 nm. This resulted in 591 mg (43%) of N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide as a light yellow solid. $^1$H-NMR (300 MHz, CD$_3$OD, ppm): δ 7.92 (d, J=7.8 Hz, 2H), 7.81 (m, 2H), 7.67 (t, J=7.8 Hz, 2H), 7.57 (m, 2H), 7.55 (d, J=6.9 Hz, 2H), 6.85 (m, 2H), 4.78 (s, 2H), 4.77 (s, 2H), 4.54 (d, J=40.2 Hz, 2H), 4.48 (s, 2H), 3.92 (m, 2H), 3.53 (m, 30H), 3.18 (s, 6H), 3.07 (t, J=5.4 Hz, 4H). MS (m/z): 603 [½M+H]$^+$.

Example 173

N1,N4-bis(2-(2-(2-(2-(3-(6,8-dichloro-2-methyl-1,2,3,4-tetrahydroisoquinolin-4-yl)phenylamino)ethoxy)ethoxy)ethoxy)ethyl)-2,3-dihydroxysuccinamide

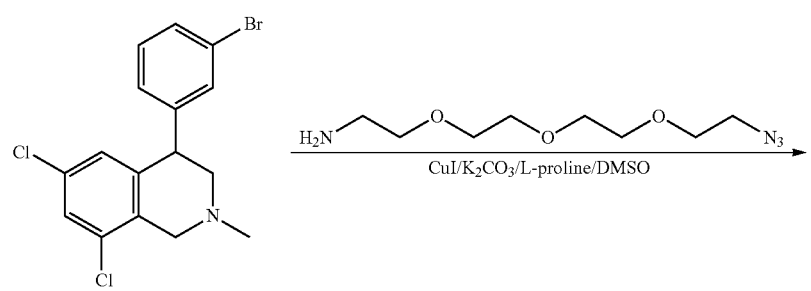

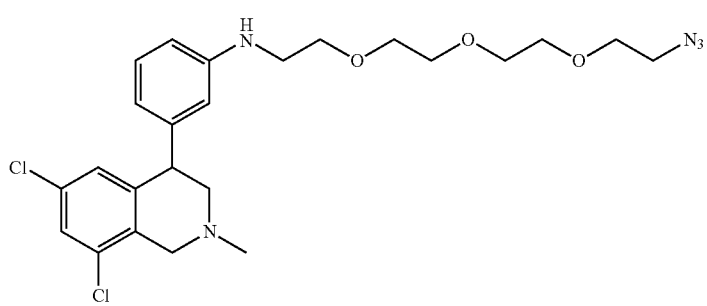

Intermediate 173.1, N-(2-(2-(2-(2-azidoethoxy)ethoxy)ethoxy)ethyl)-3-(6,8-dichloro-2-methyl-1,2,3,4-tetrahydroisoquinolin-4-yl)aniline Into a 10-mL round-bottom flask purged and maintained with an inert atmosphere of nitrogen, was placed a solution of 4-(3-bromophenyl)-6,8-dichloro-2-methyl-1,2,3,4-tetrahydroisoquinoline (intermediate 1.4) (400 mg, 1.08 mmol, 1.00 equiv) in DMSO (6 mL), 2-(2-(2-(2-azidoethoxy)ethoxy)ethoxy)ethanamine (236.11 mg, 1.08 mmol, 1.00 equiv), (S)-pyrrolidine-2-carboxylic acid (24.79 mg, 0.21 mmol, 0.20 equiv), copper(I) iodide (20.48 mg, 0.11 mmol, 0.10 equiv) and potassium carbonate (223.18 mg, 1.62 mmol, 1.50 equiv). The resulting solution was stirred at 90° C. in an oil bath and the reaction progress was monitored by LCMS. After stirring overnight the reaction mixture was cooled with a water/ice bath and then diluted with ice water. The resulting solution was extracted with 3×30 mL of ethyl acetate and the organic extracts were combined and washed with 2×20 mL of brine. The mixture was dried over anhydrous sodium sulfate and concentrated under vacuum. The residue was applied onto a silica gel column with ethyl acetate/petroleum ether (2:1). This resulted in 130 mg (24%) of N-(2-(2-(2-(2-azidoethoxy)ethoxy)ethoxy)ethyl)-3-(6,8-dichloro-2-methyl-1,2,3,4-tetrahydroisoquinolin-4-yl)benzenamine as yellow oil.

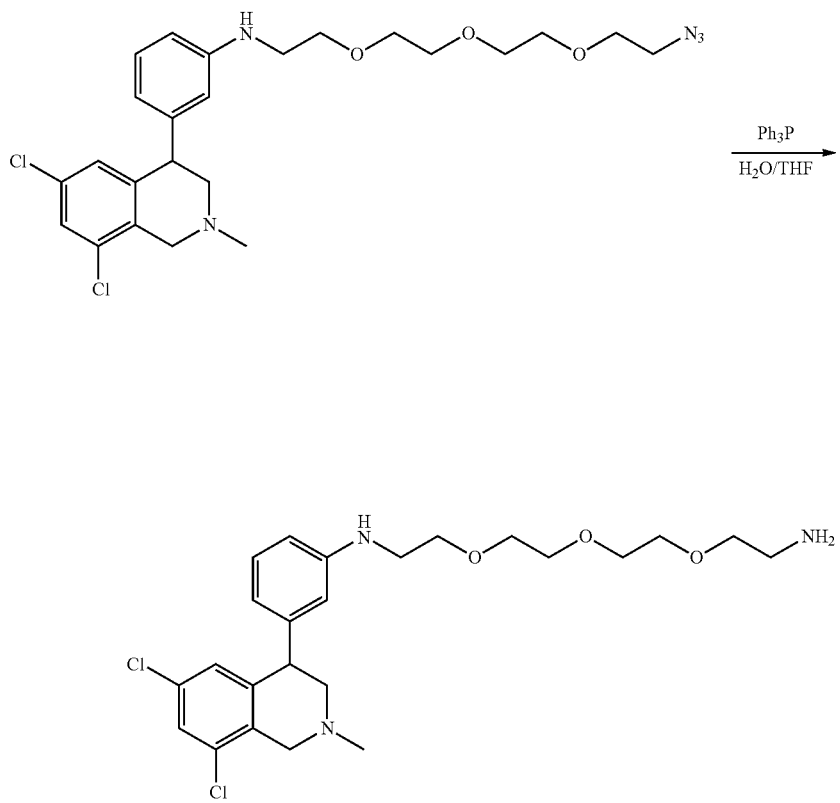

Intermediate 173.2, N-(2-(2-(2-(2-aminoethoxy)ethoxy)ethoxy)ethyl)-3-(6,8-dichloro-2-methyl-1,2,3,4-tetrahydroisoquinolin-4-yl)aniline Into a 50-mL round-bottom flask, was placed a solution of intermediate 173.1 (350 mg, 0.69 mmol, 1.00 equiv) in THF/water (4/0.4 mL) and triphenylphosphine (205 mg, 0.78 mmol, 1.20 equiv). The resulting solution was stirred overnight at 40° C. in an oil bath. The resulting mixture was then concentrated under vacuum. The pH of the solution was adjusted to 2-3 with 1N hydrogen chloride (10 ml). The resulting solution was extracted with 2×10 mL of ethyl acetate and the aqueous layers combined. The pH value of the solution was adjusted to 11 with $NH_3 \cdot H_2O$. The resulting solution was extracted with 3×30 mL of DCM and the organic layers combined. The resulting mixture was washed with 30 mL of brine. The mixture was dried over anhydrous sodium sulfate and concentrated under vacuum. This resulted in 250 mg (75%) of N-(2-(2-(2-(2-aminoethoxy)ethoxy)ethoxy)ethyl)-3-(6,8-dichloro-2-methyl-1,2,3,4-tetrahydroisoquinolin-4-yl)aniline as yellow oil.

311 312

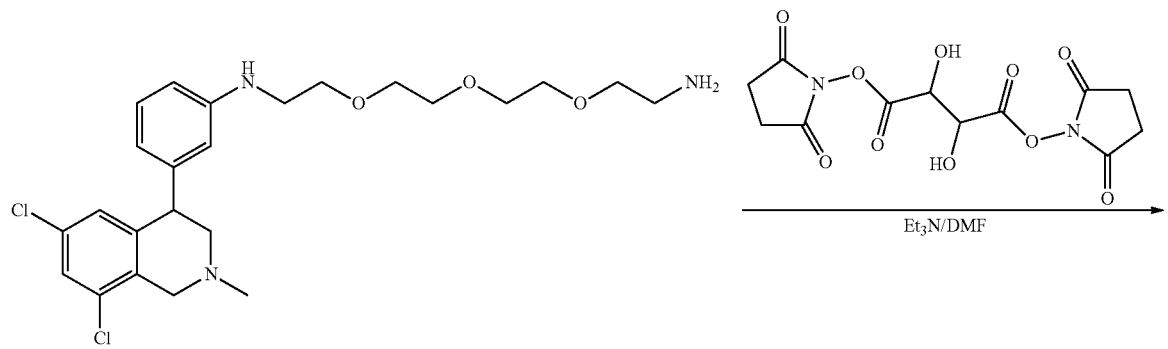

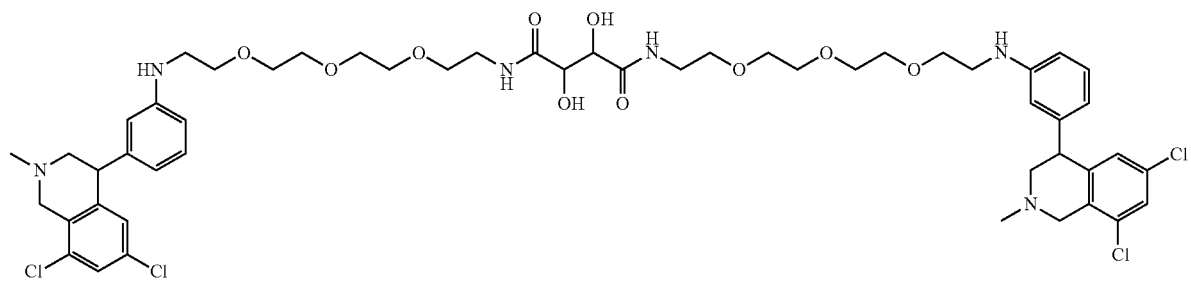

Compound 173, N1,N4-bis(2-(2-(2-(2-(3-(6,8-dichloro-2-methyl-1,2,3,4-tetrahydroisoquinolin-4-yl)phenylamino)ethoxy)ethoxy)ethoxy)ethyl)-2,3-dihydroxysuccinamide To intermediate 173.2 (240 mg, 0.50 mmol, 1.00 equiv) in DMF (5 mL) was added TEA (233 mg, 2.31 mmol, 4.50 equiv) and bis(2,5-dioxopyrrolidin-1-yl) 2,3-dihydroxybutanedioate (intermediate 168.1) (62 mg, 0.18 mmol, 0.35 equiv) and the resulting solution was stirred overnight at room temperature. The resulting mixture was concentrated under vacuum and the crude product was purified by Prep-HPLC with methanol:water (1:10). This resulted in 140 mg (26%) of N1,N4-bis(2-(2-(2-(2-(3-(6,8-dichloro-2-methyl-1,2,3,4-tetrahydroisoquinolin-4-yl)phenylamino)ethoxy)ethoxy)ethoxy)ethyl)-2,3-dihydroxysuccinamide as a white solid. $^1$H-NMR (300 MHz, DMSO, ppm): δ 7.65 (m, 4H), 7.11 (m, 2H), 6.83 (m, 2H), 6.58 (m, 2H), 6.41 (m, 4H), 4.09 (m, 32H), 3.45 (m, 17H), 3.43 (m, 5H), 3.31 (m, 9H), 2.51 (m, 6H). MS (m/z): 1079 [M+H]$^+$.

Example 174

N1,N4-bis(1-(3-(6,8-dichloro-2-methyl-1,2,3,4-tetrahydroisoquinolin-4-yl)phenylamino)-1-oxo-5,8,11-trioxa-2-azatridecan-13-yl)-2,3-dihydroxysuccinamide

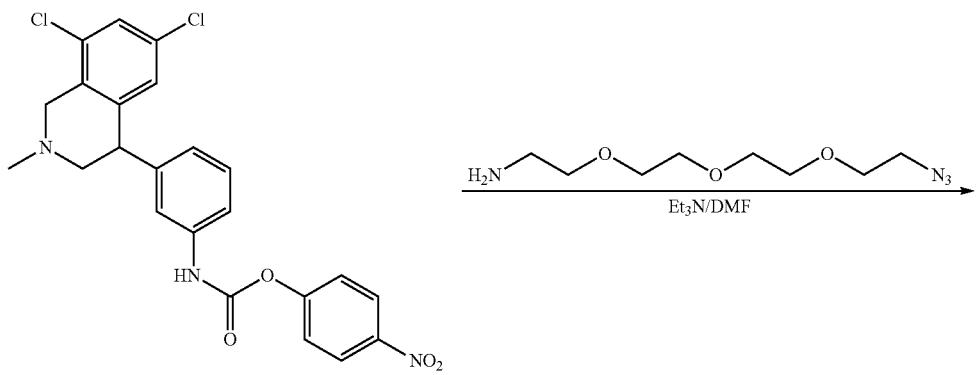

-continued

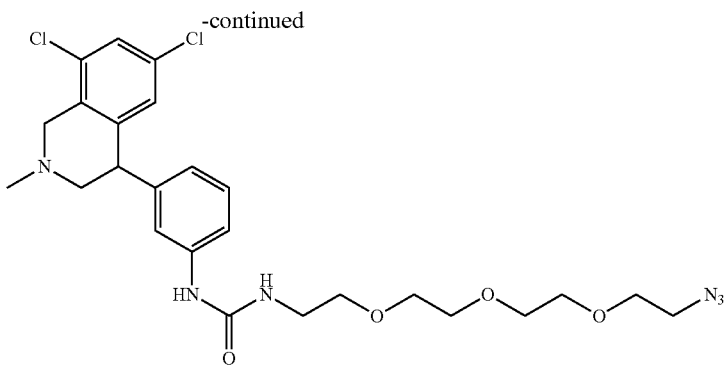

Intermediate 174.1, 1-(2-(2-(2-(2-azidoethoxy)ethoxy)ethoxy)ethyl)-3-(3-(6,8-dichloro-2-methyl-1,2,3,4-tetrahydroisoquinolin-4-yl)phenyl)urea To 4-nitrophenyl 3-(6,8-dichloro-2-methyl-1,2,3,4-tetrahydroisoquinolin-4-yl)phenylcarbamate (prepared by the procedure described in example 38) (200 mg, 0.40 mmol, 1.00 equiv, 95%) in DMF (5 mL) was added TEA (170 mg, 1.60 mmol, 4.00 equiv, 95%) and 2-(2-(2-(2-azidoethoxy)ethoxy)ethoxy)ethanamine (90 mg, 0.39 mmol, 1.00 equiv, 95%) and the resulting solution was stirred for 2 h. The mixture was then concentrated under vacuum, diluted with 10 mL of water and then extracted with 3×30 mL of ethyl acetate. The organic layers were combined, washed with 3×30 mL of brine, dried over anhydrous sodium sulfate and then evaporated. The residue was applied onto a silica gel column with ethyl acetate/petroleum ether (1:5~1:1). This resulted in 160 mg (72%) of 1-(2-(2-(2-(2-azidoethoxy)ethoxy)ethoxy)ethyl)-3-(3-(6,8-dichloro-2-methyl-1,2,3,4-tetrahydroisoquinolin-4-yl)phenyl)urea as pale-yellow oil.

Intermediate 174.2 1-(2-(2-(2-(2-aminoethoxy)ethoxy)ethoxy)ethyl)-3-(3-(6,8-dichloro-2-methyl-1,2,3,4-tetrahydroisoquinolin-4-yl)phenyl)urea Intermediate 174.2 was prepared from 1-(2-(2-(2-(2-azidoethoxy)ethoxy)ethoxy)ethyl)-3-(3-(6,8-dichloro-2-methyl-1,2,3,4-tetrahydroisoquinolin-4-yl)phenyl)urea (intermediate 174.1) using the procedure described to prepare intermediate 173.2. The crude product was purified by silica gel chromatography, eluting with DCM/methanol (50:1). This resulted in 230 mg of 1-(2-(2-(2-(2-aminoethoxy)ethoxy)ethoxy)ethyl)-3-(3-(6,8-dichloro-2-methyl-1,2,3,4-tetrahydroisoquinolin-4-yl)phenyl)urea as pale-yellow oil.

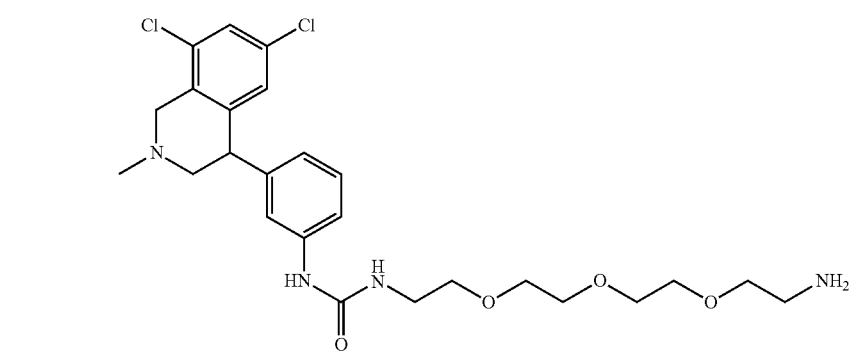

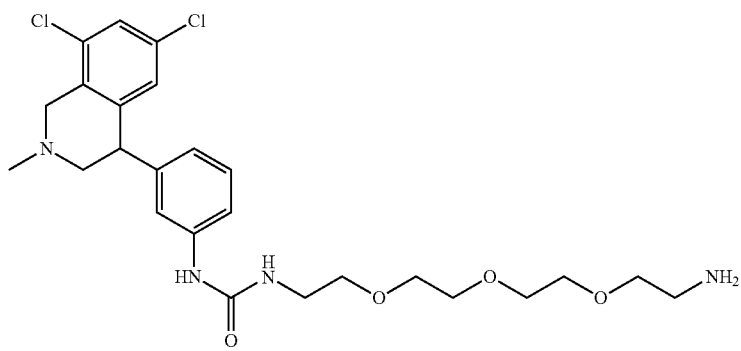

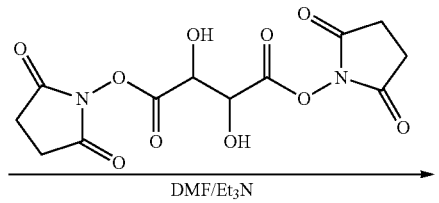

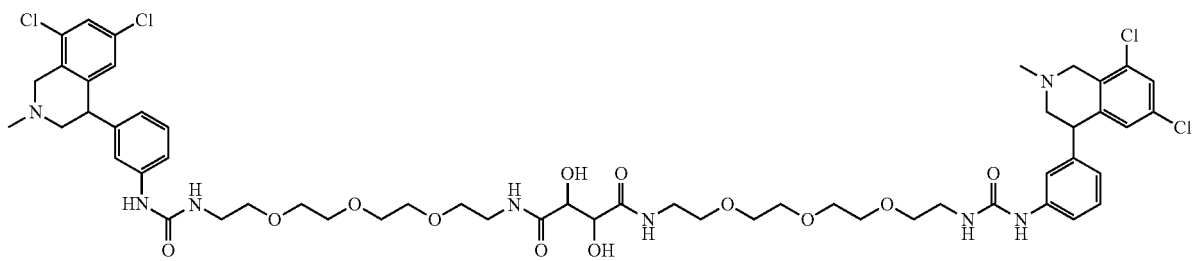

Compound 174, N1,N4-bis(1-(3-(6,8-dichloro-2-methyl-1,2,3,4-tetrahydroisoquinolin-4-yl)phenylamino)-1-oxo-5,8,11-trioxa-2-azatridecan-13-yl)-2,3-dihydroxysuccinamide Compound 174 was prepared from 1-(2-(2-(2-(2-aminoethoxy)ethoxy)ethoxy)ethyl)-3-(3-(6,8-dichloro-2-methyl-1,2,3,4-tetrahydroisoquinolin-4-yl)phenyl)urea (intermediate 174.2) using the procedures described in example 172. The crude product (400 mg) was purified by Prep-HPLC with methanol: acetonitrile=60:40. This resulted in 113 mg (23%) of N1,N4-bis(1-(3-(6,8-dichloro-2-methyl-1,2,3,4-tetrahydroisoquinolin-4-yl)phenylamino)-1-oxo-5,8,11-trioxa-2-azatridecan-13-yl)-2,3-dihydroxysuccinamide as a white solid. $^1$H-NMR (400 MHz, DMSO, ppm): δ 8.68 (s, 2H), 7.68 (s, 2H), 7.64 (t, 2H), 7.39 (s, 2H), 7.24-7.28 (m, 6H), 6.77-6.78 (m, 4H), 6.23 (s, 2H), 4.47 (s, 4H), 4.23 (s, 2H), 3.76 (s, 4H), 3.42-3.69 (m, 24H), 3.28-3.36 (m, 4H), 3.20-3.24 (m, 6H), 3.02 (s, 6H). MS (m/z): 583 [½M+1]$^+$.

Example 175

N1,N2-bis(2-(2-(2-(4-(6,8-dichloro-2-methyl-1,2,3,4-tetrahydroisoquinolin-4-yl)phenylsulfonamido)ethoxy)ethoxy)ethyl)oxalamide

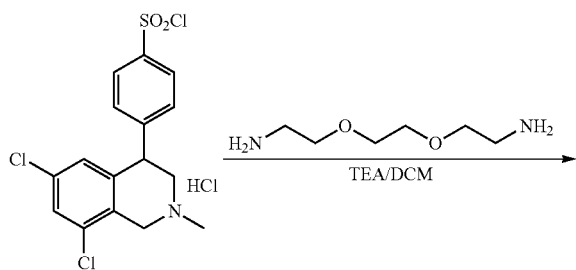

-continued

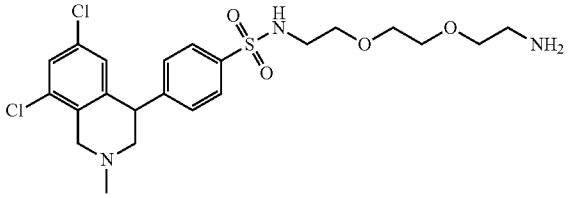

Intermediate 175.1, N-(2-(2-(2-aminoethoxy)ethoxy)ethyl)-4-(6,8-dichloro-2-methyl-1,2,3,4-tetrahydroisoquinolin-4-yl)benzenesulfonamide To 4-(6,8-dichloro-2-methyl-1,2,3,4-tetrahydroisoquinolin-4-yl)benzene-1-sulfonyl chloride hydrochloride (intermediate 10.6) (9 g, 20.02 mmol, 1.00 equiv, 95%) in DCM (200 mL) was added 2-(2-(2-aminoethoxy)ethoxy)ethanamine (15.6 g, 105.41 mmol, 5.00 equiv) and triethylamine (4.26 g, 42.18 mmol, 2.00 equiv) and the resulting solution was stirred for 3 h at room temperature. The reaction mixture was diluted with 100 mL of DCM and then washed with 2×50 mL of Brine. The mixture was dried over anhydrous sodium sulfate and concentrated under vacuum. The residue was applied onto a silica gel column with DCM/methanol (10:1). This resulted in 3 g (28%) of N-(2-(2-(2-aminoethoxy)ethoxy)ethyl)-4-(6,8-dichloro-2-methyl-1,2,3,4-tetrahydroisoquinolin-4-yl)benzenesulfonamide as brown oil.

317

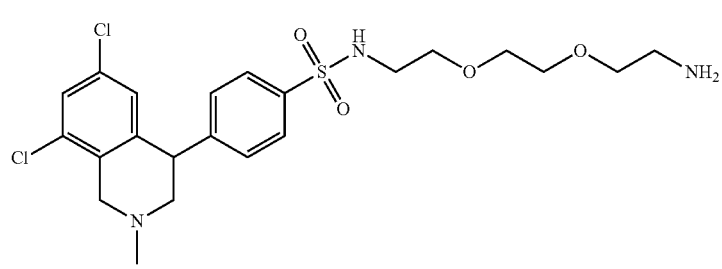 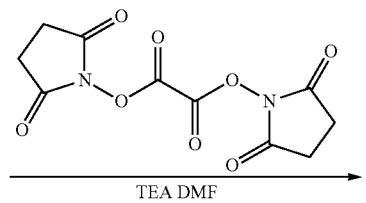

TEA DMF

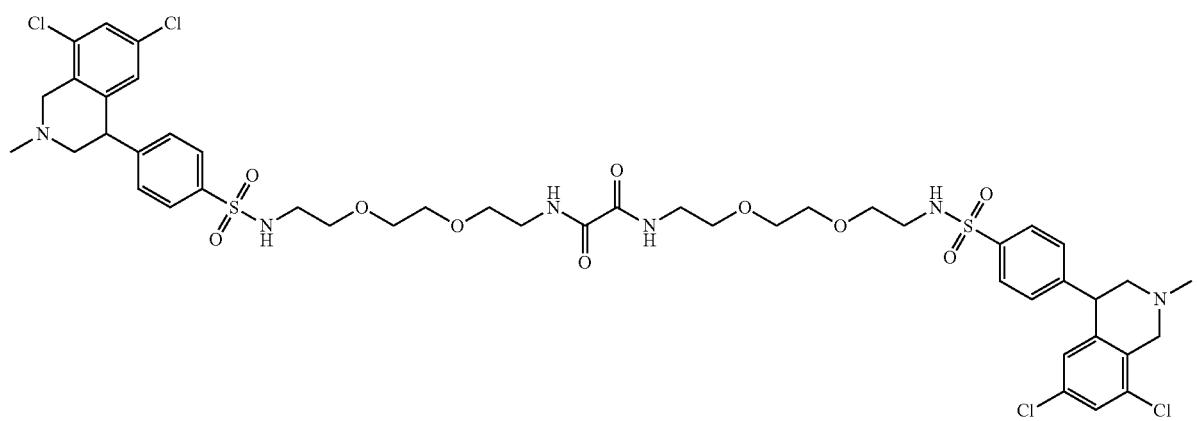

Compound 175, N1,N2-bis(2-(2-(2-(4-(6,8-dichloro-2-methyl-1,2,3,4-tetrahydroisoquinolin-4-yl)phenyl-sulfonamido)ethoxy)ethoxy)ethyl)oxalamide Into a 50-mL round-bottom flask, was placed a solution of N-(2-(2-(2-aminoethoxy)ethoxy)ethyl)-4-(6,8-dichloro-2-methyl-1,2,3,4-tetrahydroisoquinolin-4-yl)benzenesulfonamide (intermediate 175.1) (150 mg, 0.28 mmol, 2.50 equiv, 92%) in DMF (5 mL), bis(2,5-dioxopyrrolidin-1-yl) oxalate (34 mg, 0.12 mmol, 1.00 equiv) and triethylamine (49 mg, 0.49 mmol, 4.00 equiv). The resulting solution was stirred overnight at room temperature. The crude product was purified by Prep-HPLC with acetonitrile:water (0.05% CF3COOH) (10%-100%). This resulted in 97 mg (68%) of a TFA salt of N1,N2-bis(2-(2-(2-(4-(6,8-dichloro-2-methyl-1,2,3,4-tetrahydroisoquinolin-4-yl)phenylsulfonamido)ethoxy)ethoxy)ethyl)oxalamide as a white solid. $^1$H-NMR (300 MHz, CD$_3$OD, ppm): δ 7.90 (m, 4H), 7.56 (s, 2H), 7.50

318

(m, 4H), 6.85 (s, 2H), 4.77 (m, 4H), 4.53 (d, 2H), 3.90 (m, 2H), 3.88 (m, 10H), 3.58 (m, 12H), 3.31 (s, 6H), 3.12 (m, 4H). MS (m/z): 530 [½M+1]$^+$.

Example 176

N1,N4-bis(2-(2-(3-(6,8-dichloro-2-methyl-1,2,3,4-tetrahydroisoquinolin-4-yl)phenylsulfonamido)ethoxy)ethyl)-2,3-dihydroxysuccinamide

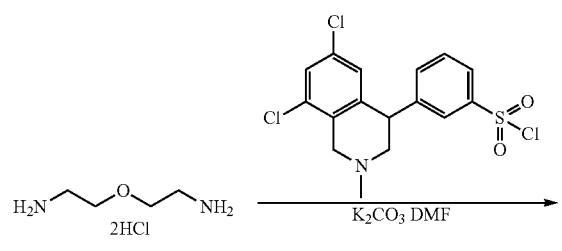

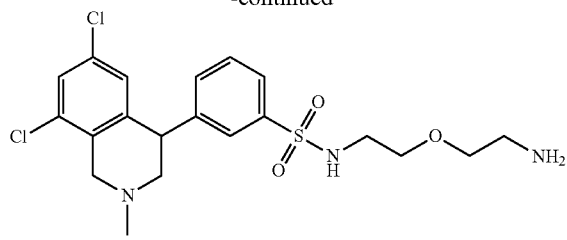

Intermediate 176.1, N-(2-(2-aminoethoxy)ethyl)-3-(6,8-dichloro-2-methyl-1,2,3,4-tetrahydroisoquinolin-4-yl)benzenesulfonamide Into a 50-mL round-bottom flask purged and maintained with an inert atmosphere of nitrogen, was placed a solution of 2-(2-aminoethoxy)ethanamine dihydrochloride (1.0 g, 5.65 mmol, 5.52 equiv) in DMF (20 mL), potassium carbonate (2.0 g, 14.39 mmol, 14.05 equiv) and 3-(6,8-dichloro-2-methyl-1,2,3,4-tetrahydroisoquinolin-4-yl)benzene-1-sulfonyl chloride (intermediate 1.6) (400 mg, 1.02 mmol, 1.00 equiv). The resulting solution was stirred overnight at room temperature at which time it was diluted with 100 mL of water. The resulting solution was extracted with 3×30 mL of ethyl acetate and the organic layers were combined and dried over sodium sulfate and concentrated under vacuum. This resulted in 60 mg (13%) of N-(2-(2-aminoethoxy)ethyl)-3-(6,8-dichloro-2-methyl-1,2,3,4-tetrahydroisoquinolin-4-yl)benzenesulfonamide as a yellow solid.

solution was stirred overnight at room temperature at which time the mixture was concentrated under vacuum. The crude product was purified by Prep-HPLC with acetonitrile:water (0.05% CF3COOH) (10%-100%). This resulted in 21 mg (13%) of a TFA salt of N1,N4-bis(2-(2-(3-(6,8-dichloro-2-methyl-1,2,3,4-tetrahydroisoquinolin-4-yl)phenylsulfonamido)ethoxy)ethyl)-2,3-dihydroxysuccinamide as a white solid. $^{1}$H-NMR (300 MHz, CD$_3$OD, ppm): δ 7.92 (d, J=7.8 Hz, 2H), 7.81 (m, 2H), 7.67 (t, J=7.8 Hz, 2H), 7.57 (m, 2H), 7.55 (d, J=6.9 Hz, 2H), 6.85 (m, 2H), 4.78 (s, 2H), 4.77 (s, 2H), 4.54 (d, J=40.2 Hz, 2H), 4.48 (s, 2H), 3.92 (m, 2H), 3.53 (m, 10H), 3.18 (s, 6H), 3.07 (t, J=5.4 Hz, 4H). MS (m/z): 517 [½M+1]$^+$.

Example 177

N1,N4-bis(2-(2-(2-(4-(6,8-dichloro-2-methyl-1,2,3,4-tetrahydroisoquinolin-4-yl)phenylsulfonamido)ethoxy)ethoxy)ethyl)succinamide

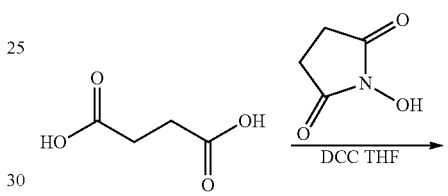

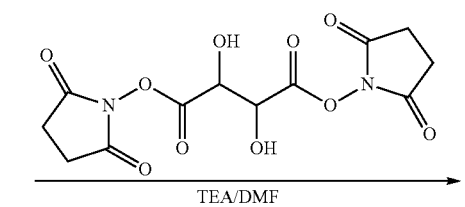

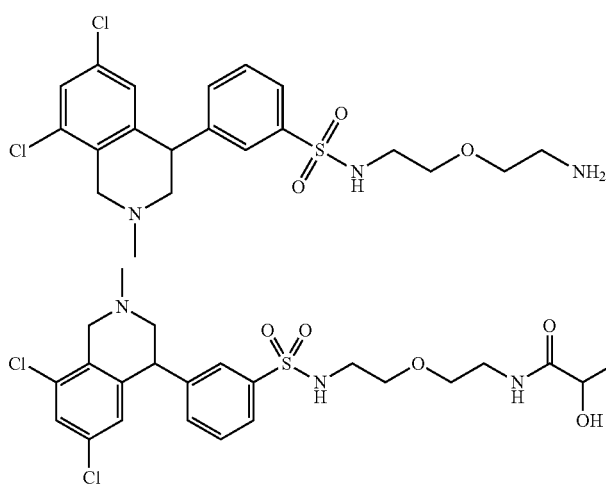

Compound 176, N1,N4-bis(2-(2-(3-(6,8-dichloro-2-methyl-1,2,3,4-tetrahydroisoquinolin-4-yl)phenylsulfonamido)ethoxy)ethyl)-2,3-dihydroxysuccinamide Into a 50-mL round-bottom flask purged and maintained with an inert atmosphere of nitrogen, was placed a solution of N-(2-(2-aminoethoxy)ethyl)-3-(6,8-dichloro-2-methyl-1,2,3,4-tetrahydroisoquinolin-4-yl)benzenesulfonamide (intermediate 176.1) (60 mg, 0.13 mmol, 1.00 equiv) in DMF (3 mL), bis(2,5-dioxopyrrolidin-1-yl) 2,3-dihydroxybutanedioate (intermediate 168.1) (21 mg, 0.06 mmol, 0.47 equiv) and triethylamine (50 mg, 0.49 mmol, 3.77 equiv). The resulting -continued

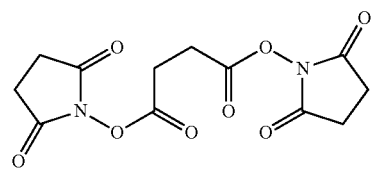

321

Intermediate 177.1, bis(2,5-dioxopyrrolidin-1-yl)succinate

To succinic acid (3.0 g, 25.42 mmol, 1.00 equiv) in THF (50 mL) was added a solution of 1-hydroxypyrrolidine-2,5-dione (6.4 g, 55.65 mmol, 2.20 equiv). This was followed by the addition of a solution of DCC (11.5 g, 55.83 mmol, 2.20 equiv) in THF (50 mL) dropwise with stirring at 0° C. The resulting solution was stirred overnight at room temperature. The reaction progress was monitored by LCMS. The solids were collected by filtration and the filtrate was concentrated to give the crude product. The resulting solids were washed with THF and ethanol. This resulted in 2.4 g (27%) of bis(2,5-dioxopyrrolidin-1-yl) succinate as a white solid.

322

Compound 177, N1,N4-bis(2-(2-(2-(4-(6,8-dichloro-2-methyl-1,2,3,4-tetrahydroisoquinolin-4-yl)phenylsulfonamido)ethoxy)ethoxy)ethyl)succinamide Compound 177 was prepared using the procedure described in example 175, substituting (2,5-dioxopyrrolidin-1-yl) succinate (intermediate 177.1) for bis(2,5-dioxopyrrolidin-1-yl) oxalate. The crude product was purified by Prep-HPLC with acetonitrile:water (0.05% CF3COOH) (10%-100%). This resulted in 32.8 mg (8%) of N1,N4-bis(2-(2-(2-(4-(6,8-dichloro-2-methyl-1,2,3,4-tetrahydroisoquinolin-4-yl)phenylsulfonamido)ethoxy)ethoxy)ethyl)succinamide as a white solid. $^{1}$H-NMR (300 MHz, CD$_3$OD, ppm): δ 7.93-7.91 (d, J=8.1 Hz, 4H), 7.57-7.56 (d, J=1.8 Hz, 2H), 7.50-7.47

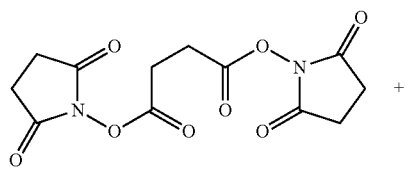

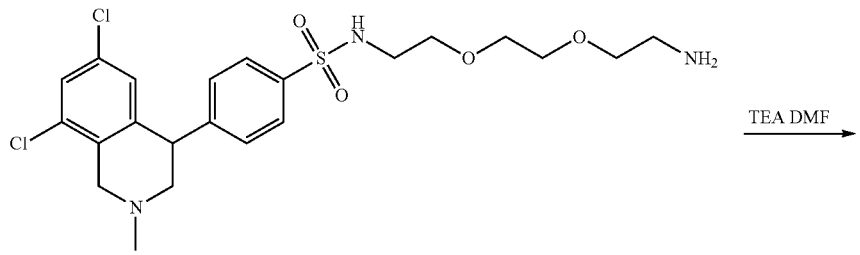

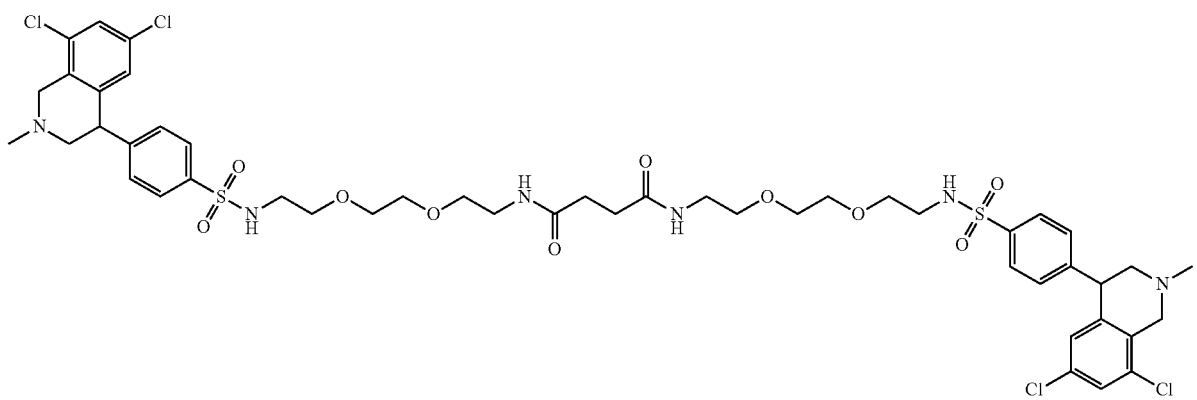

(d, J=8.4 Hz, 4H), 6.86 (s, 2H), 4.78-4.73 (d, J=13.5 Hz, 4H), 4.52 (m, 2H), 3.85 (m, 2H), 3.59-3.47 (m, 18H), 3.15-3.09 (m, 10H), 2.49 (s, 4H). MS (m/z): 544 [½M+1]⁺.

Example 178

2,2'-oxybis(N-(2-(2-(2-(4-(6,8-dichloro-2-methyl-1,2,3,4-tetrahydroisoquinolin-4-yl)phenylsulfonamido)ethoxy)ethoxy)ethyl)acetamide

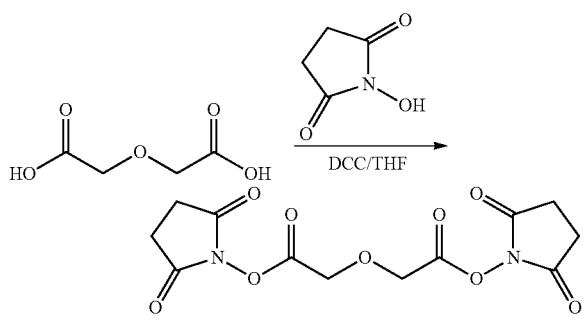

Intermediate 178.1, bis(2,5-dioxopyrrolidin-1-yl) 2,2'-oxydiacetate

Intermediate 178.1 was prepared using the procedure outlined in example 177, substituting 2,2'-oxydiacetic acid for succinic acid. The crude product was washed with ethyl acetate. This resulted in 1.5 g (19%) of Intermediate 178.1 as a white solid.

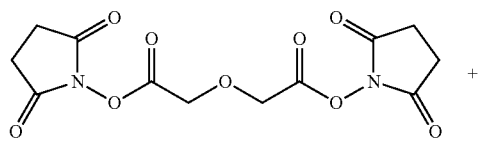

Compound 178, 2,2'-oxybis(N-(2-(2-(2-(4-(6,8-dichloro-2-methyl-1,2,3,4-tetrahydroisoquinolin-4-yl)phenylsulfonamido)ethoxy)ethoxy)ethyl)acetamide)

Compound 178 was prepared using the procedure described in example 175, substituting bis(2,5-dioxopyrrolidin-1-yl) 2,2'-oxydiacetate (intermediate 178.1) for bis(2,5-dioxopyrrolidin-1-yl) oxalate. The crude product was purified by Prep-HPLC with acetonitrile:water (0.05% CF$_3$COOH) (10%-100%). This resulted in 39.1 mg (7%) of a TFA salt of 2,2'-oxybis(N-(2-(2-(2-(4-(6,8-dichloro-2-methyl-1,2,3,4-tetrahydroisoquinolin-4-yl)phenylsulfonamido)ethoxy)ethoxy)ethyl)acetamide) as a white solid. $^1$H-NMR (300 MHz, CD$_3$OD, ppm): δ 7.94-7.91 (m, 4H), 7.57-7.56 (m, 2H), 7.51-7.48 (m, 4H), 6.87 (m, 2H), 4.82-4.76 (m, 4H), 4.54-4.49 (m, 2H), 3.93-3.91 (s, 4H), 3.89-3.87 (m, 2H), 3.66-3.42 (m, 22H), 3.17 (s, 6H), 3.13-3.09 (m, 4H). MS (m/z): 552 [½M+1]⁺.

Example 179

(2R,3R)—N1,N4-bis(2-(2-(2-(3-(3-(6,8-dichloro-2-methyl-1,2,3,4-tetrahydroisoquinolin-4-yl)phenylamino)-3-oxopropoxy)ethoxy)ethoxy)ethyl)-2,3-dihydroxysuccinamide

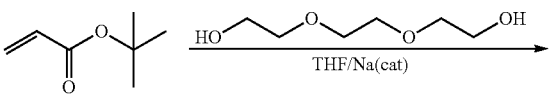

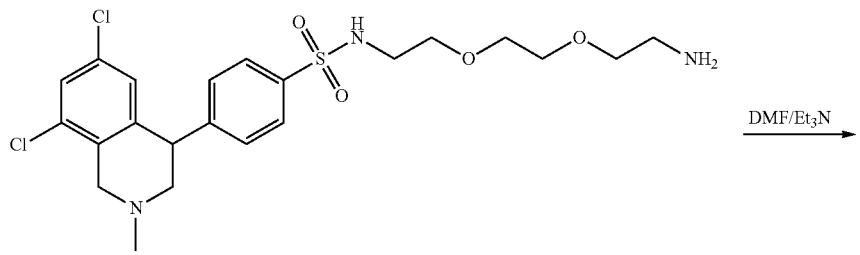

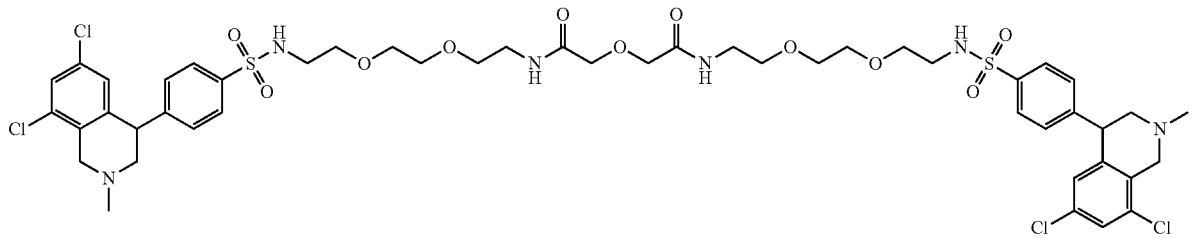

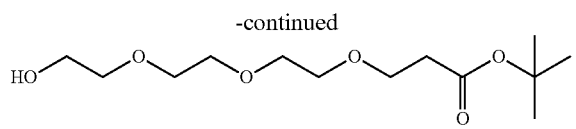

Intermediate 179.1, tert-butyl 3-(2-(2-(2-hydroxyethoxy)ethoxy)ethoxy)propanoate To triethyleneglycol (17.6 g, 117.20 mmol, 3.00 equiv) in anhydrous THF (70 mL), was added sodium (30 mg, 1.25 mmol, 0.03 equiv). Tert-butyl acrylate (5.0 g, 39.01 mmol, 1.00 equiv) was added after the sodium had dissolved. The resulting solution was stirred overnight at room temperature and then neutralized with 1.0 N hydrogen chloride. After removal of the solvent, the residue was suspended in 50 mL of brine and extracted with 3×50 mL of ethyl acetate. The combined organic layers were washed with saturated brine and dried over anhydrous sodium sulfate. After evaporation of the solvent, the tert-butyl 3-(2-(2-(2-hydroxyethoxy)ethoxy)ethoxy)propanoate (9.6 g) was isolated as a colorless oil, which was used directly for the next reaction step without further purification.

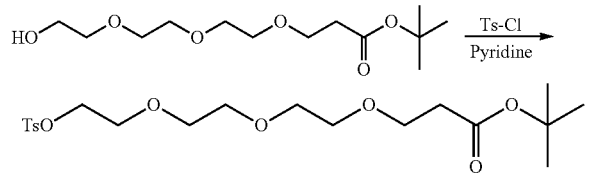

Intermediate 179.2, tert-butyl 3-(2-(2-(2-(tosyloxy)ethoxy)ethoxy)ethoxy)propanoate Into a 250-mL round-bottom flask purged and maintained with an inert atmosphere of nitrogen, was placed a solution of tert-butyl 3-(2-(2-(2-hydroxyethoxy)ethoxy)ethoxy)propanoate (intermediate 179.1) (9.6 g, 34.49 mmol, 1.00 equiv) in anhydrous pyridine (12 mL). The mixture was cooled to 0° C. and 4-methylbenzene-1-sulfonyl chloride (7.9 g, 41.44 mmol, 1.20 equiv) was added slowly in several portions. The resulting solution was stirred at 0° C. for 1-2 h and then the flask containing the reaction mixture was sealed and placed in a refrigerator at 0° C. overnight. The mixture was poured into 120 mL of water/ice, and the aqueous layer was extracted with 3×50 mL of DCM. The combined organic layers were washed with 2×50 mL of cold 1.0 N hydrogen chloride and saturated brine and dried over anhydrous sodium sulfate. The solvent was removed under vacuum to yield 13.4 g (90%) of tert-butyl 3-(2-(2-(2-(tosyloxy)ethoxy)ethoxy)ethoxy)propanoate as pale yellow oil.

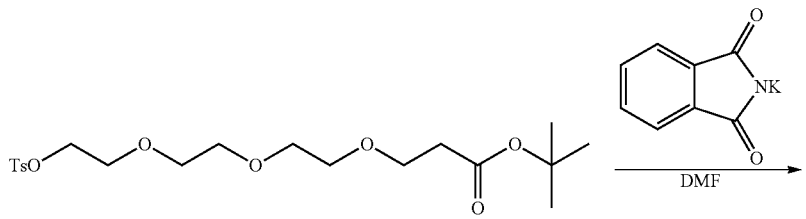

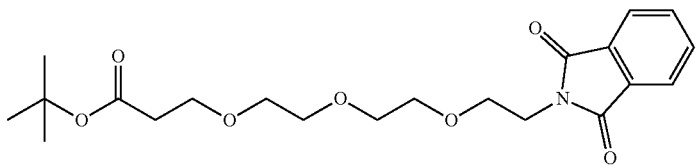

Intermediate 179.3, tert-butyl 3-(2-(2-(2-(1,3-dioxoisoindolin-2-yl)ethoxy)ethoxy)ethoxy)propanoate Into a 250-mL round-bottom flask purged and maintained with an inert atmosphere of nitrogen, was placed a solution of tert-butyl 3-(2-(2-(2-(tosyloxy)ethoxy)ethoxy)ethoxy)propanoate (13.4 g, 30.98 mmol, 1.00 equiv) in anhydrous DMF (100 mL) followed by potassium phthalimide (7.5 g, 40.49 mmol, 1.31 equiv). The resulting solution was heated to 100° C. and stirred for 3 h. The reaction progress was monitored by LCMS. The DMF was removed under vacuum to afford a brown oil residue. To the residue was added 200 mL water and the mixture was extracted with 3×50 mL of ethyl acetate. The combined organic layers were washed with saturated brine and dried over anhydrous sodium sulfate. After evaporation of solvent, The residue was applied onto a silica gel column with ethyl acetate/petroleum ether (0~1:3). The solvent was removed from fractions containing phthalimide and the residue was washed with 20% ethyl acetate/petroleum ether to yield 10.1 g (78%) of tert-butyl 3-(2-(2-(2-(1,3-dioxoisoindolin-2-yl)ethoxy)ethoxy)ethoxy)propanoate as pale yellow oil.

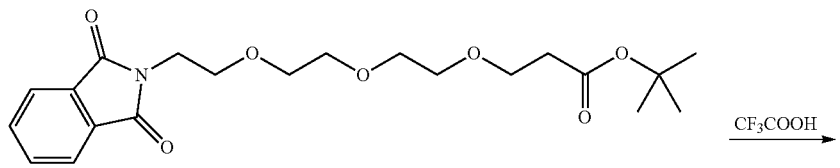

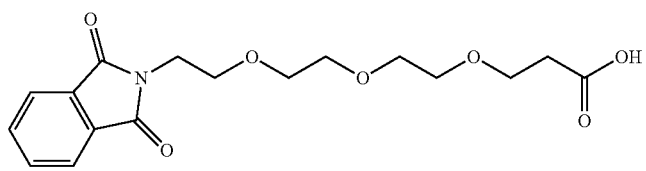

Intermediate 179.4, 3-(2-(2-(2-(1,3-dioxoisoindolin-2-yl)ethoxy)ethoxy)ethoxy)propanoic acid Into a 10-mL round-bottom flask purged and maintained with an inert atmosphere of nitrogen, was placed a solution of tert-butyl 3-(2-(2-(2-(1,3-dioxoisoindolin-2-yl)ethoxy)ethoxy)ethoxy)propanoate (intermediate 179.3) (1.5 g, 3.68 mmol, 1.00 equiv) in neat 2,2,2-trifluoroacetic acid (TFA; 2.0 mL). The resulting solution was stirred for 40 min at ambient temperature. Excess TFA was removed under vacuum to afford a pale-yellow oil residue which was purified on a silica gel column eluting with ethyl acetate/petroleum ether (1:5~1:2~2:1) to yield 1.1 g (84%) of 3-(2-(2-(2-(1,3-dioxoisoindolin-2-yl)ethoxy)ethoxy)ethoxy)propanoic acid as a white solid.

Intermediate 179.5, 3-(2-(2-(2-(1,3-dioxoisoindolin-2-yl)ethoxy)ethoxy)ethoxy)propanoyl chloride Into a 50-mL round-bottom flask purged and maintained with an inert atmosphere of nitrogen, was placed a solution of 3-(2-(2-(2-(1,3-dioxoisoindolin-2-yl)ethoxy)ethoxy)ethoxy)propanoic acid (700 mg, 1.99 mmol, 1.00 equiv) in anhydrous DCM (30.0 mL), then oxalyl dichloride (0.7 mL) was added dropwise at room temperature. Two drops of anhydrous DMF were then added. The resulting solution was heated to reflux for 40 min. The solvent was removed under vacuum to yield 750 mg of 3-(2-(2-(2-(1,3-dioxoisoindolin-2-yl)ethoxy)ethoxy)ethoxy)propanoyl chloride as pale yellow oil, which was used directly for the next reaction step without further purification.

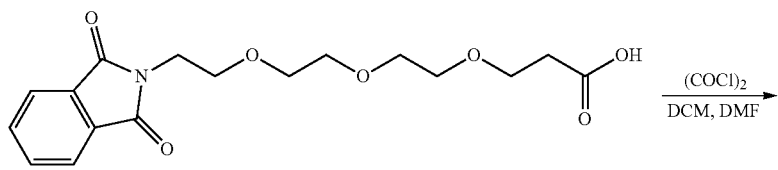

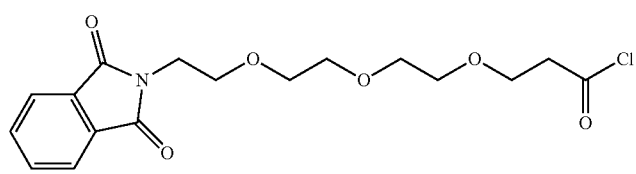

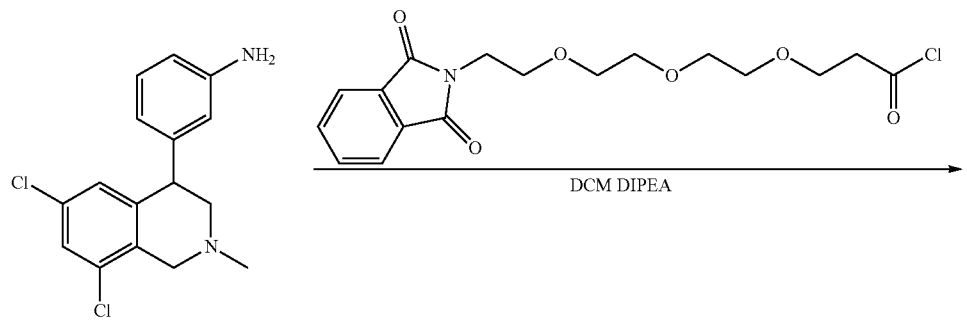

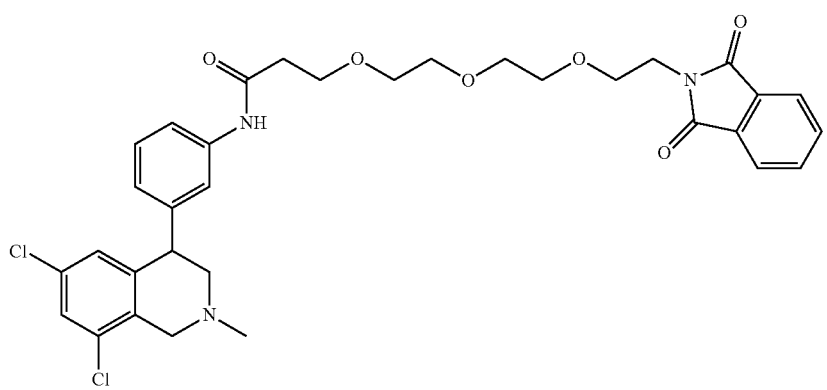

Intermediate 179.6, N-(3-(6,8-dichloro-2-methyl-1,2,3,4-tetrahydroisoquinolin-4-yl)phenyl)-3-(2-(2-(2-(1,3-dioxoisoindolin-2-yl)ethoxy)ethoxy)ethoxy)propanamide To 3-(6,8-dichloro-2-methyl-1,2,3,4-tetrahydroisoquinolin-4-yl)benzenamine (intermediate 31.5) (600.0 mg, 1.95 mmol, 1.00 equiv) in anhydrous DCM (5.0 mL) was added N-ethyl-N,N-diisopropylamine (DIEA; 0.5 mL). Then a solution of 3-(2-(2-(2-(1,3-dioxoisoindolin-2-yl)ethoxy)ethoxy)ethoxy)propanoyl chloride (intermediate 179.5) (794 mg, 2.15 mmol, 1.10 equiv) was added dropwise with stirring at room temperature. The resulting solution was stirred for 2 h at ambient temperature and then concentrated under vacuum. The residue was applied onto a silica gel column with DCM/methanol (100~50:1). This resulted in 870 mg (66%) of N-(3-(6,8-dichloro-2-methyl-1,2,3,4-tetrahydroisoquinolin-4-yl)phenyl)-3-(2-(2-(2-(1,3-dioxoisoindolin-2-yl)ethoxy)ethoxy)ethoxy)propanamide as a pale yellow syrup. The other fractions was collected and evaporated to get an additional 200 mg of impure product.

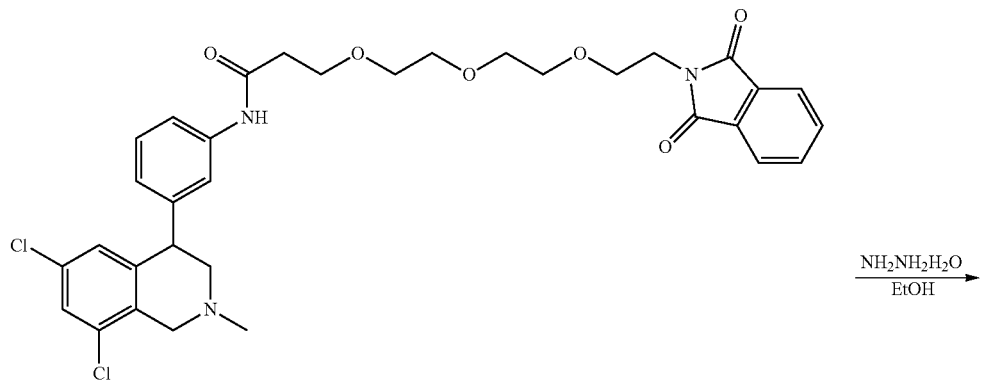

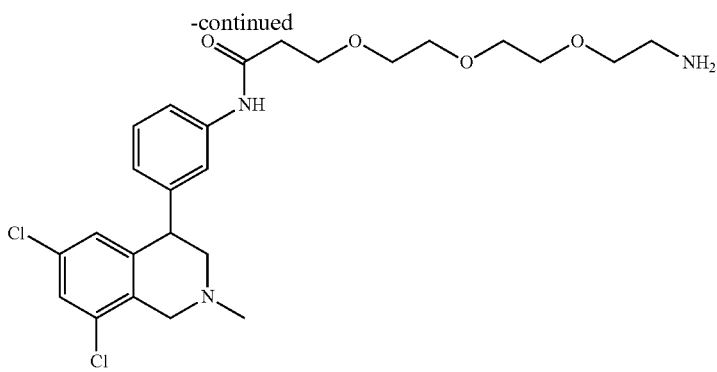

Intermediate 179.7, 3-(2-(2-(2-aminoethoxy)ethoxy)ethoxy)-N-(3-(6,8-dichloro-2-methyl-1,2,3,4-tetrahydroisoquinolin-4-yl)phenyl)propanamide Into a 100-mL round-bottom flask, was placed N-(3-(6,8-dichloro-2-methyl-1,2,3,4-tetrahydroisoquinolin-4-yl)phenyl)-3-(2-(2-(2-(1,3-dioxoisoindolin-2-yl)ethoxy)ethoxy)ethoxy)propanamide (870.0 mg, 1.36 mmol, 1.00 equiv) and 1 M hydrazine monohydrate in ethanol (30.0 mL, 30.0 mmol). The resulting solution was heated at reflux for 1 hour. The resulting mixture was cooled to room temperature and concentrated under vacuum. The residual solution was diluted with 30 mL of water and then extracted with 3×50 mL of DCM. The combined organic layers were washed with brine, dried over anhydrous sodium sulfate and concentrated under vacuum. The residue was applied onto a silica gel column with DCM/methanol (100~50:1~10:1~1:1). This resulted in 600 mg (85%) of 3-(2-(2-(2-aminoethoxy)ethoxy)ethoxy)-N-(3-(6,8-dichloro-2-methyl-1,2,3,4-tetrahydroisoquinolin-4-yl)phenyl)propanamide as a pale yellow syrup.

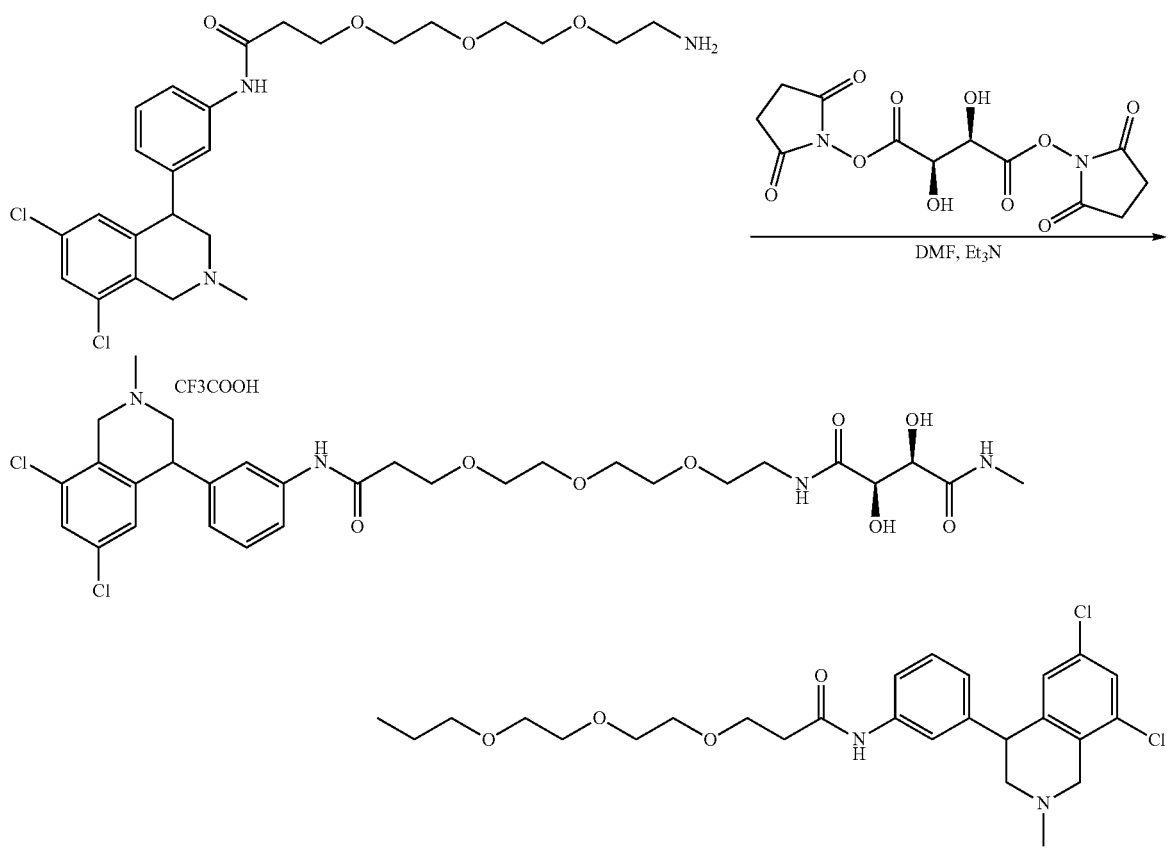

Compound 179, (2R,3R)—N1,N4-bis(2-(2-(2-(3-(3-(6,8-dichloro-2-methyl-1,2,3,4-tetrahydroisoquinolin-4-yl)phenylamino)-3-oxopropoxy)ethoxy)ethoxy)ethyl)-2,3-dihydroxysuccinamide To 3-(2-(2-(2-aminoethoxy)ethoxy)ethoxy)-N-(3-(6,8-dichloro-2-methyl-1,2,3,4-tetrahydroisoquinolin-4-yl)phenyl)propanamide (intermediate 179.7) (270 mg, 0.53 mmol, 2.00 equiv) in anhydrous DMF (5.0 mL) was added (2R,3R)-bis(2,5-dioxopyrrolidin-1-yl) 2,3-dihydroxysuccinate (prepared from (2R,3R)-tartaric acid as described in example 168) (91.0 mg, 0.26 mmol, 1.00 equiv) and triethylamine (0.3 mL) and the resulting solution was stirred for 2 h at 35° C. The resulting mixture was then concentrated under vacuum. The residue was purified by Prep-HPLC, to give 170 mg (56%) of a TFA salt of (2R,3R)—N1,N4-bis(2-(2-(2-(3-(3-(6,8-dichloro-2-methyl-1,2,3,4-tetrahydroisoquinolin-4-yl)phenylamino)-3-oxopropoxy)ethoxy)ethoxy)ethyl)-2,3-dihydroxysuccinamide as an off-white solid. $^1$H-NMR (300 MHz, CD$_3$OD, ppm): δ 7.92 (s, 1H), 7.65 (s, 2H), 7.54 (d, J=1.5 Hz, 2H), 7.36-7.46 (m, 4H), 7.02 (dd, J=7.5, 1.2 Hz, 2H), 6.90 (s, 2H), 4.83-4.75 (m, 2H), 4.65-4.60 (m, 2H), 4.53 (s, 1H), 4.46 (m, 3H), 3.88-3.80 (m, 6H), 3.64-3.51 (m, 22H), 3.41-3.35 (m, 4H), 3.16 (s, 6H), 2.64 (t, J=6.0 Hz, 4H). MS (m/z): 1136 [M+H]$^+$.

Example 180

N1,N2-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)oxalamide Compound 180, N1,N2-bis(2-(2-(2-(2-(3-(6,8-dichloro-2-methyl-1,2,3,4-tetrahydroisoquinolin-4-yl)phenylsulfonamido)ethoxy)ethoxy)ethoxy)-ethyl) oxalamide Compound 180 was prepared from compound 28 following the procedure outlined in example 175. The crude product (400 mg) was purified by Flash-Prep-HPLC with the following conditions: Column, C18 silica gel; mobile phase, CH$_3$CN/H$_2$O/CF$_3$COOH=39/100/0.05 increasing to CH$_3$CN/H$_2$O/CF$_3$COOH=39/100/0.05 within min; Detector, UV 254 nm. This resulted in 113.4 mg (11%) of a TFA salt of N1,N2-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)oxalamide as a white solid. $^1$H-NMR (300 MHz, DMSO+DCl, ppm): δ 7.766 (d, J=7.5 Hz, 2H), 7.683 (s, 2H), 7.586~7.637 (m, 4H), 7.537 (d, J=7.8 Hz, 2H), 6.644 (s, 2H), 4.834~4.889 (m, 2H), 4.598 (d, J=16.2 Hz, 2H), 4.446 (d, J=15.0 Hz, 2H), 3.602~3.763 (m, 4H), 3.299~3.436 (m, 24H), 3.224~3.263 (m, 4H), 2.975 (s, 6H), 2.825~2.863 (m, 4H). MS (m/z): 574 [M/2+H]$^+$.

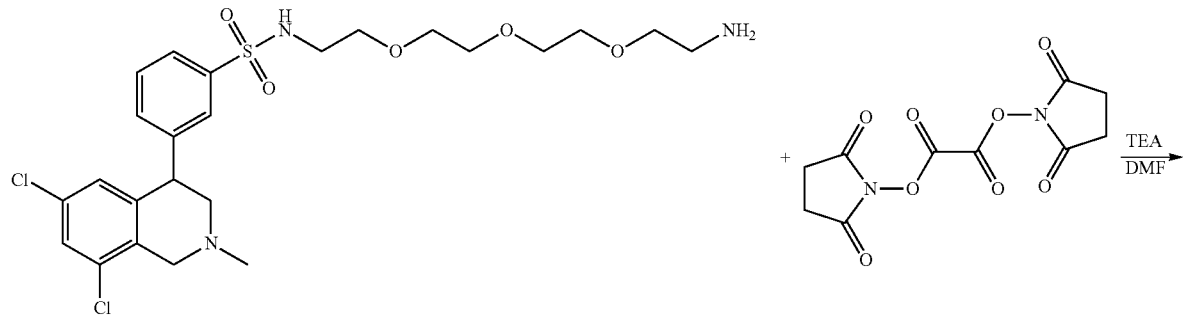

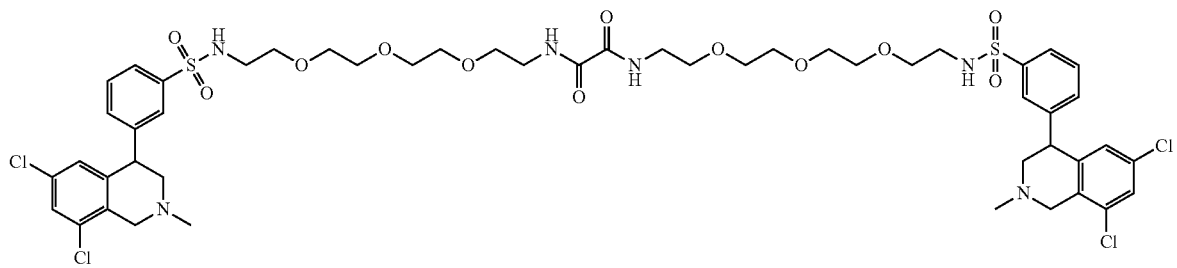

Example 181

N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)succinamide

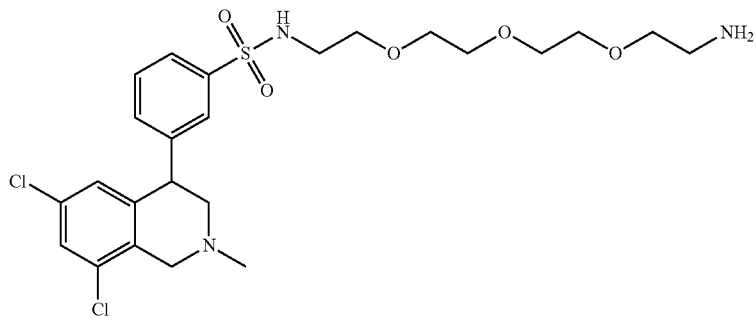

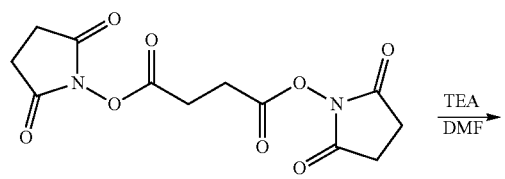

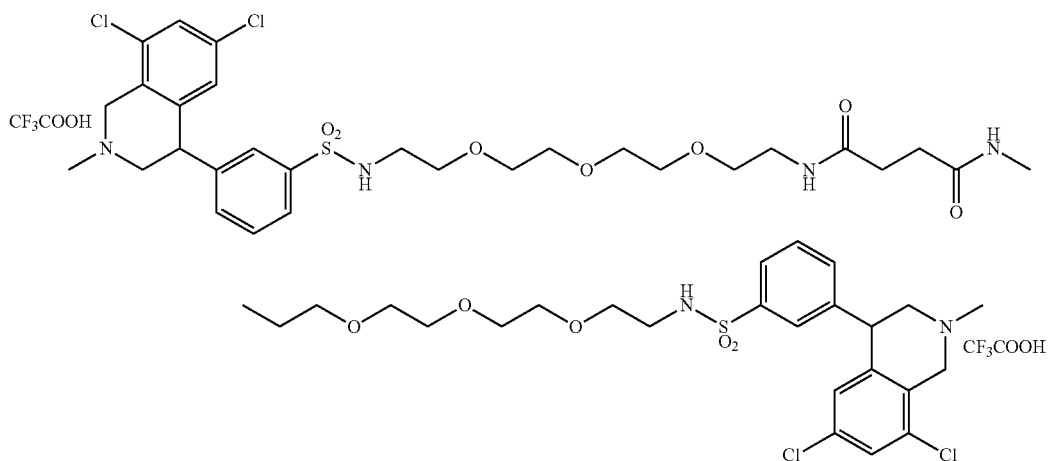

Compound 181, N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)succinamide Compound 181 was prepared from compound 28 and (2,5-dioxopyrrolidin-1-yl) succinate following the procedure outlined in example 175. The crude product (200 mg) was purified by Flash-Prep-HPLC with the following conditions: Column, C18 silica gel; mobile phase, $CH_3CN/H_2O/CF_3COOH=0.05/100/0.05$ increasing to $CH_3CN/H_2O/CF_3COOH=90/100/0.05$ within 19 min; Detector, UV 254 nm. This resulted in 201 mg (78%) of a TFA salt of N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)succinamide as a white solid. $^1$H-NMR (300 MHz, DMSO+DCl, ppm): δ 7.76 (d, J=7.5 Hz, 2H), 7.68 (s, 2H), 7.63~7.52 (m, 6H), 6.64 (s, 1H), 4.88~4.82 (m, 2H), 4.62~4.42 (m, 4H), 3.76~3.60 (m, 4H), 3.43~3.30 (m, 25H), 3.14~3.10 (m, 4H), 2.97 (s, 6H), 2.86~2.82 (m, 4H), 2.27 (s, 4H). MS (m/z): 589 [M/2+1]$^+$.

Example 182

N1,N3-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,2-dimethylmalonamide

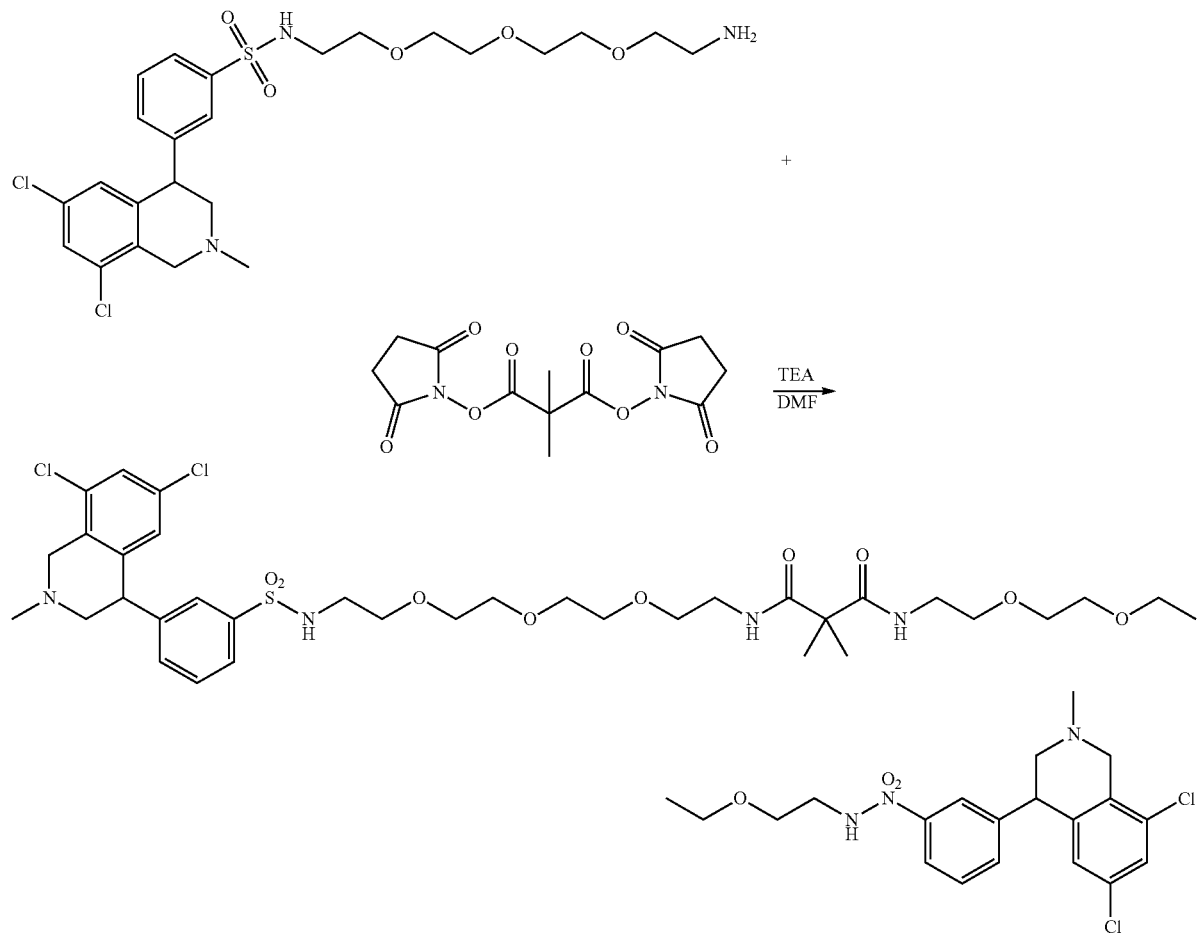

Compound 182, N1,N3-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,2-dimethylmalonamide Compound 182 was prepared from compound 28 and bis (2,5-dioxopyrrolidin-1-yl) 2,2-dimethylmalonate (prepared using the methods outlined in example 168) following the procedure outlined in example 175. The crude product (250 mg) was purified by Prep-HPLC with the following conditions: Column, C18 silica gel; mobile phase, MeCN/H$_2$O/CF$_3$COOH=39/100/0.05; Detector, UV 254 nm. This resulted in 152.3 mg (47%) of a TFA salt of N1,N3-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,2-dimethylmalonamide as a white solid. $^1$H-NMR (300 MHz, CDCl$_3$, ppm): δ 7.92~7.89 (d, J=8.1 Hz, 2H), 7.79 (s, 2H), 7.6~97.64 (m, 2H), 7.57~7.55 (d, J=7.5 Hz, 4H), 3.68 (s, 2H), 4.87~4.75 (m, 4H), 4.5~44.49 (m, 2H), 3.90~3.88 (m, 2H), 3.67~3.45 (m, 20H), 3.3~93.32 (m, 4H), 3.31 (s, 6H), 3.17~3.05 (m, 4H), 1.41 (s, 1H). MS (m/z): 1189 [M+H]$^+$.

Example 183

N1,N3-bis(2-(2-(2-(4-(6,8-dichloro-2-methyl-1,2,3,4-tetrahydroisoquinolin-4-yl)phenylsulfonamido)ethoxy)ethoxy)ethyl)-2,2-dimethylmalonamide

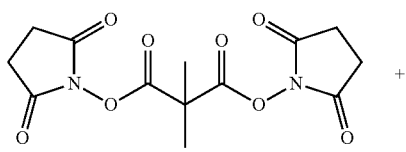

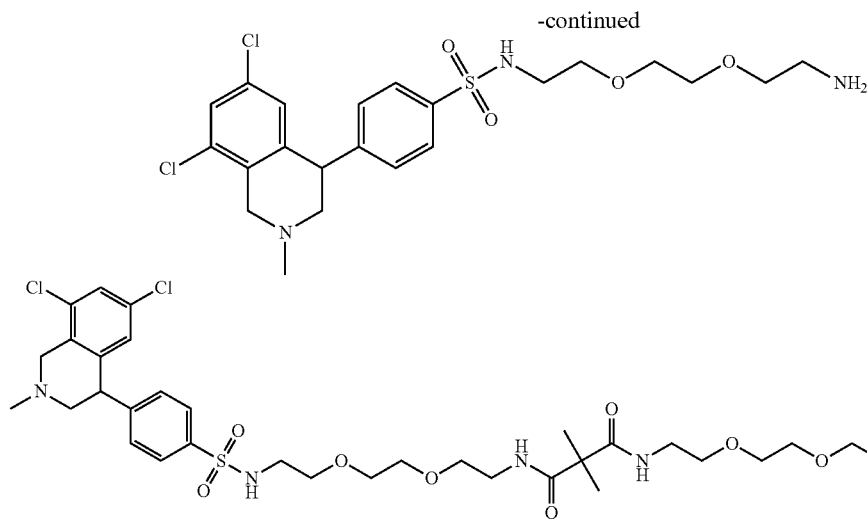

Example 183, N1,N3-bis(2-(2-(2-(4-(6,8-dichloro-2-methyl-1,2,3,4-tetrahydroisoquinolin-4-yl)phenylsulfonamido)ethoxy)ethoxy)ethyl)-2,2-dimethylmalonamide Compound 183 was prepared from intermediate 175.1 and bis(2,5-dioxopyrrolidin-1-yl) 2,2-dimethylmalonate (prepared using the methods outlined in example 168) following the procedure outlined in example 175. The crude product was purified by Prep-HPLC with acetonitrile:water (0.05% CF₃COOH)(10%-100%). This resulted in 29.5 mg (5%) of a TFA salt of N1,N3-bis(2-(2-(2-(4-(6,8-dichloro-2-methyl-1,2,3,4-tetrahydroisoquinolin-4-yl)phenylsulfonamido)ethoxy)ethyl)-2,2-dimethylmalonamide as a white solid. $^1$H-NMR (300 MHz, CD$_3$OD, ppm): δ 7.94-7.92 (m, 4H), 7.57 (m, 2H), 7.51-7.49 (m, 4H), 6.87 (m, 2H), 4.83-4.74 (m, 4H), 4.55-4.50 (m, 2H), 3.92-3.87 (m, 2H), 3.67-3.48 (m, 8H), 3.40-3.38 (m, 4H), 3.18 (s, 6H), 3.14-3.00 (m, 4H), 1.41 (s, 6H). MS (m/z): 551 [½M+H]$^+$.

Example 184

N,N'-(2,2'-(2,2'-(2,2'-(2,2'-(pyridine-2,6-diylbis(oxy))bis(ethane-2,1-diyl))bis(oxy)bis(ethane-2,1-diyl))bis(oxy)bis(ethane-2,1-diyl))bis(oxy)bis(ethane-2,1-diyl))bis(3-(6,8-dichloro-2-methyl-1,2,3,4-tetrahydroisoquinolin-4-yl)benzenesulfonamide

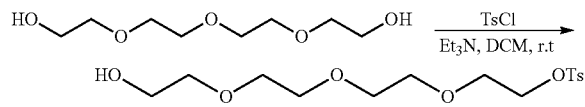

Intermediate 184.1, 2-(2-(2-(2-hydroxyethoxy)ethoxy)ethyl 4-methylbenzenesulfonate Into a 250-mL round-bottom flask was placed a solution of tetraethylene glycol (50 g, 257.47 mmol, 9.81 equiv) in DCM (150 mL) and triethylamine (8 g, 79.05 mmol, 3.01 equiv). This was followed by the addition of a solution of 4-methylbenzene-1-sulfonyl chloride (5.0 g, 26.23 mmol, 1.00 equiv) in DCM (10 mL) dropwise with stirring at 0° C. The resulting solution was stirred for 2 h at room temperature, at which time it was diluted with 200 ml of hydrogen chloride (3N aq.). The resulting solution was extracted with 2×150 mL of DCM and the combined organic layers were washed with 3×150 mL of saturated sodium bicarbonate. The mixture was dried over sodium sulfate and concentrated under vacuum. The residue was applied onto a silica gel column with ethyl acetate/petroleum ether (1:5~ethyl acetate). This resulted in 7.0 g (77%) of 2-(2-(2-(2-hydroxyethoxy)ethoxy)ethoxy)ethyl 4-methylbenzenesulfonate as colorless oil.

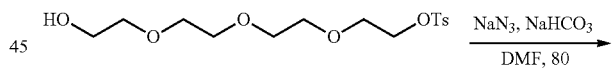

Intermediate 184.2, 2-(2-(2-(2-azidoethoxy)ethoxy)ethoxy)ethanol

To intermediate 184.1 (2.0 g, 5.74 mmol, 1.00 equiv) in DMF (40 mL) was added sodium azide (700 mg, 10.77 mmol, 1.88 equiv) and sodium bicarbonate (800 mg, 9.52 mmol, 1.66 equiv). The resulting solution was stirred for 2 h at 80° C. at which time the mixture was concentrated under vacuum. The residue was diluted with 100 mL of water and then extracted with 3×100 mL of DCM. The organic layers were combined and concentrated under vacuum to afford 1.3 g of 2-(2-(2-(2-azidoethoxy)ethoxy)ethoxy)ethanol as light yellow oil.

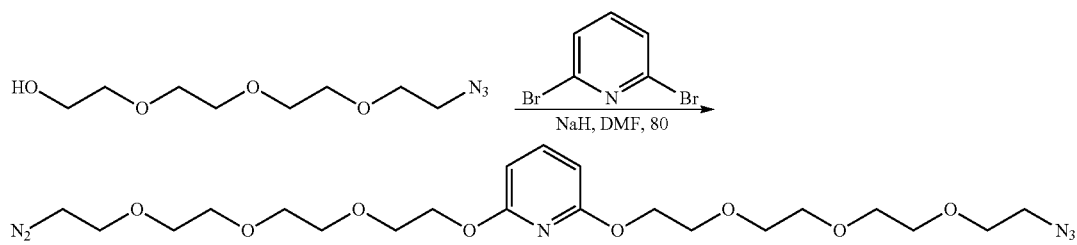

Intermediate 184.3, 2,6-bis(2-(2-(2-(2-azidoethoxy)ethoxy)ethoxy)ethoxy)pyridine Into a 50-mL round-bottom flask, was placed a solution of intermediate 184.2 (220 mg, 1.00 mmol, 2.38 equiv) in DMF (10 mL) and sodium hydride (40 mg, 1.00 mmol, 2.37 equiv, 60%). The resulting solution was stirred for 30 min at room temperature, at which time 2,6-dibromopyridine (100 mg, 0.42 mmol, 1.00 equiv) was added. The resulting solution was stirred for an additional 2 h at 80° C., and then was concentrated under vacuum. The residue was applied onto a silica gel column with DCM/methanol (50:1-30:1). This resulted in 180 mg (83%) of 2,6-bis(2-(2-(2-(2-azidoethoxy)ethoxy)ethoxy)ethoxy)pyridine as light yellow oil.

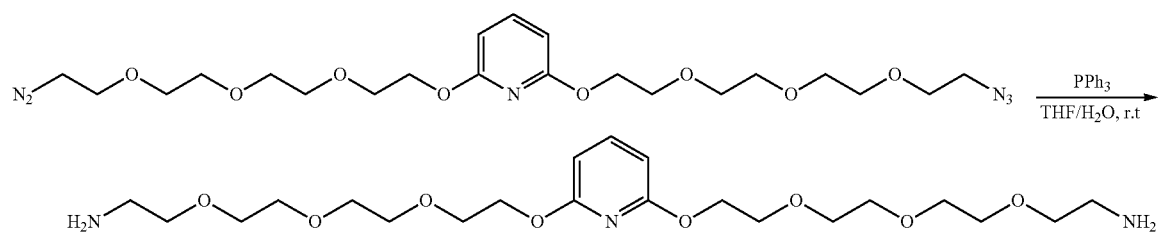

Intermediate 184.4, 2-(2-(2-(2-(6-(2-(2-(2-(2-aminoethoxy)ethoxy)ethoxy)ethoxy)pyridin-2-yloxy)ethoxy)ethoxy)ethoxy)ethanamine To intermediate 184.3 (180 mg, 0.35 mmol, 1.00 equiv) in THF/water (30/3 mL) was added triphenylphosphine (400 mg, 1.52 mmol, 4.35 equiv) and the resulting solution was stirred overnight at 40° C. After cooling to room temperature, the reaction mixture was extracted with 4×50 mL of DCM and the organic layers combined and dried over anhydrous sodium sulfate and concentrated under vacuum. The residue was applied onto a silica gel column with DCM/methanol (80:1~20:1). This resulted in 100 mg (62%) of 2-(2-(2-(2-(6-(2-(2-(2-(2-aminoethoxy)ethoxy)ethoxy)ethoxy)pyridin-2-yloxy)ethoxy)ethoxy)ethoxy)ethanamine as light yellow oil.

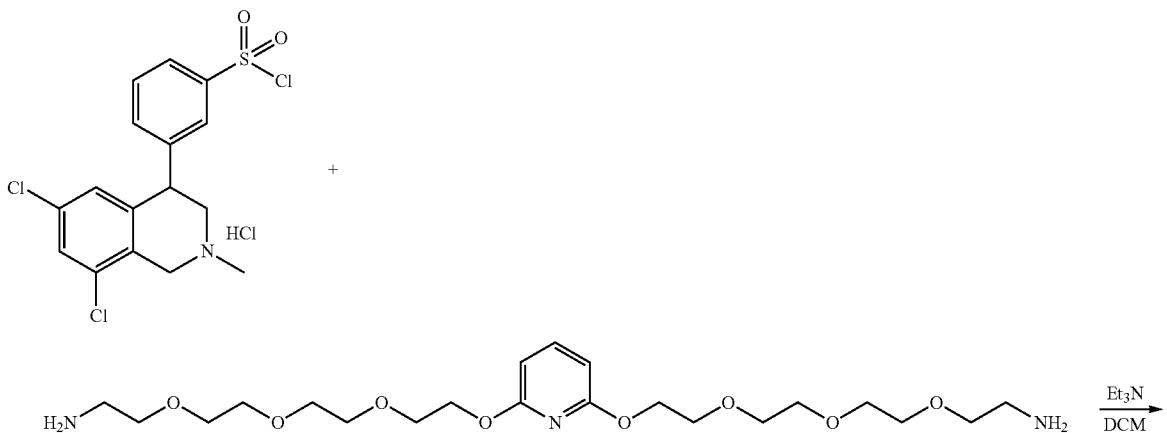

-continued

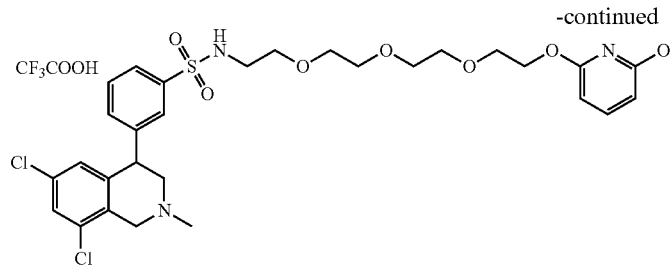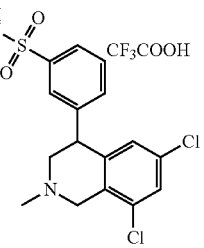

343

Compound 184, N,N'-(2,2'-(2,2'-(2,2'-(2,2'-(pyridine-2,6-diylbis(oxy))bis(ethane-2,1-diyl))bis(oxy)bis(ethane-2,1-diyl))bis(oxy)bis(ethane-2,1-diyl))bis(oxy)bis(ethane-2,1-diyl))bis(3-(6,8-dichloro-2-methyl-1,2,3,4-tetrahydroisoquinolin-4-yl)benzenesulfonamide)

To intermediate 184.4 (100 mg, 0.22 mmol, 1.00 equiv) in DCM (50 mL) was added triethylamine (70 mg, 0.69 mmol, 3.20 equiv) and 3-(6,8-dichloro-2-methyl-1,2,3,4-tetrahydroisoquinolin-4-yl)benzene-1-sulfonyl chloride (350 mg, 0.90 mmol, 4.13 equiv). The resulting solution was stirred overnight at room temperature, and then concentrated under vacuum. The residue was purified by Prep-HPLC with CH$_3$CN:H$_2$O (0.05% CF$_3$COOH)=35%-40%. This resulted in 88.4 mg (29%) of a TFA salt of the title compound as a white solid. $^1$H-NMR (300 MHz, CD$_3$OD, ppm): δ 7.91-7.88 (d, 2H), 7.78 (s, 2H), 7.67-7.50 (m, 7H), 6.86 (s, 2H), 6.34-6.31 (d, 2H), 4.90-4.75 (m, 4H), 4.52-4.46 (m, 2H), 4.42-4.39 (t, 4H), 3.90-3.81 (m, 6H), 3.71-3.43 (m, 22H), 3.16 (s, 6H), 3.07-3.03 (t, 4H). MS (m/z): 1170 [M+H]$^+$

344

Example 185

2,2'-(methylazanediyl)bis(N-(2-(2-(2-(4-(6,8-dichloro-2-methyl-1,2,3,4-tetrahydroisoquinolin-4-yl)phenylsulfonamido)ethoxy)ethoxy)ethyl)acetamide)tris(2,2,2-trifluoroacetate)

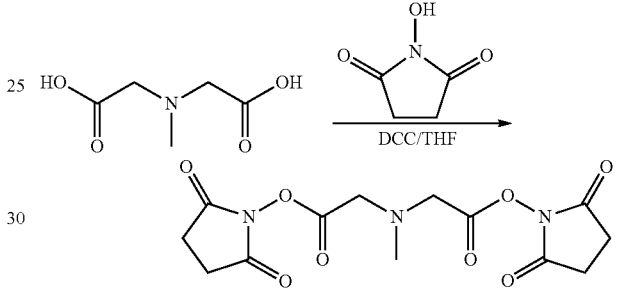

Intermediate 185.1, bis(2,5-dioxopyrrolidin-1-yl) 2,2'-(methylazanediyl)diacetate To 2-[(carboxymethyl)(methyl)amino]acetic acid (2.0 g, 13.60 mmol, 1.00 equiv) in THF (30 mL) was added DCC (6.2 g, 30.05 mmol, 2.21 equiv) and a solution of NHS (3.5 g, 30.41 mmol, 2.24 equiv) in THF (30 mL) and the reaction stirred at 0-10° C. for 2 h. The resulting solution was allowed to warm to room temperature and stirred for 16 h. The solids were then filtered out, and the resulting mixture was concentrated under vacuum. The crude product was re-crystallized from ethyl acetate/petroleum ether in the ratio of 1:10. to afford 2.0 g (21%) of the title compound as a white solid.

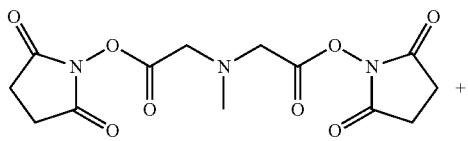 +

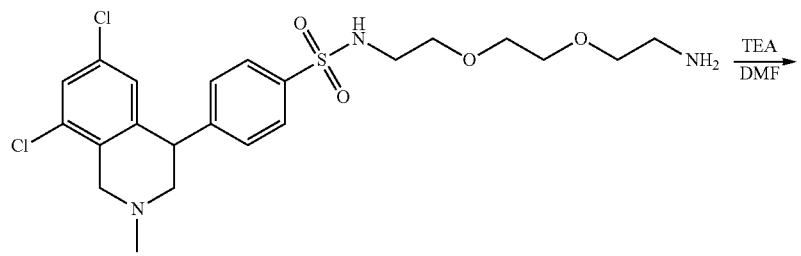

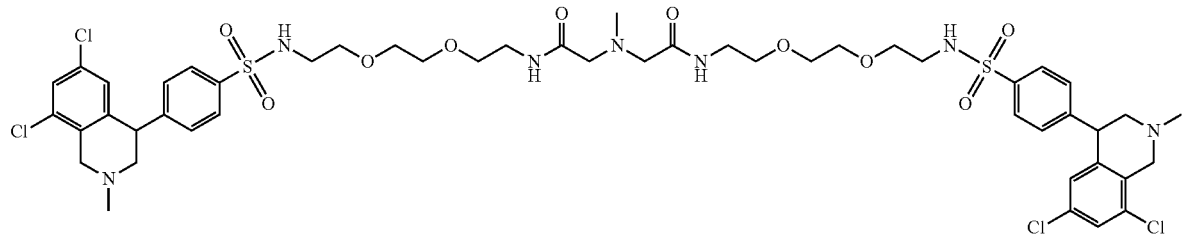

Compound 185, 2,2'-(methylazanediyl)bis(N-(2-(2-(2-(4-(6,8-dichloro-2-methyl-1,2,3,4-tetrahydroisoquinolin-4-yl)phenylsulfonamido)ethoxy)ethoxy)ethyl)-acetamide)tris(2,2,2-trifluoroacetate)

To N-(2-(2-(2-aminoethoxy)ethoxy)ethyl)-4-(6,8-dichloro-2-methyl-1,2,3,4-tetrahydroisoquinolin-4-yl)benzenesulfonamide (150 mg, 0.30 mmol, 1.00 equiv) in DMF (3 mL) was added intermediate 185.1 (106 mg, 0.15 mmol, 0.50 equiv, 48%) and triethylamine (150 mg, 1.48 mmol, 4.97 equiv) and the reaction was stirred overnight. The mixture was concentrated under vacuum and the crude product was purified by Prep-HPLC with $CH_3CN:H_2O$ (0.05% $CF_3COOH$) to afford 26.4 mg (12%) of a TFA salt of the title compound as a white solid. $^1$H-NMR (300 MHz, $CD_3OD$, ppm): δ 7.92 (m, 4H), 7.5 (m, 2H), 7.50 (m, 4H), 6.85 (s, 2H), 4.81 (m, 4H), 4.50 (m, 2H), 4.06 (s, 4H), 3.89 (m, 2H), 3.66-3.44 (m, 22H), 3.32 (s, 6H), 3.15 (m, 4H), 3.01 (s, 3H). MS (m/z): 559 [(M+2H)/2]$^+$ Example 186

5-amino-N1,N3-bis(2-(2-(2-(4-(6,8-dichloro-2-methyl-1,2,3,4-tetrahydroisoquinolin-4-yl)phenylsulfonamido)ethoxy)ethoxy)ethyl)isophthalamide tris(2,2,2-trifluoroacetate)

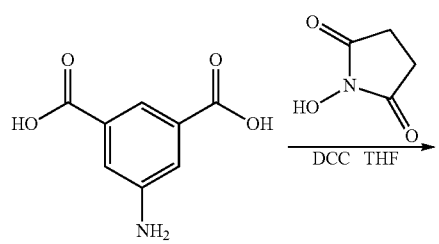

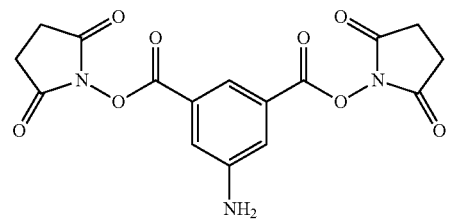

Intermediate 186.1, bis(2,5-dioxopyrrolidin-1-yl) 5-aminoisophthalate

Into a 50-mL 3-necked round-bottom flask, was placed a solution of 5-aminoisophthalic acid (300 mg, 1.66 mmol, 1.00 equiv) in THF (5 mL) and 1-hydroxypyrrolidine-2,5-dione (420 mg, 3.65 mmol, 2.20 equiv). This was followed by the addition of a solution of DCC (750 mg, 3.64 mmol, 2.20 equiv) in THF (5 mL) dropwise with stirring at 0° C. The resulting solution was stirred overnight at room temperature. The solids were removed by filtration and the filtrate was concentrated under vacuum. The crude product was purified by re-crystallization from ethanol. This resulted in 70 mg (11%) of the title compound as a light yellow solid.

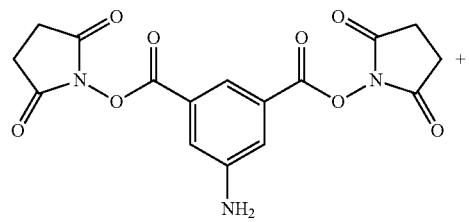
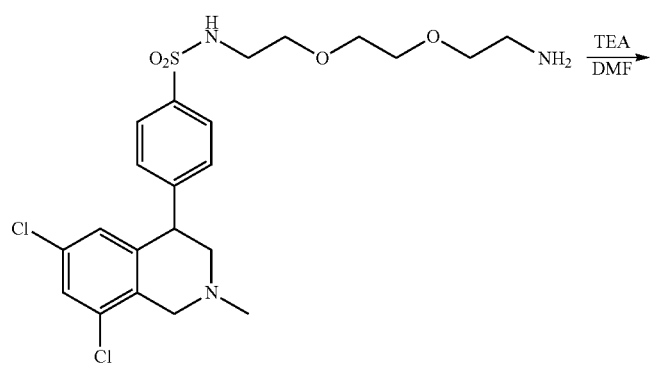

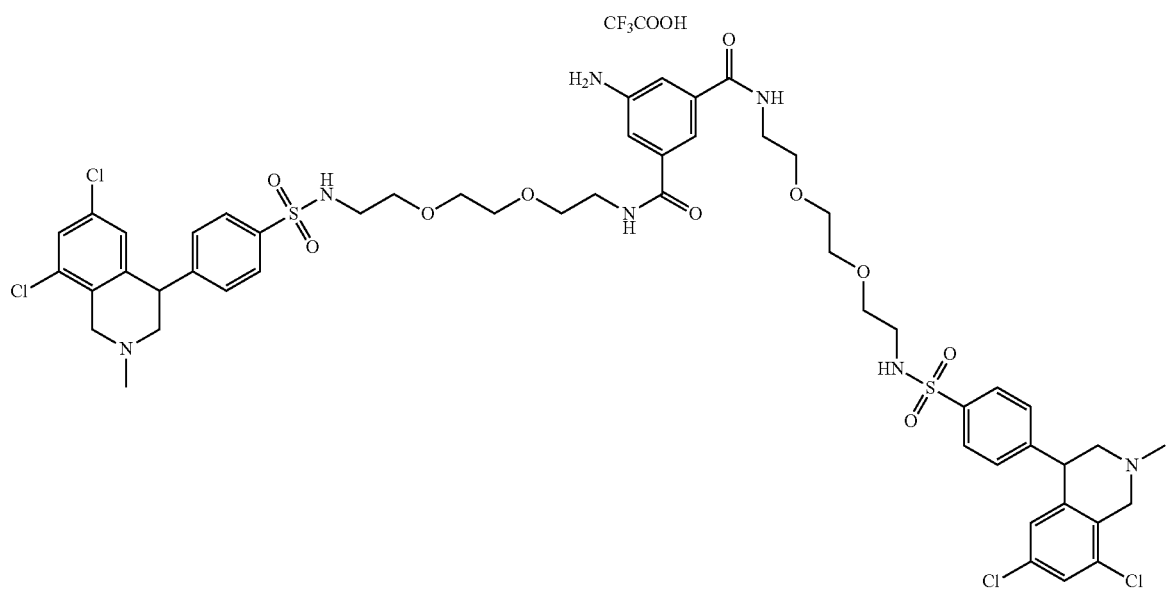

Compound 186, 5-amino-N1,N3-bis(2-(2-(2-(4-(6,8-dichloro-2-methyl-1,2,3,4-tetrahydroisoquinolin-4-yl)phenylsulfonamido)ethoxy)ethoxy)ethyl)isophthalamide tris(2,2,2-trifluoroacetate)

To N-(2-(2-(2-aminoethoxy)ethoxy)ethyl)-4-(6,8-dichloro-2-methyl-1,2,3,4-tetrahydroisoquinolin-4-yl)benzenesulfonamide (100 mg, 0.20 mmol, 1.00 equiv) in DMF (5 mL) was added intermediate 186.1 (44.8 mg, 0.12 mmol, 0.60 equiv) and triethylamine (60.4 mg, 0.60 mmol, 3.00 equiv) and the reaction was stirred overnight. The resulting mixture was concentrated under vacuum and the crude product was purified by Prep-HPLC with $CH_3CN:H_2O$ (0.05% $CF_3COOH$) to afford 32.4 mg (19%) of a TFA salt of the title compound as a white solid. $^1$H-NMR (300 MHz, $CD_3OD$, ppm): δ 7.90-7.87 (d, J=8.4 Hz, 4H), 7.60-7.54 (3H, m), 7.46-7.44 (d, J=8.4 Hz, 4H), 7.34 (d, J=1.2 Hz, 2H), 6.82 (s, 2H), 4.89-4.71 (m, 4H), 4.53-4.48 (d, J=16.2 Hz, 2H), 3.91-3.85 (m, 2H), 3.67-3.45 (m, 22H), 3.33-3.32 (m, 6H), 3.18-3.01 (m, 4H). MS (m/z): 575 [(M+2H)/2]$^+$

Example 187

2,2'-oxybis(N-(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)acetamide)

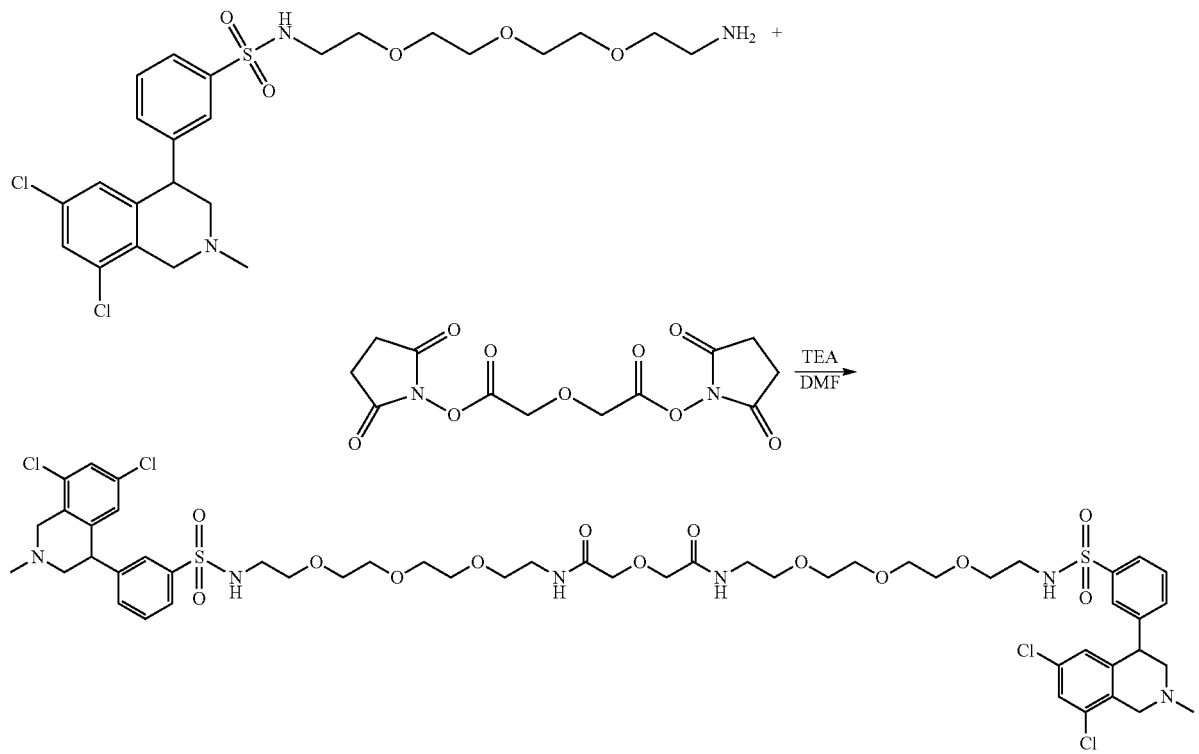

Compound 187, 2,2'-oxybis(N-(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)acetamide)

Into a 50-mL round-bottom flask, was placed a solution of N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (compound 28) (150 mg, 0.28 mmol, 1.00 equiv) in DMF (5 mL), triethylamine (56 mg, 0.55 mmol, 2.01 equiv) and bis(2,5-dioxopyrrolidin-1-yl) 2,2'-oxydiacetate (intermediate 178.1) (44 mg, 0.14 mmol, 0.49 equiv). The resulting solution was stirred overnight at room temperature, at which time the mixture was concentrated under vacuum. The crude product (150 mg) was purified by preparative HPLC with the following conditions: Column, C18 silica gel; mobile phase, methanol/water=0.05/100 increasing to methanol/water=90/100 within 19 min; Detector, UV 254 nm. This resulted in 72.4 mg (44%) of the title compound as a white solid. $^{1}$H-NMR (300 MHz, CD$_3$OD, ppm): δ 7.79 (d, J=7.2 Hz, 2H), 7.71 (s, 2H), 7.4~97.58 (m, 4H), 7.36~7.37 (m, 2H), 6.82 (s, 2H), 4.39~4.44 (m, 2H), 4.06 (s, 4H), 3.80 (d, J=16.2 Hz, 2H), 3.65 (d, J=16.2 Hz, 2H), 3.55~3.61 (m, 16H), 3.4~33.52 (m, 12H), 3.0~23.08 (m, 6H), 2.65~2.70 (m, 2H), 2.49 (s, 6H). MS (m/z): 1190 [M+H]$^+$

Example 188

5-bromo-N1,N3-bis(2-(2-(2-(4-(6,8-dichloro-2-methyl-1,2,3,4-tetrahydroisoquinolin-4-yl)phenylsulfonamido)ethoxy)ethoxy)ethyl)isophthalamide bis(2,2,2-trifluoroacetate)

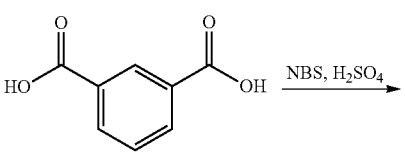

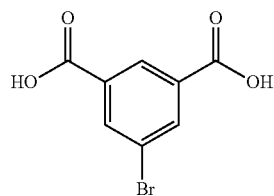

Intermediate 188.1, 5-bromoisophthalic acid

Into a 100-mL round-bottom flask, was placed a solution of isophthalic acid (10 g, 60.24 mmol, 1.00 equiv) in 98% H$_2$SO$_4$ (60 mL). This was followed by the addition of N-bromosuccinimide (12.80 g, 72.32 mmol, 1.20 equiv), in portions at 60° C. in 10 min. The resulting solution was stirred overnight at 60° C. in an oil bath. The reaction was cooled to room temperature and then quenched by the addition of water/ice. The solids were collected by filtration, and washed with 2×60 mL of hexane. The solid was dried in an oven under reduced pressure. The crude product was purified by re-crystallization from ethyl acetate to give 3 g (20%) of 5-bromoisophthalic acid as a white solid.

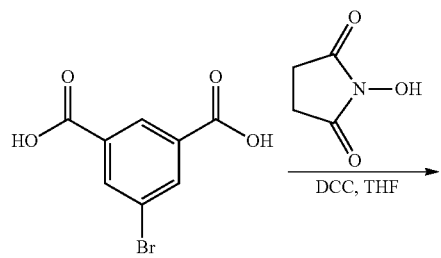

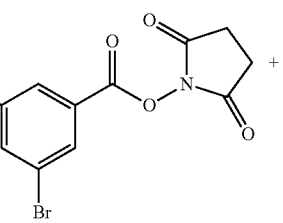

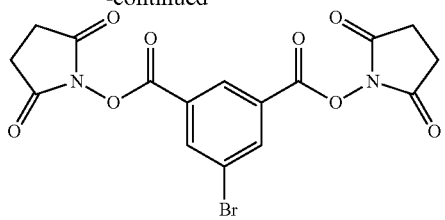

Intermediate 188.2, bis(2,5-dioxopyrrolidin-1-yl) 5-bromoisophthalate

Into a 100-mL round-bottom flask purged and maintained with an inert atmosphere of nitrogen, was placed a solution of 5-bromoisophthalic acid (3 g, 11.76 mmol, 1.00 equiv, 96%) in THF (20 mL) followed by NHS (3 g, 26.09 mmol, 2.20 equiv) at 0-5° C. To this was added a solution of DCC (5.6 g, 27.18 mmol, 2.20 equiv) in THF (20 mL) dropwise with stirring at 0-5° C. The resulting solution was stirred overnight at room temperature. The solids were filtered out and the filtrate was concentrated under vacuum. The crude product was re-crystallized from DCM/ethanol in the ratio of 1:10. This resulted in 4 g (75%) of the title compound as a white solid.

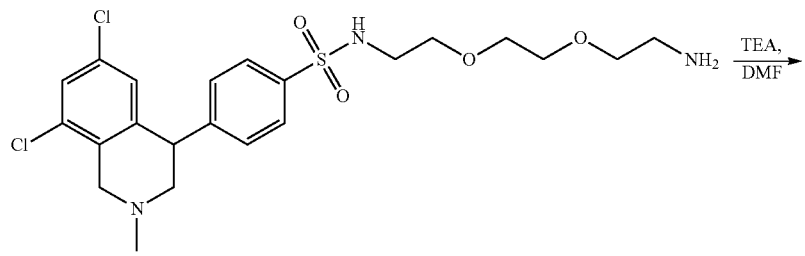

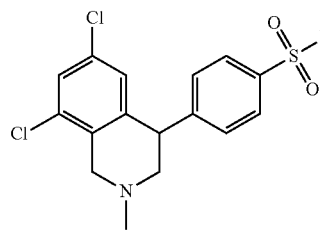

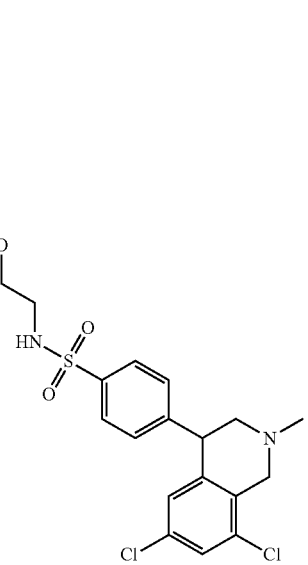

Compound 188, 5-bromo-N1,N3-bis(2-(2-(2-(4-(6,8-dichloro-2-methyl-1,2,3,4-tetrahydroisoquinolin-4-yl)phenylsulfonamido)ethoxy)ethoxy)ethyl)isophthalamide bis(2,2,2-trifluoroacetate Into a 50-mL round-bottom flask purged and maintained with an inert atmosphere of nitrogen, was placed a solution of N-(2-(2-(2-aminoethoxy)ethoxy)ethyl)-3-(6,8-dichloro-2-methyl-1,2,3,4-tetrahydroisoquinolin-4-yl)benzenesulfonamide (intermediate 175.1) (100 mg, 0.19 mmol, 2.50 equiv, 95%) in DMF (8 mL), intermediate 188.1 (35 mg, 0.08 mmol, 1.00 equiv, 98%) and triethylamine (32 mg, 0.32 mmol, 4.00 equiv). The resulting solution was stirred overnight at room temperature and then concentrated to dryness. The crude product was purified by Prep-HPLC with acetonitrile:water (0.05% CF$_3$COOH)=30%~42%. This resulted in 86 mg (75%) of a TFA salt of the title compound as a white solid. $^1$H-NMR (300 MHz, CD$_3$OD, ppm): δ 8.26 (s, 1H), 8.13 (s, 2H), 7.90 (d, J=9 Hz, 4H), 7.55 (s, 2H), 7.48 (d, J=9 Hz, 4H), 6.84 (s, 2H), 4.76 (m, 4H), 4.54 (m, 2H), 3.89 (m, 2H), 3.68 (m, 18H), 3.53 (m, 4H), 3.33 (s, 6H), 3.18 (m, 4H). MS (m/z): 609 [(M+2H)/2]$^+$ Example 189

N1,N3-bis(2-(2-(2-(4-(6,8-dichloro-2-methyl-1,2,3,4-tetrahydroisoquinolin-4-yl)phenylsulfonamido)ethoxy)ethoxy)ethyl)-2-hydroxymalonamide bis(2,2,2-trifluoroacetate)

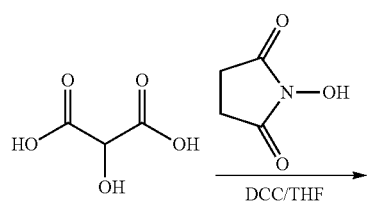

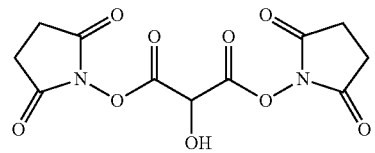

Intermediate 189.1, bis(2,5-dioxopyrrolidin-1-yl) 2-hydroxymalonate

Into a 100 ml 3-necked roundbottom flask purged and maintained with an inert atmosphere of nitrogen, was placed a solution of 2-hydroxymalonic acid (1.6 g, 13.32 mmol, 1.00 equiv) in THF (30 mL) and DCC (6.2 g, 30.05 mmol, 2.26 equiv). This was followed by the addition of a solution of NHS (3.5 g, 30.41 mmol, 2.28 equiv) in THF (30 mL) at 0-10° C. in 2 h. The resulting solution was stirred for 16 h at room temperature. The solids were then filtered out and the filtrate was concentrated under vacuum. The crude product was re-crystallized from ethanol to give 0.5 g (12%) of the title compound as a white solid.

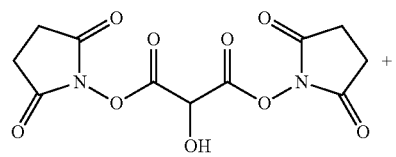
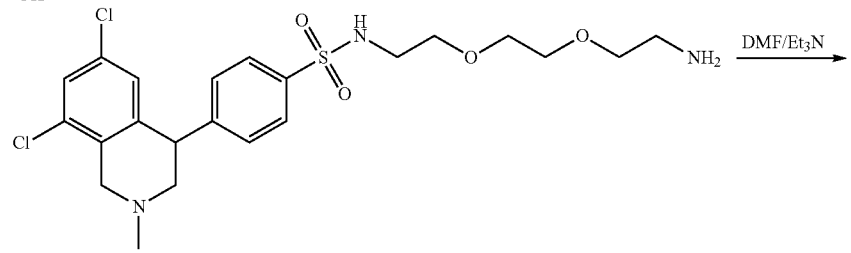
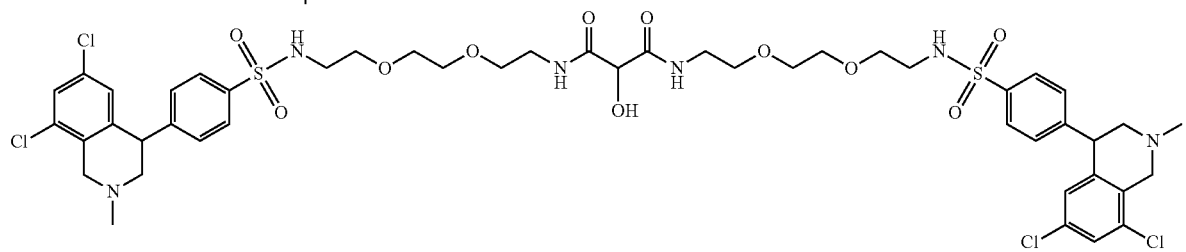

Compound 189, N1,N3-bis(2-(2-(2-(4-(6,8-dichloro-2-methyl-1,2,3,4-tetrahydroisoquinolin-4-yl)phenyl-sulfonamido)ethoxy)ethoxy)ethyl)-2-hydroxymalonamide bis(2,2,2-trifluoroacetate)

To N-(2-(2-(2-aminoethoxy)ethoxy)ethyl)-4-(6,8-dichloro-2-methyl-1,2,3,4-tetrahydroisoquinolin-4-yl)benzenesulfonamide (intermediate 175.1) (100 mg, 0.20 mmol, 1.00 equiv) in DMF (2 mL), was added Intermediate 189.1 (29 mg, 0.10 mmol, 0.45 equiv) and triethylamine (90 mg, 4.50 equiv) and the reaction was stirred for 3 h at 30° C. The mixture was concentrated under vacuum and the crude product was purified by Prep-HPLC with acetonitrile:water (0.05% CF3COOH) (10%-100%) to afford 36.5 mg (30%) of a TFA salt of the title compound as a white solid. $^1$H-NMR (300 MHz, CD$_3$OD, ppm): δ 7.94-7.91 (m, 4H), 7.57-7.56 (m, 2H), 7.51-7.48 (m, 4H), 6.87 (m, 2H), 4.82-4.76 (m, 4H), 4.54-4.49 (m, 2H), 3.93-3.91 (s, 4H), 3.89-3.87 (m, 2H), 3.66-3.42 (m, 22H), 3.17 (s, 6H), 3.13-3.09 (m, 4H). MS (m/z): 546 [(M+2H)/2]$^+$ Example 190

N1,N2-bis(2-(2-(2-(3-(6,8-dichloro-2-methyl-1,2,3,4-tetrahydroisoquinolin-4-yl)phenylsulfonamido)ethoxy)ethoxy)ethyl)oxalamide

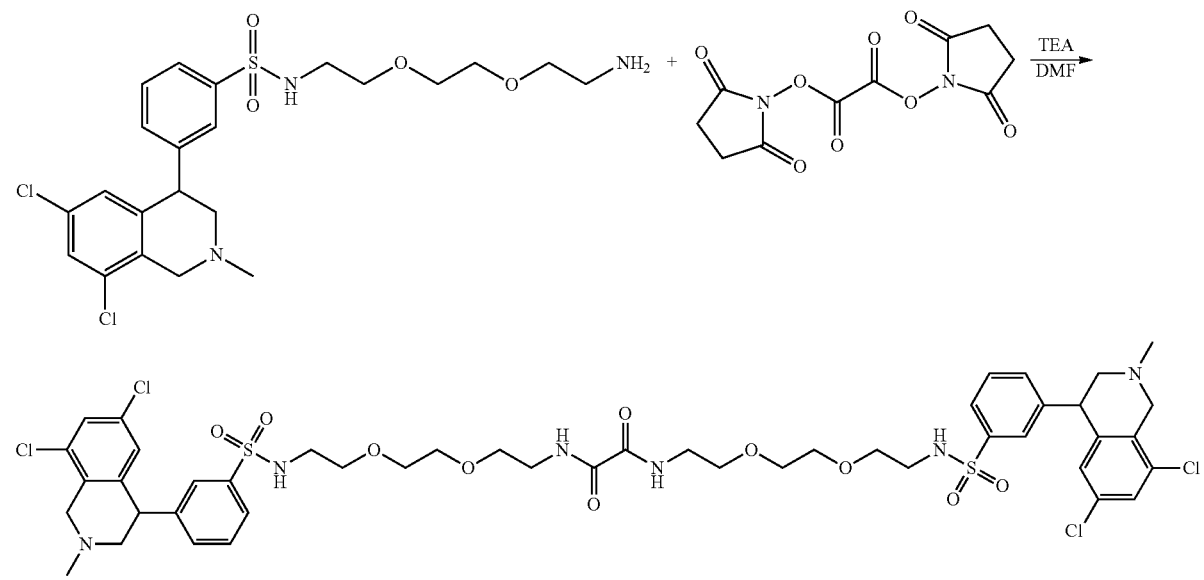

Compound 190, N1,N2-bis(2-(2-(2-(3-(6,8-dichloro-2-methyl-1,2,3,4-tetrahydroisoquinolin-4-yl)phenylsulfonamido)ethoxy)ethoxy)ethyl)oxalamide To N-(2-(2-(2-aminoethoxy)ethoxy)ethyl)-3-(6,8-dichloro-2-methyl-1,2,3,4-tetrahydroisoquinolin-4-yl)benzenesulfonamide (Intermediate 168.2) (200 mg, 0.40 mmol, 1.00 equiv) in DMF (2 mL) was added triethylamine (81 mg, 0.80 mmol, 2.01 equiv) and bis(2,5-dioxopyrrolidin-1-yl) oxalate (57 mg, 0.20 mmol, 0.50 equiv) and the resulting solution was stirred overnight. The mixture was concentrated under vacuum and the crude product (200 mg) was purified by Flash-Prep-HPLC with the following conditions: Column, C18 silica gel; mobile phase, methanol/water=0.05/100 increasing to methanol/water=90/100 within 25 min; Detector, UV 254 nm. This resulted in 72.3 mg (34%) of N1,N2-bis(2-(2-(2-(3-(6,8-dichloro-2-methyl-1,2,3,4-tetrahydroisoquinolin-4-yl)phenylsulfonamido)ethoxy)ethoxy)ethyl)oxalamide as a light yellow solid. $^1$H-NMR (300 MHz, CD$_3$OD, ppm): δ 7.77-7.81 (m, 2H), 7.72 (s, 2H), 7.48-7.57 (m, 4H), 7.35-7.36 (m, 2H), 6.81-6.82 (m, 2H), 4.39-4.43 (m, 2H), 3.79 (d, J=16.5 Hz, 2H), 3.65 (d, J=16.2 Hz, 2H), 3.55-3.60 (m, 8H), 3.43-3.50 (m, 12H), 3.02-3.09 (m, 6H), 2.64-2.71 (m, 2H), 2.49 (s, 6H). MS (m/z): 1059 [M+H]$^+$ Example 191

N1,N4-bis(2-(2-(2-(3-(6,8-dichloro-2-methyl-1,2,3,4-tetrahydroisoquinolin-4-yl)phenylsulfonamido)ethoxy)ethoxy)ethyl)succinamide Compound 191, N1,N4-bis(2-(2-(2-(3-(6,8-dichloro-2-methyl-1,2,3,4-tetrahydroisoquinolin-4-yl)phenylsulfonamido)ethoxy)ethoxy)ethyl)succinamide To N-(2-(2-(2-aminoethoxy)ethoxy)ethyl)-3-(6,8-dichloro-2-methyl-1,2,3,4-tetrahydroisoquinolin-4-yl)benzenesulfonamide (intermediate 168.2) (150 mg, 0.30 mmol, 1.00 equiv) in DMF (2 mL) was added triethylamine (60 mg, 0.59 mmol, 1.98 equiv) and intermediate 177.1 (47 mg, 0.15 mmol, 0.50 equiv) and the resulting solution was stirred overnight. The mixture was then concentrated under vacuum and the crude product (150 mg) was purified by Flash-Prep-HPLC with the following conditions: column, C18 silica gel; mobile phase, methanol/water=0.05/100 increasing to methanol/water=90/100 within 25 min; Detector, UV 254 nm. This resulted in 53.1 mg (33%) of N1,N4-bis(2-(2-(2-(3-(6,8-dichloro-2-methyl-1,2,3,4-tetrahydroisoquinolin-4-yl)phenylsulfonamido)ethoxy)ethoxy)ethyl)succinamide as a white solid. $^1$H-NMR (300 MHz, CD$_3$OD, ppm): δ 7.77-7.80 (m, 2H), 7.71 (s, 2H), 7.48-7.57 (m, 4H), 7.36-7.37 (m, 2H), 6.82 (s, 2H), 4.39-4.44 (m, 2H), 3.79 (d, J=15.9 Hz, 2H), 3.66

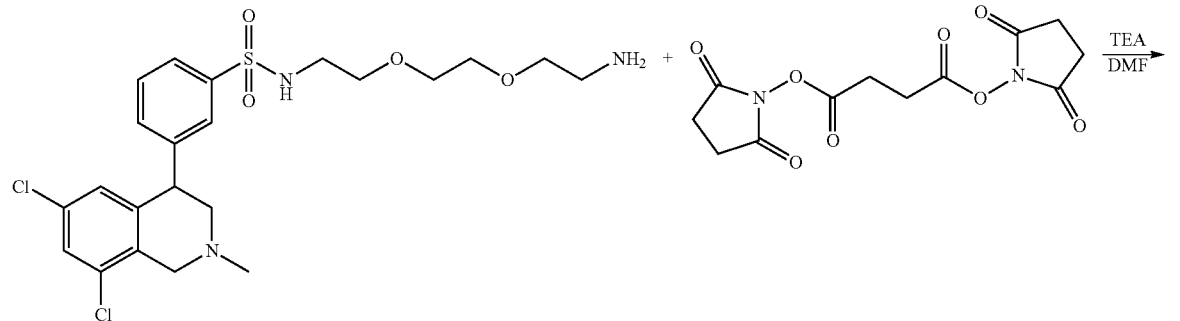

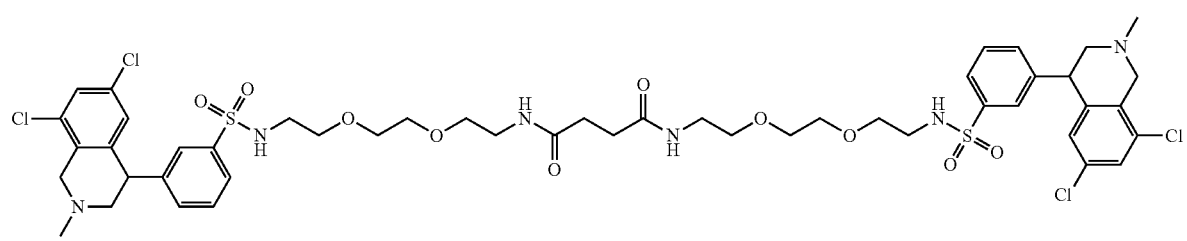

(d, J=16.2 Hz, 2H), 3.45-3.57 (m, 16H), 3.35-3.37 (m, 4H), 3.03-3.08 (m, 6H), 2.65-2.71 (m, 2H), 2.49-2.50 (m, 10H). MS (m/z): 1089 [M+H]⁺

Example 192

3,5-bis(2-(2-(2-(4-(6,8-dichloro-2-methyl-1,2,3,4-tetrahydroisoquinolin-4-yl)phenylsulfonamido)ethoxy)ethoxy)ethylcarbamoyl)benzenesulfonic acid

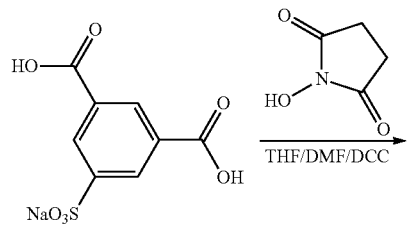

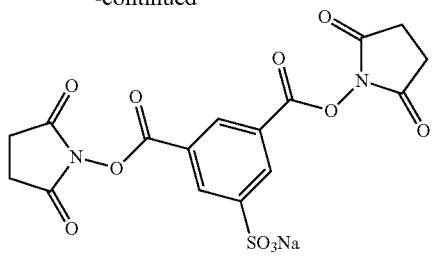

Intermediate 192.1, sodium 3,5-bis((2,5-dioxopyrrolidin-1-yloxy)carbonyl)benzenesulfonate To sodium 3,5-dicarboxybenzenesulfonate (1 g, 3.73 mmol, 1.00 equiv) and NHS (940 mg, 8.17 mmol, 2.20 equiv) in DMF (10 mL) at 0° C. was added dropwise a solution of DCC (1.69 g, 8.20 mmol, 2.20 equiv) in THF (10 mL) and the reaction stirred overnight. The solids were removed by filtration and the filtrate was concentrated under vacuum to afford 500 mg (29%) of the title compound as a white solid.

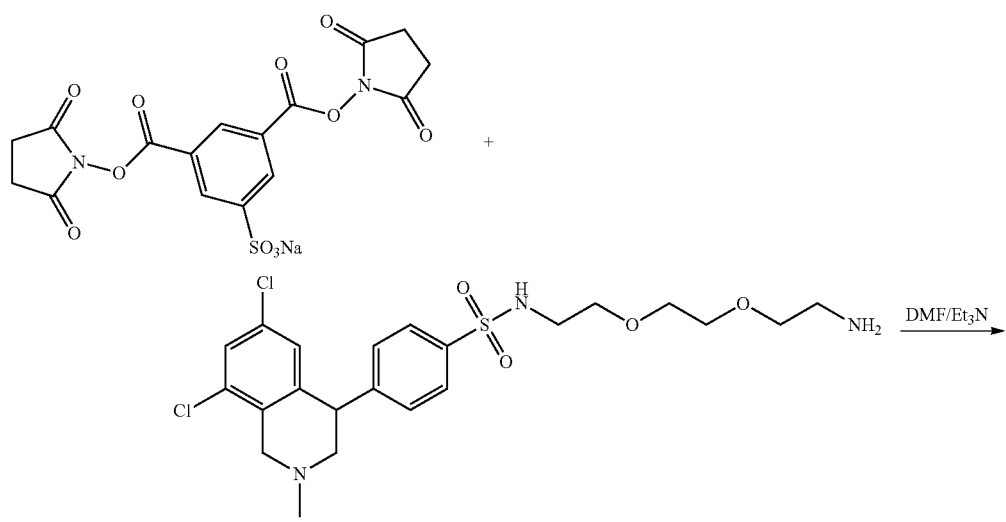

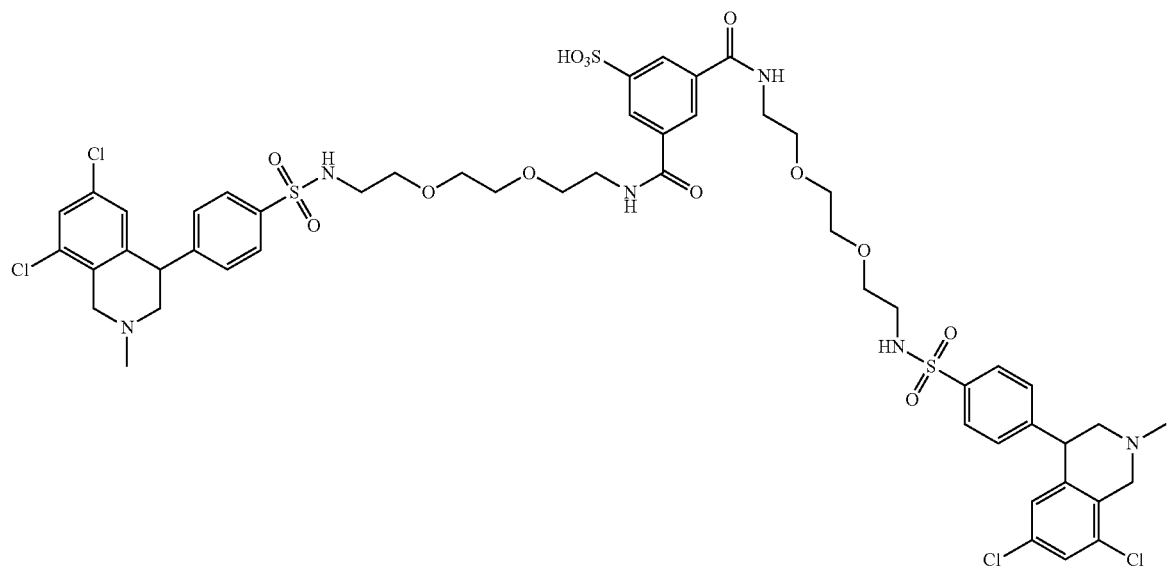

Compound 192, 3,5-bis(2-(2-(2-(4-(6,8-dichloro-2-methyl-1,2,3,4-tetrahydroisoquinolin-4-yl)phenylsulfonamido)ethoxy)ethoxy)ethyl-carbamoyl)benzenesulfonic acid To N-(2-(2-(2-aminoethoxy)ethoxy)ethyl)-4-(6,8-dichloro-2-methyl-1,2,3,4-tetrahydroisoquinolin-4-yl)benzenesulfonamide (intermediate 175.1) (100 mg, 0.20 mmol, 1.00 equiv) in DMF (2 mL) was added intermediate 192.1 (45 mg, 0.10 mmol, 0.50 equiv) and triethylamine (90 mg, 4.50 equiv) and the resulting solution was stirred overnight. The mixture was concentrated under vacuum and the crude product was purified by Prep-HPLC with acetonitrile:water (0.05% CF$_3$COOH)(10%-100%) to afford 30.6 mg (22%) of a TFA salt of the title compound as a white solid. $^1$H-NMR (300 MHz, CD$_3$OD, ppm): δ 8.35-8.34 (m, 3H), 7.84-7.81 (m, 4H), 7.48 (m, 2H), 7.41-7.38 (m, 4H), 6.75 (m, 2H), 4.87-4.70 (m, 4H), 4.56-4.50 (m, 2H), 3.92-3.85 (m, 2H), 3.70-3.42 (m, 22H), 3.37-3.32 (m, 6H), 3.20-3.06 (m, 4H). MS (m/z): 608 [[(M+2H)/2]$^+$ Example 193

N1,N3-bis(2-(2-(2-(4-(6,8-dichloro-2-methyl-1,2,3,4-tetrahydroisoquinolin-4-yl)phenylsulfonamido)ethoxy)ethoxy)ethyl)-5-hydroxyisophthalamide

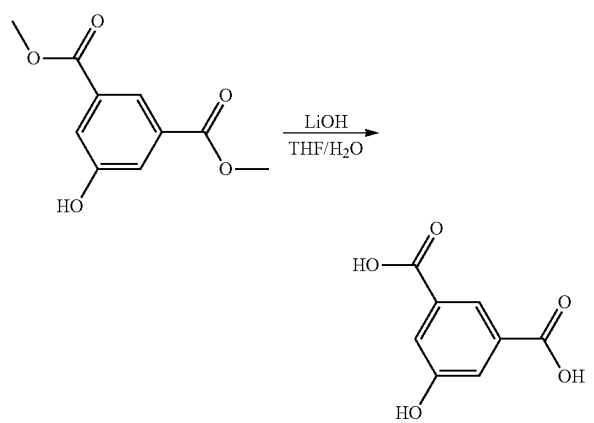

Intermediate 193.1, 5-hydroxyisophthalic acid

To dimethyl 5-hydroxyisophthalate (4.0 g, 19.03 mmol, 1.00 equiv) in THF (10 mL) was added lithium hydroxide (20 mL, 2M in water) and the resulting solution was stirred overnight at 40° C. The mixture concentrated under vacuum to remove the organic solvents and then the pH of the solution was adjusted to ~2 with 6N hydrochloric acid. The resulting solids were collected by filtration and dried in a vacuum oven to afford 2.0 g (58%) of 5-hydroxyisophthalic acid as a white solid.

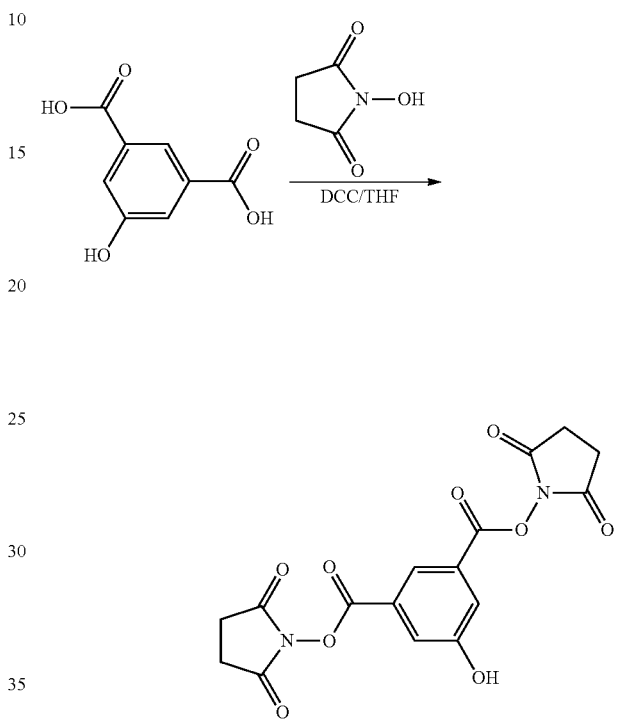

Intermediate 193.2, bis(2,5-dioxopyrrolidin-1-yl) 5-hydroxyisophthalate

To 5-hydroxyisophthalic acid (Intermediate 193.1; 1 g, 5.49 mmol, 1.00 equiv) and NHS (1.39 g, 2.20 equiv), in THF (5 mL) at 0° C. was added dropwise a solution of DCC (2.4 g, 2.20 equiv) in THF (5 mL). The resulting solution was stirred overnight at room temperature, then filtered and concentrated under vacuum to give 0.5 g (22%) of the title compound as a white solid.

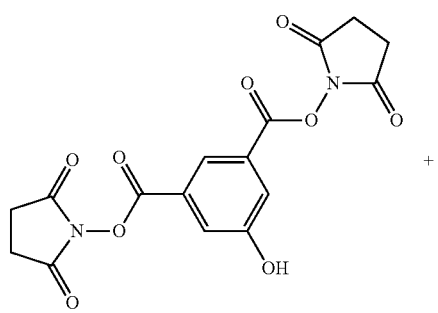

+

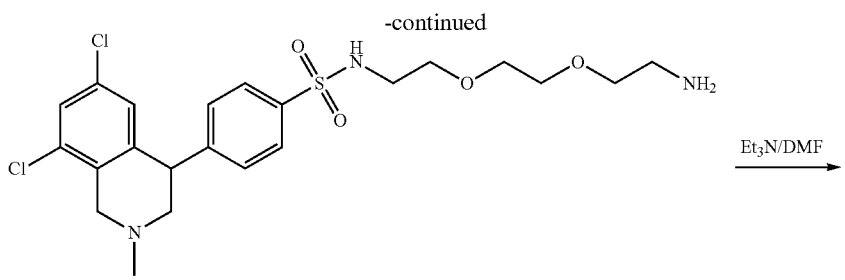

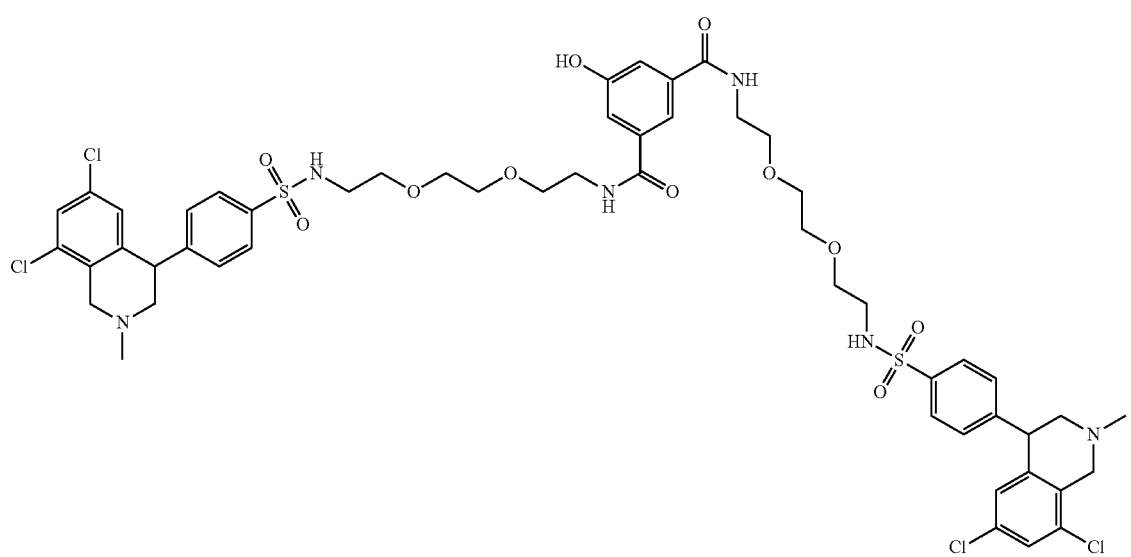

Compound 193, N1,N3-bis(2-(2-(2-(4-(6,8-dichloro-2-methyl-1,2,3,4-tetrahydroisoquinolin-4-yl)phenylsulfonamido)ethoxy)ethoxy)ethyl)-5-hydroxyisophthalamide To N-(2-(2-(2-aminoethoxy)ethoxy)ethyl)-4-(6,8-dichloro-2-methyl-1,2,3,4-tetrahydroisoquinolin-4-yl)benzenesulfonamide (intermediate 175.1) (100 mg, 0.20 mmol, 1.00 equiv) in DMF (2 mL) was added Intermediate 193.2 (34 mg, 0.09 mmol, 0.45 equiv) and triethylamine (90 mg, 4.50 equiv) and the reaction was stirred overnight. The mixture was concentrated under vacuum and the crude product was purified by Prep-HPLC with acetonitrile:water (0.05% CF$_3$COOH)(10%-100%) to afford 30 mg (24%) of a TFA salt of the title compound as a white solid. $^1$H-NMR (300 MHz, CD$_3$OD, ppm): δ 7.91-7.88 (m, 4H), 7.71-7.70 (m, 1H), 7.56-7.55 (m, 2H), 7.47-7.44 (m, 4H), 7.37-7.36 (m, 2H), 6.84 (m, 2H), 4.87-4.70 (m, 4H), 4.53-4.48 (m, 2H), 3.92-3.85 (m, 2H), 3.67-3.46 (m, 22H), 3.37-3.32 (m, 6H), 3.17-3.07 (m, 4H). MS (m/z): 576 [[(M+2H)/2]$^+$ Example 194

(2R,3R)—N1,N4-bis(3-((3-(3-(6,8-dichloro-2-methyl-1,2,3,4-tetrahydroisoquinolin-4-yl)phenylsulfonamido)propyl)(methyl)amino)propyl)-2,3-dihydroxysuccinamide

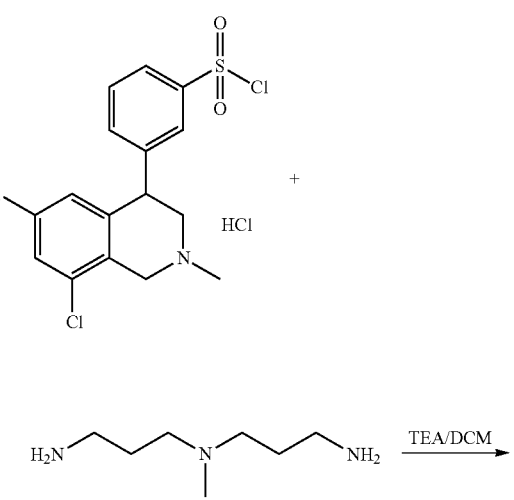

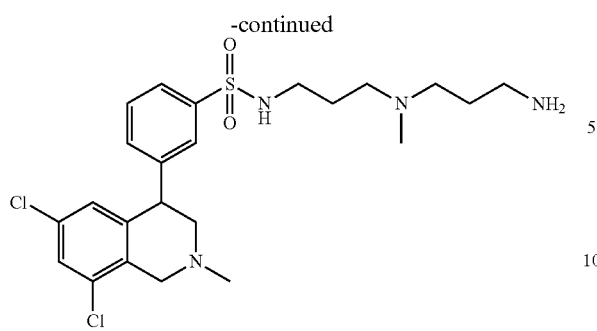

Intermediate 194.1, N-(3-((3-aminopropyl)(methyl)amino)propyl)-3-(6,8-dichloro-2-methyl-1,2,3,4-tetrahydroisoquinolin-4-yl)benzenesulfonamide To a solution of N1-(3-aminopropyl)-N1-methylpropane-1,3-diamine (560 mg, 3.85 mmol) dissolved in DCM (20 mL), was added triethylamine (300 mg, 2.96 mmol) and 3-(6,8-dichloro-2-methyl-1,2,3,4-tetrahydroisoquinolin-4-yl)benzene-1-sulfonyl chloride (300 mg, 0.77 mmol). The resulting solution was stirred for 3 h at room temperature. After removing the solvent, the resulting residue was diluted with EtOAc (50 mL), washed with water (2×10 mL) and dried over anhydrous sodium sulfate. The crude product was purified by Flash-Prep-HPLC with H₂O:MeOH (1:4) to afford 300 mg (74%) of N-(3-((3-aminopropyl)(methyl)amino)propyl)-3-(6,8-dichloro-2-methyl-1,2,3,4-tetrahydroisoquinolin-4-yl)benzenesulfonamide as a yellow oil.

Compound 194, (2R,3R)—N1,N4-bis(3-((3-(3-(6,8-dichloro-2-methyl-1,2,3,4-tetrahydroisoquinolin-4-yl)phenylsulfonamido)propyl)(methyl)amino)propyl)-2,3-dihydroxysuccinamide To a solution of N-(3-((3-aminopropyl)(methyl)amino)propyl)-3-(6,8-dichloro-2-methyl-1,2,3,4-tetrahydroisoquinolin-4-yl)benzenesulfonamide (Intermediate 194.1, 300 mg, 0.60 mmol) in DMF (2 mL) was added (2R,3R)-bis(2,5-dioxopyrrolidin-1-yl) 2,3-dihydroxysuccinate (prepared from (2R,3R)-tartaric acid as described in example 168) (91 mg, 0.27 mmol) and triethylamine (270 mg, 2.67 mmol) and the resulting solution was stirred for 2 h at room temperature and the reaction progress was monitored by LCMS. Upon completion, the mixture was concentrated under vacuum and the crude product was purified by Prep-HPLC with acetonitrile:water (0.05% CF₃COOH) (20%-29%) to afford 30.9 mg (8%) of the title compound as a TFA salt. ¹H-NMR (300 MHz, CD₃OD, ppm): 7.90-7.88 (m, 2H), 7.80 (m, 2H), 7.69-7.65 (m, 2H), 7.58-7.56 (m, 4H), 6.85 (m, 2H), 4.87-4.71 (m, 4H), 4.54-4.44 (m, 4H), 3.88-3.82 (m, 2H), 3.62-3.53 (m, 4H), 3.22 (m, 6H), 3.13-3.09 (m, 6H), 3.01-2.97 (m, 4H), 2.88 (m, 6H), 2.00-1.96 (m, 8H). LCMS (ES, m/z): 1114 [M+H]⁺.

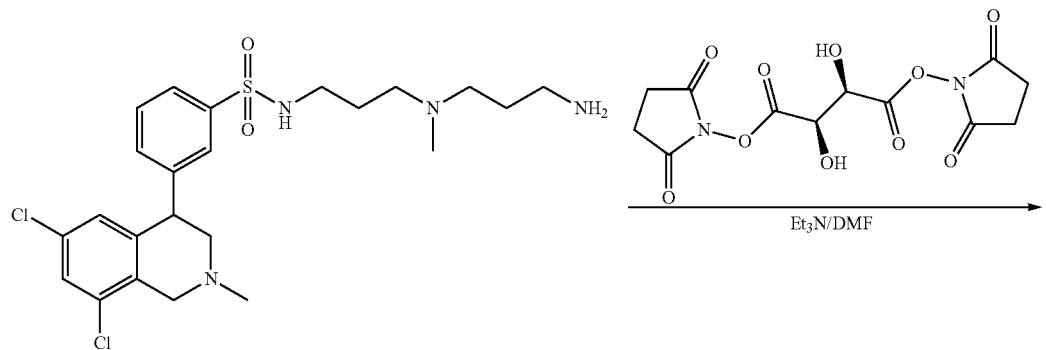

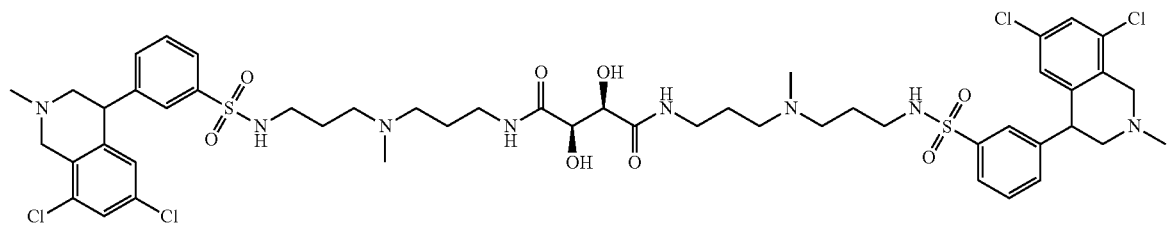

Example 195

2,2'-oxybis(N-(2-(2-(2-(3-(6,8-dichloro-2-methyl-1,2,3,4-tetrahydroisoquinolin-4-yl)phenylsulfonamido)ethoxy)ethoxy)ethyl)acetamide)

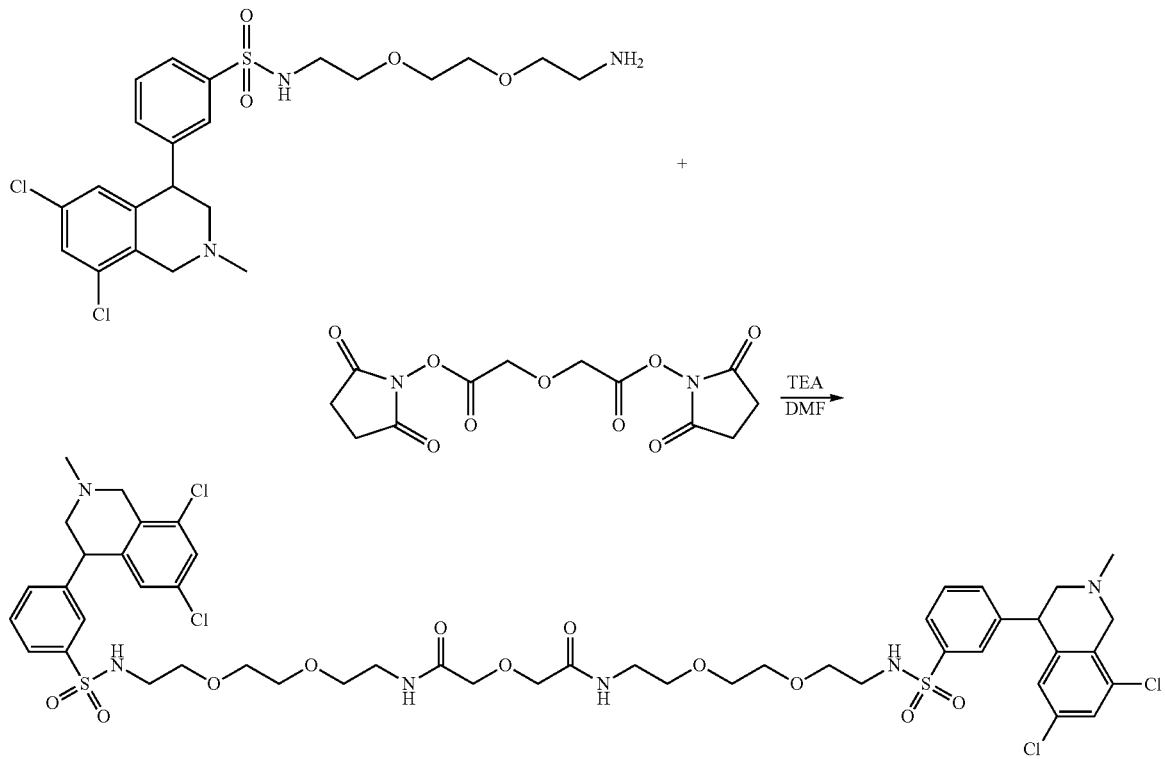

Compound 195, 2,2'-oxybis(N-(2-(2-(2-(3-(6,8-dichloro-2-methyl-1,2,3,4-tetrahydroisoquinolin-4-yl)phenylsulfonamido)ethoxy)ethoxy)ethyl)acetamide)

To a solution of N-(2-(2-(2-aminoethoxy)ethoxy)ethyl)-3-(6,8-dichloro-2-methyl-1,2,3,4-tetrahydroisoquinolin-4-yl)benzenesulfonamide (150 mg, 0.30 mmol) in DMF (2 mL) was added triethylamine (60 mg, 0.59 mmol) and bis(2,5-dioxopyrrolidin-1-yl) 2,2'-oxydiacetate (intermediate 178.1) (49 mg, 0.15 mmol) and the resulting solution was stirred overnight. After removal of the solvent, the crude product (150 mg) was purified by Flash-Prep-HPLC (C18 silica gel; methanol/water=0.05/100 increasing to methanol/water=90/100 within 25 min) to give 44.4 mg (27%) of the title compound as a TFA salt. $^1$H-NMR (300 MHz, $CD_3CD$, ppm): 7.79~7.76 (m, 2H), 7.70 (s, 2H), 7.57-7.50 (m, 4H), 7.36 (d, J=Hz, 2H), 4.89-4.41 (m, 2H), 4.06 (m, 4H), 3.81-3.62 (m, 5H), 3.59-3.42 (m, 11H), 3.33-3.31 (m, 8H), 3.07-3.01 (m, 6H), 2.71-2.64 (m, 2H), 2.48 (s, 6H). LCMS (ES, m/z): 1103 $[M+H]^+$.

Example 196

N1,N3-bis(2-(2-(2-(3-(6,8-dichloro-2-methyl-1,2,3,4-tetrahydroisoquinolin-4-yl)phenylsulfonamido)ethoxy)ethoxy)ethyl)-2,2-dimethylmalonamide

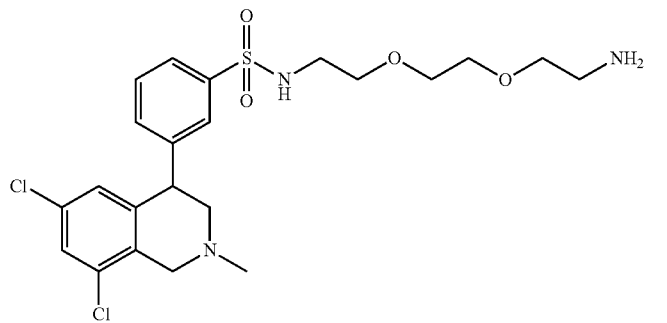

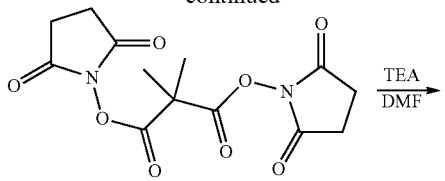

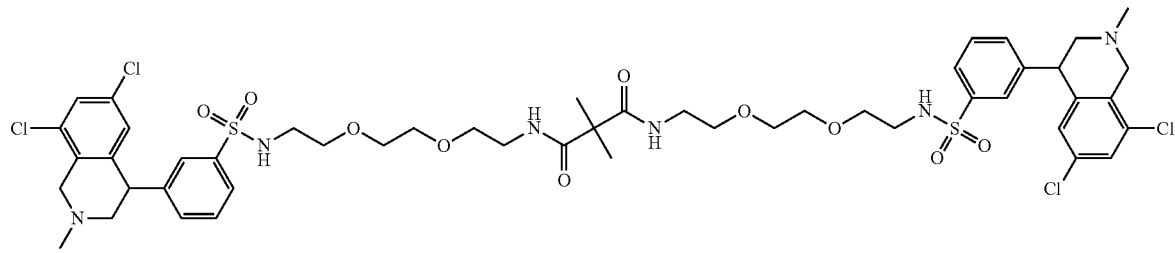

Compound 196, N1,N3-bis(2-(2-(2-(3-(6,8-dichloro-2-methyl-1,2,3,4-tetrahydroisoquinolin-4-yl)phenylsulfonamido)ethoxy)ethoxy)ethyl)-2,2-dimethylmalonamide To N-(2-(2-(2-aminoethoxy)ethoxy)ethyl)-3-(6,8-dichloro-2-methyl-1,2,3,4-tetrahydroisoquinolin-4-yl)benzenesulfonamide (150 mg, 0.30 mmol) in DMF (2 mL) was added triethylamine (60 mg, 0.59 mmol) and bis(2,5-dioxopyrrolidin-1-yl) 2,2-dimethylmalonate (prepared from 2,2-dimethylmalonic acid as described in Example 168) (49 mg, 0.15 mmol) and the resulting solution was stirred overnight. The mixture was concentrated and then purified by Flash-Prep-HPLC (C18 silica gel, methanol/water=0.05/100 increasing to methanol/water=90/100 within 25 min) to give 75.1 mg of the title compound (46%) as a TFA salt. $^1$H-NMR (300 MHz, CD$_3$OD, ppm): 7.80~7.77 (m, 2H), 7.71 (s, 2H), 7.57-7.48 (m, 4H), 7.36-7.35 (d, J=2.1 Hz, 2H), 6.81 (d, J=1.2 Hz, 2H), 4.43-4.38 (m, 2H), 3.82-3.62 (m, 4H), 3.57-~3.31 (m, 18H), 3.07-3.02 (m, 6H), 2.71-2.64 (m, 2H), 2.49 (s, 6H), 1.41 (s, 6H). LC-MS (ES, m/z): 1101 [M+H]$^+$.

Example 197

N1,N2-bis(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)oxalamide

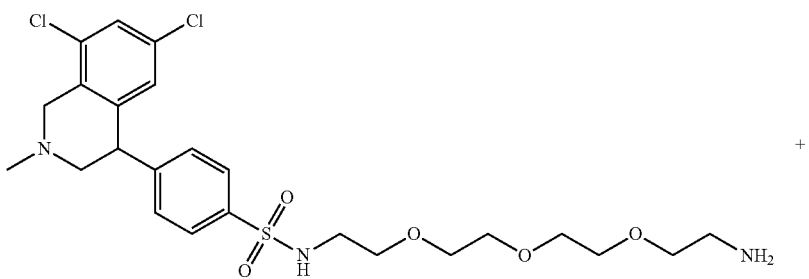

+

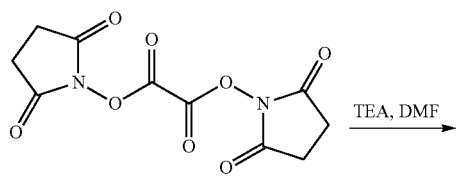

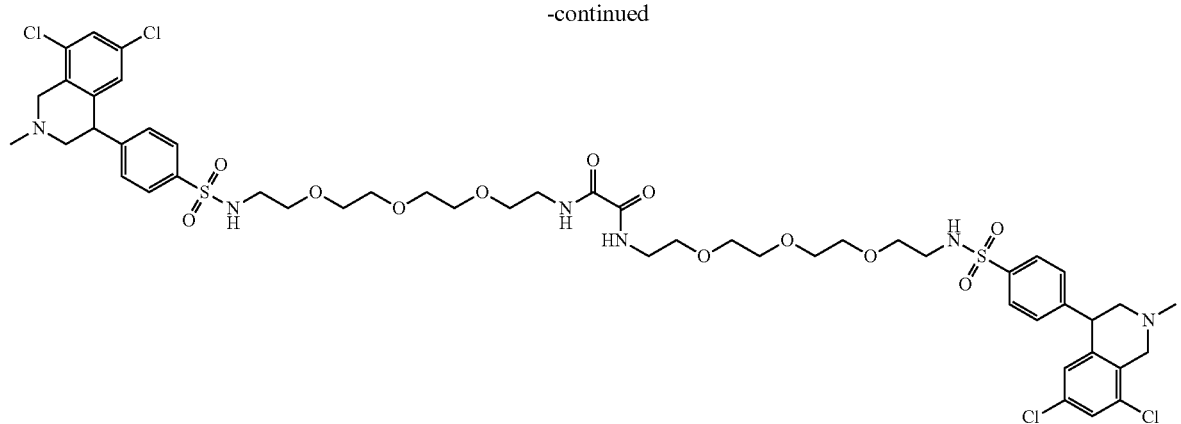

Compound 197, N1,N2-bis(2-(2-(2-(2-(4-(6,8-dichloro-2-methyl-1,2,3,4-tetrahydroisoquinolin-4-yl)phenylsulfonamido)ethoxy)ethoxy)ethoxy)-ethyl) oxalamide To a solution of N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide (compound 82) (148 mg, 0.26 mmol) in DMF (5 mL) under $N_2$ was added bis(2,5-dioxopyrrolidin-1-yl) oxalate (prepared from oxalic acid as described in Example 168) (31 mg, 0.11 mmol) and triethylamine (44 mg, 0.44 mmol) and the resulting solution was stirred overnight. The crude product was purified by Prep-HPLC with $CH_3CN:H_2O$ (0.05% $CF_3COOH$)(28%-35%) to afford 101.8 mg (68%) of the title compound as a TFA salt. $^1$H-NMR (300 Hz, $CD_3OD$, ppm): 7.94 (d, J=9 Hz, 4H), 7.58 (s, 2H), 7.50 (d, J=9 Hz, 4H), 6.88 (s, 2H), 4.80 (m, 4H), 4.53 (m, 2H), 3.90 (m, 2H), 3.59 (m, 16H), 3.52 (m, 2H), 3.49 (m, 12H), 3.13 (s, 6H), 3.09 (m, 4H). LC-MS (ES, m/z): 574 [(M+2H)/2]$^+$.

Example 198

2,2'-oxybis(N-(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)acetamide)

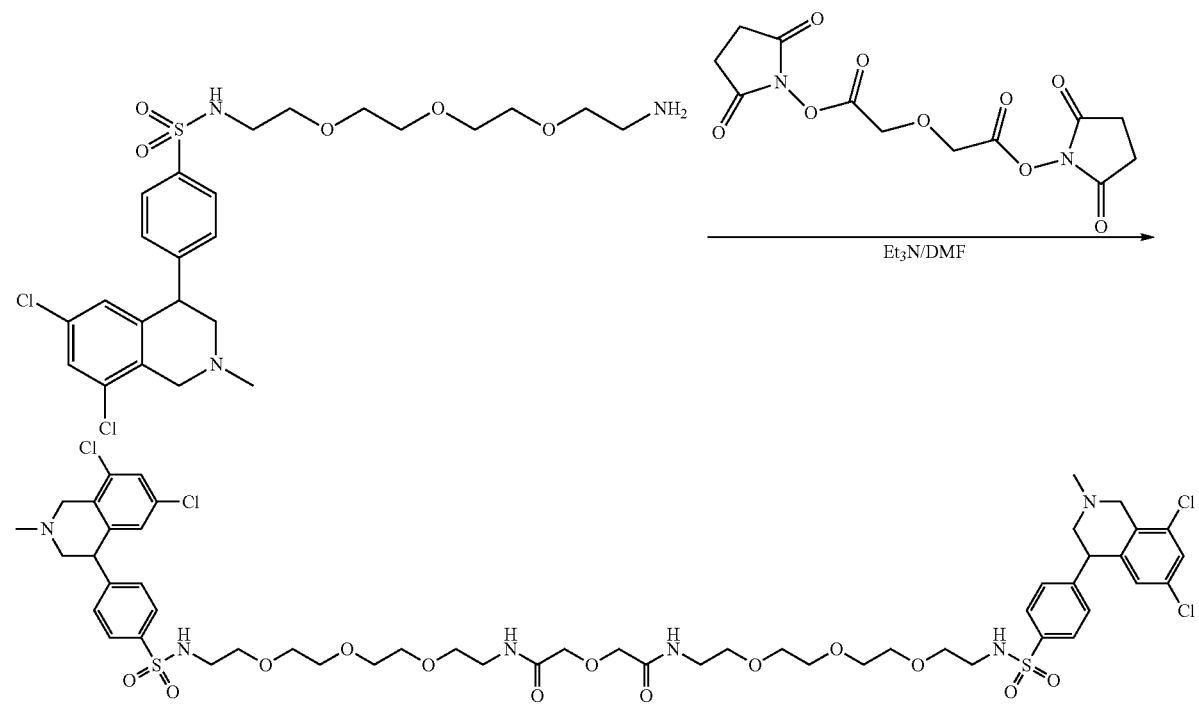

Compound 198, 2,2'-oxybis(N-(2-(2-(2-(2-(4-(6,8-dichloro-2-methyl-1,2,3,4-tetrahydroisoquinolin-4-yl)phenylsulfonamido)ethoxy)ethoxy)ethoxy)ethyl) acetamide)

To a solution of N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (Compound 82) (200 mg, 0.37 mmol) in DMF (2 mL) was added bis(2,5- dioxopyrrolidin-1-yl) 2,2'-oxydiacetate (intermediate 178.1) (60 mg) and triethylamine (184 mg). The resulting solution was stirred for 2 h at room temperature at which point LCMS indicated complete conversion. The mixture was concentrated under vacuum and the crude product was purified by Prep-HPLC with acetonitrile:water (0.05% CF$_3$COOH) (25%-35%). This resulted in 79.6 mg (31%) of the title compound as a TFA salt. $^1$H-NMR (300 MHz, CD$_3$OD, ppm): 7.94-7.91 (m, 4H), 7.58-7.57 (m, 2H), 7.51-7.48 (m, 4H), 6.88 (m, 2H), 4.82-4.74 (m, 4H), 4.52-4.47 (m, 2H), 4.06 (m, 4H), 3.90 (m, 2H), 3.64-3.42 (m, 34H), 3.15-3.13 (s, 6H), 3.11-3.09 (m, 4H). LC-MS (ES, m/z): 596 [(M+2H)/2]$^+$.

Example 199

N1,N4-bis(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)succinamide Compound 199, N1,N4-bis(2-(2-(2-(2-(4-(6,8-dichloro-2-methyl-1,2,3,4-tetrahydroisoquinolin-4-yl)phenylsulfonamido)ethoxy)ethoxy)ethoxy)-ethyl) succinamide To a solution of N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide (compound 82) (200 mg, 0.37 mmol) in dry DMF (10 mL) under N$_2$ was added bis(2,5-dioxopyrrolidin-1-yl) succinate (intermediate 177.1) (57.1 mg, 0.18 mmol) and triethylamine (111 mg, 1.10 mmol). The resulting solution was stirred for 4 h at 25° C. in an oil bath and monitored by LCMS. The resulting mixture was concentrated under vacuum and the crude product was purified by Prep-HPLC with acetonitrile:water (0.05% CF$_3$COOH)(28%-35%). This resulted in 113.8 mg (45%) of the title compound as a TFA salt. $^1$H-NMR (300 MHz, CD$_3$OD, ppm): 7.93-7.91 (d, J=8.1 Hz, 4H), 7.58-7.57 (m, 2H), 7.50-7.48 (m, 4H), 6.87 (s, 2H), 4.88-4.74 (m, 4H),

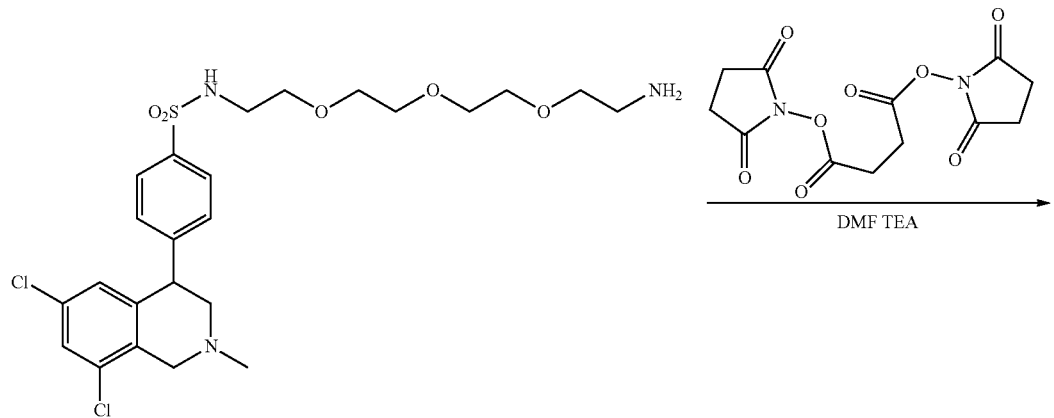

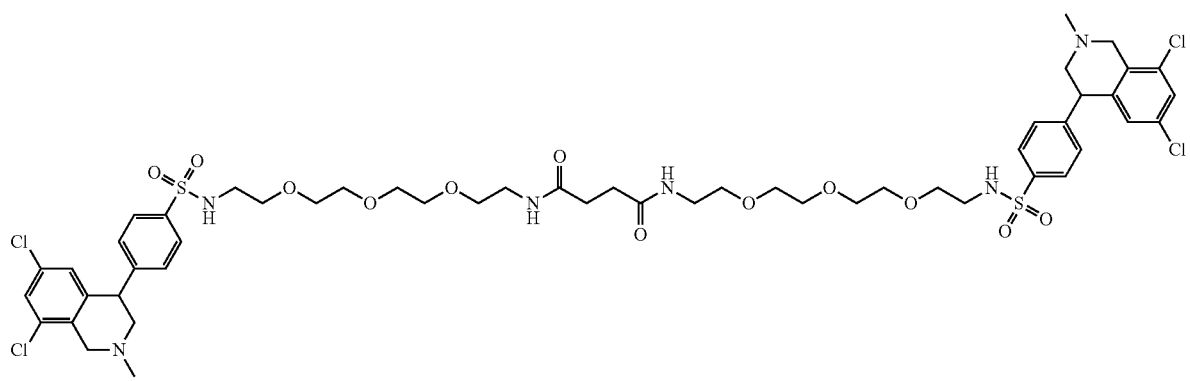

4.55-4.49 (d, J=16.2 Hz, 2H), 3.94-3.88 (m, 2H), 3.67-3.59 (m, 14H), 3.55-3.45 (m, 12H), 3.35-3.09 (m, 10H), 2.48 (s, 4H). LC-MS (ES, m/z): 588 [(M+2H)/2]+.

Example 200

N1,N4-bis(2-(2-(2-(4-((S or R)-6,8-dichloro-2-methyl-1,2,3,4-tetrahydroisoquinolin-4-yl)phenylsulfonamido)ethoxy)ethoxy)ethyl)succinamide bishydrochloride salt

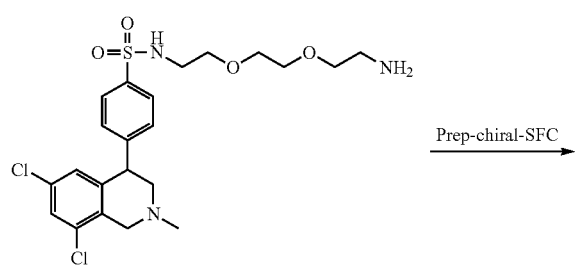

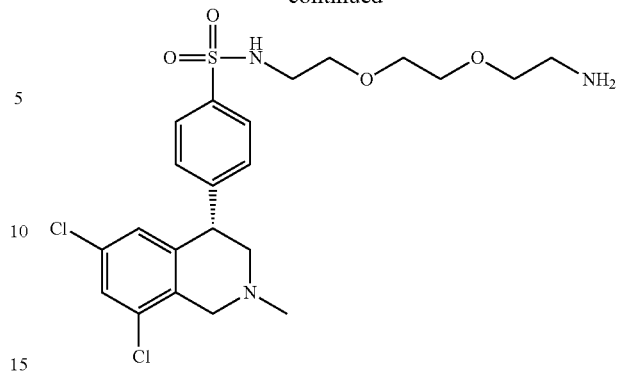

Intermediate 200.1, (S or R)—N-(2-(2-(2-aminoethoxy)ethoxy)ethyl)-4-(6,8-dichloro-2-methyl-1,2,3,4-tetrahydroisoquinolin-4-yl)benzenesulfonamide Intermediate 175.1 (3 g) was purified by Prep-SFC with the following conditions: Column, Chiralpak IA, 2*25 cm, 5 um; mobile phase, CO$_2$ (50%), iso-propanol (50%); Detector, UV 254 nm This resulted in 1 g of (S or R)—N-(2-(2-(2-aminoethoxy)ethoxy)ethyl)-4-(6,8-dichloro-2-methyl-1,2,3,4-tetrahydroisoquinolin-4-yl)benzenesulfonamide (intermediate 200.1) as a yellow solid.

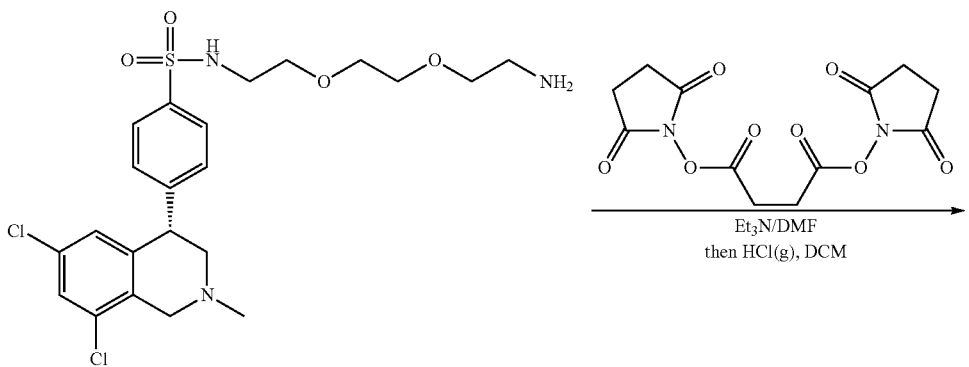

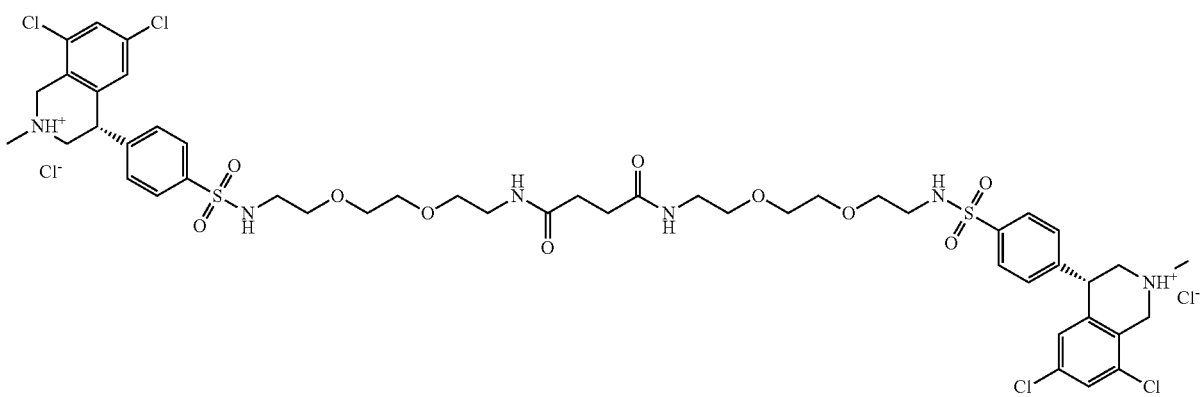

377

Compound 200, N1,N4-bis(2-(2-(2-(4-((S or R)-6,8-dichloro-2-methyl-1,2,3,4-tetrahydroisoquinolin-4-yl)phenylsulfonamido)ethoxy)ethoxy)ethyl)succinamide bis-hydrochloride salt To Intermediate 200.1 (280 mg, 0.56 mmol, 2.00 equiv) in DMF (10 mL) was added intermediate 177.1 (87 mg, 0.28 mmol, 1.00 equiv) and triethylamine (94.3 mg, 0.93 mmol, 4.00 equiv) and the reaction was stirred overnight. The resulting mixture was concentrated under vacuum and the crude product (300 mg) was purified by Prep-HPLC with CH$_3$CN:H2O (35-55%). The product was then dissolved in 15 mL of dichloromethane and gaseous hydrochloric acid was introduced for 20 minutes, then the mixture was concentrated under vacuum. The crude product was washed with 3×10 mL of ether to afford 222.4 mg of Compound 200 as a light yellow solid. $^1$H-NMR (400 MHz, CD$_3$OD, ppm): 7.94-7.92 (d, J=8 Hz, 4H), 7.56-7.52 (m, 6H), 6.82 (s, 2H), 4.89-4.84 (m, 4H), 4.52-4.48 (d, J=16.4 Hz, 2H), 3.91-3.90 (d, J=4 Hz, 2H), 3.62-3.48 (m, 18H), 3.39-3.32 (m, 4H), 3.19-3.10 (m, 10H), 2.57-2.55 (d, J=5.2 Hz, 4H). LCMS (ES, m/z): 544 [M-2HCl]/2+H$^+$.

Example 201

2,2'-oxybis(N-(2-(2-(2-(4-((S or R)-6,8-dichloro-2-methyl-1,2,3,4-tetrahydroisoquinolin-4-yl)phenylsulfonamido)ethoxy)ethoxy)ethyl)acetamide)bis-hydrochloride salt

378

Compound 201, 2,2'-oxybis(N-(2-(2-(2-(4-((S or R)-6,8-dichloro-2-methyl-1,2,3,4-tetrahydroisoquinolin-4-yl)phenylsulfonamido)ethoxy)ethoxy)ethyl)acetamide)bis-hydrochloride salt To intermediate 200.1 (500 mg, 1.00 mmol, 1.00 equiv) in DMF (3 mL) was added intermediate 178.1 (150 mg, 0.46 mmol, 0.45 equiv) and triethylamine (0.4 g, 4.50 equiv) and the resulting solution was stirred for 2 h. The crude product was purified by Prep-HPLC with CH$_3$CN/H2O (0.05% TFA) (28%-34%). The product was dissolved in 15 mL of dichloromethane and then gaseous hydrochloric acid was introduced for 20 mins. The mixture was concentrated under vacuum and the crude product was washed with 3×10 mL of ether to afford 101.1 mg (18%) of Compound 201 as a white solid. $^1$H-NMR (400 MHz, CD$_3$OD, ppm): 7.94-7.92 (m, 4H), 7.57-7.51 (m, 6H), 6.84 (s, 2H), 4.88-4.70 (m, 4H), 4.50 (s, 2H), 4.08 (s, 4H), 3.92-3.91 (m, 2H), 3.90-3.54 (m, 9H), 3.50-3.49 (m, 5H), 3.47-3.44 (m, 8H), 3.18 (s, 6H), 3.12-3.10 (m, 4H). LCMS (ES, m/z): 552 [M-2HCl]/2+H$^+$.

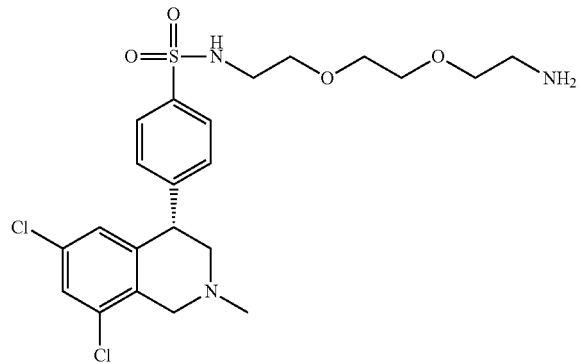

Intermediate 233.1

Example 202

(S or R)—N,N'-(10,17-dioxo-3,6,21,24-tetraoxa-9,11,16,18-tetraazahexacosane-1,26-diyl)bis(3-((S)-6,8-dichloro-2-methyl-1,2,3,4-tetrahydroisoquinolin-4-yl)benzenesulfonamide)bis-hydrochloride salt

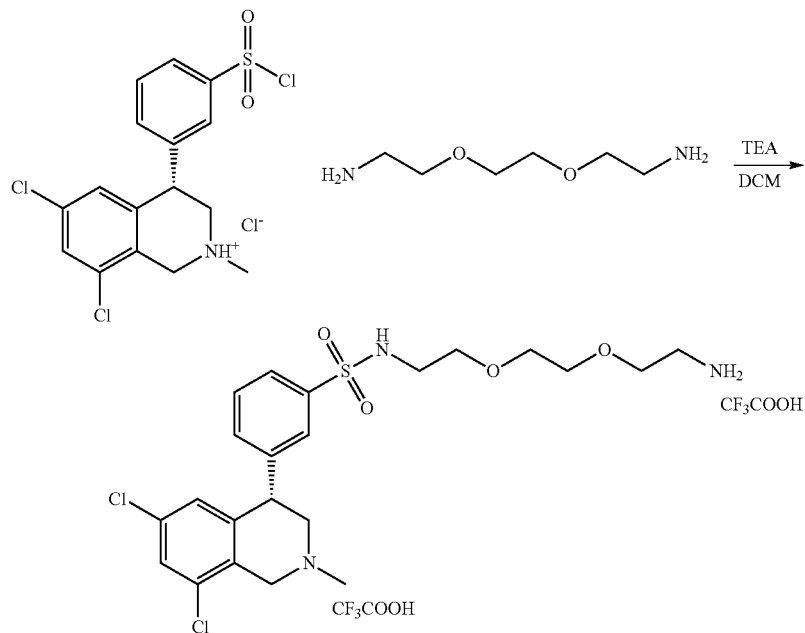

Intermediate 202.1, (S or R)—N-(2-(2-(2-aminoethoxy)ethoxy)ethyl)-3-(6,8-dichloro-2-methyl-1,2,3,4-tetrahydroisoquinolin-4-yl)benzenesulfonamide bis(2,2,2-trifluoroacetate)

To 2-(2-(2-aminoethoxy)ethoxy)ethanamine (30.4 g, 205.41 mmol, 8.01 equiv) in dichloromethane (1000 mL) was added triethylamine (5.2 g, 51.49 mmol, 2.01 equiv). This was followed by the addition of (S)-3-(6,8-dichloro-2-methyl-1,2,3,4-tetrahydroisoquinolin-4-yl)benzene-1-sulfonyl chloride hydrochloride (10 g, 23.42 mmol, 1.00 equiv; prepared from intermediate 244.1 and the procedures described in Example 1) in portions at 10° C. in 1 h. The resulting solution was stirred for 15 min at room temperature. The resulting mixture was washed with 3×500 mL of brine, dried over anhydrous sodium sulfate and concentrated under vacuum. The residue was purified by Flash-Prep-HPLC with the following conditions: Column, C18 silica gel; mobile phase, methanol/water/TFA (4/100/0.0005) increasing to 8/10/0.0005 within 30 min; Detector, UV 254 nm. This resulted in 7.2 g (42%) of intermediate 202.1 as a white solid

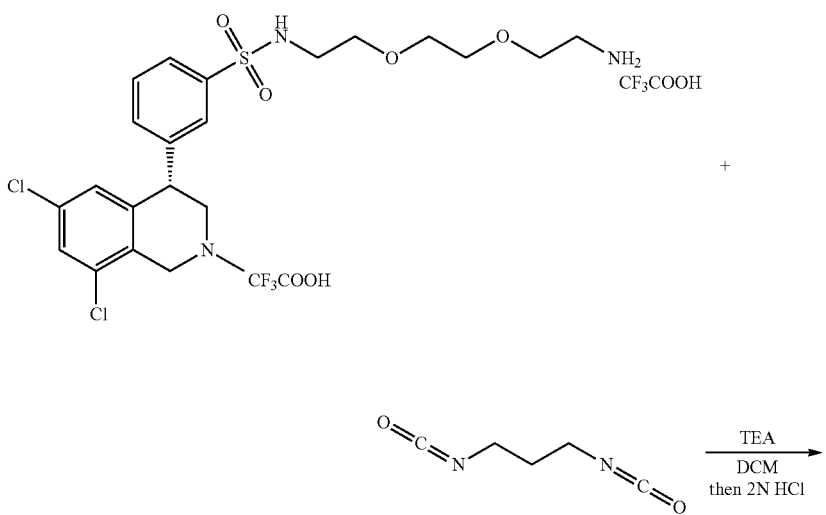

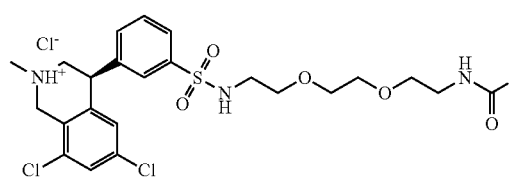

Compound 202, (S or R)—N,N'-(10,17-dioxo-3,6,21,24-tetraoxa-9,11,16,18-tetraazahexacosane-1,26-diyl)bis(3-((S)-6,8-dichloro-2-methyl-1,2,3,4-tetrahydroisoquinolin-4-yl)benzenesulfonamide)bis-hydrochloride salt To intermediate 202.1 (500 mg, 0.69 mmol, 1.00 equiv) in DCM (10 mL) was added triethylamine (138 mg, 1.37 mmol, 1.99 equiv) followed by the addition of 1,4-diisocyanatobutane (48 mg, 0.34 mmol, 0.50 equiv) in portions. The resulting solution was stirred for 10 min at room temperature then the crude product (500 mg) was purified by Flash-Prep-HPLC with the following conditions: Column, C18 silica gel; mobile phase, methanol/water=0.05/100 increasing to 90/100 within 30 min; Detector, UV 254 nm. To the product was added 0.2 mL of hydrochloric acid (2 N) and the solution lyophilized to afford 246.7 mg (59%) of Compound 202 as a white solid. $^1$H-NMR (400 MHz, CD$_3$OD, ppm): 7.92 (d, J=7.2 Hz, 2H), 7.83 (s, 2H), 7.69-7.65 (m, 2H), 7.60-7.55 (m, 4H), 6.81 (s, 2H), 4.87-4.83 (m, 4H), 4.54-4.50 (m, 2H), 3.94-3.91 (m, 2H), 3.69-3.49 (m, 18H), 3.39-3.32 (m, 4H), 3.21-3.15 (m, 10H), 3.08-3.05 (m, 4H), 1.57 (s, 4H). LCMS (ES, m/z): 1145 [M-2HCl+1]$^+$.

Example 203

(S or R)—N,N'-(2,2'-(2,2'-(2,2'-(1,4-phenylenebis(azanediyl))bis(oxomethylene)bis(azanediyl)bis(ethane-2,1-diyl))bis(oxy)bis(ethane-2,1-diyl))bis(oxy)bis(ethane-2,1-diyl))bis(3-((S or R)-6,8-dichloro-2-methyl-1,2,3,4-tetrahydroisoquinolin-4-yl)benzenesulfonamide)bis-hydrochloride salt

Compound 203, (S or R)—N,N'-(2,2'-(2,2'-(2,2'-(1,4-phenylenebis(azanediyl))bis-(oxomethylene)bis(azanediyl)bis(ethane-2,1-diyl))bis(oxy)bis(ethane-2,1-diyl))bis(oxy)bis(ethane-2,1-diyl))bis(3-((S or R)-6,8-dichloro-2-methyl-1,2,3,4-tetrahydroisoquinolin-4-yl)benzenesulfonamide)bis-hydrochloride salt To intermediate 202.1 (400 mg, 0.55 mmol, 1.00 equiv) in DCM (10 mL) was added triethylamine (111 mg, 1.10 mmol, 2.00 equiv) followed by the portionwise addition of 1,4-diisocyanatobenzene (44 mg, 0.28 mmol, 0.50 equiv). The resulting solution was stirred for 10 min and the crude product (400 mg) was purified by Flash-Prep-HPLC with the following conditions: Column, C18 silica gel; mobile phase, methanol/water (0.05/100) increasing to 90/100 within 30 min; Detector, UV 254 nm. To the product was added 0.2 mL of hydrochloric acid (2 N) and the solution lyophilized to afford 201.7 mg (59%) of Compound 203 as a white solid. $^1$H-NMR (400 MHz, CD3OD, ppm): 7.84 (d, J=7.6 Hz, 2H), 7.71 (s, 2H), 7.60-7.56 (m, 2H), 7.48-7.45 (m, 4H), 7.16 (s, 4H), 6.76 (s, 2H), 4.70-4.66 (m, 4H), 4.42-4.38 (m, 2H), 3.78-3.74 (m,

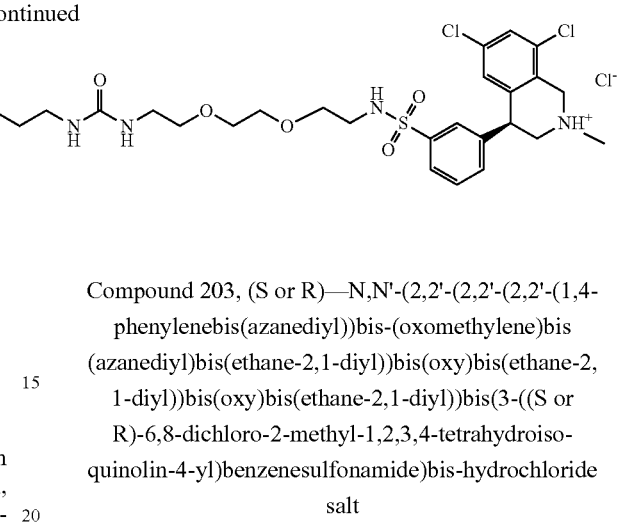

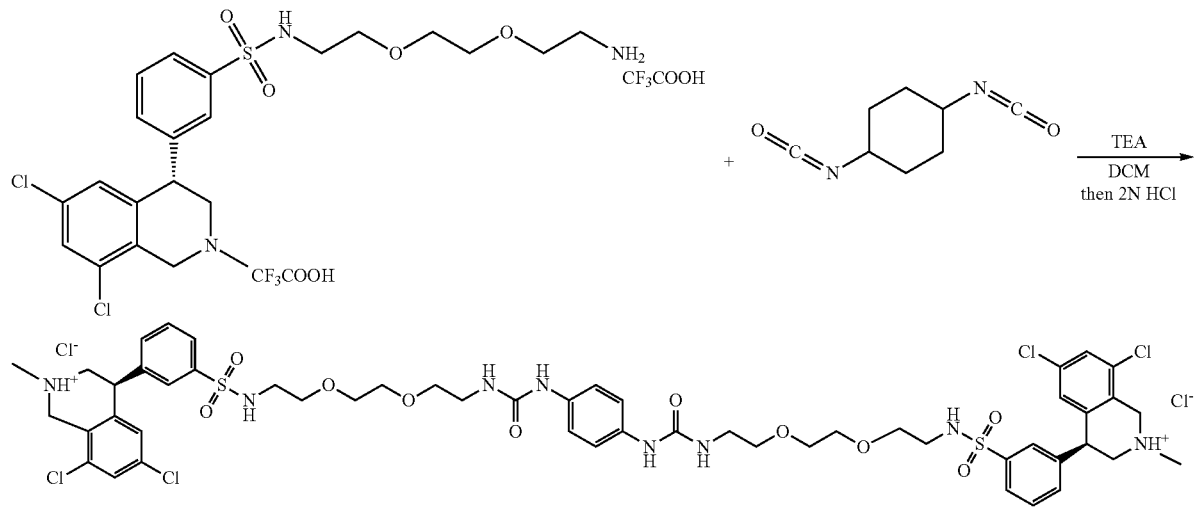

2H), 3.53-3.48 (m, 18H), 3.44-3.26 (m, 4H), 3.06-2.99 (m, 10H). LCMS (ES, m/z): 1163[M-2HCl+1]⁺.

Example 204

N,N'-(butane-1,4-diyl)bis(2-(2-(2-(4-(6,8-dichloro-2-methyl-1,2,3,4-tetrahydroisoquinolin-4-yl)phenylsulfonamido)acetamido)acetamido)acetamide)

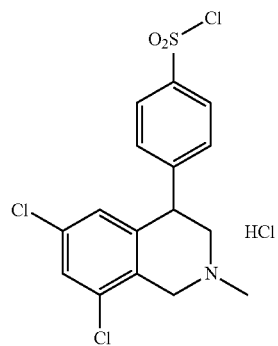
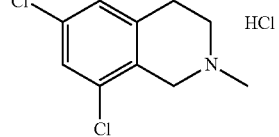

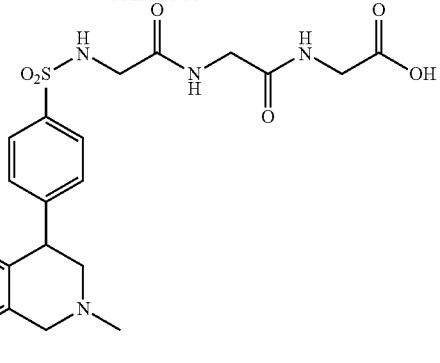

Intermediate 204.1, 2-(2-(2-(4-(6,8-dichloro-2-methyl-1,2,3,4-tetrahydroisoquinolin-4-yl)phenylsulfonamido)acetamido)acetamido)acetic acid To a slurry of 4-(6,8-dichloro-2-methyl-1,2,3,4-tetrahydroisoquinolin-4-yl)benzene-1-sulfonyl chloride hydrochloride (Intermediate 1.6) (283 mg, 0.66 mmol) and triglycine (152 mg, 0.80 mmol) in THF (1.5 mL) at 0° C. was added water (1.0 mL) followed by triethylamine (202 mg, 2.0 mmol). The reaction was allowed to warm to room temperature and stirred for 15 hours. The solvents were removed at reduced pressure and the residue was purified by preparative HPLC to give Intermediate 204.1 (122 mg) as a TFA salt.

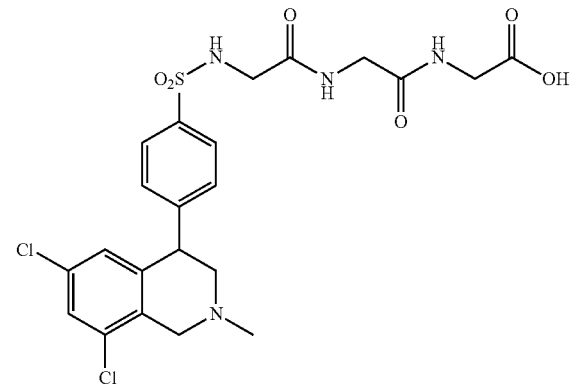

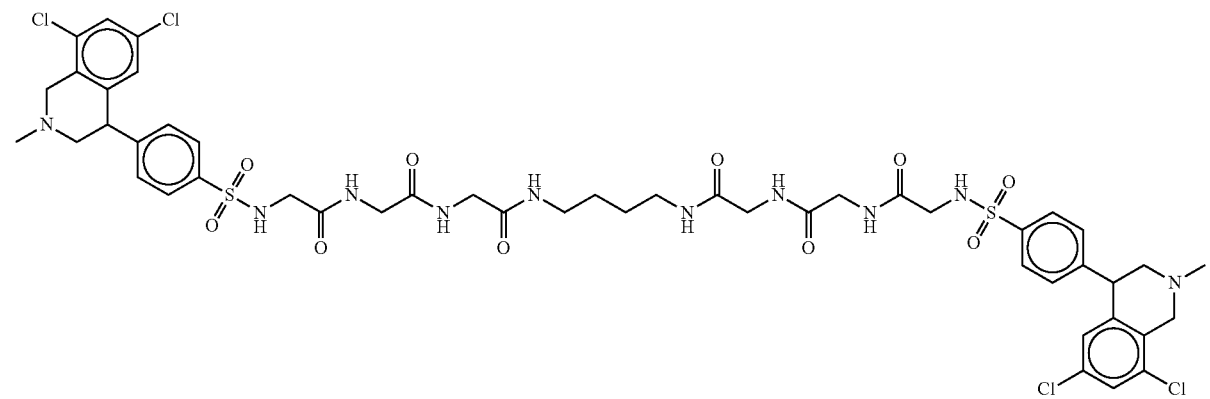

Compound 204, N,N'-(butane-1,4-diyl)bis(2-(2-(2-(4-(6,8-dichloro-2-methyl-1,2,3,4-tetrahydroisoquinolin-4-yl)phenylsulfonamido)acetamido)acetamido)acetamide)

Intermediate 204.1 (60 mg, 0.091 mmol) was dissolved in DMF (0.90 mL) followed by N-hydroxysuccinimide (12.6 mg, 0.11 mmol) and 1,4-diaminobutane (4.0 mg, 0.045 mmol). N-(3-dimethylaminopropyl)-N'-ethylcarbodiimide hydrochloride (21 mg, 0.11 mmol) was added and the reaction was stirred at room temperature for 16 hours, at which time additional 1,4-diaminobutane (1 uL) and N-(3-dimethylaminopropyl)-N'-ethylcarbodiimide hydrochloride (5 mg) were added. Two hours after the addition, solvent was removed at reduced pressure and the residue was purified by preparative HPLC. The title compound was obtained as a TFA salt (26 mg). $^1$H-NMR (400 mHz, CD3OD) δ 7.90 (d, j=8.6 Hz, 4H), 7.52 (d, j=1.8 Hz, 2H), 7.47 (d, j=8.6 Hz, 4H), 6.84 (s, 2H), 7.75 (m, 6H), 4.44 (d, J=15.6 Hz, 2H), 3.86 (s, 4H), 3.81 (s, 4H), 3.61 (s, 4H), 3.54 (m, 2H), 3.16 (m, 4H), 3.16 (s, 6H), 1.49 (m, 4H). MS (m/z): 1636.98 [M+H]$^+$.

Example 205

N1,N4-bis(2-(2-(2-(4-(6,8-dichloro-2-methyl-1,2,3,4-tetrahydroisoquinolin-4-yl)phenylsulfonamido)ethoxy)ethoxy)ethyl)-2,3-dihydroxysuccinamide Compound 205, N1,N4-bis(2-(2-(2-(4-(6,8-dichloro-2-methyl-1,2,3,4-tetrahydroisoquinolin-4-yl)phenylsulfonamido)ethoxy)ethoxy)ethyl)-2,3-dihydroxysuccinamide To a solution of N-(2-(2-(2-aminoethoxy)ethoxy)ethyl)-4-(6,8-dichloro-2-methyl-1,2,3,4-tetrahydroisoquinolin-4-yl)benzenesulfonamide (intermediate 175.1) (110 mg, 0.22 mmol) in DMF (2.0 mL) was added bis(2,5-dioxopyrrolidin-1-yl) 2,3-dihydroxysuccinate (Intermediate 168.1) (34 mg, 0.10 mmol) and the reaction was stirred for 10 minutes. The solvent was removed under vacuum and the residue was purified by preparative HPLC to give the title compound (23 mg) as a TFA salt. $^1$H-NMR (400 mHz, CD3OD) δ 7.81 (m, 4H), 7.44 (s, 1H), 7.37 (m, 2H), 6.75 (s, 1H), 4.64 (m, 4H), 4.37 (m, 4H), 3.72 (m, 2H), 3.46 (m, 10H), 3.38 (m, 12H), 3.02 (m, 10H). MS (m/z): 1117.02 [M+H]$^+$.

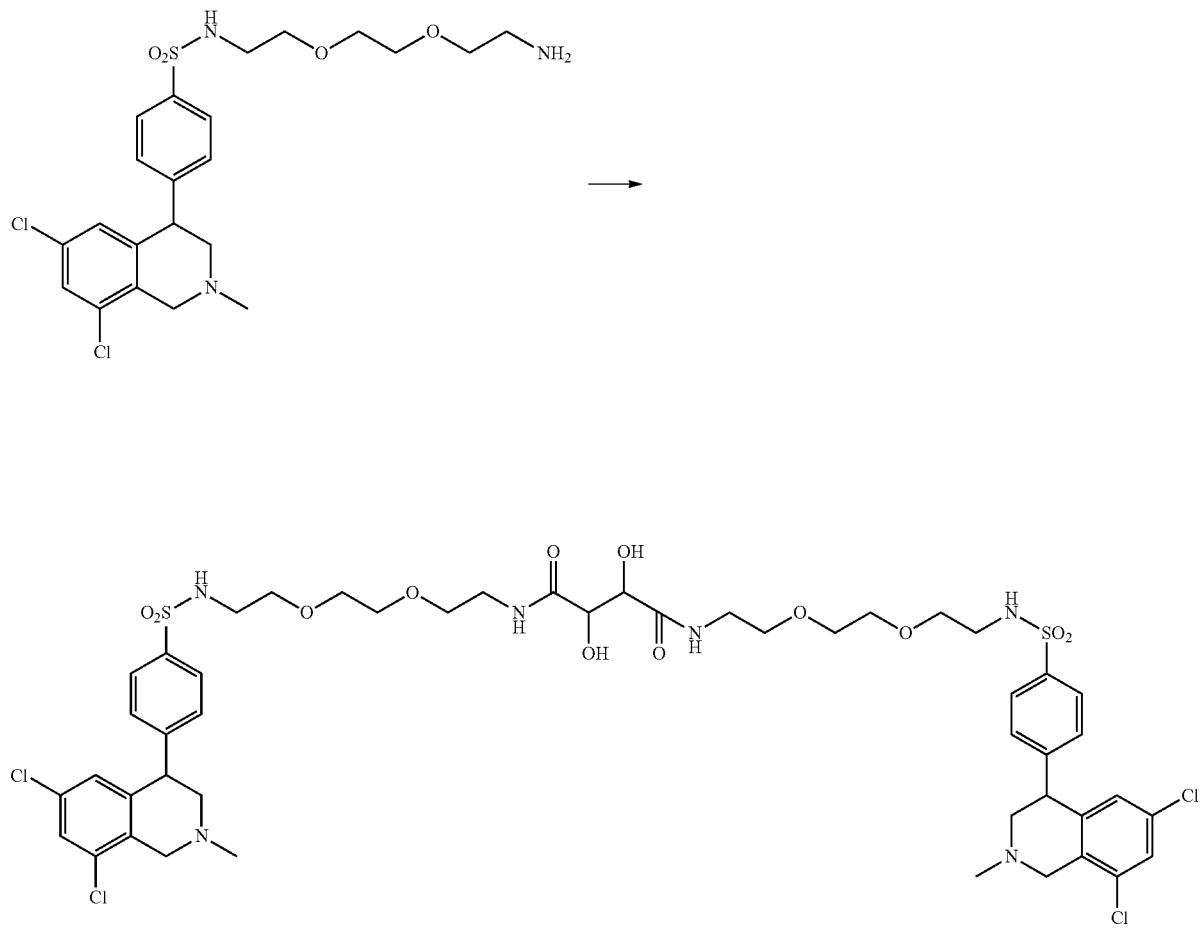

Example 206

N,N'-(2,2'-(2,2'-(2,2'-(1,4-phenylenebis(methylene))bis(azanediyl)bis(ethane-2,1-diyl))bis(oxy)bis(ethane-2,1-diyl))bis(oxy)bis(ethane-2,1-diyl))bis(3-(6,8-dichloro-2-methyl-1,2,3,4-tetrahydroisoquinolin-4-yl)benzenesulfonamide)

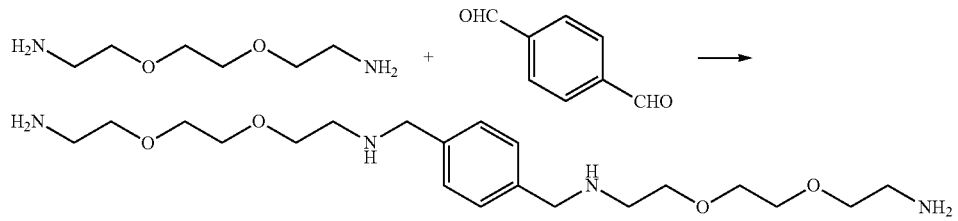

Intermediate 206.1, N,N'-(1,4-phenylenebis(methylene))bis(2-(2-(2-aminoethoxy)ethoxy)ethanamine)

A solution of terephthalaldehyde (134 mg, 1.0 mmol) and 2,2'-(ethane-1,2-diylbis(oxy))diethanamine (1.48 g, 10.0 mmol) in DCM (10 mL) was stirred at room temperature. After 15 minutes sodium triacetoxyborohydride (636 mg, 3.0 mmol) was added and the reaction was stirred for 1.5 hours. Acetic acid (600 mg, 10 mmol) was then added. After stirring for an additional 1.5 hours, acetic acid (600 mg, 10 mmol) and sodium triacetoxyborohydride (636 mg, 3.0 mmol) were added, and stirring was continued at room temperature. One hour later an additional portion of sodium triacetoxyborohydride (636 mg, 3.0 mmol) was added. Twenty hours later the reaction was quenched with 1N HCl (5 mL) and concentrated to dryness. Methanol (10 mL) and 12N HCl (3 drops) were added and the mixture was concentrated to dryness. The residue was dissolved in water (10 mL) and a portion (1.0 mL) was purified by preparative HPLC to give a TFA salt of the title compound (25 mg) as a TFA salt.

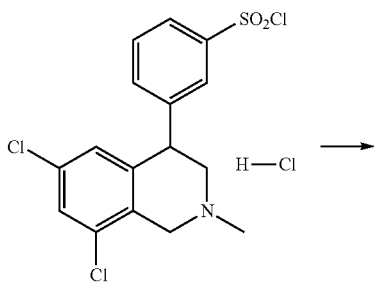

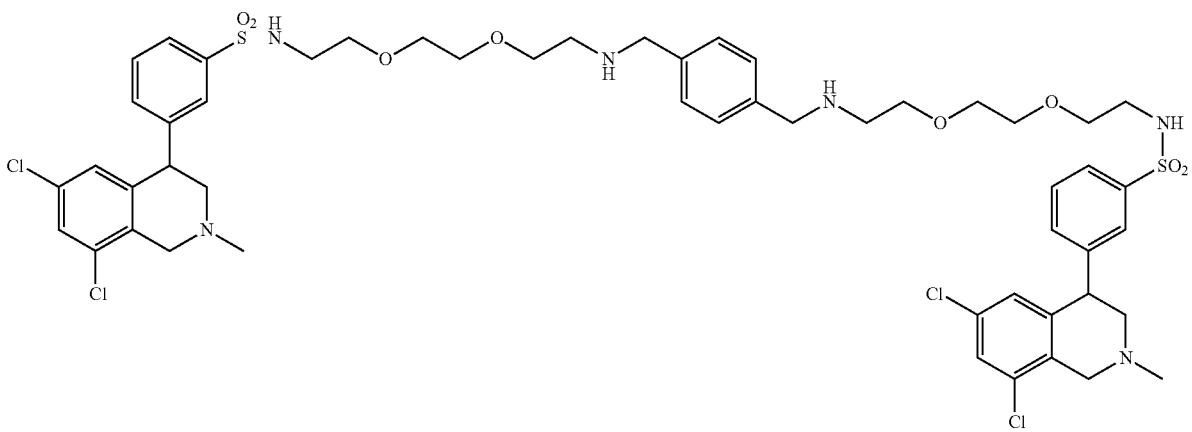

Compound 206, N,N'-(2,2'-(2,2'-(2,2'-(1,4-phenyle-nebis(methylene))bis(azanediyl)bis(ethane-2,1-diyl))bis(oxy)bis(ethane-2,1-diyl))bis(oxy)bis(ethane-2,1-diyl))bis(3-(6,8-dichloro-2-methyl-1,2,3,4-tetrahydroisoquinolin-4-yl)benzenesulfonamide)

To a solution of a TFA salt of intermediate 206.1 (25 mg, 0.029 mmol) in DCM (0.5 mL) was added of 4-(6,8-dichloro-2-methyl-1,2,3,4-tetrahydroisoquinolin-4-yl)benzene-1-sulfonyl chloride (intermediate 1.6) (25 mg, 0.06 mmol) followed by triethylamine (24.2 mg, 0.24 mmol) and the reaction was allowed to stir at room temperature for 18 hours. The reaction was concentrated to dryness, and then purified by preparative HPLC to give the title compound (8 mg) as a TFA salt. $^1$H-NMR (400 mHz, CD3OD) δ 7.85 (m, 2H), 7.74 (m, 2H), 7.62 (m, 6H), 7.53 (m, 4H), 6.80 (s, 1H), 4.74 (m, 6H), 4.44 (m, 2H), 4.30 (s, 4H), 3.83 (m, 2H), 3.76 (m, 4H), 3.62 (m, 8H), 3.50 (m, 4H), 3.23 (m, 4H), 3.10 (s, 6H), 3.02 (m, 4H). MS (m/z): 1105.05 [M+H]$^+$.

Example 207

(2R,3R)—N1,N4-bis(2-(2-(2-(4-(6,8-dichloro-2-methyl-1,2,3,4-tetrahydroisoquinolin-4-yl)phenylsulfonamido)ethoxy)ethoxy)ethyl)-2,3-dihydroxysuccinamide Compound 207, (2R,3R)—N1,N4-bis(2-(2-(2-(4-(6,8-dichloro-2-methyl-1,2,3,4-tetrahydroisoquinolin-4-yl)phenylsulfonamido)ethoxy)ethoxy)ethyl)-2,3-dihydroxysuccinamide Following the procedures outlined in example 205, compound 207 was prepared using (2R,3R)-bis(2,5-dioxopyrrolidin-1-yl) 2,3-dihydroxysuccinate. Purification by preparative HPLC gave a TFA salt of the title compound. $^1$H-NMR (400 mHz, CD3OD) δ 7.82 (m, 4H), 7.45 (m, 1H), 7.38 (m, 2H), 6.75 (s, 1H), 4.64 (m, 4H), 4.37 (m, 4H), 3.74 (m, 2H), 3.46 (m, 10H), 3.38 (m, 12H), 3.02 (m, 10H). MS (m/z): 1117.07 [M+H]$^+$.

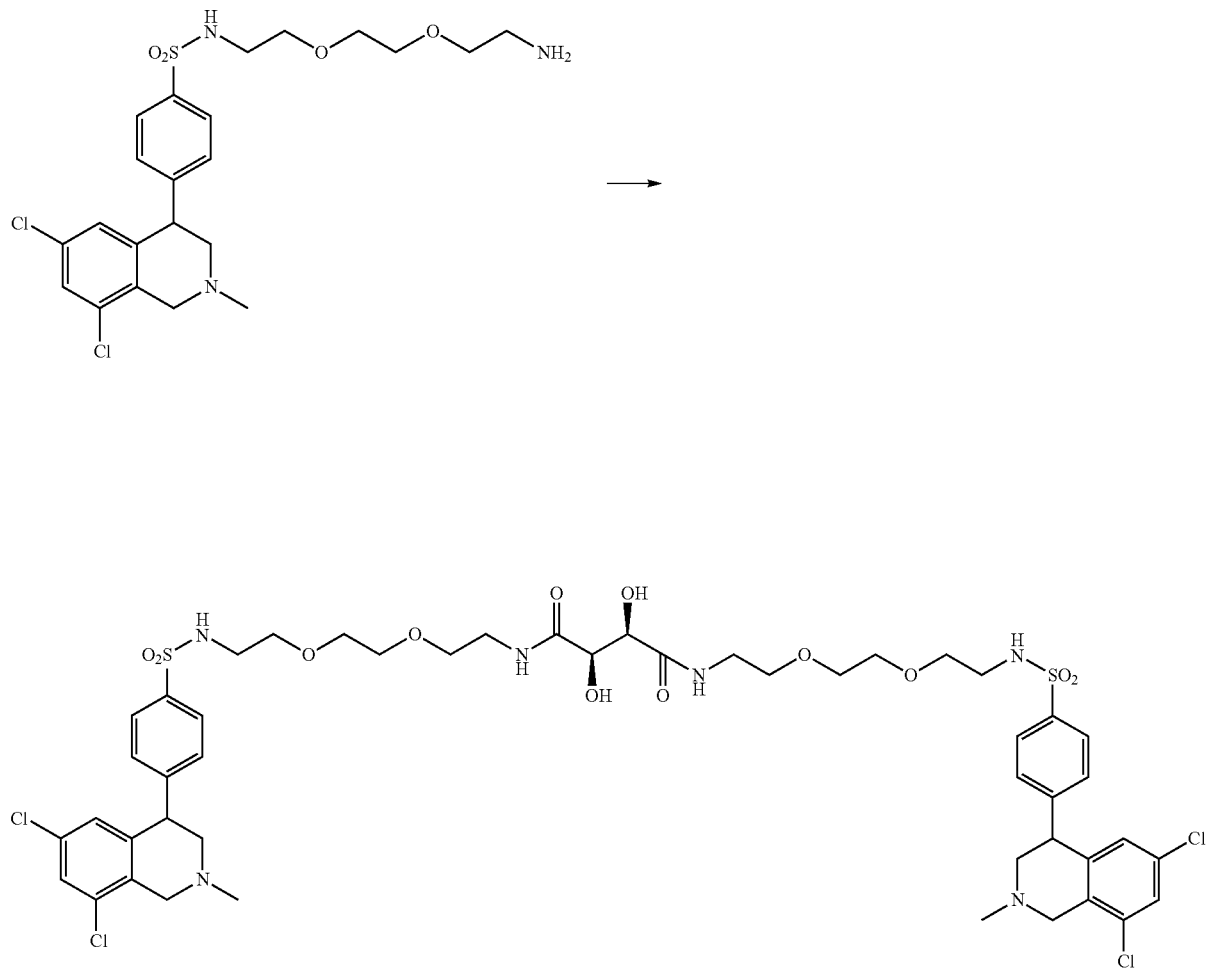

Example 208

N,N'-(13,20-dioxo-3,6,9,24,27,30-hexaoxa-12,14,19,21-tetraazadotriacontane-1,32-diyl)bis(3-(6,8-dichloro-2-methyl-1,2,3,4-tetrahydroisoquinolin-4-yl)benzenesulfonamide)

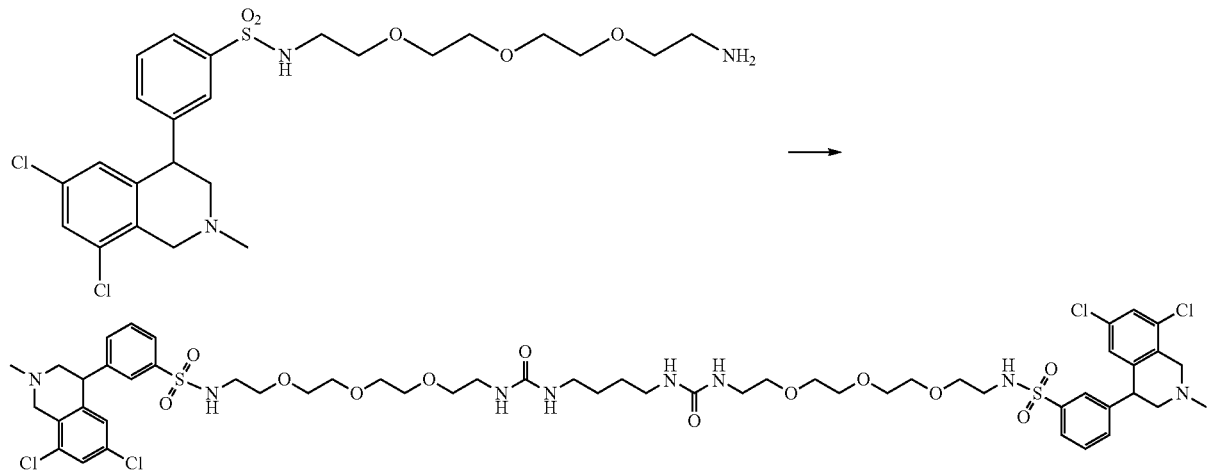

Compound 208, N,N'-(13,20-dioxo-3,6,9,24,27,30-hexaoxa-12,14,19,21-tetraazadotriacontane-1,32-diyl)bis(3-(6,8-dichloro-2-methyl-1,2,3,4-tetrahydroisoquinolin-4-yl)benzenesulfonamide)

To a solution of a TFA salt of N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (compound 28) (47 mg, 0.061 mmol) in DMF (0.20 mL) was added 1,4-diisocyanatobutane (4.0 mg, 0.03 mmol) followed by diisopropylethylamine (15 mg, 0.12 mmol). After stirring at room temperature for 30 minutes, the reaction was purified by preparative HPLC to give the title compound (31 mg) as a TFA salt. $^1$H-NMR (400 mHz, CD3OD) δ 7.88 (m, 2H), 7.75 (m, 2H), 7.63 (m, 2H), 7.54 (m, 4H), 6.83 (m, 2H), 4.74 (m, 4H), 4.48 (m, 2H), 3.87 (m, 2H), 3.62-3.55 (m, 14H), 3.51-3.43 (m, 12H), 3.24 (m, 4H), 3.14 (s, 6H), 3.05 (m, 8H), 1.43 (m, 4H). MS (m/z): 1230.99 [M+H]$^+$.

Example 209

N,N'-(1,1'-(1,4-phenylenebis(azanediyl))bis(1-oxo-5,8,11-trioxa-2-azatridecane-13,1-diyl))bis(3-(6,8-dichloro-2-methyl-1,2,3,4-tetrahydroisoquinolin-4-yl)benzenesulfonamide)

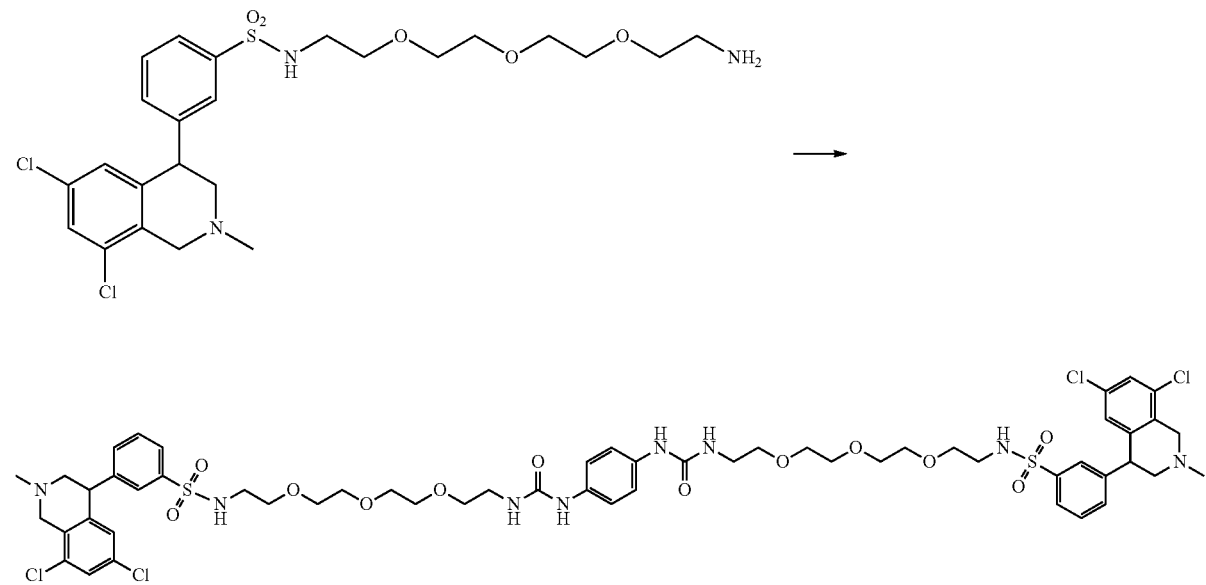

Compound 209, N,N'-(1,1'-(1,4-phenylenebis(azanediyl))bis(1-oxo-5,8,11-trioxa-2-azatridecane-13,1-diyl))bis(3-(6,8-dichloro-2-methyl-1,2,3,4-tetrahydroisoquinolin-4-yl)benzenesulfonamide)

Following the procedures outlined in example 208, compound 209 was prepared using 1,4-diisocyanatobenzene. Purification by preparative HPLC gave a TFA salt of the title compound. $^1$H-NMR (400 mHz, CD3OD) δ 7.78 (m, 2H), 7.64 (m, 2H), 7.53 (m, 2H), 7.43 (m, 2H), 7.39 (m, 2H), 7.10 (s, 4H), 6.71 (s, 2H), 4.58 (m, 4H), 4.39 (m, 2H), 3.68 (m, 2H), 3.54 (s, 8H), 3.50-3.44 (m, 8H), 3.42 (m, 6H), 3.35 (m, 4H), 2.99 (s, 6H), 2.95 (m, 4H). MS (m/z): 1250.98 [M+H]$^+$.

Example 210

(2R,3R)—N1,N4-bis(20-(4-(4-((E)-3-(diaminomethyleneamino)-2-methyl-3-oxoprop-1-enyl)-2,6-difluorophenoxy)phenylsulfonamido)-3,6,9,12,15,18-hexaoxaicosyl)-2,3-dihydroxysuccinamide

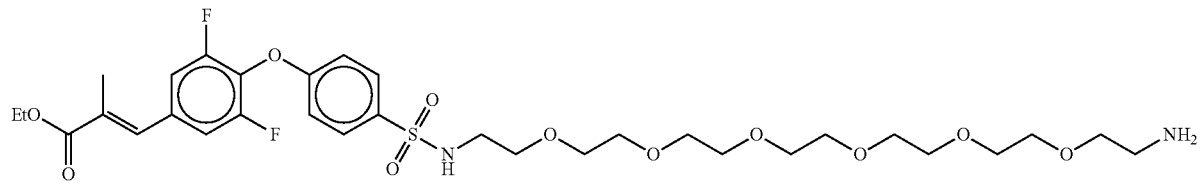

Intermediate 210.1, (E)-ethyl 3-(4-(4-(N-(20-amino-3,6,9,12,15,18-hexaoxaicosyl)sulfamoyl)phenoxy)-3,5-difluorophenyl)-2-methylacrylate Intermediate 210.1 was prepared following the procedure outlined in Example 44.2 using 20-azido-3,6,9,12,15,18-hexaoxaicosan-1-amine. The title compound was recovered in 64% yield as a yellow oil.

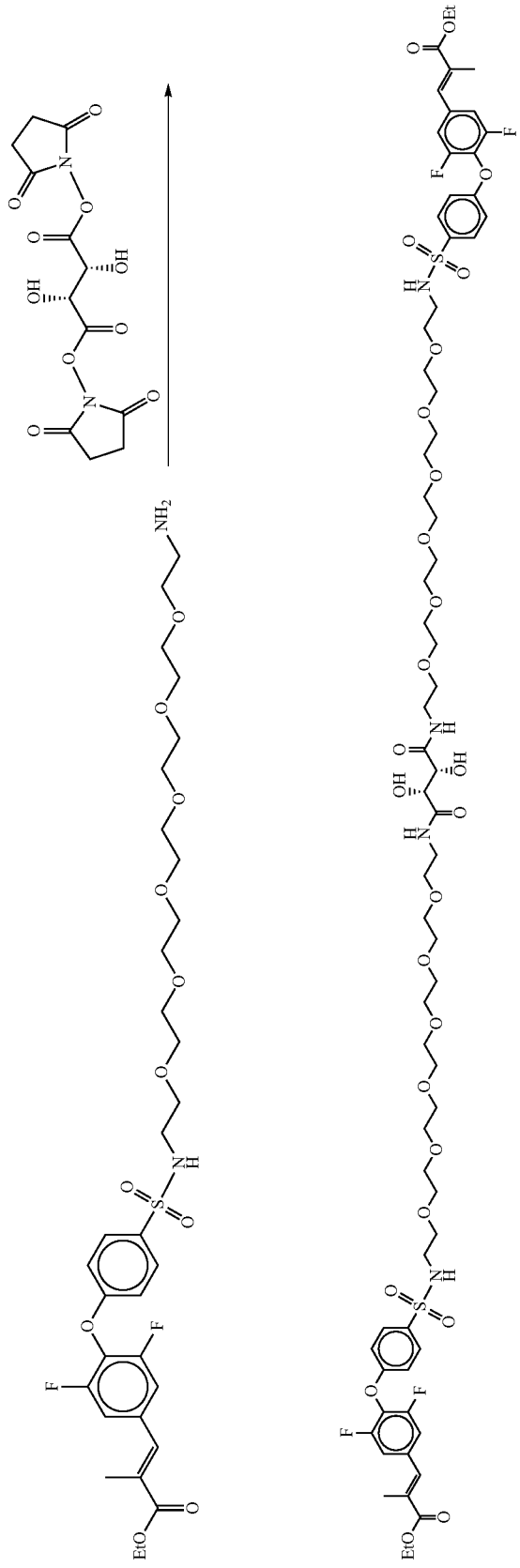

Intermediate 210.2, (2R,3R)—N1,N4-bis(20-(4-(4-((E)-4-(2-carboxyprop-1-enyl)-2,6-difluorophenoxy)phenylsulfonamido)-3,6,9,12,15,18-hexaoxaicosyl)-2,3-dihydroxysuccinamide Intermediate 210.2 was prepared following the procedure outlined in Example 168 using (2R,3R)-bis(2,5-dioxopyrrolidin-1-yl) 2,3-dihydroxysuccinate (22.4 mg, 0.065 mmol) and (E)-ethyl 3-(4-(4-(N-(20-amino-3,6,9,12,15,18-hexaoxaicosyl)sulfamoyl)phenoxy)-3,5-difluorophenyl)-2-methylacrylate (91.5 mg, 0.13 mmol). The title compound was recovered in 60% yield as a clear semi-solid.

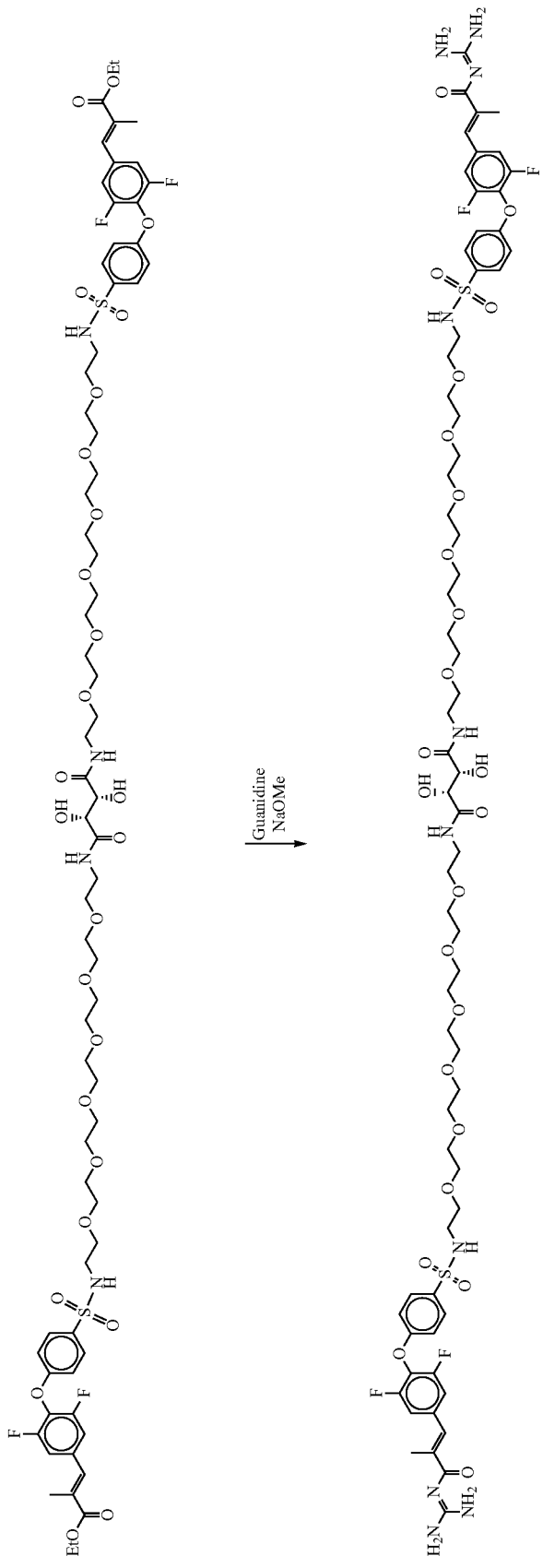

Compound 210, (2R,3R)—N1,N4-bis(20-(4-(4-((E)-3-(diaminomethyleneamino)-2-methyl-3-oxoprop-1-enyl)-2,6-difluorophenoxy)phenylsulfonamido)-3,6,9,12,15,18-hexaoxaicosyl)-2,3-dihydroxysuccinamide Compound 210 was prepared following the procedure outlined in Example 45 using Intermediate 210.2 (59.6 mg). Purification by preparative HPLC gave the title compound (10 mg) as a TFA salt. $^1$H-NMR (400 MHz, CD3OD): δ7.64 (d, 4H), 7.48 (s, 1H), 7.32 (d, 4H), 7.12 (d, 4H), 3.62-3.58 (m, 17H), 3.55-3.52 (m, 9H), 3.48-3.41 (m, 13H), 3.06 (s, 3H), 2.72 (s, 6H). MS (m/z): 1549.23 [M+H]$^+$.

Compound 211

(E)-3-(4-(4-(N-(20-amino-3,6,9,12,15,18-hexaoxaicosyl)sulfamoyl)phenoxy)-3,5-difluorophenyl)-N-(diaminomethylene)-2-methylacrylamide

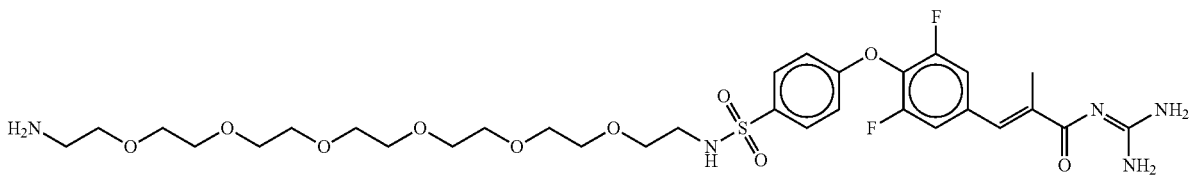

Compound 211, (E)-3-(4-(4-(N-(20-amino-3,6,9,12,15,18-hexaoxaicosyl)sulfamoyl)phenoxy)-3,5-difluorophenyl)-N-(diaminomethylene)-2-methylacrylamide Compound 211 was prepared following the procedure outlined in Example 45 using (E)-ethyl 3-(4-(4-(N-(20-amino-3,6,9,12,15,18-hexaoxaicosyl)sulfamoyl)phenoxy)-3,5-difluorophenyl)-2-methylacrylate (Intermediate 210.2, 13.2 mg). Purification by preparative HPLC gave the title compound (8.7 mg) as a TFA salt. $^1$H-NMR (400 MHz, CD3OD): δ 7.84 (d, 2H), 7.52 (s, 1H), 7.35 (d, 2H), 7.12 (d, 2H), 3.74-3.70 (m, 2H), 3.69-3.58 (m, 24H), 3.55-3.51 (m, 2H), 3.49-3.46 (m, 2H), 3.15-3.12 (m, 2H), 3.07-3.04 (m, 2H). MS (m/z): 718.28 [M+H]$^+$.

Example 212

(2R,3R)—N1,N4-bis(2-(2-(2-(2-(4-(4-((E)-3-(diaminomethyleneamino)-2-methyl-3-oxoprop-1-enyl)-2,6-difluorophenoxy)phenylsulfonamido)ethoxy)ethoxy)ethoxy)ethyl)-2,3-dihydroxysuccinamide

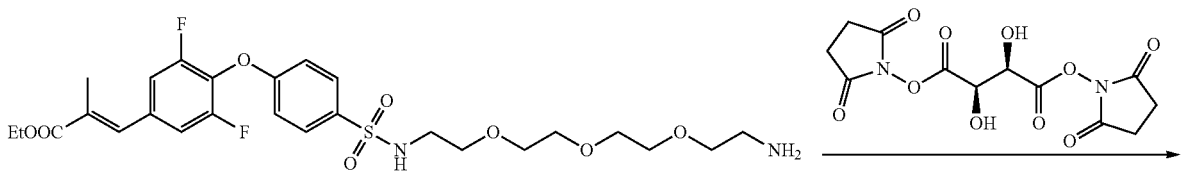

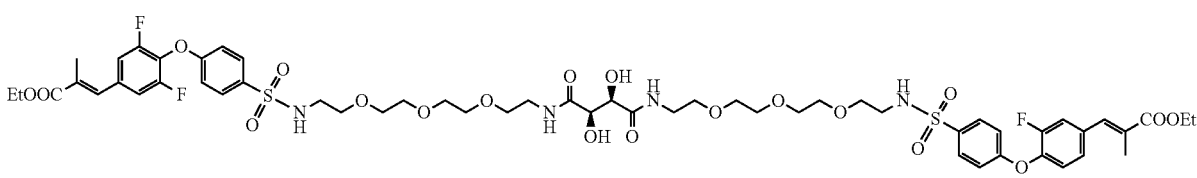

Intermediate 212.1, (E)-ethyl 3-(4-(4-(N-(2-(2-(2-(2-aminoethoxy)ethoxy)ethoxy)ethyl)sulfamoyl)phenoxy)-3,5-difluorophenyl)-2-methylacrylate Compound 44.2 (100 mg, 0.175 mmol) and (2R,3R)-bis(2,5-dioxopyrrolidin-1-yl) 2,3-dihydroxysuccinate (30.1 mg, 0.087 mmol) were dissolved in DMF (0.35 mL) with DIEA (67.7 mg, 0.525 mmol) and stirred for 2 hours at room temperature. The solvent was removed and the resulting material partitioned between EtOAc (20 mL) and water (20 mL). The organic layer was washed with saturated $NaHCO_3$ (20 mL), brine (20 mL) and dried over $Na_2SO_4$ to give the product (87.7 mg) as a yellow oil that was used without further purification.

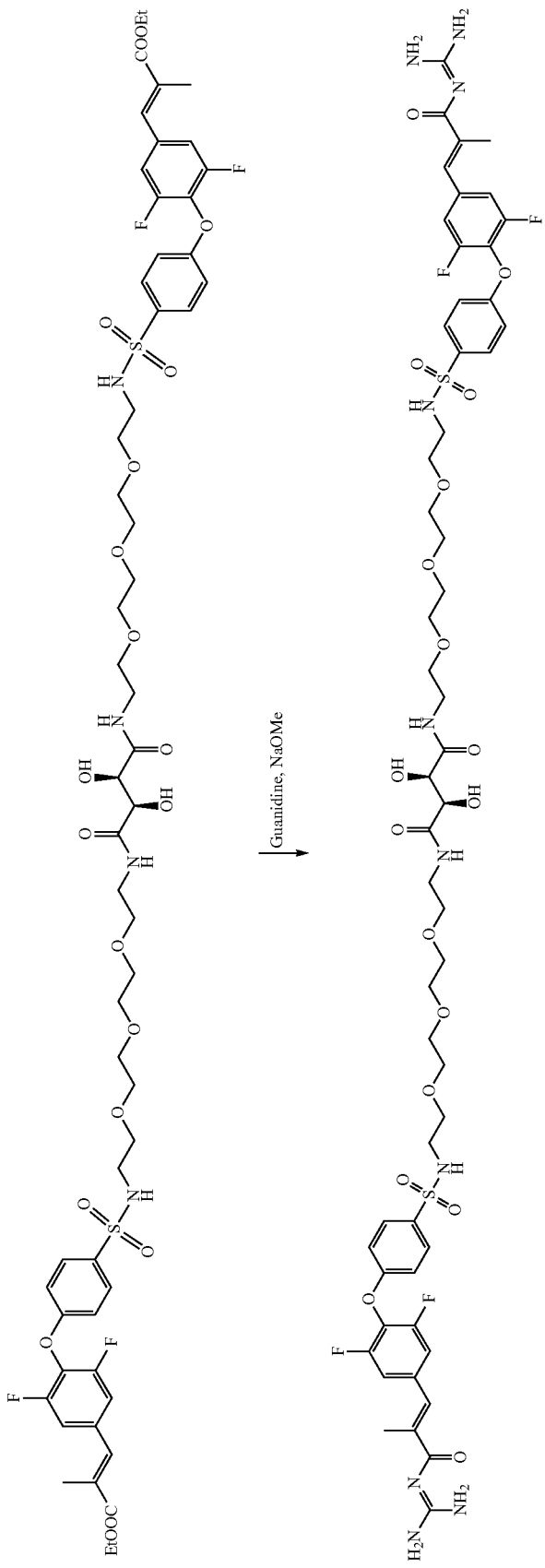

Compound 212, (2R,3R)—N1,N4-bis(2-(2-(2-(2-(4-(4-((E)-3-(diaminomethyleneamino)-2-methyl-3-oxoprop-1-enyl)-2,6-difluorophenoxy)phenylsulfonamido)ethoxy)ethoxy)ethoxy)ethyl)-2,3-dihydroxysuccinamide Compound 212 was prepared following the procedures outlined in Example 45. Purification by preparative HPLC gave 9.6 mg of the title compound as the TFA salt. $^1$H-NMR (400 MHz, CD3OD): δ 7.86 (d, 4H), 7.44 (s, 2H), 7.31 (d, 4H), 7.11 (d, 4H), 4.44 (s, 2H), 3.61-3.53 (m, 21H), 3.50-3.41 (m, 15H), 3.05 (t, 4H), 2.17 (s, 6H). MS (m/z): 1286.11 [M+H]$^+$.

Example 213

2,2',2''-nitrilotris(N-(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)acetamide)

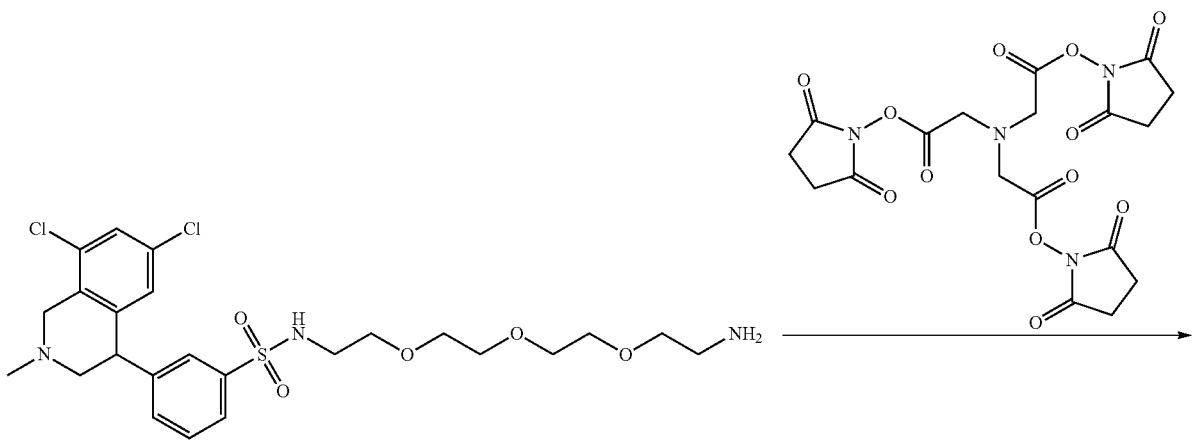

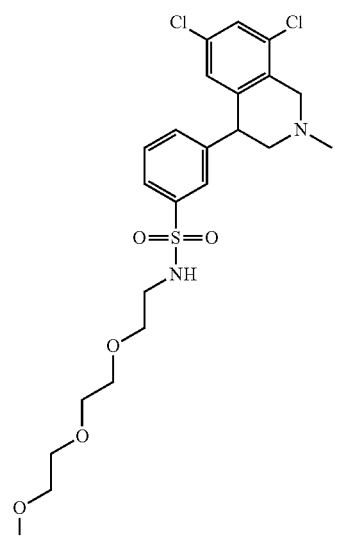

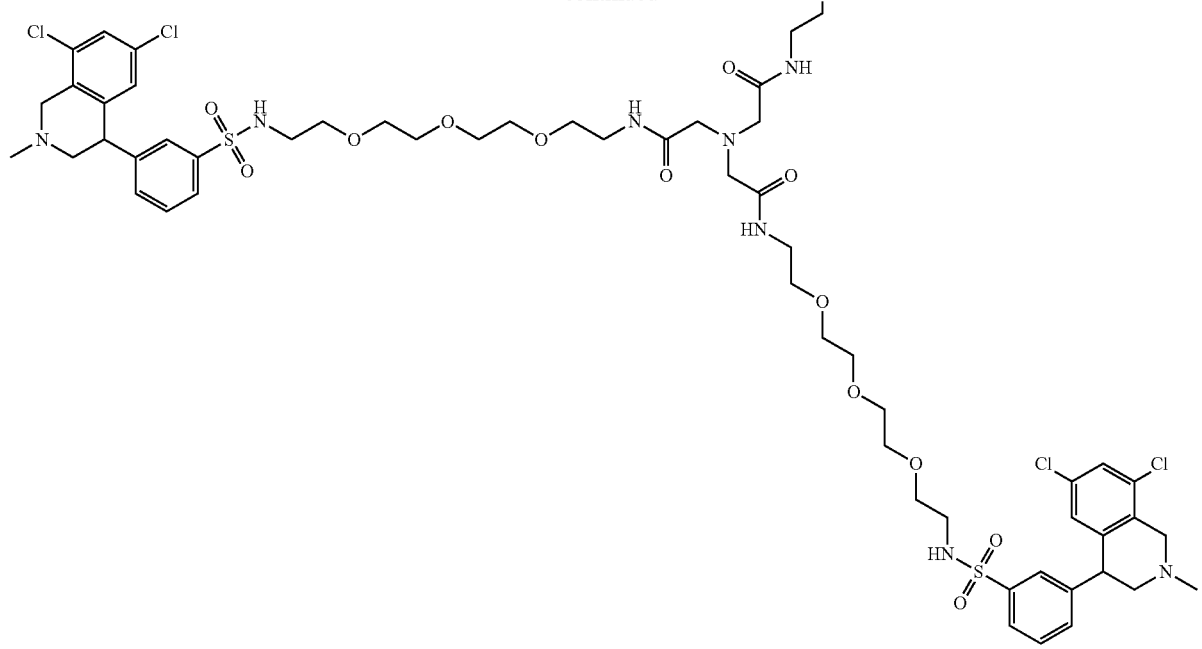

Compound 213, 2,2',2''-nitrilotris(N-(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)acetamide)

Compound 213 was prepared following the procedure outlined in Example 168 using tris(2,5-dioxopyrrolidin-1-yl) 2,2',2''-nitrilotriacetate (75 mg, 0.156 mmol) and N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (Compound 28, 254 mg, 0.467 mmol). Purification by preparative HPLC gave the title compound (32.0 mg) as the TFA salt. $^1$H-NMR (400 MHz, CD3OD): δ 7.88 (d, 3H), 7.75 (s, 3H), 7.63 (t, 3H), 7.54 (t, 6H), 6.82 (s, 3H), 4.84-4.75 (m, 6H), 4.48 (d, 3H), 3.86 (m, 3H), 3.85-3.37 (m, 54H), 3.14 (s, 9H), 3.02 (t, 6H). MS (m/z): 1777.07 [M+H]$^+$.

Example 214

N-(32-amino-3,6,9,12,15,18,21,24,27,30-decaoxadotriacontyl)-3-(6,8-dichloro-2-methyl-1,2,3,4-tetrahydroisoquinolin-4-yl)benzenesulfonamide

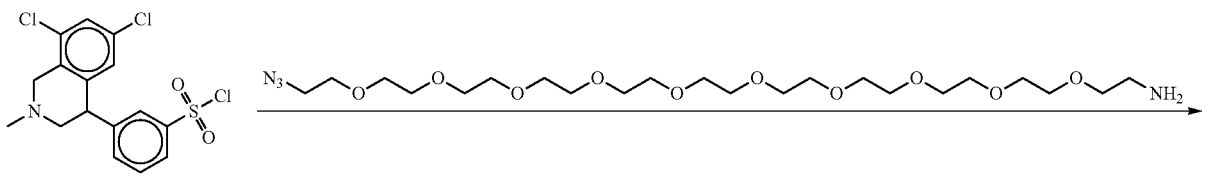

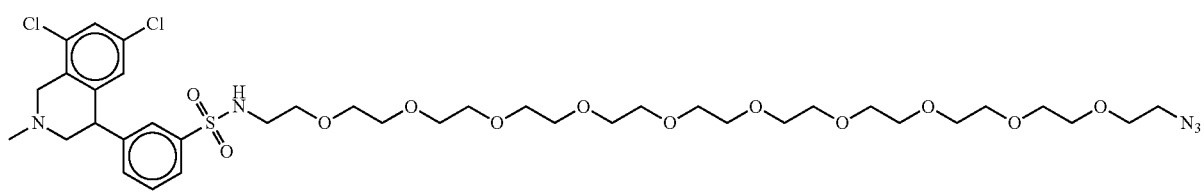

411

Intermediate 214.1, N-(32-azido-3,6,9,12,15,18,21,24,27,30-decaoxadotriacontyl)-3-(6,8-dichloro-2-methyl-1,2,3,4-tetrahydroisoquinolin-4-yl)benzenesulfonamide A solution of 32-azido-3,6,9,12,15,18,21,24,27,30-decaoxadotriacontan-1-amine (436.9 mg, 0.777 mmol) in dry DMF (3.5 mL) under $N_2$ was cooled to 0° C. A solution of 3-(6,8-dichloro-2-methyl-1,2,3,4-tetrahydroisoquinolin-4-yl)benzene-1-sulfonyl chloride (300 mg, 0.706 mmol) and DIEA (273.2 mg, 2.118 mmol) in DMF (3 mL) was added dropwise. After 60 minutes LCMS indicated complete conversion and the solvent was removed to give N-(32-azido-3,6,9,12,15,18,21,24,27,30-decaoxadotriacontyl)-3-(6,8-dichloro-2-methyl-1,2,3,4-tetrahydroisoquinolin-4-yl)benzenesulfonamide (620 mg) as a yellow oil which was used without further purification.

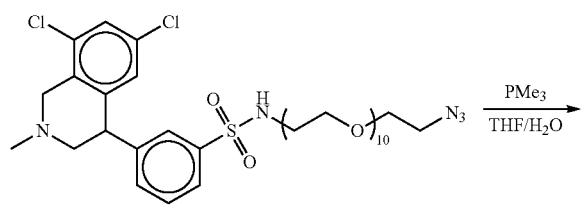

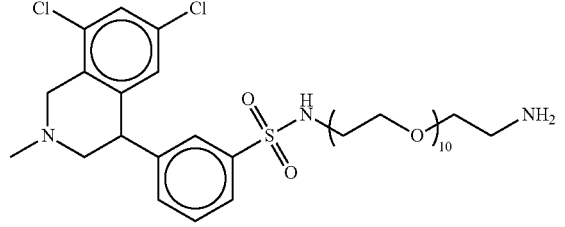

412

Compound 214, N-(32-amino-3,6,9,12,15,18,21,24,27,30-decaoxadotriacontyl)-3-(6,8-dichloro-2-methyl-1,2,3,4-tetrahydroisoquinolin-4-yl)benzenesulfonamide To a solution of N-(32-azido-3,6,9,12,15,18,21,24,27,30-decaoxadotriacontyl)-3-(6,8-dichloro-2-methyl-1,2,3,4-tetrahydroisoquinolin-4-yl)benzenesulfonamide (Intermediate 214.1, 620 mg, 0.706 mmol) in THF/$H_2O$ (10:1 v/v, 14.3 mL) under $N_2$ was added trimethylphosphine (214.8 mg, 2.82 mmol). The resulting solution was stirred overnight at which point LCMS indicated complete conversion. The solvent was removed to give 819 mg of an orange oil, a portion of which was purified by preparative HPLC to give the title compound as a TFA salt. $^1$H-NMR (400 MHz, CD3OD): δ 7.90 (d, 1H), 7.68 (s, 1H), 7.62 (t, 1H), 7.55 (m, 2H), 6.82 (s, 1H), 3.85 (m, 1H), 3.78 (q, 3H), 3.70-3.58 (m, 55H), 3.52 (m, 2H), 3.46 (t, 3H), 3.18 (t, 3H), 3.11 (s, 3H), 3.03 (t, 2H). MS (m/z): 855.24 [M+H]$^+$.

Example 215

N1,N3,N5-tris(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)benzene-1,3,5-tricarboxamide

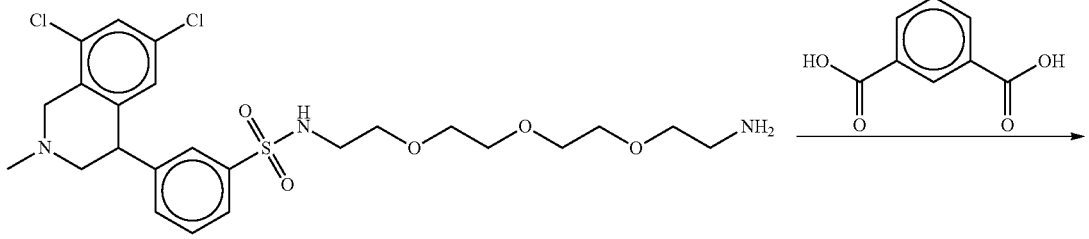

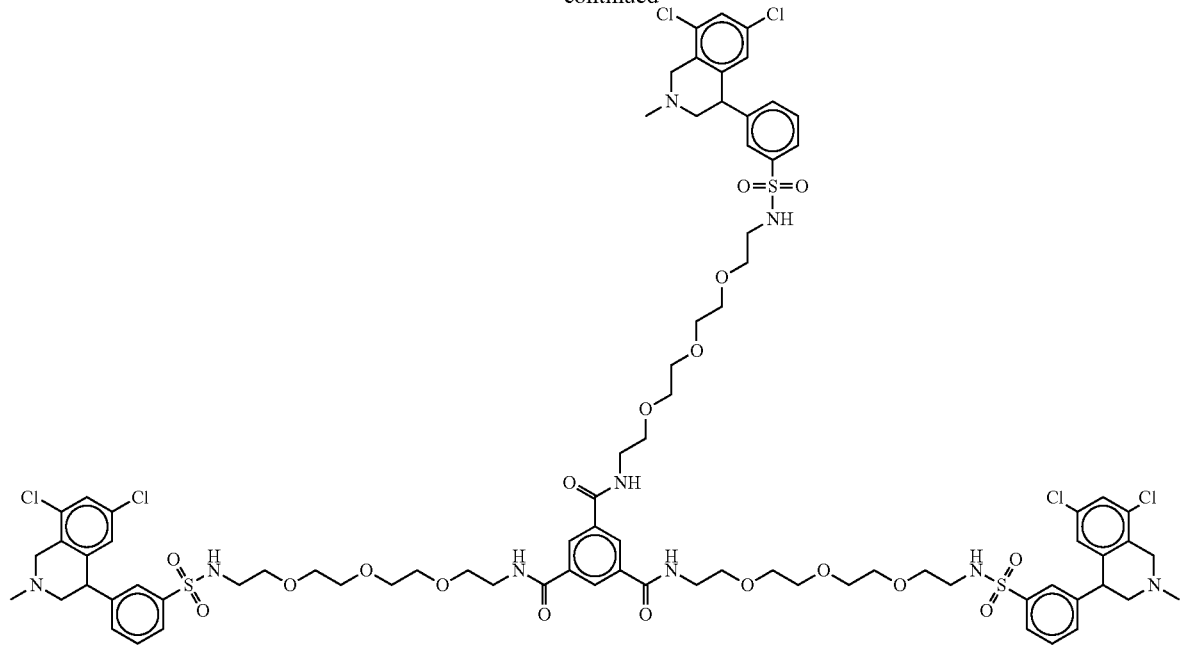

Compound 215, N1,N3,N5-tris(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)benzene-1,3,5-tricarboxamide To a solution of N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (Compound 28, 75 mg, 0.0968) in DMF (0.5 mL) was added benzene-1,3,5-tricarboxylic acid (6.7 mg, 0.0319 mmol), DIEA (37.5 mg, 0.291 mmol), and finally HATU (40.4 mg, 0.107 mmol). The reaction was stirred for 60 minutes at room temperature at which point LCMS indicated complete conversion. The resulting solution was diluted with acetonitrile/water solution (1:1 v/v) and filtered. Purification by preparative HPLC gave the title compound (37.7 mg) as a TFA salt. $^1$H-NMR (400 MHz, CD3OD): δ 8.37 (s, 3H), 7.84 (d, 2H), 7.83 (s, 2H), 7.62 (t, 2H), 7.51-7.50 (m, 4H), 6.79 (s, 2H), 4.83-4.70 (m, 5H), 4.46 (d, 2H), 3.86 (q, 2H), 3.67-3.53 (m, 27H), 3.45 (t, 5H), 3.39 (t, 5H), 3.14 (s, 7H), 2.98 (t, 4H). MS (m/z): 1797.15 [M+H]$^+$.

Example 216

N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)terephthalamide

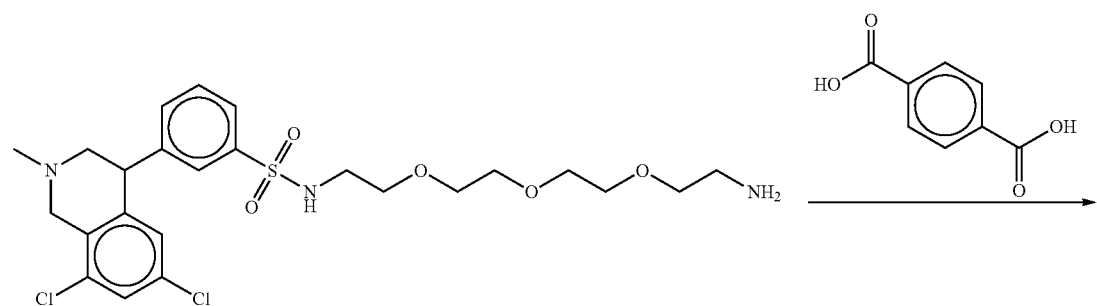

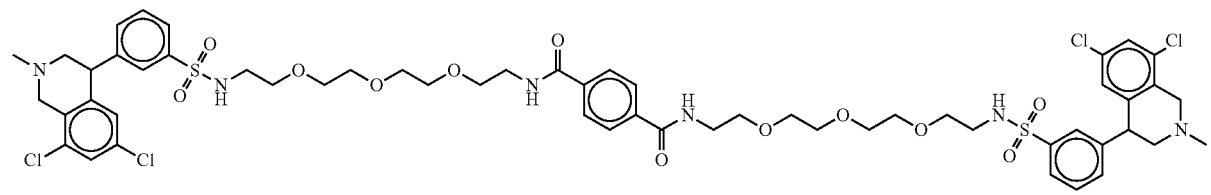

Compound 216, N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)-ethyl)terephthalamide Compound 216 was prepared following the procedure outlined in Example 215 using terephthalic acid (10.7 mg, 0.0646 mmol) and N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (Compound 28, 100 mg, 0.129 mmol). Purification by preparative HPLC gave the title compound (46.3 mg) as a TFA salt. $^1$H-NMR (400 MHz, CD3OD): δ 7.87 (m, 6H), 7.73 (s, 2H), 7.59 (t, 2H), 7.52-7.49 (m, 4H) m, 6.80 (s, 2H), 4.77-4.69 (m, 4H), 4.49 (d, 2H), 3.587 (qs, 2H), 3.67-3.54 (m, 27H), 3.45 (t, 5H), 3.40 (t, 5H), 3.13 (s, 7H), 2.99 (t, 4H). MS (m/z): 1224.34 [M+H]$^+$.

Example 217

N1,N31-bis(32-(3-(6,8-dichloro-2-methyl-1,2,3,4-tetrahydroisoquinolin-4-yl)phenylsulfonamido)-3,6,9,12,15,18,21,24,27,30-decaoxadotriacontyl)-4,7,10,13,16,19,22,25,28-nonaoxahentriacontane-1,31-diamide

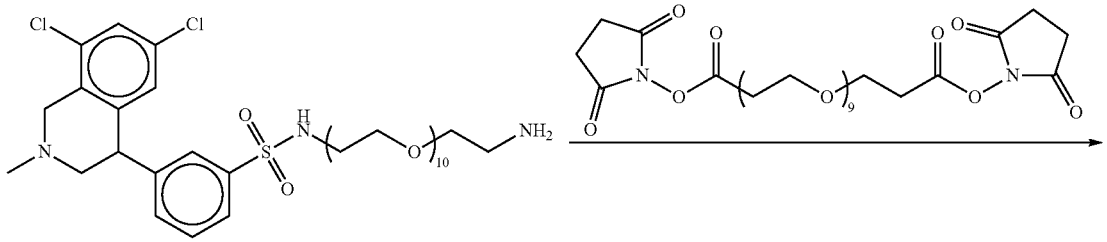

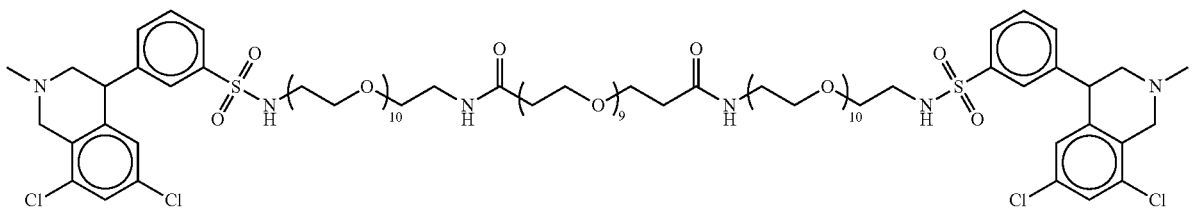

Compound 217, N1,N31-bis(32-(3-(6,8-dichloro-2-methyl-1,2,3,4-tetrahydroisoquinolin-4-yl)phenylsulfonamido)-3,6,9,12,15,18,21,24,27,30-decaoxadotriacontyl)-4,7,10,13,16,19,22,25,28-nonaoxahentriacontane-1,31-diamide Compound 217 was prepared following the procedure outlined in Example 168 using bis(2,5-dioxopyrrolidin-1-yl) 4,7,10,13,16,19,22,25,28-nonaoxahentriacontane-1,31-dioate (69.1 mg, 0.0975 mmol) and N-(32-amino-3,6,9,12,15,18,21,24,27,30-decaoxadotriacontyl)-3-(6,8-dichloro-2-methyl-1,2,3,4-tetrahydroisoquinolin-4-yl)benzenesulfonamide (Compound 214, 166.2 mg, 0.195 mmol). Purification by preparative HPLC gave the title compound (106.3 mg) as a TFA salt. $^1$H-NMR (400 MHz, CD3OD): δ 7.88 (d, 2H), 7.76 (s, 2H), 7.66 (t, 2H), 7.56 (m, 4H), 6.86 (s, 2H), 3.90 (m, 2H), 3.82 (t, 2H), 3.76 (m, 6H), 3.62-3.41 (m, 28H), 3.38 (m, 6H), 3.35-3.28 (m, 56H), 3.15 (s, 6H), 3.05 (t, 4H), 2.43 (t, 4H). MS (m/z): 1094.37 [(M+2H)/2]$^+$.

Example 218

(2R,3R)—N1,N4-bis(2-(2-(2-(3-(6,8-dichloro-2-methyl-1,2,3,4-tetrahydroisoquinolin-4-yl)phenylsulfonamido)ethoxy)ethoxy)ethyl)-2,3-dihydroxysuccinamide

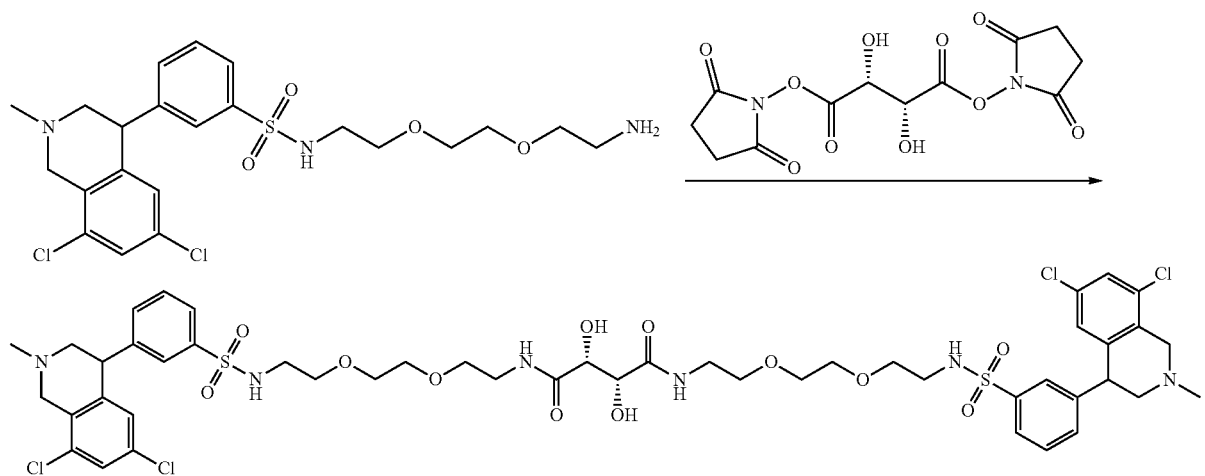

Compound 218, (2R,3R)—N1,N4-bis(2-(2-(2-(3-(6,8-dichloro-2-methyl-1,2,3,4-tetrahydroisoquinolin-4-yl)phenylsulfonamido)ethoxy)ethoxy)ethyl)-2,3-dihydroxysuccinamide Compound 218 was prepared following the procedure outlined in Example 168 using (2R,3R)-bis(2,5-dioxopyrrolidin-1-yl) 2,3-dihydroxysuccinate (10.2 mg, 0.0298 mmol) and N-(2-(2-(2-aminoethoxy)ethoxy)ethyl)-3-(6,8-dichloro-2-methyl-1,2,3,4-tetrahydroisoquinolin-4-yl)benzenesulfonamide (Compound 168.2, 30 mg, 0.0597 mmol). Purification by preparative HPLC gave the title compound (5.1 mg) as the TFA salt. $^1$H-NMR (400 MHz, CD3OD): δ 7.92 (d, J=7.8 Hz, 2H), 7.82 (m, 2H), 7.67 (t, J=7.8 Hz, 2H), 7.57 (m, 2H), 7.55 (d, J=6.9 Hz, 2H0, 6.86 (m, 2H), 4.84 (s, 2H), 4.79 (s, 2H), 4.54 (d, 2H), 4.48 (s, 2H), 3.92 (m, 2H), 3.53 (m, 22H), 3.18 (s, 6H), 3.07 (t, J=5.4 Hz, 4H). MS (m/z): 1119.04 [M+H]$^+$.

Example 219

N1,N3-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)benzene-1,3-disulfonamide

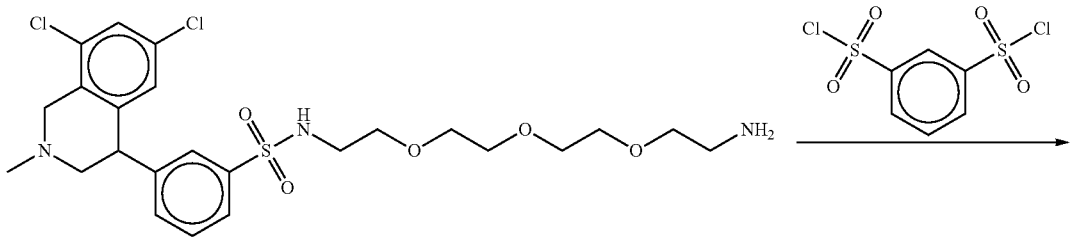

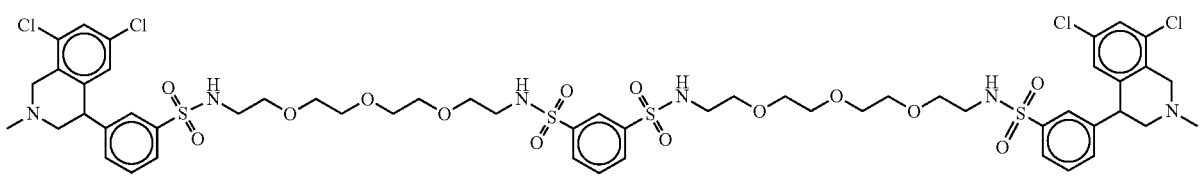

Compound 219, N1,N3-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)benzene-1,3-disulfonamide To a solution of N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (Compound 28, 50 mg, 0.0917 mmol) and DIEA (35.5 mg, 0.275 mmol) in dry DCM (0.183 mL) under N₂ was added benzene-1,3-disulfonyl dichloride (12.7 mg, 0.0459 mmol) in DCM (0.183 mL). The reaction mixture was stirred at room temperature for 60 minutes at which point LCMS indicated complete conversion. The solvent was removed and the resulting residue brought up in 4 mL ACN/H₂O solution (1:1). Filtration and purification by preparative HPLC gave the title compound (16.6 mg) as a TFA salt. ¹H-NMR (400 MHz, CD3OD): δ 8.28 (s, 1H), 8.06 (d, 1H), 7.85 (d, 2H), 7.75 (d, 2H), 7.70 (s, 1H), 7.63 (t, 2H), 7.53 (m, 3H), 6.82 (s, 1H), 4.52 (d, 1H), 3.85 (d, 1H), 3.61-3.46 (m, 28H), 3.13 (s, 6H), 3.09-3.03 (m, 7H). MS (m/z): 1294.99 [M+H]⁺.

Example 220

N4,N4'-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)biphenyl-4,4'-disulfonamide

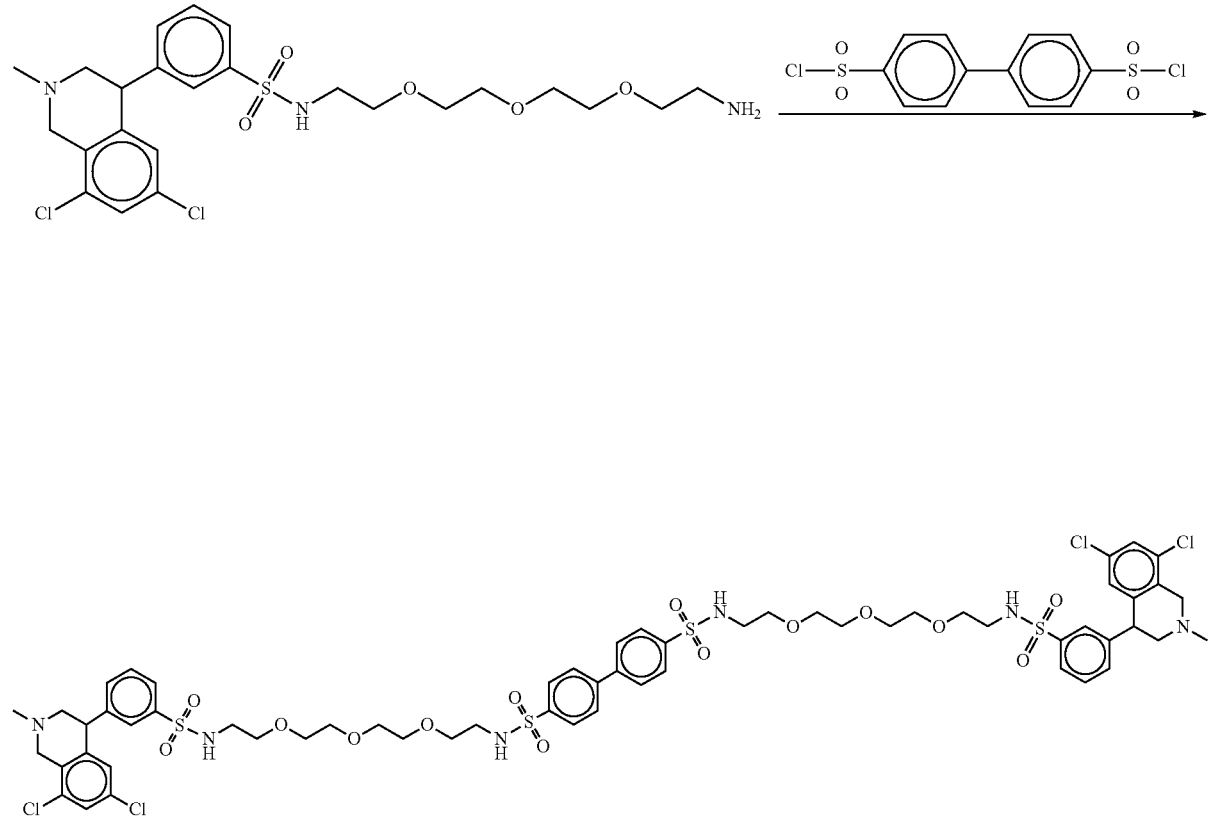

Compound 220, N4,N4'-bis(2-(2-(2-(2-(3-(6,8-dichloro-2-methyl-1,2,3,4-tetrahydroisoquinolin-4-yl)phenylsulfonamido)ethoxy)ethoxy)ethoxy)-ethyl)biphenyl-4,4'-disulfonamide Compound 220 was prepared following the procedure outlined in Example 219 using biphenyl-4,4'-disulfonyl dichloride (16.1 mg, 0.0459 mmol) and N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (Compound 28, 50 mg, 0.0917 mmol). Purification by preparative HPLC gave the title compound (16.7 mg) as a TFA salt. ¹H-NMR (400 MHz, CD3OD): δ 7.96 (d, 4H), 7.88-7.85 (m, 5H), 7.78 (s, 2H), 7.61 (t, 2H), 7.47 (d, 2H), 6.78 (s, 2H), 4.74-4.69 (m, 3H), 4.45 (d, 2H), 3.88-3.83 (m, 2H), 3.62-3.59 (m, 2H), 3.55-3.53 (m, 9H), 3.52-3.43 (m, 17H), 3.13 (s, 6H), 3.11-3.03 (m, 8H). MS (m/z): 1371.02 [M+H]⁺.

Example 221

(14R,15R)-1-(3-(6,8-dichloro-2-methyl-1,2,3,4-tetrahydroisoquinolin-4-yl)phenylsulfonamido)-14,15-dihydroxy-13-oxo-3,6,9-trioxa-12-azahexadecan-16-oic acid

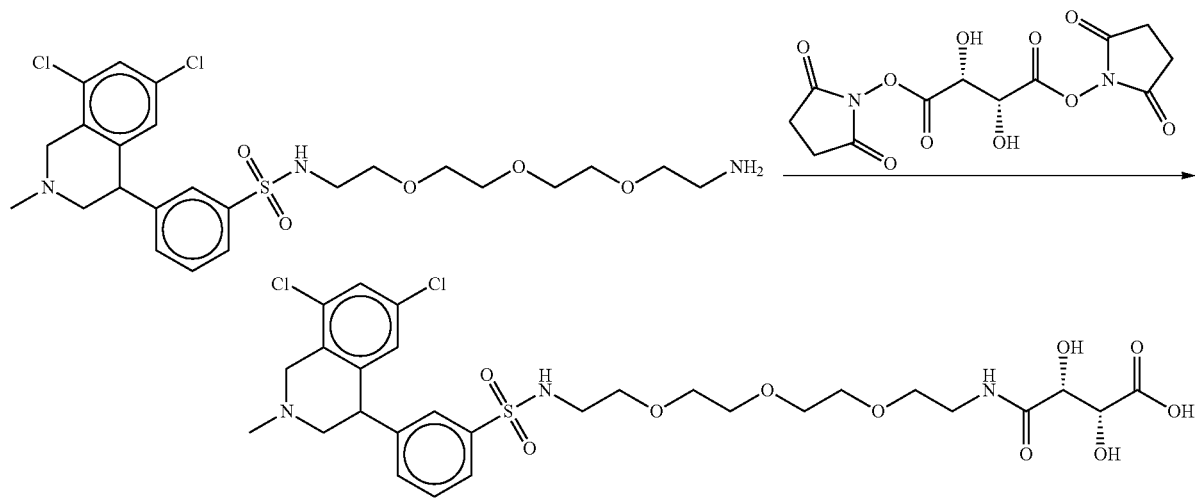

Compound 221, (14R,15R)-1-(3-(6,8-dichloro-2-methyl-1,2,3,4-tetrahydroisoquinolin-4-yl)phenylsulfonamido)-14,15-dihydroxy-13-oxo-3,6,9-trioxa-12-azahexadecan-16-oic acid Compound 221 was prepared by isolating the mono-addition byproduct from the procedure outlined in Example 168 using (2R,3R)-bis(2,5-dioxopyrrolidin-1-yl) 2,3-dihydroxysuccinate (70.4 mg, 0.205 mmol) and Compound 28 (223 mg, 0.409 mmol). Purification by preparative HPLC gave the title compound (44.4 mg) as a TFA salt. $^1$H-NMR (400 MHz, CD3OD): δ 7.89 (d, 1H), 7.81 (d, 1H), 7.63 (t, 1H), 7.55 (s, 1H), 7.50 (t, 1H), 6.84 (s, 0.5H), 3.88-3.84 (m, 1H), 3.64-3.34 (m, 22H), 3.14 (s, 4H), 3.07 (m, 2H). MS (m/z): 677.36 [M+H]$^+$.

Example 222

(2S,3S)—N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide

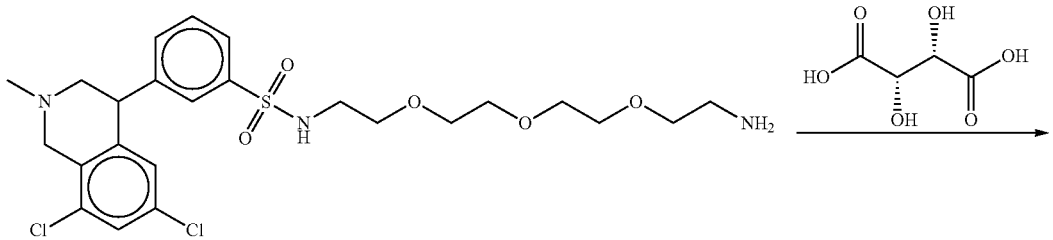

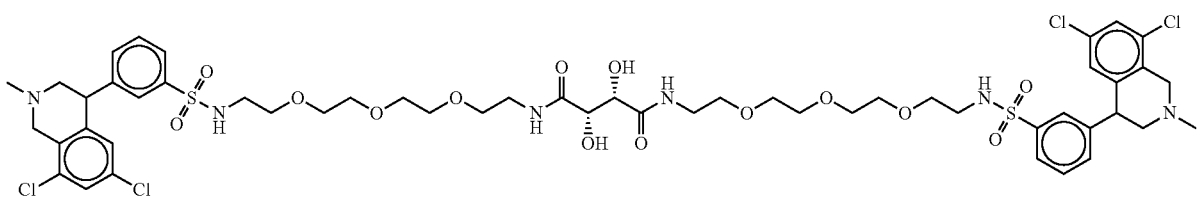

423

Compound 222, (2S,3S)—N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide Compound 222 was prepared following the procedure outlined in Example 215 using (2S,3S)-2,3-dihydroxysuccinic acid (15.5 mg, 0.103 mmol) and N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (Compound 28, 112 mg, 0.206 mmol). Purification by preparative HPLC gave the title compound (39.9 mg) as a TFA salt. $^1$H-NMR (400 MHz, CD3OD): δ 7.87 (d, 2H), 7.77 (s, 2H), 7.63 (t, 2H), 7.54-7.50 (m, 4H), 6.82 (s, 2H), 4.34 (s, 2H), 3.90-3.85 (m, 1H), 3.62-3.30 (m, 47H), 3.14 (m, 8H), 3.05 (t, 4H). MS (m/z): 1206.95 [M+H]$^+$.

Example 223

N1,N4-bis(2-(2-(2-(2-(3-((R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide

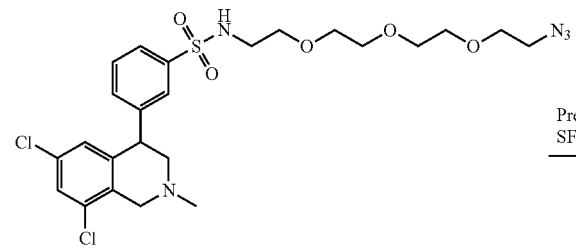

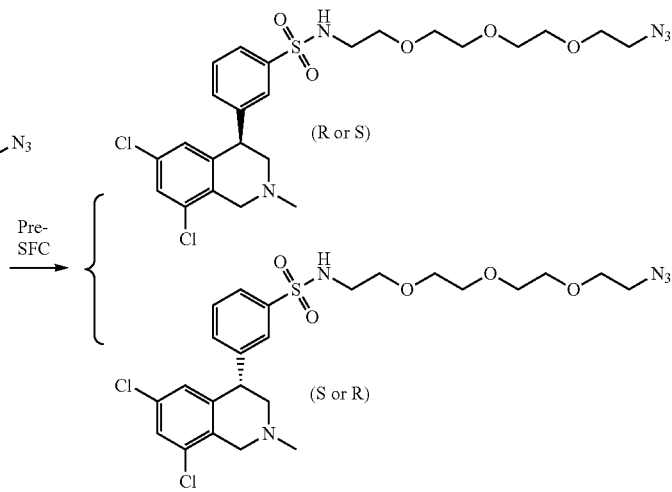

Intermediate 223.1a, (R or S)—N-(2-(2-(2-(2-azidoethoxy)ethoxy)ethoxy)ethyl)-3-(6,8-dichloro-2-methyl-1,2,3,4-tetrahydroisoquinolin-4-yl)benzenesulfonamide and 223.1b (S or R)—N-(2-(2-(2-(2-azidoethoxy)ethoxy)ethoxy)ethyl)-3-(6,8-dichloro-2-methyl-1,2,3,4-tetrahydroisoquinolin-4-yl)benzenesulfonamide N-(2-(2-(2-(2-azidoethoxy)ethoxy)ethoxy)ethyl)-3-(6,8-dichloro-2-methyl-1,2,3,4-tetrahydroisoquinolin-4-yl)benzenesulfonamide (intermediate 28.1, 4.5 g, 7.88 mmol, 1.00 equiv) was separated into its enantiomers by chiral phase preparative Supercritical Fluid Chromatography (Prep-SFC) with the following conditions: Column, Chiralpak IA, 2*25 cm, 5 um; mobile phase, CO$_2$ (80%), methanol (20%); Detector, UV 254 nm.

This resulted in 1.61 g of (R or S)—N-(2-(2-(2-(2-azidoethoxy)ethoxy)ethoxy)ethyl)-3-(6,8-dichloro-2-methyl-1,2,3,4-tetrahydroisoquinolin-4-yl)benzenesulfonamide as a yellow oil. $^1$H-NMR (300 MHz, CD$_3$OD, ppm): δ 7.79 (d, J=7.5 Hz, 1H), 7.711 (s, 1H), 7.49-7.58 (m, 2H), 7.36-7.37 (m, 1H), 6.83 (s, 1H), 4.40-4.44 (m, 1H), 3.80 (d, J=16.2 Hz, 1H), 3.58-3.69 (m, 9H), 3.40-3.52 (m, 4H), 3.33-3.38 (m, 3H), 3.03-3.09 (m, 3H), 2.66-2.72 (m, 1H), 2.50 (s, 3H). MS (m/z): 572 [M+H]$^+$.

This also gave 1.81 g of (S or R)—N-(2-(2-(2-(2-azidoethoxy)ethoxy)ethoxy)ethyl)-3-(6,8-dichloro-2-methyl-1,2,3,4-tetrahydroisoquinolin-4-yl)benzenesulfonamide as yellow oil. $^1$H-NMR (300 MHz, CD$_3$OD, ppm): δ 7.78-7.81 (m, 1H), 7.71 (s, 1H), 7.49-7.58 (m, 2H), 7.36-7.37 (m, 1H), 6.83 (s, 1H), 4.40-4.44 (m, 1H), 3.80 (d, J=15.9 Hz, 1H), 3.57-3.70 (m, 9H), 3.44-3.53 (m, 4H), 3.37-3.40 (m, 3H), 3.03-3.09 (m, 3H), 2.66-2.72 (m, 1H), 2.50 (s, 3H). MS (m/z): 572 [M+H]$^+$.

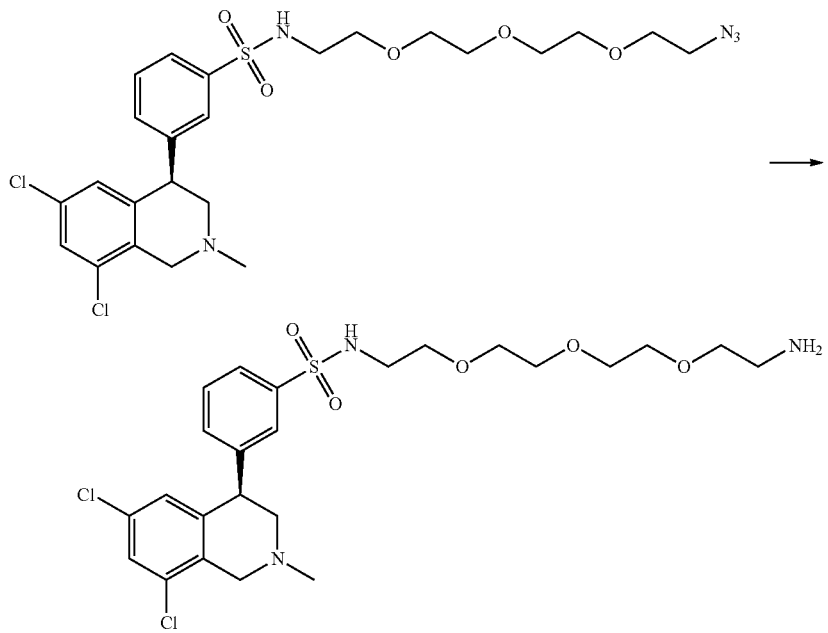

Intermediate 223.2, (R or S)—N-(2-(2-(2-(2-amino-ethoxy)ethoxy)ethoxy)ethyl)-3-(6,8-dichloro-2-methyl-1,2,3,4-tetrahydroisoquinolin-4-yl)benzenesulfonamide Following the procedure outlined in example 170, intermediate 223.1a was converted to Intermediate 223.2.

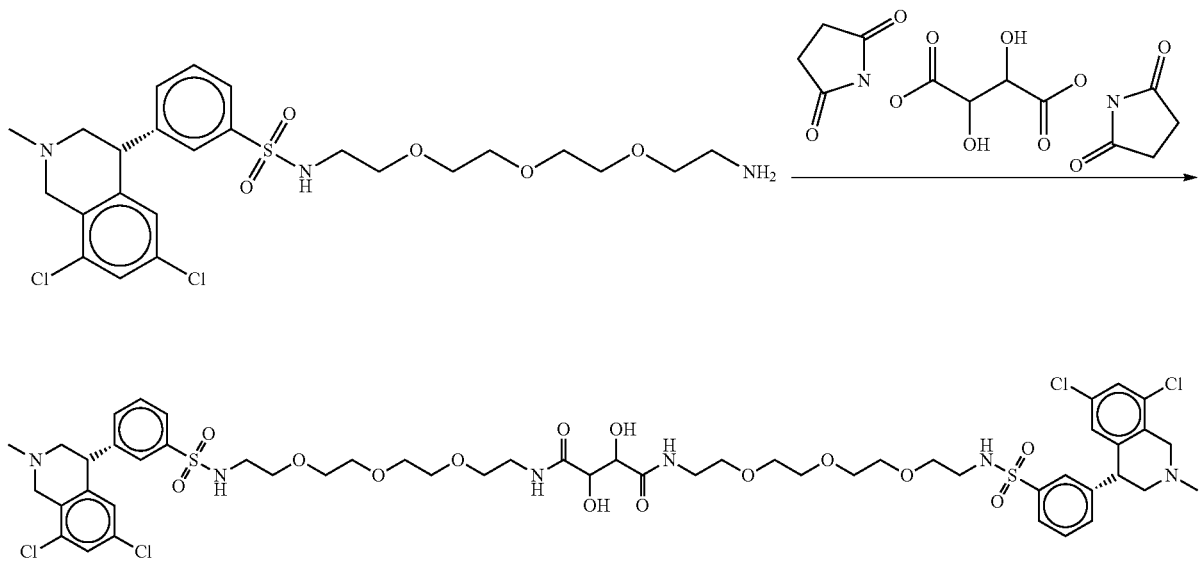

Compound 223, N1,N4-bis(2-(2-(2-(2-(3-((R or S)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide Compound 223 was prepared following the procedures outlined in Example 168 using (R or S)—N-(2-(2-(2-(2-aminoethoxy)ethoxy)ethoxy)ethyl)-3-(6,8-dichloro-2-methyl-1, 2,3,4-tetrahydroisoquinolin-4-yl)benzenesulfonamide (intermediate 223.2, 239 mg, 0.439 mmol) and bis(2,5-dioxopyrrolidin-1-yl) 2,3-dihydroxysuccinate (75.5 mg, 0.219 mmol). Purification by preparative HPLC gave the title compound (135.5 mg) as a TFA salt. $^1$H-NMR (400 MHz, CD3OD): δ 7.89 (d, 2H), 7.68 (s, 2H), 7.63 (t, 2H), 7.54-7.52 (m, 4H), 6.83 (s, 2H), 4.83-4.75 (m, 5H), 4.50-4.48 (m, 2H), 4.43 (d, 2H), 3.89-3.82 (m, 2H), 3.63-3.35 (m, 34H), 3.14 (s, 6H), 3.04 (t, 4H). MS (m/z): 1208.11 [M+H]$^+$.

Example 224

N1,N4-bis(2-(2-(2-(2-(3-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide

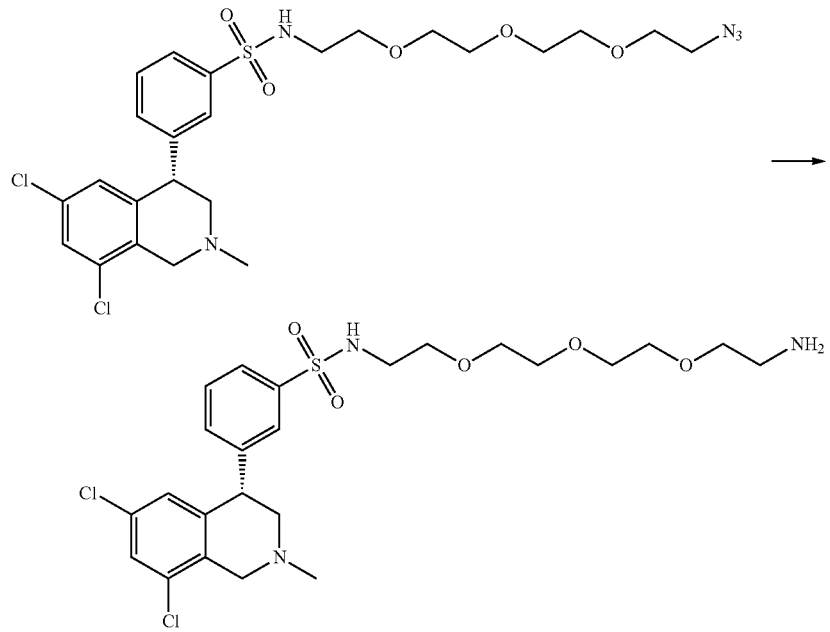

Intermediate 224.1, (S or R)—N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide Following the procedure outlined in example 170, intermediate 223.1b was converted to Intermediate 224.1.

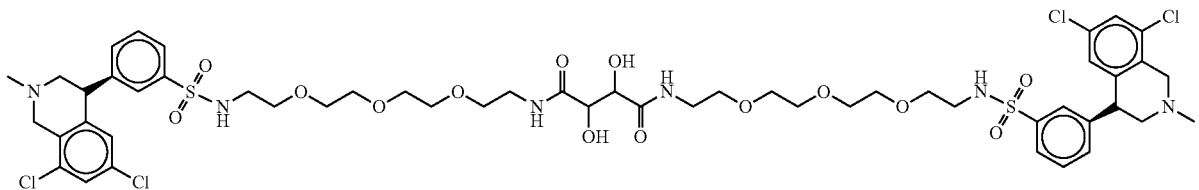

Compound 224, N1,N4-bis(2-(2-(2-(2-(3-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide Compound 224 was prepared following the procedures outlined in Example 223 using (S or R)—N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (intermediate 224.1, 274 mg, 0.502 mmol) and bis(2,5-dioxopyrrolidin-1-yl) 2,3-dihydroxysuccinate (86.4 mg, 0.251 mmol). Purification by preparative HPLC gave the title compound (159 mg) as a TFA salt. $^1$H-NMR (400 MHz, CD3OD): δ 7.87 (d, 2H), 7.77 (s, 2H), 7.63 (t, 2H), 6.54-6.51 (m, 4H), 6.83 (s, 2H), 4.84-4.75 (m, 4H), 4.50-4.43 (m, 4H), 3.90-3.85 (m, 4H), 3.62-3.28 (m, 35H), 3.14 (s, 6H), 3.04 (t, 4H). MS (m/z): 1207.11 [M+H]$^+$.

Example 225

N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide

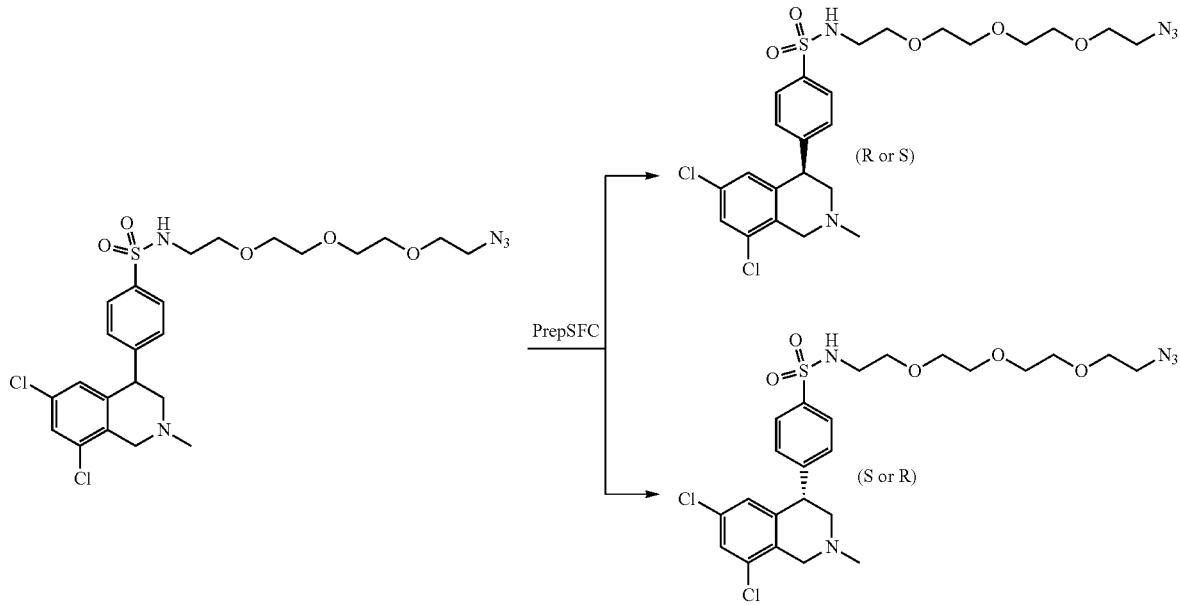 [SMILES: CN1Cc2c(Cl)cc(Cl)cc2C(c2ccc(S(=O)(=O)NCCOCCOCCOCCN=[N+]=[N-])cc2)C1 ; CN1Cc2c(Cl)cc(Cl)cc2[C@@H](c2ccc(S(=O)(=O)NCCOCCOCCOCCN=[N+]=[N-])cc2)C1 ; CN1Cc2c(Cl)cc(Cl)cc2[C@H](c2ccc(S(=O)(=O)NCCOCCOCCOCCN=[N+]=[N-])cc2)C1]

Intermediate 225.1a, (R or S)—N-(2-(2-(2-(2-azidoethoxy)ethoxy)ethoxy)ethyl)-4-(6,8-dichloro-2-methyl-1,2,3,4-tetrahydroisoquinolin-4-yl)benzenesulfonamide and intermediate 225.1b, (S or R)—N-(2-(2-(2-(2-azidoethoxy)ethoxy)ethoxy)ethyl)-4-(6,8-dichloro-2-methyl-1,2,3,4-tetrahydroisoquinolin-4-yl)benzenesulfonamide N-(2-(2-(2-(2-azidoethoxy)ethoxy)ethoxy)ethyl)-4-(6,8-dichloro-2-methyl-1,2,3,4-tetrahydroisoquinolin-4-yl)benzenesulfonamide (5 g, 8.76 mmol, 1.00 equiv) was separated into its enantiomers by Prep-SFC with the following conditions: Column, Chiralpak IA, 2*25 cm, 5 um; mobile phase, CO$_2$ (80%), ethanol (20%); Detector, UV 254 nm.

This resulted in 1.69 g of (R or S)—N-(2-(2-(2-(2-azidoethoxy)ethoxy)ethoxy)ethyl)-4-(6,8-dichloro-2-methyl-1,2,3,4-tetrahydroisoquinolin-4-yl)benzenesulfonamide as a brown oil. $^1$H-NMR (300 MHz, CD3OD, ppm): δ 7.85 (d, J=8.4 Hz, 2H), 7.40 (d, J=8.1 Hz, 2H), 7.36 (s, 1H), 6.82 (s, 1H), 4.43 (t, 1H), 3.81 (m, 1H), 3.67 (m, 9H), 3.48 (m, 4H), 3.33 (m, 2H), 3.01 (m, 1H), 2.71 (m, 1H), 2.49 (s, 3H). MS (m/z): 572 [M+H]$^+$.

Also isolated was 1.65 g of (S or R)—N-(2-(2-(2-(2-azidoethoxy)ethoxy)ethoxy)ethyl)-4-(6,8-dichloro-2-methyl-1,2,3,4-tetrahydroisoquinolin-4-yl)benzenesulfonamide as brown oil. $^1$H-NMR (300 MHz, CD3OD, ppm): δ 7.84 (d, J=8.4 Hz, 2H), 7.43 (d, J=8.1 Hz, 2H), 7.36 (s, 1H), 6.82 (s, 1H), 4.42 (t, 1H), 3.81 (m, 1H), 3.67 (m, 10H), 3.59 (m, 4H), 3.49 (m, 2H), 3.11 (m, 2H), 2.72 (m, 1H), 2.49 (s, 3H). MS (m/z): 572 [M+H]$^+$.

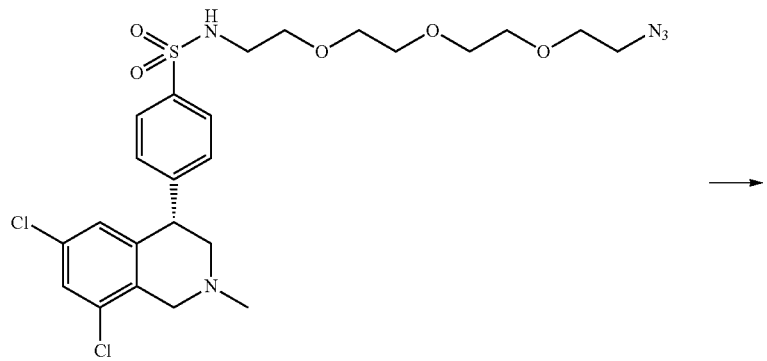

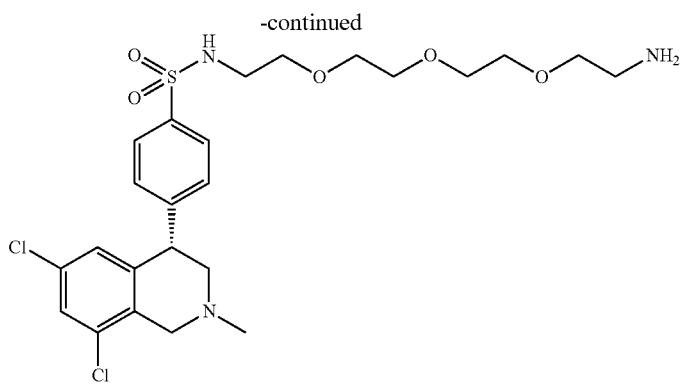

Intermediate 225.2, (S or R)—N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide Following the procedure outlined in example 170, intermediate 225.1b was converted to Intermediate 225.2.

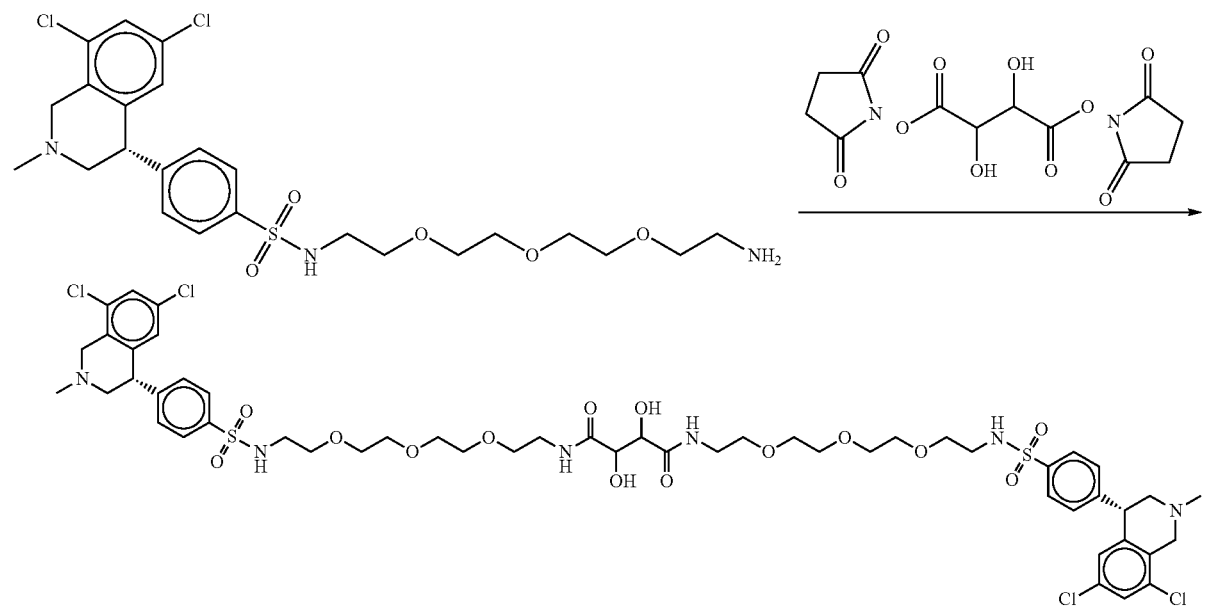

Compound 225, N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide Compound 225 was prepared following the procedures outlined in Example 168 using (S)—N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide (intermediate 225.2, 302.4 mg, 0.555 mmol) and bis(2,5-dioxopyrrolidin-1-yl) 2,3-dihydroxysuccinate (95.5 mg, 0.277 mmol). Purification by preparative HPLC gave the title compound (97.1 mg) as a TFA salt. $^1$H-NMR (400 MHz, CD3OD): δ 7.85 (d, 4H), 7.54 (s, 2H), 7.46 (d, 4H), 6.84 (s, 2H), 4.88-4.72 (m, 3H), 4.43-4.42 (m, 2H), 3.85-3.80 (m, 1H), 3.63-3.35 (m, 24H), 3.13 (s, 5H), 3.08 (t, 4H). MS (m/z): 1208.05 [M+H]$^+$.

Example 226

N1,N4-bis(2-(2-(2-(2-(4-((R or S)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide

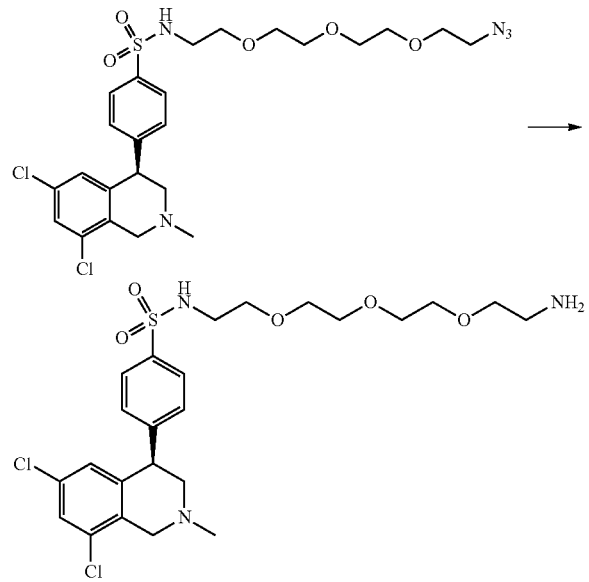

Intermediate 226.1, (R or S)—N-(2-(2-(2-(2-azidoethoxy)ethoxy)ethoxy)ethyl)-4-(6,8-dichloro-2-methyl-1,2,3,4-tetrahydroisoquinolin-4-yl)benzenesulfonamide Following the procedure outlined in example 170, intermediate 225.1a was converted to intermediate 226.1.

Compound 226, N1,N4-bis(2-(2-(2-(2-(4-((R or S)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide Compound 226 was prepared following the procedures outlined in Example 168 using (R or S)—N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide (intermediate 226.1, 267.5 mg, 0.491 mmol) and bis(2,5-dioxopyrrolidin-1-yl) 2,3-dihydroxysuccinate (84.5 mg, 0.245 mmol). Purification by preparative HPLC gave the title compound (145.4 mg) as a TFA salt. $^1$H-NMR (400 MHz, CD3OD): δ 7.89 (d, 5H), 7.54 (s, 2H), 7.48 (d, 4H), 6.84 (s, 2H), 4.84-4.73 (m, 4H), 4.50-4.43 (d, 2H), 4.18 (d, 2H), 3.85-3.80 (m, 2H), 3.64-3.40 (m, 32H), 3.13 (s, 6H), 3.08 (t, 3H). MS (m/z): 1207.10 [M+H]$^+$.

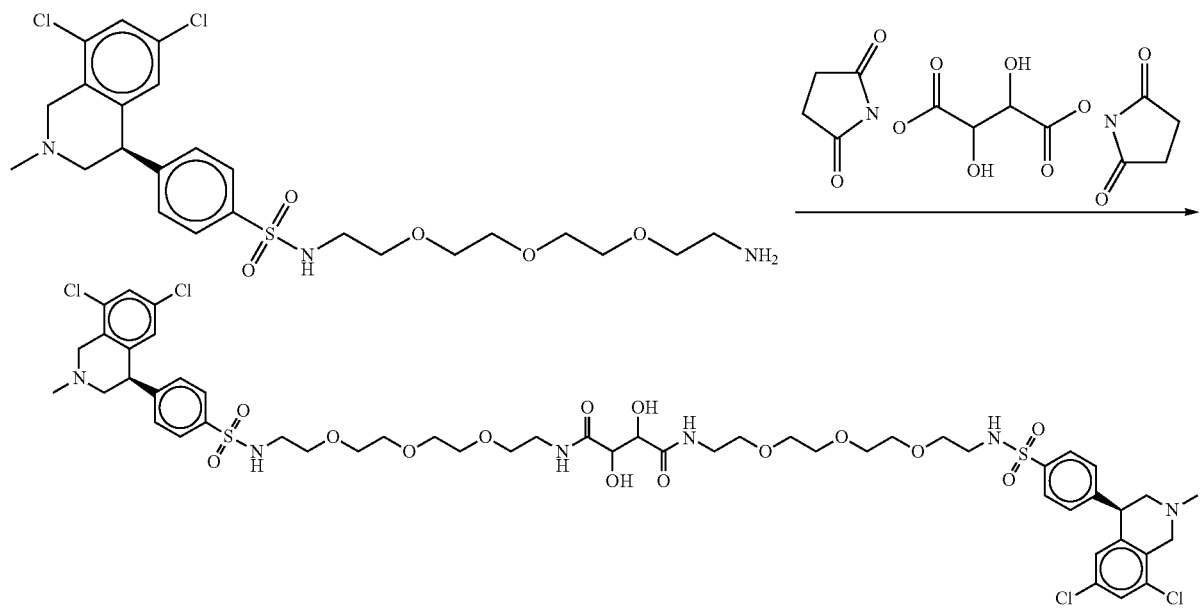

Example 227

N1,N4-bis(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide

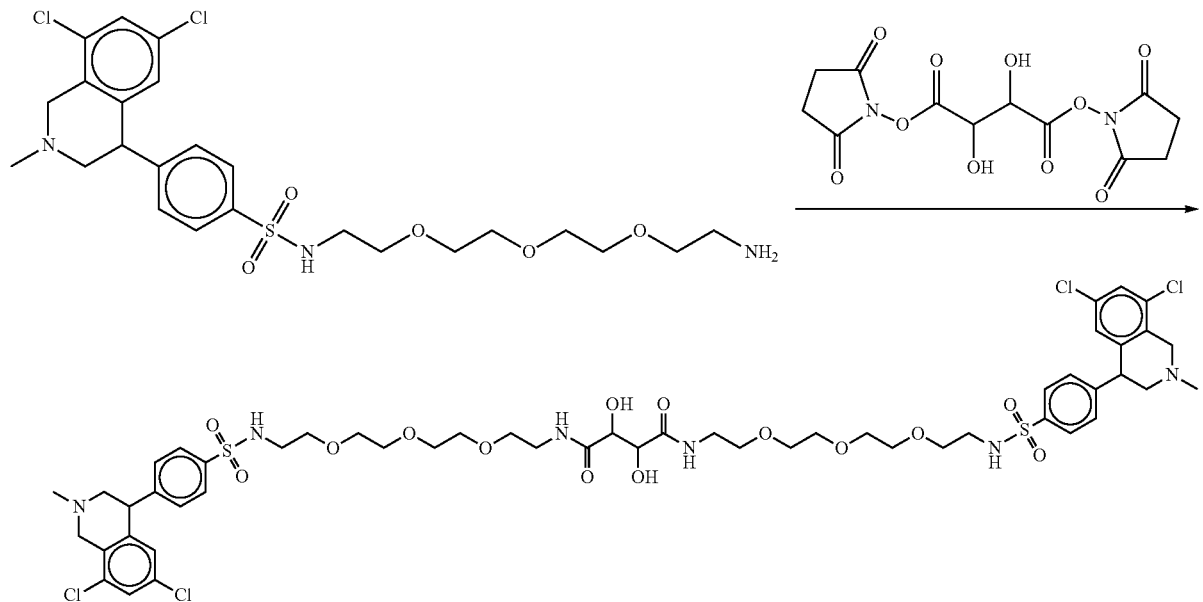

Compound 227, N1,N4-bis(2-(2-(2-(2-(4-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide Compound 227 was prepared following the procedure outlined in Example 168 using bis(2,5-dioxopyrrolidin-1-yl) 2,3-dihydroxysuccinate (49.6 mg, 0.144 mmol) and N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide (Compound 82, 157 mg, 0.288 mmol). Purification by preparative HPLC gave the title compound (34.5 mg) as a TFA salt. $^1$H-NMR (400 MHz, CD3OD): δ 7.89 (d, 4H), 7.53 (s, 2H), 7.45 (d, 4H), 6.83 (s, 2H), 4.77-4.74 (m, 6H), 4.46 (d, 2H), 4.43 (t, 2H), 3.89-3.84 (m, 2H), 3.62-3.53 (m, 19H), 3.49-3.41 (m, 13H), 3.14 (s, 6H), 3.08 (t, 4H). MS (m/z): 1206.94 [M+H]$^+$.

Example 228

N1,N3-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)isophthalamide

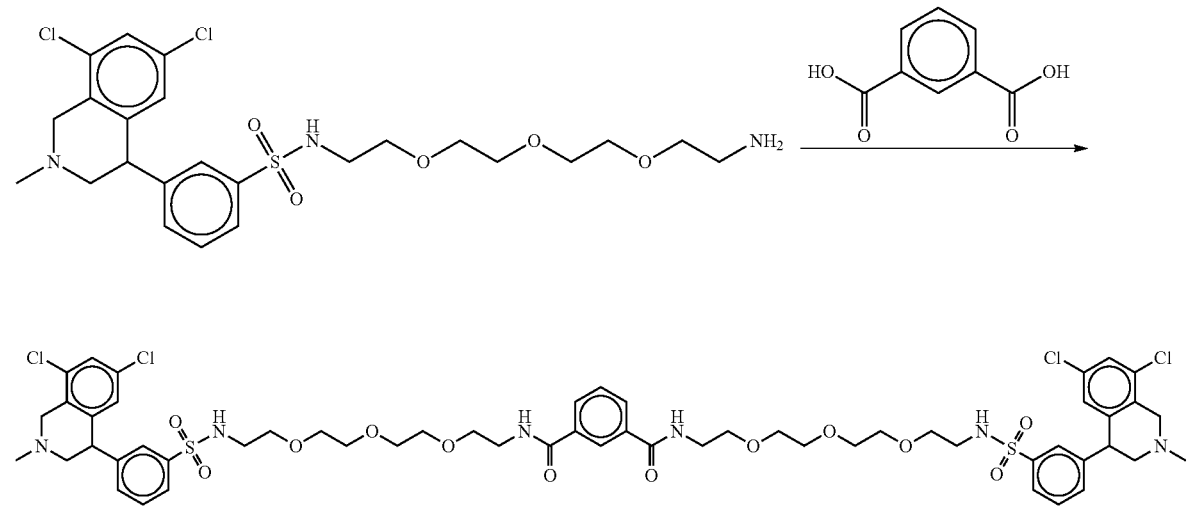

Compound 228, N1,N3-bis(2-(2-(2-(2-(3-(6,8-dichloro-2-methyl-1,2,3,4-tetrahydroisoquinolin-4-yl)phenylsulfonamido)ethoxy)ethoxy)ethoxy)-ethyl)isophthalamide Compound 228 was prepared following the procedure outlined in Example 215 using isophthalic acid (8.0 mg, 0.0484 mmol) and N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (Compound 28, 75 mg, 0.0968 mmol). Purification by preparative HPLC gave the title compound (45.6 mg) as a TFA salt. $^1$H-NMR (400 MHz, CD3OD): δ 8.25 (s, 1H), 7.92 (d, 2H), 7.85 (d, 2H), 7.73 (s, 2H), 7.58 (t, 2H), 7.49 (m, 5H), 6.81 (s, 2H), 4.83-4.71 (m, 4H), 4.49 (d, 2H), 3.87 (m, 2H), 3.67-3.54 (m, 28H), 3.45 (t, 5H), 3.44 (q, 5H), 3.14 (s, 7H), 2.99 (t, 4H). MS (m/z): 1223.19 [M+H]$^+$.

Example 229

(2R,3S)—N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide

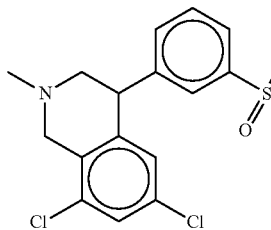
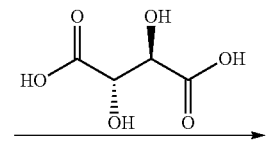

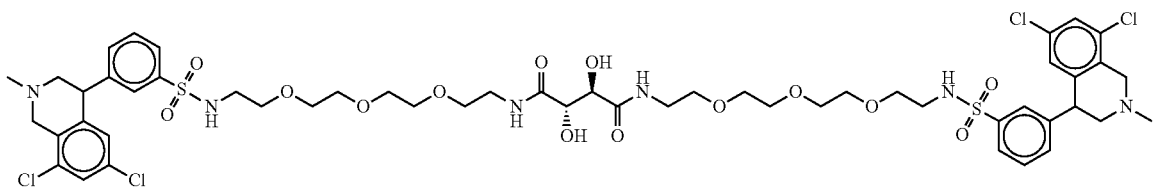

Compound 229, (2R,3S)—N1,N4-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (Compound 28, 25 mg, 0.0322 mmol) was dissolved in DMF (0.161 mL) with DIEA (12.4 mg, 0.0966 mmol) and (2R,3S)-2,3-dihydroxysuccinic acid (2.7 mg, 0.0161 mmol). Benzotriazol-1-yl-oxytripyrrolidinophosphonium hexafluorophosphate (PyBOP) (18.4 mg, 0.0354 mmol) was added and the resulting solution stirred for 60 minutes, at which point LCMS indicated complete conversion. The reaction mixture was diluted to 2 mL with acetonitrile/water (1:1) and filtered. Purification by preparative HPLC gave the title compound (8.7 mg) as a TFA salt. $^1$H-NMR (400 MHz, CD3OD): δ 7.80 (d, 2H), 7.69 (s, 2H), 7.55 (t, 2H), 7.43 (m, 4H), 6.75 (s, 2H), 4.80-4.75 (m, 3H), 4.39 (d, 2H), 4.24 (d, 2H), 3.76 (m, 2H), 3.64-3.25 (m, 33H), 3.04 (s, 7H), 2.95 (t, 4H). MS (m/z): 1207.10 [M+H]$^+$.

Example 230

N1,N2-bis(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)phthalamide

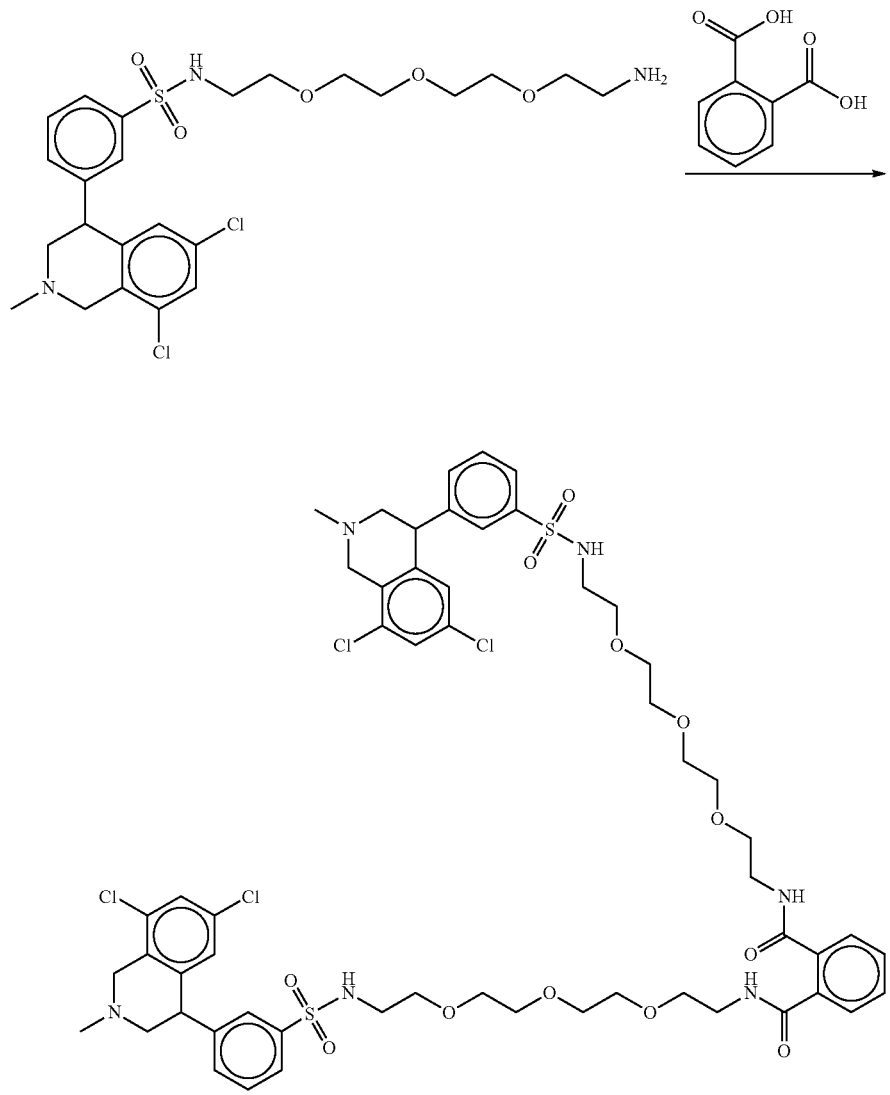

Compound 230, N1,N2-bis(2-(2-(2-(2-(3-(6,8-dichloro-2-methyl-1,2,3,4-tetrahydroisoquinolin-4-yl)phenylsulfonamido)ethoxy)ethoxy)ethoxy)-ethyl)phthalamide Compound 230 was prepared by following the procedure outlined in Example 215 using phthalic acid (8.0 mg, 0.0484 mmol) and N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (Compound 28, 75 mg, 0.0968 mmol). Purification by preparative HPLC gave the title compound (35.4 mg) as a TFA salt. $^1$H-NMR (400 MHz, CD3OD): δ 7.87 (d, 2H), 7.76 (s, 2H), 7.63 (t, 2H), 7.50 (m, 8H), 6.79 (s, 2H), 4.83-4.73 (m, 4H), 4.65 (d, 2H), 3.85 (q, 2H), 3.62-3.39 (m, 36H), 3.10 (s, 6H), 3.02 (t, 4H). MS (m/z): 1223.00 [M+H]$^+$.

Example 231

N1,N4-bis(2-(2-(2-(4-(6,8-dichloro-2-methyl-1,2,3,4-tetrahydroisoquinolin-4-yl)phenylsulfonamido)ethoxy)ethoxy)ethyl)terephthalamide

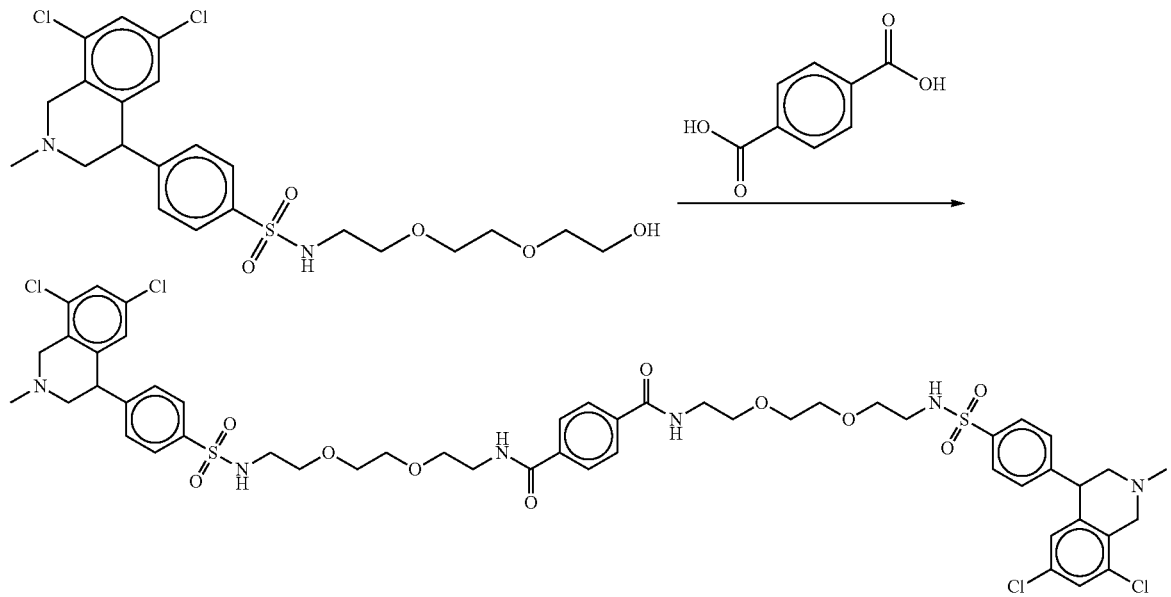

Compound 231, N1,N4-bis(2-(2-(2-(4-(6,8-dichloro-2-methyl-1,2,3,4-tetrahydroisoquinolin-4-yl)phenylsulfonamido)ethoxy)ethoxy)ethyl)-terephthalamide Compound 231 was prepared following the procedure outlined in Example 215 using terephthalic acid (11.4 mg, 0.0684 mmol) and 4-(6,8-dichloro-2-methyl-1,2,3,4-tetrahydroisoquinolin-4-yl)-N-(2-(2-(2-hydroxyethoxy)ethoxy)ethyl)benzenesulfonamide (Compound 175.1, 100 mg, 0.136 mmol). Purification by preparative HPLC gave the title compound (9.8 mg) as a TFA salt. $^1$H-NMR (400 MHz, CD3OD): δ 7.86-7.85 (m, 9H), 7.83 (s, 2H), 7.50 (s, 1H), 7.41 (d, 4H), 6.80 (s, 1H), 3.68-3.42 (m, 26H), 3.34 (m, 2H), 3.09-3.01 (m, 12H). MS (m/z): 1135.07 [M+H]$^+$.

Example 232

N,N'-(10-oxo-3,6,14,17-tetraoxa-9,11-diazanonadecane-1,19-diyl)bis(4-(6,8-dichloro-2-methyl-1,2,3,4-tetrahydroisoquinolin-4-yl)benzenesulfonamide)

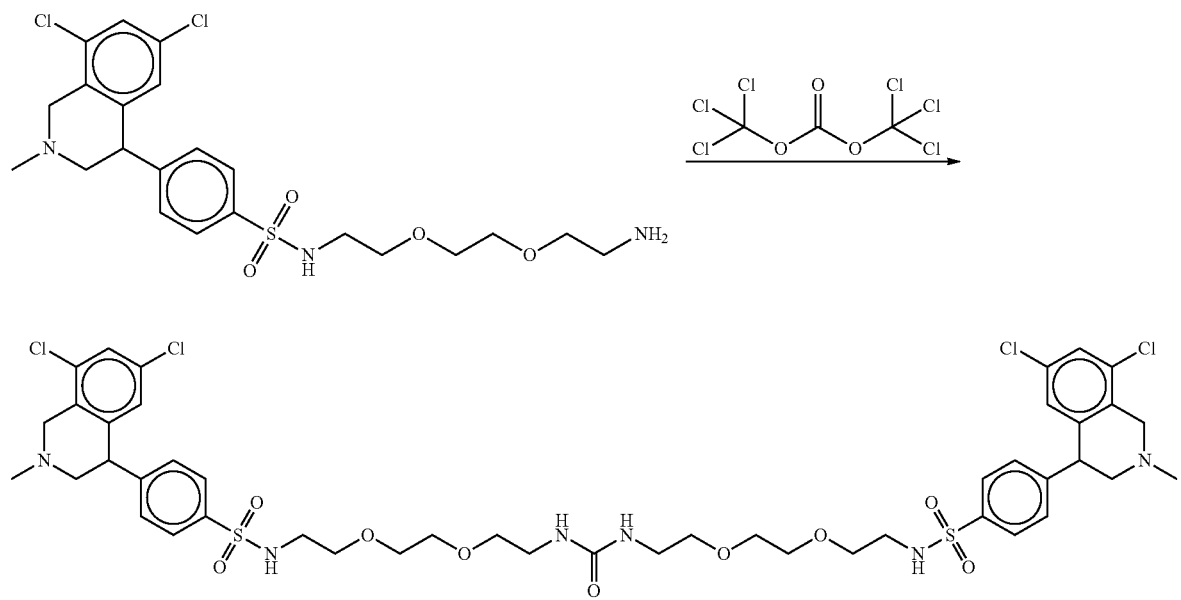

Compound 232, N,N'-(10-oxo-3,6,14,17-tetraoxa-9,11-diazanonadecane-1,19-diyl)bis(4-(6,8-dichloro-2-methyl-1,2,3,4-tetrahydroisoquinolin-4-yl)benzenesulfonamide)

N-(2-(2-(2-aminoethoxy)ethoxy)ethyl)-4-(6,8-dichloro-2-methyl-1,2,3,4-tetrahydroisoquinolin-4-yl)benzenesulfonamide (Compound 175.1, 80 mg, 0.110 mmol) and DIEA (42.1 mg, 0.330 mmol) were dissolved in dry DCM (0.5 mL) under N$_2$ and cooled to 0° C. A solution of triphosgene (4.9 mg, 0.0165 mmol) in DCM (0.2 mL) was added dropwise and the resulting solution was warmed to room temperature over 30 minutes. The solvent was removed; the resulting residue was brought up in 4 mL of acetonitrile/water (1:1) solution and filtered. Purification by preparative HPLC gave the title compound (8.5 mg) as a TFA salt. $^1$H-NMR (400 MHz, CD3OD): δ 7.90 (d, 4H), 7.60 (s, 2H), 7.47 (d, 4H), 6.84 (s, 2H), 3.58-3.42 (m, 24H), 3.12-3.05 (m, 17H). MS (m/z): 1031.96 [M+H]$^+$.

Example 233

N1,N4-bis(2-(2-(2-(2-(4-(6,8-dichloro-2-methyl-1,2,3,4-tetrahydroisoquinolin-4-yl)phenylsulfonamido)ethoxy)ethoxy)ethyl)terephthalamide

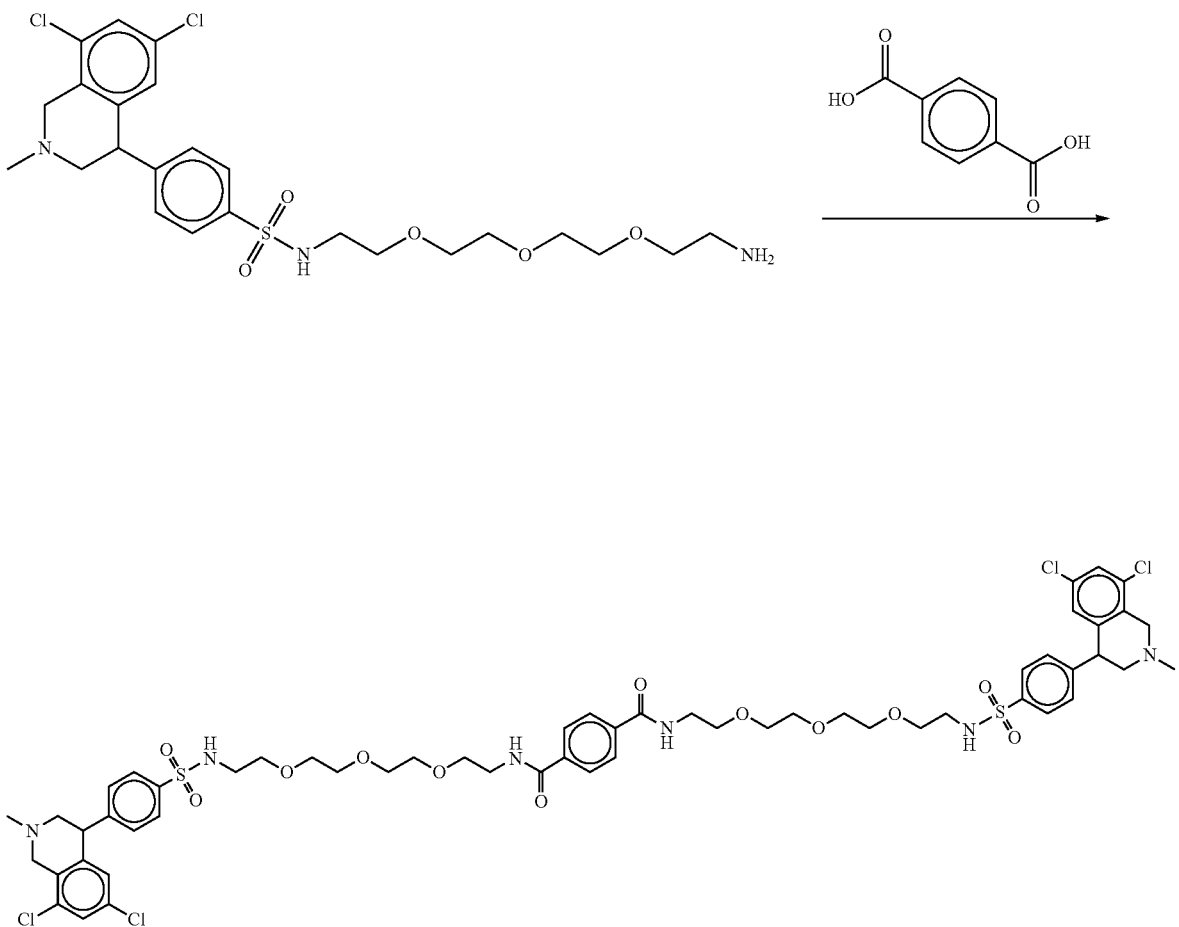

Compound 233, N1,N4-bis(2-(2-(2-(2-(4-(6,8-dichloro-2-methyl-1,2,3,4-tetrahydroisoquinolin-4-yl)phenylsulfonamido)ethoxy)ethoxy)ethoxy)-ethyl)terephthalamide Compound 233 was prepared following the procedures outlined in Example 215 using terephthalic acid (10.4 mg, 0.0628 mmol) and N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide (Compound 82, 97.2 mg, 0.1255 mmol). Purification by preparative HPLC gave the title compound (38.9 mg) as a TFA salt. $^1$H-NMR (400 MHz, CD3OD): δ 7.83 (m, 10H), 7.85 (s, 2H), 7.42 (d, 4H), 6.83 (s, 1H), 3.66-3.55 (m, 28H), 3.46-3.39 (m, 11H), 3.12 (s, 7H), 3.04 (t, 4H). MS (m/z): 1223.14 [M+H]$^+$.

Example 234

N1,N4-bis(2-(2-(2-(3-(6,8-dichloro-2-methyl-1,2,3,4-tetrahydroisoquinolin-4-yl)phenylsulfonamido)ethoxy)ethoxy)ethyl)terephthalamide

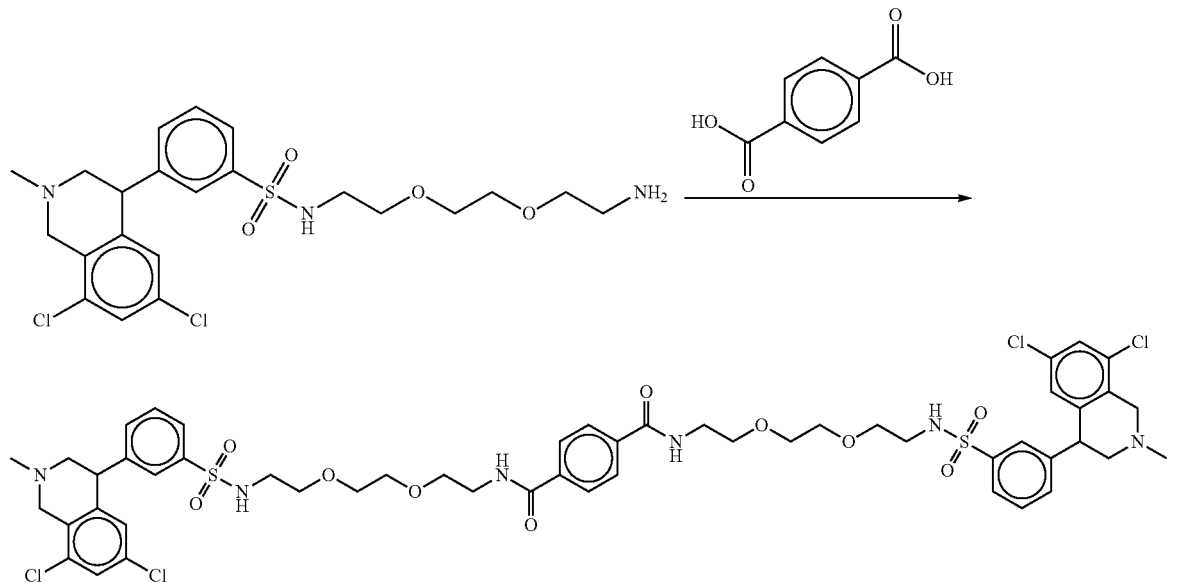

Compound 234, N1,N4-bis(2-(2-(2-(3-(6,8-dichloro-2-methyl-1,2,3,4-tetrahydroisoquinolin-4-yl)phenylsulfonamido)ethoxy)ethoxy)ethyl)-terephthalamide Compound 234 was prepared following the procedures outlined in Example 215 using terephthalic acid (13.8 mg, 0.0833 mmol) and N-(2-(2-(2-aminoethoxy)ethoxy)ethyl)-3-(6,8-dichloro-2-methyl-1,2,3,4-tetrahydroisoquinolin-4-yl)benzenesulfonamide (Compound 168.2, 121.7 mg, 0.167 mmol). Purification by preparative HPLC gave the title compound (60.0 mg) as a TFA salt. $^1$H-NMR (400 MHz, CD3OD): δ 7.88 (m, 6H), 7.72 (s, 2H), 7.61 (t, 2H), 7.51 (m, 4H), 6.80 (s, 2H), 4.88-4.75 (m, 4H), 4.75 (d, 2H), 4.74 (m, 2H), 3.85-3.42 (m, 25H), 3.12 (s, 6H), 2.99 (t, 4H). MS (m/z): 1135.11 [M+H]$^+$.

Example 235

N,N'-(10-oxo-3,6,14,17-tetraoxa-9,11-diazanonadecane-1,19-diyl)bis(3-(6,8-dichloro-2-methyl-1,2,3,4-tetrahydroisoquinolin-4-yl)benzenesulfonamide)

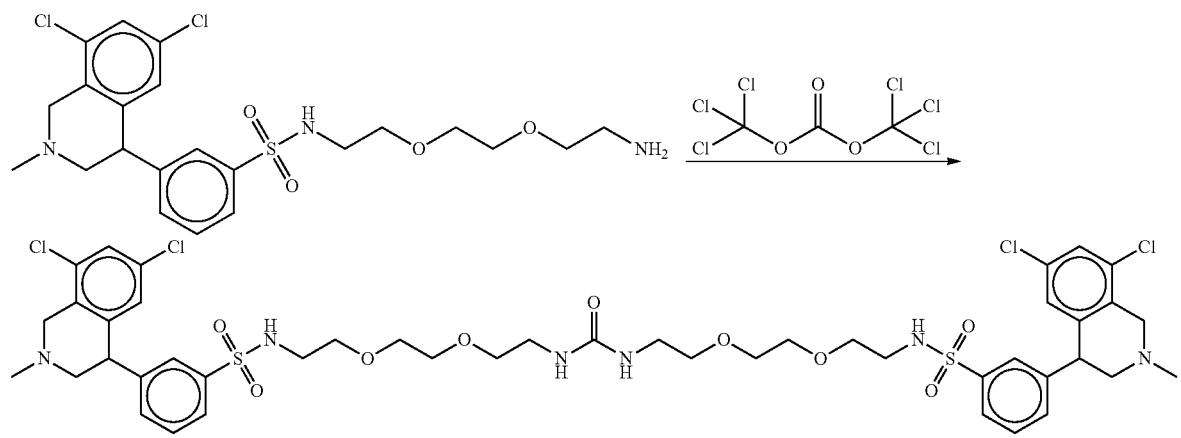

Compound 235, N,N'-(10-oxo-3,6,14,17-tetraoxa-9,11-diazanonadecane-1,19-diyl)bis(3-(6,8-dichloro-2-methyl-1,2,3,4-tetrahydroisoquinolin-4-yl)benzenesulfonamide)

Compound 235 was prepared following the procedures outlined in Example 232 using N-(2-(2-(2-aminoethoxy)ethoxy)ethyl)-3-(6,8-dichloro-2-methyl-1,2,3,4-tetrahydroisoquinolin-4-yl)benzenesulfonamide (Compound 168.2, 56.6 mg, 0.0775 mmol). Purification by preparative HPLC gave the title compound (25.0 mg) as a TFA salt. $^1$H-NMR (400 MHz, CD3OD): δ 7.88 (d, 2H), 7.75 (s, 2H), 7.65 (t, 2H), 7.53 (m, 4H), 6.83 (s, 2H), 4.89-4.68 (m, 2H), 3.88 (m, 2H), 3.62-3.43 (m, 21H), 3.30-3.27 (m, 6H), 3.11 (s, 7H), 3.03 (t, 4H). MS (m/z): 1031.07 [M+H]$^+$.

Example 236

N,N'-(10,17-dioxo-3,6,21,24-tetraoxa-9,11,16,18-tetraazahexacosane-1,26-diyl)bis(3-(6,8-dichloro-2-methyl-1,2,3,4-tetrahydroisoquinolin-4-yl)benzenesulfonamide)

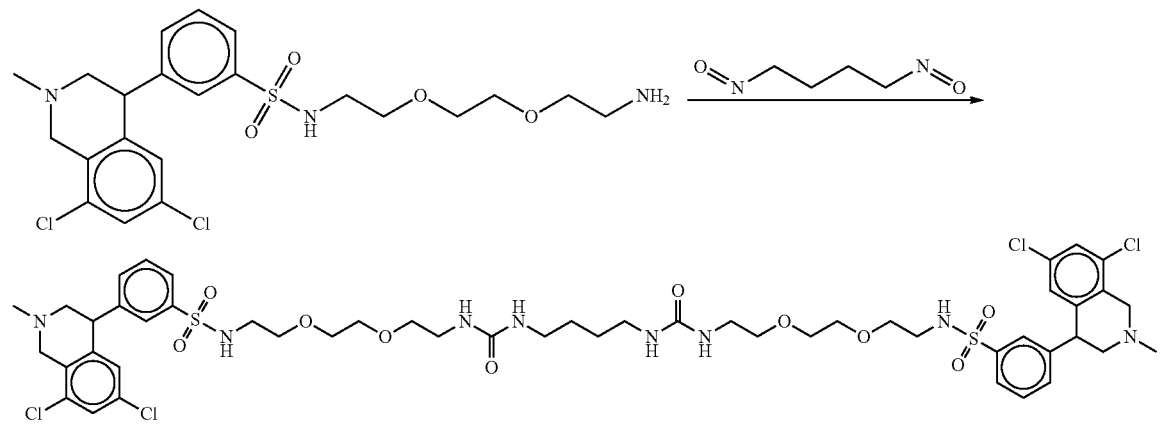

Compound 236, N,N'-(10,17-dioxo-3,6,21,24-tetraoxa-9,11,16,18-tetraazahexacosane-1,26-diyl)bis(3-(6,8-dichloro-2-methyl-1,2,3,4-tetrahydroisoquinolin-4-yl)benzenesulfonamide)

Compound 236 was prepared following the procedures outlined in Example 208 using 1,4-diisocyanatobutane (5.24 mg, 0.0374 mmol) and N-(2-(2-(2-aminoethoxy)ethoxy)ethyl)-3-(6,8-dichloro-2-methyl-1,2,3,4-tetrahydroisoquinolin-4-yl)benzenesulfonamide (Compound 168.2, 54.7 mg, 0.0749 mmol). Purification by preparative HPLC gave the title compound (27.5 mg) as a TFA salt. $^1$H-NMR (400 MHz, CD3OD): δ 7.88-7.86 (d, 2H), 7.75 (s, 2H), 7.63 (t, 2H), 7.55-7.51 (m, 4H), 4.48 (m, 2H), 3.38-3.31 (m, 1H), 3.61-3.42 (m, 17H), 3.35-3.30 (m, 4H), 3.13 (s, 6H), 3.08-3.02 (m, 7H), 1.45 (m, 2H). MS (m/z): 1145.04 [M+H]$^+$.

Example 237

N,N'-(2,2'-(2,2'-(2,2'-(1,4-phenylenebis(azanediyl)) bis(oxomethylene)bis(azanediyl)bis(ethane-2,1-diyl))bis(oxy)bis(ethane-2,1-diyl))bis(oxy)bis (ethane-2,1-diyl))bis(3-(6,8-dichloro-2-methyl-1,2,3,4-tetrahydroisoquinolin-4-yl)benzenesulfonamide)

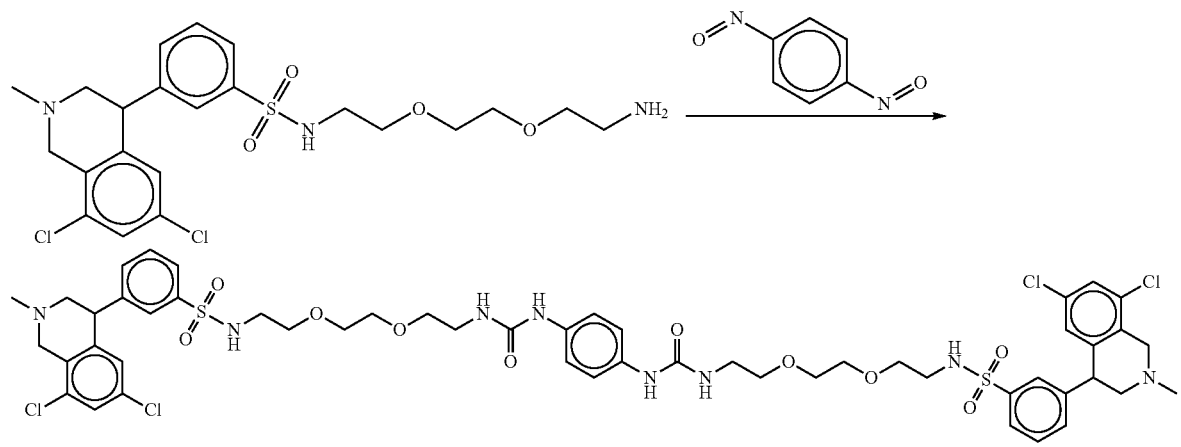

Compound 237, N,N'-(2,2'-(2,2'-(2,2'-(1,4-phenyle-nebis(azanediyl))bis(oxomethylene)bis(azanediyl)bis(ethane-2,1-diyl))bis(oxy)bis(ethane-2,1-diyl))bis(oxy)bis(ethane-2,1-diyl))bis(3-(6,8-dichloro-2-methyl-1,2,3,4-tetrahydroisoquinolin-4-yl)benzenesulfonamide)

Compound 237 was prepared following the procedure outlined in Example 208 using 1,4-diisocyanatobenzene (8.79 mg, 0.0549 mmol) and N-(2-(2-(2-aminoethoxy)ethoxy)ethyl)-3-(6,8-dichloro-2-methyl-1,2,3,4-tetrahydroisoquinolin-4-yl)benzenesulfonamide (Compound 168.2, 80.2 mg, 0.110 mmol). Purification by preparative HPLC gave the title compound (37.6 mg) as a TFA salt. $^1$H-NMR (400 MHz, CD3OD): δ 7.88 (d, 2H), 7.73 (s, 2H), 7.61 (t, 2H), 7.52 (d, 2H), 7.48 (d, 2H), 7.18 (s, 5H), 6.78 (s, 2H), 4.71-4.63 (m, 6H), 4.45-4.40 (m, 2H), 3.81-3.77 (m, 2H), 3.58-3.55 (m, 6H), 3.53-3.50 (m, 14H), 3.47-3.44 (m, 6H), 3.35-3.33 (m, 6H), 3.09 (s, 8H), 3.03 (t, 5H). MS (m/z): 1165.06 [M+H]$^+$.

Example 238

N,N'-(10,17-dioxo-3,6,21,24-tetraoxa-9,11,16,18-tetraazahexacosane-1,26-diyl)bis(4-(6,8-dichloro-2-methyl-1,2,3,4-tetrahydroisoquinolin-4-yl)benzenesulfonamide)

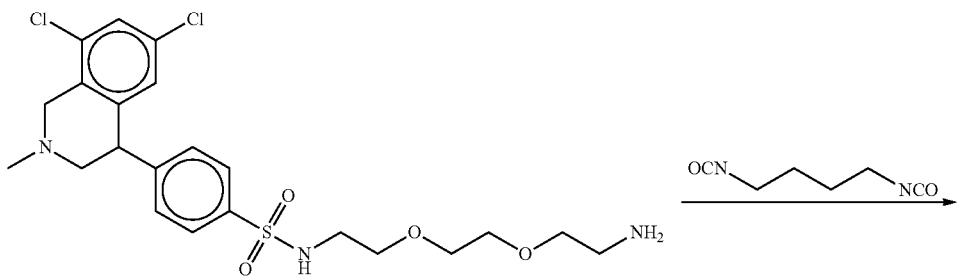

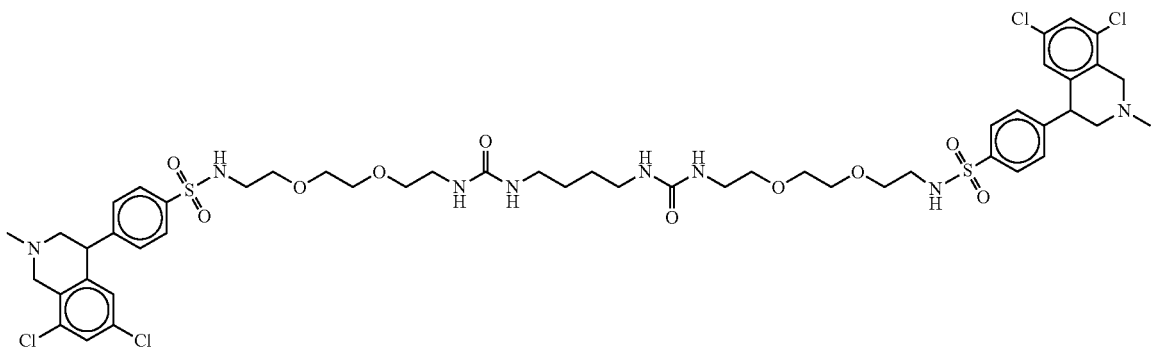

Compound 238, N,N'-(10,17-dioxo-3,6,21,24-tetraoxa-9,11,16,18-tetraazahexacosane-1,26-diyl)bis(4-(6,8-dichloro-2-methyl-1,2,3,4-tetrahydroisoquinolin-4-yl)benzenesulfonamide)

Compound 238 was prepared following the procedure outlined in Example 208 using 1,4-diisocyanatobutane (5.64 mg, 0.402 mmol) and N-(2-(2-(2-aminoethoxy)ethoxy)ethyl)-4-(6,8-dichloro-2-methyl-1,2,3,4-tetrahydroisoquinolin-4-yl)benzenesulfonamide (Compound 175.1, 58.8 mg, 0.805 mmol). Purification by preparative HPLC gave the title compound (13.8 mg) as a TFA salt. $^1$H-NMR (400 MHz, CD3OD): δ 7.86 (d, J=8 Hz, 2H), 7.72 (s, 2H), 7.61 (t, 2H), 7.52 (s, 2H), 7.47 (d, J=7 Hz, 2H), 7.18 (s, 5H), 7.78 (s, 2H), 4.77-4.68 (m, 5H), 4.48-4.40 (m, 2H), 3.35-3.28 (m, 2H), 3.56-3.51 (m, 16H), 3.45 (t, J=5 Hz, 5H), 3.35-3.32 (m, 10H), 3.09 (s, 6H), 3.03 (t, J=5 Hz, 3H). MS (m/z): 1145.01 [M+H]$^+$.

Example 239

N,N'-(2,2'-(2,2'-(2,2'-(1,4-phenylenebis(azanediyl))bis(oxomethylene)bis(azanediyl)bis(ethane-2,1-diyl))bis(oxy)bis(ethane-2,1-diyl))bis(oxy)bis(ethane-2,1-diyl))bis(4-(6,8-dichloro-2-methyl-1,2,3,4-tetrahydroisoquinolin-4-yl)benzenesulfonamide)

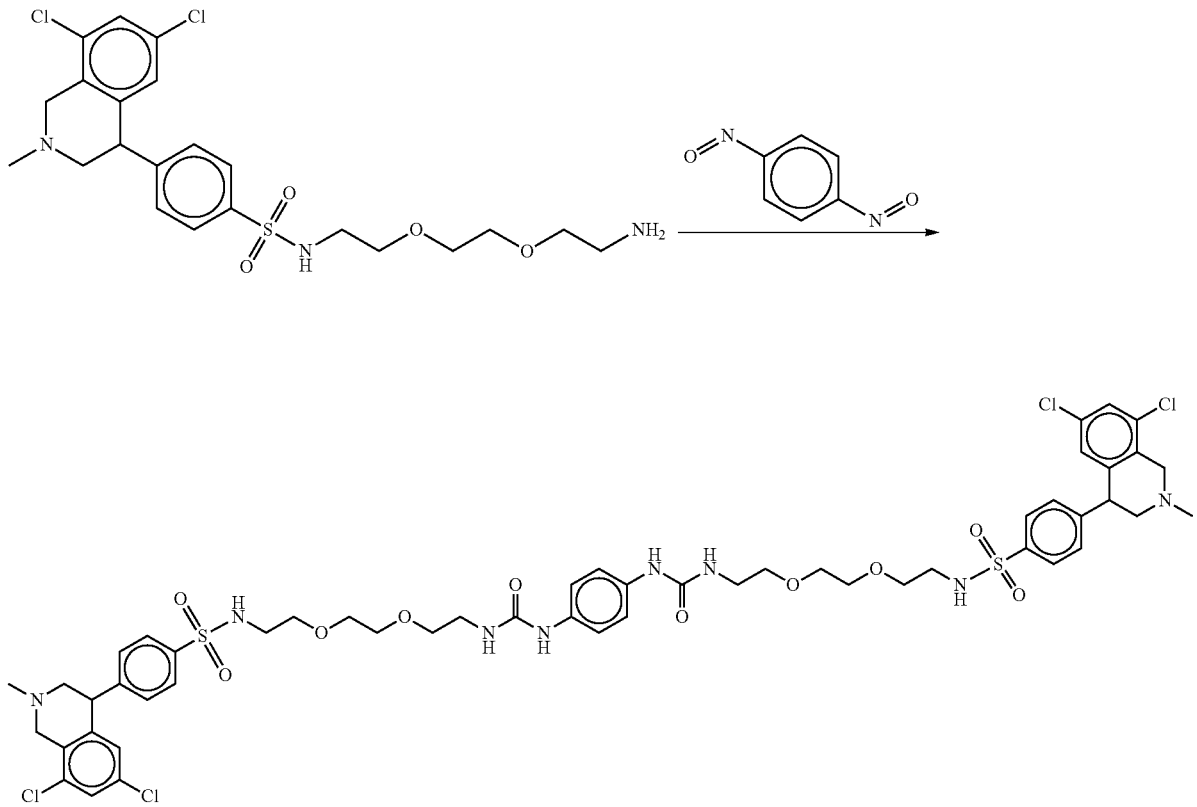

Compound 239, N,N'-(2,2'-(2,2'-(2,2'-(1,4-phenylenebis(azanediyl))bis(oxomethylene)bis(azanediyl)bis(ethane-2,1-diyl))bis(oxy)bis(ethane-2,1-diyl))bis(oxy)bis(ethane-2,1-diyl))bis(4-(6,8-dichloro-2-methyl-1,2,3,4-tetrahydroisoquinolin-4-yl)benzenesulfonamide)

Compound 239 was prepared following the procedure outlined in Example 208 using 1,4-diisocyanatobenzene (12.5 mg, 0.078 mmol) and N-(2-(2-(2-aminoethoxy)ethoxy)ethyl)-4-(6,8-dichloro-2-methyl-1,2,3,4-tetrahydroisoquinolin-4-yl)benzenesulfonamide (Compound 175.1, 113.9 mg, 0.156 mmol). Purification by preparative HPLC gave the title compound (48.9 mg) as a TFA salt. $^1$H-NMR (400 MHz, CD3OD): δ 7.87 (d, J=8 Hz, 4H), 7.52 (s, 2H), 7.40 (d, J=8 Hz, 4H), 7.18 (s, 4H), 7.69 (s, 2H), 4.70-4.62 (m, 3H), 4.48-4.40 (m, 2H), 3.82-3.76 (m, 2H), 3.58-3.43 (m, 21H), 3.35-3.30 (m, 4H), 3.11-3.06 (m, 11H). MS (m/z): 1165.12[M+H]$^+$.

Example 240

(2S,3S)—N1,N4-bis(2-(2-(2-(2-(3-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide

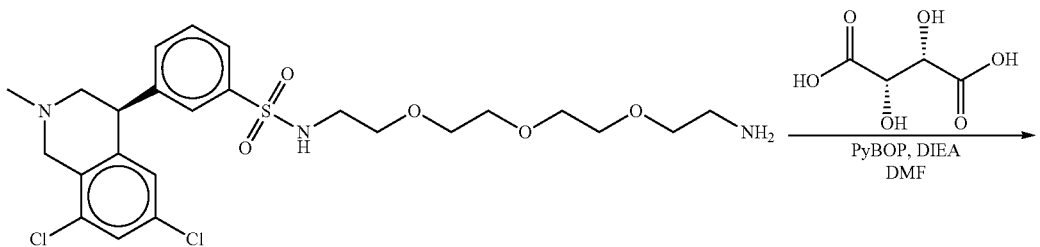

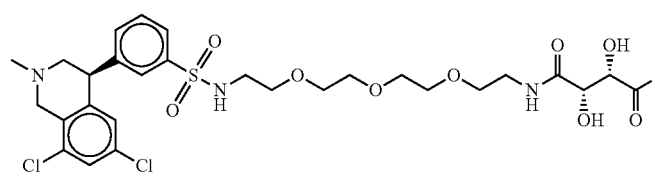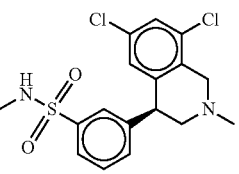

Compound 240, (2S,3S)—N1,N4-bis(2-(2-(2-(2-(3-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide Compound 240 was prepared following the procedures outlined in Example 229 using (2S,3S)-2,3-dihydroxysuccinic acid (9.6 mg, 0.057 mmol) and (S or R)—N-(2-(2-(2-(2-aminoethoxy)ethoxy)ethoxy)ethyl)-3-(6,8-dichloro-2-methyl-1,2,3,4-tetrahydroisoquinolin-4-yl) benzenesulfonamide (intermediate 224.1, 88.6 mg, 0.114 mmol). Purification by preparative HPLC gave the title compound (24.5 mg) as a TFA salt. $^1$H-NMR (400 MHz, CD3OD): δ 7.94 (t, 1H), 7.87 (d, 2H), 7.77 (s, 2H), 7.63 (t, 2H), 7.53-7.50 (m, 4H), 6.82 (s, 2H), 4.479-4.45 (m, 2H), 4.44 (s, 2H), 3.88-3.84 (m, 2H), 3.62-3.53 (m, 22H), 3.50-3.48 (m, 5H), 3.45-3.40 (m, 9H), 3.13 (s, 6H), 3.04 (t, 4H). MS (m/z): 1208.02 [M+H]$^+$.

Example 241

(2R,3R)—N1,N4-bis(2-(2-(2-(2-(3-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide

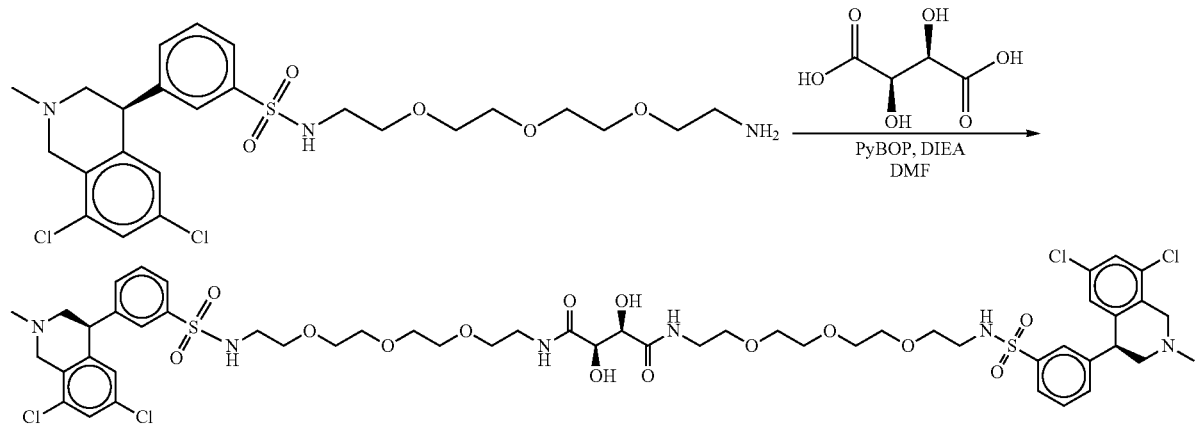

Compound 241, (2R,3R)—N1,N4-bis(2-(2-(2-(2-(3-((R or S)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide Compound 241 was prepared following the procedures outlined in Example 229 using (2R,3R)-2,3-dihydroxysuccinic acid (8.7 mg, 0.0519 mmol) and (S or R)—N-(2-(2-(2-(2-aminoethoxy)ethoxy)ethoxy)ethyl)-3-(6,8-dichloro-2-methyl-1,2,3,4-tetrahydroisoquinolin-4-yl) benzenesulfonamide (intermediate 224.1, 80.5 mg, 0.104 mmol). Purification by preparative HPLC gave the title compound (25.7) as a TFA salt. $^1$H-NMR (400 MHz, CD3OD): δ 7.87 (d, 3H), 7.76 (s, 2H), 7.63 (t, 2H), 7.54-7.51 (m, 4H), 6.83 (s, 2H), 4.78-4.73 (m, 4H), 4.49-4.42 (m, 4H), 3.89-3.85 (m, 2H), 3.62-3.53 (m, 22H), 3.51-48 (m, 5H), 3.46-3.38 (m, 9H), 3.14 (s, 6H), 3.04 (t, 4H). MS (m/z): 1208.21 [M+H]$^+$.

Example 242

(2S,3S)—N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide

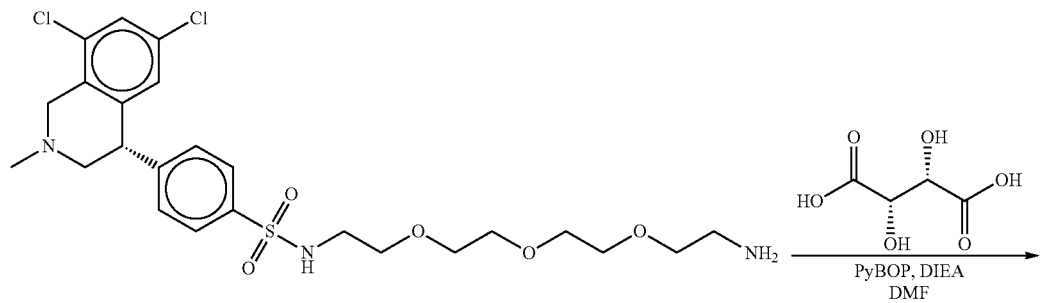

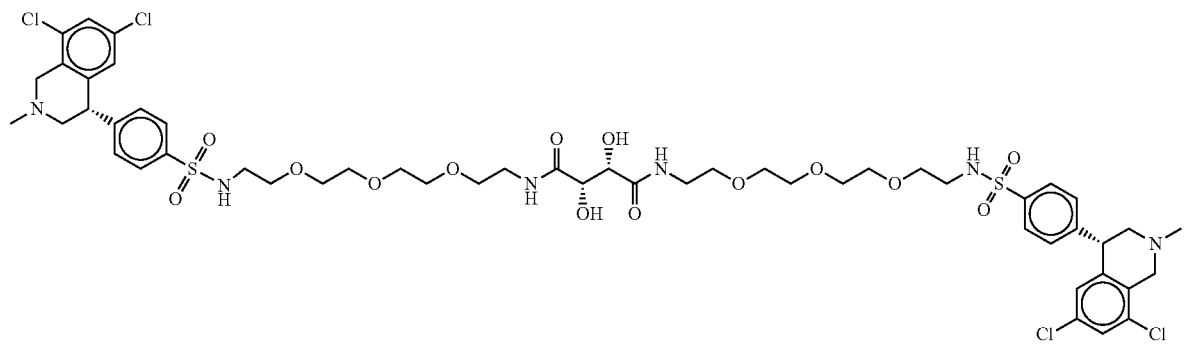

Compound 242, (2S,3S)—N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide Compound 242 was prepared following the procedures outlined in Example 229 using (2S,3S)-2,3-dihydroxysuccinic acid (6.3 mg, 0.0374 mmol) and (S or R)—N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide (intermediate 225.2, 58.0 mg, 0.0749 mmol). Purification by preparative HPLC gave the title compound (21.6 mg) as a TFA salt. $^1$H-NMR (400 MHz, CD3OD): δ 7.85 (d, 4H), 7.54 (s, 2H), 7.45 (d, 3H), 6.84 (s, 1H), 4.772-4.69 (m, 3H), 4.43 (s, 2H), 3.86-3.81 (m, 1H), 3.59-3.53 (m, 16H), 3.49-3.39 (m, 11H), 3.12 (s, 5H), 3.08 (t, 4H). MS (m/z): 1208.14 [M+H]$^+$.

Example 243

(2R,3R)—N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide

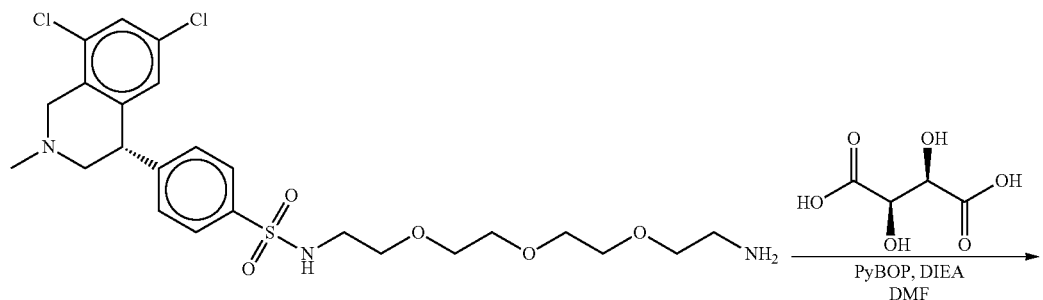

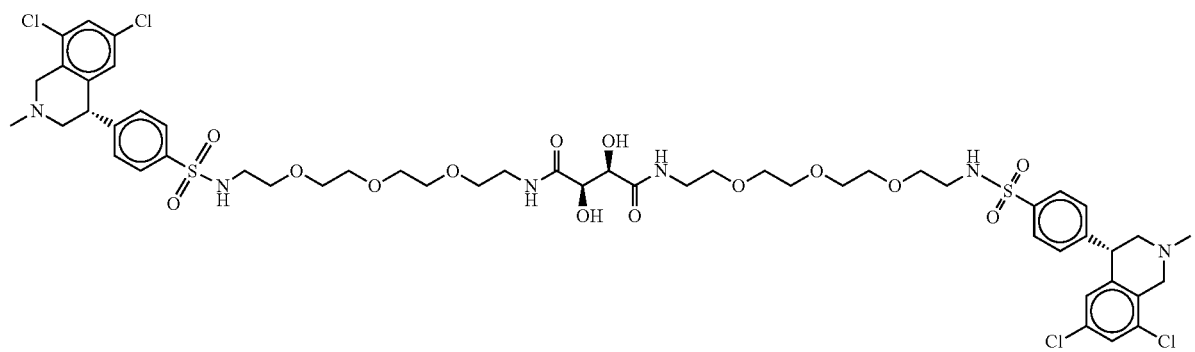

Compound 243, (2R,3R)—N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-2,3-dihydroxysuccinamide Compound 243 was prepared following the procedures outlined in Example 229 using (2R,3R)-2,3-dihydroxysuccinic acid (8.4 mg, 0.0.0499 mmol) and (S or R)—N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide (intermediate 225.2, 77.3 mg, 0.0999 mmol). Purification by preparative HPLC gave the title compound (23.4 mg) as a TFA salt. $^1$H-NMR (400 MHz, CD3OD): δ 7.89 (d, 4H), 7.53 (s, 2H), 7.45 (d, 4H), 6.83 (s, 2H), 4.81-4.71 (m, 4H), 4.49-4.41 (m, 4H), 3.89-3.83 (m, 2H), 3.60-3.53 (m, 17H), 3.49-3.38 (m, 12H), 3.13 (s, 5H), 3.08 (t, 4H). MS (m/z): 1208.09 [M+H]$^+$.

Example 244

(S or R)—N,N'-(13,20-dioxo-3,6,9,24,27,30-hexaoxa-12,14,19,21-tetraazadotriacontane-1,32-diyl)bis(3-((S or R)-6,8-dichloro-2-methyl-1,2,3,4-tetrahydroisoquinolin-4-yl)benzenesulfonamide)

Intermediate 244.1, (S or R)-4-(3-bromophenyl)-6,8-dichloro-2-methyl-1,2,3,4-tetrahydroisoquinoline

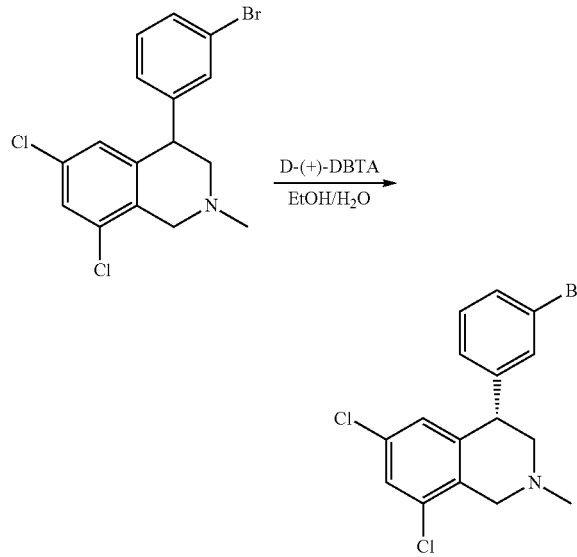

Into a 2000-mL round-bottom flask, was placed a solution of 4-(3-bromophenyl)-6,8-dichloro-2-methyl-1,2,3,4-tetrahydroisoquinoline (intermediate 1.4; 20 g, 54.20 mmol, 1.00 equiv) in ethanol (500 mL). This was followed by the addition of D-(+)-dibenzoyl tartaric acid (19 g, 53.07 mmol, 0.98 equiv), water (160 mL) and ethanol (1440 mL) at 45° C. The resulting solution was stirred for 30 min at 45° C. in an oil bath. After cooling to room temperature over 24 hours, the solids were collected by filtration. The filter cake was dissolved in potassium carbonate (saturated.) and was extracted with 2×500 mL of ethyl acetate. The combined organic layers were washed with 2×500 mL of brine, dried over anhydrous sodium sulfate and concentrated under vacuum. This gave (S or R)-4-(3-bromophenyl)-6,8-dichloro-2-methyl-1,2,3,4-tetrahydroisoquinoline as a colorless oil.

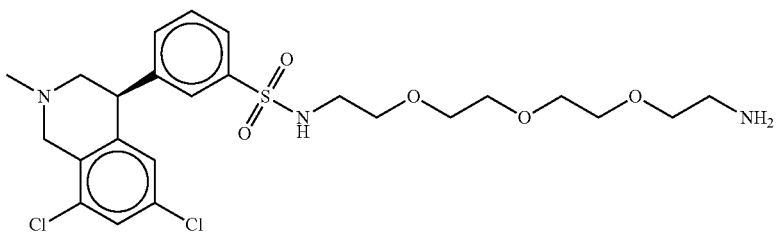

Intermediate 224.1 (alternate synthesis), (S or R)—N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (S or R)-4-(3-bromophenyl)-6,8-dichloro-2-methyl-1,2,3,4-tetrahydroisoquinoline (intermediate 244.1) was converted to (S or R)—N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (intermediate 224.1) following the procedures outlined for the racemic substrates in Example 1 and the reduction described in Example 170.

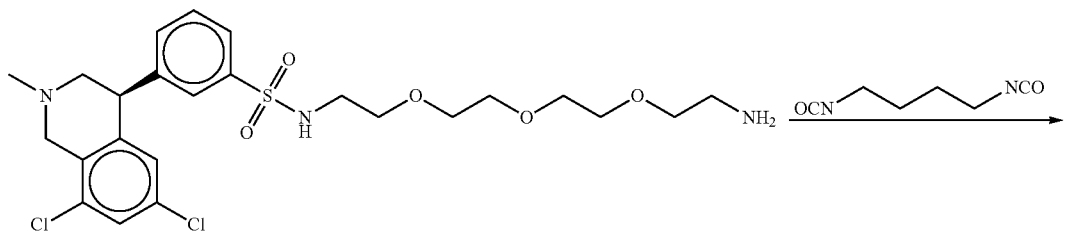

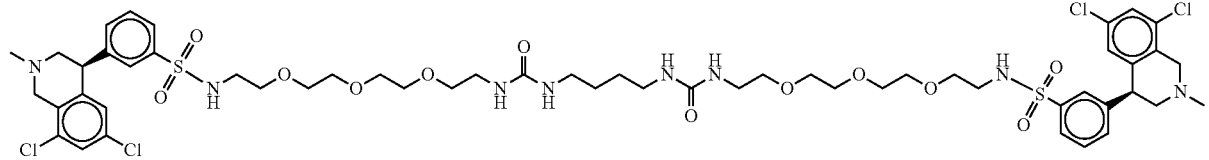

Compound 244, (S or R)—N,N'-(13,20-dioxo-3,6,9,24,27,30-hexaoxa-12,14,19,21-tetraazadotriacontane-1,32-diyl)bis(3-((S or R)-6,8-dichloro-2-methyl-1,2,3,4-tetrahydroisoquinolin-4-yl)benzenesulfonamide)

Compound 244 was prepared following the procedures outlined in Example 208 using 1,4-diisocyanatobutane (6.5 mg, 0.0471 mmol) and (S or R)—N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (Intermediate 224.1, 72.9 mg, 0.0941 mmol). Purification by preparative HPLC gave the title compound (34.9 mg) as a TFA salt. $^1$H-NMR (400 MHz, CD3OD): δ 7.89 (d, 2H), 7.75 (s, 2H), 7.63 (t, 2H), 7.55-7.51 (m, 4H), 6.83 (s, 2H), 4.48 (d, 2H), 3.90-3.85 (m, 2H), 3.59-3.55 (m, 17H), 3.51-3.43 (m, 14H), 3.31-3.23 (m, 6H), 3.14 (s, 7H), 3.04 (m, 9H), 1.43 (m, 4H). MS (m/z): 1232.99 [M+H]$^+$.

Example 245

(S or R)—N,N'-(1,1'-(1,4-phenylenebis(azanediyl))bis(1-oxo-5,8,11-trioxa-2-azatridecane-13,1-diyl))bis(3-((S or R)-6,8-dichloro-2-methyl-1,2,3,4-tetrahydroisoquinolin-4-yl)benzenesulfonamide)

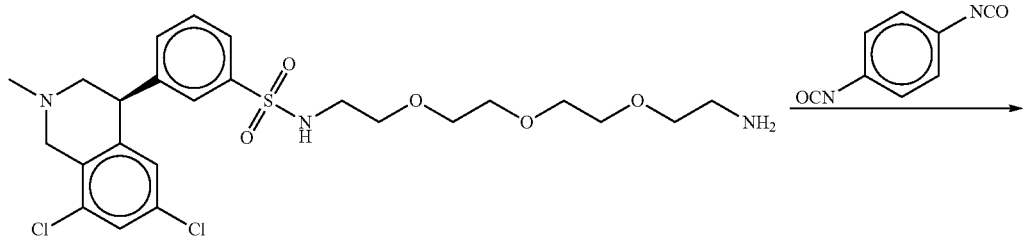

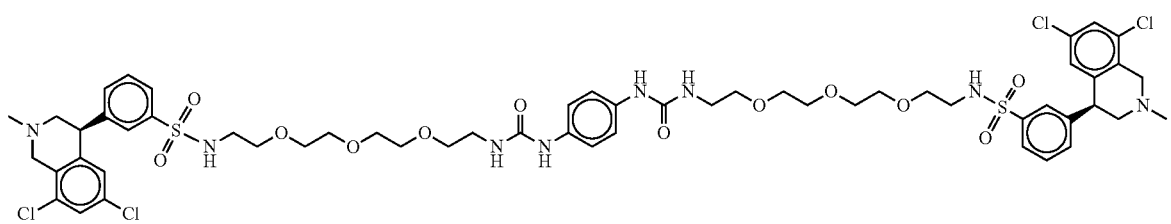

Compound 245, (S or R)—N,N'-(1,1'-(1,4-phenylenebis(azanediyl))bis(1-oxo-5,8,11-trioxa-2-azatridecane-13,1-diyl))bis(3-((S or R)-6,8-dichloro-2-methyl-1,2,3,4-tetrahydroisoquinolin-4-yl)benzenesulfonamide)

Compound 245 was prepared following the procedures outlined in Example 208 using (S or R)—N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (Intermediate 224.1, 79.1 mg, 0.102 mmol) and 1,4-diisocyanatobenzene (8.2 mg, 0.0511 mmol). Purification by preparative HPLC gave the title compound (43.2 mg) as a TFA salt. $^1$H-NMR (400 MHz, CD3OD): δ 7.87 (d, 2H), 7.72 (s, 2H), 7.61 (t, 2H), 7.51-7.46 (m, 4H), 7.17 (s, 4H), 6.78 (s, 2H), 4.44-4.39 (m, 2H), 3.82-3.77 (m, 2H), 3.61 (s, 11H), 3.57-3.53 (m, 13H), 3.49-3.48 (m, 6H), 3.44 (t, 5H), 3.35-3.29 (m, 6H), 3.09 (s, 7H), 3.03 (t, 4H). MS (m/z): 1253.01 [M+H]$^+$.

Compound 246

N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-terephthalamide HPLC gave the title compound (19.3 mg) as a TFA salt. $^1$H-NMR (400 MHz, CD3OD): δ 7.89-7.85 (m, 6H), 7.52 (s, 2H), 7.43 (d, 4H), 6.81 (s, 2H), 4.73-4.66 (m, 3H), 4.47-4.42 (m, 1H), 3.84-3.79 (m, 2H), 3.64-3.59 (m, 14H), 3.57-3.54 (m, 11H), 3.46-3.39 (m, 8H), 3.12 (s, 6H), 3.03 (t, 4H). MS (m/z): 1233.04 [M+H]$^+$.

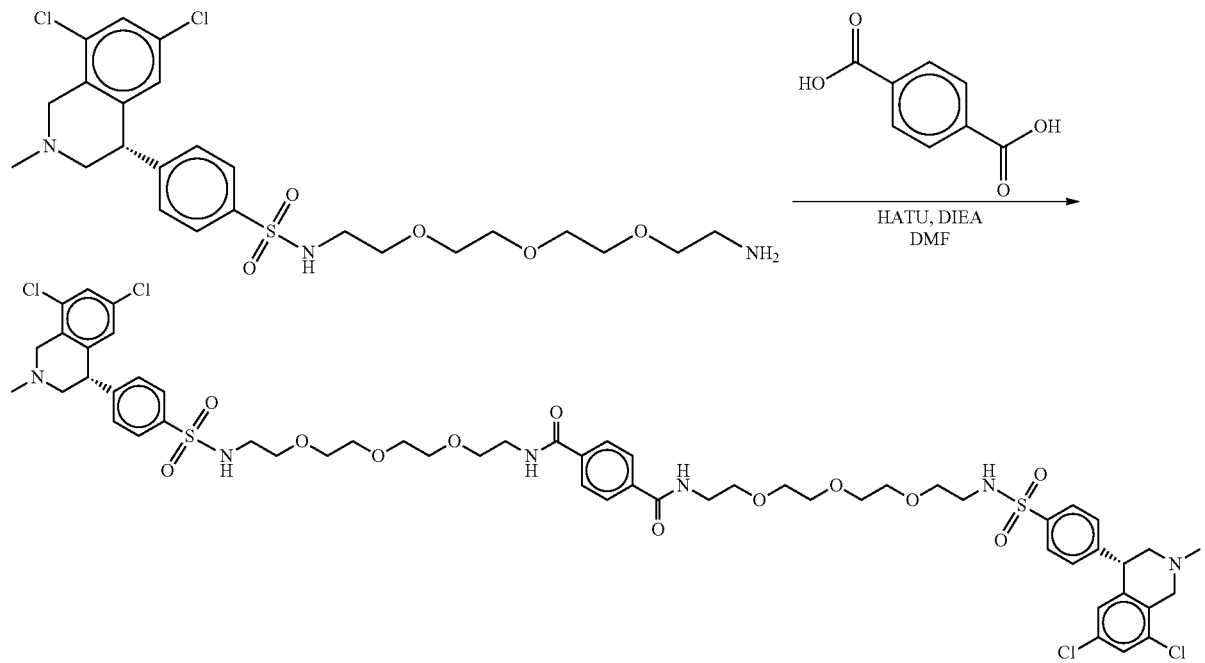

Compound 246, N1,N4-bis(2-(2-(2-(2-(4-((S or R)-6,8-dichloro-2-methyl-1,2,3,4-tetrahydroisoquinolin-4-yl)phenylsulfonamido)ethoxy)ethoxy)ethoxy)ethyl)-terephthalamide Compound 246 was prepared following the procedures outlined in Example 215 using (S or R)—N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide (Intermediate 224.1, 65.1 mg, 0.0841 mmol) and terephthalic acid (6.98 mg, 0.042 mmol). Purification by preparative

Example 247

N1-(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)succinamide

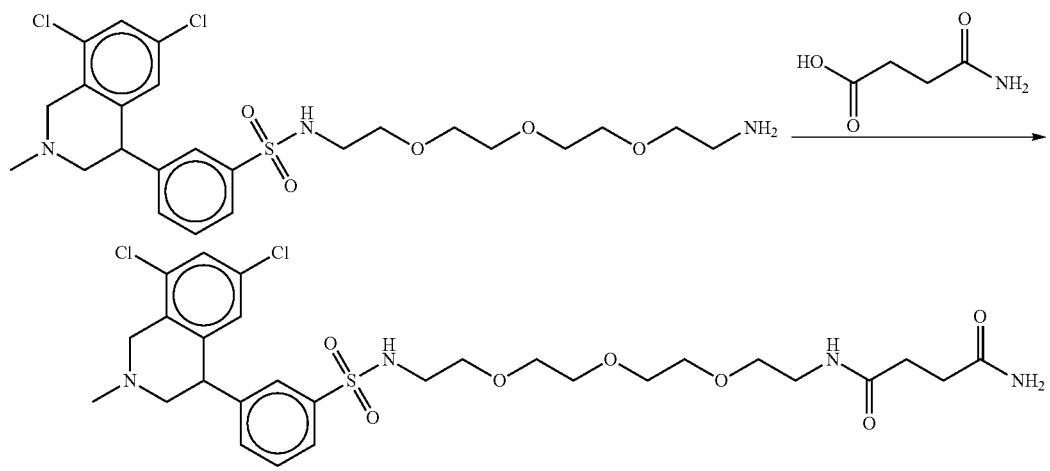

Compound 247, N1-(2-(2-(2-(2-(3-(6,8-dichloro-2-methyl-1,2,3,4-tetrahydroisoquinolin-4-yl)phenylsulfonamido)ethoxy)ethoxy)ethoxy)ethyl)succinamide Compound 247 was prepared following the procedure outlined in Example 215 using 4-amino-4-oxobutanoic acid (7.6 mg, 0.0646 mmol) and N-(2-(2-(2-(2-aminoethoxy)ethoxy)ethoxy)ethyl)-3-(6,8-dichloro-2-methyl-1,2,3,4-tetrahydroisoquinolin-4-yl)benzenesulfonamide (Compound 28, 50 mg, 0.0646 mmol). Purification by preparative HPLC gave the title compound (27.8 mg) as a TFA salt. $^1$H-NMR (400 MHz, CD3OD): δ 7.88 (d, 1H), 7.75 (s, 1H), 7.64 (t, 1H), 7.55 (s, 1H), 7.51 (d, 1H), 6.84 (s, 1H), 4.78-4.71 (m, 2H), 4.55-4.48 (m, 1H), 3.81-3.75 (m, 1H), 3.63-3.55 (m, 10H), 3.51-4.45 (m, 5H), 3.44-3.41 (m, 3H), 3.38-3.31 (m, 3H), 3.13 (s, 3H), 3.07-3.02 (t, 2H), 2.48-2.43 (m, 4H). MS (m/z): 645.32 [M+H]$^+$.

Example 248

N,N'-(13,20-dioxo-3,6,9,24,27,30-hexaoxa-12,14,19,21-tetraazadotriacontane-1,32-diyl)bis(4-(6,8-dichloro-2-methyl-1,2,3,4-tetrahydroisoquinolin-4-yl)benzenesulfonamide)

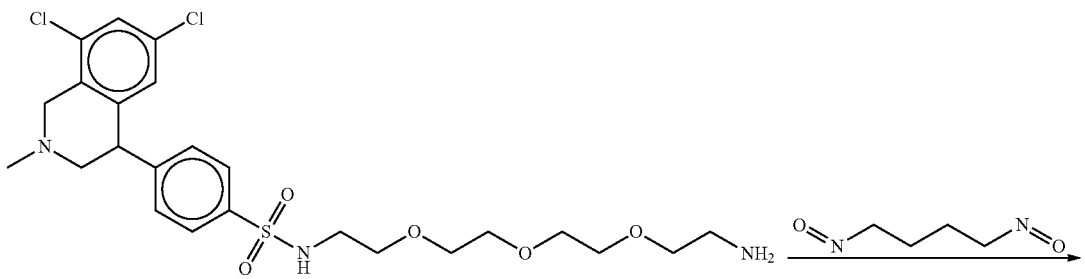

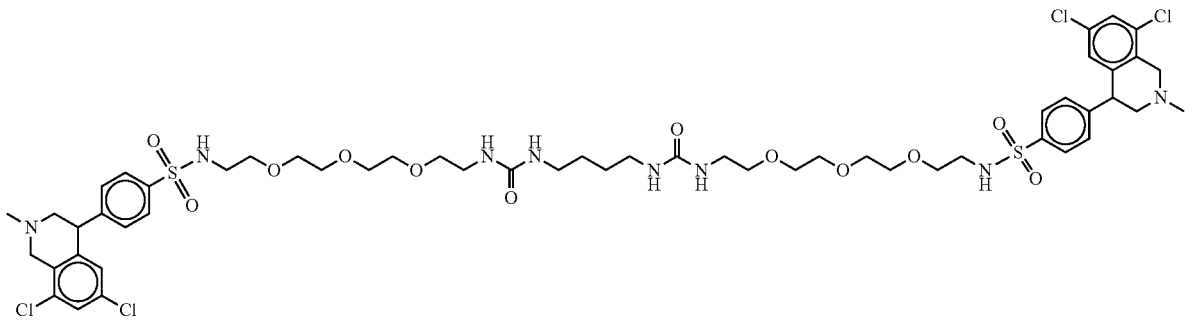

Compound 248, N,N'-(13,20-dioxo-3,6,9,24,27,30-hexaoxa-12,14,19,21-tetraazadotriacontane-1,32-diyl)bis(4-(6,8-dichloro-2-methyl-1,2,3,4-tetrahydroisoquinolin-4-yl)benzenesulfonamide)

Compound 248 was prepared following the procedure outlined in Example 208 using 1,4-diisocyanatobutane (7.64 mg, 0.545 mmol) and N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide (Compound 82, 84.4 mg, 0.109 mmol). Purification by preparative HPLC gave the title compound (43.6 mg) as a TFA salt. $^1$H-NMR (400 MHz, CD3OD): δ 7.89 (d, 4H), 7.54 (s, 2H), 7.45 (d, 4H), 6.84 (s, 2H), 4.79-4.71 (m, 4H), 3.89-3.85 (dd, 2H), 3.59-3.56 (m, 17H), 3.49-3.43 (m, 14H), 3.28-3.23 (m, 5H), 3.14 (s, 7H), 3.09-3.04 (m, 9H), 1.42 (s, 4H). MS (m/z): 1233.03 [M+H]$^+$.

Example 249

N,N'-(1,1'-(1,4-phenylenebis(azanediyl))bis(1-oxo-5,8,11-trioxa-2-azatridecane-13,1-diyl))bis(4-(6,8-dichloro-2-methyl-1,2,3,4-tetrahydroisoquinolin-4-yl)benzenesulfonamide)

gave the title compound (39.6 mg) as a TFA salt. $^1$H-NMR (400 MHz, CD3OD): δ 7.87 (d, 4H), 7.51 (s, 2H), 7.40 (d, 4H), 7.16 (s, 4H), 6.79 (s, 2H), 4.88-4.83 (m, 4H), 4.65-4.50 (m, 2H), 3.81-3.77 (m, 2H), 3.61-3.59 (m, 9H), 3.58-3.54 (m, 11H), 3.53-3.48 (m, 5H), 3.47-3.42 (m, 5H), 3.35-3.30 (m, 4H), 3.11 (s, 6H), 3.07 (t, 4H). MS (m/z): 1253.04 [M+H]$^+$.

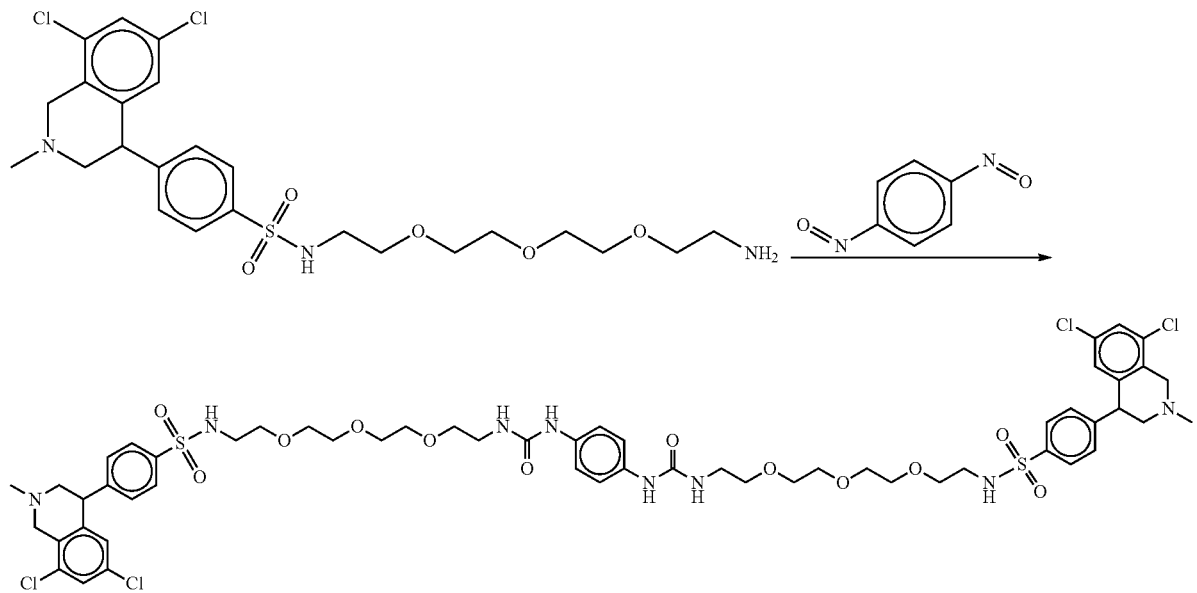

Compound 249, N,N'-(1,1'-(1,4-phenylenebis(azanediyl))bis(1-oxo-5,8,11-trioxa-2-azatridecane-13,1-diyl))bis(4-(6,8-dichloro-2-methyl-1,2,3,4-tetrahydroisoquinolin-4-yl)benzenesulfonamide)

Compound 249 was prepared following the procedure outlined in Example 208 using 1,4-diisocyanatobenzene (7.95 mg, 0.0495 mmol) and N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide (Compound 82, 76.7 mg, 0.099 mmol). Purification by preparative HPLC

Example 250

(S or R)—N,N'-(13-oxo-3,6,9,17,20,23-hexaoxa-12,14-diazapentacosane-1,25-diyl)bis(4-((S or R)-6,8-dichloro-2-methyl-1,2,3,4-tetrahydroisoquinolin-4-yl)benzenesulfonamide)

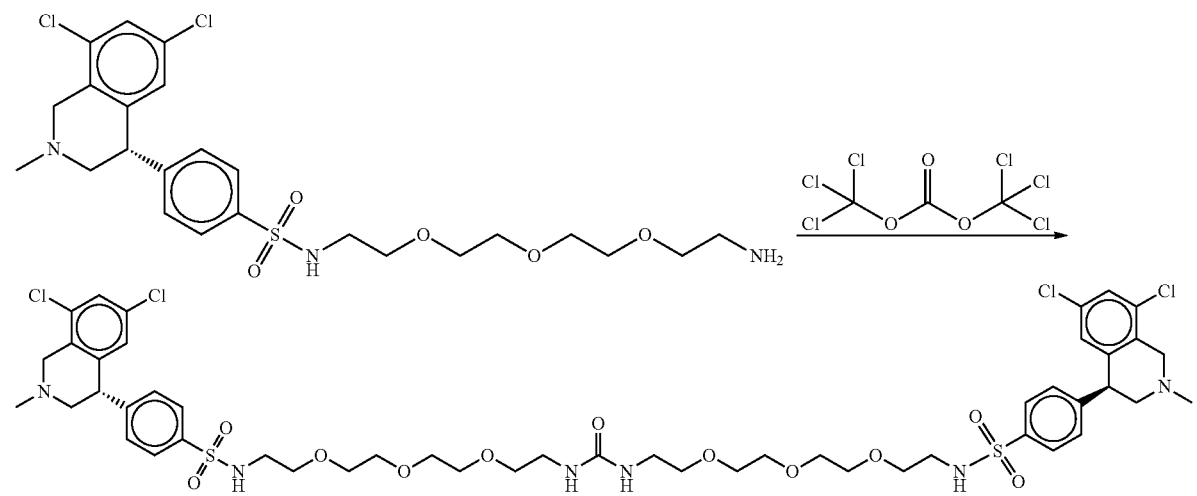

Compound 250, (S- or R)—N,N'-(13-oxo-3,6,9,17,20,23-hexaoxa-12,14-diazapentacosane-1,25-diyl)bis(4-((S or R)-6,8-dichloro-2-methyl-1,2,3,4-tetrahydroisoquinolin-4-yl)benzenesulfonamide)

Compound 250 was prepared following the procedures outlined in Example 232 using (S or R)—N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide (Intermediate 225.2, 75 mg, 0.0968 mmol). Purification by preparative HPLC gave the title compound (26.0 mg) as a TFA salt. ¹H-NMR (400 MHz, CD3OD): δ 7.88 (d, 4H), 7.54 (s, 2H), 7.45 (d, 4H), 6.84 (s, 2H), 4.79-4.72 (m, 5H), 4.48-4.42 (m, 2H), 3.87-3.83 (m, 2H), 3.58-3.54 (m, 17H), 3.49-3.43 (m, 15H), 3.24-3.22 (m, 6H), 3.12 (s. 6H), 3.08 (t, 4H). MS (m/z): 1118.96 [M+H]⁺.

Example 251

(S or R)—N,N'-(13,20-dioxo-3,6,9,24,27,30-hexaoxa-12,14,19,21-tetraazadotriacontane-1,32-diyl)bis(4-((S or R)-6,8-dichloro-2-methyl-1,2,3,4-tetrahydroisoquinolin-4-yl)benzenesulfonamide)

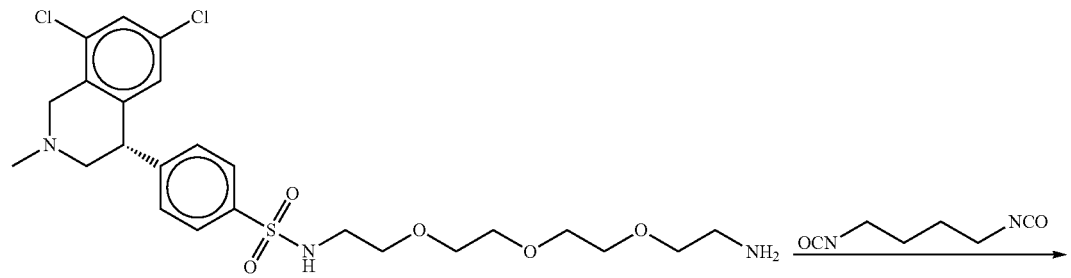

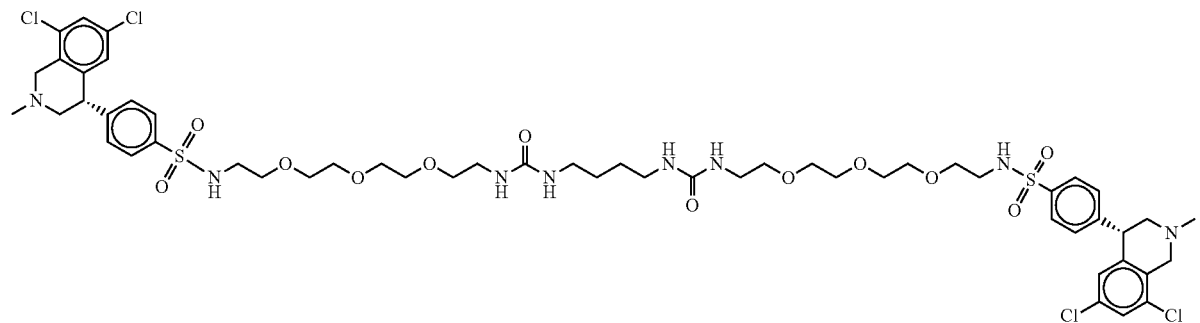

Compound 251, (S or R)—N,N'-(13,20-dioxo-3,6,9,24,27,30-hexaoxa-12,14,19,21-tetraazadotriacontane-1,32-diyl)bis(4-((S or R)-6,8-dichloro-2-methyl-1,2,3,4-tetrahydroisoquinolin-4-yl)benzenesulfonamide)

Compound 251 was prepared following the procedures outlined in Example 208 using (S or R)—N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide (intermediate 225.2, 88.1 mg, 0.114 mmol) and 1,4-diisocyanatobutane (7.9 mg, 0.0569 mmol). Purification by preparative HPLC gave the title compound (56.1 mg) as a TFA salt. ¹H-NMR (400 MHz, CD3OD): δ 7.85 (d, 4H), 7.54 (s, 2H), 7.45 (d, 4H), 6.84 (s, 2H), 4.77-4.74 (m, 4H), 4.50-4.46 (m, 2H), 3.89-3.84 (m, 2H), 3.61-3.56 (m, 17H), 3.50-3.43 (m, 14H), 3.26-3.23 (m, 6H), 3.14 (s, 7H), 3.09-3.04 (m, 10H), 1.48 (s, 4H). MS (m/z): 1233.01 [M+H]⁺.

Example 252

(S or R)—N,N'-(1,1'-(1,4-phenylenebis(azanediyl))bis(1-oxo-5,8,11-trioxa-2-azatridecane-13,1-diyl))bis(4-((S or R)-6,8-dichloro-2-methyl-1,2,3,4-tetrahydroisoquinolin-4-yl)benzenesulfonamide)

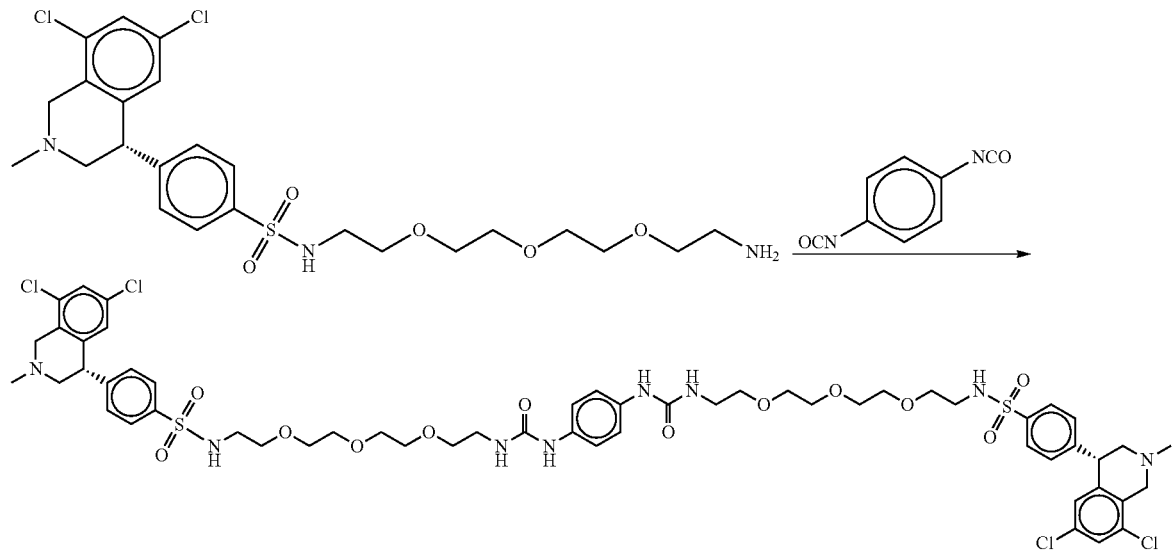

Compound 252, (S or R)—N,N'-(1,1'-(1,4-phenylenebis(azanediyl))bis(1-oxo-5,8,11-trioxa-2-azatridecane-13,1-diyl))bis(4-((S or R)-6,8-dichloro-2-methyl-1,2,3,4-tetrahydroisoquinolin-4-yl)benzenesulfonamide)

Compound 252 was prepared following the procedures outlined in Example 208 using (S)—N-(2-(2-(2-(2-aminoethoxy)ethoxy)ethoxy)ethyl)-4-(6,8-dichloro-2-methyl-1,2,3,4-tetrahydroisoquinolin-4-yl)benzenesulfonamide (intermediate 225.2, 45.2 mg, 0.0584 mmol) and 1,4-diisocyanatobenzene (4.7 mg, 0.0292 mmol). Purification by preparative HPLC gave the title compound (20.7 mg) as a TFA salt. $^1$H-NMR (400 MHz, CD3OD): δ 7.87 (d, 4H), 7.51 (s, 2H), 7.39 (d, 4H), 7.16 (s, 4H), 6.79 (s, 2H), 4.72-4.61 (m, 4H), 4.46-3.99 (m, 1H), 3.81-3.73 (m, 1H), 3.62-3.42 (m, 33H), 3.35-3.33 (m, 5H), 3.09-3.06 (m, 13H). MS (m/z): 1252.95 [M+H]$^+$.

Topological Polar Surface Area Data

Topological Polar Surface Area (tPSA) values for representative compounds in the disclosure are shown in Table 7, below. The tPSA values were calculated using the method of Ertl et al., Journal of Medicinal Chemistry, 43:3714-3717 (2000).

TABLE 7 tPSA Values of Compounds

| Example # | Topological polar surface area (Å$^2$) |
|---|---|
| Example 01 | 125 |
| Example 02 | 125 |
| Example 03 | 125 |
| Example 04 | 125 |
| Example 05 | 125 |
| Example 06 | 125 |
| Example 07 | 121 |
| Example 08 | 154 |
| Example 09 | 132 |
| Example 10 | 125 |
| Example 11 | 125 |
| Example 12 | 125 |
| Example 13 | 125 |
| Example 14 | 125 |
| Example 15 | 124 |
| Example 16 | 177 |
| Example 17 | 134 |
| Example 18 | 116 |
| Example 19 | 116 |
| Example 20 | 116 |
| Example 21 | 238 |
| Example 22 | 116 |
| Example 23 | 116 |
| Example 24 | 177 |
| Example 25 | 238 |
| Example 26 | 116 |
| Example 27 | 134 |
| Example 28 | 112 |
| Example 29 | 229 |
| Example 30 | 137 |
| Example 31 | 137 |
| Example 32 | 137 |
| Example 33 | 137 |
| Example 34 | 119 |
| Example 35 | 119 |
| Example 36 | 119 |
| Example 37 | 119 |
| Example 38 | 112 |
| Example 39 | 112 |

TABLE 7-continued tPSA Values of Compounds

| Example # | Topological polar surface area (Å²) |
|---|---|
| Example 40 | 119 |
| Example 41 | 291 |
| Example 42 | 291 |
| Example 43 | 309 |
| Example 44 | 318 |
| Example 45 | 199 |
| Example 46 | 387 |
| Example 47 | 404 |
| Example 48 | 224 |
| Example 49 | 417 |
| Example 50 | 297 |
| Example 51 | 213 |
| Example 52 | 213 |
| Example 53 | 213 |
| Example 54 | 213 |
| Example 55 | 213 |
| Example 56 | 213 |
| Example 57 | 241 |
| Example 58 | 184 |
| Example 59 | 220 |
| Example 60 | 147 |
| Example 61 | 134 |
| Example 62 | 134 |
| Example 63 | 215 |
| Example 64 | 134 |
| Example 65 | 123 |
| Example 66 | 147 |
| Example 67 | 161 |
| Example 68 | 117 |
| Example 69 | 117 |
| Example 70 | 134 |
| Example 71 | 208 |
| Example 72 | 154 |
| Example 73 | 134 |
| Example 74 | 174 |
| Example 75 | 178 |
| Example 76 | 125 |
| Example 77 | 238 |
| Example 78 | 121 |
| Example 79 | 123 |
| Example 80 | 136 |
| Example 81 | 242 |
| Example 82 | 112 |
| Example 83 | 191 |
| Example 84 | 190 |
| Example 85 | 123 |
| Example 86 | 228 |
| Example 87 | 270 |
| Example 88 | 270 |
| Example 89 | 159 |
| Example 90 | 189 |
| Example 91 | 147 |
| Example 92 | 147 |
| Example 93 | 74 |
| Example 94 | 157 |
| Example 95 | 115 |
| Example 96 | 115 |
| Example 97 | 312 |
| Example 98 | 312 |
| Example 99 | 235 |
| Example 100 | 212 |
| Example 101 | 202 |
| Example 102 | 487 |
| Example 103 | 212 |
| Example 104 | 500 |
| Example 168 | 251 |
| Example 169 | 214 |
| Example 170 | 270 |
| Example 171 | 86 |
| Example 172 | 270 |
| Example 173 | 185 |
| Example 174 | 243 |
| Example 175 | 211 |
| Example 176 | 233 |
| Example 177 | 211 |
| Example 178 | 220 |
| Example 179 | 219 |
| Example 180 | 229 |
| Example 181 | 229 |
| Example 182 | 229 |
| Example 183 | 211 |
| Example 184 | 202 |
| Example 185 | 214 |
| Example 186 | 237 |
| Example 187 | 238 |
| Example 188 | 211 |
| Example 189 | 231 |
| Example 190 | 211 |
| Example 191 | 211 |
| Example 192 | 273 |
| Example 193 | 231 |
| Example 194 | 221 |
| Example 195 | 220 |
| Example 196 | 211 |
| Example 197 | 229 |
| Example 198 | 238 |
| Example 199 | 229 |
| Example 200 | 211 |
| Example 201 | 220 |
| Example 202 | 235 |
| Example 203 | 235 |
| Example 204 | 290 |
| Example 205 | 251 |
| Example 206 | 177 |
| Example 207 | 251 |
| Example 208 | 253 |
| Example 209 | 253 |
| Example 210 | 500 |
| Example 211 | 227 |
| Example 212 | 445 |
| Example 213 | 347 |
| Example 214 | 176 |
| Example 215 | 344 |
| Example 216 | 229 |
| Example 217 | 441 |
| Example 218 | 251 |
| Example 219 | 280 |
| Example 220 | 280 |
| Example 221 | 192 |
| Example 222 | 270 |
| Example 223 | 270 |
| Example 224 | 270 |
| Example 225 | 270 |
| Example 226 | 270 |
| Example 227 | 270 |
| Example 228 | 229 |
| Example 229 | 270 |
| Example 230 | 229 |
| Example 231 | 211 |
| Example 232 | 194 |
| Example 233 | 229 |
| Example 234 | 211 |
| Example 235 | 194 |
| Example 236 | 235 |
| Example 237 | 235 |
| Example 238 | 235 |
| Example 239 | 235 |
| Example 240 | 270 |
| Example 241 | 270 |
| Example 242 | 270 |
| Example 243 | 270 |
| Example 244 | 253 |
| Example 245 | 253 |
| Example 246 | 229 |
| Example 247 | 158 |
| Example 248 | 253 |
| Example 249 | 253 |
| Example 250 | 212 |

TABLE 7-continued tPSA Values of Compounds

| Example # | Topological polar surface area (Å$^2$) |
|---|---|
| Example 251 | 253 |
| Example 252 | 253 |

Pharmacological Data

1. Pharmacological Test Example 1

Cell-Based Assay of NHE-3 Activity

Rat NHE-3-mediated Na$^+$-dependent H$^+$ antiport was measured using a modification of the pH sensitive dye method originally reported by Tsien (*Proc. Natl. Acad. Sci. USA.* (1984) 81(23): 7436-7440). Opossum kidney (OK) cells were obtained from the ATCC and propagated per their instructions. The rat NHE-3 gene was introduced into OK cells via electroporation, seeded into 96 well plates and grown overnight. Medium was aspirated from the wells, cells were washed twice with NaCl-HEPES buffer (100 mM NaCl, 50 mM HEPES, 10 mM glucose, 5 mM KCl, 2 mM CaCl$_2$, 1 mM MgCl$_2$, pH 7.4), then incubated for 30 min at room temperature with NH$_4$Cl-HEPES buffer (20 mM NH$_4$Cl, 80 mM NaCl, 50 mM HEPES, 5 mM KCl, 2 mM CaCl$_2$, 1 mM MgCl$_2$, pH 7.4) containing 5 uM BCECF-AM (Invitrogen). Cells were washed twice with Ammonium free, Na$^+$-free HEPES (100 mM choline, 50 mM HEPES, 10 mM glucose, 5 mM KCl, 2 mM CaCl$_2$, 1 mM MgCl$_2$, pH 7.4) and incubated in the same buffer for 10 minutes at room temperature to lower intracellular pH. NHE-3-mediated recovery of neutral intracellular pH was initiated by addition of Na-HEPES buffer containing 5 uM ethyl isopropyl amiloride (EIPA, a selective antagonist of NHE-1 activity that does not inhibit NHE-3) and 0-30 uM test compound, and monitoring the pH sensitive changes in BCECF fluorescence ($\lambda_{ex}$ 505 nm, $\lambda_{em}$ 538 nm) normalized to the pH insensitive BCECF fluorescence ($\lambda_{ex}$ 439 nm, $\lambda_{em}$ 538 nm). Initial rates were plotted as the average 3-6 replicates, and pIC$_{50}$ values were estimated using GraphPad Prism. The inhibitory data of many of the example compounds illustrated above are shown in Table 8, below.

TABLE 8

Inhibitory data of compounds against rat NHE-3

| Example # | rat NHE-3 Average pIC50 [1] |
|---|---|
| Example 171 | <5.0 |
| Example 174 | <5.0 |
| Example 175 | <5.0 |
| Example 223 | <5.0 |
| Example 231 | <5.0 |
| Example 232 | <5.0 |
| Example 233 | <5.0 |
| Example 235 | <5.0 |
| Example 30 | 5 to 6 |
| Example 31 | 5 to 6 |
| Example 52 | 5 to 6 |
| Example 54 | 5 to 6 |
| Example 63 | 5 to 6 |
| Example 64 | 5 to 6 |
| Example 176 | 5 to 6 |
| Example 196 | 5 to 6 |
| Example 209 | 5 to 6 |
| Example 219 | 5 to 6 |
| Example 234 | 5 to 6 |
| Example 28 | 6 to 7 |
| Example 29 | 6 to 7 |
| Example 45 | 6 to 7 |
| Example 46 | 6 to 7 |
| Example 60 | 6 to 7 |
| Example 65 | 6 to 7 |
| Example 66 | 6 to 7 |
| Example 67 | 6 to 7 |
| Example 68 | 6 to 7 |
| Example 69 | 6 to 7 |
| Example 97 | 6 to 7 |
| Example 100 | 6 to 7 |
| Example 102 | 6 to 7 |
| Example 104 | 6 to 7 |
| Example 169 | 6 to 7 |
| Example 170 | 6 to 7 |
| Example 178 | 6 to 7 |
| Example 207 | 6 to 7 |
| Example 210 | 6 to 7 |
| Example 211 | 6 to 7 |
| Example 213 | 6 to 7 |
| Example 217 | 6 to 7 |
| Example 218 | 6 to 7 |
| Example 225 | 6 to 7 |
| Example 228 | 6 to 7 |
| Example 47 | >7 |
| Example 81 | >7 |
| Example 87 | >7 |
| Example 88 | >7 |
| Example 98 | >7 |
| Example 103 | >7 |
| Example 172 | >7 |
| Example 177 | >7 |
| Example 191 | >7 |
| Example 195 | >7 |
| Example 200 | >7 |
| Example 201 | >7 |
| Example 202 | >7 |
| Example 203 | >7 |
| Example 204 | >7 |
| Example 205 | >7 |
| Example 206 | >7 |
| Example 208 | >7 |
| Example 212 | >7 |
| Example 215 | >7 |
| Example 216 | >7 |
| Example 222 | >7 |
| Example 224 | >7 |
| Example 229 | >7 |
| Example 230 | >7 |
| Example 236 | >7 |
| Example 237 | >7 |
| Example 244 | >7 |
| Example 250 | >7 |
| Example 251 | >7 |

[1] pIC50 is the negative log the IC50 value (an IC50 value of 1 micromolar corresponds to a pIC50 value of 6.0)

2. Pharmacological Test Example 2

Parallel Artificial Membrane Permeability Assay (PAMPA)

The model consists of a hydrophobic filter material coated with a mixture of lecithin/phospholipids creating an artificial lipid membrane. BD Gentest PAMPA 96-well plates (cat #353015) are warmed for 1 hr at room temperature. 1 mL of 20 uM control compounds (pooled mix of 10 mM atenolol, ranitidine, labetalol, and propranolol) in transport buffer (10 mM HEPES in HBSS pH 7.4) are prepared along with 1 mL of 20 uM test compounds in transport buffer. The PAMPA plates are separated, and 0.3 mL of compound are added in duplicate to apical side (bottom/donor plate="AP"), and 2 mL buffer are placed in the basolateral chamber (top/receiver plate="BL"). The BL plate is placed on the AP plate and incubated for 3 hrs in 37° C. incubator. At that time, samples are removed from both plates, and analyzed for compound concentration using LC/MS. A "$P_e$" (effective permeability) value is calculated using the following formula.

$$P_e = (-\ln[1 - C_A(t)/C_{eq}])/[A^*(1/V_D + 1/V_A)^*t$$

where $C_A$=concentration in acceptor well, $C_D$=concentration in donor well $V_D$=donor well volume (mL), $V_A$=acceptor well volume (mL)

A=filter area=0.3 cm$^2$, t=transport time (seconds)

$C_{eq}$=equilibrium concentration=$[C_D(t)^*V_D + C_A(t)^*V_A]/(V_D + V_A)$ $P_e$ is reported in units of cm/sec×10$^{-6}$.

Results from PAMPA testing are shown in Table 9.

TABLE 9

Papp values as determined using the PAMPA assay

| Example # | Avg Papp, A→B, cm/sec × 10$^{-6}$ |
|---|---|
| Example 01 | 0.53 |
| Example 03 | 0.8 |
| Example 07 | 0.5 |
| Example 08 | 0.2 |
| Example 13 | 0.3 |
| Example 14 | 0.4 |
| Example 15 | 0.05 |
| Example 16 | <0.02 |
| Example 23 | <0.04 |
| Example 24 | 0.03 |
| Example 26 | <0.02 |
| Example 27 | <0.02 |
| Example 30 | 0.56 |
| Example 31 | 0.61 |
| Example 34 | 0.2 |
| Example 35 | 0.17 |
| Example 36 | 0.2 |
| Example 37 | 0.1 |
| Example 38 | 0.1 |
| Example 44 | 0.1 |
| Example 47 | <0.01 |
| Example 48 | 0.9 |
| Example 51 | 0.2 |
| Example 52 | 1.61 |
| Example 53 | 1.6 |
| Example 54 | 1.3 |
| Example 56 | 0.5 |
| Example 57 | 1.65 |
| Example 58 | 0.2 |
| Example 59 | 0.1 |
| Example 60 | 0.99 |
| Example 61 | 0.1 |
| Example 63 | 0.43 |
| Example 68 | 0.35 |
| Example 69 | 0.3 |
| Example 70 | 0.4 |
| Example 71 | 0.45 |
| Example 72 | 0.2 |
| Example 73 | 0.27 |
| Example 74 | 0.45 |
| Example 75 | 0.4 |
| Example 76 | 0.2 |

Increasing values of tPSA are typically associated with lower permeability. FIG. 1 illustrates the Relationship between tPSA and Permeability (Papp, as measured in the PAMPA assay) of Example compounds. Compounds with higher tPSA values trend toward lower permeability.

3. Pharmacological Test Example 3

Figure 2B:
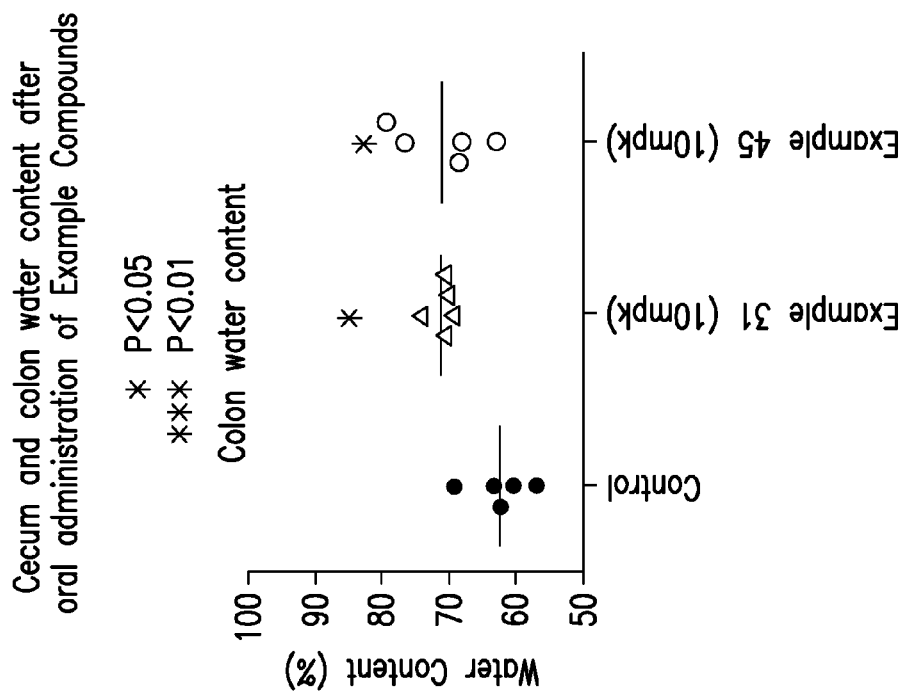
FIGS. 2A and 2B are graphs that illustrate the cecum and colon water content after oral administration of certain example compounds, as further discussed in the Examples (under the subheading "3. Pharmacological Test Example 3").
Figure 2A:
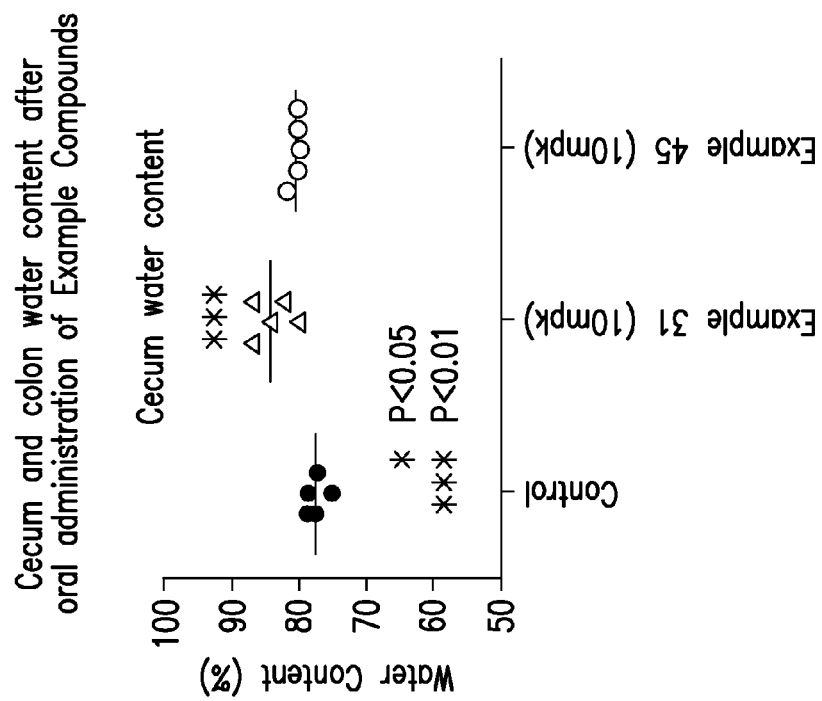

Pharmacodynamic Model: Effect of Test Compounds on Fluid Content of Intestinal Compartments Normal female Sprague Dawley rats, 7 weeks old, were acclimated for at least 2 days. The animals were fed ad lib through the experiment. Groups of 5 rats were orally gavaged with 1.5 mL of water containing a negative control compound or test compounds, adjusted to a concentration that results in a dose of 10 mg/kg. Six hours after dosing, rats were euthanized with isofluorane. The cecum and colon were ligated and then removed. After a brief rinse in saline and pat-drying, the segments were weighed. The segments were then opened, and the contents collected and weighed. The collected contents were then dried, and weighed again. The % water content was reported as 100×((Ww−Wd)/Ww) where Ww is the weight of the wet contents, and Wd is the weight of the contents after drying. The differences between groups are evaluated by one way ANOVA with Bonferroni post tests. Examples are shown in FIGS. 2A and 2B (wherein rats were dosed orally with 10 mg/kg of compound (Example or Control), and then after 6 hours, cecum and colon contents were removed, weighed and dried, and the % water in the contents was determined: *, P<0.05 and ***, P<0.01 compared to control in ANOVA analysis).

4. Pharmacological Test Example 4

Determination of Compound $C_{max}$ and AUC

Sprague-Dawley rats were orally gavaged with test article (2.5 mg/kg) and serum was collected at 0.5, 1, 2 and 4 h. Serum samples were treated with acetonitrile, precipitated proteins removed by centrifugation and supernatants analyzed by LC/MS/MS and compared against a standard curve to determine compound concentration. Table 10 illustrates data from the pharmacokinetic profiling of selected example compounds. All compounds were orally dosed at the dosage shown, and pharmacokinetic parameters determined as described in the text.

TABLE 10

Pharmacokinetic Profiling of Selected Example Compounds

| Example | Actual Oral Dose (mg/kg) | Cmax (ng/mL) | AUC (ng × hr/mL) |
|---|---|---|---|
| Example 01 | 2.1 | 21 | 53 |
| Example 16 | 1.6 | 71 | 159 |
| Example 31 | 1.3 | 11 | 56 |
| Example 35 | 2.2 | 2.4 | 5 |
| Example 50 | 2.3 | 93 | 242 |
| Example 52 | 4.6 | 14 | 9 |
| Example 55 | 2.2 | 9 | 23 |
| Example 60 | 2.4 | 2 | 0 |
| Example 63 | 2.4 | 0 | 0 |
| Example 211 | 0.7 | <2.3 | <3.0 |
| Example 212 | 1.5 | <2.7 | <4.4 |
| Example 213 | 9.5 | <5.0 | <5.0 |
| Example 214 | 2.6 | <5.0 | <5.0 |
| Example 215 | 7.7 | <2.0 | <2.0 |
| Example 216 | 1.9 | <4.0 | <8.3 |
| Example 217 | 9.1 | <10.0 | <10.0 |
| Example 204 | 10.9 | <2.0 | <2.0 |
| Example 218 | 9 | <1.0 | <1.0 |

TABLE 10-continued

Pharmacokinetic Profiling of Selected Example Compounds

| Example | Actual Oral Dose (mg/kg) | Cmax (ng/mL) | AUC (ng × hr/mL) |
|---|---|---|---|
| Example 169 | 11 | <3.5 | <4.0 |
| Example 205 | 10.7 | <2.0 | <2.0 |
| Example 225 | 27 | <3.5 | <5.3 |
| Example 226 | 31 | <3.0 | <5.0 |
| Example 172 | 26 | <2.0 | <2.0 |
| Example 228 | 23 | <5.0 | <5.0 |
| Example 230 | 17 | <5.0 | <5.0 |
| Example 173 | 28 | 23 | 19 |
| Example 174 | 27 | <5.4 | <5.0 |
| Example 208 | 12 | <5.0 | <5.0 |
| Example 231 | 23 | <2.5 | <3.0 |
| Example 232 | 17 | <2.0 | <2.0 |
| Example 233 | 19 | <2.6 | <6.8 |
| Example 234 | 22 | <2.0 | <2.0 |
| Example 235 | 11 | <5.0 | <5.0 |
| Example 175 | 28 | 8 | 6 |
| Example 177 | 14 | <3.2 | <4.0 |
| Example 178 | 18 | <2.0 | <2.0 |
| Example 179 | 27 | <16.0 | <35.0 |
| Example 180 | 25 | <10.0 | <19.0 |
| Example 181 | 28 | <2.0 | <2.0 |
| Example 185 | 17 | <2.0 | <2.0 |
| Example 186 | 15 | <3.4 | <5.0 |
| Example 244 | 16 | <7.0 | <15.0 |
| Example 245 | 21 | <2.0 | <2.0 |

5. Pharmacological Test Example 5

Evaluation of NHE-3-Inhibitory Compounds in Disease Models with Na/H$_2$O Retention: CRF/ESRD Model Male Sprague-Dawley rats with subtotal (5/6$^{th}$) nephrectomy, 7 weeks old and weighing 175-200 g at surgery time, are purchased from Charles River Laboratories. The animals are subjected to acclimation for 7 days, and randomly grouped (using random number table) before proceeding to experiments. During acclimation, all animals are fed with base diet HD8728CM. The rats are housed in holding cages (2/cage) during the acclimation period and the time between sample collections. The rats are transferred to metabolic cages on the days of sample collections. Food and water is provided ad libitum.

Chronic renal failure is induced in the rats by subtotal (5/6th) nephrectomy (Nx) followed by intravenous (IV) injection of adriamycin (ADR) at 2 weeks post-nephrectomy, at a dose of 3.5 mg/kg body weight. Animals are then randomized into control and treatment groups with 10 rats per group. Rats in untreated group are fed with base diet and rats in the treatment groups are fed the same chow supplemented with NHE-3 inhibitor/fluid holding polymer at various doses. All the groups are maintained for 28 days.

Serum samples are collected at day (−1) (1 days before ADR injection), days 14 and 28 post ADR treatment. Twenty four hour urine and fecal samples are collected at day (−1), days 14 and 28 post ADR treatment and stored at −20° C. for later analysis. Body weight, food and water consumption are measured at the same time points as urine collections. Serum and urine chemistry (Na, K, Ca, Cl) are determined using an ACE Clinical Chemistry System (ALFA WASSER MANN Diagnostic Technologies, LLC). Fecal electrolyte (Na, K, Ca, Cl) excretions are determined by IC. Fluid balance are also determined via amount of fluid intake (in drinking water) subtracted by combined fecal water amount and urine volume. Tissues (heart, kidney and small intestine) are harvested at the end of experiments for later histopathological analysis. The third space (pleural fluids and ascites) body fluid accumulation are scored semi-quantitatively as follows: grade 0, no fluid accumulation; grade 1, trace amount of fluids; grade 2, obvious amount of fluids; grade 3, both cavities full of fluids; grade 4, fluids overflowed once the cavities are opened. Each score of body fluid accumulation is confirmed and agreed on by 2 investigators.

Animals treated with NHE-3 inhibitor/fluid holding polymer show decreased serum aldosterone, decreased 24 hr urine volume and decreased urine K excretion, and increased urine Na excretion compared to no treatment group. Treated animals also have increased fecal Na and fluid excretion, compared to control group. Compared to untreated rats which show positive fluid balance of 4 g per day, animals treated with NHE-3 inhibitor/fluid holding polymer demonstrate a fluid loss of 5 g per day.

Treatment of NHE-3 inhibitor/fluid holding polymer in CRF rats is associated with less edema in heart, kidney and small intestine tissues, less hypertrophy in heart, less third space fluid accumulation, and lower body weight at the end of experiment compared to untreated group.

6. Pharmacological Test Example 6

Evaluation of NHE-3-Inhibitory Compounds in Disease Models with Na/H2O Retention: Congestive Heart Failure Model CHFs are introduced to male Sprague Dawley rats, 7-8 weeks old fed ad lib regular diet and ad lib 10% ethanol in drinking water, and gavaged with a daily dose of 6.3 mg cobalt acetate for 7 days. Then CHF rats are gavaged with a daily dose of 4 mg of furosemide for 5 days, inducing resistance to furosemide diuretic effects. The rats are then randomly divided into 2 groups, control and treatment, and the treatment group administered NHE-3 inhibitor/fluid holding polymer for 7 days. Day 0 and day 7 post treatment serum aldosterone levels, urine volume, urine Na and K excretions are measured. Fluid balance is also determined via amount of fluid intake (in drinking water) subtracted by combined fecal fluid amount and urine volume.

Animals treated with NHE-3 inhibitor/fluid holding polymer have decreased serum aldosterone levels, decreased 24 hr urine volume and urine K excretion, and increased urine Na excretion compared to control group. Animals treated with NHE-3 inhibitor/fluid holding polymer have, for example, increased fecal Na and fluid excretion. Compared to untreated rats, which show a positive fluid balance of, for example, 4 g per day, treated animals demonstrate a fluid loss of 5 g per day.

7. Pharmacological Test Example 7

Evaluation of NHE-3-Inhibitory Compounds in Disease Models with Na/H2O Retention: Hypertension Model Male Dahl salt-sensitive rats are obtained from Harlan Teklad. After acclimation, animals are randomly grouped and fed diet containing 8% NaCl±NHE-3 inhibitor/fluid holding polymer for 7 days. Day 0 and day 7 post treatment systolic BP, serum aldosterone levels, urine volume, urine Na and K excretions are measured. Fluid balance is also determined via amount of fluid intake (in drinking water) subtracted by combined fecal fluid amount and urine volume.

Animals treated with NHE-3 inhibitor/fluid holding polymer would show decreased systolic BP, serum aldosterone levels, 24 hr urine volume and urine K excretion, and increased urine Na excretion compared to no treatment group. Animals treated with NHE-3 inhibitor/fluid holding polymer would also show increased fecal fluid excretion. Compared to untreated rats which would show positive fluid balance of 4 g per day, animals treated with NHE-3 inhibitor/fluid holding polymer demonstrate a fluid loss of 2 g per day.

8. Pharmacological Test Example 8

Na Transport Inhibition Study on Colonic Tissues

Immediately following euthanasia and exsanguinations of the rats, the entire distal colon is removed, cleansed in ice-cold isotonic saline, and partially stripped of the serosal muscularis using blunt dissection. Flat sheets of tissue are mounted in modified Ussing chambers with an exposed tissue area of 0.64 cm². Transepithelial fluxes of $^{22}Na^+$ (Perkin Elmer Life Sciences, Boston, Mass.) are measured across colonic tissues bathed on both sides by 10 ml of buffered saline (pH 7.4) at 37° C. and circulated by bubbling with 95% $O_2$–5% $CO_2$. The standard saline contains the following solutes (in mmol/1): 139.4 $Na^+$, 5.4 K, 1.2 $Mg^{2+}$, 123.2 $Cl^-$, 21.0 $HCO_3^-$, 1.2 $Ca^{2+}$, 0.6 $H_2PO_4^-$, 2.4 $HPO^{2-}$, and 10 glucose. The magnitude and direction of the net flux (Jnet Na) is calculated as the difference between the two unidirectional fluxes (mucosal to serosal, Jms Na and serosal to mucosal, Jsm Na) measured at 15-min intervals for a control period of 45 min (Per I), under short-circuit conditions. In some series, Per I is followed by a second 45-min flux period (Per II) to determine the acute effects of NHE inhibitors.

9. Pharmacological Test Example 9

Pharmacodynamic Model: Effect of Test Compounds and FAP on Consistency and Form of Rat Stools Normal rats are given a NHE-3 inhibiting compound and optionally a fluid-absorbing or -holding polymer mixed in their diet at escalated doses. Distilled water is available at libitum. Clinical data monitored are body weight, food intake, water intake, fecal and urinary output. Urinary Na, K and creatinine are measured by a Clinical Analyzer (VetAce; Alfa Wassermann Diagnostic Technologies, LLC, West Caldwell, N.J.). The consistency of the stools expelled within 24 h after the administration of each drug or vehicle is reported as follows: when the feces are unformed, i.e., muddy or watery, this is judged to be diarrhea and the percentage diarrhea is reported as the ratio of the number of animals producing unformed stools to the number tested. All of the feces is collected just after each evacuation and put into a covered vessel prepared for each animal in order to prevent the feces from drying. To investigate the duration of activity of each drug, the feces collected over each 8-h period is dried for more than 8 h at 70° C. in a ventilated oven after the wet weight is measured. The fecal fluid content is calculated from the difference between the fecal wet weight and the dry weight. Fecal Na and K is analyzed by ion Chromatography (Dionex) after acid digestion of the feces specimen.

10. Pharmacological Test Example 10

Effect of Test Compounds and FAP on CKD Rats

Male Sprague-Dawley rats (275-300 g; Harlan, Indianapolis, Ind.) are used and have free access to water and Purina rat chow 5001 at all times. A ⅚ nephrectomy is performed to produce a surgical resection CRF model and the treatment study is performed 6 wk after this procedure. In one control group, CRF rats are given access to Purina rat chow; in treated groups, CRF rats are given access to Purina rat chow mixed with the article, i.e. a NHE-3 inhibiting compound and optionally a fluid-absorbing or -holding polymer. The treatment period is 30 days. Systolic blood pressure is monitored in all animals with the use of a tail sphygmomanometer (Harvard Apparatus, South Natick, Mass.). All rats are euthanatized by an intraperitoneal injection of pentobarbital (150 mg/kg body wt), and blood is collected by cardiac puncture for serum $Na^+$ (Roche Hitachi Modular P800 chemistry analyzer; Roche Diagnostics, Indianapolis, Ind.) and creatinine determination (kit 555A; Sigma Chemical, St. Louis, Mo.). Sodium and creatinine is also determined in a urine specimen collected over 24 h immediately before euthanasia.

11. Pharmacological Test Example 11

Effect of Test Compounds on Intestinal Fluid Accumulation in Suckling Mice

Institute of Cancer Research/Harlan Sprague-Dawley (ICR-HSD) suckling mice, 2 to 4 days old (2.1±1.0 g), are dosed orally with 0.1 mL of test solution (vehicle (1 mmol/L HEPES) or NHE inhibitor dissolved in vehicle). After dosing, the mice are kept at room temperature for 3 hours, then killed, the intestinal and body weights measured, and a ratio of the intestinal weight to remaining body weight is calculated. A ratio of 0.0875 represents one mouse unit of activity, indicating significant fluid accumulation in the intestine.

12. Pharmacological Test Example 12

Determination of Water-Absorbing Capacity

This test is designed to measure the ability of a polymer to absorb 0.9% saline solution against a pressure of 50 g/cm² or 5 kPa. The superabsorbent is put into a plastic cylinder that has a screen fabric as bottom. A weight giving the desired pressure is put on top. The cylinder arrangement is then placed on a liquid source. The superabsorbent soaks for one hour, and the absorption capacity is determined in g/g.

This test principle is described in the European Disposables And Nonwovens Association (EDANA) standard EDANA ERT 442—Gravimetric Determination of Absorption under Pressure or Absorbency Under Load (AUL), or in the AUL-test found in column 12 in U.S. Pat. No. 5,601,542, the entire contents of which are incorporated herein by reference for all relevant and consistent purposes. Any of these two methods can be used, or the simplified method described below.

Equipment:

A plastic cylinder having a screen fabric made of steel or nylon glued to the bottom. The fabric can have mesh openings of 36 μm (designated "400 mesh"), or in any case smaller than the smallest tested particles. The cylinder can have an internal diameter of 25.4 mm, and a height of 40 mm. A larger cylinder can also be used, such as the apparatus in the EDANA standard ERT 442—Gravimetric Determination of Absorption under Pressure.

A plastic piston or spacer disc with a diameter slightly smaller than the cylinder's inner diameter. For a cup with a 25.4 mm inner diameter the disc can be 25.2 mm wide, 8 mm high, and weigh about 4.4 g.

A weight that exerts a 50 g/cm² pressure on the superabsorbent (in combination with the piston). For a 25.4 mm inner diameter cylinder (=5.067 cm²) and a 4.4 g piston, the weight should have a mass of 249 g.

Glass or ceramic filter plate (porosity=0). The plate is at least 5 mm high, and it has a larger diameter than the cylinder.

Filter paper with a larger diameter than the cylinder. Pore size <25 μm.

Petri dish or tray 0.9% NaCl solution

Procedure:

Put the glass filter plate in a Petri dish, and place a filter paper on top.

Fill the Petri dish with 0.9% NaCl solution—up to the edge of the filter plate.

Weigh a superabsorbent sample that corresponds to a 0.032 g/cm² coverage on the cylinder's screen fabric (=0.16 g for a cylinder with a 25.4 mm inner diameter). Record the exact weight of the sample (A). Carefully distribute the sample on the screen fabric.

Place the plastic piston on top of the distributed sample, and weigh the cylinder assembly (B). Then mount the weight onto the piston.

Place the assembly on the filter paper, and let the superabsorbent soak for 60 minutes.

Remove the weight, and weigh the assembly with the swollen superabsorbent (C).

Calculate the AUL in g/g according to this formula: C−B.

13. Pharmacological Test Example 13

Pharmacodynamic Model: Effect of Test Compounds on Fecal Water Content

Normal female Sprague Dawley rats (Charles-River laboratories international, Hollister, Calif.), 7-8 weeks old with body weight 175-200 g were acclimated for at least 3 days before proceeding to experiments. The animals were provided food (Harlan Teklad 2018c) and water ad lib. through the experiment. Animals were randomly grouped with 6 rats per group.

The experiments were initiated by orally dosing test compounds at 3 mg/kg in volume of 10 ml/kg. Rats from control group were gavaged with the same volume of vehicle (water). After dosing, rats were placed in metabolic cages for 16 hrs (overnight). Food and water consumption were monitored. After sixteen hours, feces and urine were collected. The percent of fecal water was measured by weighing fecal samples before and after drying.

Representative data of % fecal water content are shown in Table 11 (data are expressed as means, with 6 animals per data point). The differences between control and treated groups were evaluated by one way ANOVA with Dunnett post tests. Results are significant if $p<0.05$.

TABLE 11

| Example | % Fecal water | % Fecal water (% of control) | Significant? |
| --- | --- | --- | --- |
| 224 | 65% | 125% | Y |
| 234 | 58% | 117% | Y |
| 239 | 58% | 114% | Y |
| 178 | 59% | 118% | Y |
| 237 | 60% | 120% | Y |
| 238 | 60% | 121% | Y |
| 177 | 60% | 121% | Y |
| 244 | 61% | 118% | Y |
| 236 | 64% | 128% | Y |
| 250 | 60% | 120% | Y |
| 200 | 62% | 124% | Y |
| 201 | 63% | 127% | Y |
| 202 | 63% | 134% | Y |
| 203 | 61% | 130% | Y |

14. Pharmacological Test Example 14

Pharmacodynamic Model: Effect of Test Compounds on Urinary Sodium Levels

Figures 3A, 3B:
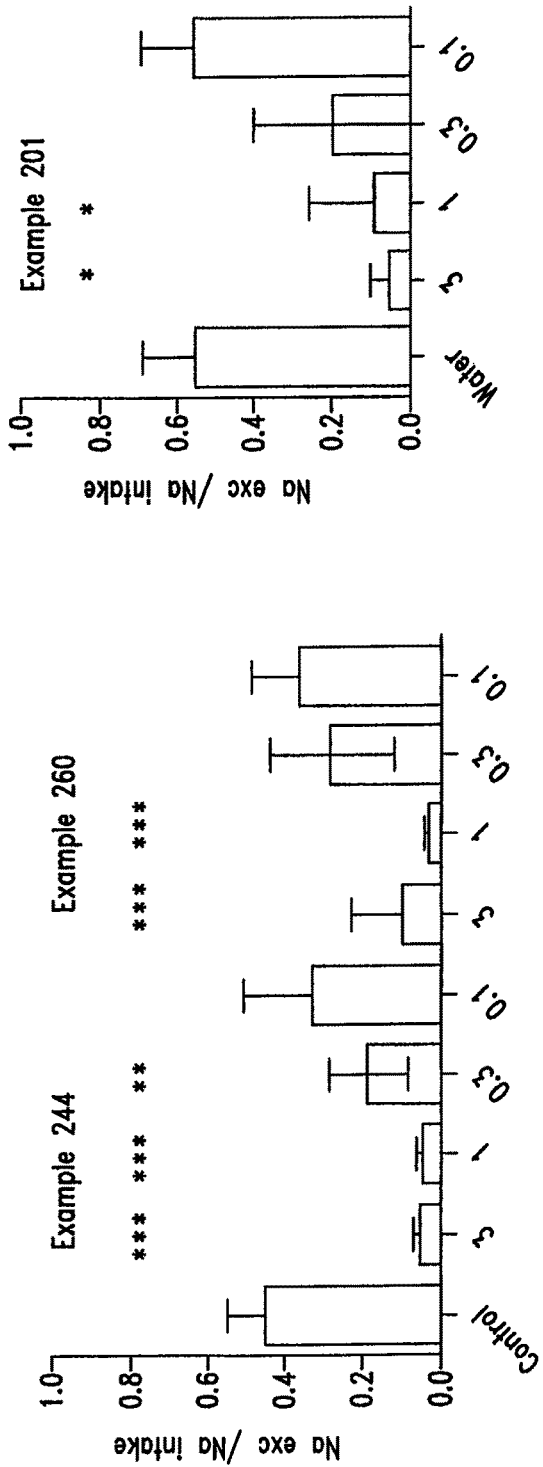
FIGS. 3A and 3B are graphs that illustrate the dose dependent decrease of urinary salt levels after administration of certain example compounds, as further discussed in the Examples (under the subheading "14. Pharmacological Test Example 14").

It is anticipated that the reduction of absorption of sodium from the intestine will be reflected in reduced levels of sodium in the urine. To test this, the protocols in Example 13 were repeated, but urine was collected in addition to feces. Urine sodium levels were analyzed by ion chromatography (IC), and the amount of sodium excreted in the urine was corrected for variations in sodium intake by measuring food consumption. In addition, test compounds were administered at several dose levels to demonstrate a dose-response relationship. As shown in FIGS. 3A and 3B for Examples 201, 244, and 260, where as rats excrete about half the sodium they consume in urine, in rats treated with increasing doses of NHE-3 inhibitor, the amount of sodium excreted in the urine diminishes significantly and dose dependently.

15. Pharmacological Test Example 15

Figure 4:
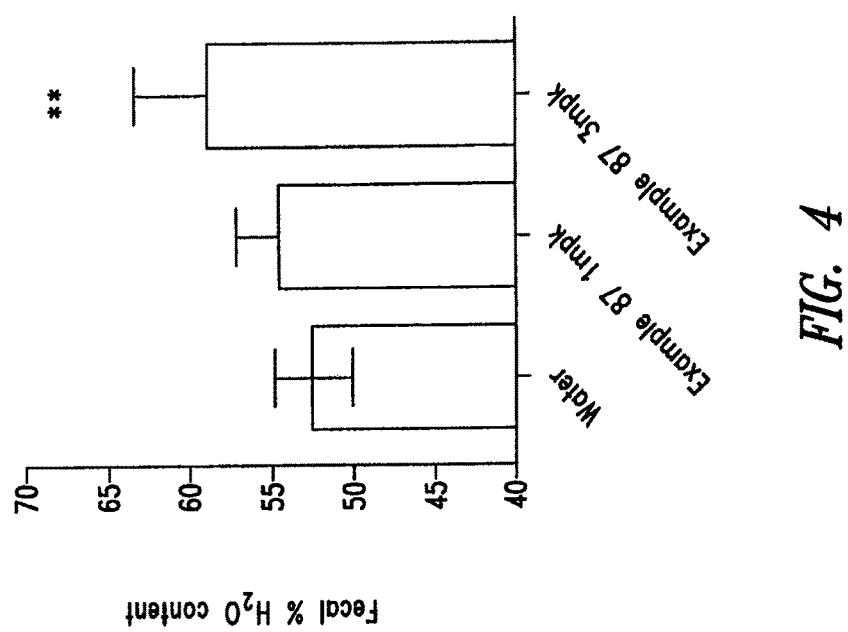
FIG. 4 is a graph that illustrates a dose dependent increase in fecal water content after administration of a certain example compound, as further discussed in the Examples (under the subheading "15. Pharmacological Test Example 15").

Pharmacodynamic Model: Dose Dependent Effect of Test Compound on Fecal Water Content Rats were monitored for fecal water content as in Example 13, and the test compound was administered at several dose levels to demonstrate a dose-response relationship. As shown in FIG. 4, in rats treated with increasing doses of the NHE-3 inhibitor tested (i.e., Example 87), the fecal water content increased significantly and dose dependently.

16. Pharmacological Test Example 16

Pharmacodynamic Model: Addition of a Fluid Absorbing Polymer to Chow

Figure 5A:
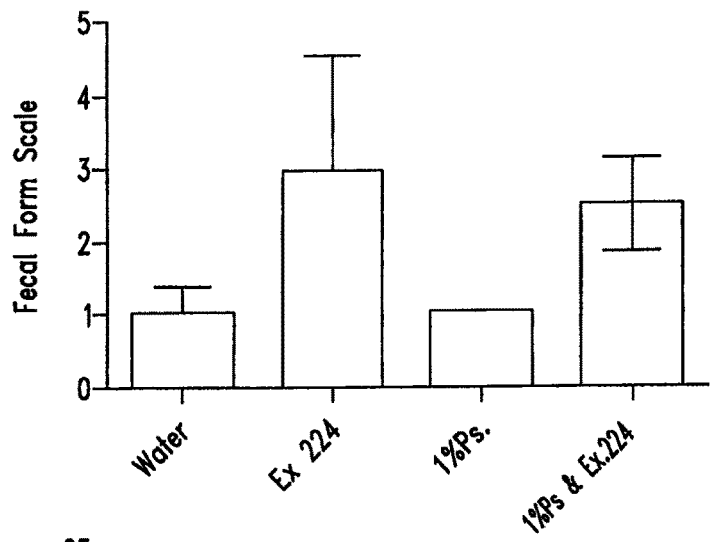
FIGS. 5A, 5B and 5C are graphs that illustrate that supplementing the diet with Psyllium results in a slight reduction of fecal stool form, but without impacting the ability of a certain example compound to increase fecal water content or decrease urinary sodium, as further discussed in the Examples (under the subheading "16. Pharmacological Test Example 16").
Figure 5B:
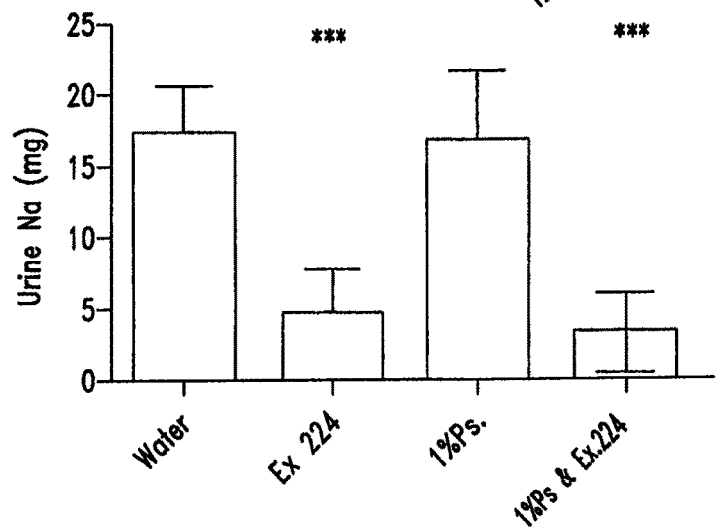
Figure 5C:
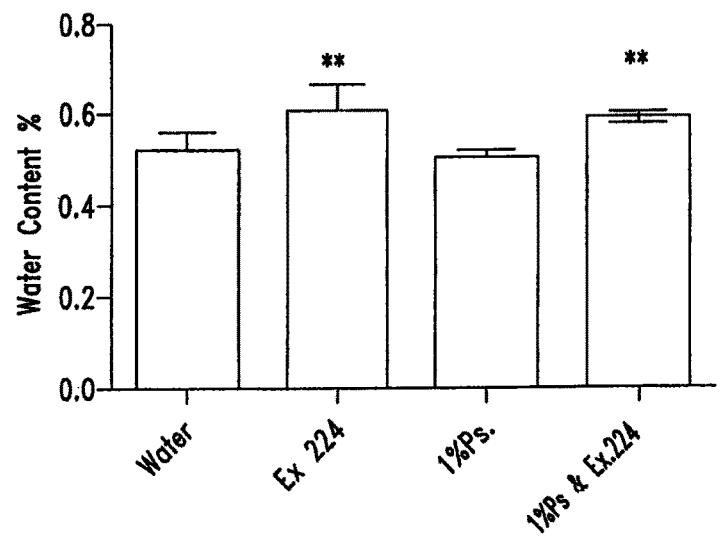

Rats were monitored for fecal water content as in Example 13, with the addition of a second group that were fed chow with the addition of 1% Psyllium to their diet. In addition to fecal water and urinary sodium, fecal form was monitored on a scale of 1-5, where 1 is a normal pellet, 3 indicates soft and unformed pellets, and 5 indicates watery feces. As shown in FIGS. 5A, 5B and 5C, supplementing the diet with Psyllium resulted in a slight reduction of fecal stool form, but without impacting the ability of the test compound (i.e., Example 224) to increase fecal water content or decrease urinary sodium.

17. Pharmacological Test Example 17

Pharmacodynamic Model: Effect of Test Compounds on Acute Stress-Induced Visceral Hypersensitivity in Female Wistar Rats Female Wistar rats weighing 220-250 g were prepared for electromyography. The animals were anaesthetized, and three pairs of nichrome wire electrodes were implanted bilaterally in the striated muscles at 3 cm laterally from the midline. The free ends of electrodes were exteriorised on the back of the neck and protected by a glass tube attached to the skin. Electromyographic recordings (EMG) were begun 5 days after surgery. The electrical activity of the abdominal striated muscles were recorded with an electromyograph machine (Mini VIII; Alvar, Paris, France) using a short time constant (0.03 sec.) to remove low-frequency signals (<3 Hz).

Partial restraint stress (PRS), a relatively mild stress, was performed as follows. Briefly, animals were lightly anaesthetized with ethyl-ether, and their freeholders, upper forelimbs and thoracic trunk were wrapped in a confining harness of paper tape to restrict, but not prevent their body movements and placed in their home cage for 2 hours. Control sham-stress animals were anaesthetized but not wrapped. PRS was performed between 10:00 and 12:00 AM.

Colorectal distension (CRD) was accomplished as follows: rats were placed in a plastic tunnel, where they were not allowed to move or escape daily during 3 consecutive days (3 h/day) before any CRD. The balloon used for distension was 4 cm in long and made from a latex condom inserted in the rectum at 1 cm of the anus and fixed at the tail. The balloon, connected to a barostat was inflated progressively by steps of 15 mmHg, from 0, 15, 45 and 60 mmHg, each step of inflation lasting 5 min. CRD was performed at T+2 h15 as a measure of PRS induced visceral hyperalgesia±test compound or vehicle. To determine the antinociceptive effect of test compounds on stress-induced visceral hypersensitivity, test compounds were administered 1 h before CRD in 6 groups of 8 female rats. For each parameter studied (the number of abdominal contractions for each 5-min period during rectal distension) data is expressed as mean±SEM. Comparisons between the different treatments were performed using an analysis of variance (ANOVA) followed by a Dunnett post test. The criterion for statistical significance is $p<0.05$.

Figure 6:
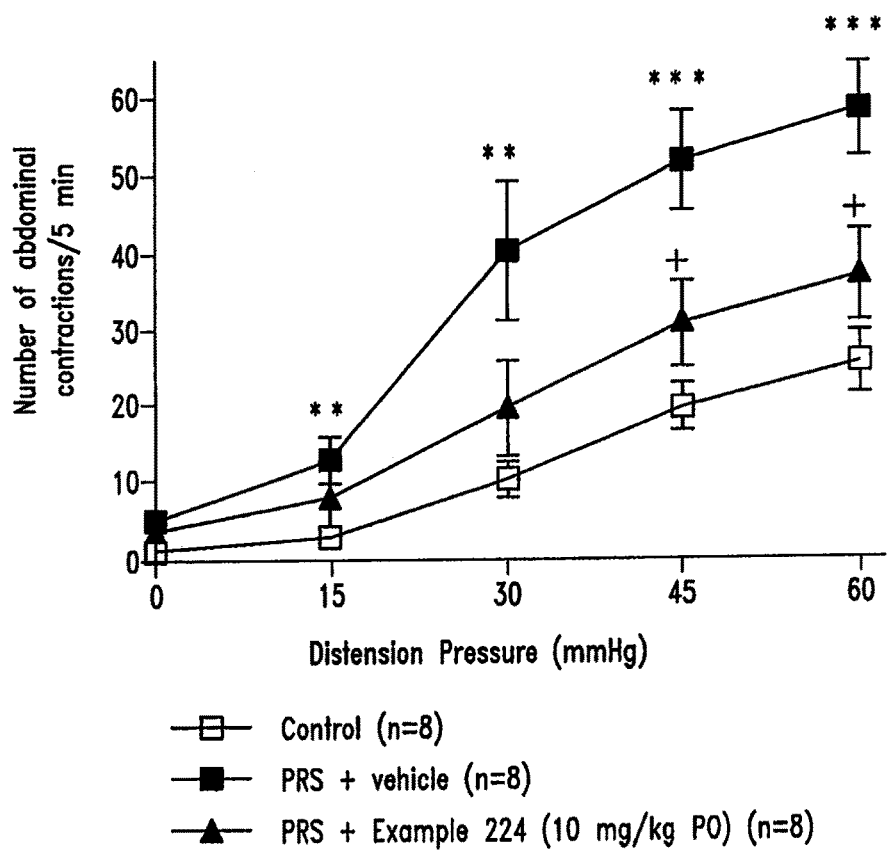
FIG. 6 is a graph that illustrates that inhibition of NHE-3 reduces hypersensitivity to distention, as further discussed in the Examples (under the subheading "17. Pharmacological Test Example 17").

FIG. 6 shows the results of this test using the compound illustrated in Example 224 dosed orally at 10 mg/kg, and shows that at 45 and 60 mm Hg, inhibition of NHE-3 in rats surprisingly reduces visceral hypersensitivity to distension ($p<0.05$).

18. Pharmacological Test Example 18

Pharmacodynamic Model: Effect of Test Compounds on Fecal Sodium Levels

Figure 7B:
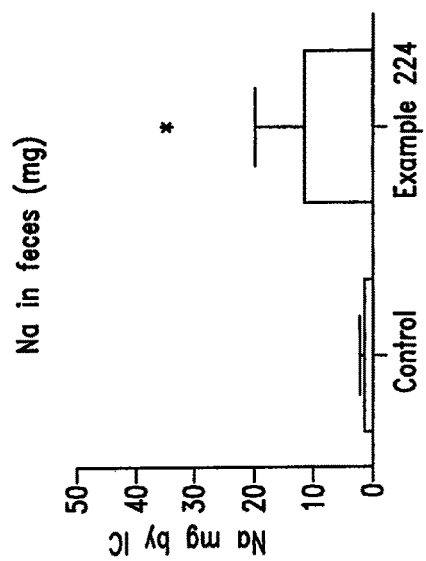
FIGS. 7A and 7B are graphs that illustrate that inhibition of NHE-3 increases the amount of sodium excreted in feces, as further discussed in the Examples (under subheading "18. Pharmacological Test Example 18").
Figure 7A:
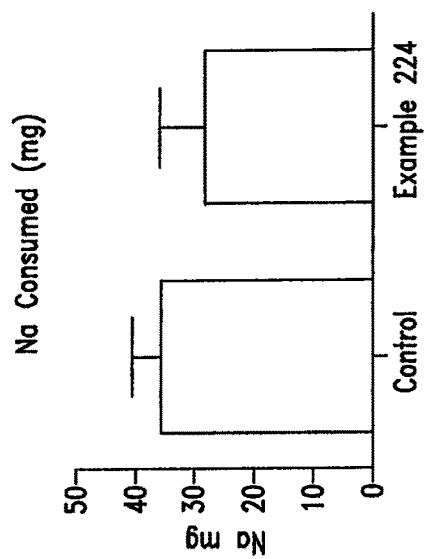

It is anticipated that the reduction of absorption of sodium from the intestine will be reflected in increase levels of sodium in the feces. To test this, the protocols in Example 13 were repeated. After drying of feces to determine water content, 1M HCl was added to dried ground feces to a concentration of 50 mg/mL and extracted at room temperature on rotator for 5 days. Sodium content was analyzed by ion chromatography (IC). As shown in FIGS. 7A and 7B for Example 224, in rats treated with an NHE-3 inhibitor, the amount of sodium excreted in the feces significantly ($p<0.05$ by t-test).

19. Pharmacological Test Example 19

Determination of Compound Remaining in Feces

Sprague-Dawley rats were orally gavaged with test article. A low dose of compound (0.1 mg/kg) was selected so that feces would remain solid and practical to collect. For both Examples 202 and 203, three rats were dosed, and following dosage of compounds, the rats were placed in metabolic cages for 72 hours. After 72 hours, fecal samples were recovered and dried for 48 hours. Dried fecal samples were ground to a powdered from, and for each rat, 10 replicates of 50 mg samples were extracted with acetonitrile. Insoluble materials were removed by centrifugation and supernatants analyzed by LC/MS/MS and compared against a standard curve to determine compound concentration. The amount of compound actually dosed was determined by LC/MS/MS analysis of the dosing solutions. The total amount of compound present in the 72-hour fecal samples was compared to the total amount of compound dosed, and reported as percentage of total dose recovered. The results, shown in Table 12, demonstrate near quantitative recovery of Examples 202 and 203 in 72-hour fecal samples.

TABLE 12

Recovery of dosed compounds from 72-hour fecal samples

| | % Recovery ± SD | |
|---|---|---|
| | Example 202 | Example 203 |
| Rat 1 | 93.8 ± 11.8 | 100.3 ± 6.7 |
| Rat 2 | 90.5 ± 5.5 | 75.8 ± 8.2 |
| Rat 3 | 92.4 ± 10.6 | 104.4 ± 7.1 |

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for treating irritable bowel syndrome in a subject in need thereof comprising administering a compound, or a pharmaceutically acceptable salt thereof, wherein the compound has the following structure (X):

$$\text{Core-(-L-NHE)}_n \qquad (X)$$

wherein:
n is 2;
NHE has the structure

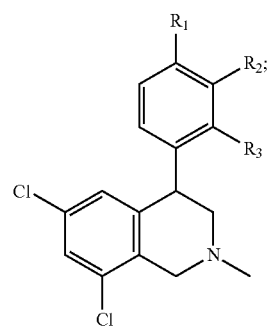

wherein:
$R^1$ is H or —SO2-$NR_7R_8$—;
$R^2$ is selected from H, —$NR_7$(CO)$R_8$, —$SO_2$—$NR_7R_8$— and —$NR_7R_8$;

R³ is hydrogen;
R⁷ is hydrogen;
R⁸ is a bond linking to L;
L is a polyalkylene glycol linker; and
Core has the following structure:

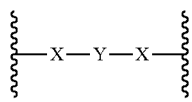

wherein:
X is selected from the group consisting of a bond, —O—, —NH—, NHC(=O)—, —NHC(=O)NH—, and —NHSO₂—;
Y is selected from the group consisting of a bond, optionally substituted $C_{1-6}$ alkylene, optionally substituted phenyl, pyridinyl, a polyethylene glycol linker and —(CH₂)$_{1-6}$O(CH₂)$_{1-6}$—.

2. A method of claim 1, wherein the NHE has one of the following structures:

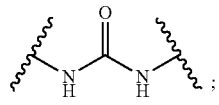 or

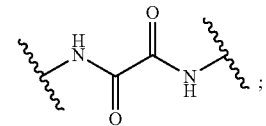

or pharmaceutically acceptable salt thereof.

3. The method of claim 1, or a pharmaceutically acceptable salt thereof, wherein L is a polyethylene glycol linker.

4. The method of claim 1, or a pharmaceutically acceptable salt thereof, wherein the Core is selected from the group consisting of:

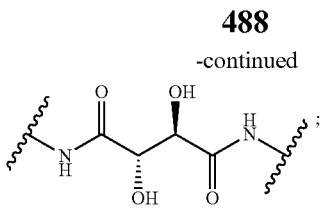

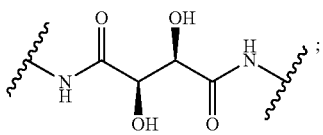

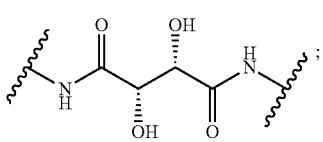

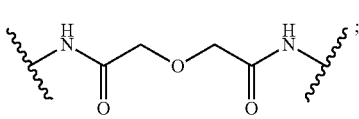

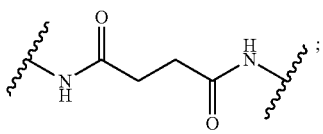

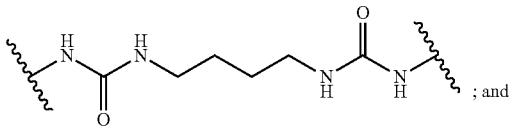; and

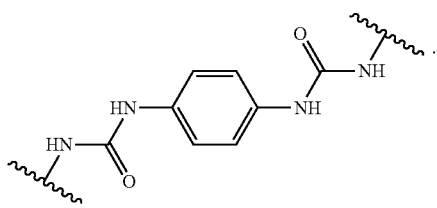

5. The method of claim 1, wherein the compound is selected from:
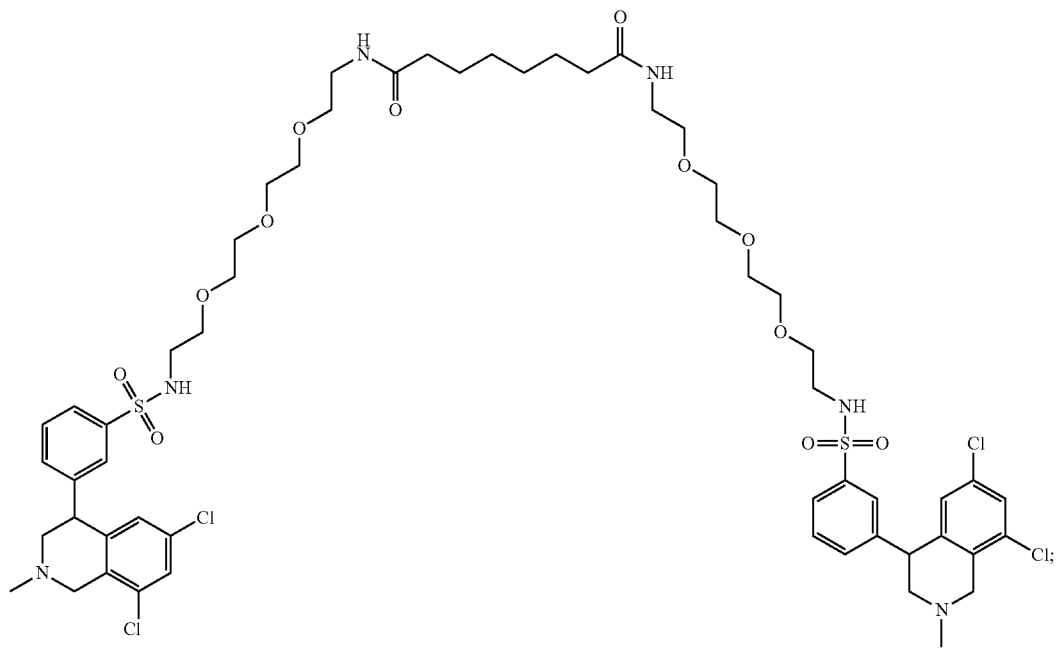
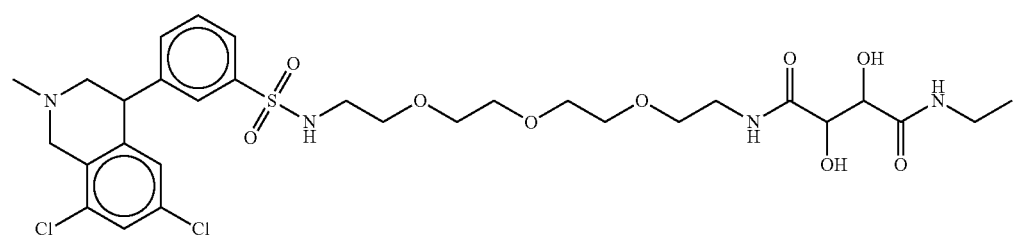
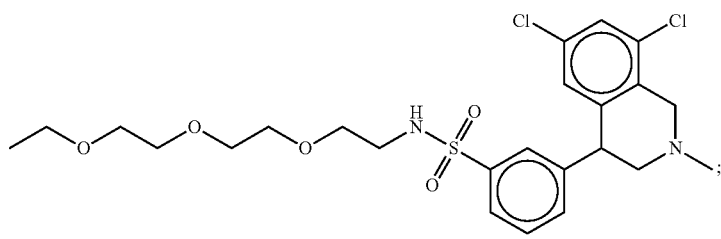
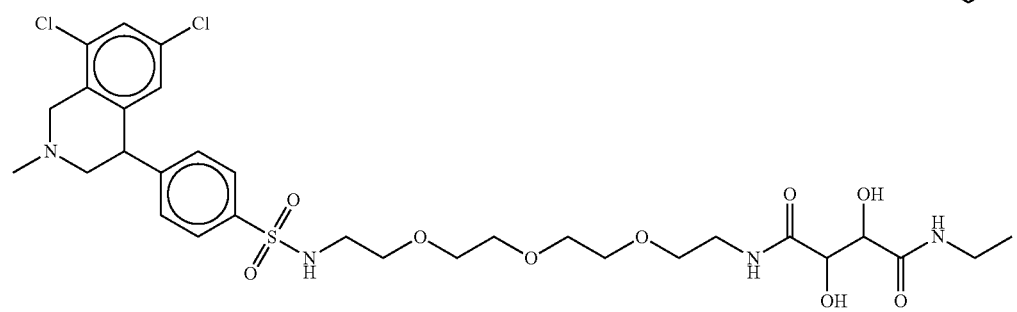

491 492
-continued
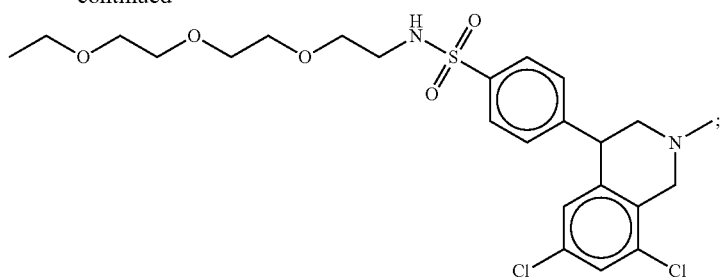
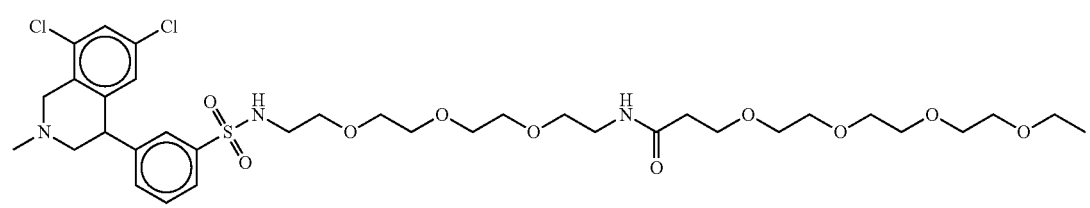
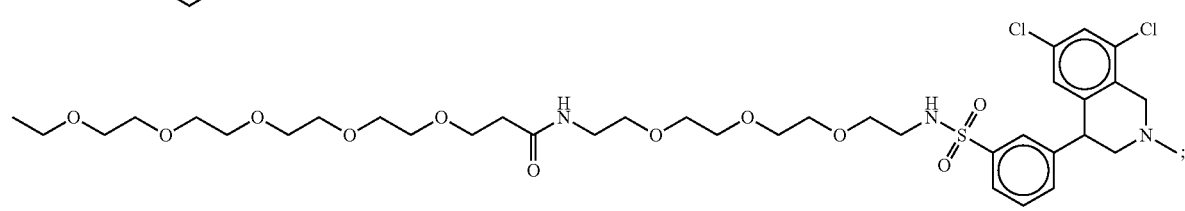
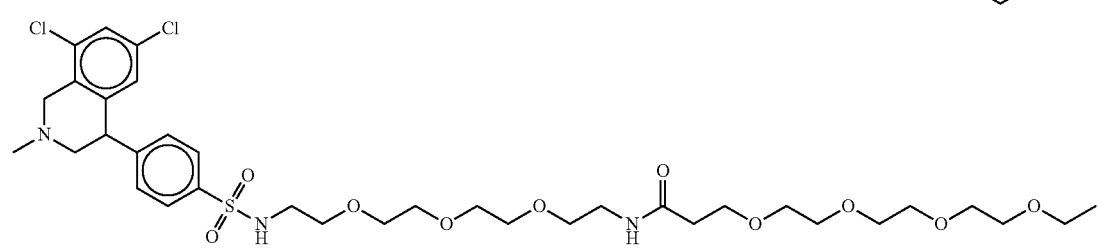
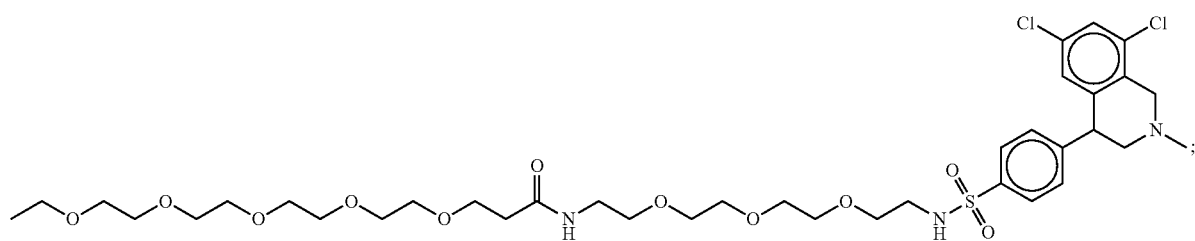
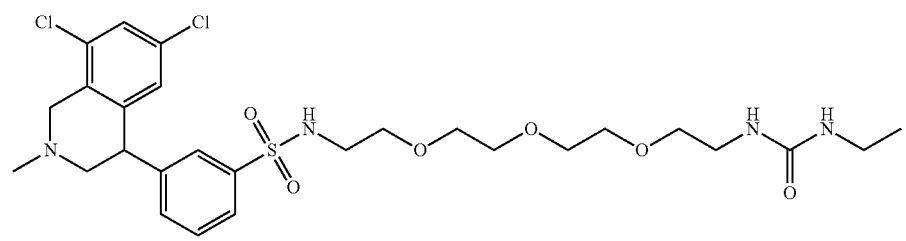
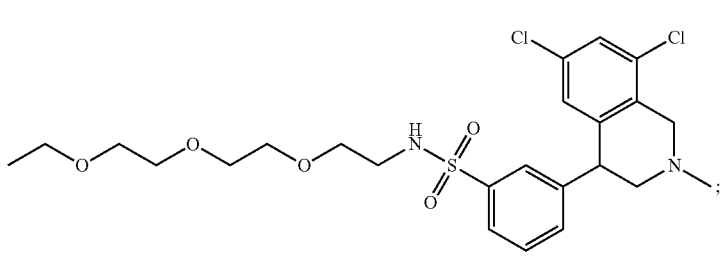

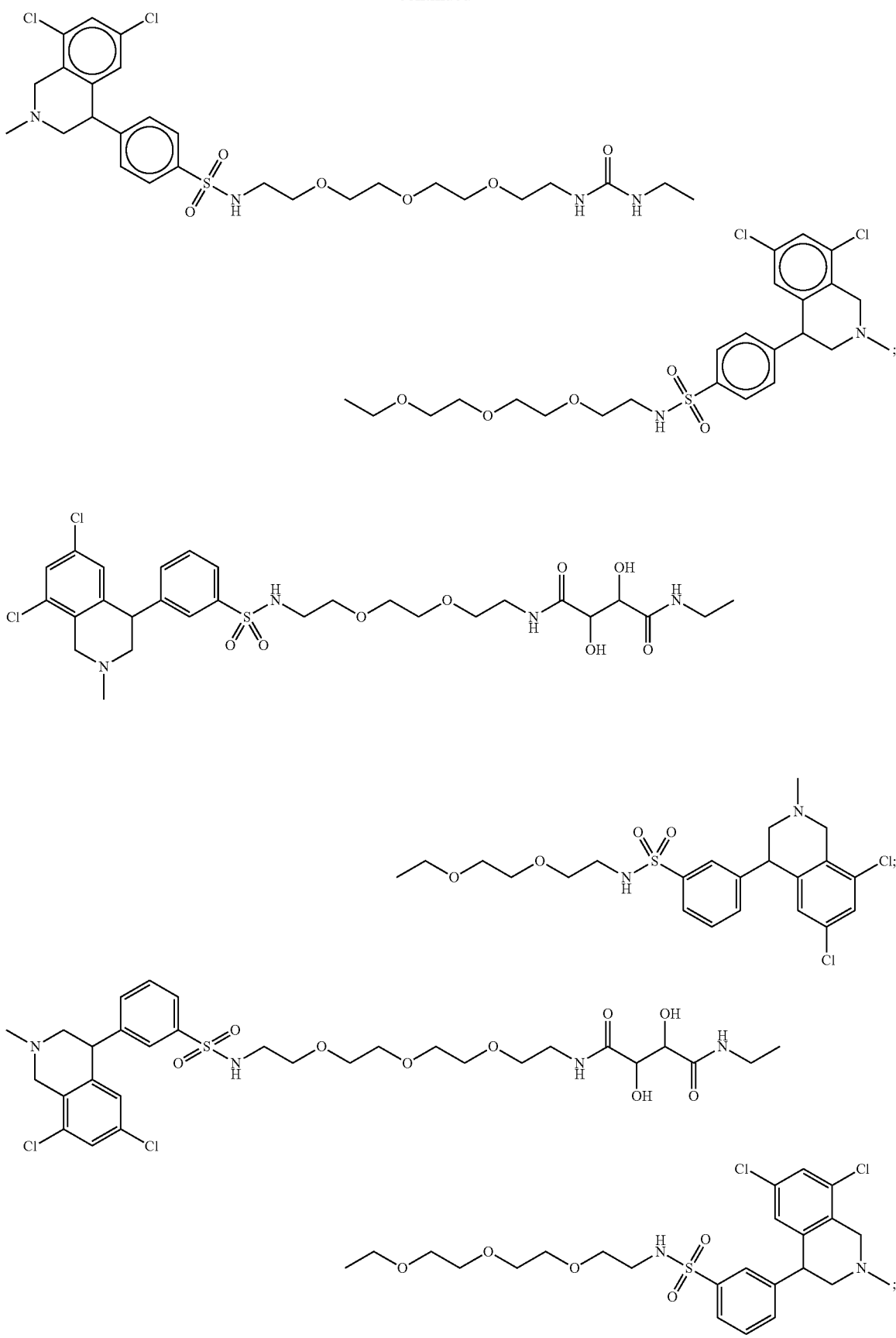

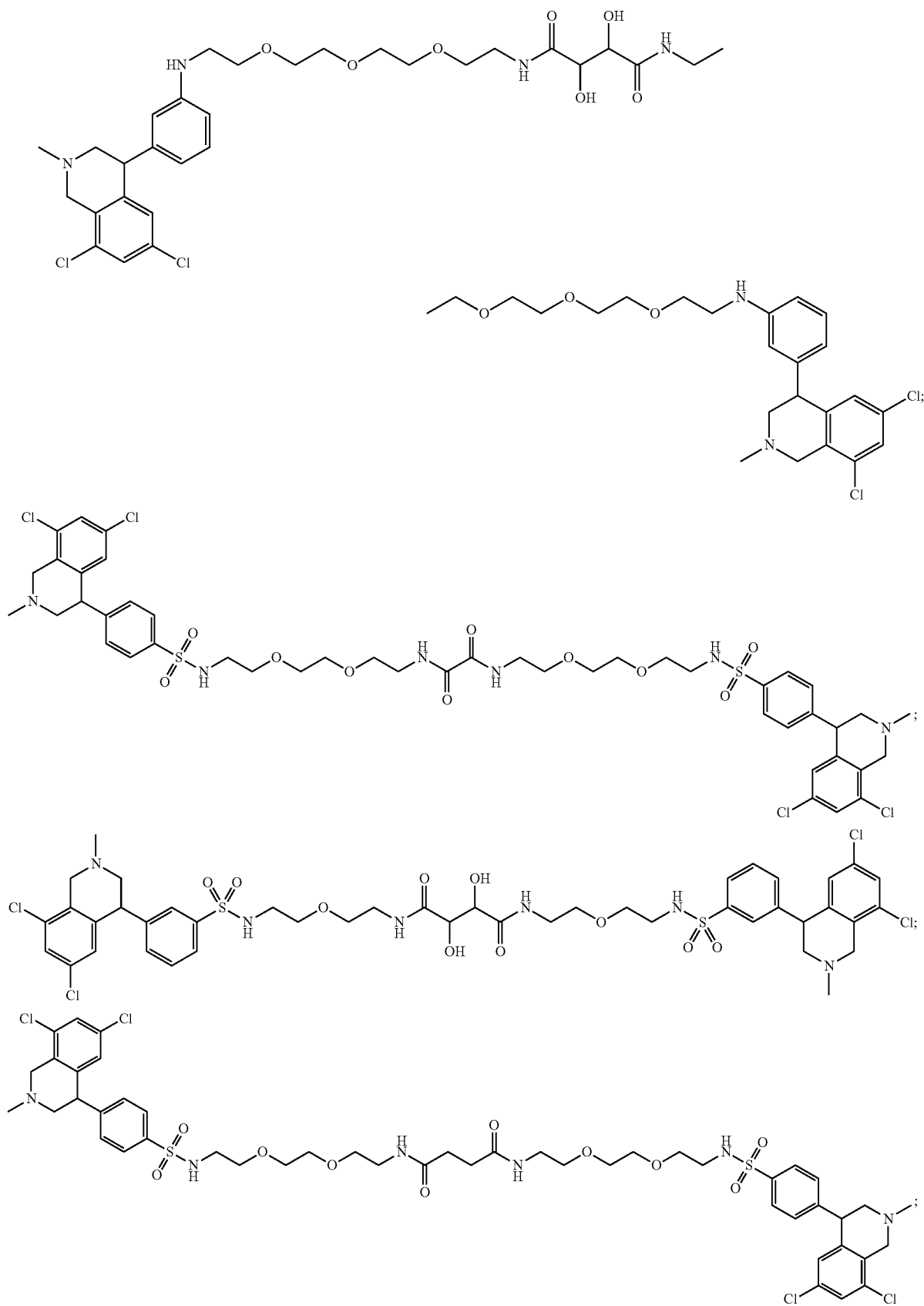

497 498
-continued
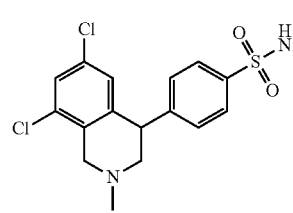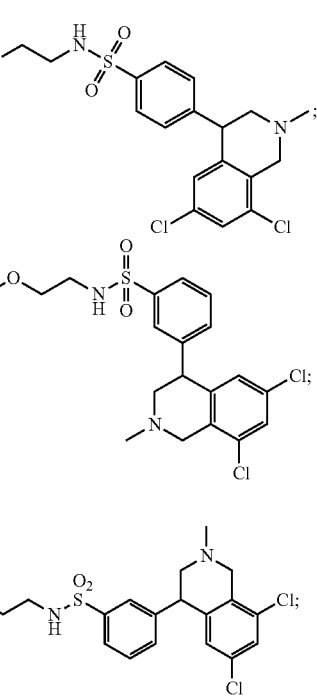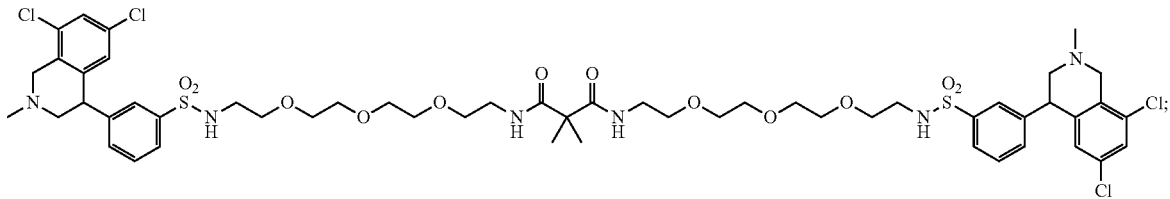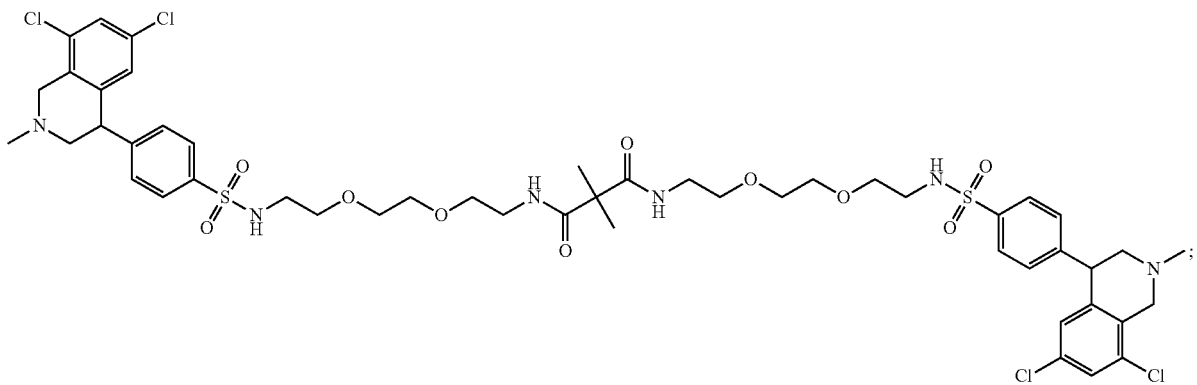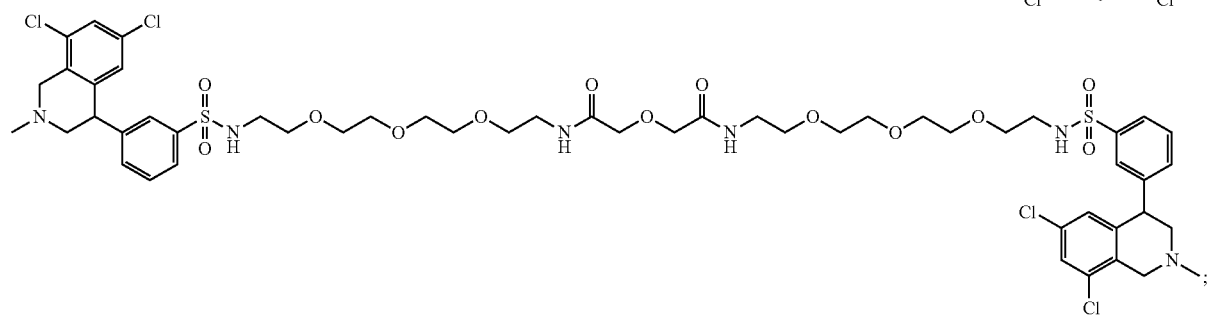

499 500
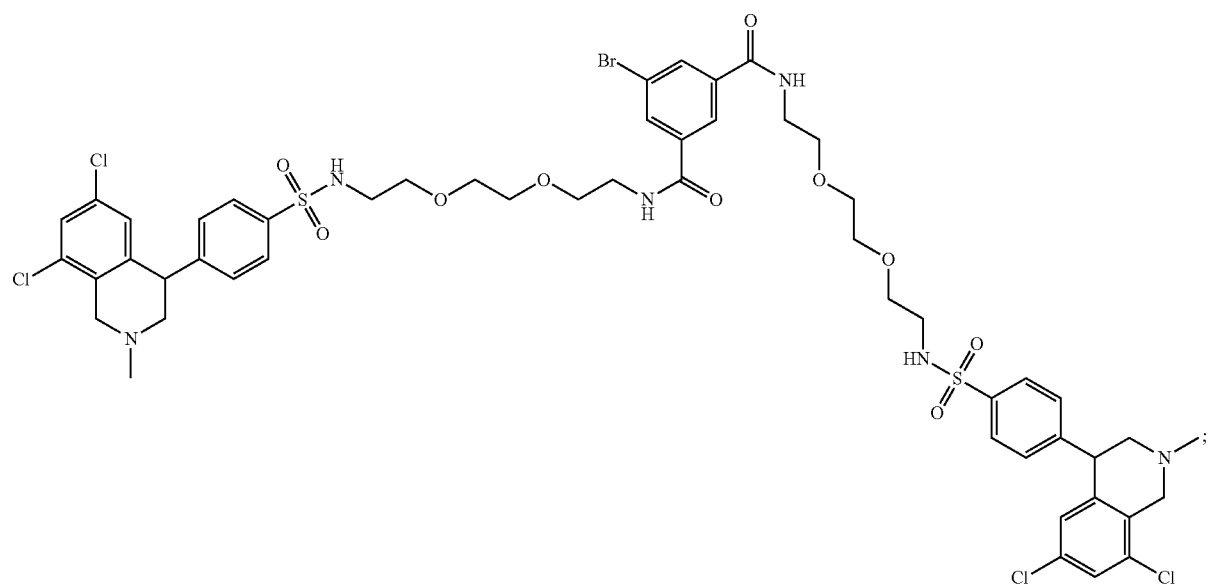
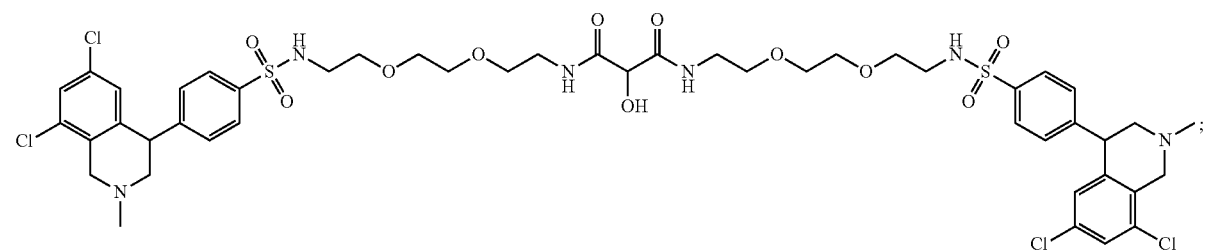
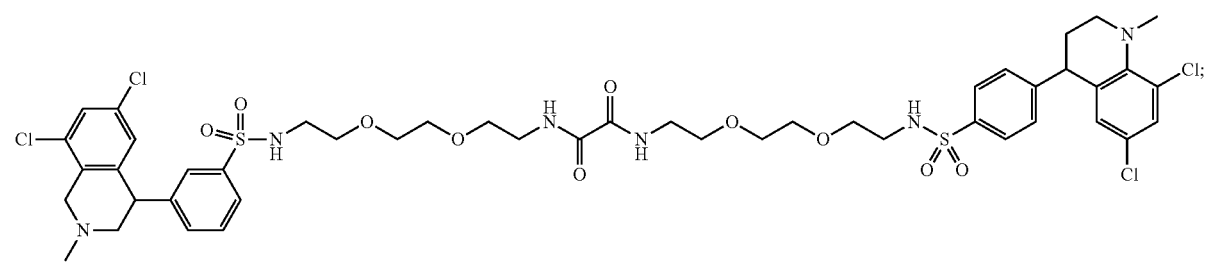
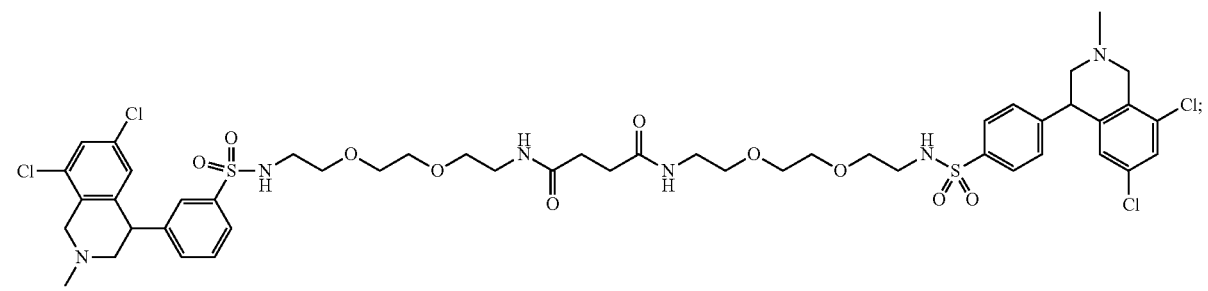

-continued
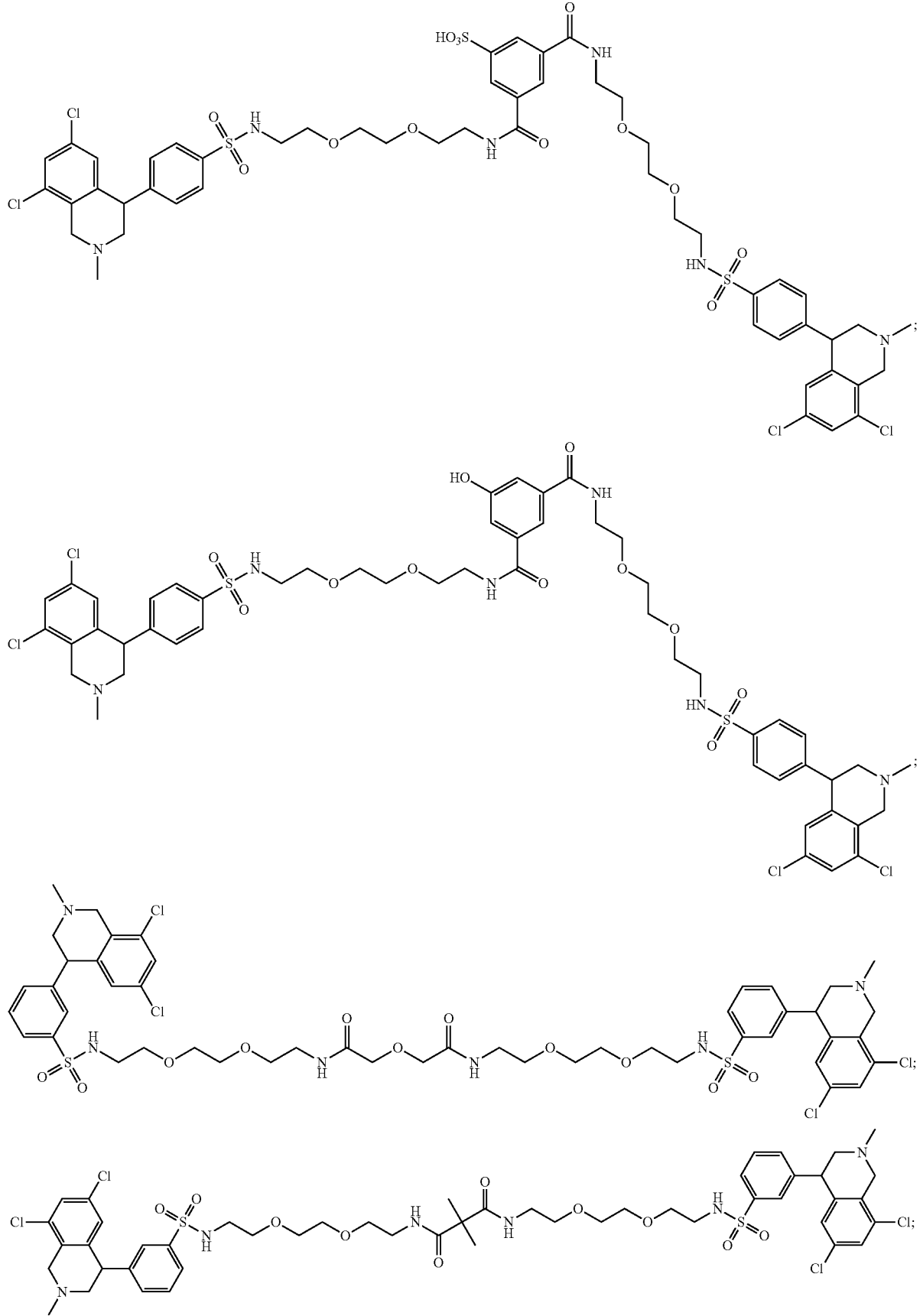

503                                                                                       504
-continued
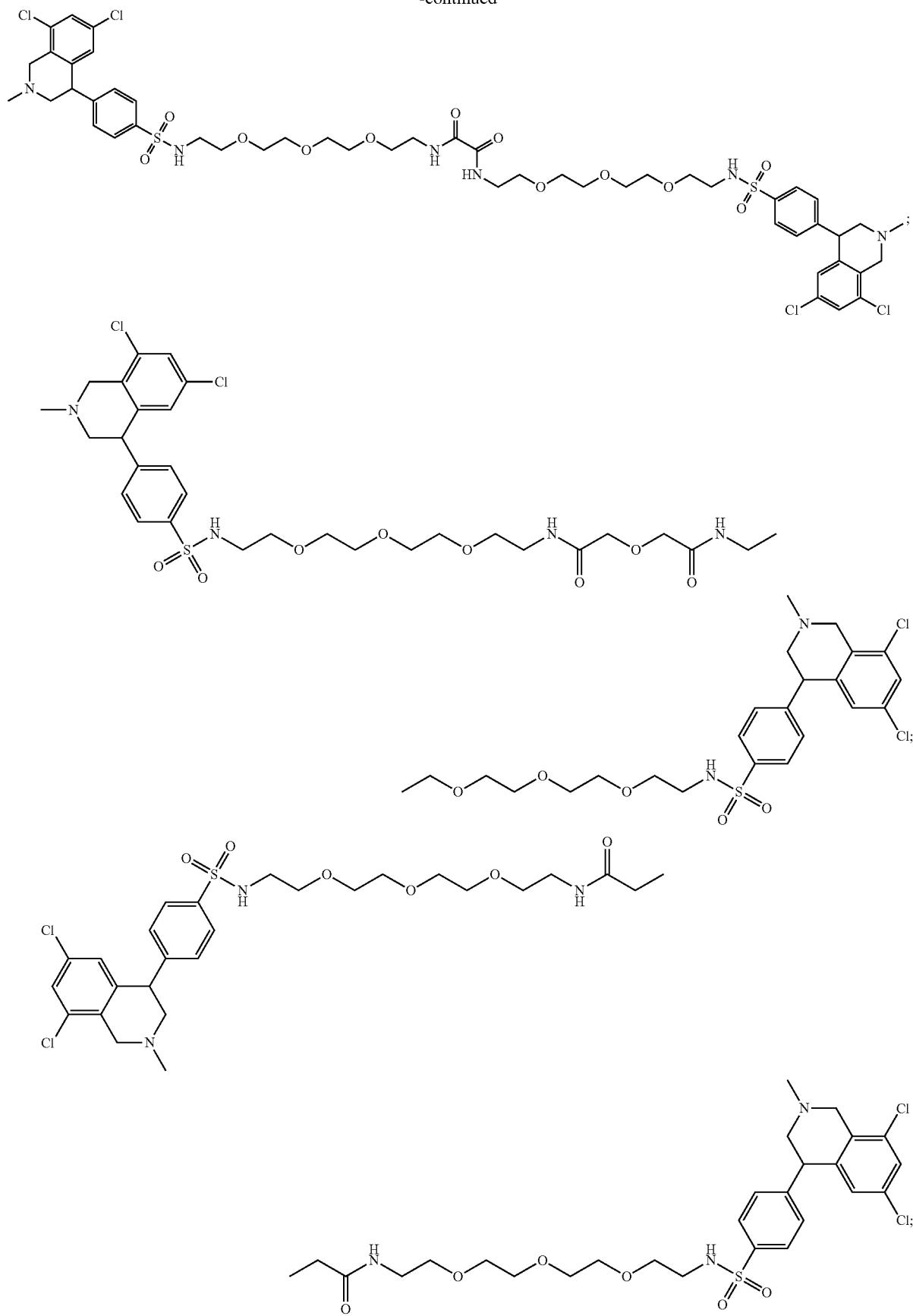

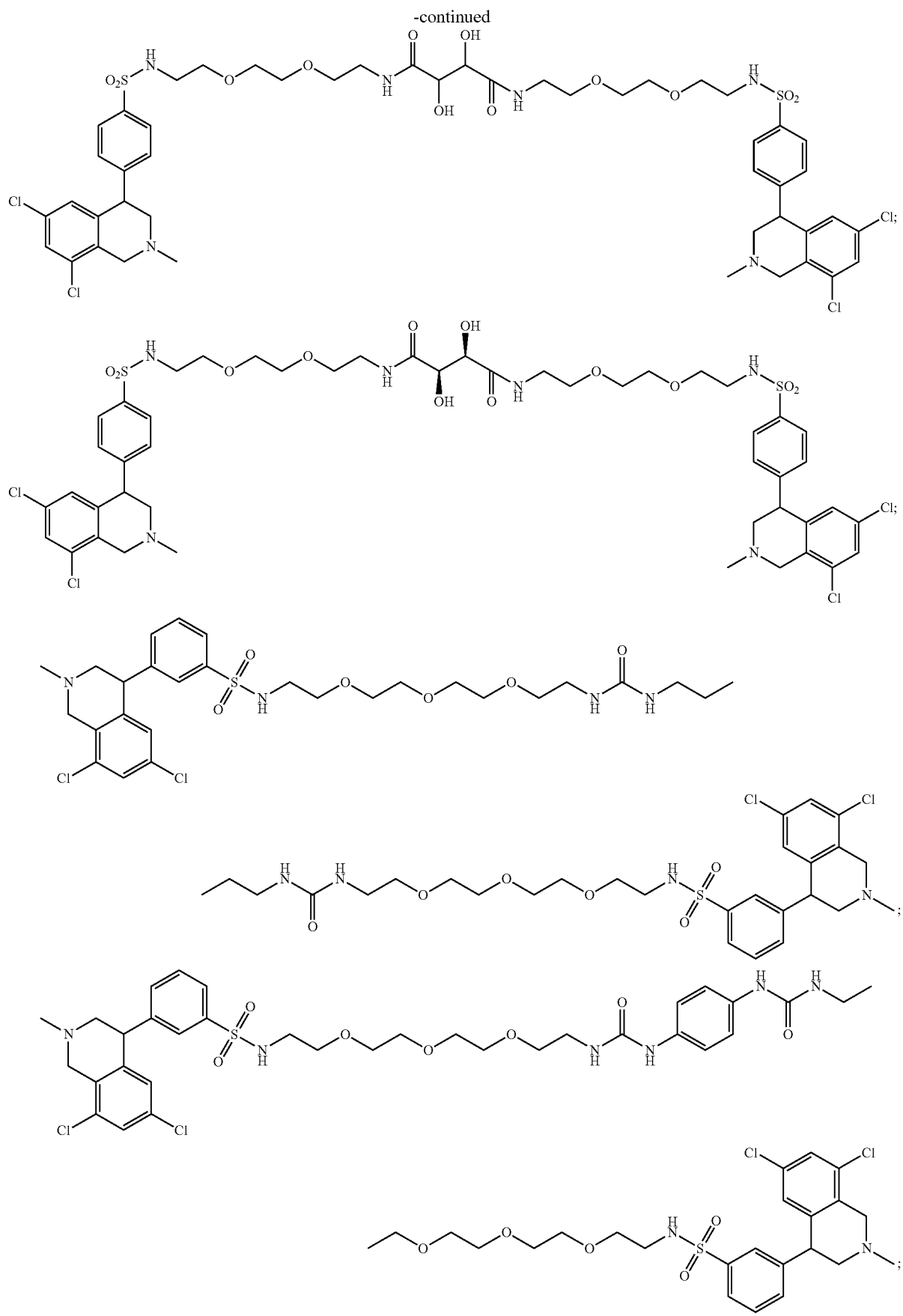

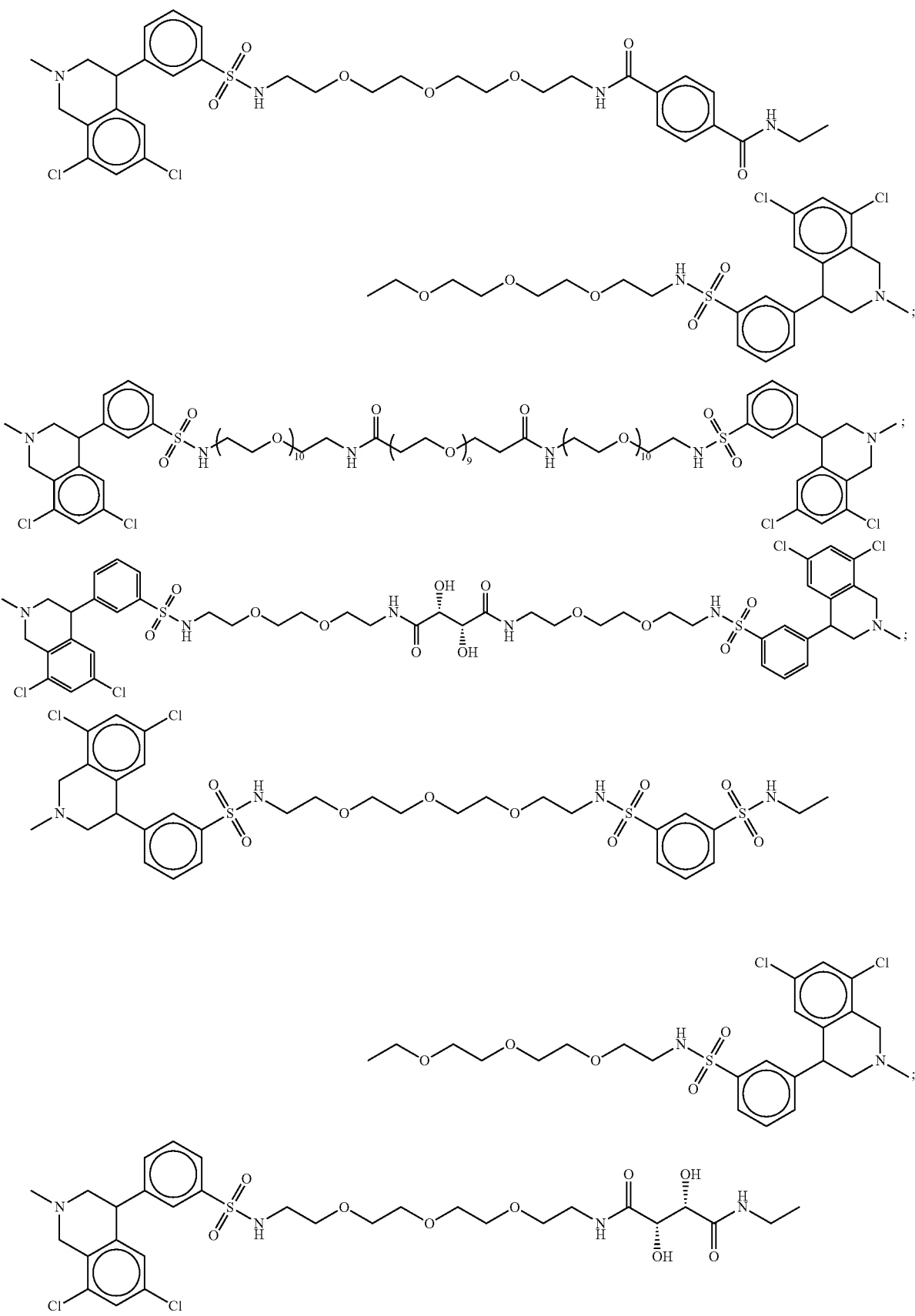

-continued
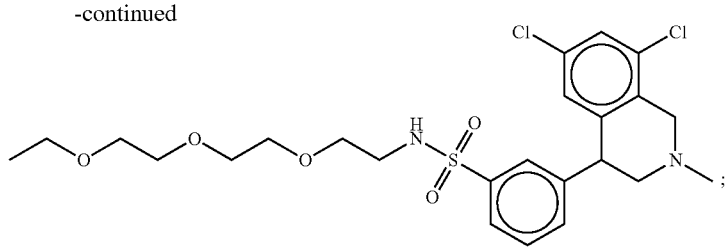
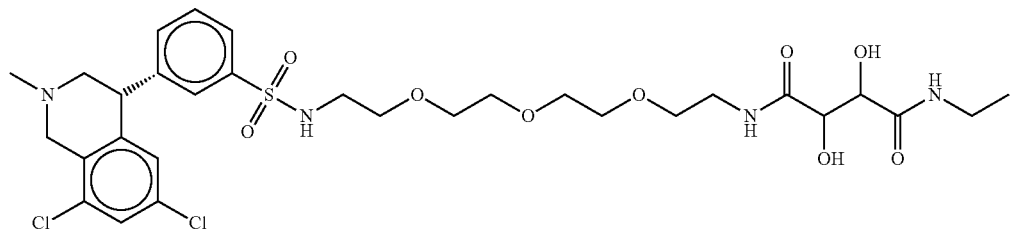
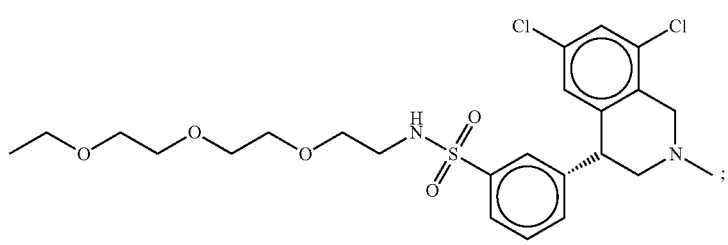
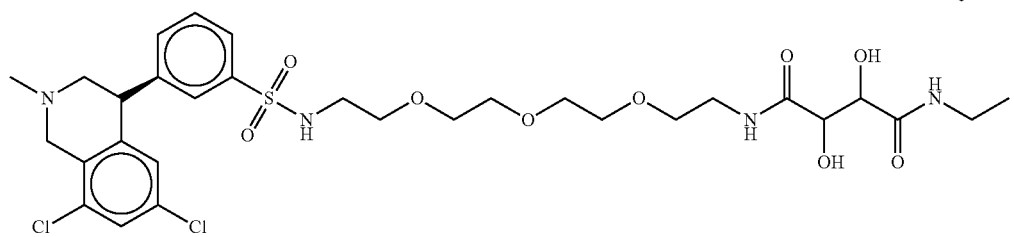
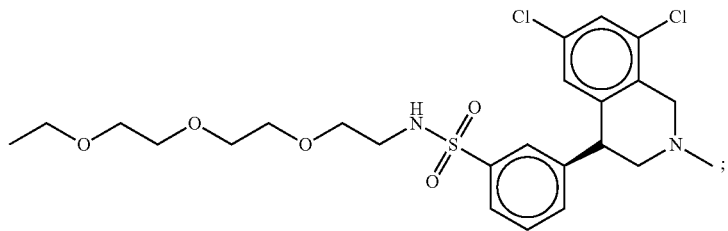
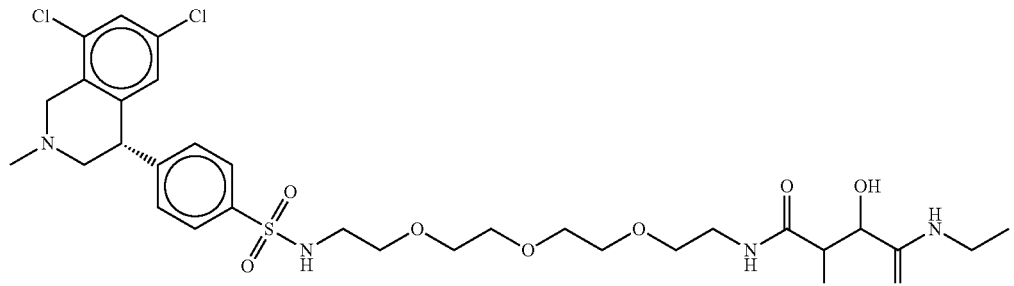
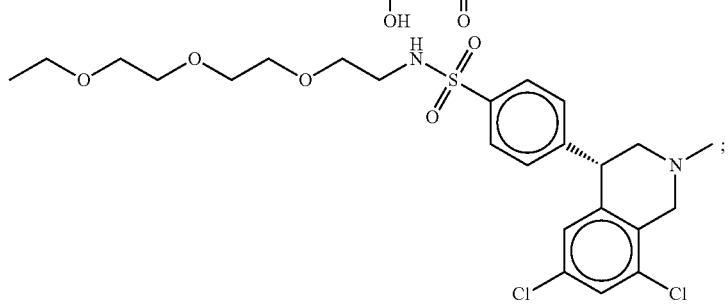

511 512
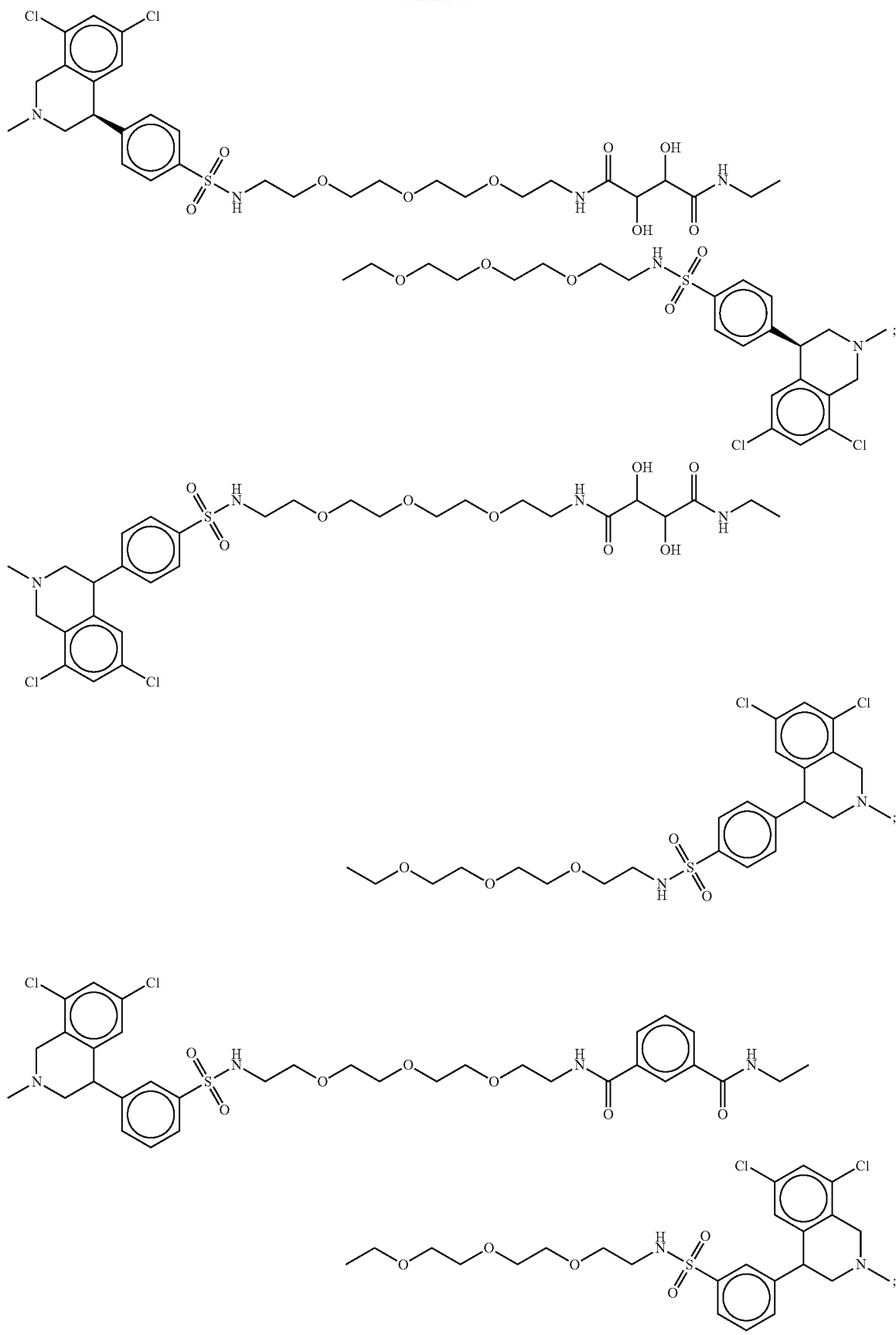

513   514
-continued
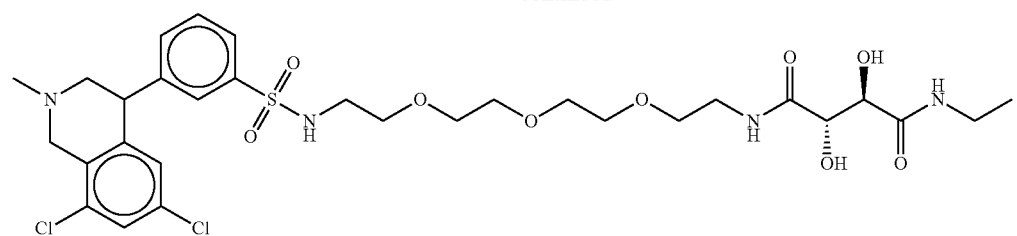
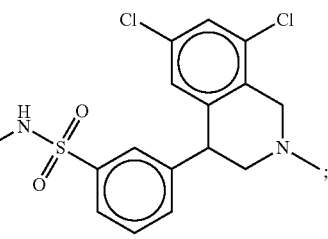
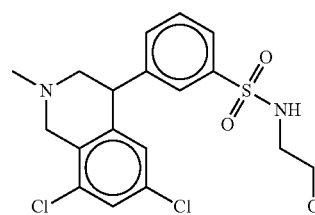
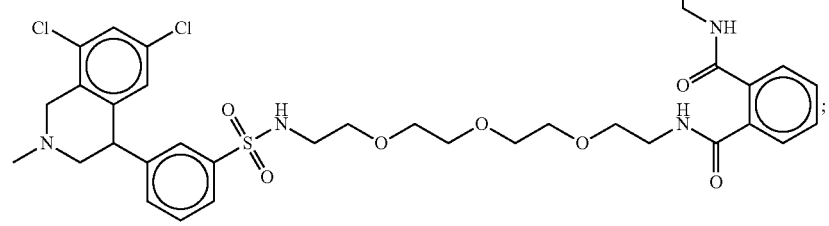
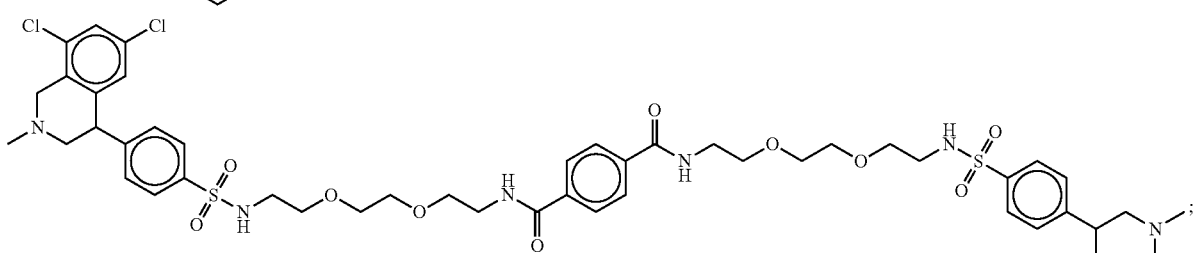
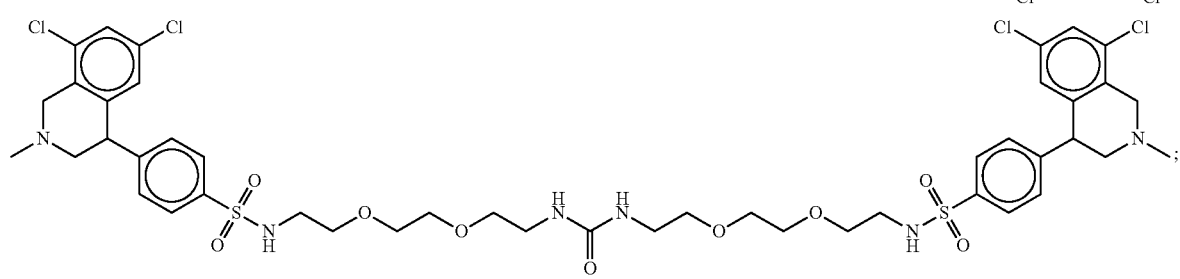

515 516
-continued
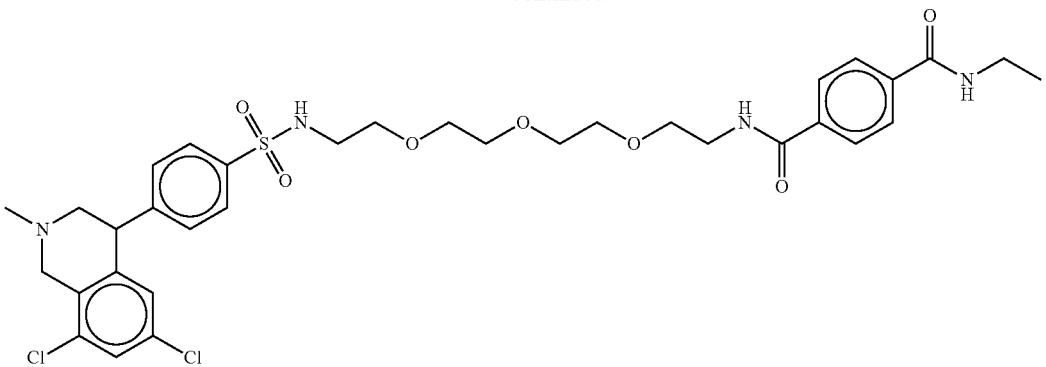
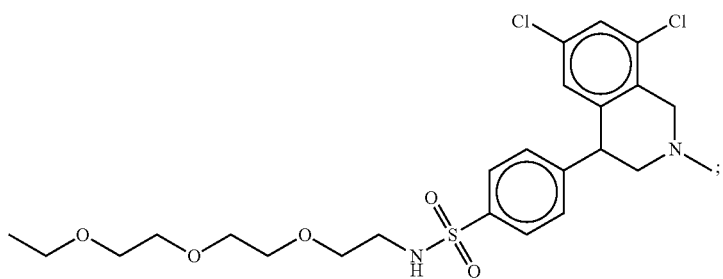
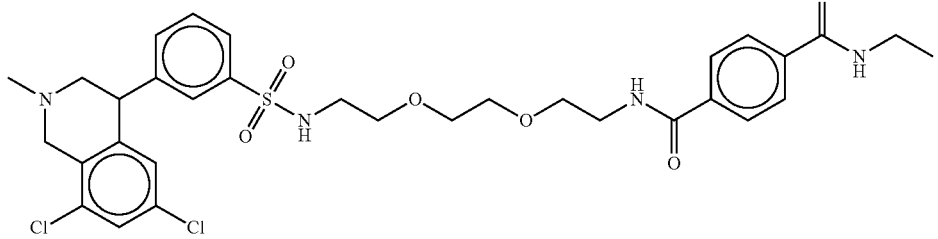
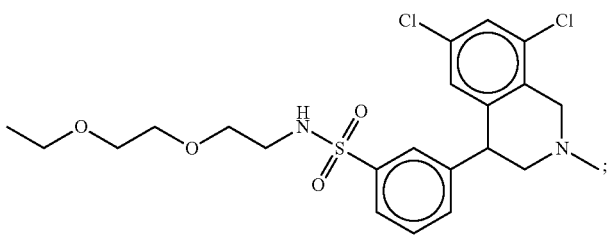
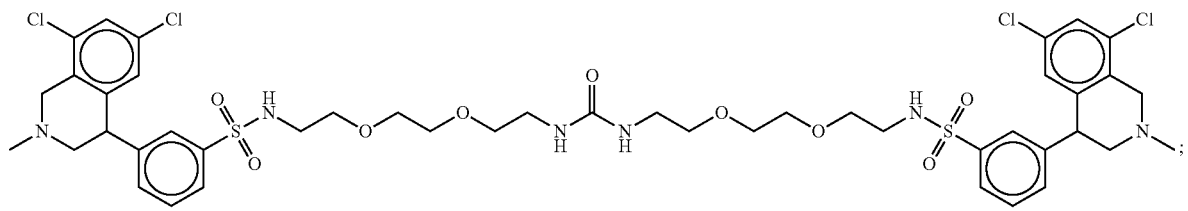
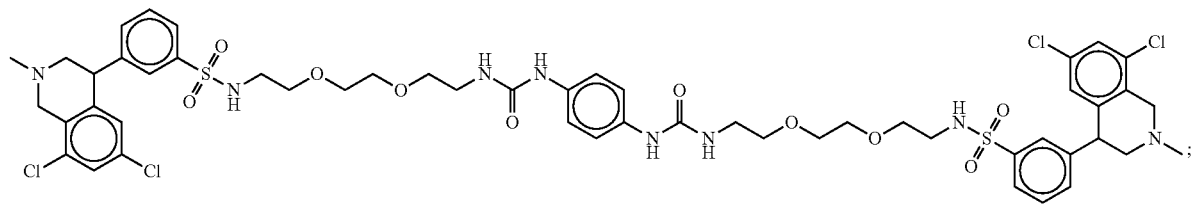

517                                   518
-continued
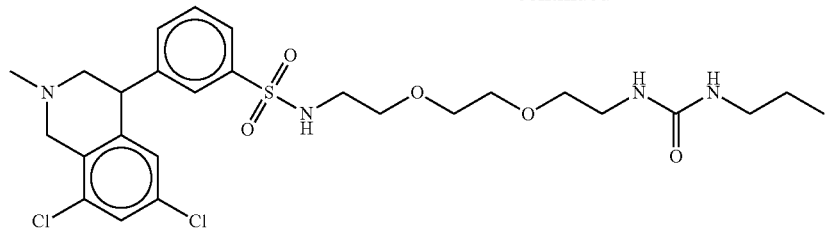
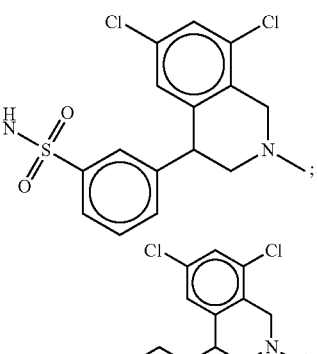
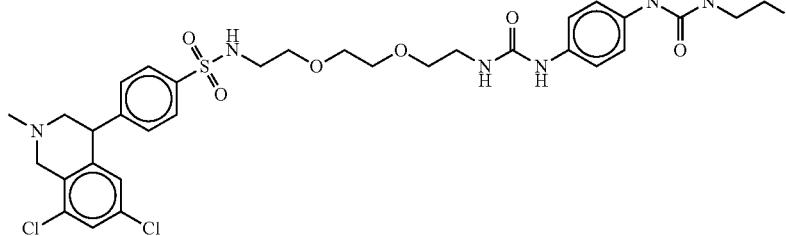
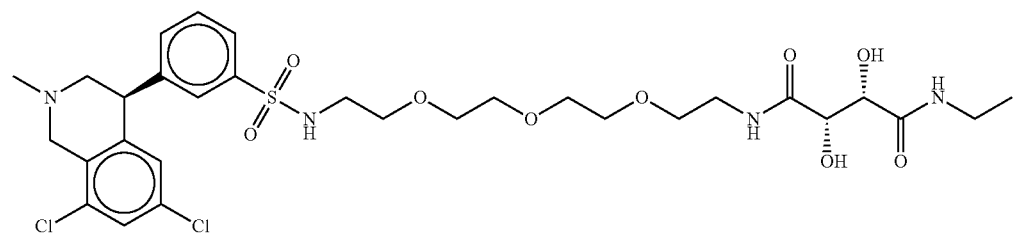
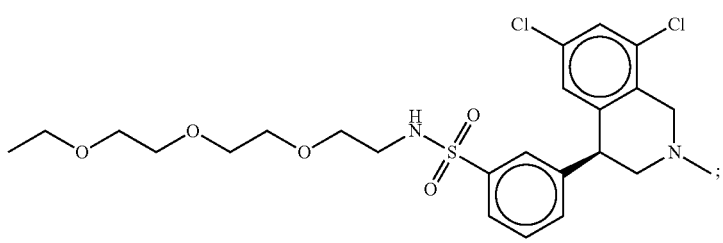
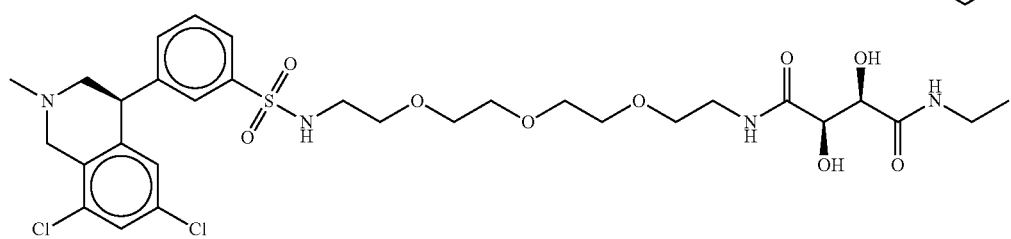

-continued
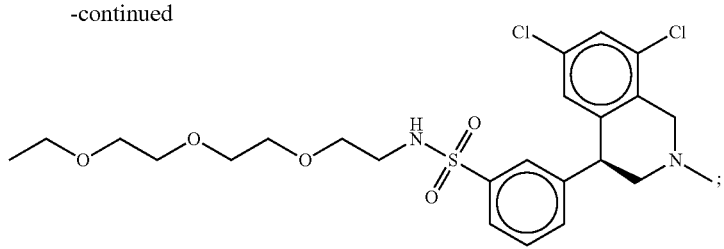
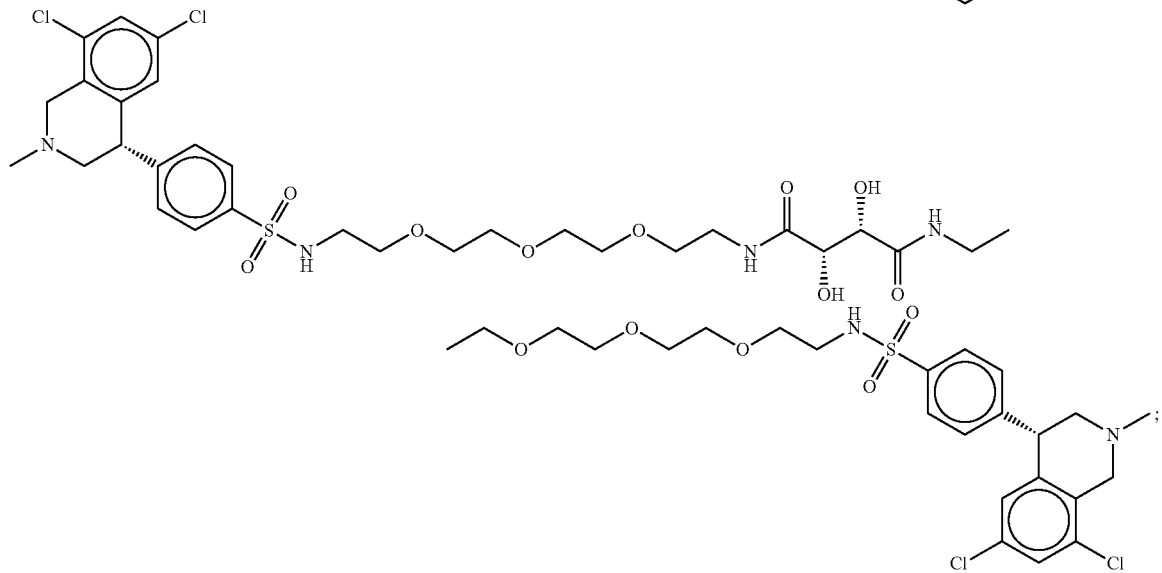
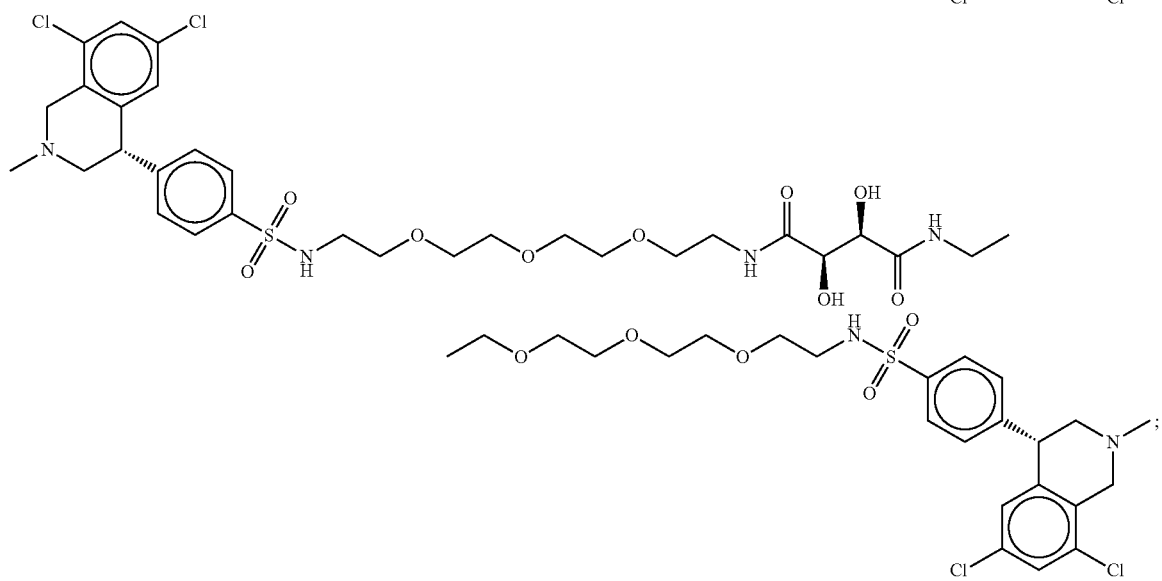
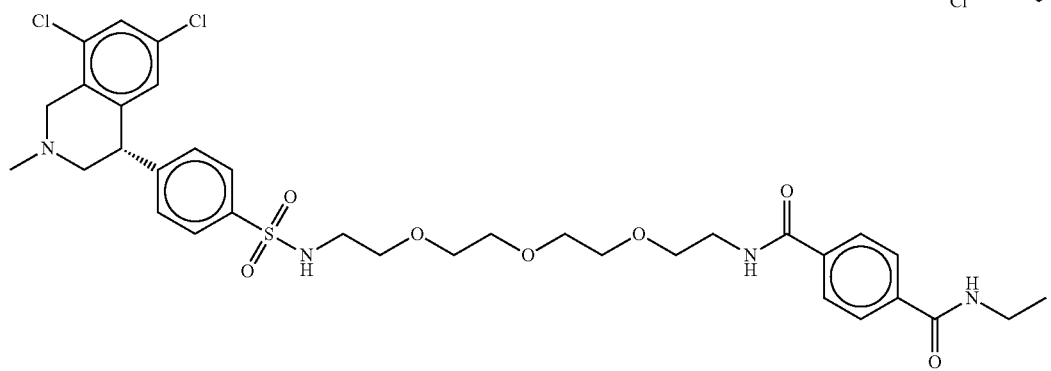

-continued
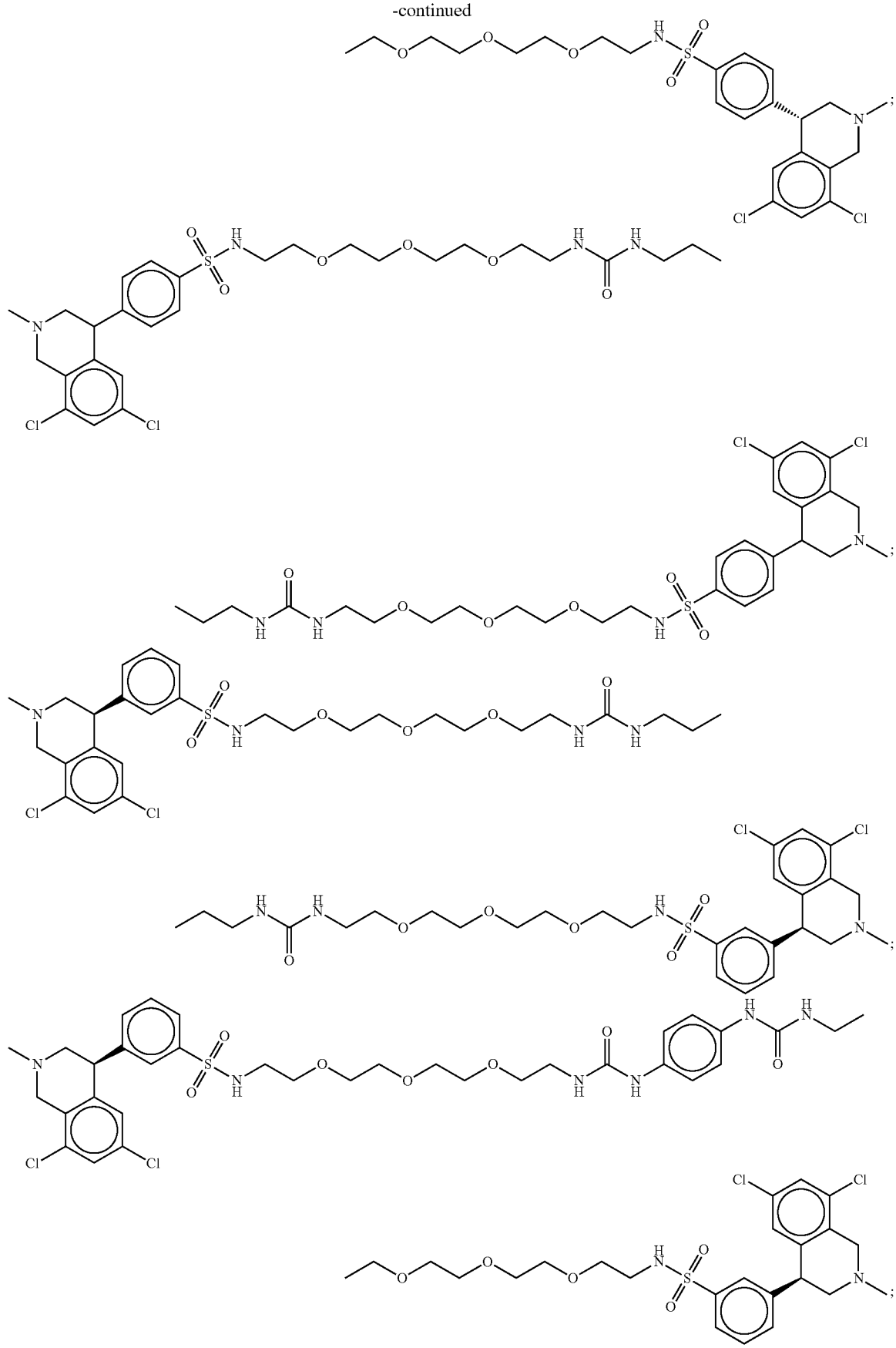

-continued
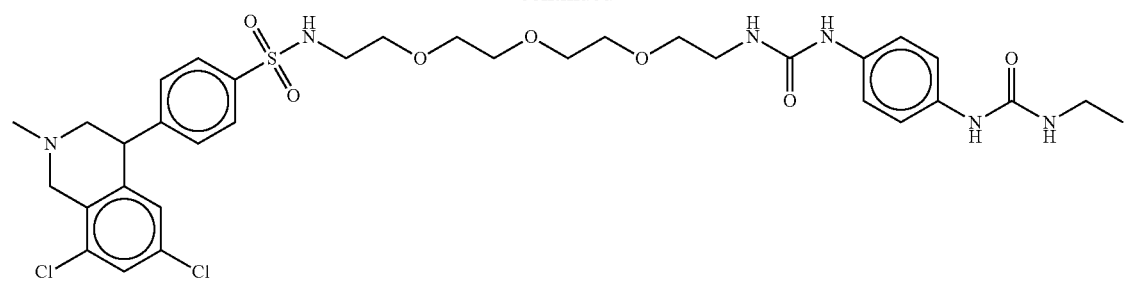
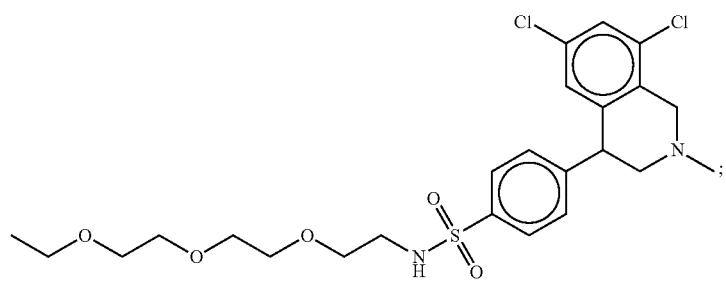
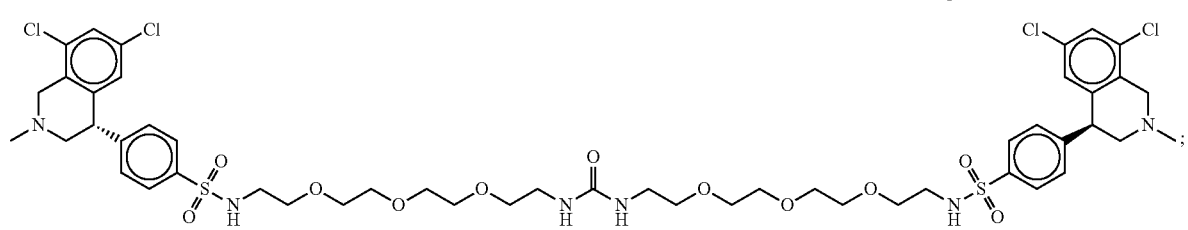
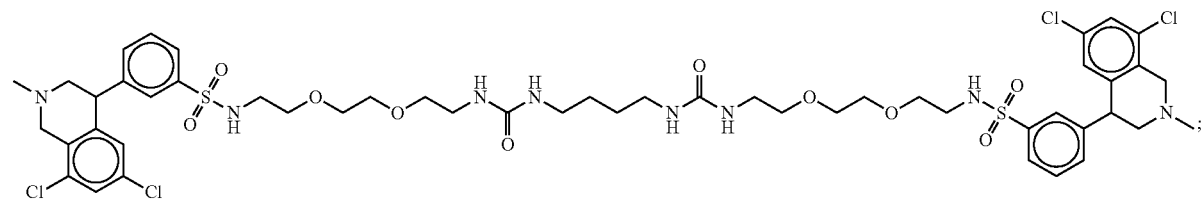
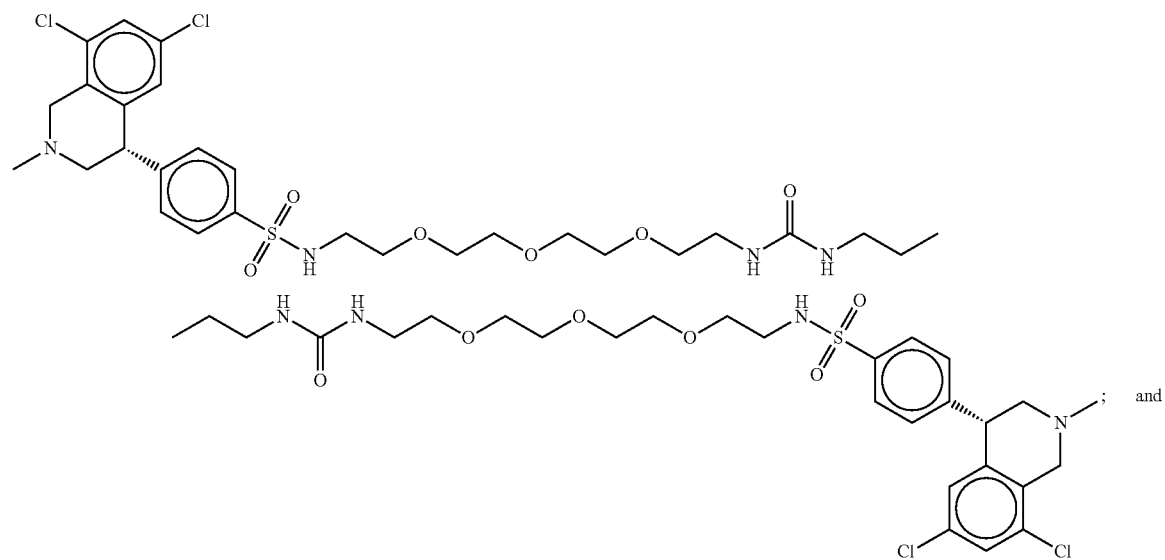

-continued
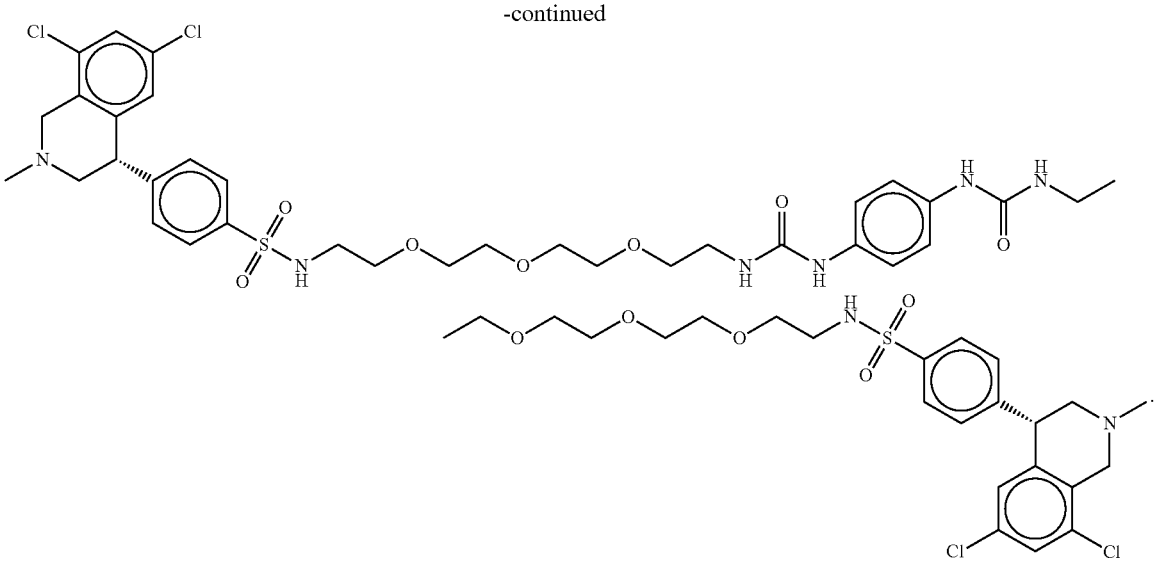
6. The method of claim 1, wherein the pharmaceutically acceptable salt is selected from:
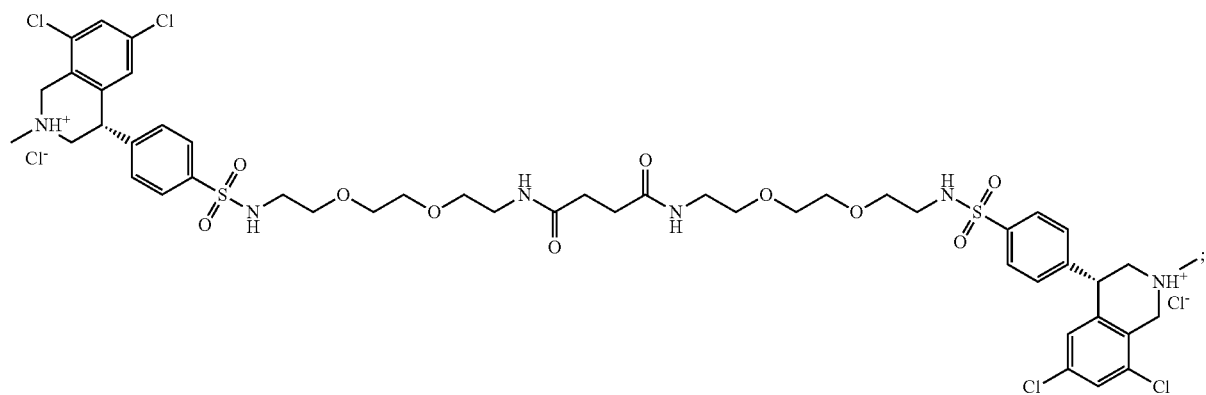
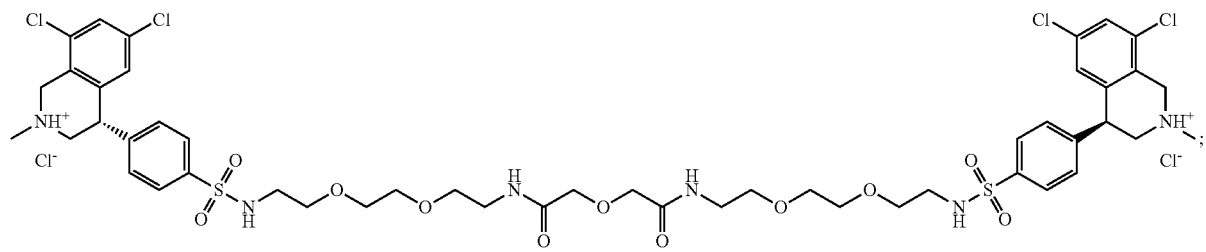
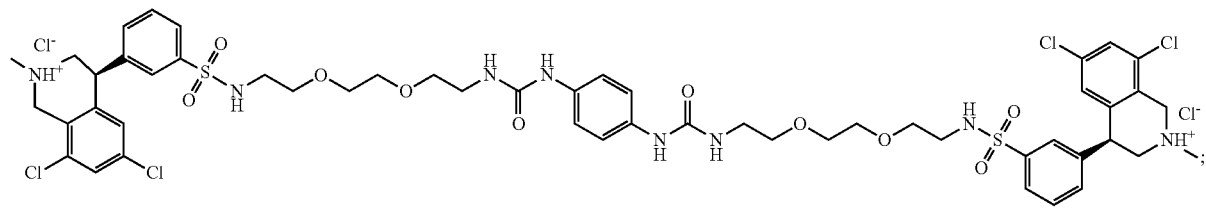

-continued